US005082767A

United States Patent [19]

Hatfield et al.

[11] Patent Number: 5,082,767

[45] Date of Patent: Jan. 21, 1992

[54] CODON PAIR UTILIZATION

[76] Inventors: G. Wesley Hatfield, 718 Goldenrod, Corona Del Mar, Calif. 92625; George A. Gutman, 3080 Tyler Way, Costa Mesa, Calif. 92626

[21] Appl. No.: 316,321

[22] Filed: Feb. 27, 1989

[51] Int. Cl.$^5$ ..................... C12Q 1/68

[52] U.S. Cl. ..................... 435/6; 435/69.1; 435/91; 435/172.3; 436/501; 536/26; 536/27; 536/28; 935/17; 935/78; 935/88

[58] Field of Search ............ 435/6, 91, 69.1, 172.3; 436/501; 536/26, 27, 28; 935/17, 78, 88

[56] References Cited

U.S. PATENT DOCUMENTS

| | | | |
|---|---|---|---|
| 4,184,917 | 1/1980 | Dorner et al. | 435/68 |
| 4,190,495 | 2/1980 | Curtiss, III | 435/172 |
| 4,262,090 | 4/1981 | Colby, Jr. et al. | 435/91 |
| 4,293,652 | 10/1981 | Cohen | 435/172 |
| 4,321,365 | 3/1982 | Wu et al. | 536/27 |
| 4,332,892 | 6/1982 | Ptashne et al. | 435/68 |
| 4,332,898 | 6/1982 | Reusser | 435/172 |
| 4,338,397 | 7/1982 | Gilbert et al. | 435/68 |
| 4,342,832 | 8/1982 | Goeddel et al. | 435/172 |
| 4,348,477 | 9/1982 | Nakano et al. | 435/172 |
| 4,349,629 | 9/1982 | Carey et al. | 435/172 |
| 4,350,764 | 9/1982 | Baxter et al. | 435/69 |
| 4,351,901 | 9/1982 | Bahl | 435/91 |
| 4,356,270 | 10/1982 | Itakura | 435/317 |
| 4,359,535 | 11/1982 | Pieczenick | 435/317 |
| 4,363,877 | 12/1982 | Goodman et al. | 435/317 |
| 4,371,625 | 2/1983 | Tiollais | 435/317 |
| 4,394,443 | 7/1983 | Weissman et al. | 435/6 |
| 4,396,601 | 8/1983 | Salser et al. | 424/94 |
| 4,399,216 | 8/1983 | Axel et al. | 435/6 |
| 4,403,035 | 9/1983 | Anderson et al. | 435/172 |
| 4,468,464 | 8/1984 | Cohen et al. | 435/317 |

OTHER PUBLICATIONS

Shaper, "Constraints on Codon Context in *Escherichia coli* Genes, Their Possible Role in Modulating the Efficiency of Translation", *J. Mol. Biol.* 188:555-564 (1985).
Yarus et al., "Sense Codons Are Found in Specific Contexts", *J. Mol. Biol.* 182:529-540 (1985).
Ausubel et al., Current Protocols in Molecular Biology, vol. 1, Chap. 8, (Wiley Interscience, 1988).
Staden, R., *Nucleic Acids Res.* 12:551-567 (1984).
R. Nussinov, "Eukaryotic Dinucleotide Preference Rules and Their Implications for Degenerate Codon Usage", J. Mol. Biol. 149:125-131 (1981).
Bossi, L. and J. R. Roth, "The Influence of Codon Context on Genetic Code Translation", Nature 286:123-127 (1980).
Taniguchi, T. and C. Weissman, "Inhibition of Qβ RNA 70S Ribosome Initiation Complex Formation by an Oligonucleotide Complementary to the 3' Terminal Region of *E. coli* 16S Ribosomal RNA", Nature 275:770-772 (1978).
Kolaskar, A. S. and B. V. B. Reddy, "Contextual Constraints on Codon Pair Usage: Structural and Biological Implications", Journal of Biomolecular Structure and Dynamics 3(4):725-738 (1986).
Hatfield et al., "Codon Pair Utilization in *E. coli* is Non-Random", Journal of Cellular Biochemistry, Supplement 13 C, (1989).

*Primary Examiner*—Robert A. Wax
*Assistant Examiner*—Ardin H. Marschel
*Attorney, Agent, or Firm*—Knobbe, Martens, Olson & Bear

[57] ABSTRACT

A method for determining the pattern of nonrandom codon pair usage of an organism, comprising the steps of obtaining nucleotide sequence data for the organism, determining from the data the number of codons represented in at least a portion of the sequence and the frequency of usage of at least some codons in the portion, determining from the frequency the expected number of occurrences of at least some codon pairs, if they are paired in a random manner, and comparing the expected number with the actual number of occurrences to determine relative codon pairing preferences. The codon pairings of organisms are highly nonrandom, and differ from organism to organism. This information is used to construct and express altered or synthetic genes having desired levels of translational efficiency, to determine which regions in a genome are protein coding regions, to introduce translational pause sites into heterologous genes, and to ascertain relationship or ancestral origin of nucleotide sequences.

44 Claims, 4 Drawing Sheets

CODON PAIR UTILIZATION

GOVERNMENT INTEREST IN THE INVENTION

This invention was made with Government support under

Grant Nos. GM24330 and AI21366, awarded by the National Institutes of Health. The Government has certain rights in this invention.

FIELD OF THE INVENTION

The present invention relates to a new discovery in the field of genetics regarding codon pair preferences in organisms, the ascertaining of those preferences, and using that information in altering or constructing genes for purposes of expression in other organisms or to modify the translational efficiency of at least portions of the genes.

BACKGROUND OF THE INVENTION

The expression of foreign heterologous genes in transformed organisms is now commonplace. A large number of mammalian genes, including, for example, murine and human genes, have been successfully inserted into single celled organisms. Standard techniques in this regard include introduction of the foreign gene to be expressed into a vector such as a plasmid or a phage and utilizing that vector to insert the gene into an organism. The native promoters for such genes are commonly replaced with strong promoters compatible with the host into which the gene is inserted. Protein sequencing machinery is widely available that permits elucidation of the amino acid sequences of even minute quantities of native protein. From these sequences, DNA sequences coding for those proteins can be inferred. DNA synthesis is also a rapidly developing art, and synthetic genes corresponding to those inferred DNA sequences can be readily constructed.

Despite the burgeoning knowledge of expression systems and recombinant DNA, significant obstacles remain when one attempts to express a foreign or synthetic gene in an organism. Many native, active proteins, for example, are glycosylated in a manner different from that which occurs when they are expressed in a foreign host. For this reason, eukaryotic expression hosts such as yeast are preferred over bacterial hosts for expressing many mammalian genes. The glycosylation problem is the subject of continuing research.

There is another major problem in this area, however, that is much more poorly understood. Oftentimes, translation of a synthetic gene, even when coupled with a strong promoter, proceeds much more slowly than would be expected. The same is frequently true of exogenous genes foreign to the expression organism. And even when the gene is translated in a sufficiently efficient manner that recoverable quantities of the translation product are produced, the protein is often inactive or otherwise different in properties from the native protein.

It is recognized that the latter problem is commonly due to differences in protein folding in various organisms. The solution to this problem has been elusive, and the mechanisms controlling protein folding are poorly understood.

The problems related to translational efficiency, on the other hand, are commonly believed to be related to codon context effects. The protein coding regions of genes in all organisms are subject to a wide variety of functional constraints, some of which depend on the requirement for encoding a properly functioning protein, as well as appropriate translational start and stop signals. However, several features of protein coding regions have been discerned which are not readily understood in terms of these constraints: two important classes of such features are those involving codon usage and codon context.

It has been known for a considerable time that codon utilization is highly biased and varies considerably between different organisms. Codon usage patterns have been shown to be related to the relative abundance of tRNA isoacceptors, and genes encoding proteins of high versus low abundance show differences in their codon preferences. The possibility that biases in codon usage can alter peptide elongation rates has been widely discussed, but while differences in codon use are thought to be associated with differences in translation rates, direct effects of codon choice on translation have been difficult to demonstrate. Additional proposed constraints on codon usage patterns include maximizing the fidelity of translation and optimizing the kinetic efficiency of protein synthesis.

Apart from the non-random use of codons, considerable evidence has accumulated that codon/anticodon recognition is influenced by sequences outside the codon itself, a phenomenon termed "codon context." There exists a strong influence of nearby nucleotides on the efficiency of suppression of nonsense codons as well as missense codons. Clearly, the abundance of suppressor activity in natural bacterial populations, as well as the use of "termination" codons to encode selenocysteine and phosphoserine require that termination be context-dependent. Similar context effects have been shown to influence the fidelity of translation, as well as the efficiency of translation initiation.

Statistical analyses of protein coding regions of *E. coli* have demonstrated yet another manifestation of "codon context." The presence of a particular codon at one position has been shown to strongly influence the frequency of occurrence of certain nucleotides in neighboring codons, and these context constraints differ markedly for genes expressed at high versus low levels. See, e.g., Shpaer, Constraints on Codon Context in *Escherichia coli* Genes, J. Mol. Biol. 188:555-564 (1985) (choice of synonymous codons in highly expressed genes depends on adjacent nucleotides); Yarus, et al., *Sense Codons are Found in Specific Contexts,* J. Mol. Biol. 182:529-540 (1985) (nonrandomness in nucleotides adjacent to codons in weakly and highly expressed genes). Although the context effect has been recognized by previous researchers, the predictive value of the statistical rules relating to preferred nucleotides adjacent to codons is relatively low. This, in turn, has severely limited the utility of such nucleotide preference data for selecting codons to effect desired levels of translational efficiency.

The advent of automated nucleotide sequencing equipment has made available large quantities of sequence data for a wide variety of organisms. The amount of sequence data available is increasing exponentially, and particularly rapid growth is expected in human sequence data as the sequencing of the human genome proceeds. Understanding those data, however, presents substantial difficulties. For example, it is important to identify the coding regions of the genome in order to relate the genetic sequence data to protein sequences. In addition, the ancestry of the genome in particular organisms is of substantial interest. Indeed, it is now known that genomes of some organisms are of mixed ancestry. Some sequences that are originally viral in origin, for example, are now stably incorporated into the genome of eukaryotic organisms. And the viral sequences themselves possibly originated in another substantially unrelated species. An understanding of the ancestry of a gene can be important in drawing proper analogies between related genes and their translation products in other organisms.

Thus, there is a need for a better understanding of codon context effects on translation, and for a method for determining the appropriate codons for any desired translational effect. There is also a need for a method for identifying coding regions of the genome from nucleotide sequence data. Furthermore, a method for controlling protein folding, and for insuring that a foreign gene will fold appropriately when expressed in a host, would represent a major advance in the art. Similarly, methods for determining the ancestry of genes, and for determining the genus or species from which a particular unknown gene comes, are also highly desirable. Finally, genes altered or constructed in accordance with desired translational efficiencies would be of significant worth. All of these needs are addressed by the present invention.

SUMMARY OF THE INVENTION

At the heart of the present invention is a focus on the native preferences in various organisms for codon pairs. This is a significant shift from the focus of the prior art on context effects related to adjacent nucleotides. The results of that shift in focus are dramatic. We have examined the use of codon pairs in a large number of prokaryotic and eukaryotic protein-coding genes. We find that codon pair utilization is highly biased, reflecting over-representation or under-representation of many pairs. This effect is independent of non-randomness in the use of amino acid pairs (which itself is highly evident); it is much weaker when non-adjacent codon pairs are examined, and virtually disappears when pairs separated by two or three intervening codons are evaluated. Moreover, there is virtually no between the preference rules in different types of organisms. There appears to be a high degree of directionality in this bias; any particular codon tends to make both over- and under-represented pairs, but preferentially as a left- or right-hand member. We have shown a relationship between codon pair utilization patterns and levels of gene expression: genes encoding proteins expressed at low levels tend to favor less abundant but more highly over-represented codon pairs, relative to their more highly expressed counterparts.

The non-random utilization of codon pairs appears to be a consequence of their effects on translational efficiency, which in turn may be related to the compatibility of adjacent aminoacyl-tRNA isoacceptors at the A and P sites of a ribosome in a translation complex. We suggest that non-random codon pair utilization is the consequence of protein-coding regions of an organism co-evolving with its protein synthetic machinery, and that this co-evolution is responsible for the species-specific patterns of the number, abundance and chemical and structural modifications of tRNA isoacceptors, as well as codon and codon pair utilization (codon context) patterns. Such co-evolution is believed to provide each organism with the ability to optimize the regulation of translational efficiency while imposing minimal constraints on the structure or function of the encoded proteins.

Our observations regarding codon pair preferences in organisms can be applied in a number of ways to determine and utilize those preferences. The codon pair bias between highly expressed and poorly expressed genes and between organisms can be utilized to greatly facilitate a number of aspects of modern recombinant DNA technology.

Thus, in accordance with one aspect of the present invention, there is provided a method for determining relative native codon pairing preferences in an organism, comprising the steps of obtaining nucleotide sequence data for the organism, determining from the data the number of codons represented in at least a portion of the sequence and the frequency of usage of at least some codons in the portion, determining from the frequency the expected number of occurrences of at least some codon pairs, if the codons are paired in a random manner, and comparing the expected number with the actual number of occurrences to determine the relative codon pairing preferences. Advantageously, the method may further comprise the step of correcting for preferred amino acid pairings of the organism prior to determining the codon pairing preferences. In one preferred embodiment, the method includes the step of altering a gene for expression in the organism by substituting at least one codon for an existing codon in the gene to alter codon pairing in accordance with the codon pairing preferences to change the translational efficiency of the gene in a predetermined manner. For example, the codon pairing may be altered to increase the translational efficiency of at least a portion of the gene. The codon pairing may be altered to increase the number of codon pairs that, in comparison to random codon pair usage, are the more abundant and yet more under-represented codon pairs in the organism. Alternatively, the codon pairing is altered to decrease the translational efficiency of the gene. This may be done by increasing the number of codon pairs that, in comparison to random codon pair usage, are the less abundant and yet more over-represented codon pairs in the organism. When altering codon pairs to change translational efficiency, a single codon may be altered; alternatively, two, three, or four codons, or even as much as 5%, 10%, 15%, or even 20% or more of the codon pairs in the gene can be altered. The invention also includes the step of constructing a synthetic gene coding for a predetermined polypeptide for expression in the organism, and selecting codons for amino acids of the polypeptide in accordance with the relative native codon pairing preferences of the organism to achieve a desired level of translational efficiency of the gene. Codon pair selection can follow the rules and affect the number of genes previously discussed.

In one preferred embodiment, the method includes the step of separately determining the codon pair preferences of a first group of genes that are expressed above a certain level, and a second group of genes that are expressed below the level. These data then become useful in selecting the codon pairs that correspond to the inferred greater translational efficiency of highly expressed genes, or lower translational efficiency of genes expressed at a lower level.

The present invention also includes a method for making at least a portion of a synthetic gene coding for a polypeptide, wherein the gene is intended for expression in a particular organism, comprising the steps of obtaining information regarding the relationship between codon pairing and translational efficiency for the organism, and for at least one amino acid pair in the polypeptide, selecting from among possible codon pairs a pair that provides a desired level of translational efficiency, and providing the selected codon pair in the gene. It is preferred that at least two o three codon pairs are selected and provided in accordance with the information. In one embodiment, the selected codon pair is preferred by the organism in genes expressed at low levels of less than about 1000 copies per cell. In another, the selected codon pair is preferred by the organism in genes expressed at intermediate levels of from about 1000 to about 10,000 copies per cell. In still another embodiment, the selected codon pair is preferred by the organism in genes expressed at high levels of greater than about 10,000 copies per cell. In one embodiment, the selecting step affects at least 5%, 10%, or even 15% or more of the codons of the gene.

In accordance with still another aspect of the present invention, there is provided a method for altering a gene of a first organism for expression in a second organism, comprising the steps of obtaining information regarding native codon pairing preferences for at least some genes of the second organism, and for at least one codon pair in the gene, replacing one or more existing codon pairs in accordance with the codon pair preference information with more preferred codon pairs coding for the same amino acids to alter the translational efficiency of the pairs in a predetermined manner. In one preferred embodiment, the replacing step affects at least 5%, 10%, 15%, or even 20% or more of the codons of the organism. The replacing step may be designed to either increase or decrease the translational efficiency of the codon pairs. Effecting both a local increase and a local decrease in translational efficiency in the gene is also contemplated by the present invention, for example, to assist in protein folding during translation.

The present invention also includes a method for expressing a gene in an organism, the gene having an altered translational efficiency, comprising the steps of introducing a gene prepared according to one of the foregoing methods into the organism, and expressing the gene in the organism.

A further aspect of the present invention is an exogenous gene coding for a predetermined polypeptide for expression in a first organism, comprising a plurality of codon pairs coding for amino acid pairs of the polypeptide, wherein at least three of the pairs have been selected from among possible codon pairs to correspond to codon pairs preferred by the first organism in genes expressed at levels greater than about 10,000 copies per cell. In one preferred embodiment, at least 5%, 10%, 15%, or even 20% or more of the pairs have been selected from among possible codon pairs coding for the amino acid pairs to correspond to codon pairs preferred by the first organism in genes expressed at levels greater than about 10,000 copies per cell.

A complementary aspect of the invention is an exogenous gene coding for a predetermined polypeptide for expression in an organism, comprising a plurality of codon pairs coding for amino acid pairs of the polypeptide, wherein at least three of the pairs have been selected from among possible codon pairs to correspond to codon pairs preferred by the first organism in genes expressed at levels less than about 1000 copies per cell. Similarly, the invention includes an exogenous gene coding for a predetermined polypeptide for expression in an organism, comprising a plurality of codon pairs coding for amino acid pairs of the polypeptide, wherein at least three of the pairs have been selected from among possible codon pairs to correspond to codon pairs preferred by the first organism in genes expressed at levels between about 1000 and about 10,000 copies per cell per. Yet another aspect of the present invention is a gene altered for expression in a host organism other than the one to which the gene is native, wherein at least three codon pairs of the native gene have been changed to correspond to codon pairs preferred by the host organism in genes expressed at levels greater than about 10,000 copies per cell.

Also included within the scope of the present invention is an organism expressing an exogenous gene native to a different species, wherein the exogenous gene has been tailored for expression in the organism by rational replacement of existing codon pairs with codon pairs producing desired translational efficiency in the organism. These codon pairs may be those that, in comparison to random codon pair usage, are the more abundant and are under-represented in the organism. Alternatively, they may be those that, in comparison to random codon pair usage, are the less abundant and are over-represented in the organism.

Still another aspect of this invention is a method for determining probable protein-coding sequences in the genome of an organism, comprising the steps of obtaining, for the organism, information regarding codon pairing preferences in known coding regions of the genome, and comparing the information with nucleotide sequence data for a region of interest in the genome to determine whether the region has the codon pairings expected in a coding region.

Still another use for the discovery set forth herein is the utilization of the data regarding codon pair preference in a method for determining the type of organism from which a sample of nucleic acid originated. The steps of such a method comprise determining the nucleotide sequence of the sample, and comparing the codon pairings in the sequence with codon pairing preferences for several possible organisms.

Similarly, the invention contemplates a method for determining the evolutionary origin of a nucleic acid sample, comprising the steps of determining the nucleotide sequence of the sample, and comparing the codon pairings in the sequence with codon pairing preferences of genes to which the sample may be related.

One particular use for the codon pair preference rules discovered by the present inventors is in altering the translational efficiency of only a portion of a gene. This method comprises obtaining, for an organism in which the gene is to be expressed, data regarding the relationship between codon pairing and translational efficiency, and altering at least one codon pairing in the portion in accordance with the data. For example, protein folding may be enhanced when the codon pair alteration introduces a translational pause in a portion of a gene. Similarly, it may be desirable to have the alteration increase the speed at which the portion is translated.

The codon pair preference relationships reported herein also provide a method for inferring the relative level of expression of a gene in an organism, comprising the steps of obtaining nucleotide sequence data for the gene, obtaining data relating codon pair preferences to the level of expression of genes in the organism, and comparing the codon pairings of the gene with the data.

In the expression of an exogenous gene in an engineered organism, the present invention facilitates the proper folding of translation product in a method comprising the steps of obtaining data relating to codon pair preferences and relative representation of codon pairs for both a first organism to which the gene is native and a second organism in which the gene is to be expressed, identifying at least on codon pair in the gene that is over-represented to a greater extent in the first organism than in the second organism, altering the identified codon pair to a pair coding for the same amino acids that is over-represented to a greater extent in the second organism, and expressing the gene having the altered codon pair in the second organism.

Related to the foregoing is a method for introducing a translational pause site into a gene to be expressed in a particular organism, comprising the steps of obtaining, for the organism, information regarding codon pair preferences and relative representation of codon pairs, and introducing into the pause site an over-represented codon pair.

DETAILED DESCRIPTION OF THE INVENTION

Figure 1:
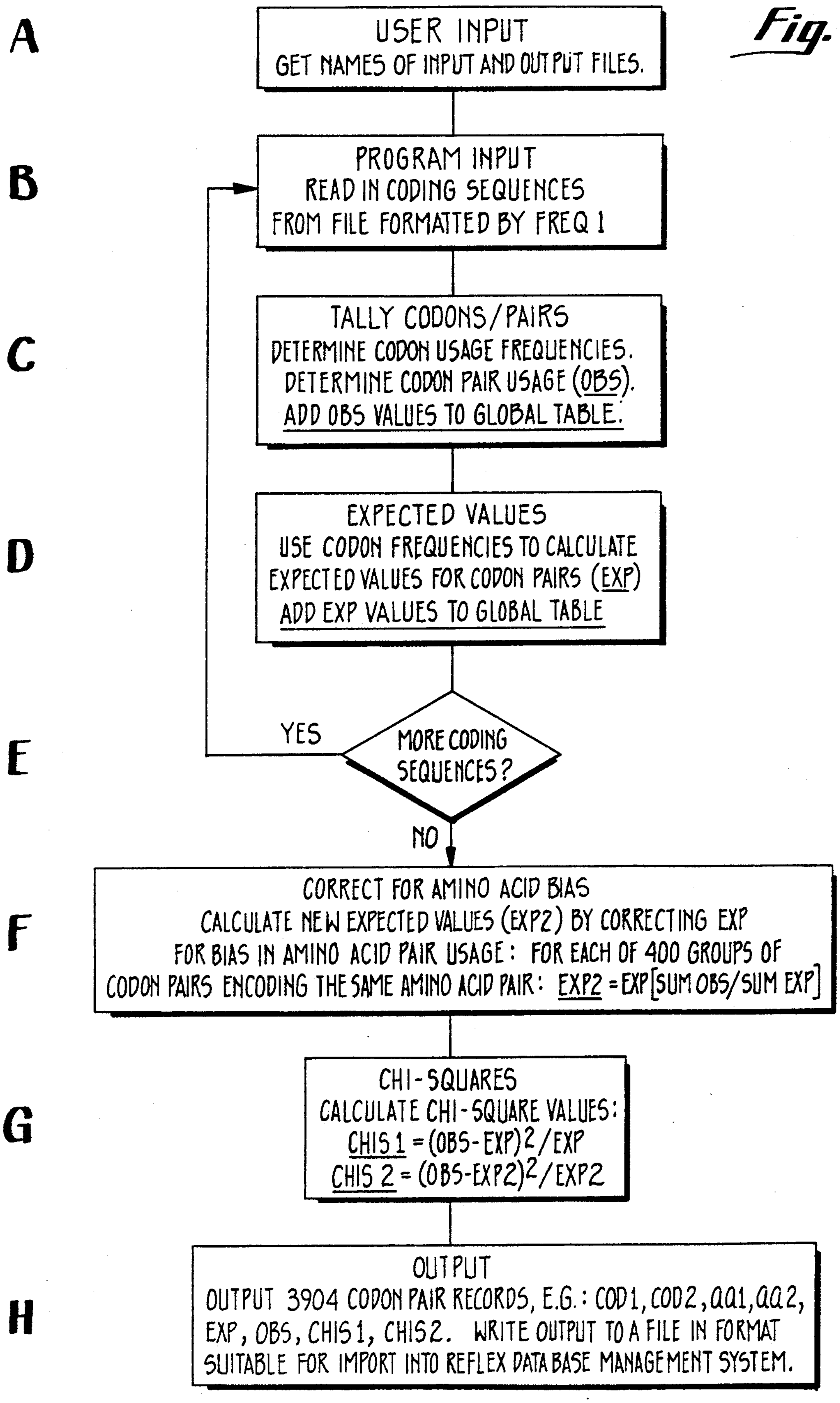
FIG. 1 is a flow diagram for a computer program for determining codon pair preferences.

We have now analyzed the pattern of codon pair utilization in DNA sequences specifying protein-coding genes of the bacterium *E. coli* and the yeast *S. cerevisiae.* Such pairs are utilized in a highly non-random fashion, and there are many pairs which are extremely over- or under-represented compared with their random expectation. This non-randomness of codon pairs is independent of non-randomness in the utilization of amino acid pairs, which itself is also highly evident. In addition, patterns of codon pair utilization differ between genes whose protein products are expressed at high versus low levels. Further, the codon pair utilization is dramatically different between the analyzed yeast and bacteria genomes.

Computer Analysis of Preference Patterns

An important first step in practicing the present invention is obtaining information relating to the codon pair preferences for the particular organism of interest. Broadly, this involves obtaining codon sequence data for the organism, preferably on a gene-by-gene basis. The analysis is preferably focused only on the coding regions of the genome. Of course, because the analysis is a statistical one, a large database is preferred. Additionally, for some aspects of the present invention, differentiation between the relative levels of expression of the various native genes yields valuable information.

Initially, the total number of codons is determined and the number of times each of the 61 common codons appears is determined. From this information, the expected frequency of each of the 3721 ($61^2$) possible codon pairs is calculated, preferably by multiplying together the frequencies with which each of the component codons appears. This frequency analysis can be carried out on a global basis, analyzing all of the sequences in the database together; however, it is preferably done on a local basis, analyzing each sequence individually. This will tend to minimize the statistical effect of an unusually high proportion of rare codons in a sequence. After the frequency data is obtained, for each sequence in the database, the expected number of occurrences of each codon pair is calculated by multiplying the expected frequency by the number of pairs in the sequence. This information is then added to a global table, and each next succeeding sequence is analyzed in like manner.

This analysis results in a table of expected and observed values for each of the 3271 codon pairs. The statistical significance of the variation between the expected and observed values may then be calculated, and the resulting information is used in further practice of the various aspects of the present invention. If desired, the data can be corrected for nonrandomness of amino acid pair usage, and data from rare codon pairs can be eliminated if it is not of sufficient statistical significance.

When the codon pair usage patterns of *E. coli* and *S. cerevisiae* were evaluated and compared in accordance with Examples 2 and 3, below, several features became apparent:

Codon Pairs. Our analyses show that many codon pairs are highly over- or under-utilized compared with their random expectations, and that this effect is independent of any contribution by non-randomness in codon use or in amino acid pair utilization. We conclude that powerful constraints must therefore exist on the utilization of codon pairs. Our findings are generally consistent with those of others who have described non-random features of coding region context, although our analysis more closely defines the nature of the non-random patterns. Discussion of the many known constraints on codon use and on codon context can thus be extended to the evaluation of constraints on specific codon pairs. Our results strongly suggest that codon usage is closely related to control of translational efficiency.

Consequences of Codon Pair Non-Randomness. The codon pair non-randomness we have described acts only over a short distance, affecting the adjacent codon very strongly, the next one more weakly (although still highly significantly) and the next two non-discernably.

We nave also found a high degree of directionality in codon pair non-randomness; codons which tend to make highly non-random pairs do so preferentially as right- or left-hand members. Both of these features are consistent with the view that the effect is mediated via interactions between aminoacyl-tRNAs bound to adjacent codons on the translation complex, a concept which has been invoked to explain the context effect on termination suppression. In fact, variation in chemical modification of tRNAs (with the potential for altering their steric interactions) can markedly affect the efficiency of termination suppression and peptide elongation rates. The relationship between specific codo pairs and translation initiation and elongation rates, as well as the influence of tRNA modification, are potentially fruitful areas for investigation made possible by our invention.

One area in which the ability to control translation efficiency is of special importance is the expression of eukaryotic genes in *E. coli*. We have demonstrated that patterns of codon Pair utilization turn out to differ substantially between the two species we have analyzed. It is expected that this will hold true in general as additional species are analyzed. Thus, our invention provides simple rules for modifying coding sequences, or generating synthetic genes, for the purpose of controlling translation efficiency in genetically engineered expression systems.

Another increasingly important contemporary problem is the need to identify true protein-coding regions in open reading frames of DNA sequences, particularly given the current exponential increase in published nucleotide sequences, and the planned project for sequencing the human genome. Several approaches have been described, taking advantage of non-random features of codon utilization, as well as other statistical features which characterize protein-coding regions, but none has proven completely satisfactory. Application of the non-random features we have described, both for codon pairs and amino acid pairs, can contribute significantly to such analyses.

The general view to which we subscribe regards protein coding regions within an organism as co-evolving in a complex fashion with the protein synthetic machinery. The relative abundance of tRNA isoacceptors, their anticodons and secondary structure, and the variety of their chemical modifications, all affect (and are affected by) the pattern of utilization of codons and codon pairs. This mutual influence is believed to result in highly species-specific patterns of metabolic coordination that operates without placing excessive constraints on the structure and function of the encoded proteins.

Tailoring Codon Pairings of Heterologous Gene to Expression System

Figure 3:
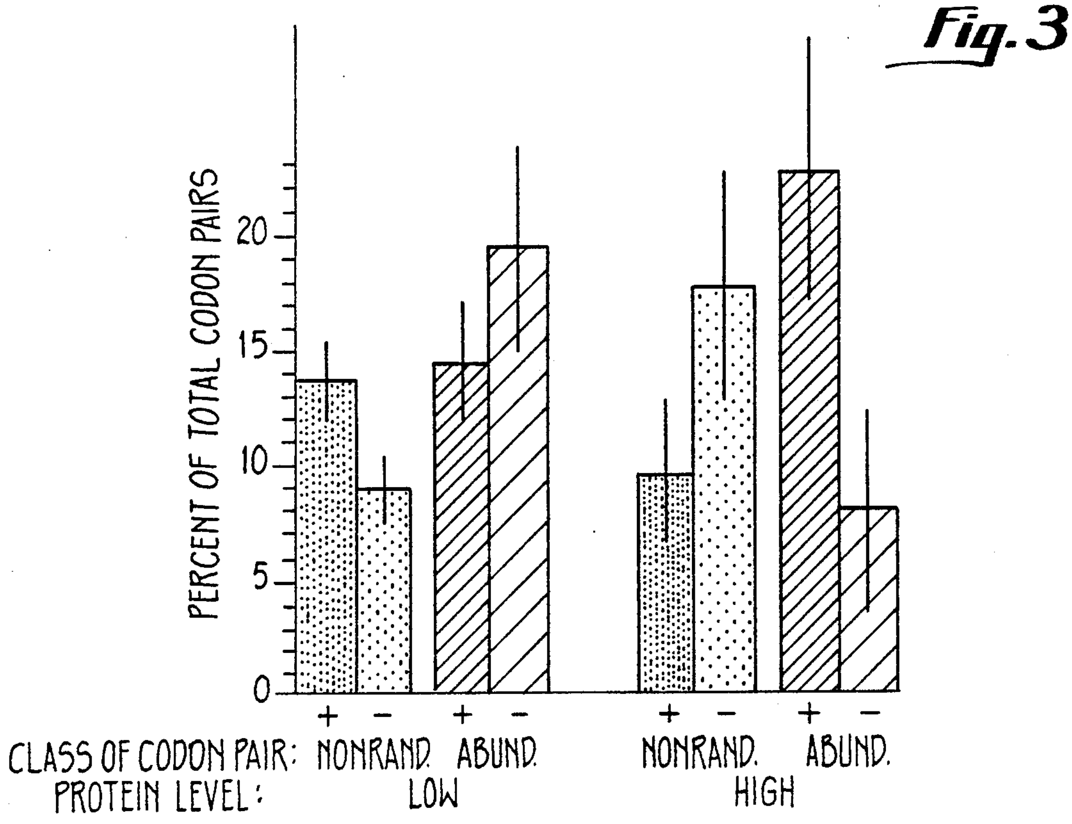
FIG. 3 is a graph showing, for *E. coli* genes expressed at low levels and those expressed at high levels, the percentages of over-represented codon pairs (NONRAND+)(chis2≧12) and under-represented pairs (NONRAND-)(chis2≧3) and the percentages of pairs used abundantly (≧90x; ABUND+) and infrequently (≦15x; ABUND−) in the *E. coli* database. Lengths of the vertical lines represent ±1 standard deviation. The numbers above each pair of bars represents the ratio of high (+) and low (−) values.

The information we can now generate regarding codon preference patterns for a particular type of gene in an organism is of significant value in tailoring genes for expression in a particular organism. This is particularly true when the analysis described above and exemplified in Examples 1-3 below is performed on a subset of the genes in an organism. As reported in Examples 2 and 3, and as shown in FIG. 3, we have discovered significant differences in codon pair utilization between genes that are expressed at high levels and those that are expressed at low levels. These data, we believe, are reflective of translational efficiency. Thus, we have derived a simple set of rules that can be used in analyzing native translational patterns, in altering native genes, and in constructing synthetic genes. Those rules are that for high translational efficiency, a nucleic acid sequence should utilize under-represented codon pairs, preferably those that are more abundant. Conversely, for low translational efficiency, one uses over-represented codon pairs, preferably those that are less abundant. In particular, it appears that an over-represented abundant pair will result in slow translation; an under-represented abundant pair will result in very fast translation; an over-represented less abundant pair will result in very slow translation, and an under-represented less abundant pair will result in fast translation. Relative abundance can be determined in comparison to the mean number of occurrences of one codon pair in the database. The more abundant codon pairs will occur more often than the mean; the less abundant codon pairs will occur less often than the mean. And one can arbitrarily require, for example, that the difference from the mean meet some minimum criterion, such as a one or two standard deviation difference.

Based on the foregoing, a less abundant, over-represented codon pair is believed to introduce a translational pause into the protein synthesis process. Nature apparently uses translational regulation through codon pair selection to control the folding of proteins. This is supported by Example 4, where apparent pauses are found before and/or after folded protein regions in nucleic acid binding proteins with a helix-turn-helix configuration.

As used herein, a codon pair is considered to be over-represented or under-represented if its chi-square value is greater than 4. Also, a gene is considered to be expressed at high levels if it is expressed at levels greater than about 10,000 copies per cell. A gene is considered to be expressed at low levels if it is expressed at levels less than about 1000 copies per cell. Genes are considered to be expressed at an intermediate level if expressed at between 1000 and 10,000 copies per cell. Separate analysis of genes in each category to determine the codon pair preferences therein is also a part of the present invention. Of course, the definition of high, intermediate, and low levels of expression may be altered to suit any particular situation or organism without departing from the principle of separately determining codon pair preferences within each category.

In accordance with these concepts, a gene of one organism may be altered for expression in another, and is expressed in that other organism, where the two organisms have different patterns of codon pair usage. For example, when high levels of translation are desired, the codon pairs of the native gene are altered to replace those that are over-represented in the expression organism with under-represented codon pairs, preferably pairs that are also relatively abundant. The particular codon pairs to be altered can be determined by reference to a table of codon pair preferences, such as the one for *E. coli* attached as Appendix 3. As an example, reference to Appendix 3 shows that one of the two most over-represented codon pairs in the *E. coli* database is ACG CTG, coding for the amino acid pair Thr Leu. A synonymous codon pair (i.e., coding for the same amino acid pair) is ACC CTG, which is the most under-represented codon pair in that database. Using genes altered with conventional techniques, we have generated initial data which demonstrate the predicted effects on translation rate when the genes differ only in the substitution of ACC CTG for ACG CTG.

Even without a complete understanding of the exact translational effect of any given codon pair in any particular organism, the codon pair preference data generated in accordance with the present invention can be utilized in connection with recombinant DNA techniques to tailor genes for expression in any particular organism. In accordance with one preferred embodiment of the invention, the pattern of nonrandom codon pair usage in a gene is determined for the organism to which the gene is native. This may be done graphically, for example, by plotting the chi-square values for each of the codon pairs, as shown in FIGS. 4A-4D. Then, one compares the codon pair usage in that gene with the preference pattern of the organism in which it is to be expressed, and alters the codon pair usage, changing amino acid usage either not at all or only to a small degree, to achieve a gene having the same pattern of nonrandom usage in the expression organism. In this way, the translational kinetics of the gene in the native organism can be conserved to a substantial degree in the expression organism. In addition, protein folding can be permitted to occur in the same manner as in the organism to which the gene is native. Thus, for example, the gene can be altered to provide translational pauses in the same places as in the native organism.

When altering a gene for expression in another organism, one may tailor all of the codon pairs to correspond closely (in terms of overall representation in the genome of the expression organism) to the preference patterns of the expression organism. However, it may not be necessary to alter all of the codon pairs, or even a large percentage of them. Often, alteration of a single pair, or two or three pairs, can be sufficient to achieve the desired change in translational kinetics.

It should be noted that the present invention is not dependent on and not directed to any one particular technique for constructing and/or altering nucleotide sequences. Several suitable techniques are known in the prior art, and include, for example, oligonucleotide-directed mutagenesis, mutagenesis with degenerate oligonucleotides, and region-specific mutagenesis. All of these techniques are explained in Ausubel, et al., Current Protocols in Molecular Biology, Vol. 1, Ch.8 (Wiley Interscience 1988). Moreover, suitable techniques for altering DNA are set forth, for example, in U.S. Pat. Nos. 4,184,917, 4,321,365, and 4,351,901, which are incorporated herein by this reference. Instead of altering an existing gene, any desired sequence Can now be synthesized de novo using readily available machinery. Sequential synthesis of DNA is described, for example, in U.S. Pat. No. 4,293,652, which is incorporated herein by this reference.

Similarly, the expression of genes in heterologous systems is now well known, and the present invention is not directed to or dependent on any particular expression system or technique. Rather, genes prepared with the modifications set forth herein may be used to transform an expression cell or organism in any suitable manner in conjunction with any suitable vector, and the genes may be expressed with known promoters in any conventional manner. Suitable vector construction, transformation, and expression techniques are disclosed, for example, in U.S. Pat. Nos. 4,468,464, 4,403,035, 4,332,901, 4,399,216, 4,396,601, 4,394,443, 4,371,625, 4,363,877, 4,359,535, 4,356,270, 4,350,764, 4,349,629, 4,399,216, 4,348,477, 4,342,832, 4,338,397, 4,332,898, 4,332,892, 4,321,365, 4,262,090, and 4,190,495, which are incorporated here in by this reference.

Determination of Protein Codino Regions in a Genome

The present invention also includes a method of distinguishing protein coding regions from non-coding regions of a genome. This is done by comparing the codon usage and codon pair usage of any unknown region to known patterns. Although this analysis may be implemented in any number of ways, one preferred embodiment involves a modification of the technique described by R. Staden, Nucleic Acids Res. 12:551-567 (1984), which is hereby incorporated by reference. In our technique, the codon usage in a sliding window (e.g., 25 codons long) is compared to that of a known codon pair usage table of the type set forth in Appendices 4 and 5 hereto. For a given codon sequence a1a2a3a4...an, one calculates the probability of selecting this particular sequence given a particular pattern of codon pair preference. This probability can be calculated as:

$$p1 = Fa1a2 \times Fa2a3 \times Fa3a4 \times \ldots x\ Fa(n-1)an$$

where Fa1a2 is the frequency of codon pair a1a2 from the table and n is the length of the window, in codons. Next, one repeats the calculation, shifting the window first one nucleotide (b1b2b3b4 . . . bn) and then two nucleotides (c1c2c3c4 . . . cn) to generate probabilities p2 and p3, respectively. One then calculates the probability that appearance of this particular sequence in each of the frames is the result of its being a protein coding sequence. This probability for the first frame is calculated as:

$$P1 = p1/(p1 + p2 + p3)$$

Similar calculations for each of the other two frames are also carried out, giving values P2 and P3. Then, plotting log(P/(1-P)) for each of the frames P1, P2, P3 as one moves through the sequence being analyzed yields a series of three graphs, each showing the probability that this reading frame represents a protein coding sequence. If the plot of one reading frame is consistently higher than the two others, it indicates the likelihood that the region in question represents a protein coding region.

The Staden technique referred to above generates similar data based on the codon preferences (as opposed to the codon pair preferences) of a particular organism. Use of both techniques in parallel to identify protein coding regions is also contemplated as a part of the present invention.

These same techniques can be used to infer the relative level of native expression of a gene, by comparing the codon usage pattern of that gene with the pattern used by the organism in genes expressed at different levels.

Determination of Source or Ancestral Origin of RNA or DNA

In another variation of the present invention, one may use codon pair preference data to determine the extent to which a particular nucleic acid sequence is related to the genomes of various species. By comparing the actual codon pair usage in a protein coding region of such a sequence with codon pair preference data for several species, the degree to which the codon pair usage corresponds to that of each species can be determined, and from that information inferences can be drawn regarding the and actual or ancestral origins of the sequence.

EXAMPLE 1

COMPUTER PROGRAM FOR ANALYZING CODON PAIR PREFERENCES

In general, an appropriate computer program for analyzing codon pair preferences for any particular organism may correspond to the flow chart set forth in FIG. 1. We have implemented the codon pair analysis in a set of programs we refer to as CODPAIR, which are written in TURBO PASCAL (Borland International, Scotts Valley, California) running in an MS-DOS environment. Program listings for CODPAIR are set forth in Appendix 1 attached hereto.

For each sequence in the database, CODPAIR enumerates the total number of codons, the frequency of each codon and the number of occurrences of each codon pair. The expected frequency of each codon pair is then calculated as the product of the frequencies of its two component codons, assuming they are used randomly; the expected number of occurrences of each codon pair is the product of its expected frequency and the total number of codon pairs in the sequence. CODPAIR adds the values for observed and expected occurrences of codon pairs to two global tables, then goes on to the next sequence.

While our initial approach was to calculate the expected values using global codon usage frequencies, the use of locally evaluated frequencies is a more conservative approach. If, for example, a sequence has an unusually high proportion of rare codons, it will also tend to have a high proportion of rare codon Pairs made up of these codons, simply by virtue of their local abundance.

The result of these calculations is a list of 3,721 codon pairs, each with an expected and observed value, together with a value for chi-square (chis1):

$$chis1 = (observed-expected)^2/expected$$

The sum of these chi-squares is that of a distribution with 3,720 degrees of freedom (DF). According to the Central Limit Theorem, the expected value of chi-square is equal to the number of degrees of freedom, N (where N is large), with a variance of 2N.

In order to remove the contribution to this chi-square of non-randomness in amino acid pairs, a new value (chis2) was calculated in the following manner. For each group of codon pairs encoding the same amino acid pair (i.e., 400 groups), the sums of the expected and observed values were tallied; any non-randomness in amino acid pairs is reflected in the difference between these two values. Therefore, each of the expected values within the group was multiplied by the factor [sum observed/sum expected], so that the sums of the expected and observed values with the group were now equal. The new chi-square, chis2, was evaluated using these new expected values. This manipulation reduces the number of degrees of freedom by 400, resulting in a distribution with 3,320 degrees of freedom.

The CODPAIR program shown in Appendix 1 includes two subprograms, or modules, FREQMODI and FREQMOD2. The FREQMOD1 module is a preprocessor which inputs a portion of the GENBANK database (currently provided by Intelligenetics, Mountain View, California) in INTELLIGENETICS format and formats a coding sequence database comprising the sequence name and the protein coding regions found in sequences of DNA and RNA. An example input database file for FREQMOD1, in INTELLIGENETICS format, is presented in Appendix 2. An example coding sequence, or CODPAIR, database file, the file in Appendix 2 after being preprocessed by FREQMODI, is presented in Appendix 3. Since the function of the FREQMOD module is not substantive to the utilization of codon pairs, it will only be discussed for the purpose of describing the coding sequence database.

The FREQMOD2 module is the subprogram which performs a statistical analysis on the coding sequence database for codon pair utilization. The program statements in FREQMOD2 (Appendix 1) can be cross-referenced against the flow chart symbols of FIG. 1 by the letters (A-H) which have been placed in the left-hand margin of both references.

With reference to FIG. 1, the first block, USER INPUT (A), of FREQMOD2 is a request to the user for input and output filenames. In the preferred embodiment of Appendix 1, this block is programmed as the INIT1 procedure. File variable INDBNAME designates the input database file created by FREQMODI and this file must have a "OTD" file extension. The output filenames, as described in the introductory comments of FREQMOD2, use the same root as the input filename but differ in file extensions.

The flow control loop containing blocks B-D and conditional diamond E is located in procedure PROCESSIT. PROCESSIT relies on a coding sequence database file with a file structure determined by procedure STORECODE in FREQMOD1. PROGRAM INPUT (B) is executed when FREQMOD2 calls procedure PROCESSIT which in turn calls procedure REGIONIN. For each coding sequence in the coding sequence database, all protein coding regions are read in one by one, by a call to procedure REGIONIN. REGIONIN uses dynamic memory to build a linked list of bases. Linked lists are first-in-first-out data structures which are well known to those skilled in the art of programming. The head of the linked list is defined by variable BASE. A base is defined as one of the letters in the following set: (G,T,C,A). The number of bases in the coding region under consideration is accumulated and stored in the variable NUMREGNOW.

TALLY CODONS/PAIRS (C) block is implemented in the FREQMOD2 module by procedure COUNTIT which is executed by a call from procedure PROCESSIT immediately after each call to procedure REGIONIN. The first step of TALLY CODONS/PAIRS (C.1) is to determine codon usage frequencies. Codons are defined by concatenating the letters which define three bases. The variable CDNI holds a codon character string, for example, GAC, which also happens to represents the amino acid Asparagine.

Each of the sixty-four possible codons has at this point already been assigned an index into a codon character string table, CODON (see Appendix 1, FREQMOD2, page 2-3). Continuing with the last example, GAC is seen to be defined as CODON number forty-eight (48). Furthermore, in the amino acid character string table, CDN, each codon is mapped to one of the twenty possible protein forming amino acids or one of the three possible special initiating or terminating codons. In this example, CDN [48], or position forty-eight of the amino acid character string table, is defined to be the character string 'Asp'.

After CDN1 is defined in procedure COUNTIT, the first codon is configured as a possible left side of a codon pair by being assigned to the character string variable CDNL. The index into the CODON table of CDNL is found by calling the utility procedure FINDNUM, and the resulting value is assigned to the integer variable CODL. The local codon observed usage table, LTABLE, is incremented at the appropriate codon index defined by CODL. For example, since the protein coding region ATG-GCC- . . . begins with the codon represented by 'ATG', LTABLE [21] is incremented from 0 to 1.

In all but the first codon, the local codon usage table, LTABLE, is indexed using the integer variable CODR. CODR is the index equivalent of the character string variable CDNR. For example, in the preceding example, LTABLE is indexed with the integer equivalent of GCC, or 32, and incremented from 0 to 1. Global expected codon usage table, TABLE 1, updated with the corresponding local table data.

The second step of the TALLY CODONS/PAIRS block (C.2) is to determine the observed codon pair usage in the subject protein coding region. This is accomplished by saving the last codon processed in character string variable CODL, and keeping the current codon processed in character string variable CODR. Hence, all codons except the first (neglecting the special initiating codon) are possible members of two codon pairs, first as a left member and second as right member. Global expected codon pair usage table, TABLE2, is thus indexed by variables CODL and CODR, and incremented accordingly. Using the preceding example, the first possible pair of the sequence ATG-GCC . . . causes TABLE2 [21,32] to be incremented.

The next block of the flow chart shown in FIG. 1 is EXPECTED VALUES (D). The functionality of EXPECTED VALUES (D) is implemented in procedure COMPUTE which is local to, and called by, procedure COUNTIT. Local codon frequencies are established by dividing all local codon counts, stored in local codon usage table LTABLE, by the total number of codons in a given region. As an example, if a region has four occurrences of the codon 'CCC', and the entire region contains one hundred codons, then the observed frequency of 'CCC' in the given region is 4%.

The expected codon pair usage is then calculated for each codon, as either a left member or a right member, by multiplying the observed frequency of both pair members, and then multiplying by the total number of pairs. This value is summed in the expected codon pair usage table, ETABLE2. In the last example, if the region has ten occurrences of the codon 'CAT', then, assuming independent variables, we expect to find (0.04) * (0.10) * 100=0.4 pairs (this is of course a theoretical number) of CCC-CAT, and the same number of CAT-CCC pairs.

Conditional diamond MORE CODING SEQUENCES (E) is implemented in the FREQMOD2 module by the WHILE-loop which terminates on finding either the end-of-database string '//' or an end-of-file condition, indicating no more coding sequences to process.

In the flow chart of FIG. 1, blocks F-H correspond to procedure CONVERSION in FREQMOD2. In the CORRECT FOR AMINO ACID BIAS (F) block, new expected codon pair usage values are calculated to correct for bias in amino acid pairs. As shown in the CONVERSION procedure of module FREQMOD2, the bias correction is accomplished by, for each amino acid or special codon, first summing observed (variable SUMOBS) and expected (variable SUMEXP) codon pairs stored, respectively, in tables TABLE2 and ETABLE2. The new expected codon pair usage (variable NEWEXP) is then defined by multiplying the expected codon pair usage, ETABLE2, by the following bias adjustment coefficient: (SUMOBS)/(SUMEXP).

The CHI-SQUARES (G) block is implemented in FREQMOD2, procedure CONVERSION, by programming the formulas shown in the flow chart of FIG. 1. The OUTPUT (H) block follows as the last functional block. The REFLEX file variable, shown in procedure CONVERSION, identifies an output file in REFLEX format. REFLEX is a database management system sold by Borland International. REFLEX is used for sorting, selecting, listing and performing like manipulations on a database.

EXAMPLE 2

ANALYSIS OF *E. COLI* CODON PAIR PREFERENCES

The CODPAIR program described in Example 1 was used to analyze the *E. coli* genome. The source of DNA sequences was the GENBANK database (Release 40.0, Rev. 1986, Bolt Beranek and Newman, Inc., Cambridge, Massachusetts). Two hundred thirty seven chromosomal *E. coli* protein coding regions greater than 100 bp in length were used for analysis (212 contained a termination codon) encompassing a total of 235,845 nucleotides and 78,403 codon pairs.

The analysis proceeded generally as outlined in Example 1. However, we omitted from these calculations all codon pairs for which the expected value was less than 3, to avoid high chi-squares generated simply by very low expected values (e.g., an expected value of 0.1 with an observed value of 2 yields a chi-square of 36!). In our analysis of the *E. coli* genome, this correction resulted in a loss of 507 records, leaving 2,713 degrees of freedom; the chi-square for this distribution (calculated as described above) has an expected mean of 2,713 with a standard deviation of 75.

A printout of the codon pair preference data for this analysis of the *E. coli* genome, comparing expected and observed values for all of the possible codon pairs, together with chis1 and chis2 calculations for each pair, is set forth in full in Appendix 4.

The distribution of amino acid pair occurrences was also evaluated; the sums of the expected and observed values for codon pairs corresponding to each of the 400 amino acid pairs were used to calculate a chi-square value for this distribution, with 399 degrees of freedom.

A tabular example of the output of CODPAIR is shown in Appendix 4 (additional examples can be seen in Appendix 5, discussed below). Each line shows the two adjacent codons of a pair and their cognate amino acids, the expected number of occurrences of that codon pair (calculated under the assumption that they are used randomly), and the observed number of occurrences of that pair in the database. "Chis1" is the chi-square value generated by the expected and observed values shown, while "chis2" is the chi-square re-calculated to remove any influence of non-randomness in amino acid pair frequencies (see Methods). It is evident that while many codon pairs occur at levels close to those expected, some are highly over-represented (e.g., CTG-GCA, CTG-GCG) or under-represented (CTG-GAC, CTG-GCC). Examples can also be seen of the effect of correcting chisl for amino acid pair non-randomness to yield chis2. In the case of CTG-GCG, chis2 is very much smaller than chisl (although still extremely high at 54); in the case of AAC-CCG, the very large value of 41 for chis1 is reduced to only 2.9 for chis2. In the ensuing discussion we shall deal only with this latter value, chis2. While this is a conservative approach (as discussed in Methods), it is important to note that the difference between chis1 and chis2 does not necessarily imply that part of the codon pair non-randomness is the consequence of amino acid pair non-randomness; the direction of causation is indeterminate, and it is equally possible that the amino acid pair non-randomness is driven by selection on codon pairs.

Figure 2:
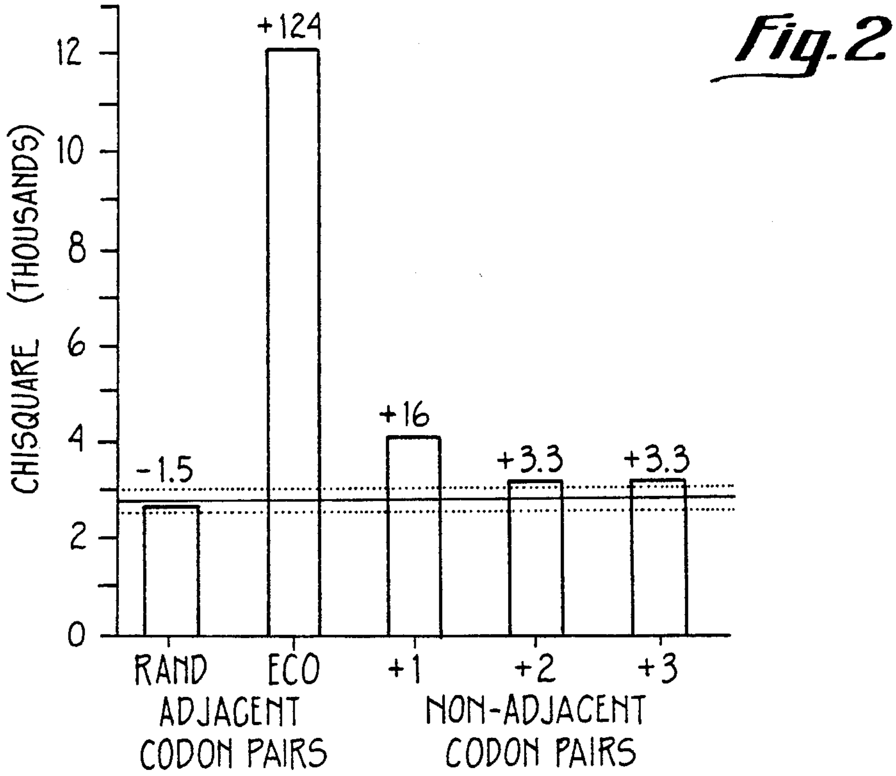
FIG. 2 is a graph comparing the sums of codon pair chi-square (chis2) values for a randomized data base, the *E. coli* database, and the chi-square values of codons separated by 1, 2, and 3 intervening codons. The solid horizontal line represents the expected mean of the chisquare values; the broken lines represent + and − 3 standard deviations. +1, +2, and +3 are evaluations of nonadjacent codon pairs separated by the indicated number of intervening codons. ECO indicates the *E. coli* database; RAND indicates the randomized *E. coli* database.

As illustrated in FIG. 2, the sum of the chi-squares for the *E. coli* database (ECO) is 12,105, which is 124 standard deviations higher than its expected mean. Although over-represented codon pairs represent a minority of all records (45%), they contribute almost 60% of the total chi-square; over-represented pairs are thus more over-represented than the remainder are under-represented.

Two kinds of controls were evaluated. First, a "jumbled" database was generated by randomizing the order of the codons (excluding the initiating AUG and termination codon) in each sequence. The result was a database with the same number of codons and expected values for codon pairs—only the observed codon pair values were different. Running CODPAIR using this randomized database (RAND, FIG. 2) yields a chi-square value of 2,701, which is within 2 standard deviations (SD) of its expected mean. The distributions of chi-square values derived from these two databases (not shown) ar strikingly different; in ECO there are 552 records with chi-square values greater than 6, and 149 with values greater than 15; RAND, however, yields only 25 chi-square values greater than 6 and none greater than 15.

A second control involved evaluating codon pairs separated by one, two or three intervening codons; this allowed us to determine if non-randomness extended to non-neighboring codon pairs. As seen in FIG. 2, separation by a single codon (+1) reduces the chi-square derived from ECO to only 4,031; this is considerably lower than the original 12,105, but still 16 SD away from its expected mean. Separation by two or three intervening codons (+2, 3) reduces the chi-square to 3,062 and 3,047, respectively, only 3 SD away from the expected mean. Thus, whatever influence is driving the non-randomness in codon pair utilization, it appears to act only over a very short distance.

Codon Pair Utilization and Codon Context. Others have described non-random patterns of codon contexts in *E. coli* protein-coding regions. Shpaer, J. Mol. Biol. 188:555-564 (1985) reported (for example) that the codon AAA(Lys) is preferentially followed by GXX, and AAG(Lys) by CSS. These results are amply confirmed by our own findings (chis2=36 and 88, respectively); in addition, we find a highly significant deficit in pairs of the form AAG-GXX (chis232 80), but a random representation of AAA-CXX (chis2=1.5). While our data are therefore quite consistent with those of Shpaer, our results more closely define the nature of the non-random patterns. As an example, Table 1 shows our results for the AAA-GXX pairs.

TABLE 1

| CODON AAA(Lys) PRECEDING GXX* | | | |
|---|---|---|---|
| cod2 | exp | obs | chis2 |
| GAA (Glu) | 154.8 | 137** | 1.7 |
| GAC (Asp) | 81.1 | 105 | 4.0 |
| GAG (Glu) | 58.8 | 125 | 77.2 |
| GAT (Asp) | 91.0 | 113 | 2.7 |
| GCA (Ala) | 71.3 | 71 | 0.1 |
| GCC (Ala) | 64.1 | 78 | 2.2 |
| GCG (Ala) | 99.7 | 153 | 24.8 |
| GCT (Ala) | 72.1 | 51** | 7.2 |
| GGA (Gly) | 15.8 | 11** | 1.3 |
| GGC (Gly) | 94.1 | 113 | 4.8 |
| GGG (Gly) | 22.1 | 40 | 15.8 |
| GGT (Gly) | 104.6 | 94** | 0.6 |
| GTA (Val) | 44.9 | 39** | 1.6 |
| GTC (Val) | 37.6 | 43 | 0.3 |
| GTG (Val) | 66.8 | 104 | 15.3 |
| GTT (Val) | 81.1 | 86 | 0.0 |
| Totals: | 1159.5 | 1363 | |

*Expected, observed and chis2 values for all codon pairs consisting of AAA(Lys) followed by a codon beginning with G (see Appendix 4). Pairs of this form are found, overall, more frequently than expected (chis2 = 35.7), although several pairs, marked by double asterisks,** are under-represented (AAA-GCT significantly), and several more are observed close to their random expectation.

It is evident that the high degree of over-representation of this category of sixteen pairs is due mainly to only five or six of the sixteen; one pair is markedly under-represented (AAA-GCT), while most are close to random. Similar results hold for the codon pair AAG-CXX (not shown). A similar situation exists for at least some of the results of Yarus and Folley, J. Mol. Biol. 182:529-540 (1985). For instance, their finding of an excess of pairs of the form GCC-XGX is confirmed by our results (chis2=64; data not shown); however, while eight of these sixteen codon pairs are substantially over-represented (chis2 ranges from 9 to 88), several occur at levels close to their random expectations, and one (GCC-GGC) is grossly under-represented (chis2=39).

Thus, while analysis of codon context may correctly describe the "average" behavior of sequences adjacent to particular codons, representation of particular codon pairs may differ markedly from this average.

Non-Random Utilization of Amino Acid Pairs. Table 2 lists the six most highly over-represented (top half) and under-represented (bottom half) amino acid pairs in our *E. coli* database, together with their expected, observed and chi-square values. The sum of the chi-square values derived from the amino acid pair distribution is 1,129, more than 29 SD away from its expected mean. (The difference between the totals of chis1 and chis2 for the codon pair table (see Appendix 4), which we have interpreted as representing the contribution due to non-randomness in amino acid pairs, gives a value very close to this, namely 1,323.) Thus, there exists a highly significant degree of non-randomness in the occurrence of amino acid pairs in *E. coli* proteins.

TABLE 2

| MOST HIGHLY NON-RANDOM AMINO ACID PAIRS* | | | | |
|---|---|---|---|---|
| aa1 | aa2 | exp | obs | chis2 |
| Asn | Pro | 126.5 | 202 | 45.1 |
| Trp | Gln | 38.8 | 68 | 22.0 |
| Ser | Gly | 332.7 | 415 | 20.4 |
| Ile | Asn | 185.1 | 246 | 20.0 |
| Glu | Gln | 230.6 | 296 | 18.5 |
| Gln | Gln | 171.7 | 226 | 17.2 |
| Gly | Pro | 236.1 | 152 | 30.0 |
| Ile | Gln | 196.0 | 123 | 27.2 |
| Phe | Met | 74.6 | 38 | 18.0 |
| Glu | Asp | 292.8 | 226 | 15.2 |
| Leu | Gln | 336.4 | 266 | 14.7 |

TABLE 2-continued

| MOST HIGHLY NON-RANDOM AMINO ACID PAIRS* | | | | |
|---|---|---|---|---|
| aa1 | aa2 | exp | obs | chis2 |
| Ile | Ile | 291.3 | 227 | 14.2 |

*The six most highly over-represented (top half) and under-represented (bottom half) amino acid pairs in the *E. coli* database. aa1, aa2: left and right amino acids of a pair; exp, obs: expected and observed number of occurrences of each pair; chis2: chi-square based on the indicated expected and observed values. The sum of the chi-square values for the entire distribution (399 DF) is 1219, or 29 SD higher than its expected mean.

Codon Pair Utilization in Proteins of High Versus Low Abundance. Coding regions for *E. coli* proteins expressed at high versus low levels are known to differ in both codon usage and codon context. Therefore, we have examined the utilization of codon pairs in these two classes of proteins. We have arbitrarily defined "over-represented" codon pairs as those with chi-square values greater than or equal to 12, "under-represented" codon pairs as those with chi-square values greater than or equal to 3, "abundant" pairs as those occurring at least 90 times and "non-abundant" pairs as those occurring no more than 15 times in the database. (The chi-square values differ for under- and over-represented pairs in order to approximately balance the number of pairs in each category. Each category now represents about 18% of all pairs. "Over-represented" and "under-represented" pairs each comprise about 11% of all pairs.) "High" and "low" levels of gene expression are as defined by Yarus, et al., J. Mol. Biol. 182:529-540 (1985). Of course, other cutoffs for abundance and representation can be used, such as having each category represent 5%, 10%, 15%, 20%, or even 25% of the pairs in the database.

FIG. 3 shows the proportion of abundant versus nonabundant pairs (ABUND+and ABUND-), as well as over-represented versus under-represented pairs (NONRAND+ and NONRAND−), in the two classes of proteins. Codon pairs that are abundant in the database as a whole are used almost three times more frequently than rare ones in highly expressed proteins, but are used less frequently than rare ones in genes of low expression; this may be, at least in part, a reflection of the known avoidance of rare codons in genes for proteins expressed at high levels. Highly under-represented pairs are used almost twice as frequently as over-represented ones in highly expressed genes, while in poorly expressed genes over-represented pairs are used more frequently. Thus, proteins expressed at low levels tend to favor less abundant, but more highly over-represented codon pairs: conversely, proteins expressed at high levels favor more abundant but more highly under-represented pairs.

EXAMPLE 3

ANALYSIS OF *S. CEREVISIAE* CODON PAIR PREFERENCES

In order to compare the utilization of codon pairs in a eukaryotic organism with the data generated in Example 2 for the prokaryotic *E. coli*, we conducted a corresponding analysis of the genome of *S. cerevisiae*, using data from release 56.0 of the GENBANK database. (At that time, the database was provided by the University of Wisconsin, Genetics Computer Group.) We analyzed a total of 75,458 codon pairs (omitting stops), approximately the same number of pairs as we analyzed for coli. The codon pair preference data we generated are attached hereto as Appendix 5.

The overall chis2 for the yeast database was 5,748, which is 34 standard deviations higher than expected. This is highly nonrandom, although less striking than the 124 standard deviation value of *E. coli.* The yeast data show 308 chi-square values greater than 6, and 40 values greater than 15. (The corresponding *E. coli* values were 552 and 149, respectively.)

There is little correlation between non-random representation of individual codon pairs in the two species. A poor correlation exists between the observed number of occurrences of codon pairs in the two species ($r=0.29$), and almost no correlation exists between the values of chis2 ($r=0.06-0.09$.)

Consistent with previously published results, our analysis of codon usage also revealed marked differences between the two species. Particularly notable differences were seen for codons for Ala, Arg, Gln, Leu, Pro, and Thr. On the other hand, amino acid usage was very similar between the two.

Analysis of the usage of amino acid pairs for *S. cerevisiae* yielded a total chi-square of 1045, or 23 standard deviations higher than expected. (The value for *E. coli* was 1219, or 29 standard deviations high.)

The patterns of over- and under-representation between the two species are quite different. Among the twenty homodimers, for example, yeast has 12 values of chi-square greater than 2, 9 of which are over-represented, while 3 are under-represented. Only 4 of these values are concordant with nonrandom representation in *E. coli* (which has 6 values greater than 2, of which all but two are under-represented).

Overall, there is a poor correlation between amino acid pair chi-square values for *E. coli* and *S. cerevisiae*, $r=0.23$ for signed values, and $r=0.10$ for absolute values. However, a good correlation exists between observed number of occurrences of amino acid pairs in yeast and *E. coli*, $r=0.84$. This may at least partially reflect the fact that amino acid usage does not differ markedly between the two species.

EXAMPLE 4

APPARENT CONTROL OF PROTEIN FOLDING THROUGH CODON-PAIR MEDIATED TRANSLATIONAL PAUSES

In order to illustrate the correlation between translational kinetics (as inferred from codon pair utilization) and tertiary structure of polypeptide translation products, the codon pair utilization patterns of four *E. coli* genes were analyzed. These genes all code for DNA binding proteins having a characteristic helix-turn-helix tertiary structure, which is involved in DNA binding. In particular, progressing from the amino terminus along the polypeptide chain of these proteins, one finds a helix ("helix 2"), a "turn" region where the chain is folded, and another helix ("helix 3"). Based on the analysis below, we suggest that effective folding of the helical regions of these proteins requires a translational pause.

Figure 4A:
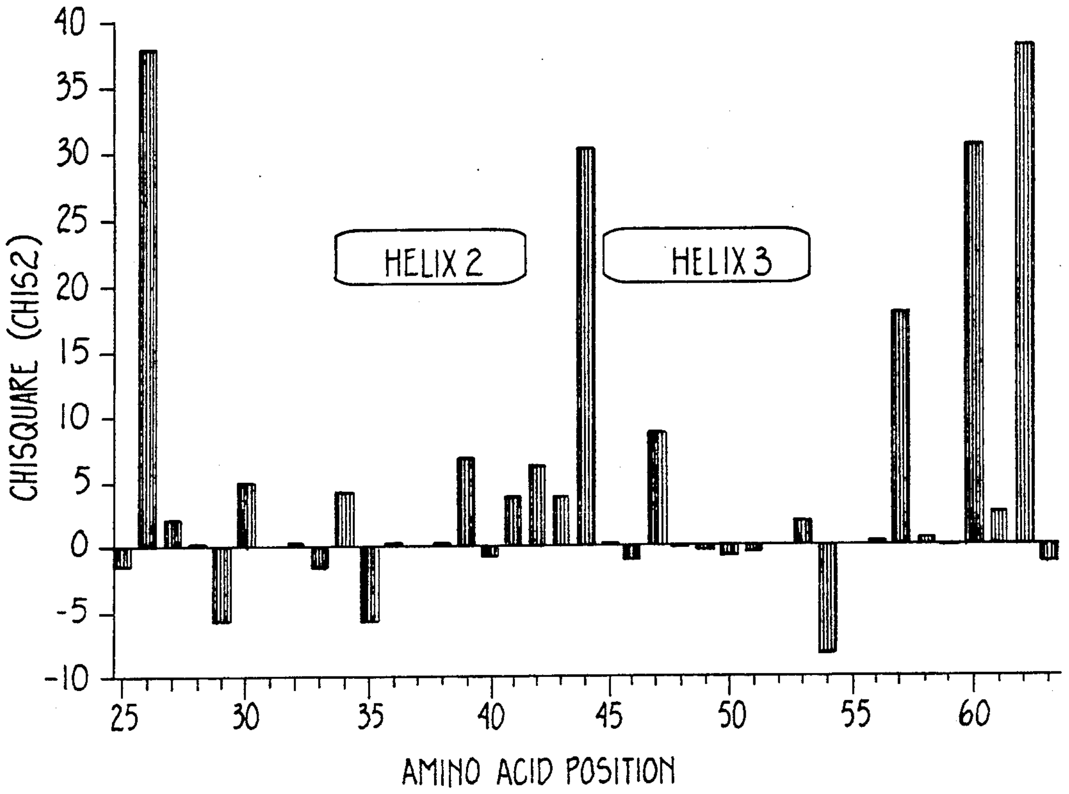
FIGS. 4A-4D are graphs correlating the locations of highly nonrandom codon pairs in four *E. coli* genes with the tertiary structure of four DNA binding proteins encoded thereby.
Figure 4B:
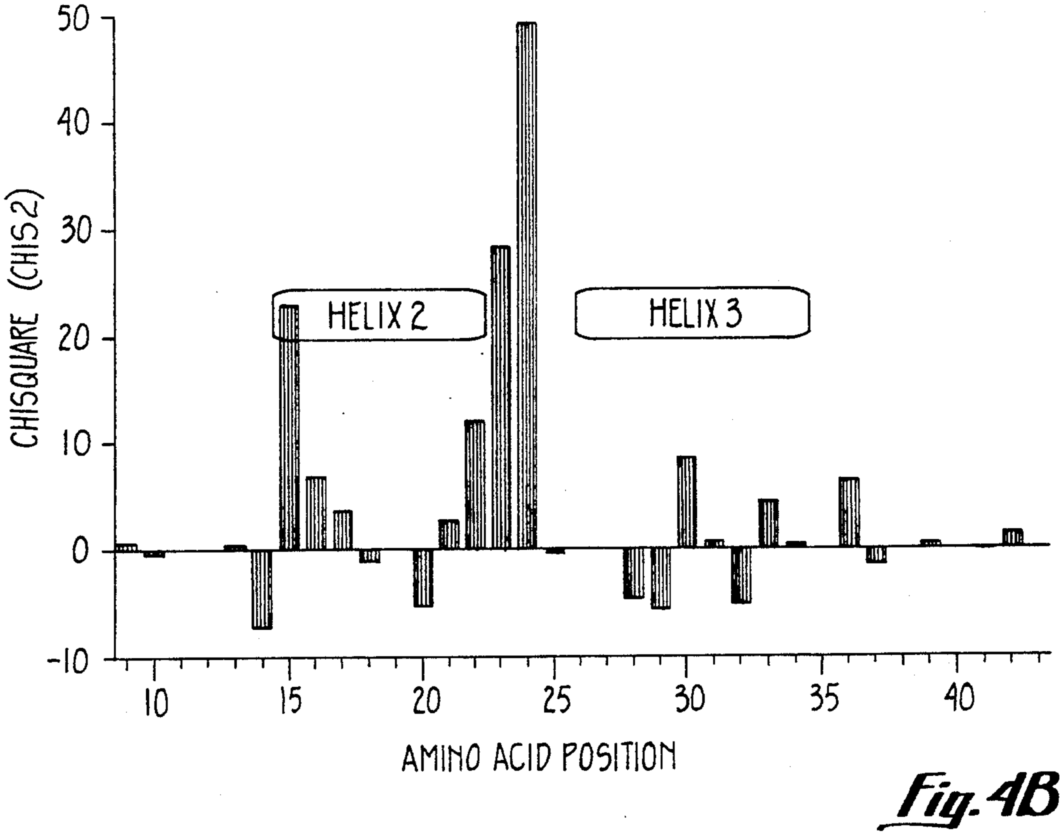
Figure 4C:
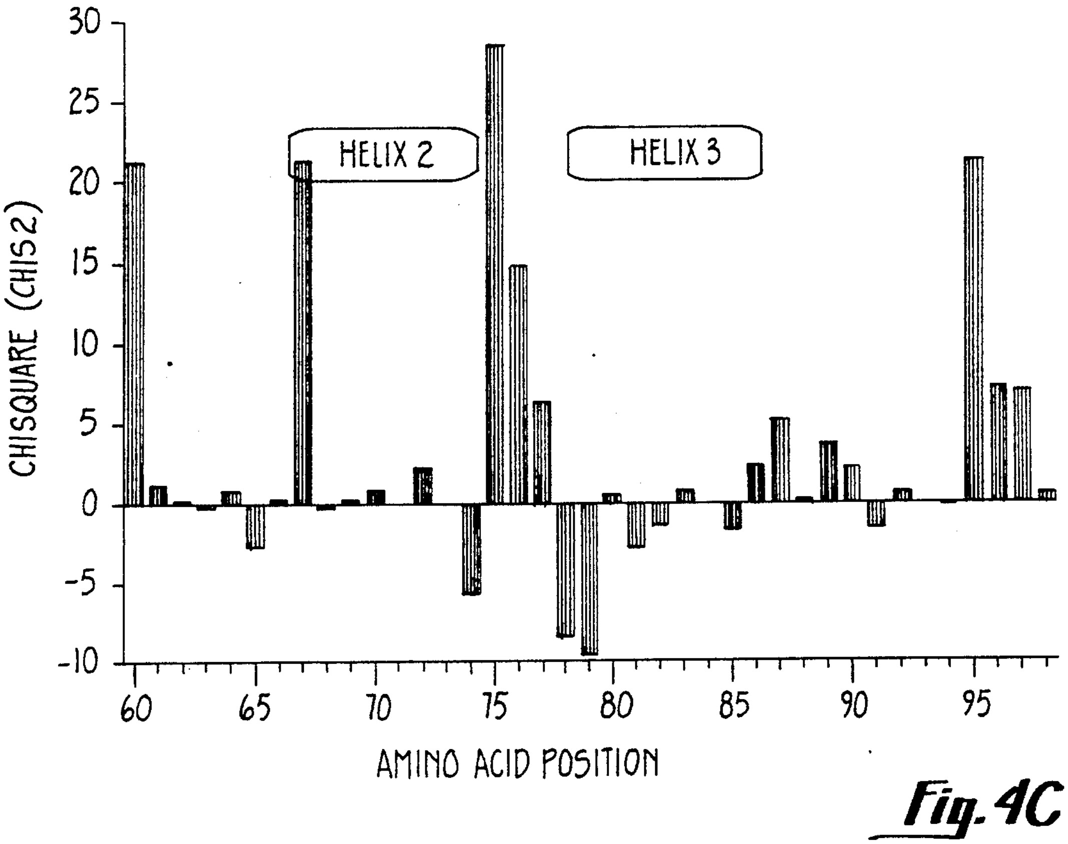
Figure 4D:
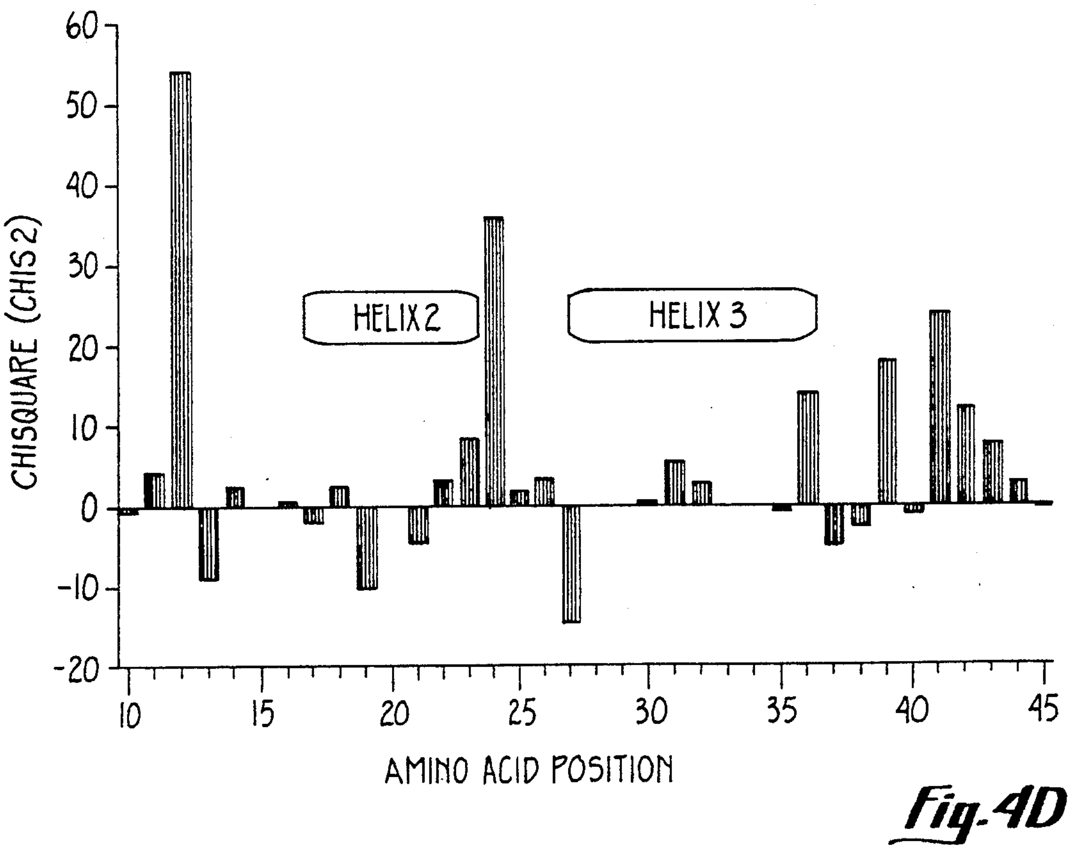

FIGS. 4A–4D graphically illustrate chi-square (chis2) values for codon pairs corresponding to the helix and turn regions of these proteins. In particular, FIG. 4 A corresponds to lambda cI protein, FIG. 4B corresponds to lambda cro protein; FIG. 4C corresponds to troR protein, and FIG. 4D corresponds to ilvY protein. The abscissa in each figure represents the amino acid position of the protein; the ordinate represents the chi-square values of the corresponding codon pairs as calculated in Example 2. Chi-square values are given as positive for over-represented pairs and negative for under-represented pairs. Boxes representing helix 2 and helix 3 are uniformly positioned at chi-square=20.

As the figures illustrate, the "turn" region in between the helices invariably shows one or more highly over-represented pairs. In addition, over-represented pairs are often seen before the first helix and after the second helix. Finally, over-represented pairs are avoided inside either helix, except at one end or the other.

These data suggest that nonrandomness of codon pairs is related to protein structure and folding. We propose that the highly over-represented pair or pairs in the "turn" are responsible for a translational pause, and that proper protein folding may be facilitated by the pause.

In summary, these results demonstrate a high degree of non-randomness in the occurrence of codon pairs in *E. coli* and *S. cerevisiae,* reflected in both over- and under-representation of individual pairs. The bias in utilization of codon pairs is only weakly correlated with their absolute abundance, and is over and above any contribution by non-randomness of amino acid pairs. This bias is much less evident in non-adjacent codon pairs, and virtually disappears when pairs separated by two or three intervening codons are evaluated. There appears to be a high degree of directionality in this bias, which may be important in understanding its biochemical basis.

At the same time, the bias in utilization of codon pairs differs markedly from species to species. Consequently, a foreign gene inserted into the genome of an organism is unlikely to utilize the appropriate codon pairs necessary to permit it to exhibit its native translational efficiency and protein folding pattern when expressed.

APPENDIX 1

```
{***************************************************************************}
{*                     Frequency Generation Module One                     *}
{*                                                                         *}
{*                                                                         *}
{*     This program allows the user to create a coding region database    *}
{* consisting of the sequence name and the protein coding regions found   *}
{* in that sequence of DNA or RNA.  It takes input from an input list     *}
{* and an input database.                                                 *}
{*     The input list is a list of all the sequences to be added to the  *}
{* database and the starting and stopping locations of all the protein    *}
{* coding regions within each region.                                     *}
{*     The input database contains the actual DNA or RNA sequences along  *}
{* with their secondary data, i.e. name, size, purpose, etc.              *}
{*     The output consists of three files.  One is a list of all sequences*}
{* which have been processed and the other is the actual coding regions   *}
{* from these sequences.  The former file is called the output list and   *}
{* the latter, the output database.  By the way, the output list is       *}
{* alphabetically sorted.                                                 *}
{*     The files which we have encountered thus far are specially marked  *}
{* by means of their extensions.  The files for input will all have the   *}
{* same prefix, but will be distinguished by their extensions.  For       *}
{* instance, the input list files have the extension INL while the input  *}
{* database files have the extension IND.  The output files are           *}
{* distinguished in a similar fashion.  The output list has the OTA       *}
{* extension while the output database has the OTD extension.             *}
{*                                                                         *}
{***************************************************************************}
PROGRAM FREQMOD1;
{$I+}
{$C+}
  TYPE name1      =    STRING[20];
       name2      =    array [ 1..14 ] of Char;
       standard   =    STRING[255];
       inputlist1 = Record                {Contains one sequence description}
         seqname      :NAME1;
         num_cd_reg   :Integer;
         cd_strt_stp  :Array [ 1..20 ] of Name1;
         inverse      :Array [ 1..20 ] of BOOLEAN;
       End;
       pointto     =^Sequence;            {Points to a base in sequence.seqb}
       sequence    = Record               {Contains a base and the pointer to}
           seqb        :Char;             {the next base in sequence.        }
           next        :pointto;
       End;
       sequ1       = Record               {Contains the entire sequence}
           name        :String[10];
           nameline    :Standard;
           defnline    :Standard;
           header      :pointto;
           sequen1     :Sequence;
           numchars    :Integer;
       End;
       regions     = RECORD               {Contains one coding region}
            header     :Pointto;
            strt_stp   :Name1;
            codereg    :Sequence;
            numchar    :Integer;
       End;
       seqlist     = Record              {Contains all the coding regions in any}
                                         {given sequence.                       }
         seqname       :Name1;
         nameline      :Standard;
         defnline      :Standard;
         num_cd_reg    :Integer;
         regT          :Array[ 1..20 ] of Regions
       End;
       Outdb       = File of Seqlist;
       Outs        = Record
           seqname     :Name1;
           posinfile   :Integer;
       End;
       Outsorts    = File of Outs;
       recsorts = Array[1..300] of Outs;
```

```
VAR
     inlistname,
     indbname,
     outdbname,
     errorlog         :TEXT;
     inputlist        :INPUTLIST1;
     seq1             :SEQU1;
     out1             :OUTS;
     codereg1         :SEQLIST;
     alpha1,
     hashed           :Outsorts;
     a1               :Recsorts;
     head,tail,base   :Pointto;
     inlist,
     indbase,
     outdbase,
     c,
     D,
     outalpha,
     outhash          :NAME1;
     temporary        :STANDARD;
     error,
     start,
     inverse,
     lastfound,
     runlog1          :Boolean;
     fn1,
     strt,
     stop,
     num,
     nument,
     count,
     ct1,
     stat,
     mem1             :Integer;
     memo             :Real;
{*********************************************************************}
{* This procedure makes a pause by displaying hit return and requiring a  *}
{* linefeed.                                                          *}
{*********************************************************************}
PROCEDURE pause;
  VAR cont:CHAR;
  Begin
    WriteLn;
    Write('                    ** Hit ''Return'' to Continue **');
    ReadLn(cont);
  End;
{*********************************************************************}
{* This procedure creates a runtime log of errors which occurred on the  *}
{* system during execution.                                           *}
{*********************************************************************}
PROCEDURE errorrep(code:STANDARD;infilename,sequence:NAME1);
  VAR stemp : String[255];
  Begin
    error := TRUE;
    stemp := '';
    stemp := CONCAT('ERROR: ',code,' in ',sequence,' sequence, from ',inlist,' file.');
    WriteLn(errorlog,stemp);
  End;
{*********************************************************************}
{* This procedure takes any string and returns its uppercase equivalent.  *}
{*********************************************************************}
PROCEDURE changecase(VAR str1:NAME1);
  VAR count:Integer;
  Begin
    FOR count := 1 to LENGTH(str1) DO
       str1[count] := upcase(str1[count]);
  End;
{*********************************************************************}
{* This function comes from the turbo-pascal utilities disk and it gets a *}
{* directory listing of the current logged drive.                     *}
{*********************************************************************}
PROCEDURE DIRLIST;
  TYPE
    string20  = STRING[20];
    Char12arr = Array [ 1..12 ] of CHAR;
    RegRec    =
      record
        AX,BX,CX,DX,BP,SI,DI,DS,ES,Flags:Integer;
      End;
  VAR
    Regs        :RegRec;
    DTA         :array [ 1..43 ] of Byte;
    Mask        :Char12arr;
    NamR        :String20;
    Error,
    I,
    num,
    tab1        :Integer;
  Begin {Main body of procedure dirlist}
    FillChar(DTA,SizeOf(DTA),0);          { Initialize the DTA buffer }
    FillChar(Mask,SizeOf(Mask),0);        { Initialize the mask }
    FillChar(NamR,SizeOf(NamR),0);        { Initialize the file name }
    WriteLn;
    Regs.Ax := $1A00;               { Function used to set the DTA}
    Regs.DS := Seg(DTA);            { Store the parameter segment in DS}
    Regs.DX := Ofs(DTA);            {   "      "     "    offset in DX}
    MSDos(Regs);                    { Set the DTA location}
    Error := 0;
    Mask := '????????.???';
    Regs.Ax := $4E00;               { Get first directory entry  }
    Regs.DS := Seg(Mask);           { Point to the file Mask }
    Regs.DX := Ofs(Mask);
    Regs.CX := 22;                  { Store the option }
    MSDos (Regs);                   { Execute MSDos call}
    Error := Regs.AX and $FF;       { Get Error return }
    I := 1;                         { initialize 'I' to the first element }
    num := 1;
    tab1 := 15;
    if (Error = 0 ) then
```

```
Repeat
  NamR[I] := Chr(Mem[Seg(DTA):Ofs(DTA)+29+I]);
  I := I + 1;
     Until not(NamR[I-1] in [' '..'~']) or (I>20);
   NamR[0] := Chr(I-1);         { set string length because assigning}
                                { by element does not set lenght }
   while (Error = 0) do begin
     Error := 0;
     Regs.AX := $4F00;          { Function used to get the next }
                                { directory entry }
     Regs.CX := 22;             { Set the file option }
     MSDos( Regs );             { Call MSDos }
     Error := Regs.AX and $FF;  { get the Error return }
     I := 1;
     repeat
       NamR[I] := Chr(Mem[Seg(DTA):Ofs(DTA)+29+I]);
       I := I + 1;
     until not(NamR[I-1] in [' '..'~']) or (I > 20);
     NamR[0] := Chr(I-1);
     if (Error = 0) then
       Begin
         IF num = 6 THEN
           Begin
             WriteLn;
             tab1 := 15;
             num := 1;
           End;
         Write(NamR:tab1);
         tab1 := tab1;
         num := num + 1;
       END;
  end;
 end; {main procedure}
{*************************************************************************}
{* This algorithm gets a set of records from disk.                       *}
{*************************************************************************}
Procedure Retrieve(VAR a1:Recsorts;VAR count:INTEGER; VAR fl1:Outsorts);
   Var q:Integer;
   Begin
     Reset(fl1);
     count := 0;
     WriteLn;
     WriteLn('Now loading list of already processed sequences...');
     While NOT(eof(fl1)) Do
       Begin
         q := filepos(fl1);
         WriteLn;
         Count := count + 1;
         Read(fl1,a1[count]);
         WriteLn('Sequence is ',a1[count].seqname);
       End;
     Close(fl1);
     Erase(fl1);
   End;
{*************************************************************************}
{* This algorithm stores a set of records to disk.                       *}
{*************************************************************************}
Procedure Storeit1(VAR a1:Recsorts;VAR count:INTEGER; VAR fl1:Outsorts);
  Var step :Integer;
      q    :Integer;
  Begin
    Rewrite(fl1);
    WriteLn;
    WriteLn('Now saving a list of all sequences which have been processed to date...');
    For step := 1 to count Do
      Begin
        q := filepos(fl1);
        WriteLn;
        Write(fl1,a1[step]);
        WriteLn('Record #',step,' is ',a1[step].seqname);
      End;
    Close(fl1);
  End;
{**********************************************************************}
{* This function comes from the turbo-pascal manual and determines whether*}
{* a file exists already or not                                        *}
{**********************************************************************}
FUNCTION exist(filename:NAME1):Boolean;
  VAR fil   :FILE;
  Begin
    ASSIGN(fil,filename);
    {$I-}
    RESET(FIL);
    {I+}
    EXIST := (IOresult = 0)
  End;
{**********************************************************************}
{* This procedure copies a text file into another text file. It deletes *}
{* the first file, and renames the second file after copying.          *}
{**********************************************************************}
PROCEDURE copyit(filename:NAME1;VAR nument:INTEGER);
  VAR t1       : TEXT;
      exists   : Boolean;
      block1   : Standard;
      ch1      : Char;
      i,
      amt      : Real;
  Begin {copy it}
    CLRSCR;
    i := 0;
    GOTOXY(10,5);
    WriteLn('Now Copying original database.... Please Standby');
    GOTOXY(10,12);
    WriteLn('    Already copied    ');
    block1 := 'tempfile';
    nument := 0;
    exists := EXIST(block1);
    Assign(t1,block1);
    If exists Then
      Erase(t1);
```

```
      Assign(t1,filename);
      Rename(t1,block1);
      Assign(outdbname,filename);
      Reset(t1);
      Rewrite(outdbname);
      While Not(Eof(t1)) DO
        Begin
          Read(t1,ch1);
          Write(outdbname,ch1);
          i := i + 1;
          amt := i / 1024;
          GotoXy(34,12);
          Write(amt:5:2,' K');
          IF ch1 = '\' THEN
            nument := nument + 1;
        End;
      nument := nument - 1;
      Close(t1);
      ERASE(T1);
    End; {copy it}
{***********************************************************************}
{* This procedure copies a text file into another text file. It deletes   *}
{* the first file, and renames the second file after copying.            *}
{***********************************************************************}
PROCEDURE copyrunlog;
  VAR t1        : TEXT;
      exists    : Boolean;
      block1    : Standard;
      ch1       : Char;
  Begin {Copy runlog}
    block1 := 'tempfile';
    exists := EXIST(block1);
    Assign(t1,block1);
    If exists Then
      Erase(t1);
    Assign(t1,'run.log');
    Rename(t1,block1);
    Assign(errorlog,'run.log');
    Reset(t1);
    Rewrite(errorlog);
    While Not(Eof(t1)) DO
      Begin
        Read(t1,ch1);
        Write(errorlog,ch1);
      End;
    Close(t1);
    ERASE(T1);
  End; {copy run log}
{***********************************************************************}
{* This algorithm checks filenames to find out if they exist on the disk  *}
{***********************************************************************}
FUNCTION getfilenames(typein:Integer):NAME1;
  VAR
      invalid,
      exists,
      exist1     :Boolean;
      go         :Name1;
      dummy      :CHAR; {A dummy variable}
      dir1       :STRING[255]; {contains directory}
      drive,
      count      :Integer;
      filename   :NAME1;
      mask1      :NAME2;
  Begin
    Repeat
      TEXTMODE(BW80);
      error := FALSE;
(*      CLRSCR;
      {CASE typein OF
        0:mask1 := '????????.inl';
        1:mask1 := '????????.ind';
      End;}                                    *)
      CLRSCR;
      REPEAT
        LowVideo;
        WRITE('Enter the filename for the ');
        NormVideo;
        CASE typein OF
          0:WriteLn('INPUT LIST: ');
          1:WriteLn('INPUT DATABASE: ');
          2:WriteLn('OUTPUT DATABASE: ');
        End;
        LowVideo;
        WriteLn;
        Write(' (Please specify a filename with the ');
        NormVideo;
        Case typein Of
          0: Write('.INL');
          1: Write('.IND');
          2: Write('.OTD');
        End;
        LowVideo;
        WriteLn(' suffix, but do not write the suffix.)');
        WriteLn(' (For example:  Test.otd is a file. You would write only Test )');
        WriteLn;
        WriteLn('          Hit ''Return'' to get a directory listing');
        {GOTOXY(5,12);}
        WriteLn;
        NormVideo;
        Write('FILENAME:');
        {GOTOXY(15,12);}
        {WRITE('____________');
        GOTOXY(15,12);}
        READLN(filename);
        IF filename = '' THEN
          Begin
            CLRSCR;
            LowVideo;
            DIRLIST;
            WRITELN;
            WRITELN;
          End;
```

```
{TEXTBACKGROUND(0);}
invalid := FALSE;
count := 0;
IF (length(filename) > 8) THEN
  invalid := TRUE;
WHILE (NOT(INVALID)) AND (count <= LENGTH(filename)) DO
  Begin
    If (filename[count] = '.') THEN
      invalid := TRUE
    Else
      count := count + 1;
  End;
UNTIL (filename <> '') and not(invalid);
CASE typein OF
  0: filename := filename + '.inl';
  1: filename := filename + '.ind';
  2: Begin
       outalpha := filename + '.ota';
       filename := filename + '.otd';
     End;
END;
exists := EXIST(filename);
If typein = 2 Then
  exist1 := EXIST(outalpha);
IF not(exists) and (typein IN [0,1]) THEN
  Begin
    WriteLn;
    WriteLn('** ERROR: THE FILENAME YOU ENTERED DOES NOT EXIST, PLEASE RE-ENTER **');
    WriteLn;
    PAUSE
  End
ELSE
 IF typein = 2 THEN
   IF exists and exist1 THEN
     Begin
       copyit(filename,nument);
       go := 'Y';
       Assign(alpha1,outalpha);
       Retrieve(a1,ct1,alpha1);
       nument := ct1;
     End
   ELSE
     Begin
       WriteLn;
       WriteLn('  The filename which you entered for the output database does not exist. ');
       WriteLn;
       Write('        Would you like me to create it? (Y/N) ');
       go := '';
       ReadLn(GO);
       ChangeCase(go);
       If go = 'Y' THEN
         Begin
           Assign(outdbname,filename);
           Rewrite(outdbname);
           WriteLn(outdbname,'\');
           nument := 0;
           Assign(alpha1,outalpha);
           ct1 := 0;
         End;
     End;
     Until (exists and (typein IN [0,1])) or (GO = 'Y');
     getfilenames := filename;
   End;
{*********************************************************************}
{* This algorithm converts a given string of numbers separated by a comma *}
{* into two numbers, i.e. a start and a stop.                          *}
{*********************************************************************}
PROCEDURE convertstr(VAR cdreg,sequence:NAME1; VAR start,stop:Integer; VAR inverse:Boolean);
  VAR step,              {A integer loop counting variable}
      err1,
      temp      :Integer;
      current   :String[7]; {A temporary holding variable}
      found1    :Boolean; {Indicates a section has been found}
  Begin
    step    := 1;
    err1    := 0;
    current := '';
    temp    := 0;
    error   := FALSE;
    found1  := FALSE;
    start   := 0;
    stop    := 0;
    inverse := FALSE;
    WHILE (step <= LENGTH(cdreg)) AND NOT(error) DO
      Begin
        IF cdreg[step] in ['<','>',' '] THEN
          step := step + 1
        ELSE
          IF cdreg[step] = ','  THEN
            Begin
              IF found1 THEN
                errorrep('Coding region format is incorrect -- too many commas',inlist,sequence)
              ELSE
                IF current = ''  THEN
                  errorrep('Coding region format is incorrect -- nothing before comma.',inlist,sequence)
                ELSE
                  Begin
                    found1 := TRUE;
                    VAL(current,start,err1);
                    current := '';
                    step := step + 1;
                  End
            End
          ELSE
            Begin
              current := current + cdreg[step];
              step := step + 1;
            End;
      End; {while}
    VAL(current,stop,err1);
    IF (start > stop) THEN    {Non-message strand has been found-- Inverse Complement}
```

```
      Begin
        inverse := TRUE;
        temp    := start;
        start   := stop;
        stop    := temp;
      End
    ELSE
      IF start = stop THEN
        errorrep('Start is equal to stop, no bases in region.',inlist,sequence);
    IF not(error) THEN
      IF (((stop - start) +1) MOD 3) <> 0 THEN
        errorrep('Coding region is not divisible by 3.',inlist,sequence);
  End;
{*********************************************************************}
{* This algorithm gets the necessary sequence information from a pre-made *}
{* file and passes it to the main input routine                          *}
{*********************************************************************}
PROCEDURE READINLIST(VAR inputlist:INPUTLIST1);
  VAR count    :Integer;
      temp     :STRING[40];
  FUNCTION checkerr(VAR info:NAME1):Boolean;
    VAR x      :Integer;
        error1 :Boolean;
    Begin
      x := 1;
      error1 := FALSE;
      WHILE (X <= LENGTH(info)) and NOT(error1) DO
        Begin
          error1 := NOT(info[x] in ['0','1','2','3','4','5','6','7','8','9','>','<','\',',']);
          x := x + 1;
        End;
      IF error1 THEN
        errorrep('Unrecognized character in start and stop',inlist,inputlist.seqname);
      checkerr := error1;
    End;
  Begin {readinlist}
    error := false; {global}
    With inputlist DO
      Begin
        seqname := 'non-sequence';
        READLN(inlistname,seqname);
        seqname := COPY(seqname,1,10);
         IF length(seqname) < 10 THEN    {Add spaces to the name to make it 10}
           FOR count := 1 to (10 - LENGTH(SEQNAME)) DO
               seqname := seqname + ' ';
         count := 0;
         CHANGECASE(seqname);
         IF ((EOF(inlistname)) and START) THEN
           errorrep('File is empty',inlist,seqname)
         ELSE
          IF NOT(eof(inlistname)) THEN
           Begin
            start := FALSE;
            count := count + 1;
            READLN(inlistname,cd_strt_stp[count]);
            IF NOT(EOF(INLISTNAME)) THEN
              error := checkerr(cd_strt_stp[count]);
            IF (cd_strt_stp[count] = '') OR (cd_strt_stp[count] = '\\') OR EOF(INLISTNAME) THEN
              errorrep('Sequence followed by no coding regions',inlist,seqname)
            ELSE
             Begin
              REPEAT
               Begin
                count := count + 1;
                READLN(inlistname,cd_strt_stp[count]);
                IF NOT(EOF(INLISTNAME)) THEN
                  error := checkerr(cd_strt_stp[count]);
                IF cd_strt_stp[count] = '' THEN
                  errorrep('A blank start and stop was found',inlist,seqname); {no starts and stops}
               End;
              UNTIL error OR (cd_strt_stp[count] = '\\') OR (EOF(INLISTNAME));
             num_cd_reg := count - 1;
            End;
          End;
      End;
  End; {READINLIST}
{*********************************************************************}
{* This algorithm inputs the data from the sequence containing database.  *}
{* It then passes this data to a special record,and then to a new database*}
{*********************************************************************}
PROCEDURE readindbase(VAR inputlist:INPUTLIST1; VAR seq1:SEQU1);
{Alterations:
    make Check 7 characters long, get name from 15 /10 instead of 14,
    look for TOIG lin instead of LOCUS line for error              }
  VAR count,
      len,
      step            :Integer;
      tail,base,head  :Pointto;
      name,
      check           :NAME1;
      temp            :Char;
      temp1,
      temp2           :STANDARD;
      notfound,
      found,
      endseq          :Boolean;
  Begin
    {Assume the input database file has already been opened}
    seq1.name := inputlist.seqname;
    endseq    := False;
    notfound  := False;
    found     := False;
    count     := 0;
    len       := LENGTH(seq1.name);
    step      := 1;
    check     := '';
    IF lastfound THEN
      Begin
        readln(indbname,temporary);
        check := COPY(temporary,1,7);
        ChangeCase(check);
        WHILE (check <> '; LOCUS') and NOT(EOF(indbname))  DO  {Eliminate blanks from beginning of the file}
```

```
      Begin
        readln(indbname,temporary);
        check := Copy(temporary,1,7);
        ChangeCase(check)
      End;
   End;
IF EOF(indbname) THEN
   errorrep('Untimely end of database file',indbase,seq1.name);
IF not(EOF(indbname)) THEN
 Begin
   name := Copy(temporary,15,10);  {Copy name of sequence out of database}
   seq1.nameline := temporary;
   ChangeCase(name);
   IF seq1.name < name THEN    {If the sequence is not found}
     notfound := TRUE
   ELSE
     IF seq1.name = name THEN  {If the sequence is found, name = name}
       found := TRUE
     ELSE
      Begin
        WHILE  NOT(notfound) and NOT(found) and NOT(EOF(indbname)) DO
          Begin
            readln(indbname,temporary);
                check := COPY(temporary,1,7);
                ChangeCase(check);
                WHILE (check <> '; LOCUS') and (NOT(EOF(indbname)))  DO  {Eliminate blanks from beginning of the file}
                  Begin
                    readln(indbname,temporary);
                    check := Copy(temporary,1,7);
                    ChangeCase(check)
                  End;
                IF not(EOF(indbname)) THEN
                  Begin
                    name := Copy(temporary,15,10);  {Copy name of sequence out of database}
                    seq1.nameline := temporary;
                    ChangeCase(name);
                    IF seq1.name > name THEN
                      notfound := TRUE
                    ELSE
                      IF seq1.name = name THEN
                        found := TRUE;
                  End;
              End;
          End;
      IF found THEN  {Found the sequence}
        Begin
          lastfound := TRUE;
          With seq1 DO
            Begin
              Readln(indbname,temporary);  {    Move to the right place in the seq }
              check := Copy(temporary,1,7);
                  ChangeCase(check);
              WHILE (temporary[1] = ';') and NOT(error) and NOT(temporary = '') DO
                Begin
                  IF check = '; DEFIN' Then
                    defnline := temporary;
                  Readln(indbname,temporary);
                  check := Copy(temporary,1,7);
                  ChangeCase(check);
                  IF check = ';   TOI' THEN
                    errorrep('No coding region -- error in database',indbase,name);
                End;
              NEW(header);
              tail := header;
              base := header;
              base^.next := NIL;
              Repeat
                Readln(indbname,temp1);
                step := 1;
                IF (temp1 = '') or (EOF(indbname) AND (temp1[length(temp1)] <> '1')) THEN
                  errorrep('Too many blank lines or Untimely end of dbase file ',indbase,name)
                ELSE
                 Begin
                  Repeat
                    base^.seqb := temp1[step];
                    IF (NOT(base^.seqb IN ['A','G','C','T','N','1'])) THEN
                      begin
                        errorrep('Not a permissible character in database',indbase,name);
                        temp2 := '';
                        temp2 := CONCAT('the character is ',base^.seqb);
                        WriteLn(errorlog,temp2);
                      end;
                    If not(error) THEN
                      IF (base^.seqb IN ['A','G','C','T','N'])   THEN
                        Begin
                          count := count + 1;
                          NEW(base);
                          tail^.next := base;
                          tail := base;
                          base^.next := nil;
                          step := step + 1;
                        End
                      ELSE
                        IF (base^.seqb = '1') THEN
                          endseq := TRUE;
                  Until (base^.seqb = '1') or error or (step > length(temp1));
                 End;
              Until Error Or Endseq;
            numchars := count;
            End
        End
      ELSE
        Begin
          errorrep('Sequence was not found in database',name,inputlist.seqname);
          lastfound := FALSE;
        End;
     End;
```

```
  End;
{*****************************************************************************}
{* This algorithm erases or frees dynamically allocated memory by using     *}
{* certain given commands of the Pascal language.                          *}
{*****************************************************************************}
PROCEDURE erasereg(VAR reg:REGIONS);
  VAR tail,base:Pointto;
  Begin
    With reg DO
      Begin
        base := header;
        tail := base^.next;
        WHILE tail <> NIL DO
          Begin
            DISPOSE(BASE);
            base := tail;
            tail := base^.next;
          End;
        strt_stp := '';
        numchar := 0;
      End;
  End;
{*****************************************************************************}
{* This algorithm selects the indicated coding regions from the given      *}
{* base sequence.  If there are any errors, it will not go on with the     *}
{* sequence and subsequently move to the next sequence.                    *}
{*****************************************************************************}
PROCEDURE selectregions(VAR inputlist:InputList1; VAR seq1:Sequ1; VAR start,stop:Integer; VAR Reg:REGIONS; num:Integer
  Var
      count,
      length1,
      count1      :Integer;
      flip        :Array [ 1..7000 ] of Char;
      head1,
      head2,
      base1,
      base2,
      tail1,
      tail2       :Pointto;
  Begin (Select regions)
    count := 0;
    With seq1 DO
      Begin
        IF (start >= seq1.numchars) and (stop > seq1.numchars) THEN
          errorrep('Start or Stop exceed length of sequence ',inlist,name)
        ELSE
          Begin
            base1 := seq1.header;
            count := 1;
            WHILE (count <> start) and (base1^.next <> nil) DO
              Begin
                base1 := base1^.next;
                count := count + 1;
              End;
          End;
      End;
    IF Not(Error) THEN
      Begin
        NEW(reg.header);
        tail2           := reg.header;
        base2           := reg.header;
        base2^.next     := nil;
        While (base1^.next <> nil) and (count <> (stop +1)) DO
          Begin
            base2^.seqb  := base1^.seqb;
            NEW(base2);
            tail2^.next  := base2;
            tail2        := base2;
            base2^.next  := nil;
            base1        := base1^.next;
            count        := count +1;
          End;
        reg.strt_stp        := inputlist.cd_strt_stp[NUM];
        reg.numchar         := ABS(stop - start) + 1;
      End;
    If inputlist.inverse[num] Then      (Inverse complement handling)
      Begin (Inverse)
        base1 := reg.header;
        length1 := 0;
        While base1^.next <> nil Do
          Begin
            Case base1^.seqb Of
              'A': base1^.seqb := 'T';
              'T': base1^.seqb := 'A';
              'G': base1^.seqb := 'C';
              'C': base1^.seqb := 'G';
            End;
            length1 := length1 + 1;
            flip[length1] := base1^.seqb;
            base1 := base1^.next;
          End;
        base1 := reg.header;
        For count1 := length1 downto 1 Do
          Begin
            base1^.seqb := flip[count1];
            base1 := base1^.next;
          End;
      End; (Inverse )
  End; (Select regions)
{*****************************************************************************}
{* This algorithm erases or frees dynamically allocated memory by using     *}
{* certain given commands of the Pascal language.                          *}
{*****************************************************************************}
PROCEDURE eraseseq(VAR seq:SEQU1);
  VAR tail,base:Pointto;
  Begin  ( Erase Seq )
    With seq DO
      Begin
        base := header;
        tail := base^.next;
        WHILE tail <> NIL DO
```

```
        Begin
          DISPOSE(BASE);
          base := tail;
          tail := base^.next;
        End;
      DISPOSE(BASE);
    End;
  End;  { Erase Seq }
{**********************************************************************}
{* This algorithm switches a pair of records around                   *}
{**********************************************************************}
Procedure Switch(VAR a,b:Outs);
  VAR temp:Outs;
  Begin { Switch }
    temp := a;
    a    := b;
    b    := temp;
  End;  { Switch }
{**********************************************************************}
{* This algorithm performs a bubble sort by comparing all elements and *}
{* switching at the appropriate times.  It is efficient for small array sizes*}
{* and is typically used in conjunction with a quicksort algorithm.  This  *}
{* particular routine was taken from Introduction to Pascal by Rodney Zaks. *}
{**********************************************************************}
Procedure BSORT(start,top:INTEGER; VAR a1:Recsorts);
  Var index     :Integer;
      switched  :Boolean;
  Begin  {Bubble Sort}
      Repeat
        switched := False;
        For index := start to (top-1) Do
          Begin
            If a1[index].seqname > a1[index+1].seqname Then
              Begin
                switch(a1[index],a1[index+1]);
                switched := True
              End
          End;
      Until NOT(switched);
  End;  {Bubble Sort}
{**********************************************************************}
{* This algorithm finds a good median value in array and places it at the   *}
{* beginning in accordance with the principles of the quick sort technique.  *}
{*This particular routine was taken from Introduction to Pascal by Rodney Zaks.   *}
{**********************************************************************}
Procedure FindMedian(start,top:Integer; Var a1:Recsorts);
  Var middle    : Integer;
      sorted    : Recsorts;
  Begin {Find Median}
    middle    := (start + top) div 2;
    sorted[1].seqname := a1[start].seqname;
    sorted[2].seqname := a1[top].seqname;
    sorted[3].seqname := a1[middle].seqname;
    bsort(1,3,sorted);
    If sorted[2].seqname = a1[middle].seqname Then
      switch (a1[start],a1[middle])
    Else
      If sorted[2].seqname = a1[top].seqname Then
        switch (a1[start],a1[top]);
  End;  {Find Median}
{**********************************************************************}
{* This algorithm performs a quick sort on a given array.  It works by first *}
{* splitting the range of values into two sets, one set greater than a    *}
{* a previously determined median value and the other set less than the value*}
{* . The algorithm then sorts each section separately and combines them into *}
{* one set subsequently.  In practice, the idea is DIVIDE AND CONQUER.  By   *}
{* dividing range of values into smaller subranges and then using a bubble   *}
{* sort, the greatest efficiency is achieved.  This particular implementation*}
{* of the concept comes from Introduction to Pascal by Rodney Zaks.  It has  *}
{* been modified in this program for using arrays of records.               *}
{**********************************************************************}
Procedure SortSection(start,top : Integer);
  Var swapup : Boolean;
      S,E,M  : Integer;
  Begin  {Sortsection}
    If top - start < 6 Then  { Sort small section with the bubble sort }
      Bsort ( start, top, a1 )
    Else
      Begin
        findmedian (start,top,a1);
        swapup := True;
        { Start Scanning from array top }
        s := start; { Lower Comparison Limit }
        e := top;   { Upper Comparison Limit }
        m := start; { Location of comparison value }
        While e > s Do
          Begin
            If swapup Then
              { Scan downward from partition top    }
              { and exchange if smaller than median }
              Begin
                While (a1[e].seqname >= a1[m].seqname) and (e>m) Do
                  e := e - 1;
                If e > m Then
                  Begin
                    switch (a1[e],a1[m]);
                    m := e
                  End;
                swapup := False
              End
            Else
              { Scan upward from partition start    }
              { and exchange if larger than median  }
              Begin
                While (a1[s].seqname <= a1[m].seqname) and (s < m) Do
                  s := s + 1;
                If s < m Then
                  Begin
                    Switch(a1[s],a1[m]);
                    m := s
                  End;
                Swapup := True
              End
```

```
        End;
      Sortsection(start,m-1); { Sort Lower half of partition }
      Sortsection(m+1,top);   { Sort Upper half of partition }
    End
  End; { Sortsection }
{****************************************************************************}
{* This algorithm alphabetically sorts a list of names given as records     *}
{****************************************************************************}
Procedure AlphaSort;
  Begin
    Sortsection(1,nument);
    Assign(alpha1,outalpha);
    Storeit1(a1,nument,alpha1);
  End;
{****************************************************************************}
{* This algorithm saves the given coding regions as indexed by the          *}
{* sequences they came from, in the order they came in.  In addition, two   *}
{* separate files will be created which contain the indexes for an alphabet-*}
{* -ically sorted list and a hashed list.                                    *}
{****************************************************************************}
Procedure Storecode(Var codereg1:SEQLIST; Var a1:Recsorts);
  Var count : Integer;
      base  : Pointto;
  Begin
    {Assume that the file has been opened in main loop}
    nument          := nument + 1;
    ct1             := ct1 + 1;
    a1[ct1].posinfile := nument;
    a1[ct1].seqname   := codereg1.seqname;
    Sortsection(1,ct1);
    WriteLn(outdbname,nument);
    WITH codereg1 DO
      Begin
        WriteLn(outdbname,nameline);
        WriteLn(outdbname,defnline);
        WriteLn(outdbname,num_cd_reg);
        FOR count := 1 to num_cd_reg DO
          With reg1[count] DO
            Begin
              WriteLn(outdbname,strt_stp);
              With codereg DO
                Begin
                  base := header;
                  While (base^.next <> nil) DO
                    Begin
                      Write(outdbname,base^.seqb);
                      base := base^.next;
                    End;
                End;
              WriteLn(outdbname,'1');
            End;
      End;
  End;
{*************************************************************************}
{*  This algorithm uses a binary search routine which divides the array   *}
{* of names into half and then again...until it finds the name or fails to*}
{*************************************************************************}
Procedure search(Var name:Name1; Var a1:Recsorts; Var nument:Integer);
    Var
        left,        {The left endpoint}
        right,       {The right endpoint}
        index : Integer;
        found : Boolean;
    Begin
        found  := False;
        left   := 0;
        right  := nument + 1;
        index  := (left + right) div 2;
        WHILE (index <> left) and (not(found)) DO
          Begin
            If a1[index].seqname = name Then
              Found := True
            Else
              Begin
                If (name < a1[index].seqname)  Then
                    right := index
                Else
                 If (name > a1[index].seqname) Then
                    left  := index;
                index  := (left + right) div 2
              End;
          End;
        If found Then
          errorrep('The sequence has already been processed',inlist,name);
      End;
   {*********************************************************************}
   {* This procedure creates an alarm.  It comes from the turbo disk,     *}
   {* courtesy of Borland of course...                                    *}
   {*  Play the notes G and D in octave three 7 times each with a         *}
   {* duration of 70 milliseconds.                                        *}
   {*********************************************************************}
   Procedure SoftAlarm;
   type
     NoteRecord = record
                    C,CF,D,DF,E,F,FF,G,GF,A,AF,B: integer;
                  end;
   const
     Notes: NoteRecord =
          (C:1;CF:2;D:3;DF:4;E:5;F:6;FF:7;G:8;GF:9;A:10;AF:11;B:12);
   var
     ch : char;
     I: integer;
   procedure Play(Octave,Note,Duration: integer);
   { Play Note in Octave Duration milliseconds
     Frequency computed by first computing C in
     Octave then increasing frequency by Note-1
     times the twelfth root of 2. (1.059463994)
     If Duration is zero  Note will be played
     until you activate procedure NoSound       }
     var
```

```
      Frequency : real;
      I         : integer;
    begin
      Frequency := 32.625;
      for I := 1 to Octave do          { Compute C in Octave              }
        Frequency := Frequency * 2;
      for I := 1 to Note - 1 do        { Increase frequency Note-1 times }
        Frequency := Frequency * 1.059463094;
      if Duration <> 0 then
      begin
        Sound(Round(Frequency));
        Delay(Duration);
        NoSound;
      end
      else Sound(Round(Frequency));
    end;
    begin {Soft Alarm}
      for I := 1 to 7 do
        with Notes do
        begin
          Play(4,G,70);
          Play(4,D,70);
        end;
        delay(1000);
    end;  {Soft Alarm}
{***************************************************************************}
{*                 M  A  I  N     P  R  O  G  R  A  M                      *}
{***************************************************************************}
  Begin { M A I N  P R O G R A M }
    error := False;
    lastfound := TRUE;
    start := true;
    stat := 0;
ClrScr;
WriteLn('FROMOD1, uses .INL list of sequence names, and .IND sequence file');
WriteLn('        to generate .OTD output database used by FREQ2.');
WriteLn;
WriteLn('      (modified 6/88 to operate on IG file generated by ');
WriteLn('                    UWGCG utility program TOIG.)');
WriteLn;
WriteLn;
WriteLn('Hit any key to continue');
ReadLn(c);
    inlist := GETFILENAMES(0);
    ASSIGN(inlistname,inlist);
    indbase := GETFILENAMES(1);
    ASSIGN(indbname,indbase);
    outdbase := GETFILENAMES(2);
    ASSIGN(errorlog,'run.log');
    runlog1 := Exist('run.log');
    IF runlog1 THEN
      copyrunlog
    Else
      ReWrite(errorlog);
    WriteLn(errorlog,'Input list file is ',inlist);
    WriteLn(errorlog,'Input database file is ',indbase);
    WriteLn(errorlog,'Output database file is ',outdbase);
    ReSet(inlistname);
    ReSet(indbname);
    CLRSCR;
    GotoXY(5,10);
    Write('Please Standby, Now Processing...');
    SoftAlarm;
    readinlist(INPUTLIST);
    If NOT(EOF(inlistname)) Then
     Repeat
      Begin
{       freemem(base,mem1);
       WriteLn;
       WriteLn('Free memory : ',mem1);}
       stat := stat + 1;
       GotoXY(40,10);
{       Write(stat);}
       in1 := 1;
       search(inputlist.seqname,a1,nument);
       IF not(error) THEN
         BEGIN
           readindbase(inputlist,seq1);
           IF not(error) Then
             Begin
               num := 1;
               codereg1.seqname   := inputlist.seqname;
               codereg1.nameline  := seq1.nameline;
               codereg1.defnline  := seq1.defnline;
               codereg1.num_cd_reg := inputlist.num_cd_reg;
               WriteLn;
               WriteLn('Now on ');
               WriteLn(seq1.nameline);
               WriteLn(seq1.defnline);
               WriteLn(inputlist.num_cd_reg,' coding region(s)');
             End;
           WHILE not(error) and (num <= inputlist.num_cd_reg) DO
             Begin
               convertstr(inputlist.cd_strt_stp[num],inputlist.seqname,strt,stop,inputlist.inverse[num]);
               SelectRegions(inputlist,seq1,strt,stop,codereg1.reg1[num],num);
               num := num + 1;
             End;
           If not(error) Then
             Begin
               Storecode(codereg1,a1);
               FOR num := 1 to inputlist.num_cd_reg DO
                 With codereg1 DO
                   erasereg(reg1[num]);
             End;
           Eraseseq(seq1);
         End;
      error := false;
      readinlist(INPUTLIST);
      IF (EOF(INDBNAME)) AND NOT(EOF(INLISTNAME)) THEN
        errorrep('The input list is no longer in the dbase ',inlist,inputlist.seqname);
      If EOF(inlistname) Then
        WriteLn(outdbname,'\\')
```

```
      Else
        WriteLn(outdbname,'\');
      End;
    Until Eof(inlistname);
   Alphasort;
   CLOSE(errorlog);
   CLOSE(inlistname);
   CLOSE(indbname);
   CLOSE(outdbname);
   WriteLn('                      ...Done Processing...End of Run');
   WriteLn;
   WriteLn('                              Wake up, I''m done');
   WriteLn;
   Write('                         Hit Any Key to Quit!');
   Repeat
     SoftAlarm;
   Until KeyPressed;
 End.
{***************************************************************************}
{*Frequency Generation Module Two with Local Region and Amino Acid Bias     *}
{*                             "Freq2Loc"                                   *}
{*                                                                          *}
{*     This program allows the user to generate codon and codon pair        *}
{* frequencies when given a database containing protein coding regions.     *}
{* These frequencies take into account local coding regions and amino       *}
{* acid usage. The program takes input from the output database generated  *}
{* by module one.                                                           *}
{*     The output consists of six  files.  The first is a table of codon    *}
{* usage within a given set of coding regions. The second and third are     *}
{* tables of observed and expected codon usage respectively.                *}
{*    The fourth is a file containing the number of                         *}
{* codons processed, the number of codon pairs processed, the number of     *}
{* protein coding regions processed, and the number of sequences processed*}
{* -- in that order. The fifth file contains a list of all the sequences    *}
{* which have been processed by module two.  The sixth file is a run log    *}
{* which states which files were used during a run and errors encountered   *}
{* during that run of this module.                                          *}
{*     The files which we have encountered thus far are specially marked    *}
{* by means of their extensions.  The output files will all have the        *}
{* same prefix, but will be distinguished by their extensions.  For         *}
{* instance, the table one file is labeled .TB1, table 2 & 3 are .TB2,.TB3*}
{* The codon numbers file is labeled .NUM, the sequences processed file is*}
{* labeled .TBI (for table information), and the run log is labeled         *}
{* RUN.LOG.  The input file is labeled .OTD from the previous module.       *}
{*     After the program finds the frequencies, it computes statistical     *}
{* data from this information.  The new information is stored in a sixth   *}
{* file with the extension .PRN.  This file is saved under a Reflex         *}
{* database compatible format.                                              *}
{***************************************************************************}
Program FreqMod2;
{$I+}
{$C+}
  TYPE name1      =    STRING[20];
       name2      =    array [ 1..14 ] of Char;
       standard   =    STRING[255];
       CodonUse   = Array [ 1..64 ] Of Real;
       CodonPrUse = Array [ 1..64 , 1..64 ] Of Real;
       Cdnuse     = File of CodonUse;
       Cdnpruse   = File of CodonPrUse;
       Seqlist    = File of String[20];
       Recsorts   = Array[1..300] of String[20];
       Pointto    = ^Base1;
       Base1      = Record
         seqb  :Char;
         Next  :Pointto
       End;
       Region     = Record
         header    :Pointto;
         numregnow :Integer;
         reg       :Base1;
       End;

       codty      = String[3];
       AminoAcids = Record
         start     :Integer;
         stop      :Integer;
       End;

 VAR
       codon           :Array[1..64] of Codty;  {Contains the actual codons}
       cdn             :Array[1..64] of Codty;  {Contains the amino acids}
       regnow          :Region;     {The coding region under examination}
       head,tail,base  :Pointto;
       numregnow       :Integer;
       Table1          :CodonUse;
       Table2,
       Etable2         :CodonPrUse;
       Valid           :Seqlist;
       Valid1          :Recsorts;
       cdnl,
       cdnr,
       cdn1            :Codty;  {The actual codons}
       AA              :Array[1..23] of AminoAcids; {Information on amino acids}
       indbname,
       errorlog,
       numberi,
       reflex          :TEXT;
       outtab1         :CdnUse;
       outtab2,
       outtab3         :CdnPrUse;

       indbase,
       outtable1,
       outtable2,
       outtable3,
       outalpha,
       validname,
       numbers,
       Seqname,
       Check,
       reflx1,
```

```
      ref1           :Name1;
      temporary      :STANDARD;
      error,
      inverse,
      runlog1,
      noend,
      codon1         :Boolean;
      strt,
      stop,
      spare,
      num,
      numreg,
      ct1,
      ct2,
      ct3,
      ct4,
      count,
      vnum,
      codl,
      codr,
      count1           :Integer;
      numcdns,     {Number of codons}
      numprs,      {Number of Pairs}
      numtreg,     {Number of coding regions}
      numprc,      {Number of sequences}
      numexp,       {Expected number of occurrences}
      numobs:Real;  {Observed number of occurrences}
{*************************************************************************}
{* This procedure takes any string and returns its uppercase equivalent.  *}
{*************************************************************************}
PROCEDURE changecase(VAR str1:NAME1);
  VAR count:Integer;
  Begin
    FOR count := 1 to LENGTH(str1) DO
        str1[count] := upcase(str1[count]);
  End;

{*************************************************************************}
{*  This algorithm creates a table of codons in a 1 by 64 matrix.         *}
{*************************************************************************}
Procedure CreateTable;
  Begin {CreateTable}
       CODON[1]  := 'TTT';
       CODON[2]  := 'TTC';
       CODON[3]  := 'TTA';
       CODON[4]  := 'TTG';
       CODON[5]  := 'CTT';
       CODON[6]  := 'CTC';
       CODON[7]  := 'CTA';
       CODON[8]  := 'CTG';
       CODON[9]  := 'ATT';
       CODON[10] := 'ATC';
       CODON[11] := 'ATA';
       CODON[12] := 'ATG';
       CODON[13] := 'GTT';
       CODON[14] := 'GTC';
       CODON[15] := 'GTA';
       CODON[16] := 'GTG';
       CODON[17] := 'TCT';
       CODON[18] := 'TCC';
       CODON[19] := 'TCA';
       CODON[20] := 'TCG';
       CODON[21] := 'AGT';
       CODON[22] := 'AGC';
       CODON[23] := 'CCT';
       CODON[24] := 'CCC';
       CODON[25] := 'CCA';
       CODON[26] := 'CCG';
       CODON[27] := 'ACT';
       CODON[28] := 'ACC';
       CODON[29] := 'ACA';
       CODON[30] := 'ACG';
       CODON[31] := 'GCT';
       CODON[32] := 'GCC';
       CODON[33] := 'GCA';
       CODON[34] := 'GCG';
       CODON[35] := 'TAT';
       CODON[36] := 'TAC';
       CODON[37] := 'TAA';
       CODON[38] := 'TAG';
       CODON[39] := 'CAT';
       CODON[40] := 'CAC';
       CODON[41] := 'CAA';
       CODON[42] := 'CAG';
       CODON[43] := 'AAT';
       CODON[44] := 'AAC';
       CODON[45] := 'AAA';
       CODON[46] := 'AAG';
       CODON[47] := 'GAT';
       CODON[48] := 'GAC';
       CODON[49] := 'GAA';
       CODON[50] := 'GAG';
       CODON[51] := 'TGT';
       CODON[52] := 'TGC';
       CODON[53] := 'TGA';
       CODON[54] := 'TGG';
       CODON[55] := 'CGT';
       CODON[56] := 'CGC';
       CODON[57] := 'CGA';
       CODON[58] := 'CGG';
       CODON[59] := 'AGA';
       CODON[60] := 'AGG';
       CODON[61] := 'GGT';
       CODON[62] := 'GGC';
       CODON[63] := 'GGA';
       CODON[64] := 'GGG';
       CDN[1]  := 'Phe';
       CDN[2]  := 'Phe';
       CDN[3]  := 'Leu';
       CDN[4]  := 'Leu';
       CDN[5]  := 'Leu';
       CDN[6]  := 'Leu';
       CDN[7]  := 'Leu';
```

```
        CDN[8] := 'Leu';
        CDN[9] := 'Ile';
        CDN[10]:= 'Ile';
        CDN[11]:= 'Ile';
        CDN[12]:= 'Met';
        CDN[13]:= 'Val';
        CDN[14]:= 'Val';
        CDN[15]:= 'Val';
        CDN[16]:= 'Val';
        CDN[17]:= 'Ser';
        CDN[18]:= 'Ser';
        CDN[19]:= 'Ser';
        CDN[20]:= 'Ser';
        CDN[21]:= 'Ser';
        CDN[22]:= 'Ser';
        CDN[23]:= 'Pro';
        CDN[24]:= 'Pro';
        CDN[25]:= 'Pro';
        CDN[26]:= 'Pro';
        CDN[27]:= 'Thr';
        CDN[28]:= 'Thr';
        CDN[29]:= 'Thr';
        CDN[30]:= 'Thr';
        CDN[31]:= 'Ala';
        CDN[32]:= 'Ala';
        CDN[33]:= 'Ala';
        CDN[34]:= 'Ala';
        CDN[35]:= 'Tyr';
        CDN[36]:= 'Tyr';
        CDN[37]:= 'Ocr';
        CDN[38]:= 'Amb';
        CDN[39]:= 'His';
        CDN[40]:= 'His';
        CDN[41]:= 'Gln';
        CDN[42]:= 'Gln';
        CDN[43]:= 'Asn';
        CDN[44]:= 'Asn';
        CDN[45]:= 'Lys';
        CDN[46]:= 'Lys';
        CDN[47]:= 'Asp';
        CDN[48]:= 'Asp';
        CDN[49]:= 'Glu';
        CDN[50]:= 'Glu';
        CDN[51]:= 'Cys';
        CDN[52]:= 'Cys';
        CDN[53]:= 'Umb';
        CDN[54]:= 'Trp';
        CDN[55]:= 'Arg';
        CDN[56]:= 'Arg';
        CDN[57]:= 'Arg';
        CDN[58]:= 'Arg';
        CDN[59]:= 'Arg';
        CDN[60]:= 'Arg';
        CDN[61]:= 'Gly';
        CDN[62]:= 'Gly';
        CDN[63]:= 'Gly';
        CDN[64]:= 'Gly';
        AA[1].Start := 1;
        AA[1].Stop  := 2;
        AA[2].Start  :=3;
        AA[2].Stop   :=8;
        AA[3].Start  :=9;
        AA[3].Stop   :=11;
        AA[4].Start  :=12;
        AA[4].Stop   :=12;
        AA[5].Start  :=13;
        AA[5].Stop   :=16;
        AA[6].Start  :=17;
        AA[6].Stop   :=22;
        AA[7].Start  :=23;
        AA[7].Stop   :=26;
        AA[8].Start  :=27;
        AA[8].Stop   :=30;
        AA[9].Start  :=31;
        AA[9].Stop   :=34;
        AA[10].Start  :=35;
        AA[10].Stop   :=36;
        AA[11].Start  :=39;
        AA[11].Stop   :=40;
        AA[12].Start  :=41;
        AA[12].Stop   :=42;
        AA[13].Start  :=43;
        AA[13].Stop   :=44;
        AA[14].Start  :=45;
        AA[14].Stop   :=46;
        AA[15].Start  :=47;
        AA[15].Stop   :=48;
        AA[16].Start  :=49;
        AA[16].Stop   :=50;
        AA[17].Start  :=51;
        AA[17].Stop   :=52;
        AA[18].Start  :=54;
        AA[18].Stop   :=54;
        AA[19].Start  :=55;
        AA[19].Stop   :=60;
        AA[20].Start  :=61;
        AA[20].Stop   :=64;
        AA[21].Start  :=37;
        AA[21].Stop   :=37;
        AA[22].Start  :=38;
        AA[22].Stop   :=38;
        AA[23].Start  :=53;
        AA[23].Stop   :=53;

  End;  {CreateTable}

{***********************************************************************}
{* This procedure makes a pause by displaying hit return and requiring a *}
{* linefeed.                                                              *}
{***********************************************************************}
PROCEDURE pause;
  VAR cont:CHAR;
```

```
  Begin
    WriteLn;
    Write('                    ** Hit ''Return'' to Continue **');
    ReadLn(cont);
  End;

{***************************************************************************}
{* This procedure creates a runtime log of errors which occurred on the   *}
{* system during execution.                                                *}
{***************************************************************************}
PROCEDURE errorrep(code:STANDARD;infilename,sequence:NAME1);
  VAR stemp : String[255];
  Begin
    error := TRUE;
    stemp := '';
    stemp := CONCAT('ERROR: ',code,' in ',sequence,' sequence, from ',indbase,' file.');
    WriteLn(errorlog,stemp);
  End;

{*******************************************************************}
{* This procedure creates an alarm.  It comes from the turbo disk,   *}
{* courtesy of Borland of course...                                 *}
{*  Play the notes G and D in octave three 7 times each with a      *}
{* duration of 70 milliseconds.                                     *}
{*******************************************************************}
Procedure SoftAlarm;
type
  NoteRecord = record
                 C,CF,D,DF,E,F,FF,G,GF,A,AF,B: integer;
               end;
const
  Notes: NoteRecord =
        (C:1;CF:2;D:3;DF:4;E:5;F:6;FF:7;G:8;GF:9;A:10;AF:11;B:12);
var
  ch : char;
  I: integer;
procedure Play(Octave,Note,Duration: integer);
{ Play Note in Octave Duration milliseconds
  Frequency computed by first computing C in
  Octave then increasing frequency by Note-1
  times the twelfth root of 2. (1.059463994)
  If Duration is zero  Note will be played
  until you activate procedure NoSound       }
  var
    Frequency : real;
    I         : integer;
  begin
    Frequency := 32.625;
    for I := 1 to Octave do             { Compute C in Octave             }
      Frequency := Frequency * 2;
    for I := 1 to Note - 1 do           { Increase frequency Note-1 times }
      Frequency := Frequency * 1.059463094;
    if Duration <> 0 then
    begin
      Sound(Round(Frequency));
      Delay(Duration);
      NoSound;
    end
    else Sound(Round(Frequency));
  end;
  begin {Soft Alarm}
    for I := 1 to 7 do
      with Notes do
      begin
        Play(4,G,70);
        Play(4,D,70);
      end;
      delay(1000);
  end;  {Soft Alarm}

{***************************************************************************}
{* This function comes from the turbo-pascal utilities disk and it gets a *}
{* directory listing of the current logged drive.                          *}
{***************************************************************************}
PROCEDURE DIRLIST;
  TYPE
    string20  = STRING[20];
    Char12arr = Array [ 1..12 ] of CHAR;
    RegRec    =
      record
        AX,BX,CX,DX,BP,SI,DI,DS,ES,Flags:Integer;
      End;
  VAR
    Regs        :RegRec;
    DTA         :array [ 1..43 ] of Byte;
    Mask        :Char12arr;
    NamR        :String20;
    Error,
    I,
    num,
    tab1        :Integer;
  Begin {Main body of procedure dirlist}
    FillChar(DTA,SizeOf(DTA),0);           { Initialize the DTA buffer }
    FillChar(Mask,SizeOf(Mask),0);         { Initialize the mask }
    FillChar(NamR,SizeOf(NamR),0);         { Initialize the file name }
    WriteLn;
    Regs.AX := $1A00;            { Function used to set the DTA}
    Regs.DS := Seg(DTA);         { Store the parameter segment in DS}
    Regs.DX := Ofs(DTA);         {   "     ";    "     offset in DX}
    MSDos(Regs);                 { Set the DTA location}
    Error := 0;
    Mask := '????????.???';
    Regs.AX := $4E00;            { Get first directory entry  }
    Regs.DS := Seg(Mask);        { Point to the file Mask }
    Regs.DX := Ofs(Mask);
    Regs.CX := 22;               { Store the option }
    MSDos (Regs);                { Execute MSDos call}
    Error := Regs.AX and $FF;    { Get Error return }
    I := 1;                      { initialize 'I' to the first element }
    num := 1;
    tab1 := 15;
    if (Error = 0 ) then
```

```
      Repeat
        NamR[I] := Chr(Mem[Seg(DTA):Ofs(DTA)+29+I]);
        I := I + 1;
      Until not(NamR[I-1] in [' '..'~']) or (I>20);
    NamR[0] := Chr(I-1);         { set string length because assigning}
                                 { by element does not set lenght }
    while (Error = 0) do begin
      Error := 0;
      Regs.AX := $4F00;          { Function used to get the next }
                                 { directory entry }
      Regs.CX := 22;             { Set the file option }
      MSDos( Regs );             { Call MSDos }
      Error := Regs.Ax and $FF;  { get the Error return }
      I := 1;
      repeat
        NamR[I] := Chr(Mem[Seg(DTA):Ofs(DTA)+29+I]);
        I := I + 1;
      until not(NamR[I-1] in [' '..'~']) or (I > 20);
      NamR[0] := Chr(I-1);
      if (Error = 0) then
        Begin
          IF num = 6 THEN
            Begin
              WriteLn;
              tab1 := 15;
              num := 1;
            End;
          Write(NamR:tab1);
          tab1 := tab1;
          num := num + 1;
        END;
    end;
  end; {main procedure}
{*************************************************************************}
{* This algorithm gets a set of records from disk.                      *}
{*************************************************************************}
Procedure Retrieve(VAR Valid1:Recsorts;VAR Vnum:INTEGER; VAR Valid:Seqlist);
   Var q:Integer;
   Begin
     Reset(Valid);
     Vnum := 0;
     WriteLn;
     WriteLn('      Now loading a list of previously processed sequences...');
     While NOT(eof(Valid)) Do
       Begin
         q := filepos(Valid);
         WriteLn;
         Vnum := Vnum + 1;
         Read(Valid,Valid1[Vnum]);
         WriteLn('Sequence is ',Valid1[Vnum]);
       End;
     Close(Valid);
     Erase(Valid);
   End;

{*************************************************************************}
{* This algorithm stores a set of records to disk.                      *}
{*************************************************************************}
Procedure Storeit1(VAR Valid1:Recsorts;VAR Vnum:INTEGER; VAR Valid:Seqlist);
  Var step :Integer;
      q    :Integer;
  Begin
    Rewrite(Valid);
    WriteLn;
    WriteLn('       Now writing a list of sequences processed to date');
    For step := 1 to Vnum Do
      Begin
        q := filepos(Valid);
        WriteLn;
        Write(Valid,Valid1[step]);
        WriteLn('Record #',step,' is ',Valid1[step]);
      End;
    Close(Valid);
  End;

{*************************************************************************}
{* This function comes from the turbo-pascal manual and determines whether*}
{* a file exists already or not                                          *}
{*************************************************************************}
FUNCTION exist(filename:NAME1):Boolean;
  VAR fil   :FILE;
  Begin
    ASSIGN(fil,filename);
    {$I-}
    RESET(FIL);
    {I+}
    EXIST := (IOresult = 0)
  End;

{*************************************************************************}
{* This procedure copies a text file into another text file. It deletes *}
{* the first file, and renames the second file after copying.           *}
{*************************************************************************}
PROCEDURE copyrunlog;
  VAR t1       : TEXT;
      exists   : Boolean;
      block1   : Standard;
      ch1      : Char;
  Begin {Copy runlog}
    block1 := 'tempfile';
    exists := EXIST(block1);
    Assign(t1,block1);
    If exists Then
      Erase(t1);
    Assign(t1,'run.log');
    Rename(t1,block1);
    Assign(errorlog,'run.log');
    Reset(t1);
    Rewrite(errorlog);
    While Not(Eof(t1)) DO
      Begin
        Read(t1,ch1);
        Write(errorlog,ch1);
      End;
```

```
    Close(t1);
    ERASE(T1);
  End; (copy run log)

{*************************************************************************}
{* This algorithm checks filenames to find out if they exist on the disk *}
{*************************************************************************}
Function getfilenames(typein:Integer):Name1;
  VAR
      invalid,
      exists,
      exist1,
      exist2,
      exist3,
      exist4     :Boolean;
      go         :Name1;
      dummy      :CHAR; (A dummy variable)

      dir1       :STRING[255]; (contains directory)
      drive,
      count,
      count1,
      count2     :Integer;
      filename   :NAME1;
      mask1      :NAME2;

  Begin
    GO := 'N';
    Repeat
      TEXTMODE(BW80);
      error := FALSE;
      CLRSCR;
      REPEAT
        LowVideo;
        WRITE('Enter the filename for the ');
        NormVideo;
        CASE typein OF
          0:WriteLn('INPUT DATABASE: ');
          1:WriteLn('OUTPUT DATA');
        End;
        LowVideo;
        WriteLn;
        Write(' (Please specify a filename with the ');
        NormVideo;
        Case typein Of
          0: Write('.OTD');
          1: Write('.TB1');
        End;
        LowVideo;
        WriteLn(' suffix, but do not write the suffix.)');
        WriteLn(' (For example:  Test.otd is a file. You would write only Test )');
        WriteLn(' Note: You may create a output data file set with any new name');
        WriteLn;
        WriteLn('          Hit ''Return'' to get a directory listing');
        (GOTOXY(5,12);)
        WriteLn;
        NormVideo;
        Write('FILENAME:');
        (GOTOXY(15,12);)
        (WRITE('______________');
        GOTOXY(15,12);)
        READLN(filename);
        IF filename = '' THEN
          Begin
            CLRSCR;
            LowVideo;
            DIRLIST;
            WRITELN;
            WRITELN;
          End;
        (TEXTBACKGROUND(0);)
        invalid := FALSE;
        count := 0;
        IF (length(filename) > 8) THEN
          invalid := TRUE;

        WHILE (NOT(INVALID)) AND (count <= LENGTH(filename)) DO
          Begin
            If (filename[count] = '.') THEN
              invalid := TRUE
            Else
              count := count + 1;
          End;

      UNTIL (filename <> '') and not(invalid);

      CASE typein OF
        0: Begin
             filename := filename + '.OTD';
           End;
        1: Begin
             outtable3 := filename + '.TB3';
             outtable2 := filename + '.TB2';
             validname := filename + '.TBI';
             numbers   := filename + '.NUM';
             reflx1    := filename + '.PRN';
             filename  := filename + '.TB1';
             outtable1 := filename;
           End;
      END;

      exists := EXIST(filename);
      If typein = 1 Then
        Begin
          exist1 := Exist(outtable2);
          exist2 := Exist(validname);
          exist3 := Exist(numbers);
          exist4 := Exist(outtable3);
        End;
```

```
        IF not(exists) and (typein = 0) THEN
          Begin
            WriteLn;
            WriteLn('** ERROR: THE FILENAME ENTERED DOES NOT EXIST, PLEASE RE-ENTER **');
            WriteLn;
            PAUSE
          End
        ELSE
         IF (typein = 1) THEN
           IF exists and exist1 and exist2 and exist3 and exist4 THEN
             Begin
               Assign(outtab1,filename);
               Reset(outtab1);
               Read(outtab1,table1);
               Assign(outtab2,outtable2);
               Reset(outtab2);
               Read(outtab2,table2);
               Assign(outtab3,outtable3);
               Reset(outtab3);
               Read(outtab3,Etable2);
               Assign(valid,validname);
               Retrieve(valid1,vnum,valid);
               Assign(numberi,numbers);
               Reset(numberi);
               ReadLn(numberi,numcdns);
               ReadLn(numberi,numprs);
               ReadLn(numberi,numtreg);
               ReadLn(numberi,numprc);
               Close(numberi);
               Erase(numberi);
               go := 'Y';
             End
           ELSE
             Begin
               WriteLn;
               WriteLn('  The filename which you entered for the Output Data does not exist. ');
               WriteLn;
               Write('         Would you like me to create it? (Y/N) ');
               go := '';
               ReadLn(GO);
               ChangeCase(go);
               If go = 'Y' Then
                Begin
                 Assign(outtab1,filename);
                 Rewrite(outtab1);
                 Assign(outtab2,outtable2);
                 Rewrite(outtab2);
                 Assign(outtab3,outtable3);
                 Rewrite(outtab3);
                 For count1 := 1 to 64 Do
                   Begin
                     table1[count1] := 0;
                     For count2 := 1 to 64 Do
                       Begin
                         table2[count2,count1] := 0;
                         Etable2[count2,count1] := 0
                       End
                   End;
                 Assign(valid,validname);
                 Rewrite(valid);
                 Vnum    := 0;
                 numcdns := 0;
                 numprs  := 0;
                 numtreg  := 0;
                 numprc  := 0;
                 go      := 'Y';
                End
             End;
    Until (exists and (typein IN [0])) or (GO = 'Y');
    getfilenames := filename;
  End;

{***************************************************************************}
{* This algorithm converts a given string of numbers separated by a comma *}
{* into two numbers, i.e. a start and a stop.                              *}
{***************************************************************************}
PROCEDURE convertstr(VAR cdreg:Standard; Var sequence:NAME1; VAR start,stop:Integer; VAR inverse,stop1:Boolean);
  VAR step,              (A integer loop counting variable)
      err1,
      temp       :Integer;
      current    :String[7]; (A temporary holding variable)
      found1,
      start1,
      temp1      :Boolean; (Indicates a section has been found)
  Begin
    step    := 1;
    err1    := 0;
    current := '';
    temp    := 0;
    error   := FALSE;
    found1  := FALSE;
    start   := 0;
    stop    := 0;
    start1  := False;
    stop1   := False;
    inverse := FALSE;
    WHILE (step <= LENGTH(cdreg)) AND NOT(error) DO
      Begin
        IF cdreg[step] in ['<','>',' '] THEN
          Begin
            If cdreg[step] in ['<','>'] Then   (Checks to see if there is a stop codon)
              If found1 Then
                stop1 := True
              Else
                start1 := True;
            step := step + 1
          End
        ELSE
          IF cdreg[step] = ','  THEN
            Begin
              IF found1 THEN
                errorrep('Coding region format is incorrect -- too many commas',indbase,sequence)
              ELSE
```

```
                IF current = ''  THEN
                  errorrep('Coding region format is incorrect -- nothing before comma.',indbase,sequence)
                ELSE
                  Begin
                    found1 := TRUE;
                    VAL(current,start,err1);
                    current := '';
                    step := step + 1;
                  End
              End
            ELSE
              Begin
                current := current + cdreg[step];
                step := step + 1;
              End;
        End; {while}
      VAL(current,stop,err1);
      IF (start > stop) THEN    {Non-message strand has been found-- Inverse Complement}
        Begin
          inverse := TRUE;
          temp    := start;
          start   := stop;
          stop    := temp;
        End
      ELSE
          IF start = stop THEN
            errorrep('Start is equal to stop, no bases in region.',indbase,sequence);
      IF not(error) THEN
        IF (((stop - start) +1) MOD 3) <> 0 THEN
          errorrep('Coding region is not divisible by 3.',indbase,sequence);

  End; {CONVERT STRING}

{**************************************************************************}
{*  This algorithm uses a binary search routine which divides the array   *}
{* of names into half and then again...until it finds the name or fails to*}
{**************************************************************************}
Procedure search(Var name:Name1; Var valid1:Recsorts; Var nument:Integer);
    Var
        left,        {The left endpoint}
        right,       {The right endpoint}
        index : Integer;
        found : Boolean;
    Begin {Binary Search}
      found  := False;
      left   := 0;
      right  := nument + 1;
      index  := (left + right) div 2;
      WHILE (index <> left) and (not(found)) DO
        Begin
          If valid1[index] = name Then
            Found := True
          Else
            Begin
              If (name < valid1[index])  Then
                  right := index
              Else
               If (name > valid1[index]) Then
                  left  := index;
              index  := (left + right) div 2
            End;
        End;
      If found Then
        errorrep('The sequence has already been processed',indbase,name);
    End; {Binary Search}

{**************************************************************************}
{*  This algorithm finds the array number of any given codons by searching*}
{**************************************************************************}
Function Findnum(Var x:Codty):Integer;
  Var cnt:Integer;
      found:Boolean;
  Begin {Find Num}
    cnt := 1;
    found := False;
    While not(found) and (cnt<=64) Do
      If x = codon[cnt] Then
        Begin
          found := True;
          findnum := cnt;
        End
      Else
        cnt := cnt + 1;
  End; {Find Num}


{**************************************************************************}
{*  This algorithm moves file pointer to next sequence.                   *}
{**************************************************************************}
Procedure FastFwd;
  Begin
    ReadLn(indbname,temporary);
    While  (temporary[1] <> '\') and  (temporary[1] <> '\\') Do    {Fast forward}
      ReadLn(indbname,temporary);
  End;

{**************************************************************************}
{*  This algorithm erases or frees dynamically allocated memory by using  *}
{*  certain given commands of the Pascal Language.                        *}
{**************************************************************************}
Procedure EraseReg;
  Begin {Erase Region}
    With Regnow Do
      Begin
        base := header;
        tail := base^.next;
        While tail <> NIL Do
          Begin
            DISPOSE(BASE);
            base := tail;
            tail := base^.next;
          End
      End
  End;   {Erase Region}
```

```
{************************************************************************}
{*  This algorithm reads in exactly one coding region.                  *}
{************************************************************************}
Procedure RegionIn;
  Var Ch1:Standard;
      Temp :Char;

   Begin {RegionIn}
       ReadLn(indbname,temporary);  {Pulls in the start and stop}
       convertstr(temporary,seqname,strt,stop,inverse,noend);
      With regnow Do
       Begin
         numregnow := 0;
         New(header);
         tail := header;
         base := header;
         base^.next := NIL;
         Read(indbname,temp);
         While (temp <> '1') and not(error) Do
            Begin
              base^.seqb := temp;
              numregnow := numregnow + 1;
              New(base);
              tail^.next := base;
              tail       := base;
              base^.next := NIL;
              Read(indbname,temp);
            End;
         IF NOT(ERROR) Then {Gets rid of last character and linefeed on coding region line}
           ReadLn(indbname,ch1);
         WriteLn;
       End;
   End; {RegionIn}

{************************************************************************}
{*  This algorithm tabulates the necessary information.                 *}
{************************************************************************}
Procedure Countit;
  Var Ltable1  :CodonUse;   {Local codon usage table}
        Step  :Integer;     {Integer loop counter}
        NUMIN :REAL;          {NUMBER OF CODONS IN}
  {************************************************************************}
  {*  This algorithm initializes the local codon usage table and other vars.*}
  {************************************************************************}
  Procedure Init;
    Var count : Integer;
    Begin
      For count := 1 to 64 Do
        Ltable1[count] := 0;
    End;

  {************************************************************************}
  {*  This algorithm computes the expected number of codon pairs.          *}
  {************************************************************************}
  Procedure Compute;
    Var totalprs,             {The total number of pairs in the coding region}
        totalcdns,
        test1,
        test2
                   :Real;   {The total number of codons in the coding region}
           step,            { Integer Loop Counters }
          step1    :Integer; { Integer Loop Counters }
             f1,             { The frequency of occurrence of the left codon }
             f2    :Real;    { The frequency of occurrence of the right codon }
    Begin {Compute}
      totalcdns := NUMCDNS - NUMIN; {regnow.numregnow DIV 3;}
      totalprs  := totalcdns - 1;
      {test1 := 0;
      For step := 1 to 64 Do
        test1 := test1 + ltable1[step];}

 {     test2   := test1 - 1;
      WriteLn('Codonmeth1 :',totalcdns,'    , Codonmeth2:',test1);
      pause;}
  {    TEST2:=0;}
      For step := 1 to 64 Do { Compute Frequencies }
        bEGIN
          ltable1[step] := (ltable1[step]/totalcdns);
{          TEST2  := TEST2 + LTABLE1[STEP];}
        eND;
{       WRITELN('LTABLE ADDS TO :',TEST2);
      PAUSE;
      TEST1:= 0; TEST2 := 0;}
      For step := 1 to 64 Do
        If NOT(step = 37) AND NOT(step = 38) AND NOT(step = 53) Then
          For step1 := 1 to 64 Do
            Begin
              If NOT(step1 = 37) AND NOT(step1 = 38) AND NOT(step1 = 53) Then
D -------------- Etable2[step,step1] := Etable2[step,step1] + (Ltable1[step] * Ltable1[step1] * totalPRS);
   {            WriteLn('Observed Pairs :',Table2[step,step1],',  Expected Pairs:  ',Etable2[step,step1]);
              TEST1 := TEST1 +TABLE2[STEP,STEP1];
              TEST2 := TEST2 +ETABLE2[STEP,STEP1];}
            End;
{      WriteLn('Codon Pair Total: ',test1,'  Exp. CP Total: ',test2);}
    End;  {Compute}

  Begin {Countit}
    NUMIN := NUMCDNS;
    Init;
    codon1 := False; {Flag for first left codon}
    cdnl   := '';
    cdnr   := '';
    ct3 := 0;          {Counter for the coding region}
    base := Regnow.header;
    While (ct3 < regnow.numregnow) and NOT(error) Do
      Begin
        numcdns := numcdns + 1;
        cdn1 := '';
        For ct4 := 1 to 3 Do
          Begin
            cdn1 := cdn1 + base^.seqb;
            base := base^.next;
          End;
```

```
        ct3  := ct3 + 3; {Adds a codon consisting of 3 bases to position in sequence}
        If Not(codon1) Then
          Begin
            cdnl := cdn1;
            codl := Findnum(cdnl);
C.1 ------- Ltable1[codl] := Ltable1[codl] + 1;
            codon1 := True;
            codr := codl;
          End
        Else
          Begin
            codl   := codr;
            cdnr   := cdn1;
            codr   := Findnum(cdnr);
C.2 ------- Table2[codl,codr] := Table2[codl,codr] + 1;
            If NOT(CODR = 37) AND NOT(CODR = 38) AND NOT(CODR = 53) Then
C.1 -----------   Ltable1[codr] := Ltable1[codr] + 1
            ELSE
              Begin
                NUMCDNS := NUMCDNS -1;    {REMOVES STOP CODON FROM TOTAL NUMBER}
                table1[codr] := table1[codr] +1    {Add stop codon into global table}
              End;
            numprs := numprs + 1
          End;
      End;
    For step := 1 to 64 Do
C.3 ------ Table1[step] := Table1[step] + Ltable1[step];  {Add local codon usage to global table}
    Compute; {number of pairs expected}
    EraseReg; {Release the memory used in the region}

  End; {Procedure CountIt}

{****************************************************************************}
{*  This algorithm checks if there is a stop codon at the end.              *}
{****************************************************************************}
Procedure CheckStop;
  Var base1, base2, base3 :Pointto;
      count1,
      hell     : Integer;

  Begin {CheckStop}
    cdn1  := '';
    hell  := regnow.numregnow - 3 ;
    base1 := regnow.header;
      For count1 := 1 to hell Do
        Begin
          base1 := base1^.next;
        End;

      base2 := base1^.next;
      base3 := base2^.next;
    cdn1 := base1^.seqb + base2^.seqb + base3^.seqb;

    If (cdn1 <> 'TAA') and (cdn1 <> 'TGA') and (cdn1 <> 'TAG') Then
       errorrep('Region does not have a stop codon',indbase,seqname);
  End;  {CheckStop}

{****************************************************************************}
{*  This algorithm processes the input database by using sub procedures.    *}
{****************************************************************************}
Procedure ProcessIt;
  Begin {ProcessIt}
    WriteLn;
    ReadLn(indbname,temporary);   {Find first delimiter}
    While (TEMPORARY <> '\\') AND NOT(Eof(indbname)) Do
      Begin
        error := False;
        ReadLn(indbname,temporary);    {Look for number in file}
        ReadLn(indbname,temporary);    {Look for sequence}
        WriteLn(temporary);
        seqname := COPY(temporary,14,10);
        If vnum > 0 Then
          search(seqname,valid1,vnum);
        ReadLn(indbname,temporary);    {Look for definition}
        WriteLn(temporary);
        If not(error) Then
          Begin
            ReadLn(indbname,temporary);    {Look for number of regions}
            Val(temporary,numreg,spare);
            WriteLn('number of regions is ',numreg);
            ct1 := 0;
            ct2 := 0;
            ct3 := 0;
            Repeat
              ct1 := ct1 + 1;
B ----------- RegionIn;
              If not(noend) and not(error) Then  {Check for stop codons at end}
                Begin
                  CheckStop
                End;
              If not(error) then CountIt;   {don't count if no stop codon, etc}
E ----------- Until (ct1 = numreg) OR (error); {Examine regions}
          End;
        Fastfwd;
        If Not(error) Then
          Begin
            numtreg := numtreg + numreg;
            numprc  := numprc + 1;
            vnum    := vnum + 1;
            valid1[vnum] := seqname
          End;
      End;
  End; {ProcessIt}

{****************************************************************************}
{*  This algorithm displays the information found in the program.           *}
{****************************************************************************}
Procedure DisplayInfo;
  VAR nc, np :Real;
      i,i1     :Integer;
  Begin  {Display Info}
    nc := 0;
    np := 0;
    For i := 1 to 64 Do
      Begin
```

```
        nc := nc + table1[i];
        For i1 := 1 to 64 Do
          np := np + table2[i,i1]
      End;
    Clrscr;
    WriteLn;
    WriteLn('Data is as follows:');
    WriteLn('   Number of codons   : ',numcdns:10:0);
    WriteLn('   Number of pairs    : ',numprs:10:0);
    WriteLn('   Number of regions  : ',numtreg:10:0);
    WriteLn('   Number of sequences: ',numprc:10:0);
    WriteLn;
    Writeln('   Number of cdns from table: ',nc:10:0);
    Writeln('   Number of cdn prs from table: ',np:10:0);
    WriteLn;
    WriteLn(' And now for the table...');
    pause;
    WriteLn('Codon Usage:');
    WriteLn;
    Delay(500);
    For ct1 := 1 to 64 Do
      WriteLn('Number of ',codon[ct1],' is ',table1[ct1]:3:0);
  End; {Display Info}
{**************************************************************************}
{* This algorithm switches a pair of records around                      *}
{**************************************************************************}
Procedure Switch(VAR a,b:Name1);
  VAR temp:Name1;
  Begin { Switch }
    temp := a;
    a    := b;
    b    := temp;
  End;  { Switch }
{**************************************************************************}
{* This algorithm performs a bubble sort by comparing all elements and   *}
{* switching at the appropriate times.  It is efficient for small array sizes*}
{* and is typically used in conjunction with a quicksort algorithm.  This *}
{* particular routine was taken from Introduction to Pascal by Rodney Zaks. *}
{**************************************************************************}
Procedure BSORT(start,top:INTEGER; VAR valid1:Recsorts);
  Var index     :Integer;
      switched  :Boolean;
  Begin  {Bubble Sort}
      Repeat
        switched := False;
        For index := start to (top-1) Do
          Begin
            If valid1[index] > valid1[index+1] Then
              Begin
                switch(valid1[index],valid1[index+1]);
                switched := True
              End
          End;
      Until NOT(switched);
  End;  {Bubble Sort}

{**************************************************************************}
{* This algorithm finds a good median value in array and places it at the  *}
{* beginning in accordance with the principles of the quick sort technique. *}
{*This particular routine was taken from Introduction to Pascal by Rodney Zaks.  *}
{**************************************************************************}
Procedure FindMedian(start,top:Integer; Var valid1:Recsorts);
  Var middle   : Integer;
      sorted   : Recsorts;
  Begin {Find Median}
    middle    := (start + top) div 2;
    sorted[1] := valid1[start];
    sorted[2] := valid1[top];
    sorted[3] := valid1[middle];
    bsort(1,3,sorted);
    If sorted[2] = valid1[middle] Then
      switch (valid1[start],valid1[middle])
    Else
  -   If sorted[2] = valid1[top] Then
        switch (valid1[start],valid1[top]);
  End;  {Find Median}

{**************************************************************************}
{* This algorithm performs a quick sort on a given array.  It works by first *}
{* splitting the range of values into two sets, one set greater than a    *}
{* a previously determined median value and the other set less than the value*}
{* . The algorithm then sorts each section separately and combines them into *}
{* one set subsequently.  In practice, the idea is DIVIDE AND CONQUER.  By  *}
{* dividing range of values into smaller subranges and then using a bubble  *}
{* sort, the greatest efficiency is achieved.  This particular implementation*}
{* of the concept comes from Introduction to Pascal by Rodney Zaks.  It has  *}
{* been modified in this program for using arrays of records.             *}
{**************************************************************************}
Procedure SortSection(start,top : Integer);
  Var swapup : Boolean;
      S,E,M  : Integer;
  Begin  {Sortsection}
    If top - start < 6 Then  { Sort small section with the bubble sort }
      Bsort ( start, top, valid1 )
    Else
      Begin
        findmedian (start,top,valid1);
        swapup := True;
        { Start Scanning from array top }
        s := start; { Lower Comparison Limit }
        e := top;   { Upper Comparison Limit }
        m := start; { Location of comparison value }
        While e > s Do
          Begin
            If swapup Then
              { Scan downward from partition top    }
              { and exchange if smaller than median }
              Begin
                While (valid1[e] >= valid1[m]) and (e>m) Do
                  e := e - 1;
                If e > m Then
                  Begin
                    switch (valid1[e],valid1[m]);
                    m := e
                  End;
```

```
            swapup := False
          End
        Else
          { Scan upward from partition start    }
          { and exchange if larger than median  }
          Begin
            While (valid1[s] <= valid1[m]) and (s < m) Do
              s := s + 1;
            If s < m Then
              Begin
                Switch(valid1[s],valid1[m]);
                m := s
              End;
            Swapup := True
          End
      End;
    Sortsection(start,m-1); { Sort Lower half of partition }
    Sortsection(m+1,top);   { Sort Upper half of partition }
  End
End; { Sortsection }

{***********************************************************************}
{* This algorithm alphabetically sorts a list of names given as records *}
{***********************************************************************}
Procedure AlphaSort;
  Begin
    Sortsection(1,vnum);
    Assign(valid,validname);
    Storeit1(valid1,vnum,valid);
  End;

{*********************************************************************}
{*  This algorithm closes all files and prepares for the end of run. *}
{*********************************************************************}
Procedure EndRun;
  Begin (End Run)
    Write(outtab1,table1);
    Write(outtab2,table2);
    Write(outtab3,Etable2);
    Assign(numberi,numbers);
    Rewrite(numberi);
    WriteLn(numberi,numcdns:10:0);
    WriteLn(numberi,numprs:10:0);
    WriteLn(numberi,numtreg:10:0);
    WriteLn(numberi,numprc:10:0);
    Close(outtab1);
    Close(outtab2);
    Close(outtab3);
    Close(numberi);
    Close(errorlog);
    Close(indbname);
  End; (End Run)
{*********************************************************************}
{*  This algorithm raises a number to a power.                       *}
{*********************************************************************}
Function PwrUp(num,pwr:Real):Real;
  Begin (PwrUp)
    pwrup := Exp(pwr * (Ln(num)));
  End;  (PwrUp)

{*********************************************************************}
{*  This algorithm writes a comma to the reflex file.                *}
{*********************************************************************}
Procedure C;
  Begin (c)
    Write(reflex,' ');
  End;  (c)


{*********************************************************************}
{*  This algorithm converts all of the data to a reflex standard and also *}
{*  finds certain statistical data as given by a formula.            *}
{*********************************************************************}
Procedure Conversion;
  VAR response  : Name1;
           cnt,
          cnt1,
             x,
             y  : Integer;
           Chi,
        Chinew,
        newexp,
        sumexp,
        sumobs  : Real;
  Begin  (Conversion)
    (response := 'Y';
    Repeat
      WriteLn;
      WriteLn;
      Write('          ' Would you like me to display the pairs while processing? (Y/N)');
      ReadLn(response);
      ChangeCase(response);
    Until response[1] in ['Y','N'];)
    Assign(reflex,reflx1);
    Rewrite(reflex);
    WriteLn;
    WriteLn('                         >>    Now processing pairs   <<');
    WriteLn;
    For cnt := 1 to 20 Do
      Begin
        For cnt1 := 1 to 23 Do
          Begin
            sumobs := 0;
            sumexp := 0;
            For x := AA[cnt].Start to AA[cnt].Stop Do
              For y := AA[cnt1].Start to AA[cnt1].Stop Do
                Begin
                  sumobs := sumobs + table2[x,y];
                  sumexp := sumexp + Etable2[x,y];
                End;
            For x := AA[cnt].Start to AA[cnt].Stop Do
              For y := AA[cnt1].Start to AA[cnt1].Stop Do
                Begin
```

```
                    numexp := Etable2[x,y];
                    numobs := table2[x,y];
                    If sumexp <> 0 Then
F -------------      newexp := (etable2[x,y]/(sumexp))*(sumobs)
                    Else
                      newexp := 0;
                    If numexp <> 0 Then
G.1 -----------      Chi := ((Sqr(numobs - numexp))/numexp)  {Chi-square}
                    Else
                      Chi := 0;
                    If newexp <> 0 Then
G.2 -----------      Chinew := ((Sqr(numobs - newexp))/newexp)  {Chi-square new}
                    Else
                      Chinew := 0;
                    Write(reflex,cdn[x]);
                    C;
                    Write(reflex,cdn[y]);
                    C;
                    Write(reflex,codon[x]);
H ------            C;
                    Write(reflex,codon[y]);
                    C;
                    Write(reflex,numexp:6:2);
                    C;
                    Write(reflex,numobs:4:0);
                    C;
                    Write(reflex,Chi:8:4);
                    C;
                    WriteLn(reflex,Chinew:8:4)
                  End;
              End;
          End;
        Close(reflex)
      End; {Conversion}

{****************************************************************************}
{*  This algorithm initializes data and opens files respectively.           *}
{****************************************************************************}
Procedure Init1;
  Begin {Init1}
    CreateTable;
    error   := False;
    numcdns := 0;
    numprs  := 0;
    numtreg := 0;
    numprc  := 0;
    noend   := False;
    ref1 := 'N';
    Repeat
      CLRSCR;
          GotoXY(1,12);
          Write('Would you like to only generate a Reflex File? (Y/N) ');
          ReadLn(ref1);
          ChangeCase(ref1);
        Until (ref1[1] in ['Y','N']);
        If ref1 = 'N' Then
          Begin
            indbase := GETFILENAMES(0);
            ASSIGN(indbname,indbase);
            ReSet(indbname);
          End;
        outtable1 := GETFILENAMES(1);
        ASSIGN(errorlog,'run.log');
        runlog1 := Exist('run.log');
        IF runlog1 THEN
          copyrunlog
        Else
          ReWrite(errorlog);
        WriteLn(errorlog);
        WriteLn(errorlog,'Currently running FREQMOD2special');
        WriteLn(errorlog);
        If ref1 = 'N' THEN
          WriteLn(errorlog,'Input database file is ',indbase);
        WriteLn(errorlog,'Output data has the root: ',outtable1);
        WriteLn(errorlog);

    End;  {Init1}

    {****************************************************************************}
    {*               M  A  I  N     P  R  O  G  R  A  M                          *}
    {****************************************************************************}
    Begin { M A I N  P R O G R A M }
A ------ Init1;
      CLRSCR;
      GotoXY(5,10);
      Write('             Please Standby, Module Two Now Processing...');
      WriteLn;
      SoftAlarm;
      If ref1 = 'N' Then
        Begin
          ProcessIt;
          Alphasort;
          EndRun
        End;
      DisplayInfo;
      WriteLn;
      If ref1 = 'N' Then
        Repeat
          CLRSCR;
          GotoXY(1,12);
          Write('Would you like to generate a Reflex file? (Y/N)');
          ReadLn(ref1);
          ChangeCase(ref1);
        Until (ref1[1] in ['Y','N']);
      If ref1 = 'Y' Then
        Begin
          ClrScr;
          GotoXY(1,12);
          Write('                Standby, Now converting to REFLEX standard');
          Conversion;
        End;
```

```
      WriteLn;
      WriteLn('                    ...Done Processing...End of Run');
      WriteLn;
      WriteLn('                         Wake up, I''m done');
      WriteLn;
      Write('                         Press Any Key to Quit!');
      Repeat
        SoftAlarm;
      Until KeyPressed;
   End. {Main Program : FreqMod2}
```

```
ECOACE
186,896
1109,3769
3784,5676
6001,7425
\\
ECOADA
102,1166
\\
ECOALAS
1,2631
\\
```

```
;LOCUS       ECOACE       7740 bp    DNA             updated   01/07/85
;DEFINITION  E.coli aceE  acdF  lpd and    :nes (ace operon) coding for pyruva
```

```
GTCTACATTTGTGCATAGTTACAACTTTGAAACGTTATATATGTCAAGTTGTTAAAATGT
GCACAGTTTCATGATTTCAATCAAAACCTGTATGGACATAAGGTGAATACTTGTTACTTT
AGCGGTCACAGACATGAAATTGGTAAGACCAATTGACTTCGGCAAGTGGCTTAAGACAGG
AACTCATGGCCTACAGCAAAATCCGCCAACCAAAACTCTCCGATGTGATTGAGCAGCAAC
TGGAGTTTTTGATCCTCGAAGGCACTCTCCGCCCGGGCGAAAAACTCCCACCGGAACGCG
AACTGGCAAAACAGTTTGACGTCTCCCGTCCCTCCTTGCGTGAGGCGATTCAACGTCTCG
AAGCGAAGGGCTTGTTGCTTCGTCGCCAGGGTGGCGGCACTTTTGTCCAGAGCAGCCTAT
GGCAAAGCTTCAGCGATCCGCTGGTGGAGCTGCTCTCCGACCATCCTGAGTCACAGTATG
ACTTGCTCGAAACACGACACGCCCTGGAAGGTATCGCCGCTTATTACGCCGCGCTGCGTA
GTACCGATGAAGACAAGGAACGCATCCGTGAACTCCACCACGCCATAGAGCTGGCGCAGC
AGTCTGGCGATCTGGACGCGGAATCAAACGCCGTACTCCAGTATCAGATTGCCGTCACCG
AAGCGGCCCACAATGTGGTTCTGCTTCATCTGCTAAGGTGTATGGAGCCGATGTTGGCCC
AGAATGTCCGCCAGAACTTCGAATTGCTCTATTCGCGTCGCGAGATGCTGCCGCTGGTGA
GTAGTCACCGCACCCGCATATTTGAAGCGATTATGGCCGGTAAGCCGGAAGAAGCGCGCG
AAGCATCGCATCGCCATCTGGCCTTTATCGAAGATTTTGCTCGACAGAAGTCGTGAAGAG
AGCCGCCGTGAGCGTTCTCTGCGTCGTCTGGAGCAACGAAAGAATTAGTGATTTTTCTGG
TAAAAATTATCCAGAAGATGTTGTAAATCAAGCGCATATAAAAGCGCGGCAACTAAACGT
AGAACCTGTCTTATTGAGCTTTCCGGCGAGAGTTCAATGGGACAGGTTCCAGAAAACTCA
ACGTTATTAGATAGATAAGGAATAACCCATGTCAGAACGTTTCCCAAATGACGTGGATCC
GATCGAAACTCGCGACTGGCTCCAGGCGATCGAATCGGTCATCCGTGAAGAAGGTGTTGA
GCGTGCTCAGTATCTGATCGACCAACTGCTTGCTGAAGCCCGCAAAGGCGGTGTAAACGT
AGCCGCAGGCACAGGTATCAGCAACTACATCAACACCATCCCCGTTGAAGAACAACCGGA
GTATCCGGGTAATCTGGAACTGGAACGCCGTATTCGTTCAGCTATCCGCTGGAACGCCAT
CATGACGGTGCTGCGTGCGTCGAAAAAAGACCTCGAACTGGGCGGCCATATGGCGTCCTT
CCAGTCTTCCGCAACCATTTATGATGTGTGCTTTAACCACTTCTTCCGTGCACGCAACGA
GCAGGATGGCGGCGACCTGGTTTACTTCCAGGGCCACATCTCCCGGGGCGTGTACGCTCG
TGCTTTCCTGGAAGGTCGTCTGACTCAGGAGCAGCTGGATAACTTCCGTCAGGAAGTTCA
CGGCAATGGCCTCTCTTCCTATCCGCACCCGAAACTGATGCCGGAATTCTGGCAGTTCCC
GACCGTATCTATGGGTCTGGGTCCGATTGGTGCTATTTACCAGGCTAAATTCCTGAAATA
TCTGGAACACCGTGGCCTGAAAGATACCTCTAAACAAACCGTTTACGCGTTCCTCGGTGA
CGGTGAAATGGACGAACCGGAATCCAAAGGTGCGATCACCATCGCTACCCGTGAAAAACT
GGATAACCTGGTCTTCGTTATCAACTGTAACCTGCAGCGTCTTGACGGCCCGGTCACCGG
TAACGGCAAGATCAACGAACTGGAAGGCATCTTCGAAGGTGCTGGCTGGAACGTGATCAA
AGTGATGTGGGGTAGCCGTTGGGATGAACTGCTGCGTAAGGATACCAGCGGTAAACTGAT
CCAGCTGATGAACGAAACCGTTGACGGCGACTACCAGACCTTCAAATCGAAAGATGGTGC
GTACGTTCGTGAACACTTCTTCGGTAAATATCCTGAAACCGCAGCACTGGTTGCAGACTG
GACTGACGAGCAGATCTGGGCACTGAACCGTGGTGGTCACGATCCGAAGAAAATCTACGC
TGCATTCAAGAAAGCGCAGGAAACCAAAGGCAAAGCGACAGTAATCCTTGCTCATACCAT
TAAAGGTTACGGCATGGGCGACGCGGCTGAAGGTAAAAACATCGCGCACCAGGTTAAGAA
AATGAACATGGACGGTGTGCGTCATATCCGCGACCGTTTCAATGTGCCGGTGTCTGATGC
AGATATCGAAAAACTGCCGTACATCACCTTCCCGGAAGGTTCTGAAGAGCATACCTATCT
GCACGCTCAGCGTCAGAAACTGCACGGTTATCTGCCAAGCCGTCAGCCGAACTTCACCGA
GAAGCTTGAGCTGCCGAGCCTGCAAGACTTCGGCGCGCTGTTGGAAGAGCAGAGCAAAGA
GATCTCTACCACTATCGCTTTCGTTCGTGCTCTGAACGTGATGCTGAAGAACAAGTCGAT
CAAAGATCGTCTGGTACCGATCATCGCCGACGAAGCGCGTACTTTCGGTATGGAAGGTCT
GTTCCGTCAGATTGGTATTTACAGCCCGAACGGTCAGCAGTACACCCCGCAGGACCGCGA
GCAGGTTGCTTACTATAAAGAAGACGAGAAAGGTCAGATTCTGCAGGAAGGGATCAACGA
GCTGGGCGCAGGTTGTTCCTGGCTGGCAGCGGCGACCTCTTACAGCACCAACAATCTGCC
GATGATCCCGTTCTACATCTATTACTCGATGTTCGGCTTCCAGCGTATTGGCGATCTGTG
CTGGGCGGCTGGCGACCAGCAAGCGCGTGGCTTCCTGATCGGCGGTACTTCCGGTCGTAC
CACCCTGAACGGCGAAGGTCTGCAGCACGAAGATGGTCACAGCCACATTCAGTCGCTGAC
TATCCCGAACTGTATCTCTTACGACCCGGCTTACGCTTACGAAGTTGCTGTCATCATGCA
TGACGGTCTGGAGCGTATGTACGGTGAAAAACAAGAGAACGTTTACTACTACATCACTAC
GCTGAACGAAAACTACCACATGCCGGCAATGCCGGAAGGTGCTGAGGAAGGTATCCGTAA
AGGTATCTACAAACTCGAAACTATTGAAGGTAGCAAAGGTAAAGTTCAGCTGCTCGGCTC
CGGTTCTATCCTGCGTCACGTCCGTGAAGCAGCTGAGATCCTGGCGAAAGATTACGGCGT
AGGTTCTGACGTTTATAGCGTGACCTCCTTCACCGAGCTGGCGCGTGATGGTCAGGATTG
TGAACGCTGGAACATGCTGCACCCGCTGGAAACTCCGCGCGTTCCGTATATCGCTCAGGT
GATGAACGACGCTCCGGCAGTGGCATCTACCGACTATATGAAACTGTTCGCTGAGCAGGT
CCGTACTTACGTACCGGCTGACGACTACCGCGTACTGGGTACTGATGGCTTCGGTCGTTC
CGACAGCCGTGAGAACCTGCGTCACCACTTCGAAGTTGATGCTTCTTATGTCGTGGTTGC
GGCGCTGGGCGAACTGGCTAAACGTGGCGAAATCGATAAGAAAGTGGTTGCTGACGCAAT
CGCCAAATTCAACATCGATGCAGATAAAGTTAACCCGCGTCTGGCGTAAGAGGTAAAAGA
ATAATGGCTATCGAAATCAAAGTACCGGACATCGGGGCTGATGAAGTTGAAATCACCGAG
ATCCTGGTCAAAGTGGGCGACAAAGTTGAAGCCGAACAGTCGCTGATCACCGTAGAAGGC
GACAAAGCCTCTATGGAAGTTCCGTCTCCGCAGGCGGGTATCGTTAAAGAGATCAAAGTC
TCTGTTGGCGATAAAACCCAGACCGGCGCACTGATTATGATTTTCGATTCCGCCGACGGT
GCAGCAGACGCTGCACCTGCTCAGGCAGAAGAGAAGAAAGAAGCAGCTCCGGCAGCAGCA
CCAGCGGCTGCGGCGGCAAAAGACGTTAACGTTCCGGATATCGGCAGCGACGAAGTTGAA
GTGACCGAAATCCTGGTGAAAGTTGGCGATAAAGTTGAAGCTGAACAGTCGCTGATCACC
GTAGAAGGCGACAAGGCTTCTATGGAAGTTCCGGCTCCGTTTGCTGGCACCGTGAAAGAG
ATCAAAGTGAACGTGGGTGACAAAGTGTCTACCGGCTCGCTGATTATGGTCTTCGAAGTC
GCGGGTGAAGCAGGCGCGGCAGCTCCGGCCGCTAAACAGGAAGCAGCTCCGGCAGCGGCC
CCTGCACCAGCGGCTGGCGTGAAAGAAGTTAACGTTCCGGATATCGGCGGTGACGAAGTT
GAAGTGACTGAAGTGATGGTGAAAGTGGGCGACAAAGTTGCCGCTGAACAGTCACTGATC
ACCGTAGAAGGCGACAAAGCTTCTATGGAAGTTCCGGCGCCGTTTGCAGGCGTCGTGAAG
GAACTGAAAGTCAACGTTGGCGATAAAGTGAAAACTGGCTCGCTGATTATGATCTTCGAA
GTTGAAGGCGCAGCGCCTGCGGCAGCTCCTGCGAAACAGGAAGCGGCAGCGCCGGCACCG
GCAGCAAAAGCTGAAGCCCCGGCAGCAGCACCAGCTGCGAAAGCGGAAGGCAAATCTGAA
TTTGCTGAAAACGACGCTTATGTTCACGCGACTCCGCTGATCCGCCGTCTGGCACGCGAG
TTTGGTGTTAACCTTGCGAAAGTGAAGGGCACTGGCCGTAAAGGTCGTATCCTGCGCGAA
GACGTTCAGGCTTACGTGAAAGAAGCTATCAAACGTGCAGAAGCAGCTCCGGCAGCGACT
GGCGGTGGTATCCCTGGCATGCTGCCGTGGCCGAAGGTGGACTTCAGCAAGTTTGGTGAA
ATCGAAGAAGTGGAACTGGGCCGCATCCAGAAAATCTCTGGTGCGAACCTGAGCCGTAAC
```

TGGGTAATGATCCCGCATGTTACTCACTTCGACAAAACCGATATCACCGAGTTGGAAGCG
TTCCGTAAACAGCAGAACGAAGAAGCGGCGAAACGTAAGCTGGATGTGAAGATCACCCCG
GTTGTCTTCATCATGAAAGCCGTTGCTGCAGCTCTTGAGCAGATGCCTCGCTTCAATAGT
TCGCTGTCGGAAGACGGTCAGCGTCTGACCCTGAAGAAATACATCAACATCGGTGTGGCG
GTGGATACCCCGAACGGTCTGGTTGTTCCGGTATTCAAAGACGTCAACAAGAAAGGCATC
ATCGAGCTGTCTCGCGAGCTGATGACTATTTCTAAGAAAGCGCGTGACGGTAAGCTGACT
GCGGGCGAAATGCAGGGCGGTTGCTTCACCATCTCCAGCATCGGCGGCCTGGGTACTACC
CACTTCGCGCCGATTGTGAACGCGCCGGAAGTGGCTAT[illegible]GCGTTTCCAAGTCCGCG
ATGGAGCCGGTGTGGAATGGTAAAGAGTTCGTGCCGCGTC[illegible]GCTGCCGATTTCTCTC
TCCTTCGACCACCGCGTGATCGACGGTGCTGATGGTGCCC[illegible]TCATTACCATCATTAAC
AACACGCTGTCTGACATTCGCCGTCTGGTGATGTAAGTAAAAGAGCCGGCCCAACGGCCG
GCTTTTTTCTGGTAATCTCATGAATGTATTGAGGTTATTAGCGAATAGACAAATCGGTTG
CCGTTTGTTGTTTAAAAATTGTTAACAATTTTGTAAAATACCGACGGATAGAACGACCCG
GTGGTGGTTAGGGTATTACTTCACATACCCTATGGATTTCTGGGTGCAGCAAGGTAGCAA
GCGCCAGAATCCCCAGGAGCTTACATAAGTAAGTGACTGGGGTGAGGGCGTGAAGCTAAC
GCCGCTGCGGCCTGAAAGACGACGGGTATGACCGCCGGAGATAAATATATAGAGGTCATG
ATGAGTACTGAAATCAAAACTCAGGTCGTGGTACTTGGGGCAGGCCCCGCAGGTTACTCC
GCTGCCTTCCGTTGCGCTGATTTAGGTCTGGAAACCGTAATCGTAGAACGTTACAACACC
CTTGGCGGTGTTTGCCTGAACGTCGGCTGTATCCCTTCTAAAGCACTGCTGCACGTAGCA
AAAGTTATCGAAGAAGCCAAAGCGCTGGCTGAACACGGTATCGTCTTCGGCGAACCGAAA
ACCGATATCGACAAGATTCGTACCTGGAAAGAGAAAGTGATCAATCAGCTGACCGGTGGT
CTGGCTGGTATGGCGAAAGGCCGCAAAGTCAAAGTGGTCAACGGTCTGGGTAAATTCACC
GGGGCTAACACCCTGGAAGTTGAAGGTGAGAACGGCAAAACCGTGATCAACTTCGACAAC
GCGATCATTGCAGCGGGTTCTCGCCCGATCCAACTGCCGTTTATTCCGCATGAAGATCCG
CGTATCTGGGACTCCACTGACGCGCTGGAACTGAAAGAAGTACCAGAACGCCTGCTGGTA
ATGGGTGGCGGTATCATCGGTCTGGAAATGGGCACCGTTTACCACGCGCTGGGTTCACAG
ATTGACGTGGTTGAAATGTTCGACCAGGTTATCCCGGCAGCTGACAAAGACATCGTTAAA
GTCTTCACCAAGCGTATCAGCAAGAAATTCAACCTGATGCTGGAAACCAAAGTTACCGCC
GTTGAAGCGAAAGAAGACGGCATTTATGTGACGATGGAAGGCAAAAAAGCACCCGCTGAA
CCGCAGCGTTACGACGCCGTGCTGGTAGCGATTGGTCGTGTGCCGAACGGTAAAAACCTC
GACGCAGGCAAAGCAGGCGTGGAAGTTGACGACCGTGGTTTCATCCGCGTTGACAAACAG
CTGCGTACCAACGTACCGCACATCTTTGCTATCGGCGATATCGTCGGTCAACCGATGCTG
GCACACAAAGGTGTTCACGAAGGTCACGTTGCCGCTGAAGTTATCGCCGGTAAGAAACAC
TACTTCGATCCGAAAGTTATCCCGTCCATCGCCTATACCGAACCAGAAGTTGCATGGGTG
GGTCTGACTGAGAAAGAAGCGAAAGAGAAAGGCATCAGCTATGAAACCGCCACCTTCCCG
TGGGCTGCTTCTGGTCGTGCTATCGCTTCCGACTGCGCAGACGGTATGACCAAGCTGATT
TTCGACAAAGAATCTCACCGTGTGATCGGTGGTGCGATTGTCGGTACTAACGGCGGCGAG
CTGCTGGGTGAAATCGGCCTGGCAATCGAAATGGGTTGTGATGCTGAAGACATCGCACTG
ACCATCCACGCGCACCCGACTCTGCACGAGTCTGTGGGCCTGGCGGCAGAAGTGTTCGAA
GGTAGCATTACCGACCTGCCGAACCCGAAAGCGAAGAAGAAGTAATTTTTCGTTTGCCGG
AACATCCGGCAATTAAAAAAGCGGCTAACCACGCCGCTTTTTTTACGTCTGCAATTTACC
TTTCCAGTCTTCTTGCTCCACGTTCAGAGAGACGTTCGCATACTGCTGACCGTTGCCTCG
TTATTCAGCCTGACAGTATGGTTACTGTCGTTTAGACGTTGTGGGCGGCTCTCCTGAACT
TTCTCCCGAAAAACCTGACGTTGTTCAGGTGATGCCGATTGAACAGCTGGCGGGCGTTAT
CACGTTGCTGTTGATTCAGTGGGCGCTGCTGTACTTTTTCCTTAAACACCTGGCGCTGCT
1
;LOCUS ECOADA 1324 bp ds-DNA entered 02/03/86
;DEFINITION E.coli ada gene coding for Ada protein regulatory protein of AAGCTTCCTTGTCAGCGAAAAAAATTAAAGCGCAAGATTGTTGGTTTTTGCGTGATGGTG
ACCGGGCAGCCTAAAGGCTATCCTTAACCAGGGAGCTGATTATGAAAAAAGCCACATGCT
TAACTGACGATCAACGCTGGCAATCTGTCTTAGCCCGCGACCCGAATGCCGACGGCGAAT
TCGTTTTCGCCGTGCGTACCACAGGCATCTTTTGCCGTCCGTCTTGCCGCGCCAGACATG
CTTTGCGGGAAAACGTCTCCTTCTACGCAAATGCCAGCGAGGCACTCGCCGCTGGCTTTC
GCCCCTGCAAACGTTGTCAGCCAGAAAAAGCCAATGCCCAGCAACATCGGTTGGATAAAA
TCACCCACGCGTGTCGACTGCTGGAACAGGAAACGCCTGTAACGCTGGAAGCCTTAGCCG
ACCAGGTGGCGATGAGTCCATTTCATCTACATCGGTTGTTTAAAGCGACTACCGGAATGA
CGCCTAAAGCCTGGCAACAGCGCTGGCGCGCTCGCCGTTTGCGCGAATCGCTGGCGAAAG
GGGAGAGCGTGACGACGTCTATTCTTAACGCCGGATTCCCCGACAGCAGCAGTTACTATC
GCAAAGCTGACGAAACGCTGGGCATGACGGCTAAACAATTCCGTCACGGTGGCGAAAATC
TGGCGGTGCGTTACGCGCTGGCTGATTGTGAGCTGGGTCGTTGCCTGGTGGCAGAAAGCG
AGCGGGGGATTTGCGCGATATTGCTGGGCGATGATGACGCGACACTAATCAGCGAGTTGC
AGCAGATGTTTCCCGCTGCCGACAACGCGCCTGCCGATCTGATGTTTCAGCAACATGTGC
GTGAAGTGATCGCCAGCCTCAATCAACGCGATACGCCGCTGACGTTACCGCTGGACATTC
GCGGCACTGCTTTTCAGCAACAAGTCTGGCAGGCACTGCGCACGATACCTTGCGGTGAAA
CCGTCAGTTATCAGCAACTGGCTAACGCCATCGGCAAACCGAAAGCGGTACGGGCCGTTG
CCAGCGCCTGTGCCGCCAACAAGCTGGCTATCATAATACCCTGTCATCGGGTGGTCCGTG
GTGATGGCACACTTTCCGGTTACCGCTGGGGCGTGTCGCGTAAAGCGCAACTGCTGCGCC
GCGAAGCTGAAAATGAGGAGAGGTAATGTTGGATCTGTTTGCCGATGCTGAACCGTGGCA
AGAGCCACTGGCGGCTGGTGCGGTAATTTTACGGCGTTTTGCTTTTAACGCTGCGGAGCA
ACTGATCCGCGATATTAATGACGTTGCCAGCCAGTCGCCGTTTCGCCAGATGGTCACCCC
CGGG1
;LOCUS ECOALAS 2767 bp ds-DNA updated 12/16/85
;DEFINITION E.coli alaS gene coding for alanyl-tRNA synthetase.

AGCAAGAGCACCGCTGAGATCCGTCAGGCGTTTCTCGACTTTTTCCATAGTAAGGGACAT
CAGGTAGTTGCCAGCAGCTCCAGGTACCCCATAACCGACCCAACTTTGTTGTTTACCAAC
GCCGGGATGAACCAGTTCAAGGATGTGTTCCTTGGGCTCGACAAGCGTAATTATTCCCGC
GCTACCACTTCCCAACGCTGCGTGCGTGCGGGTGGTAAACACAACGACCTGGAAAACGTC
GGTTACACCGCGCGTCACCATACCTTCTTCGAAATGCTGGGCAACTTCAGCTTCGGCGAC
TATTTCAAACACGATGCCATTCAGTTTGCATGGGAACTGCTGACCAGCGAAAAATGGTTT
GCCCTGCCGAAAGAGCGTCTGTGGGTTACCGTCTATGAAAGCGACGACGAAGCCTACGAA
ATCTGGGAAAAAGAAGTAGGGATCCCGCGCGAACGTATTATTCGCATCAACGATAACAAG
GGTGCGCCATACGCATCTGGCAACTTCTGGCGGATGGGTGGCACTGGTCCGTGCGACCCG
TGCACCGAAATCTTCTACGATCACGGCGACCACATTTGGGGGGGCCCTCCGGGAAGCCCG
GAAGAAGACGGCGACCGCTACATTGAGATCTGGAACATCGTCTTCATGCAGTTCAACCGC
CAGGCCGATGGCACGATGGAACCGCTGCCGAAGCCGTCTGTAGATACCGGTATGGGTCTG
GAGCGTATTGCTGCGGTGCTGCAACACGTTAACTCTAACTATGACATCGACCTGTTCCGC
ACGCTGATCCAGGCGGTAGCGAAAGTCACTGGCGCAACCGATCTGAGCAATAAATCGCTG
CGCGTAATCGCTGACCACATTCGTTCTTGTGCGTTCCTGATCGCGGATGGCGTAATGCCG
TCCAATGAAAACCGTGGTTATGTACTGCGTCGTATCATTCGTCGCGCAGTGCGTCACGGT
AATATGCTCGGCGCGAAAGAAACCTTCTTCTACAAACTGGTTGGTCCGCTGATCGACGTT
ATGGGCTCTGCGGGTGAAGACCTGAAACGCCAGCAGGCGCAGGTTGAGCAGGTGCTGAAG
ACTGAAGAAGAGCAGTTTGCTCGTACTCTGGAGCGCGGTCTGGCGTTGCTGGATGAAGAG
CTGGCAAAACTTTCTGGTGATACGCTGGATGGTGAAACTGCTTTCCGTCTGTACGACACC
TATGGCTTCCCGGTTGACCTGACGGCTGATGTTTGTCGTGAGCGCAACATCAAAGTTGAC
GAAGCTGGTTTTGAAGCTGCAATGGAAGAGCAGCGTCGTCGCGCGCGCGAAGCCAGCGGC
TTTGGTGCCGATTACAACGCAATGATCCGTGTTGACAGTGCATCTGAATTTAAAGGCTAT
GACCATCTGGAACTGAACGGCAAAGTGACTGCGCTGTTTGTTGATGGTAAAGCGGTTGAT
GCCATCAATGCAGGCCAGGAAGCTGTGGTCGTGCTGGATCAAACGCCATTCTATGCGGAA
TCCGGCGGTCAGGTTGGCGATAAAGGCGAACTGAAAGGCGCTAACTTCTCCTTTGCGGTG
GAAGATACGCAGAAATACGGCCAGGCGATTGGTCACATCG[illegible]ACTTGCTGCGGGTTCT
CTGAAAGTGGGCGACGCGGTGCAGGCTGATGTTGATGAGG[illegible]TCGCGCCCGTATTCGT
CTGAATCACTCCGCAACGCACCTGATGCACGCTGCGCTGCG[illegible]AGGTTCTGGGTACTCAT
GTATCGCATAAAGGTTCACTGGTTAACGACAAGGTGCTGCGCTTCGACTTCTCACACAAC
GAAGCGATGAAACCAGAAGAGATTCGTGCGGTCGAAGACCTGGTGAACACACTGATTCGT
CGCAATTTGCCGATCGAAACCAACATCATGGATCTCGAAGCGGCGAAAGCGAAAGGTGCG
ATGGCGCTGTTCGGCGAGAAGTATGATGAGCGCGTACGCGTGCTGAGCATGGGCGATTTC
TCTACCGAGTTGTGTGGCGGTACTCACGCCAGCCGCACTGGTGATATTGGTCTGTTCCGC
ATCATCTCTGAATCGGGTACTGCTGCAGGCGTTCGTCGTATCGAAGCGGTAACCGGAGAA
GGTGCTATCGCCACCGTTCATGCAGACAGCGATCGCTTAAGCGAAGTCGCGCATCTGCTG AAAGGCGATAGCAATAATCTGGCTGATAAAGTGCGCTCAGTACTGGAACGTACGCGTCAG
CTGGAAAAAGAGTTACAACAGCTTAAAGAACAAGCTGCCGCACAGGAGAGCGCAAATCTT
TCCAGTAAGGCAATTGATGTTAATGGTGTTAAGCTGTTGGTTAGCGAGCTTAGCGGTGTT
GAGCCGAAAAATGTTGCGTACCATGGTTGACGATTTAAAAAATCAGCTGGGGTCGACAATT
ATCGTGCTGGCAACGGTAGTCGAAGGTAAGGTTTCTCTGATTGCAGGCGTATCTAAGGAC
GTCACAGATCGTGTGAAAGCAGGGGAACTGATTGGTATGGTCGCTCAGCAGGTGGGCGGC
AAGGGTGGTGGACGTCCTGACATGGCGCAAGCCGGTGGTACGGATGCTGCGGCCTTACCT
GCAGCGTTAGCCAGTGTGAAAGGCTGGGTCAGCGCGAAATTGCAATAATATAAGCGTCAG
GCAACGCCGTGGACTCGCTTCACGGCATTCGCATTAACGCTATCGACAACGATAAAGTCA
GGTTGAAGTTGTGTATATCGCGTAAACTTAGGTTTAACAGAATGTAATGCCATGACTGCT
TAGATGT1

\
1
;LOCUS ECOACE 7740 bp DNA updated 01/07/85
;DEFINITION E.coli aceE acdF lpd and A genes (ace operon) coding for pyruva
4
186,896
ATGGCCTACAGCAAAATCCGCCAACCAAAACTCTCCGATGTGATTGAGCAGCAACTGGAGTTTTTGATCCTCGAAGGCACTCTCCGCCCGGGCGAAAAACTCCCACCGGAACGCGAACTGGCA
AAACAGTTTGACGTCTCCCGTCCCTCCTTGCGTGAGGCGATTCAACGTCTCGAAGCGAAGGGCTTGTTGCTTCGTCGCCAGGGTGGCGGCACTTTTGTCCAGAGCAGCCTATGGCAAAGCTTC
AGCGATCCGCTGGTGGAGCTGCTCTCCGACCATCCTGAGTCACAGTATGACTTGCTCGAAACACGACACGCCCTGGAAGGTATCGCCGCTTATTACGCCGCGCTGCGTAGTACCGATGAAGAC
AAGGAACGCATCCGTGAACTCCACCACGCCATAGAGCTGGCGCAGCAGTCTGGCGATCTGGACGCGGAATCAAACGCCGTACTCCAGTATCAGATTGCCGTCACCGAAGCGGCCCACAATGTG
GTTCTGCTTCATCTGCTAAGGTGTATGGAGCCGATGTTGGCCCAGAATGTCCGCCAGAACTTCGAATTGCTCTATTCGCGTCGCGAGATGCTGCCGCTGGTGAGTAGTCACCGCACCCGCATA
TTTGAAGCGATTATGGCCGGTAAGCCGGAAGAAGCGCGCGAAGCATCGCATCGCCATCTGGCCTTTATCGAAGATTTTGCTCGACAGAAGTCGTGA1
1109,3769
ATGTCAGAACGTTTCCCAAATGACGTGGATCCGATCGAAACTCGCGACTGGCTCCAGGCGATCGAATCGGTCATCCGTGAAGAAGGTGTTGAGCGTGCTCAGTATCTGATCGACCAACTGCTT
GCTGAAGCCCGCAAAGGCGGTGTAAACGTAGCCGCAGGCACAGGTATCAGCAACTACATCAACACCATCCCCGTTGAAGAACAACCGGAGTATCCGGGTAATCTGGAACTGGAACGCCGTATT
CGTTCAGCTATCCGCTGGAACGCCATCATGACGGTGCTGCGTGCGTCGAAAAAAGACCTCGAACTGGGCGGCCATATGGCGTCCTTCCAGTCTTCCGCAACCATTTATGATGTGTGCTTTAAC
CACTTCTTCCGTGCACGCAACGAGCAGGATGGCGGCGACCTGGTTTACTTCCAGGGCCACATCTCCCGGGGCGTGTACGCTCGTGCTTTCCTGGAAGGTCGTCTGACTCAGGAGCAGCTGGAT
AACTTCCGTCAGGAAGTTCACGGCAATGGCCTCTCTTCCTATCCGCACCCGAAACTGATGCCGGAATTCTGGCAGTTCCCGACCGTATCTATGGGTCTGGGTCCGATTGGTGCTATTTACCAG
GCTAAATTCCTGAAATATCTGGAACACCGTGGCCTGAAAGATACCTCTAAACAAACCGTTTACGCGTTCCTCGGTGACGGTGAAATGGACGAACCGGAATCCAAAGGTGCGATCACCATCGCT
ACCCGTGAAAAACTGGATAACCTGGTCTTCGTTATCAACTGTAACCTGCAGCGTCTTGACGGCCCGGTCACCGGTAACGGCAAGATCAACGAACTGGAAGGCATCTTCGAAGGTGCTGGCTGG
AACGTGATCAAAGTGATGTGGGGTAGCCGTTGGGATGAACTGCTGCGTAAGGATACCAGCGGTAAACTGATCCAGCTGATGAACGAAACCGTTGACGGCGACTACCAGACCTTCAAATCGAAA
GATGGTGCGTACGTTCGTGAACACTTCTTCGGTAAATATCCTGAAACCGCAGCACTGGTTGCAGACTGGACTGACGAGCAGATCTGGGCACTGAACCGTGGTGGTCACGATCCGAAGAAAATC
TACGCTGCATTCAAGAAAGCGCAGGAAACCAAAGGCAAAGCGACAGTAATCCTTGCTCATACCATTAAAGGTTACGGCATGGGCGACGCGGCTGAAGGTAAAAACATCGCGCACCAGGTTAAG
AAAATGAACATGGACGGTGTGCGTCATATCCGCGACCGTTTCAATGTGCCGGTGTCTGATGCAGATATCGAAAAACTGCCGTACATCACCTTCCCGGAAGGTTCTGAAGAGCATACCTATCTG
CACGCTCAGCGTCAGAAACTGCACGGTTATCTGCCAAGCCGTCAGCCGAACTTCACCGAGAAGCTTGAGCTGCCGAGCCTGCAAGACTTCGGCGCGCTGTTGGAAGAGCAGAGCAAAGAGATC
TCTACCACTATCGCTTTCGTTCGTGCTCTGAACGTGATGCTGAAGAACAAGTCGATCAAAGATCGTCTGGTACCGATCATCGCCGACGAAGCGCGTACTTTCGGTATGGAAGGTCTGTTCCGT
CAGATTGGTATTTACAGCCCGAACGGTCAGCAGTACACCCCGCAGGACCGCGAGCAGGTTGCTTACTATAAAGAAGACGAGAAAGGTCAGATTCTGCAGGAAGGGATCAACGAGCTGGGCGCA
GGTTGTTCCTGGCTGGCAGCGGCGACCTCTTACAGCACCAACAATCTGCCGATGATCCCGTTCTACATCTATTACTCGATGTTCGGCTTCCAGCGTATTGGCGATCTGTGCTGGGCGGCTGGC
GACCAGCAAGCGCGTGGCTTCCTGATCGGCGGTACTTCCGGTCGTACCACCCTGAACGGCGAAGGTCTGCAGCACGAAGATGGTCACAGCCACATTCAGTCGCTGACTATCCCGAACTGTATC
TCTTACGACCCGGCTTACGCTTACGAAGTTGCTGTCATCATGCATGACGGTCTGGAGCGTATGTACGGTGAAAAACAAGAGAACGTTTACTACTACATCACTACGCTGAACGAAAACTACCAC
ATGCCGGCAATGCCGGAAGGTGCTGAGGAAGGTATCCGTAAAGGTATCTACAAACTCGAAACTATTGAAGGTAGCAAAGGTAAAGTTCAGCTGCTCGGCTCCGGTTCTATCCTGCGTCACGTC
CGTGAAGCAGCTGAGATCCTGGCGAAAGATTACGGCGTAGGTTCTGACGTTTATAGCGTGACCTCCTTCACCGAGCTGGCGCGTGATGGTCAGGATTGTGAACGCTGGAACATGCTGCACCCG
CTGGAAACTCCGCGCGTTCCGTATATCGCTCAGGTGATGAACGACGCTCCGGCAGTGGCATCTACCGACTATATGAAACTGTTCGCTGAGCAGGTCCGTACTTACGTACCGGCTGACGACTAC
CGCGTACTGGGTACTGATGGCTTCGGTCGTTCCGACAGCCGTGAGAACCTGCGTCACCACTTCGAAGTTGATGCTTCTTATGTCGTGGTTGCGGCGCTGGGCGAACTGGCTAAACGTGGCGAA
ATCGATAAGAAAGTGGTTGCTGACGCAATCGCCAAATTCAACATCGATGCAGATAAAGTTAACCCGCGTCTGGCGTAA1
3784,5676
ATGGCTATCGAAATCAAAGTACCGGACATCGGGGCTGATGAAGTTGAAATCACCGAGATCCTGGTCAAAGTGGGCGACAAAGTTGAAGCCGAACAGTCGCTGATCACCGTAGAAGGCGACAAA
GCCTCTATGGAAGTTCCGTCTCCGCAGGCGGGTATCGTTAAAGAGATCAAAGTCTCTGTTGGCGATAAAACCCAGACCGGCGCACTGATTATGATTTTCGATTCCGCCGACGGTGCAGCAGAC
GCTGCACCTGCTCAGGCAGAAGAGAAGAAAGAAGCAGCTCCGGCAGCAGCACCAGCGGCTGCGGCGGCAAAAGACGTTAACGTTCCGGATATCGGCAGCGACGAAGTTGAAGTGACCGAAATC
CTGGTGAAAGTTGGCGATAAAGTTGAAGCTGAACAGTCGCTGATCACCGTAGAAGGCGACAAGGCTTCTATGGAAGTTCCGGCTCCGTTTGCTGGCACCGTGAAAGAGATCAAAGTGAACGTG
GGTGACAAAGTGTCTACCGGCTCGCTGATTATGGTCTTCGAAGTCGCGGGTGAAGCAGGCGCGGCAGCTCCGGCCGCTAAACAGGAAGCAGCTCCGGCAGCGGCCCCTGCACCAGCGGCTGGC
GTGAAAGAAGTTAACGTTCCGGATATCGGCGGTGACGAAGTTGAAGTGACTGAAGTGATGGTGAAAGTGGGCGACAAAGTTGCCGCTGAACAGTCACTGATCACCGTAGAAGGCGACAAAGCT
TCTATGGAAGTTCCGGCGCCGTTTGCAGGCGTCGTGAAGGAACTGAAAGTCAACGTTGGCGATAAAGTGAAAACTGGCTCGCTGATTATGATCTTCGAAGTTGAAGGCGCAGCGCCTGCGGCA
GCTCCTGCGAAACAGGAAGCGGCAGCGCCGGCACCGGCAGCAAAAGCTGAAGCCCCGGCAGCAGCACCAGCTGCGAAAGCGGAAGGCAAATCTGAATTTGCTGAAAACGACGCTTATGTTCAC
GCGACTCCGCTGATCCGCCGTCTGGCACGCGAGTTTGGTGTTAACCTTGCGAAAGTGAAGGGCACTGGCCGTAAAGGTCGTATCCTGCGCGAAGACGTTCAGGCTTACGTGAAAGAAGCTATC
AAACGTGCAGAAGCAGCTCCGGCAGCGACTGGCGGTGGTATCCCTGGCATGCTGCCGTGGCCGAAGGTGGACTTCAGCAAGTTTGGTGAAATCGAAGAAGTGGAACTGGGCCGCATCCAGAAA
ATCTCTGGTGCGAACCTGAGCCGTAACTGGGTAATGATCCCGCATGTTACTCACTTCGACAAAACCGATATCACCGAGTTGGAAGCGTTCCGTAAACAGCAGAACGAAGAAGCGGCGAAACGT
AAGCTGGATGTGAAGATCACCCCGGTTGTCTTCATCATGAAAGCCGTTGCTGCAGCTCTTGAGCAGATGCCTCGCTTCAATAGTTCGCTGTCGGAAGACGGTCAGCGTCTGACCCTGAAGAAA
TACATCAACATCGGTGTGGCGGTGGATACCCCGAACGGTCTGGTTGTTCCGGTATTCAAAGACGTCAACAAGAAAGGCATCATCGAGCTGTCTCGCGAGCTGATGACTATTTCTAAGAAAGCG
CGTGACGGTAAGCTGACTGCGGGCGAAATGCAGGGCGGTTGCTTCACCATCTCCAGCATCGGCGGCCTGGGTACTACCCACTTCGCGCCGATTGTGAACGCGCCGGAAGTGGCTATCCTCGGC
GTTTCCAAGTCCGCGATGGAGCCGGTGTGGAATGGTAAAGAGTTCGTGCCGCGTCTGATGCTGCCGATTTCTCTCTCCTTCGACCACCGCGTGATCGACGGTGCTGATGGTGCCCGTTTCATT
ACCATCATTAACAACACGCTGTCTGACATTCGCCGTCTGGTGATGTAA1
6001,7425
ATGAGTACTGAAATCAAAACTCAGGTCGTGGTACTTGGGGCAGGCCCCGCAGGTTACTCCGCTGCCTTCCGTTGCGCTGATTTAGGTCTGGAAACCGTAATCGTAGAACGTTACAACACCCTT
GGCGGTGTTTGCCTGAACGTCGGCTGTATCCCTTCTAAAGCACTGCTGCACGTAGCAAAAGTTATCGAAGAAGCCAAAGCGCTGGCTGAACACGGTATCGTCTTCGGCGAACCGAAAACCGAT
ATCGACAAGATTCGTACCTGGAAAGAGAAAGTGATCAATCAGCTGACCGGTGGTCTGGCTGGTATGGCGAAAGGCCGCAAAGTCAAAGTGGTCAACGGTCTGGGTAAATTCACCGGGGCTAAC
ACCCTGGAAGTTGAAGGTGAGAACGGCAAAACCGTGATCAACTTCGACAACGCGATCATTGCAGCGGGTTCTCGCCCGATCCAACTGCCGTTTATTCCGCATGAAGATCCGCGTATCTGGGAC
TCCACTGACGCGCTGGAACTGAAAGAAGTACCAGAACGCCTGCTGGTAATGGGTGGCGGTATCATCGGTCTGGAAATGGGCACCGTTTACCACGCGCTGGGTTCACAGATTGACGTGGTTGAA
ATGTTCGACCAGGTTATCCCGGCAGCTGACAAAGACATCGTTAAAGTCTTCACCAAGCGTATCAGCAAGAAATTCAACCTGATGCTGGAAACCAAAGTTACCGCCGTTGAAGCGAAAGAAGAC
GGCATTTATGTGACGATGGAAGGCAAAAAAGCACCCGCTGAACCGCAGCGTTACGACGCCGTGCTGGTAGCGATTGGTCGTGTGCCGAACGGTAAAAACCTCGACGCAGGCAAAGCAGGCGTG
GAAGTTGACGACCGTGGTTTCATCCGCGTTGACAAACAGCTGCGTACCAACGTACCGCACATCTTTGCTATCGGCGATATCGTCGGTCAACCGATGCTGGCACACAAAGGTGTTCACGAAGGT
CACGTTGCCGCTGAAGTTATCGCCGGTAAGAAACACTACTTCGATCCGAAAGTTATCCCGTCCATCGCCTATACCGAACCAGAAGTTGCATGGGTGGGTCTGACTGAGAAAGAAGCGAAAGAG
AAAGGCATCAGCTATGAAACCGCCACCTTCCCGTGGGCTGCTTCTGGTCGTGCTATCGCTTCCGACTGCGCAGACGGTATGACCAAGCTGATTTTCGACAAAGAATCTCACCGTGTGATCGGT
GGTGCGATTGTCGGTACTAACGGCGGCGAGCTGCTGGGTGAAATCGGCCTGGCAATCGAAATGGGTTGTGATGCTGAAGACATCGCACTGACCATCCACGCGCACCCGACTCTGCACGAGTCT
GTGGGCCTGGCGGCAGAAGTGTTCGAAGGTAGCATTACCGACCTGCCGAACCCGAAAGCGAAGAAGAAGTAA1

\
2
;LOCUS ECOADA 1324 bp ds-DNA entered 02/03/86
;DEFINITION E.coli ada gene coding for Ada protein regulatory protein of
1
102,1166
ATGAAAAAAGCCACATGCTTAACTGACGATCAACGCTGGCAATCTGTCTTAGCCCGCGACCCGAATGCCGACGGCGAATTCGTTTTCGCCGTGCGTACCACAGGCATCTTTTGCCGTCCGTCT
TGCCGCGCCAGACATGCTTTGCGGGAAAACGTCTCCTTCTACGCAAATGCCAGCGAGGCACTCGCCGCTGGCTTTCGCCCCTGCAAACGTTGTCAGCCAGAAAAAGCCAATGCCCAGCAACAT
CGGTTGGATAAAATCACCCACGCGTGTCGACTGCTGGAACAGGAAACGCCTGTAACGCTGGAAGCCTTAGCCGACCAGGTGGCGATGAGTCCATTTCATCTACATCGGTTGTTTAAAGCGACT
ACCGGAATGACGCCTAAAGCCTGGCAACAGGCGTGGCGCGCTCGCCGTTTGCGCGAATCGCTGGCGAAAGGGGAGCGTGACGACGTCTATTCTTAACGCCGGATTCCCCGACAGCAGCAGT
TACTATCGCAAAGCTGACGAAACGCTGGGCATGACGGCTAAACAATTCCGTCACGGTGGCGAAAATCTGGCGGTGCGTTACGCGCTGGCTGATTGTGAGCTGGGTCGTTGCCTGGTGGCAGAA
AGCGAGCGGGGGATTTGCGCSATATTGCTGGGCGATGATGACGCCACACTAATCAGCGAGTTGCAGCAGATGTTTCCCGCTGCCGACAACGCGCCTGCCGATCTGATGTTTCAGCAACATGTG
CGTGAAGTGATCGCCAGCCTCAATCAACGCGACGCCGCTGACGTTACCGCTGGACATTCGCGGCACTGCTTTTCAGCAACAAGTCTGGCAGGCACTGCGCACGATACCTTGCGGTGAAACC
GTCAGTTATCAGCAACTGGCTAACGCCATCGGCAAACCGAAAGCGGTACGGGCCGTTGCCAGCGCCTGTGCCGCCAACAAGCTGGCTATCATAATACCCTGTCATCGGGTGGTCCGTGGTGAT
GGCACACTTTCCGGTTACCGCTGGGGCGTGTCGCGTAAAGCGCAACTGCTGCGCCGCGAAGCTGAAAATGAGGAGAGGTAA1

\
3
;LOCUS ECOALAS 2767 bp ds-DNA updated 12/16/85
;DEFINITION E.coli alaS gene coding for alanyl-tRNA synthetase.
1
<1,2628
AGCAAGAGCACCGCTGAGATCCGTCAGGCGTTTCTCGACTTTTTCCATAGTAAGGGACATCAGGTAGTTGCCAGCAGCTCCAGGTACCCCATAACCGACCCAACTTTGTTGTTTACCAACGCC
GGGATGAACCAGTTCAAGGATGTGTTCCTTGGGCTCGACAAGCGTAATTATTCCCGCGCTACCACTTCCCAACGCTGCGTGCGTGCGGGTGGTAAACACAACGACCTGGAAAACGTCGGTTAC
ACCGCGCGTCACCATACCTTCTTCGAAATGCTGGGCAACTTCAGCTTCGGCGACTATTTCAAACACGATGCCATTCAGTTTGCATGGGAACTGCTGACCAGCGAAAAATGGTTTGCCCTGCCG
AAAGAGCGTCTGTGGGTTACCGTCTATGAAAGCGACGACGAAGCCTACGAAATCTGGGAAAAAGAAGTAGGGATCCCGCGCGAACGTATTATTCGCATCAACGATAACAAGGGTGCGCCATAC
GCATCTGGCAACTTCTGGCGGATGGGTGGCACTGGTCCGTGCGACCCGTGCACCGAAATCTTCTACGATCACGGCGACCACATTTGGGGGGGCCCTCCGGGAAGCCCGGAAGAGACGGCGAT
CGCTACATTGAGATCTGGAACATCGTCTTCATGCAGTTCAACCGCCAGGCCGATGGCACGATGGAACCGCTGCCGAAGCCGTCTGTAGATACCGGTATGGGTCTGGAGCGTATTGCTGCGGTG
CTGCAACACGTTAACTCTAACTATGACATCGACCTGTTCCGCACGCTGATCCAGGCGGTAGCGAAAGTCACTGGCGCAACCGATCTGAGCAATAAATCGCTGCGCGTAATCGCTGACCACATT
CGTTCTTGTGCGTTCCTGATCGCGGATGGCGTAATGCCGTCCAATGAAAACCGTGGTTATGTACTGCGTCGTATCATTCGTCGCGCAGTGCGTCACGTTAATATGCTCGGCGCGAAAGAAACC
TTCTTCTACAAACTGGTTGGTCCGCTGATCGACGTTATG CTGCGGGTGAAGACCTGAAACGCCAGCAGGCGCAGGTTGAGC /GCTGAAGACTGAAGAAGAGCAGTTTGCTCGTACT
CTGGAGCGCGGTCTGGCGTTGCTGGATGAAGAGCTGGCA4 ACTTTCTGGTGATACGCTGGATGGTGAAACTGCTTTCCGTCTGTA GACACCTATGGCTTCCCGGTTGACCTGACGGCTGAT
GTTTGTCGTGAGCGCAACATCAAAGTTGACGAGCTGGTTTTGAAGCTGCAATGGAGAGCAGCTCGTCGCGCGCGAAGCCAGCGGCTTTGGTGCCGATTACAACGCAATGATCCGTGTT
GACAGTGCATCTGAATTTAAAGGCTATGACCATCTGGAACTGAACGGCAAAGTGACTGCGCTGTTTGTTGATGGTAAAGCGGTTGATGCCATCAATGCAGGCCAGGAAGCTGTGGTCGTGCTG
GATCAAACGCCATTCTATGCGGAATCCGGCGGTCAGGTTGGCGATAAAGGCGAACTGAAAGGCGCTAACTTCTCCTTTGCGGTGGAAGATACGCAGAAATACGGCCAGGCGATTGGTCACATC
GGTAAACTTGCTGCGGGTTCTCTGAAAGTGGGCGACGCGGTGCAGGCTGATGTTGATGAGGCTCGTCGCGCCCGTATTCGTCTGAATCACTCCGCAACGCACCTGATGCACGCTGCGCTGCGC CAGGTTCTGGGTACTCATGTATCGCATAAAGGTTCACTGGTTAACGACAAGGTGCTGCGCTTCGACTTCTCACACAACGAAGCGATGAAACCAGAAGAGATTCGTGCGGTCGAAGACCTGGTG
AACACACTGATTCGTCGCAATTTGCCGATCGAAACCAACATCATGGATCTCGAAGCGGCGAAAGCGAAAGGTGCGATGGCGCTGTTCGGCGAGAAGTATGATGAGCGCGTACGCGTGCTGAGC
ATGGGCGATTTCTCTACCGAGTTGTGTGGCGGTACTCACGCCAGCCGCACTGGTGATATTGGTCTGTTCCGCATCATCTCTGAATCGGGTACTGCTGCAGGCGTTCGTCGTATCGAAGCGGTA
ACCGGAGAAGGTGCTATCGCCACCGTTCATGCAGACAGCGATCGCTTAAGCGAAGTCGCGCATCTGCTGAAAGGCGATAGCAATAATCTGGCTGATAAAGTGCGCTCAGTACTGGAACGTACG
CGTCAGCTGGAAAAAGAGTTACAACAGCTTAAAGAACAAGCTGCCGCACAGGAGAGCGCAAATCTTTCCAGTAAGGCAATTGATGTTAATGGTGTTAAGCTGTTGGTTAGCGAGCTTAGCGGT
GTTGAGCCGAAAAATGTTGCGTACCATGGTTGACGATTTAAAAAATCAGCTGGGGTCGACAATTATCGTGCTGGCAACGGTAGTCGAAGGTAAGGTTTCTCTGATTGCAGGCGTATCTAAGGAC
GTCACAGATCGTGTGAAAGCAGGGGAACTGATTGGTATGGTCGCTCAGCAGGTGGGCGGCAAGGGTGGTGGACGTCCTGACATGGCGCAAGCCGGTGGTACGGATGCTGCGGCCTTACCTGCA
GCGTTAGCCAGTGTGAAAGGCTGGGTCAGCGCGAAATTGCAATAA ECOO.RXD/CPLIST.RXR January 11, 1989

| aa1 | aa2 | cod1 | cod2 | exp | obs | chis1 | chis2 |
|---|---|---|---|---|---|---|---|
| Lys | Lys | AAA | AAA | 143.2 | 103 | -11.3 | -7.2 |
| Lys | Asn | AAA | AAC | 85.8 | 77 | -0.9 | -0.4 |
| Lys | Lys | AAA | AAG | 40.7 | 30 | -2.8 | -1.7 |
| Lys | Asn | AAA | AAT | 41.2 | 49 | 1.5 | 2.2 |
| Lys | Thr | AAA | ACA | 17.0 | 22 | 1.5 | 1.8 |
| Lys | Thr | AAA | ACC | 76.0 | 87 | 1.6 | 2.3 |
| Lys | Thr | AAA | ACG | 30.4 | 35 | 0.7 | 1.0 |
| Lys | Thr | AAA | ACT | 38.6 | 34 | -0.6 | -0.3 |
| Lys | Arg | AAA | AGA | 4.1 | 7 | 2.1 | 1.6 |
| Lys | Ser | AAA | AGC | 42.8 | 32 | -2.7 | -0.2 |
| Lys | Arg | AAA | AGG | 2.7 | 1 | -1.1 | -1.2 |
| Lys | Ser | AAA | AGT | 17.5 | 9 | -4.1 | -1.8 |
| Lys | Ile | AAA | ATA | 9.6 | 12 | 0.6 | 1.1 |
| Lys | Ile | AAA | ATC | 101.2 | 89 | -1.5 | -0.3 |
| Lys | Met | AAA | ATG | 79.0 | 58 | -5.6 | -0.3 |
| Lys | Ile | AAA | ATT | 72.6 | 56 | -3.8 | -2.0 |
| Lys | Gln | AAA | CAA | 37.0 | 39 | 0.1 | 0.4 |
| Lys | His | AAA | CAC | 35.2 | 32 | -0.3 | -0.6 |
| Lys | Gln | AAA | CAG | 93.9 | 84 | -1.0 | -5.6 |
| Lys | His | AAA | CAT | 26.1 | 25 | -0.0 | -0.2 |
| Lys | Pro | AAA | CCA | 22.7 | 24 | 0.1 | 0.2 |
| Lys | Pro | AAA | CCC | 8.9 | 15 | 4.2 | 2.1 |
| Lys | Pro | AAA | CCG | 73.6 | 60 | -2.5 | -7.6 |
| Lys | Pro | AAA | CCT | 16.3 | 11 | -1.7 | -3.3 |
| Lys | Arg | AAA | CGA | 6.3 | 4 | -0.8 | -1.1 |
| Lys | Arg | AAA | CGC | 59.8 | 64 | 0.3 | 0.0 |
| Lys | Arg | AAA | CGG | 8.3 | 9 | 0.1 | 0.0 |
| Lys | Arg | AAA | CGT | 88.3 | 75 | -2.0 | -3.9 |
| Lys | Leu | AAA | CTA | 6.9 | 6 | -0.1 | -0.3 |
| Lys | Leu | AAA | CTC | 25.0 | 40 | 9.1 | 6.3 |
| Lys | Leu | AAA | CTG | 174.0 | 163 | -0.7 | -3.4 |
| Lys | Leu | AAA | CTT | 24.4 | 23 | -0.1 | -0.4 |
| Lys | Glu | AAA | GAA | 154.8 | 137 | -2.0 | -1.7 |
| Lys | Asp | AAA | GAC | 81.1 | 105 | 7.0 | 4.0 |
| Lys | Glu | AAA | GAG | 58.8 | 125 | 74.7 | 77.2 |
| Lys | Asp | AAA | GAT | 91.0 | 113 | 5.3 | 2.7 |
| Lys | Ala | AAA | GCA | 71.3 | 71 | -0.0 | -0.1 |
| Lys | Ala | AAA | GCC | 64.1 | 78 | 3.0 | 2.2 |
| Lys | Ala | AAA | GCG | 99.7 | 153 | 28.5 | 24.8 |
| Lys | Ala | AAA | GCT | 72.1 | 51 | -6.1 | -7.2 |
| Lys | Gly | AAA | GGA | 15.8 | 11 | -1.5 | -1.3 |
| Lys | Gly | AAA | GGC | 94.1 | 113 | 3.8 | 4.8 |
| Lys | Gly | AAA | GGG | 22.1 | 40 | 14.6 | 15.8 |
| Lys | Gly | AAA | GGT | 104.5 | 94 | -1.0 | -0.6 |
| Lys | Val | AAA | GTA | 44.9 | 39 | -0.8 | -1.6 |
| Lys | Val | AAA | GTC | 37.5 | 43 | 0.8 | 0.3 |
| Lys | Val | AAA | GTG | 66.8 | 104 | 20.7 | 15.3 |
| Lys | Val | AAA | GTT | 81.1 | 86 | 0.3 | 0.0 |
| Lys | Ocr | AAA | TAA | 0.0 | 15 | 0.0 | 0.0 |
| Lys | Tyr | AAA | TAC | 43.8 | 44 | 0.0 | 0.0 |
| Lys | Amb | AAA | TAG | 0.0 | 0 | 0.0 | 0.0 |
| Lys | Tyr | AAA | TAT | 42.2 | 45 | 0.2 | 0.3 |
| Lys | Ser | AAA | TCA | 16.3 | 10 | -2.4 | -0.7 |
| Lys | Ser | AAA | TCC | 35.1 | 20 | -6.5 | -2.4 |
| Lys | Ser | AAA | TCG | 19.3 | 22 | 0.4 | 2.6 |
| Lys | Ser | AAA | TCT | 39.3 | 31 | -1.7 | -0.0 |
| Lys | Umb | AAA | TGA | 0.0 | 0 | 0.0 | 0.0 |
| Lys | Cys | AAA | TGC | 16.0 | 12 | -1.0 | -0.0 |
| Lys | Trp | AAA | TGG | 31.2 | 29 | -0.2 | -0.0 |
| Lys | Cys | AAA | TGT | 12.0 | 6 | -3.0 | -1.2 |
| Lys | Leu | AAA | TTA | 28.3 | 22 | -1.4 | -2.4 |
| Lys | Phe | AAA | TTC | 60.2 | 48 | -2.5 | -0.0 |
| Lys | Leu | AAA | TTG | 27.4 | 24 | -0.4 | -1.1 |
| Lys | Phe | AAA | TTT | 46.4 | 30 | -5.8 | -1.3 |
| | Page Totals: | | | 3085.9 | 3096 | 261.1 | 232.6 |

PAGE 1

ECOO.RXD/CPLIST.RXR January 11, 1989

| aa1 | aa2 | cod1 | cod2 | exp | obs | chis1 | chis2 |
|---|---|---|---|---|---|---|---|
| Asn | Lys | AAC | AAA | 85.8 | 92 | 0.5 | 0.5 |
| Asn | Asn | AAC | AAC | 67.1 | 66 | -0.0 | 0.0 |
| Asn | Lys | AAC | AAG | 26.4 | 35 | 2.8 | 0.7 |
| Asn | Asn | AAC | AAT | 26.1 | 22 | -0.6 | -0.5 |
| Asn | Thr | AAC | ACA | 10.3 | 7 | -1.0 | -0.1 |
| Asn | Thr | AAC | ACC | 53.8 | 48 | -0.6 | -0.8 |
| Asn | Thr | AAC | ACG | 21.5 | 8 | -8.5 | -4.6 |
| Asn | Thr | AAC | ACT | 24.7 | 16 | -3.1 | -0.6 |
| Asn | Arg | AAC | AGA | 2.3 | 6 | 5.8 | 7.7 |
| Asn | Ser | AAC | AGC | 30.7 | 37 | 1.3 | 5.2 |
| Asn | Arg | AAC | AGG | 1.4 | 3 | 1.7 | 2.4 |
| Asn | Ser | AAC | AGT | 11.7 | 18 | 3.3 | 7.0 |
| Asn | Ile | AAC | ATA | 4.7 | 3 | -0.6 | -1.0 |
| Asn | Ile | AAC | ATC | 67.4 | 70 | 0.1 | 0.5 |
| Asn | Met | AAC | ATG | 54.5 | 42 | -2.9 | -1.8 |
| Asn | Ile | AAC | ATT | 46.8 | 37 | -2.1 | -4.9 |
| Asn | Gln | AAC | CAA | 24.4 | 14 | -4.4 | -2.5 |
| Asn | His | AAC | CAC | 23.9 | 20 | -0.6 | -0.1 |
| Asn | Gln | AAC | CAG | 67.1 | 50 | -4.3 | -1.3 |
| Asn | His | AAC | CAT | 17.8 | 19 | 0.1 | 0.6 |
| Asn | Pro | AAC | CCA | 14.8 | 15 | 0.0 | 3.1 |
| Asn | Pro | AAC | CCC | 5.7 | 5 | -0.1 | -1.8 |
| Asn | Pro | AAC | CCG | 51.8 | 98 | 41.3 | 2.9 |
| Asn | Pro | AAC | CCT | 10.3 | 13 | 0.7 | 0.7 |
| Asn | Arg | AAC | CGA | 4.1 | 2 | -1.1 | -0.7 |
| Asn | Arg | AAC | CGC | 42.4 | 40 | -0.1 | -0.2 |
| Asn | Arg | AAC | CGG | 5.4 | 5 | -0.0 | -0.0 |
| Asn | Arg | AAC | CGT | 61.9 | 69 | 0.8 | 4.0 |
| Asn | Leu | AAC | CTA | 4.5 | 1 | -2.7 | -2.6 |
| Asn | Leu | AAC | CTC | 17.6 | 19 | 0.1 | 0.2 |
| Asn | Leu | AAC | CTG | 122.0 | 124 | 0.0 | 0.3 |
| Asn | Leu | AAC | CTT | 15.8 | 22 | 2.5 | 3.0 |
| Asn | Glu | AAC | GAA | 100.0 | 76 | -5.7 | -0.9 |
| Asn | Asp | AAC | GAC | 56.7 | 56 | -0.0 | -0.1 |
| Asn | Glu | AAC | GAG | 38.5 | 35 | -0.3 | -0.2 |
| Asn | Asp | AAC | GAT | 62.2 | 58 | -0.3 | -0.6 |
| Asn | Ala | AAC | GCA | 44.8 | 25 | -8.7 | -9.2 |
| Asn | Ala | AAC | GCC | 44.0 | 86 | 40.0 | 38.0 |
| Asn | Ala | AAC | GCG | 69.2 | 52 | -4.3 | -4.8 |
| Asn | Ala | AAC | GCT | 45.8 | 34 | -3.0 | -3.4 |
| Asn | Gly | AAC | GGA | 9.1 | 6 | -1.1 | -1.5 |
| Asn | Gly | AAC | GGC | 65.8 | 76 | 1.6 | 0.4 |
| Asn | Gly | AAC | GGG | 14.6 | 13 | -0.2 | -0.5 |
| Asn | Gly | AAC | GGT | 72.5 | 80 | 0.8 | 0.1 |
| Asn | Val | AAC | GTA | 28.2 | 27 | -0.1 | -0.0 |
| Asn | Val | AAC | GTC | 25.5 | 43 | 12.0 | 13.1 |
| Asn | Val | AAC | GTG | 47.2 | 50 | 0.2 | 0.3 |
| Asn | Val | AAC | GTT | 52.9 | 43 | -1.8 | -1.5 |
| Asn | Ocr | AAC | TAA | 0.0 | 2 | 0.0 | 0.0 |
| Asn | Tyr | AAC | TAC | 34.4 | 40 | 0.9 | 1.3 |
| Asn | Amb | AAC | TAG | 0.0 | 2 | 0.0 | 0.0 |
| Asn | Tyr | AAC | TAT | 28.9 | 26 | -0.3 | -0.2 |
| Asn | Ser | AAC | TCA | 9.8 | 9 | -0.1 | -0.1 |
| Asn | Ser | AAC | TCC | 24.8 | 21 | -0.6 | -0.0 |
| Asn | Ser | AAC | TCG | 14.2 | 13 | -0.1 | -0.1 |
| Asn | Ser | AAC | TCT | 25.4 | 18 | -2.2 | -0.5 |
| Asn | Umb | AAC | TGA | 0.0 | 1 | 0.0 | 0.0 |
| Asn | Cys | AAC | TGC | 11.5 | 21 | 7.8 | 3.2 |
| Asn | Trp | AAC | TGG | 22.8 | 44 | 19.8 | 7.6 |
| Asn | Cys | AAC | TGT | 8.3 | 11 | 0.9 | 0.1 |
| Asn | Leu | AAC | TTA | 17.0 | 10 | -2.9 | -2.5 |
| Asn | Phe | AAC | TTC | 43.6 | 53 | 2.0 | 1.9 |
| Asn | Leu | AAC | TTG | 19.4 | 10 | -4.6 | -4.1 |
| Asn | Phe | AAC | TTT | 30.8 | 32 | 0.0 | 0.0 |
| | Page Totals: | | | 2092.8 | 2099 | 216.1 | 158.3 |

PAGE 2

ECOO.RXD/CPLIST.RXR January 11, 1989

| aa1 | aa2 | cod1 | cod2 | exp | obs | chis1 | chis2 |
|---|---|---|---|---|---|---|---|
| Lys | Lys | AAG | AAA | 40.7 | 76 | 30.7 | 37.7 |
| Lys | Asn | AAG | AAC | 26.4 | 17 | -3.4 | -2.8 |
| Lys | Lys | AAG | AAG | 17.8 | 18 | 0.0 | 0.1 |
| Lys | Asn | AAG | AAT | 13.1 | 17 | 1.2 | 1.6 |
| Lys | Thr | AAG | ACA | 5.7 | 3 | -1.3 | -1.2 |
| Lys | Thr | AAG | ACC | 22.7 | 9 | -8.3 | -7.7 |
| Lys | Thr | AAG | ACG | 10.2 | 9 | -0.1 | -0.1 |
| Lys | Thr | AAG | ACT | 11.1 | 7 | -1.5 | -1.3 |
| Lys | Arg | AAG | AGA | 1.4 | 0 | -1.3 | -1.4 |
| Lys | Ser | AAG | AGC | 13.8 | 16 | 0.4 | 2.2 |
| Lys | Arg | AAG | AGG | 1.0 | 4 | 8.6 | 7.7 |
| Lys | Ser | AAG | AGT | 5.7 | 4 | -0.5 | -0.1 |
| Lys | Ile | AAG | ATA | 3.0 | 4 | 0.4 | 0.6 |
| Lys | Ile | AAG | ATC | 31.1 | 40 | 2.6 | 4.2 |
| Lys | Met | AAG | ATG | 25.1 | 24 | -0.1 | -0.9 |
| Lys | Ile | AAG | ATT | 22.6 | 23 | 0.0 | 0.2 |
| Lys | Gln | AAG | CAA | 11.2 | 23 | 12.5 | 7.8 |
| Lys | His | AAG | CAC | 11.0 | 19 | 5.7 | 4.9 |
| Lys | Gln | AAG | CAG | 30.6 | 54 | 17.9 | 9.8 |
| Lys | His | AAG | CAT | 8.2 | 8 | -0.0 | -0.0 |
| Lys | Pro | AAG | CCA | 7.0 | 11 | 2.4 | 1.1 |
| Lys | Pro | AAG | CCC | 2.9 | 5 | 1.6 | 0.8 |
| Lys | Pro | AAG | CCG | 23.7 | 50 | 29.1 | 18.3 |
| Lys | Pro | AAG | CCT | 5.1 | 10 | 4.6 | 2.8 |
| Lys | Arg | AAG | CGA | 2.3 | 6 | 5.7 | 4.9 |
| Lys | Arg | AAG | CGC | 19.9 | 22 | 0.2 | 0.0 |
| Lys | Arg | AAG | CGG | 3.1 | 4 | 0.3 | 0.2 |
| Lys | Arg | AAG | CGT | 28.9 | 45 | 9.0 | 6.6 |
| Lys | Leu | AAG | CTA | 2.1 | 5 | 4.0 | 3.3 |
| Lys | Leu | AAG | CTC | 8.6 | 15 | 4.8 | 3.5 |
| Lys | Leu | AAG | CTG | 54.5 | 82 | 13.9 | 9.1 |
| Lys | Leu | AAG | CTT | 8.4 | 10 | 0.3 | 0.1 |
| Lys | Glu | AAG | GAA | 48.7 | 9 | -32.3 | -31.8 |
| Lys | Asp | AAG | GAC | 24.8 | 11 | -7.7 | -9.0 |
| Lys | Glu | AAG | GAG | 20.1 | 8 | -7.3 | -7.1 |
| Lys | Asp | AAG | GAT | 28.6 | 11 | -10.8 | -12.4 |
| Lys | Ala | AAG | GCA | 21.3 | 11 | -4.9 | -5.4 |
| Lys | Ala | AAG | GCC | 19.8 | 10 | -4.8 | -5.3 |
| Lys | Ala | AAG | GCG | 31.4 | 25 | -1.3 | -1.6 |
| Lys | Ala | AAG | GCT | 20.8 | 13 | -2.9 | -3.3 |
| Lys | Gly | AAG | GGA | 5.1 | 6 | 0.2 | 0.2 |
| Lys | Gly | AAG | GGC | 28.6 | 21 | -2.0 | -1.7 |
| Lys | Gly | AAG | GGG | 6.9 | 6 | -0.1 | -0.1 |
| Lys | Gly | AAG | GGT | 31.1 | 10 | -14.3 | -13.7 |
| Lys | Val | AAG | GTA | 13.3 | 7 | -3.0 | -3.6 |
| Lys | Val | AAG | GTC | 11.8 | 8 | -1.2 | -1.7 |
| Lys | Val | AAG | GTG | 21.8 | 19 | -0.4 | -0.3 |
| Lys | Val | AAG | GTT | 23.8 | 14 | -4.0 | -5.0 |
| Lys | Ocr | AAG | TAA | 0.0 | 9 | 0.0 | 0.0 |
| Lys | Tyr | AAG | TAC | 13.5 | 9 | -1.5 | -1.4 |
| Lys | Amb | AAG | TAG | 0.0 | 1 | 0.0 | 0.0 |
| Lys | Tyr | AAG | TAT | 13.3 | 13 | -0.0 | -0.0 |
| Lys | Ser | AAG | TCA | 5.3 | 3 | -1.0 | -0.4 |
| Lys | Ser | AAG | TCC | 10.9 | 6 | -2.2 | -0.9 |
| Lys | Ser | AAG | TCG | 6.6 | 11 | 3.0 | 6.2 |
| Lys | Ser | AAG | TCT | 12.1 | 17 | 2.0 | 5.4 |
| Lys | Umb | AAG | TGA | 0.0 | 2 | 0.0 | 0.0 |
| Lys | Cys | AAG | TGC | 5.5 | 8 | 1.1 | 3.2 |
| Lys | Trp | AAG | TGG | 9.8 | 9 | -0.1 | -0.0 |
| Lys | Cys | AAG | TGT | 3.9 | 3 | -0.2 | 0.0 |
| Lys | Leu | AAG | TTA | 8.7 | 11 | 0.6 | 0.3 |
| Lys | Phe | AAG | TTC | 19.0 | 15 | -0.9 | -0.0 |
| Lys | Leu | AAG | TTG | 9.3 | 7 | -0.6 | -0.9 |
| Lys | Phe | AAG | TTT | 14.7 | 19 | 1.3 | 4.6 |
| | | Page Totals: | | 968.7 | 972 | 284.1 | 268.5 |

PAGE 3

ECOO.RXD/CPLIST.RXR January 11, 1989

| aa1 | aa2 | cod1 | cod2 | exp | obs | chis1 | chis2 |
|---|---|---|---|---|---|---|---|
| Asn | Lys | AAT | AAA | 41.2 | 50 | 1.9 | 0.1 |
| Asn | Asn | AAT | AAC | 26.1 | 26 | -0.0 | -0.0 |
| Asn | Lys | AAT | AAG | 13.1 | 15 | 0.3 | 0.0 |
| Asn | Asn | AAT | AAT | 26.0 | 29 | 0.3 | 0.5 |
| Asn | Thr | AAT | ACA | 9.1 | 7 | -0.5 | -0.0 |
| Asn | Thr | AAT | ACC | 23.2 | 28 | 1.0 | 5.4 |
| Asn | Thr | AAT | ACG | 14.2 | 12 | -0.3 | -0.1 |
| Asn | Thr | AAT | ACT | 11.9 | 6 | -2.9 | -1.2 |
| Asn | Arg | AAT | AGA | 3.6 | 0 | -3.6 | -3.1 |
| Asn | Ser | AAT | AGC | 18.0 | 13 | -1.4 | -0.2 |
| Asn | Arg | AAT | AGG | 1.9 | 0 | -1.9 | -1.7 |
| Asn | Ser | AAT | AGT | 10.0 | 5 | -2.5 | -1.3 |
| Asn | Ile | AAT | ATA | 6.4 | 8 | 0.4 | 0.1 |
| Asn | Ile | AAT | ATC | 27.8 | 48 | 14.6 | 8.5 |
| Asn | Met | AAT | ATG | 27.8 | 36 | 2.4 | 3.5 |
| Asn | Ile | AAT | ATT | 32.0 | 44 | 4.5 | 1.7 |
| Asn | Gln | AAT | CAA | 17.8 | 24 | 2.2 | 4.6 |
| Asn | His | AAT | CAC | 10.7 | 11 | 0.0 | 0.2 |
| Asn | Gln | AAT | CAG | 33.8 | 37 | 0.3 | 1.9 |
| Asn | His | AAT | CAT | 12.6 | 8 | -1.7 | -0.9 |
| Asn | Pro | AAT | CCA | 9.9 | 21 | 12.6 | 1.8 |
| Asn | Pro | AAT | CCC | 5.0 | 10 | 5.1 | 0.5 |
| Asn | Pro | AAT | CCG | 22.3 | 32 | 4.2 | 0.4 |
| Asn | Pro | AAT | CCT | 6.8 | 8 | 0.2 | 0.8 |
| Asn | Arg | AAT | CGA | 3.4 | 1 | -1.7 | -1.3 |
| Asn | Arg | AAT | CGC | 22.8 | 17 | -1.5 | -0.4 |
| Asn | Arg | AAT | CGG | 4.8 | 1 | -3.0 | -2.5 |
| Asn | Arg | AAT | CGT | 24.9 | 13 | -5.7 | -3.6 |
| Asn | Leu | AAT | CTA | 3.5 | 1 | -1.8 | -1.7 |
| Asn | Leu | AAT | CTC | 10.4 | 19 | 7.2 | 5.1 |
| Asn | Leu | AAT | CTG | 54.4 | 58 | 0.2 | 0.6 |
| Asn | Leu | AAT | CTT | 12.1 | 14 | 0.3 | 0.4 |
| Asn | Glu | AAT | GAA | 47.2 | 38 | -1.8 | -0.1 |
| Asn | Asp | AAT | GAC | 21.5 | 30 | 3.3 | 2.8 |
| Asn | Glu | AAT | GAG | 21.3 | 26 | 1.0 | 3.5 |
| Asn | Asp | AAT | GAT | 36.5 | 38 | 0.1 | 0.0 |
| Asn | Ala | AAT | GCA | 24.5 | 27 | 0.3 | 0.2 |
| Asn | Ala | AAT | GCC | 27.8 | 41 | 6.3 | 5.7 |
| Asn | Ala | AAT | GCG | 34.8 | 32 | -0.2 | -0.3 |
| Asn | Ala | AAT | GCT | 20.0 | 19 | -0.1 | -0.1 |
| Asn | Gly | AAT | GGA | 9.5 | 10 | 0.0 | 0.0 |
| Asn | Gly | AAT | GGC | 30.2 | 40 | 3.2 | 1.8 |
| Asn | Gly | AAT | GGG | 10.8 | 6 | -2.1 | -2.7 |
| Asn | Gly | AAT | GGT | 32.2 | 32 | -0.0 | -0.2 |
| Asn | Val | AAT | GTA | 13.7 | 14 | 0.0 | 0.0 |
| Asn | Val | AAT | GTC | 15.4 | 14 | -0.1 | -0.1 |
| Asn | Val | AAT | GTG | 24.5 | 15 | -3.7 | -3.4 |
| Asn | Val | AAT | GTT | 23.5 | 20 | -0.5 | -0.4 |
| Asn | Ocr | AAT | TAA | 0.0 | 1 | 0.0 | 0.0 |
| Asn | Tyr | AAT | TAC | 13.9 | 15 | 0.1 | 0.2 |
| Asn | Amb | AAT | TAG | 0.0 | 0 | 0.0 | 0.0 |
| Asn | Tyr | AAT | TAT | 20.3 | 14 | -1.9 | -1.7 |
| Asn | Ser | AAT | TCA | 9.4 | 6 | -1.3 | -0.4 |
| Asn | Ser | AAT | TCC | 10.7 | 4 | -4.2 | -2.6 |
| Asn | Ser | AAT | TCG | 9.5 | 5 | -2.1 | -1.1 |
| Asn | Ser | AAT | TCT | 12.6 | 6 | -3.4 | -1.9 |
| Asn | Umb | AAT | TGA | 0.0 | 1 | 0.0 | 0.0 |
| Asn | Cys | AAT | TGC | 5.9 | 4 | -0.6 | -1.5 |
| Asn | Trp | AAT | TGG | 13.2 | 2 | -9.5 | -13.1 |
| Asn | Cys | AAT | TGT | 5.1 | 2 | -1.8 | -2.9 |
| Asn | Leu | AAT | TTA | 16.8 | 14 | -0.5 | -0.3 |
| Asn | Phe | AAT | TTC | 18.9 | 15 | -0.8 | -0.9 |
| Asn | Leu | AAT | TTG | 13.7 | 5 | -5.6 | -5.2 |
| Asn | Phe | AAT | TTT | 21.7 | 16 | -1.5 | -1.6 |
| | | Page Totals: | | 1112.1 | 1114 | 142.1 | 111.4 |

PAGE 4

ECOO.RXD/CPLIST.RXR January 11, 1989

| aa1 | aa2 | cod1 | cod2 | exp | obs | chis1 | chis2 |
|---|---|---|---|---|---|---|---|
| Thr | Lys | ACA | AAA. | 17.0 | 17 | 0.0 | -1.0 |
| Thr | Asn | ACA | AAC | 10.3 | 8 | -0.5 | -0.0 |
| Thr | Lys | ACA | AAG | 5.7 | 5 | -0.1 | -0.1 |
| Thr | Asn | ACA | AAT | 9.1 | 5 | -1.8 | -0.8 |
| Thr | Thr | ACA | ACA | 5.5 | 9 | 2.2 | 3.1 |
| Thr | Thr | ACA | ACC | 9.4 | 5 | -2.1 | -1.5 |
| Thr | Thr | ACA | ACG | 5.5 | 8 | 1.2 | 1.8 |
| Thr | Thr | ACA | ACT | 4.8 | 5 | 0.0 | 0.1 |
| Thr | Arg | ACA | AGA | 1.6 | 0 | -1.6 | -1.6 |
| Thr | Ser | ACA | AGC | 6.7 | 0 | -6.7 | -6.6 |
| Thr | Arg | ACA | AGG | 0.9 | 1 | 0.0 | 0.0 |
| Thr | Ser | ACA | AGT | 4.0 | 2 | -1.0 | -1.0 |
| Thr | Ile | ACA | ATA | 3.0 | 5 | 1.4 | 1.3 |
| Thr | Ile | ACA | ATC | 11.1 | 13 | 0.3 | 0.2 |
| Thr | Met | ACA | ATG | 10.4 | 7 | -1.1 | -0.0 |
| Thr | Ile | ACA | ATT | 12.4 | 12 | -0.0 | -0.0 |
| Thr | Gln | ACA | CAA | 7.1 | 18 | 16.6 | 18.0 |
| Thr | His | ACA | CAC | 4.2 | 2 | -1.1 | -0.9 |
| Thr | Gln | ACA | CAG | 12.6 | 7 | -2.5 | -2.2 |
| Thr | His | ACA | CAT | 4.7 | 3 | -0.6 | -0.4 |
| Thr | Pro | ACA | CCA | 3.6 | 13 | 24.1 | 15.7 |
| Thr | Pro | ACA | CCC | 2.3 | 5 | 3.3 | 1.6 |
| Thr | Pro | ACA | CCG | 8.3 | 11 | 0.9 | 0.0 |
| Thr | Pro | ACA | CCT | 2.8 | 3 | 0.0 | 0.1 |
| Thr | Arg | ACA | CGA | 1.4 | 1 | -0.1 | -0.1 |
| Thr | Arg | ACA | CGC | 8.4 | 6 | -0.7 | -0.9 |
| Thr | Arg | ACA | CGG | 2.0 | 0 | -2.0 | -2.1 |
| Thr | Arg | ACA | CGT | 9.9 | 8 | -0.4 | -0.5 |
| Thr | Leu | ACA | CTA | 1.7 | 3 | 1.1 | 0.5 |
| Thr | Leu | ACA | CTC | 4.2 | 10 | 8.2 | 4.9 |
| Thr | Leu | ACA | CTG | 21.0 | 20 | -0.1 | -1.1 |
| Thr | Leu | ACA | CTT | 4.8 | 8 | 2.1 | 0.8 |
| Thr | Glu | ACA | GAA | 18.7 | 14 | -1.2 | -0.0 |
| Thr | Asp | ACA | GAC | 8.5 | 11 | 0.7 | 0.5 |
| Thr | Glu | ACA | GAG | 8.2 | 8 | -0.0 | -0.4 |
| Thr | Asp | ACA | GAT | 13.8 | 7 | -3.3 | -3.7 |
| Thr | Ala | ACA | GCA | 9.9 | 10 | 0.0 | 0.1 |
| Thr | Ala | ACA | GCC | 9.9 | 4 | -3.5 | -2.9 |
| Thr | Ala | ACA | GCG | 12.9 | 13 | 0.0 | 0.1 |
| Thr | Ala | ACA | GCT | 8.0 | 8 | 0.0 | -0.0 |
| Thr | Gly | ACA | GGA | 3.9 | 3 | -0.2 | -0.5 |
| Thr | Gly | ACA | GGC | 11.6 | 9 | -0.6 | -1.4 |
| Thr | Gly | ACA | GGG | 4.1 | 5 | 0.2 | 0.0 |
| Thr | Gly | ACA | GGT | 12.3 | 18 | 2.6 | 1.0 |
| Thr | Val | ACA | GTA | 5.7 | 11 | 5.0 | 4.2 |
| Thr | Val | ACA | GTC | 5.9 | 0 | -5.8 | -6.1 |
| Thr | Val | ACA | GTG | 9.0 | 3 | -4.0 | -4.4 |
| Thr | Val | ACA | GTT | 9.8 | 9 | -0.1 | -0.2 |
| Thr | Ocr | ACA | TAA | 0.0 | 0 | 0.0 | 0.0 |
| Thr | Tyr | ACA | TAC | 5.1 | 2 | -1.9 | -2.0 |
| Thr | Amb | ACA | TAG | 0.0 | 0 | 0.0 | 0.0 |
| Thr | Tyr | ACA | TAT | 8.1 | 7 | -0.1 | -0.2 |
| Thr | Ser | ACA | TCA | 3.6 | 8 | 5.3 | 5.5 |
| Thr | Ser | ACA | TCC | 4.2 | 3 | -0.3 | -0.3 |
| Thr | Ser | ACA | TCG | 3.4 | 5 | 0.7 | 0.8 |
| Thr | Ser | ACA | TCT | 4.9 | 6 | 0.2 | 0.3 |
| Thr | Umb | ACA | TGA | 0.0 | 0 | 0.0 | 0.0 |
| Thr | Cys | ACA | TGC | 2.3 | 1 | -0.8 | -0.6 |
| Thr | Trp | ACA | TGG | 5.0 | 5 | 0.0 | 0.1 |
| Thr | Cys | ACA | TGT | 2.1 | 2 | -0.0 | -0.0 |
| Thr | Leu | ACA | TTA | 7.1 | 10 | 1.2 | 0.2 |
| Thr | Phe | ACA | TTC | 7.0 | 8 | 0.1 | 0.0 |
| Thr | Leu | ACA | TTG | 4.8 | 5 | 0.0 | 0.1 |
| Thr | Phe | ACA | TTT | 8.4 | 21 | 18.8 | 13.4 |
| | Page Totals: | | | 434.4 | 436 | 140.3 | 118.5 |

ECOO.RXD/CPLIST.RXR January 11, 1989

| aa1 | aa2 | cod1 | cod2 | exp | obs | chis1 | chis2 |
|---|---|---|---|---|---|---|---|
| Thr | Lys | ACC | AAA | 76.0 | 70 | -0.5 | -1.7 |
| Thr | Asn | ACC | AAC | 53.8 | 55 | 0.0 | 2.4 |
| Thr | Lys | ACC | AAG | 22.7 | 26 | 0.5 | 3.7 |
| Thr | Asn | ACC | AAT | 23.2 | 24 | 0.0 | 1.2 |
| Thr | Thr | ACC | ACA | 9.4 | 9 | -0.0 | -0.0 |
| Thr | Thr | ACC | ACC | 58.0 | 59 | 0.0 | 0.8 |
| Thr | Thr | ACC | ACG | 19.5 | 14 | -1.5 | -0.8 |
| Thr | Thr | ACC | ACT | 21.4 | 27 | 1.5 | 2.9 |
| Thr | Arg | ACC | AGA | 2.1 | 2 | -0.0 | -0.0 |
| Thr | Ser | ACC | AGC | 29.0 | 59 | 31.2 | 32.5 |
| Thr | Arg | ACC | AGG | 1.2 | 3 | 2.9 | 2.6 |
| Thr | Ser | ACC | AGT | 10.5 | 17 | 4.0 | 4.3 |
| Thr | Ile | ACC | ATA | 3.8 | 6 | 1.2 | 1.1 |
| Thr | Ile | ACC | ATC | 62.5 | 82 | 6.1 | 5.3 |
| Thr | Met | ACC | ATG | 51.0 | 45 | -0.7 | -1.8 |
| Thr | Ile | ACC | ATT | 45.4 | 57 | 3.0 | 2.5 |
| Thr | Gln | ACC | CAA | 22.4 | 11 | -5.8 | -5.2 |
| Thr | His | ACC | CAC | 22.9 | 19 | -0.6 | -0.2 |
| Thr | Gln | ACC | CAG | 60.7 | 44 | -4.6 | -3.6 |
| Thr | His | ACC | CAT | 16.8 | 11 | -2.0 | -1.3 |
| Thr | Pro | ACC | CCA | 13.2 | 6 | -3.9 | -6.7 |
| Thr | Pro | ACC | CCC | 5.6 | 7 | 0.4 | 0.0 |
| Thr | Pro | ACC | CCG | 49.4 | 29 | -8.5 | -17.4 |
| Thr | Pro | ACC | CCT | 9.4 | 3 | -4.3 | -6.5 |
| Thr | Arg | ACC | CGA | 3.7 | 6 | 1.5 | 1.2 |
| Thr | Arg | ACC | CGC | 39.7 | 44 | 0.5 | 0.1 |
| Thr | Arg | ACC | CGG | 4.9 | 5 | 0.0 | 0.0 |
| Thr | Arg | ACC | CGT | 55.2 | 53 | -0.1 | -0.4 |
| Thr | Leu | ACC | CTA | 4.1 | 3 | -0.3 | -0.7 |
| Thr | Leu | ACC | CTC | 16.8 | 10 | -2.8 | -5.2 |
| Thr | Leu | ACC | CTG | 112.9 | 60 | -24.8 | -42.4 |
| Thr | Leu | ACC | CTT | 13.8 | 13 | -0.0 | -0.8 |
| Thr | Glu | ACC | GAA | 93.4 | 65 | -8.6 | -1.0 |
| Thr | Asp | ACC | GAC | 50.7 | 64 | 3.5 | 2.5 |
| Thr | Glu | ACC | GAG | 36.1 | 37 | 0.0 | 2.6 |
| Thr | Asp | ACC | GAT | 56.9 | 58 | 0.0 | 0.0 |
| Thr | Ala | ACC | GCA | 40.7 | 40 | -0.0 | -0.1 |
| Thr | Ala | ACC | GCC | 42.0 | 49 | 1.2 | 2.6 |
| Thr | Ala | ACC | GCG | 66.6 | 41 | -9.9 | -6.9 |
| Thr | Ala | ACC | GCT | 39.5 | 33 | -1.1 | -0.3 |
| Thr | Gly | ACC | GGA | 8.8 | 18 | 9.6 | 5.9 |
| Thr | Gly | ACC | GGC | 61.0 | 58 | -0.1 | -2.3 |
| Thr | Gly | ACC | GGG | 13.6 | 24 | 7.9 | 4.2 |
| Thr | Gly | ACC | GGT | 65.9 | 102 | 19.7 | 8.5 |
| Thr | Val | ACC | GTA | 25.3 | 25 | -0.0 | -0.1 |
| Thr | Val | ACC | GTC | 24.7 | 26 | 0.1 | 0.0 |
| Thr | Val | ACC | GTG | 44.4 | 32 | -3.4 | -4.6 |
| Thr | Val | ACC | GTT | 47.5 | 81 | 23.5 | 19.3 |
| Thr | Ocr | ACC | TAA | 0.0 | 0 | 0.0 | 0.0 |
| Thr | Tyr | ACC | TAC | 29.3 | 37 | 2.0 | 1.3 |
| Thr | Amb | ACC | TAG | 0.0 | 0 | 0.0 | 0.0 |
| Thr | Tyr | ACC | TAT | 25.4 | 27 | 0.1 | 0.0 |
| Thr | Ser | ACC | TCA | 8.6 | 8 | -0.0 | -0.0 |
| Thr | Ser | ACC | TCC | 21.9 | 18 | -0.7 | -0.6 |
| Thr | Ser | ACC | TCG | 12.9 | 11 | -0.3 | -0.2 |
| Thr | Ser | ACC | TCT | 23.7 | 16 | -2.5 | -2.3 |
| Thr | Umb | ACC | TGA | 0.0 | 0 | 0.0 | 0.0 |
| Thr | Cys | ACC | TGC | 10.7 | 8 | -0.7 | -0.4 |
| Thr | Trp | ACC | TGG | 19.9 | 40 | 20.2 | 12.8 |
| Thr | Cys | ACC | TGT | 7.9 | 19 | 15.7 | 18.3 |
| Thr | Leu | ACC | TTA | 15.4 | 15 | -0.0 | -0.7 |
| Thr | Phe | ACC | TTC | 38.8 | 53 | 5.2 | 1.7 |
| Thr | Leu | ACC | TTG | 17.0 | 10 | -2.9 | -5.3 |
| Thr | Phe | ACC | TTT | 27.9 | 28 | 0.0 | 0.5 |
| | Page Totals: | | | 1917.0 | 1922 | 252.0 | 260.4 |

ECOO.RXD/CPLIST.RXR January 11, 1989

| aa1 | aa2 | cod1 | cod2 | exp | obs | chis1 | chis2 |
|---|---|---|---|---|---|---|---|
| Thr | Lys | ACG | AAA | 30.4 | 15 | -7.8 | -3.4 |
| Thr | Asn | ACG | AAC | 21.5 | 8 | -8.5 | -5.4 |
| Thr | Lys | ACG | AAG | 10.2 | 6 | -1.7 | -0.5 |
| Thr | Asn | ACG | AAT | 14.2 | 3 | -8.8 | -6.5 |
| Thr | Thr | ACG | ACA | 5.5 | 6 | 0.0 | 0.2 |
| Thr | Thr | ACG | ACC | 19.5 | 7 | -8.0 | -6.5 |
| Thr | Thr | ACG | ACG | 13.6 | 12 | -0.2 | -0.0 |
| Thr | Thr | ACG | ACT | 8.2 | 8 | -0.0 | -0.0 |
| Thr | Arg | ACG | AGA | 1.3 | 1 | -0.1 | -0.1 |
| Thr | Ser | ACG | AGC | 14.2 | 4 | -7.3 | -7.1 |
| Thr | Arg | ACG | AGG | 0.8 | 0 | -0.8 | -0.9 |
| Thr | Ser | ACG | AGT | 6.3 | 3 | -1.7 | -1.7 |
| Thr | Ile | ACG | ATA | 2.7 | 3 | 0.0 | 0.0 |
| Thr | Ile | ACG | ATC | 23.8 | 7 | -11.9 | -12.3 |
| Thr | Met | ACG | ATG | 22.6 | 20 | -0.3 | -0.8 |
| Thr | Ile | ACG | ATT | 22.9 | 15 | -2.7 | -3.0 |
| Thr | Gln | ACG | CAA | 12.2 | 31 | 29.0 | 31.4 |
| Thr | His | ACG | CAC | 9.0 | 11 | 0.5 | 0.9 |
| Thr | Gln | ACG | CAG | 26.7 | 21 | -1.2 | -0.9 |
| Thr | His | ACG | CAT | 9.4 | 10 | 0.0 | 0.2 |
| Thr | Pro | ACG | CCA | 6.7 | 26 | 56.2 | 37.5 |
| Thr | Pro | ACG | CCC | 3.6 | 4 | 0.1 | 0.0 |
| Thr | Pro | ACG | CCG | 20.0 | 47 | 36.3 | 19.2 |
| Thr | Pro | ACG | CCT | 5.0 | 14 | 16.4 | 9.7 |
| Thr | Arg | ACG | CGA | 2.2 | 6 | 6.4 | 5.8 |
| Thr | Arg | ACG | CGC | 19.0 | 19 | 0.0 | 0.0 |
| Thr | Arg | ACG | CGG | 3.7 | 4 | 0.0 | 0.0 |
| Thr | Arg | ACG | CGT | 21.8 | 27 | 1.2 | 0.7 |
| Thr | Leu | ACG | CTA | 2.6 | 9 | 15.9 | 11.1 |
| Thr | Leu | ACG | CTC | 8.1 | 17 | 9.7 | 5.3 |
| Thr | Leu | ACG | CTG | 48.5 | 144 | 188.2 | 125.7 |
| Thr | Leu | ACG | CTT | 7.9 | 21 | 21.7 | 13.8 |
| Thr | Glu | ACG | GAA | 36.9 | 21 | -6.9 | -2.3 |
| Thr | Asp | ACG | GAC | 18.2 | 10 | -3.7 | -4.2 |
| Thr | Glu | ACG | GAG | 17.1 | 4 | -10.0 | -6.6 |
| Thr | Asp | ACG | GAT | 26.2 | 15 | -4.8 | -5.4 |
| Thr | Ala | ACG | GCA | 17.3 | 17 | -0.0 | -0.1 |
| Thr | Ala | ACG | GCC | 21.8 | 10 | -6.4 | -5.1 |
| Thr | Ala | ACG | GCG | 30.1 | 37 | 1.6 | 3.0 |
| Thr | Ala | ACG | GCT | 14.0 | 11 | -0.6 | -0.3 |
| Thr | Gly | ACG | GGA | 5.3 | 10 | 4.1 | 2.4 |
| Thr | Gly | ACG | GGC | 24.8 | 14 | -4.7 | -7.6 |
| Thr | Gly | ACG | GGG | 8.0 | 4 | -2.0 | -3.0 |
| Thr | Gly | ACG | GGT | 24.1 | 12 | -6.1 | -9.1 |
| Thr | Val | ACG | GTA | 10.3 | 24 | 18.2 | 16.0 |
| Thr | Val | ACG | GTC | 11.6 | 14 | 0.5 | 0.3 |
| Thr | Val | ACG | GTG | 21.5 | 23 | 0.1 | 0.0 |
| Thr | Val | ACG | GTT | 16.6 | 15 | -0.2 | -0.3 |
| Thr | Ocr | ACG | TAA | 0.0 | 0 | 0.0 | 0.0 |
| Thr | Tyr | ACG | TAC | 11.2 | 2 | -7.5 | -8.0 |
| Thr | Amb | ACG | TAG | 0.0 | 0 | 0.0 | 0.0 |
| Thr | Tyr | ACG | TAT | 13.7 | 9 | -1.6 | -2.0 |
| Thr | Ser | ACG | TCA | 5.3 | 6 | 0.1 | 0.1 |
| Thr | Ser | ACG | TCC | 8.4 | 3 | -3.5 | -3.3 |
| Thr | Ser | ACG | TCG | 7.4 | 4 | -1.6 | -1.5 |
| Thr | Ser | ACG | TCT | 9.3 | 5 | -2.0 | -1.9 |
| Thr | Umb | ACG | TGA | 0.0 | 0 | 0.0 | 0.0 |
| Thr | Cys | ACG | TGC | 5.5 | 1 | -3.7 | -3.3 |
| Thr | Trp | ACG | TGG | 10.0 | 4 | -3.6 | -4.9 |
| Thr | Cys | ACG | TGT | 3.5 | 1 | -1.8 | -1.6 |
| Thr | Leu | ACG | TTA | 9.4 | 14 | 2.3 | 0.7 |
| Thr | Phe | ACG | TTC | 15.5 | 7 | -4.7 | -6.5 |
| Thr | Leu | ACG | TTG | 10.0 | 17 | 5.0 | 2.1 |
| Thr | Phe | ACG | TTT | 15.7 | 12 | -0.9 | -2.0 |
| | | Page Totals: | | 852.6 | 855 | 550.5 | 414.4 |

PAGE 7

ECOO.RXD/CPLIST.RXR January 11, 1989

| aa1 | aa2 | cod1 | cod2 | exp | obs | chis1 | chis2 |
|---|---|---|---|---|---|---|---|
| Thr | Lys | ACT | AAA | 38.6 | 25 | -4.8 | -1.0 |
| Thr | Asn | ACT | AAC | 24.7 | 27 | 0.2 | 2.0 |
| Thr | Lys | ACT | AAG | 11.1 | 3 | -5.9 | -3.8 |
| Thr | Asn | ACT | AAT | 11.9 | 10 | -0.3 | -0.0 |
| Thr | Thr | ACT | ACA | 4.8 | 3 | -0.6 | -0.4 |
| Thr | Thr | ACT | ACC | 21.4 | 17 | -0.9 | -0.3 |
| Thr | Thr | ACT | ACG | 8.2 | 11 | 0.9 | 1.7 |
| Thr | Thr | ACT | ACT | 15.4 | 9 | -2.7 | -1.8 |
| Thr | Arg | ACT | AGA | 1.6 | 0 | -1.6 | -1.7 |
| Thr | Ser | ACT | AGC | 11.8 | 0 | -11.8 | -11.7 |
| Thr | Arg | ACT | AGG | 0.9 | 0 | -0.9 | -1.0 |
| Thr | Ser | ACT | AGT | 5.1 | 3 | -0.8 | -0.8 |
| Thr | Ile | ACT | ATA | 2.6 | 4 | 0.7 | 0.6 |
| Thr | Ile | ACT | ATC | 29.0 | 20 | -2.8 | -3.1 |
| Thr | Met | ACT | ATG | 22.7 | 5 | -13.8 | -7.9 |
| Thr | Ile | ACT | ATT | 20.4 | 20 | -0.0 | -0.0 |
| Thr | Gln | ACT | CAA | 10.0 | 10 | 0.0 | 0.0 |
| Thr | His | ACT | CAC | 9.9 | 13 | 1.0 | 1.7 |
| Thr | Gln | ACT | CAG | 27.5 | 31 | 0.4 | 0.7 |
| Thr | His | ACT | CAT | 7.3 | 8 | 0.1 | 0.3 |
| Thr | Pro | ACT | CCA | 6.3 | 1 | -4.4 | -5.9 |
| Thr | Pro | ACT | CCC | 2.4 | 3 | 0.2 | 0.0 |
| Thr | Pro | ACT | CCG | 21.0 | 25 | 0.8 | 0.1 |
| Thr | Pro | ACT | CCT | 4.4 | 8 | 2.9 | 1.1 |
| Thr | Arg | ACT | CGA | 1.8 | 0 | -1.8 | -1.9 |
| Thr | Arg | ACT | CGC | 16.2 | 21 | 1.4 | 1.0 |
| Thr | Arg | ACT | CGG | 2.3 | 1 | -0.8 | -0.9 |
| Thr | Arg | ACT | CGT | 26.4 | 32 | 1.2 | 0.7 |
| Thr | Leu | ACT | CTA | 2.1 | 2 | -0.0 | -0.1 |
| Thr | Leu | ACT | CTC | 7.0 | 4 | -1.3 | -2.3 |
| Thr | Leu | ACT | CTG | 49.8 | 54 | 0.4 | 0.6 |
| Thr | Leu | ACT | CTT | 6.7 | 7 | 0.0 | 0.1 |
| Thr | Glu | ACT | GAA | 42.5 | 52 | 2.1 | 10.2 |
| Thr | Asp | ACT | GAC | 23.9 | 44 | 16.9 | 14.9 |
| Thr | Glu | ACT | GAG | 16.0 | 11 | -1.5 | -0.2 |
| Thr | Asp | ACT | GAT | 25.5 | 23 | -0.3 | -0.5 |
| Thr | Ala | ACT | GCA | 21.1 | 25 | 0.7 | 1.5 |
| Thr | Ala | ACT | GCC | 17.1 | 22 | 1.4 | 2.4 |
| Thr | Ala | ACT | GCG | 26.6 | 29 | 0.2 | 0.8 |
| Thr | Ala | ACT | GCT | 22.5 | 21 | -0.1 | -0.0 |
| Thr | Gly | ACT | GGA | 4.7 | 6 | 0.4 | 0.1 |
| Thr | Gly | ACT | GGC | 26.2 | 43 | 10.8 | 5.3 |
| Thr | Gly | ACT | GGG | 5.9 | 6 | 0.0 | 0.1 |
| Thr | Gly | ACT | GGT | 32.7 | 31 | -0.1 | -1.3 |
| Thr | Val | ACT | GTA | 13.8 | 10 | -1.0 | -1.4 |
| Thr | Val | ACT | GTC | 9.9 | 10 | 0.0 | 0.0 |
| Thr | Val | ACT | GTG | 17.8 | 6 | -7.8 | -8.7 |
| Thr | Val | ACT | GTT | 25.0 | 25 | 0.0 | 0.1 |
| Thr | Ocr | ACT | TAA | 0.0 | 0 | 0.0 | 0.0 |
| Thr | Tyr | ACT | TAC | 13.2 | 23 | 7.4 | 6.3 |
| Thr | Amb | ACT | TAG | 0.0 | 0 | 0.0 | 0.0 |
| Thr | Tyr | ACT | TAT | 12.0 | 16 | 1.3 | 1.0 |
| Thr | Ser | ACT | TCA | 4.8 | 8 | 2.1 | 2.3 |
| Thr | Ser | ACT | TCC | 10.3 | 16 | 3.1 | 3.3 |
| Thr | Ser | ACT | TCG | 5.1 | 2 | -1.9 | -1.8 |
| Thr | Ser | ACT | TCT | 12.1 | 23 | 9.9 | 10.4 |
| Thr | Umb | ACT | TGA | 0.0 | 0 | 0.0 | 0.0 |
| Thr | Cys | ACT | TGC | 4.3 | 2 | -1.2 | -1.0 |
| Thr | Trp | ACT | TGG | 8.7 | 1 | -6.8 | -8.1 |
| Thr | Cys | ACT | TGT | 3.2 | 3 | -0.0 | -0.0 |
| Thr | Leu | ACT | TTA | 7.9 | 7 | -0.1 | -0.6 |
| Thr | Phe | ACT | TTC | 17.7 | 22 | 1.0 | 0.2 |
| Thr | Leu | ACT | TTG | 7.2 | 7 | -0.0 | -0.3 |
| Thr | Phe | ACT | TTT | 13.3 | 14 | 0.0 | 0.1 |
| | | Page Totals: | | 882.0 | 885 | 143.8 | 137.6 |

PAGE 8

ECOO.RXD/CPLIST.RXR January 11, 1989

| aa1 | aa2 | cod1 | cod2 | exp | obs | chis1 | chis2 |
|---|---|---|---|---|---|---|---|
| Arg | Lys | AGA | AAA | 4.1 | 3 | -0.3 | -0.3 |
| Arg | Asn | AGA | AAC | 2.3 | 3 | 0.2 | 0.2 |
| Arg | Lys | AGA | AAG | 1.4 | 2 | 0.3 | 0.3 |
| Arg | Asn | AGA | AAT | 3.6 | 9 | 8.3 | 8.4 |
| Arg | Thr | AGA | ACA | 1.6 | 3 | 1.3 | 1.7 |
| Arg | Thr | AGA | ACC | 2.1 | 2 | -0.0 | -0.0 |
| Arg | Thr | AGA | ACG | 1.3 | 2 | 0.4 | 0.6 |
| Arg | Thr | AGA | ACT | 1.6 | 3 | 1.3 | 1.6 |
| Arg | Arg | AGA | AGA | 2.0 | 2 | 0.0 | 0.0 |
| Arg | Ser | AGA | AGC | 1.7 | 0 | -1.7 | -1.4 |
| Arg | Arg | AGA | AGG | 0.5 | 0 | -0.5 | -0.5 |
| Arg | Ser | AGA | AGT | 1.2 | 2 | 0.5 | 1.0 |
| Arg | Ile | AGA | ATA | 2.0 | 3 | 0.5 | 0.4 |
| Arg | Ile | AGA | ATC | 2.3 | 3 | 0.2 | 0.1 |
| Arg | Met | AGA | ATG | 2.7 | 1 | -1.1 | -0.7 |
| Arg | Ile | AGA | ATT | 3.7 | 3 | -0.1 | -0.2 |
| Arg | Gln | AGA | CAA | 2.0 | 2 | 0.0 | -0.1 |
| Arg | His | AGA | CAC | 1.3 | 0 | -1.3 | -1.6 |
| Arg | Gln | AGA | CAG | 3.3 | 2 | -0.5 | -1.1 |
| Arg | His | AGA | CAT | 1.5 | 1 | -0.1 | -0.4 |
| Arg | Pro | AGA | CCA | 1.5 | 1 | -0.2 | -0.1 |
| Arg | Pro | AGA | CCC | 0.9 | 3 | 5.5 | 6.2 |
| Arg | Pro | AGA | CCG | 1.8 | 2 | 0.0 | 0.1 |
| Arg | Pro | AGA | CCT | 0.9 | 1 | 0.0 | 0.0 |
| Arg | Arg | AGA | CGA | 0.4 | 0 | -0.4 | -0.4 |
| Arg | Arg | AGA | CGC | 1.9 | 0 | -1.9 | -1.7 |
| Arg | Arg | AGA | CGG | 0.8 | 1 | 0.1 | 0.1 |
| Arg | Arg | AGA | CGT | 2.2 | 0 | -2.2 | -2.0 |
| Arg | Leu | AGA | CTA | 0.5 | 0 | -0.5 | -0.6 |
| Arg | Leu | AGA | CTC | 1.1 | 2 | 0.8 | 0.7 |
| Arg | Leu | AGA | CTG | 4.1 | 6 | 0.9 | 0.7 |
| Arg | Leu | AGA | CTT | 1.5 | 2 | 0.2 | 0.1 |
| Arg | Glu | AGA | GAA | 4.8 | 11 | 8.2 | 6.3 |
| Arg | Asp | AGA | GAC | 2.3 | 2 | -0.0 | 0.0 |
| Arg | Glu | AGA | GAG | 2.5 | 1 | -0.9 | -1.1 |
| Arg | Asp | AGA | GAT | 4.1 | 1 | -2.3 | -1.9 |
| Arg | Ala | AGA | GCA | 2.7 | 4 | 0.6 | 1.0 |
| Arg | Ala | AGA | GCC | 2.1 | 2 | -0.0 | -0.0 |
| Arg | Ala | AGA | GCG | 2.8 | 3 | 0.0 | 0.1 |
| Arg | Ala | AGA | GCT | 1.9 | 2 | 0.0 | 0.0 |
| Arg | Gly | AGA | GGA | 1.7 | 4 | 3.1 | 4.0 |
| Arg | Gly | AGA | GGC | 2.4 | 3 | 0.2 | 0.4 |
| Arg | Gly | AGA | GGG | 1.0 | 1 | 0.0 | 0.0 |
| Arg | Gly | AGA | GGT | 3.3 | 1 | -1.6 | -1.3 |
| Arg | Val | AGA | GTA | 1.6 | 2 | 0.1 | 0.1 |
| Arg | Val | AGA | GTC | 1.7 | 2 | 0.1 | 0.0 |
| Arg | Val | AGA | GTG | 1.9 | 1 | -0.4 | -0.5 |
| Arg | Val | AGA | GTT | 3.0 | 2 | -0.3 | -0.4 |
| Arg | Ocr | AGA | TAA | 0.0 | 0 | 0.0 | 0.0 |
| Arg | Tyr | AGA | TAC | 1.5 | 0 | -1.5 | -1.6 |
| Arg | Amb | AGA | TAG | 0.0 | 0 | 0.0 | 0.0 |
| Arg | Tyr | AGA | TAT | 3.6 | 3 | -0.1 | -0.2 |
| Arg | Ser | AGA | TCA | 1.6 | 1 | -0.2 | -0.1 |
| Arg | Ser | AGA | TCC | 1.2 | 0 | -1.2 | -0.9 |
| Arg | Ser | AGA | TCG | 0.9 | 1 | 0.0 | 0.1 |
| Arg | Ser | AGA | TCT | 1.7 | 2 | 0.1 | 0.3 |
| Arg | Umb | AGA | TGA | 0.0 | 0 | 0.0 | 0.0 |
| Arg | Cys | AGA | TGC | 0.5 | 0 | -0.5 | -0.5 |
| Arg | Trp | AGA | TGG | 1.5 | 1 | -0.2 | -0.4 |
| Arg | Cys | AGA | TGT | 0.8 | 0 | -0.8 | -0.7 |
| Arg | Leu | AGA | TTA | 2.9 | 3 | 0.0 | 0.0 |
| Arg | Phe | AGA | TTC | 1.8 | 0 | -1.8 | -2.3 |
| Arg | Leu | AGA | TTG | 1.2 | 1 | -0.0 | -0.0 |
| Arg | Phe | AGA | TTT | 2.6 | 3 | 0.1 | 0.0 |
| | Page Totals: | | | 120.5 | 121 | 55.4 | 57.4 |

PAGE 9

ECOO.RXD/CPLIST.RXR January 11, 1989

| aa1 | aa2 | cod1 | cod2 | exp | obs | chis1 | chis2 |
|---|---|---|---|---|---|---|---|
| Ser | Lys | AGC | AAA | 42.8 | 39 | -0.3 | -0.5 |
| Ser | Asn | AGC | AAC | 30.7 | 35 | 0.6 | 1.4 |
| Ser | Lys | AGC | AAG | 13.8 | 15 | 0.1 | 1.3 |
| Ser | Asn | AGC | AAT | 18.0 | 23 | 1.4 | 2.3 |
| Ser | Thr | AGC | ACA | 6.7 | 9 | 0.8 | 0.6 |
| Ser | Thr | AGC | ACC | 29.0 | 36 | 1.7 | 1.1 |
| Ser | Thr | AGC | ACG | 14.2 | 7 | -3.6 | -4.1 |
| Ser | Thr | AGC | ACT | 11.8 | 11 | -0.1 | -0.2 |
| Ser | Arg | AGC | AGA | 1.7 | 1 | -0.3 | -0.4 |
| Ser | Ser | AGC | AGC | 24.3 | 11 | -7.3 | -6.1 |
| Ser | Arg | AGC | AGG | 1.1 | 0 | -1.1 | -1.2 |
| Ser | Ser | AGC | AGT | 8.0 | 10 | 0.5 | 0.9 |
| Ser | Ile | AGC | ATA | 3.3 | 0 | -3.3 | -3.0 |
| Ser | Ile | AGC | ATC | 34.3 | 27 | -1.6 | -0.6 |
| Ser | Met | AGC | ATG | 32.0 | 18 | -6.1 | -1.5 |
| Ser | Ile | AGC | ATT | 30.7 | 19 | -4.5 | -3.0 |
| Ser | Gln | AGC | CAA | 16.7 | 8 | -4.5 | -4.2 |
| Ser | His | AGC | CAC | 12.9 | 20 | 3.9 | 3.3 |
| Ser | Gln | AGC | CAG | 38.6 | 66 | 19.5 | 21.3 |
| Ser | His | AGC | CAT | 12.5 | 15 | 0.5 | 0.3 |
| Ser | Pro | AGC | CCA | 8.7 | 7 | -0.3 | -0.0 |
| Ser | Pro | AGC | CCC | 4.5 | 2 | -1.4 | -0.8 |
| Ser | Pro | AGC | CCG | 28.4 | 23 | -1.0 | -0.0 |
| Ser | Pro | AGC | CCT | 6.6 | 7 | 0.0 | 0.4 |
| Ser | Arg | AGC | CGA | 3.0 | 2 | -0.3 | -0.5 |
| Ser | Arg | AGC | CGC | 27.3 | 33 | 1.2 | 0.2 |
| Ser | Arg | AGC | CGG | 4.5 | 6 | 0.5 | 0.2 |
| Ser | Arg | AGC | CGT | 31.6 | 43 | 4.1 | 1.6 |
| Ser | Leu | AGC | CTA | 3.1 | 1 | -1.4 | -1.7 |
| Ser | Leu | AGC | CTC | 11.9 | 12 | 0.0 | 0.1 |
| Ser | Leu | AGC | CTG | 69.5 | 73 | 0.2 | 0.1 |
| Ser | Leu | AGC | CTT | 10.8 | 14 | 1.0 | 0.5 |
| Ser | Glu | AGC | GAA | 54.0 | 60 | 0.7 | 3.2 |
| Ser | Asp | AGC | GAC | 27.2 | 21 | -1.4 | -0.3 |
| Ser | Glu | AGC | GAG | 23.4 | 21 | -0.2 | -0.0 |
| Ser | Asp | AGC | GAT | 37.3 | 41 | 0.4 | 2.5 |
| Ser | Ala | AGC | GCA | 23.7 | 16 | -2.5 | -3.2 |
| Ser | Ala | AGC | GCC | 30.4 | 49 | 11.4 | 9.1 |
| Ser | Ala | AGC | GCG | 41.2 | 29 | -3.6 | -4.7 |
| Ser | Ala | AGC | GCT | 21.8 | 13 | -3.5 | -4.3 |
| Ser | Gly | AGC | GGA | 6.5 | 10 | 1.9 | 0.4 |
| Ser | Gly | AGC | GGC | 35.5 | 52 | 7.6 | 1.3 |
| Ser | Gly | AGC | GGG | 10.7 | 18 | 5.1 | 1.7 |
| Ser | Gly | AGC | GGT | 35.2 | 57 | 13.5 | 3.9 |
| Ser | Val | AGC | GTA | 14.8 | 14 | -0.0 | -0.1 |
| Ser | Val | AGC | GTC | 16.8 | 18 | 0.1 | 0.0 |
| Ser | Val | AGC | GTG | 29.1 | 31 | 0.1 | 0.0 |
| Ser | Val | AGC | GTT | 25.4 | 19 | -1.6 | -2.0 |
| Ser | Ocr | AGC | TAA | 0.0 | 1 | 0.0 | 0.0 |
| Ser | Tyr | AGC | TAC | 16.2 | 25 | 4.9 | 2.8 |
| Ser | Amb | AGC | TAG | 0.0 | 0 | 0.0 | 0.0 |
| Ser | Tyr | AGC | TAT | 17.3 | 16 | -0.1 | -0.5 |
| Ser | Ser | AGC | TCA | 6.7 | 2 | -3.3 | -2.9 |
| Ser | Ser | AGC | TCC | 12.4 | 12 | -0.0 | -0.0 |
| Ser | Ser | AGC | TCG | 9.7 | 4 | -3.3 | -2.8 |
| Ser | Ser | AGC | TCT | 12.9 | 4 | -6.1 | -5.4 |
| Ser | Umb | AGC | TGA | 0.0 | 0 | 0.0 | 0.0 |
| Ser | Cys | AGC | TGC | 7.2 | 8 | 0.1 | 0.2 |
| Ser | Trp | AGC | TGG | 13.7 | 18 | 1.3 | 0.4 |
| Ser | Cys | AGC | TGT | 5.1 | 3 | -0.9 | -2.0 |
| Ser | Leu | AGC | TTA | 12.2 | 2 | -8.5 | -9.5 |
| Ser | Phe | AGC | TTC | 22.6 | 27 | 0.9 | 1.3 |
| Ser | Leu | AGC | TTG | 13.3 | 3 | -8.0 | -9.0 |
| Ser | Phe | AGC | TTT | 19.7 | 12 | -3.0 | -2.5 |
| | Page Totals: | | | 1194.8 | 1199 | 167.4 | 139.7 |

PAGE 10

ECOO.RXD/CPLIST.RXR January 11, 1989

| aa1 | aa2 | cod1 | cod2 | exp | obs | chis1 | chis2 |
|---|---|---|---|---|---|---|---|
| Arg | Lys | AGG | AAA | 2.7 | 4 | 0.7 | 0.7 |
| Arg | Asn | AGG | AAC | 1.4 | 1 | -0.1 | -0.1 |
| Arg | Lys | AGG | AAG | 1.0 | 0 | -1.0 | -1.0 |
| Arg | Asn | AGG | AAT | 1.9 | 0 | -1.9 | -1.9 |
| Arg | Thr | AGG | ACA | 0.9 | 2 | 1.2 | 1.5 |
| Arg | Thr | AGG | ACC | 1.2 | 1 | -0.0 | -0.0 |
| Arg | Thr | AGG | ACG | 0.8 | 1 | 0.0 | 0.1 |
| Arg | Thr | AGG | ACT | 0.9 | 1 | 0.0 | 0.0 |
| Arg | Arg | AGG | AGA | 0.5 | 0 | -0.5 | -0.5 |
| Arg | Ser | AGG | AGC | 1.1 | 1 | -0.0 | -0.0 |
| Arg | Arg | AGG | AGG | 0.6 | 1 | 0.3 | 0.4 |
| Arg | Ser | AGG | AGT | 0.9 | 0 | -0.9 | -0.7 |
| Arg | Ile | AGG | ATA | 0.9 | 3 | 5.3 | 4.9 |
| Arg | Ile | AGG | ATC | 1.5 | 2 | 0.2 | 0.1 |
| Arg | Met | AGG | ATG | 1.6 | 3 | 1.1 | 1.9 |
| Arg | Ile | AGG | ATT | 2.3 | 1 | -0.7 | -0.8 |
| Arg | Gln | AGG | CAA | 1.2 | 2 | 0.6 | 0.2 |
| Arg | His | AGG | CAC | 0.5 | 0 | -0.5 | -0.6 |
| Arg | Gln | AGG | CAG | 2.1 | 5 | 4.2 | 2.2 |
| Arg | His | AGG | CAT | 0.7 | 0 | -0.7 | -0.9 |
| Arg | Pro | AGG | CCA | 0.6 | 0 | -0.6 | -0.6 |
| Arg | Pro | AGG | CCC | 0.4 | 0 | -0.4 | -0.3 |
| Arg | Pro | AGG | CCG | 1.0 | 3 | 3.7 | 4.2 |
| Arg | Pro | AGG | CCT | 0.5 | 0 | -0.5 | -0.4 |
| Arg | Arg | AGG | CGA | 0.5 | 2 | 4.5 | 5.4 |
| Arg | Arg | AGG | CGC | 1.1 | 1 | -0.0 | -0.0 |
| Arg | Arg | AGG | CGG | 0.4 | 2 | 6.1 | 7.2 |
| Arg | Arg | AGG | CGT | 1.4 | 0 | -1.4 | -1.3 |
| Arg | Leu | AGG | CTA | 0.2 | 1 | 2.4 | 2.2 |
| Arg | Leu | AGG | CTC | 0.7 | 0 | -0.7 | -0.7 |
| Arg | Leu | AGG | CTG | 2.9 | 2 | -0.3 | -0.3 |
| Arg | Leu | AGG | CTT | 1.0 | 1 | 0.0 | 0.0 |
| Arg | Glu | AGG | GAA | 2.6 | 5 | 2.2 | 1.6 |
| Arg | Asp | AGG | GAC | 1.4 | 0 | -1.4 | -1.2 |
| Arg | Glu | AGG | GAG | 1.5 | 0 | -1.5 | -1.6 |
| Arg | Asp | AGG | GAT | 2.3 | 2 | -0.0 | -0.0 |
| Arg | Ala | AGG | GCA | 1.7 | 0 | -1.7 | -1.5 |
| Arg | Ala | AGG | GCC | 1.6 | 2 | 0.1 | 0.2 |
| Arg | Ala | AGG | GCG | 1.8 | 1 | -0.3 | -0.2 |
| Arg | Ala | AGG | GCT | 1.2 | 0 | -1.2 | -1.1 |
| Arg | Gly | AGG | GGA | 0.9 | 1 | 0.0 | 0.0 |
| Arg | Gly | AGG | GGC | 1.4 | 1 | -0.1 | -0.0 |
| Arg | Gly | AGG | GGG | 0.7 | 0 | -0.7 | -0.6 |
| Arg | Gly | AGG | GGT | 1.7 | 2 | 0.0 | 0.1 |
| Arg | Val | AGG | GTA | 0.9 | 2 | 1.4 | 1.2 |
| Arg | Val | AGG | GTC | 1.0 | 0 | -1.0 | -1.0 |
| Arg | Val | AGG | GTG | 1.3 | 1 | -0.1 | -0.1 |
| Arg | Val | AGG | GTT | 1.5 | 1 | -0.2 | -0.2 |
| Arg | Ocr | AGG | TAA | 0.0 | 1 | 0.0 | 0.0 |
| Arg | Tyr | AGG | TAC | 0.8 | 1 | 0.1 | 0.0 |
| Arg | Amb | AGG | TAG | 0.0 | 0 | 0.0 | 0.0 |
| Arg | Tyr | AGG | TAT | 1.7 | 0 | -1.7 | -1.8 |
| Arg | Ser | AGG | TCA | 0.8 | 0 | -0.8 | -0.7 |
| Arg | Ser | AGG | TCC | 0.6 | 0 | -0.6 | -0.5 |
| Arg | Ser | AGG | TCG | 0.7 | 0 | -0.7 | -0.5 |
| Arg | Ser | AGG | TCT | 1.0 | 0 | -1.0 | -0.8 |
| Arg | Umb | AGG | TGA | 0.0 | 1 | 0.0 | 0.0 |
| Arg | Cys | AGG | TGC | 0.3 | 0 | -0.3 | -0.3 |
| Arg | Trp | AGG | TGG | 0.8 | 2 | 2.0 | 1.0 |
| Arg | Cys | AGG | TGT | 0.4 | 1 | 0.8 | 0.8 |
| Arg | Leu | AGG | TTA | 1.6 | 2 | 0.1 | 0.0 |
| Arg | Phe | AGG | TTC | 1.2 | 0 | -1.2 | -1.5 |
| Arg | Leu | AGG | TTG | 0.9 | 3 | 5.4 | 4.9 |
| Arg | Phe | AGG | TTT | 1.4 | 2 | 0.2 | 0.0 |
| | | Page Totals: | | 70.7 | 71 | 67.3 | 65.1 |

PAGE 11

ECOO.RXD/CPLIST.RXR January 11, 1989

| aa1 | aa2 | cod1 | cod2 | exp | obs | chis1 | chis2 |
|---|---|---|---|---|---|---|---|
| Ser | Lys | AGT | AAA | 17.5 | 16 | -0.1 | -0.2 |
| Ser | Asn | AGT | AAC | 11.7 | 10 | -0.3 | -0.1 |
| Ser | Lys | AGT | AAG | 5.7 | 5 | -0.1 | -0.0 |
| Ser | Asn | AGT | AAT | 10.0 | 11 | 0.1 | 0.3 |
| Ser | Thr | AGT | ACA | 4.0 | 2 | -1.0 | -1.2 |
| Ser | Thr | AGT | ACC | 10.5 | 9 | -0.2 | -0.4 |
| Ser | Thr | AGT | ACG | 6.3 | 2 | -2.9 | -3.2 |
| Ser | Thr | AGT | ACT | 5.1 | 4 | -0.2 | -0.3 |
| Ser | Arg | AGT | AGA | 1.2 | 1 | -0.0 | -0.1 |
| Ser | Ser | AGT | AGC | 8.0 | 5 | -1.1 | -0.8 |
| Ser | Arg | AGT | AGG | 0.9 | 0 | -0.9 | -1.0 |
| Ser | Ser | AGT | AGT | 6.4 | 2 | -3.1 | -2.7 |
| Ser | Ile | AGT | ATA | 2.5 | 2 | -0.1 | -0.0 |
| Ser | Ile | AGT | ATC | 12.0 | 10 | -0.3 | -0.1 |
| Ser | Met | AGT | ATG | 11.9 | 9 | -0.7 | -0.0 |
| Ser | Ile | AGT | ATT | 13.8 | 15 | 0.1 | 0.4 |
| Ser | Gln | AGT | CAA | 8.1 | 10 | 0.5 | 0.6 |
| Ser | His | AGT | CAC | 4.8 | 5 | 0.0 | 0.0 |
| Ser | Gln | AGT | CAG | 15.5 | 6 | -5.9 | -5.6 |
| Ser | His | AGT | CAT | 5.2 | 3 | -0.9 | -1.1 |
| Ser | Pro | AGT | CCA | 3.9 | 3 | -0.2 | -0.0 |
| Ser | Pro | AGT | CCC | 2.4 | 2 | -0.1 | 0.0 |
| Ser | Pro | AGT | CCG | 9.6 | 8 | -0.3 | -0.0 |
| Ser | Pro | AGT | CCT | 3.0 | 0 | -3.0 | -2.5 |
| Ser | Arg | AGT | CGA | 2.0 | 7 | 13.0 | 10.5 |
| Ser | Arg | AGT | CGC | 10.0 | 8 | -0.4 | -0.9 |
| Ser | Arg | AGT | CGG | 2.3 | 2 | -0.0 | -0.1 |
| Ser | Arg | AGT | CGT | 10.7 | 13 | 0.5 | 0.1 |
| Ser | Leu | AGT | CTA | 1.6 | 3 | 1.3 | 1.0 |
| Ser | Leu | AGT | CTC | 5.0 | 4 | -0.2 | -0.3 |
| Ser | Leu | AGT | CTG | 23.8 | 26 | 0.2 | 0.0 |
| Ser | Leu | AGT | CTT | 5.3 | 4 | -0.3 | -0.5 |
| Ser | Glu | AGT | GAA | 19.8 | 29 | 4.2 | 7.6 |
| Ser | Asp | AGT | GAC | 9.3 | 6 | -1.2 | -0.5 |
| Ser | Glu | AGT | GAG | 9.2 | 6 | -1.1 | -0.5 |
| Ser | Asp | AGT | GAT | 15.5 | 14 | -0.1 | -0.0 |
| Ser | Ala | AGT | GCA | 11.0 | 6 | -2.3 | -2.7 |
| Ser | Ala | AGT | GCC | 12.7 | 13 | 0.0 | 0.0 |
| Ser | Ala | AGT | GCG | 16.7 | 24 | 3.2 | 2.4 |
| Ser | Ala | AGT | GCT | 8.4 | 16 | 6.9 | 5.9 |
| Ser | Gly | AGT | GGA | 4.0 | 3 | -0.2 | -0.8 |
| Ser | Gly | AGT | GGC | 13.1 | 12 | -0.1 | -1.2 |
| Ser | Gly | AGT | GGG | 4.8 | 6 | 0.3 | 0.0 |
| Ser | Gly | AGT | GGT | 13.1 | 13 | -0.0 | -0.7 |
| Ser | Val | AGT | GTA | 5.9 | 7 | 0.2 | 0.1 |
| Ser | Val | AGT | GTC | 7.1 | 5 | -0.6 | -0.7 |
| Ser | Val | AGT | GTG | 11.3 | 11 | -0.0 | -0.0 |
| Ser | Val | AGT | GTT | 9.9 | 3 | -4.8 | -5.1 |
| Ser | Ocr | AGT | TAA | 0.0 | 1 | 0.0 | 0.0 |
| Ser | Tyr | AGT | TAC | 5.9 | 10 | 2.9 | 1.9 |
| Ser | Amb | AGT | TAG | 0.0 | 0 | 0.0 | 0.0 |
| Ser | Tyr | AGT | TAT | 8.6 | 17 | 8.4 | 6.0 |
| Ser | Ser | AGT | TCA | 4.0 | 6 | 1.0 | 1.4 |
| Ser | Ser | AGT | TCC | 4.7 | 2 | -1.5 | -1.3 |
| Ser | Ser | AGT | TCG | 4.3 | 10 | 7.4 | 8.7 |
| Ser | Ser | AGT | TCT | 5.7 | 10 | 3.3 | 4.1 |
| Ser | Umb | AGT | TGA | 0.0 | 0 | 0.0 | 0.0 |
| Ser | Cys | AGT | TGC | 2.5 | 1 | -0.9 | -1.5 |
| Ser | Trp | AGT | TGG | 5.8 | 4 | -0.5 | -1.0 |
| Ser | Cys | AGT | TGT | 2.3 | 3 | 0.2 | 0.0 |
| Ser | Leu | AGT | TTA | 7.4 | 9 | 0.3 | 0.1 |
| Ser | Phe | AGT | TTC | 7.8 | 12 | 2.3 | 2.8 |
| Ser | Leu | AGT | TTG | 6.3 | 9 | 1.2 | 0.7 |
| Ser | Phe | AGT | TTT | 10.0 | 14 | 1.6 | 2.1 |
| | | Page Totals: | | 487.3 | 489 | 94.9 | 93.8 |

PAGE 12

ECOO.RXD/CPLIST.RXR January 11, 1989

| aa1 | aa2 | cod1 | cod2 | exp | obs | chis1 | chis2 |
|---|---|---|---|---|---|---|---|
| Ile | Lys | ATA | AAA | 9.6 | 15 | 3.1 | 2.6 |
| Ile | Asn | ATA | AAC | 4.7 | 3 | -0.6 | -1.7 |
| Ile | Lys | ATA | AAG | 3.0 | 3 | 0.0 | 0.0 |
| Ile | Asn | ATA | AAT | 6.4 | 12 | 5.0 | 1.5 |
| Ile | Thr | ATA | ACA | 3.0 | 2 | -0.3 | -0.7 |
| Ile | Thr | ATA | ACC | 3.8 | 9 | 6.9 | 4.1 |
| Ile | Thr | ATA | ACG | 2.7 | 8 | 10.1 | 6.7 |
| Ile | Thr | ATA | ACT | 2.6 | 7 | 7.2 | 4.6 |
| Ile | Arg | ATA | AGA | 2.0 | 2 | 0.0 | 0.0 |
| Ile | Ser | ATA | AGC | 3.3 | 8 | 6.7 | 4.8 |
| Ile | Arg | ATA | AGG | 0.9 | 0 | -0.9 | -0.9 |
| Ile | Ser | ATA | AGT | 2.5 | 0 | -2.5 | -2.9 |
| Ile | Ile | ATA | ATA | 4.0 | 2 | -1.0 | -0.4 |
| Ile | Ile | ATA | ATC | 4.9 | 1 | -3.1 | -2.1 |
| Ile | Met | ATA | ATG | 4.9 | 2 | -1.7 | -0.6 |
| Ile | Ile | ATA | ATT | 6.7 | 3 | -2.0 | -0.9 |
| Ile | Gln | ATA | CAA | 4.2 | 5 | 0.1 | 2.1 |
| Ile | His | ATA | CAC | 2.3 | 0 | -2.3 | -2.2 |
| Ile | Gln | ATA | CAG | 6.3 | 2 | -2.9 | -1.0 |
| Ile | His | ATA | CAT | 2.8 | 1 | -1.1 | -1.0 |
| Ile | Pro | ATA | CCA | 2.6 | 6 | 4.6 | 3.7 |
| Ile | Pro | ATA | CCC | 1.5 | 1 | -0.2 | -0.2 |
| Ile | Pro | ATA | CCG | 3.3 | 5 | 0.8 | 0.5 |
| Ile | Pro | ATA | CCT | 1.8 | 2 | 0.0 | 0.0 |
| Ile | Arg | ATA | CGA | 1.0 | 0 | -0.9 | -1.0 |
| Ile | Arg | ATA | CGC | 3.9 | 2 | -0.9 | -1.0 |
| Ile | Arg | ATA | CGG | 1.5 | 2 | 0.2 | 0.1 |
| Ile | Arg | ATA | CGT | 4.4 | 4 | -0.0 | -0.1 |
| Ile | Leu | ATA | CTA | 1.1 | 4 | 8.3 | 10.3 |
| Ile | Leu | ATA | CTC | 2.3 | 2 | -0.0 | -0.0 |
| Ile | Leu | ATA | CTG | 8.8 | 6 | -0.9 | -0.4 |
| Ile | Leu | ATA | CTT | 3.2 | 3 | -0.0 | -0.0 |
| Ile | Glu | ATA | GAA | 9.4 | 9 | -0.0 | -0.3 |
| Ile | Asp | ATA | GAC | 4.1 | 6 | 0.9 | 0.4 |
| Ile | Glu | ATA | GAG | 4.6 | 8 | 2.5 | 1.3 |
| Ile | Asp | ATA | GAT | 7.7 | 6 | -0.4 | -0.9 |
| Ile | Ala | ATA | GCA | 5.4 | 4 | -0.3 | -0.5 |
| Ile | Ala | ATA | GCC | 5.0 | 8 | 1.8 | 1.4 |
| Ile | Ala | ATA | GCG | 5.8 | 8 | 0.8 | 0.6 |
| Ile | Ala | ATA | GCT | 4.0 | 2 | -1.0 | -1.1 |
| Ile | Gly | ATA | GGA | 2.9 | 1 | -1.2 | -1.4 |
| Ile | Gly | ATA | GGC | 4.9 | 3 | -0.8 | -1.0 |
| Ile | Gly | ATA | GGG | 2.4 | 2 | -0.1 | -0.1 |
| Ile | Gly | ATA | GGT | 5.6 | 5 | -0.1 | -0.2 |
| Ile | Val | ATA | GTA | 2.9 | 1 | -1.3 | -1.0 |
| Ile | Val | ATA | GTC | 3.3 | 3 | -0.0 | 0.0 |
| Ile | Val | ATA | GTG | 4.2 | 2 | -1.1 | -0.8 |
| Ile | Val | ATA | GTT | 5.4 | 3 | -1.1 | -0.7 |
| Ile | Ocr | ATA | TAA | 0.0 | 0 | 0.0 | 0.0 |
| Ile | Tyr | ATA | TAC | 2.6 | 0 | -2.6 | -2.7 |
| Ile | Amb | ATA | TAG | 0.0 | 0 | 0.0 | 0.0 |
| Ile | Tyr | ATA | TAT | 5.4 | 12 | 8.0 | 7.3 |
| Ile | Ser | ATA | TCA | 2.7 | 1 | -1.0 | -1.4 |
| Ile | Ser | ATA | TCC | 2.1 | 1 | -0.6 | -0.8 |
| Ile | Ser | ATA | TCG | 1.8 | 1 | -0.3 | -0.5 |
| Ile | Ser | ATA | TCT | 2.9 | 2 | -0.3 | -0.5 |
| Ile | Umb | ATA | TGA | 0.0 | 0 | 0.0 | 0.0 |
| Ile | Cys | ATA | TGC | 1.0 | 0 | -1.0 | -1.0 |
| Ile | Trp | ATA | TGG | 3.1 | 3 | -0.0 | -0.0 |
| Ile | Cys | ATA | TGT | 1.5 | 1 | -0.2 | -0.2 |
| Ile | Leu | ATA | TTA | 5.6 | 5 | -0.1 | -0.0 |
| Ile | Phe | ATA | TTC | 3.9 | 1 | -2.2 | -1.4 |
| Ile | Leu | ATA | TTG | 3.3 | 4 | 0.1 | 0.4 |
| Ile | Phe | ATA | TTT | 5.7 | 12 | 7.0 | 12.4 |
| | Page Totals: | | | 235.0 | 236 | 111.5 | 98.4 |

PAGE 13

ECOO.RXD/CPLIST.RXR January 11, 1989

| aa1 | aa2 | cod1 | cod2 | exp | obs | chis1 | chis2 |
|---|---|---|---|---|---|---|---|
| Ile | Lys | ATC | AAA | 101.2 | 107 | 0.3 | 0.0 |
| Ile | Asn | ATC | AAC | 67.4 | 117 | 36.5 | 8.4 |
| Ile | Lys | ATC | AAG | 31.1 | 31 | -0.0 | -0.1 |
| Ile | Asn | ATC | AAT | 27.8 | 36 | 2.4 | 0.0 |
| Ile | Thr | ATC | ACA | 11.1 | 11 | -0.0 | -0.5 |
| Ile | Thr | ATC | ACC | 62.5 | 98 | 20.1 | 6.6 |
| Ile | Thr | ATC | ACG | 23.8 | 10 | -8.0 | -12.3 |
| Ile | Thr | ATC | ACT | 29.0 | 42 | 5.9 | 1.4 |
| Ile | Arg | ATC | AGA | 2.3 | 1 | -0.8 | -0.8 |
| Ile | Ser | ATC | AGC | 34.3 | 62 | 22.3 | 13.4 |
| Ile | Arg | ATC | AGG | 1.5 | 5 | 8.3 | 7.8 |
| Ile | Ser | ATC | AGT | 12.0 | 18 | 3.0 | 1.3 |
| Ile | Ile | ATC | ATA | 4.9 | 1 | -3.1 | -2.1 |
| Ile | Ile | ATC | ATC | 93.6 | 75 | -3.7 | -0.1 |
| Ile | Met | ATC | ATG | 66.2 | 52 | -3.0 | -0.8 |
| Ile | Ile | ATC | ATT | 55.6 | 47 | -1.3 | -0.3 |
| Ile | Gln | ATC | CAA | 26.1 | 8 | -12.6 | -4.3 |
| Ile | His | ATC | CAC | 29.2 | 26 | -0.3 | -0.1 |
| Ile | Gln | ATC | CAG | 75.4 | 41 | -15.7 | -0.8 |
| Ile | His | ATC | CAT | 19.6 | 22 | 0.3 | 0.5 |
| Ile | Pro | ATC | CCA | 16.3 | 16 | -0.0 | -0.2 |
| Ile | Pro | ATC | CCC | 6.0 | 9 | 1.6 | 1.0 |
| Ile | Pro | ATC | CCG | 62.1 | 57 | -0.4 | -1.6 |
| Ile | Pro | ATC | CCT | 11.9 | 9 | -0.7 | -1.2 |
| Ile | Arg | ATC | CGA | 4.6 | 4 | -0.1 | -0.1 |
| Ile | Arg | ATC | CGC | 47.9 | 45 | -0.2 | -0.4 |
| Ile | Arg | ATC | CGG | 6.1 | 8 | 0.6 | 0.5 |
| Ile | Arg | ATC | CGT | 73.9 | 68 | -0.5 | -1.0 |
| Ile | Leu | ATC | CTA | 4.8 | 0 | -4.8 | -4.2 |
| Ile | Leu | ATC | CTC | 20.6 | 46 | 31.4 | 43.3 |
| Ile | Leu | ATC | CTG | 146.4 | 107 | -10.6 | -3.5 |
| Ile | Leu | ATC | CTT | 18.0 | 18 | 0.0 | 0.3 |
| Ile | Glu | ATC | GAA | 122.7 | 136 | 1.4 | 0.3 |
| Ile | Asp | ATC | GAC | 66.8 | 100 | 16.5 | 7.0 |
| Ile | Glu | ATC | GAG | 46.3 | 49 | 0.2 | 0.4 |
| Ile | Asp | ATC | GAT | 69.7 | 77 | 0.8 | 0.1 |
| Ile | Ala | ATC | GCA | 52.1 | 30 | -9.4 | -10.9 |
| Ile | Ala | ATC | GCC | 50.9 | 81 | 17.8 | 14.6 |
| Ile | Ala | ATC | GCG | 81.1 | 56 | -7.7 | -9.7 |
| Ile | Ala | ATC | GCT | 54.4 | 50 | -0.3 | -0.8 |
| Ile | Gly | ATC | GGA | 10.1 | 2 | -6.5 | -7.1 |
| Ile | Gly | ATC | GGC | 75.6 | 84 | 0.9 | 0.2 |
| Ile | Gly | ATC | GGG | 15.9 | 13 | -0.5 | -0.9 |
| Ile | Gly | ATC | GGT | 86.1 | 98 | 1.6 | 0.4 |
| Ile | Val | ATC | GTA | 35.3 | 19 | -7.5 | -5.1 |
| Ile | Val | ATC | GTC | 29.3 | 58 | 28.0 | 38.1 |
| Ile | Val | ATC | GTG | 55.7 | 27 | -14.8 | -10.6 |
| Ile | Val | ATC | GTT | 63.9 | 72 | 1.0 | 3.7 |
| Ile | Ocr | ATC | TAA | 0.0 | 2 | 0.0 | 0.0 |
| Ile | Tyr | ATC | TAC | 36.3 | 38 | 0.1 | 0.0 |
| Ile | Amb | ATC | TAG | 0.0 | 0 | 0.0 | 0.0 |
| Ile | Tyr | ATC | TAT | 30.2 | 33 | 0.3 | 0.1 |
| Ile | Ser | ATC | TCA | 10.6 | 1 | -8.7 | -10.1 |
| Ile | Ser | ATC | TCC | 29.1 | 58 | 28.8 | 18.7 |
| Ile | Ser | ATC | TCG | 15.6 | 5 | -7.2 | -9.2 |
| Ile | Ser | ATC | TCT | 30.4 | 23 | -1.8 | -3.9 |
| Ile | Umb | ATC | TGA | 0.0 | 1 | 0.0 | 0.0 |
| Ile | Cys | ATC | TGC | 13.1 | 16 | 0.6 | 0.8 |
| Ile | Trp | ATC | TGG | 23.6 | 32 | 3.0 | 6.2 |
| Ile | Cys | ATC | TGT | 9.6 | 8 | -0.3 | -0.2 |
| Ile | Leu | ATC | TTA | 17.8 | 7 | -6.5 | -4.7 |
| Ile | Phe | ATC | TTC | 50.5 | 45 | -0.6 | -0.6 |
| Ile | Leu | ATC | TTG | 20.0 | 3 | -14.4 | -12.0 |
| Ile | Phe | ATC | TTT | 33.9 | 15 | -10.5 | -5.3 |
| | Page Totals: | | | 2429.9 | 2436 | 396.2 | 300.8 |

PAGE 14

ECOO.RXD/CPLIST.RXR January 11, 1989

| aa1 | aa2 | cod1 | cod2 | exp | obs | chis1 | chis2 |
|---|---|---|---|---|---|---|---|
| Met | Lys | ATG | AAA | 79.0 | 86 | 0.6 | 0.0 |
| Met | Asn | ATG | AAC | 54.5 | 54 | -0.0 | -0.0 |
| Met | Lys | ATG | AAG | 25.1 | 30 | 0.9 | 0.1 |
| Met | Asn | ATG | AAT | 27.8 | 27 | -0.0 | -0.0 |
| Met | Thr | ATG | ACA | 10.4 | 13 | 0.6 | 0.2 |
| Met | Thr | ATG | ACC | 51.0 | 53 | 0.1 | 0.3 |
| Met | Thr | ATG | ACG | 22.6 | 23 | 0.0 | 0.2 |
| Met | Thr | ATG | ACT | 22.7 | 30 | 2.3 | 0.9 |
| Met | Arg | ATG | AGA | 2.7 | 4 | 0.6 | 0.8 |
| Met | Ser | ATG | AGC | 32.0 | 34 | 0.1 | 0.3 |
| Met | Arg | ATG | AGG | 1.6 | 0 | -1.6 | -1.6 |
| Met | Ser | ATG | AGT | 11.9 | 24 | 12.5 | 7.4 |
| Met | Ile | ATG | ATA | 4.9 | 3 | -0.8 | -0.4 |
| Met | Ile | ATG | ATC | 66.2 | 61 | -0.4 | -0.1 |
| Met | Met | ATG | ATG | 64.7 | 64 | -0.0 | 0.0 |
| Met | Ile | ATG | ATT | 51.3 | 44 | -1.0 | -0.0 |
| Met | Gln | ATG | CAA | 25.1 | 30 | 0.9 | 0.5 |
| Met | His | ATG | CAC | 23.8 | 25 | 0.1 | 1.7 |
| Met | Gln | ATG | CAG | 64.5 | 64 | -0.0 | -0.2 |
| Met | His | ATG | CAT | 19.6 | 10 | -4.7 | -2.1 |
| Met | Pro | ATG | CCA | 15.1 | 30 | 14.6 | 4.5 |
| Met | Pro | ATG | CCC | 6.5 | 7 | 0.0 | 0.4 |
| Met | Pro | ATG | CCG | 51.7 | 66 | 4.0 | 0.2 |
| Met | Pro | ATG | CCT | 11.0 | 11 | 0.0 | 1.0 |
| Met | Arg | ATG | CGA | 4.7 | 5 | 0.0 | 0.1 |
| Met | Arg | ATG | CGC | 43.4 | 41 | -0.1 | -0.0 |
| Met | Arg | ATG | CGG | 6.3 | 4 | -0.9 | -0.7 |
| Met | Arg | ATG | CGT | 57.8 | 58 | 0.0 | 0.1 |
| Met | Leu | ATG | CTA | 5.0 | 7 | 0.8 | 1.9 |
| Met | Leu | ATG | CTC | 19.0 | 12 | -2.6 | -1.0 |
| Met | Leu | ATG | CTG | 121.2 | 97 | -4.8 | -0.2 |
| Met | Leu | ATG | CTT | 16.5 | 13 | -0.8 | -0.1 |
| Met | Glu | ATG | GAA | 98.2 | 99 | 0.0 | 0.4 |
| Met | Asp | ATG | GAC | 50.4 | 38 | -3.1 | -0.5 |
| Met | Glu | ATG | GAG | 39.5 | 31 | -1.8 | -1.1 |
| Met | Asp | ATG | GAT | 60.3 | 56 | -0.3 | -0.4 |
| Met | Ala | ATG | GCA | 43.2 | 53 | 2.2 | 0.9 |
| Met | Ala | ATG | GCC | 46.5 | 24 | -10.9 | -13.7 |
| Met | Ala | ATG | GCG | 71.8 | 94 | 6.9 | 3.5 |
| Met | Ala | ATG | GCT | 42.3 | 49 | 1.1 | 0.2 |
| Met | Gly | ATG | GGA | 10.0 | 13 | 0.9 | 0.7 |
| Met | Gly | ATG | GGC | 64.2 | 80 | 3.9 | 2.8 |
| Met | Gly | ATG | GGG | 15.7 | 24 | 4.4 | 3.8 |
| Met | Gly | ATG | GGT | 66.9 | 45 | -7.2 | -8.4 |
| Met | Val | ATG | GTA | 27.7 | 22 | -1.2 | -1.1 |
| Met | Val | ATG | GTC | 28.0 | 29 | 0.0 | 0.1 |
| Met | Val | ATG | GTG | 49.2 | 50 | 0.0 | 0.0 |
| Met | Val | ATG | GTT | 48.7 | 51 | 0.1 | 0.2 |
| Met | Ocr | ATG | TAA | 0.0 | 2 | 0.0 | 0.0 |
| Met | Tyr | ATG | TAC | 29.2 | 27 | -0.2 | -0.0 |
| Met | Amb | ATG | TAG | 0.0 | 0 | 0.0 | 0.0 |
| Met | Tyr | ATG | TAT | 28.3 | 28 | -0.0 | -0.0 |
| Met | Ser | ATG | TCA | 10.8 | 15 | 1.6 | 0.4 |
| Met | Ser | ATG | TCC | 23.2 | 25 | 0.1 | 0.2 |
| Met | Ser | ATG | TCG | 15.2 | 20 | 1.5 | 0.3 |
| Met | Ser | ATG | TCT | 24.1 | 19 | -1.1 | -3.0 |
| Met | Umb | ATG | TGA | 0.0 | 1 | 0.0 | 0.0 |
| Met | Cys | ATG | TGC | 11.3 | 10 | -0.1 | -0.1 |
| Met | Trp | ATG | TGG | 22.1 | 21 | -0.1 | 0.0 |
| Met | Cys | ATG | TGT | 8.8 | 10 | 0.2 | 0.2 |
| Met | Leu | ATG | TTA | 18.0 | 11 | -2.7 | -1.1 |
| Met | Phe | ATG | TTC | 41.7 | 36 | -0.8 | -0.3 |
| Met | Leu | ATG | TTG | 20.2 | 28 | 3.0 | 7.1 |
| Met | Phe | ATG | TTT | 32.9 | 35 | 0.1 | 0.4 |
| | Page Totals: | | | 2068.0 | 2076 | 111.5 | 78.1 |

PAGE 15

ECOO.RXD/CPLIST.RXR January 11, 1989

| aa1 | aa2 | cod1 | cod2 | exp | obs | chis1 | chis2 |
|---|---|---|---|---|---|---|---|
| Ile | Lys | ATT | AAA | 72.6 | 75 | 0.1 | 0.0 |
| Ile | Asn | ATT | AAC | 46.8 | 50 | 0.2 | 2.4 |
| Ile | Lys | ATT | AAG | 22.6 | 19 | -0.6 | -0.9 |
| Ile | Asn | ATT | AAT | 32.0 | 28 | -0.5 | -4.9 |
| Ile | Thr | ATT | ACA | 12.4 | 13 | 0.0 | 0.3 |
| Ile | Thr | ATT | ACC | 45.4 | 49 | 0.3 | 0.6 |
| Ile | Thr | ATT | ACG | 22.9 | 21 | -0.2 | -1.6 |
| Ile | Thr | ATT | ACT | 20.4 | 20 | -0.0 | -0.9 |
| Ile | Arg | ATT | AGA | 3.7 | 1 | -1.9 | -2.1 |
| Ile | Ser | ATT | AGC | 30.7 | 24 | -1.5 | -3.4 |
| Ile | Arg | ATT | AGG | 2.3 | 0 | -2.3 | -2.3 |
| Ile | Ser | ATT | AGT | 13.8 | 5 | -5.6 | -7.3 |
| Ile | Ile | ATT | ATA | 6.7 | 4 | -1.1 | -0.3 |
| Ile | Ile | ATT | ATC | 55.6 | 54 | -0.0 | -2.6 |
| Ile | Met | ATT | ATG | 51.3 | 31 | -8.0 | -0.6 |
| Ile | Ile | ATT | ATT | 59.1 | 40 | -6.2 | -0.8 |
| Ile | Gln | ATT | CAA | 25.9 | 8 | -12.4 | -4.2 |
| Ile | His | ATT | CAC | 20.2 | 20 | -0.0 | -0.0 |
| Ile | Gln | ATT | CAG | 58.0 | 59 | 0.0 | 14.0 |
| Ile | His | ATT | CAT | 19.8 | 21 | 0.1 | 0.2 |
| Ile | Pro | ATT | CCA | 15.1 | 14 | -0.1 | -0.3 |
| Ile | Pro | ATT | CCC | 7.4 | 8 | 0.0 | 0.0 |
| Ile | Pro | ATT | CCG | 44.0 | 54 | 2.3 | 0.8 |
| Ile | Pro | ATT | CCT | 11.0 | 18 | 4.5 | 3.1 |
| Ile | Arg | ATT | CGA | 5.0 | 3 | -0.8 | -0.9 |
| Ile | Arg | ATT | CGC | 40.4 | 57 | 6.8 | 5.4 |
| Ile | Arg | ATT | CGG | 6.7 | 5 | -0.4 | -0.6 |
| Ile | Arg | ATT | CGT | 48.4 | 59 | 2.3 | 1.5 |
| Ile | Leu | ATT | CTA | 5.3 | 4 | -0.3 | -0.1 |
| Ile | Leu | ATT | CTC | 18.0 | 28 | 5.6 | 9.6 |
| Ile | Leu | ATT | CTG | 106.3 | 90 | -2.5 | -0.1 |
| Ile | Leu | ATT | CTT | 18.1 | 20 | 0.2 | 1.1 |
| Ile | Glu | ATT | GAA | 86.5 | 106 | 4.4 | 0.3 |
| Ile | Asp | ATT | GAC | 41.7 | 32 | -2.2 | -5.3 |
| Ile | Glu | ATT | GAG | 36.5 | 47 | 3.0 | 0.5 |
| Ile | Asp | ATT | GAT | 59.7 | 66 | 0.7 | 0.1 |
| Ile | Ala | ATT | GCA | 40.7 | 35 | -0.8 | -1.3 |
| Ile | Ala | ATT | GCC | 46.4 | 75 | 17.6 | 14.5 |
| Ile | Ala | ATT | GCG | 64.7 | 47 | -4.8 | -6.3 |
| Ile | Ala | ATT | GCT | 35.9 | 70 | 32.4 | 28.2 |
| Ile | Gly | ATT | GGA | 13.1 | 2 | -9.4 | -10.2 |
| Ile | Gly | ATT | GGC | 55.6 | 70 | 3.7 | 2.0 |
| Ile | Gly | ATT | GGG | 17.2 | 4 | -10.1 | -11.1 |
| Ile | Gly | ATT | GGT | 57.4 | 85 | 13.3 | 9.4 |
| Ile | Val | ATT | GTA | 25.1 | 10 | -9.1 | -7.0 |
| Ile | Val | ATT | GTC | 27.1 | 38 | 4.4 | 7.7 |
| Ile | Val | ATT | GTG | 45.1 | 31 | -4.4 | -2.2 |
| Ile | Val | ATT | GTT | 42.4 | 41 | -0.0 | -0.2 |
| Ile | Ocr | ATT | TAA | 0.0 | 1 | 0.0 | 0.0 |
| Ile | Tyr | ATT | TAC | 24.7 | 18 | -1.8 | -2.2 |
| Ile | Amb | ATT | TAG | 0.0 | 0 | 0.0 | 0.0 |
| Ile | Tyr | ATT | TAT | 29.6 | 32 | 0.2 | 0.1 |
| Ile | Ser | ATT | TCA | 12.4 | 14 | 0.2 | 0.0 |
| Ile | Ser | ATT | TCC | 19.6 | 26 | 2.1 | 0.6 |
| Ile | Ser | ATT | TCG | 15.4 | 19 | 0.9 | 0.1 |
| Ile | Ser | ATT | TCT | 22.3 | 30 | 2.7 | 0.8 |
| Ile | Umb | ATT | TGA | 0.0 | 0 | 0.0 | 0.0 |
| Ile | Cys | ATT | TGC | 10.6 | 17 | 3.9 | 4.2 |
| Ile | Trp | ATT | TGG | 21.2 | 7 | -9.5 | -7.2 |
| Ile | Cys | ATT | TGT | 8.1 | 1 | -6.2 | -6.0 |
| Ile | Leu | ATT | TTA | 22.8 | 19 | -0.6 | -0.1 |
| Ile | Phe | ATT | TTC | 35.6 | 30 | -0.9 | -0.1 |
| Ile | Leu | ATT | TTG | 20.6 | 22 | 0.1 | 0.9 |
| Ile | Phe | ATT | TTT | 34.0 | 27 | -1.4 | 0.0 |
| | Page Totals: | | | 1919.8 | 1924 | 217.6 | 201.7 |

PAGE 16

ECOO.RXD/CPLIST.RXR January 11, 1989

| aa1 | aa2 | cod1 | cod2 | exp | obs | chis1 | chis2 |
|---|---|---|---|---|---|---|---|
| Gln | Lys | CAA | AAA | 37.0 | 46 | 2.2 | 7.7 |
| Gln | Asn | CAA | AAC | 24.4 | 32 | 2.4 | 2.9 |
| Gln | Lys | CAA | AAG | 11.2 | 6 | -2.4 | -1.1 |
| Gln | Asn | CAA | AAT | 17.8 | 24 | 2.2 | 2.6 |
| Gln | Thr | CAA | ACA | 7.1 | 8 | 0.1 | 0.2 |
| Gln | Thr | CAA | ACC | 22.4 | 34 | 6.0 | 6.9 |
| Gln | Thr | CAA | ACG | 12.2 | 19 | 3.8 | 4.3 |
| Gln | Thr | CAA | ACT | 10.0 | 15 | 2.5 | 2.9 |
| Gln | Arg | CAA | AGA | 2.0 | 4 | 2.0 | 1.9 |
| Gln | Ser | CAA | AGC | 16.7 | 15 | -0.2 | -0.0 |
| Gln | Arg | CAA | AGG | 1.2 | 0 | -1.2 | -1.2 |
| Gln | Ser | CAA | AGT | 8.1 | 11 | 1.1 | 1.6 |
| Gln | Ile | CAA | ATA | 4.2 | 8 | 3.4 | 2.6 |
| Gln | Ile | CAA | ATC | 26.1 | 42 | 9.6 | 6.8 |
| Gln | Met | CAA | ATG | 25.1 | 19 | -1.5 | -0.4 |
| Gln | Ile | CAA | ATT | 25.9 | 24 | -0.1 | -0.6 |
| Gln | Gln | CAA | CAA | 18.7 | 41 | 26.6 | 10.9 |
| Gln | His | CAA | CAC | 10.3 | 15 | 2.2 | 1.6 |
| Gln | Gln | CAA | CAG | 31.8 | 35 | 0.3 | 1.1 |
| Gln | His | CAA | CAT | 11.2 | 16 | 2.0 | 1.5 |
| Gln | Pro | CAA | CCA | 8.0 | 9 | 0.1 | 0.2 |
| Gln | Pro | CAA | CCC | 4.5 | 6 | 0.5 | 0.6 |
| Gln | Pro | CAA | CCG | 21.7 | 24 | 0.2 | 0.4 |
| Gln | Pro | CAA | CCT | 6.3 | 9 | 1.2 | 1.3 |
| Gln | Arg | CAA | CGA | 3.0 | 7 | 5.3 | 5.1 |
| Gln | Arg | CAA | CGC | 21.6 | 24 | 0.3 | 0.2 |
| Gln | Arg | CAA | CGG | 4.0 | 4 | 0.0 | 0.0 |
| Gln | Arg | CAA | CGT | 24.8 | 40 | 9.4 | 9.0 |
| Gln | Leu | CAA | CTA | 3.2 | 3 | -0.0 | -0.1 |
| Gln | Leu | CAA | CTC | 9.6 | 21 | 13.7 | 9.3 |
| Gln | Leu | CAA | CTG | 51.7 | 94 | 34.7 | 20.6 |
| Gln | Leu | CAA | CTT | 10.4 | 8 | -0.6 | -1.3 |
| Gln | Glu | CAA | GAA | 44.7 | 21 | -12.6 | -8.7 |
| Gln | Asp | CAA | GAC | 20.6 | 10 | -5.5 | -2.1 |
| Gln | Glu | CAA | GAG | 19.4 | 16 | -0.6 | -0.1 |
| Gln | Asp | CAA | GAT | 31.6 | 14 | -9.8 | -4.3 |
| Gln | Ala | CAA | GCA | 21.5 | 9 | -7.2 | -7.5 |
| Gln | Ala | CAA | GCC | 25.3 | 20 | -1.1 | -1.2 |
| Gln | Ala | CAA | GCG | 33.5 | 23 | -3.3 | -3.5 |
| Gln | Ala | CAA | GCT | 17.9 | 7 | -6.6 | -6.8 |
| Gln | Gly | CAA | GGA | 6.7 | 6 | -0.1 | -0.0 |
| Gln | Gly | CAA | GGC | 28.2 | 15 | -6.2 | -4.5 |
| Gln | Gly | CAA | GGG | 9.4 | 11 | 0.3 | 0.7 |
| Gln | Gly | CAA | GGT | 27.8 | 16 | -5.0 | -3.4 |
| Gln | Val | CAA | GTA | 12.2 | 2 | -8.5 | -8.6 |
| Gln | Val | CAA | GTC | 14.0 | 6 | -4.6 | -4.6 |
| Gln | Val | CAA | GTG | 22.7 | 10 | -7.1 | -7.2 |
| Gln | Val | CAA | GTT | 20.5 | 16 | -1.0 | -1.0 |
| Gln | Ocr | CAA | TAA | 0.0 | 5 | 0.0 | 0.0 |
| Gln | Tyr | CAA | TAC | 12.8 | 13 | 0.0 | 0.6 |
| Gln | Amb | CAA | TAG | 0.0 | 0 | 0.0 | 0.0 |
| Gln | Tyr | CAA | TAT | 15.9 | 19 | 0.6 | 0.1 |
| Gln | Ser | CAA | TCA | 7.2 | 9 | 0.4 | 0.8 |
| Gln | Ser | CAA | TCC | 9.9 | 12 | 0.5 | 0.8 |
| Gln | Ser | CAA | TCG | 7.8 | 6 | -0.4 | -0.2 |
| Gln | Ser | CAA | TCT | 10.9 | 10 | -0.1 | -0.0 |
| Gln | Umb | CAA | TGA | 0.0 | 1 | 0.0 | 0.0 |
| Gln | Cys | CAA | TGC | 5.2 | 2 | -2.0 | -1.0 |
| Gln | Trp | CAA | TGG | 11.8 | 8 | -1.2 | -1.3 |
| Gln | Cys | CAA | TGT | 4.5 | 4 | -0.1 | -0.1 |
| Gln | Leu | CAA | TTA | 13.0 | 8 | -1.9 | -3.2 |
| Gln | Phe | CAA | TTC | 16.3 | 10 | -2.4 | -3.1 |
| Gln | Leu | CAA | TTG | 12.1 | 13 | 0.1 | 0.1 |
| Gln | Phe | CAA | TTT | 17.6 | 11 | -2.5 | -3.2 |
| | Page Totals: | | | 992.9 | 996 | 229.2 | 185.7 |

PAGE 17

ECOO.RXD/CPLIST.RXR January 11, 1989

| aa1 | aa2 | cod1 | cod2 | exp | obs | chis1 | chis2 |
|---|---|---|---|---|---|---|---|
| His | Lys | CAC | AAA | 35.2 | 19 | -7.4 | -4.9 |
| His | Asn | CAC | AAC | 23.9 | 31 | 2.1 | 1.9 |
| His | Lys | CAC | AAG | 11.0 | 8 | -0.8 | -0.4 |
| His | Asn | CAC | AAT | 10.7 | 8 | -0.7 | -0.8 |
| His | Thr | CAC | ACA | 4.2 | 1 | -2.4 | -1.9 |
| His | Thr | CAC | ACC | 22.9 | 28 | 1.2 | 3.4 |
| His | Thr | CAC | ACG | 9.0 | 6 | -1.0 | -0.4 |
| His | Thr | CAC | ACT | 9.9 | 7 | -0.8 | -0.3 |
| His | Arg | CAC | AGA | 1.3 | 1 | -0.1 | -0.0 |
| His | Ser | CAC | AGC | 12.9 | 18 | 2.0 | 2.0 |
| His | Arg | CAC | AGG | 0.5 | 1 | 0.5 | 0.7 |
| His | Ser | CAC | AGT | 4.8 | 3 | -0.6 | -0.7 |
| His | Ile | CAC | ATA | 2.3 | 3 | 0.2 | 0.0 |
| His | Ile | CAC | ATC | 29.2 | 26 | -0.3 | -2.4 |
| His | Met | CAC | ATG | 23.8 | 16 | -2.6 | -4.4 |
| His | Ile | CAC | ATT | 20.2 | 26 | 1.7 | 0.1 |
| His | Gln | CAC | CAA | 10.3 | 5 | -2.7 | -3.7 |
| His | His | CAC | CAC | 15.3 | 14 | -0.1 | -0.1 |
| His | Gln | CAC | CAG | 28.1 | 35 | 1.7 | 0.4 |
| His | His | CAC | CAT | 8.8 | 9 | 0.0 | 0.0 |
| His | Pro | CAC | CCA | 6.1 | 4 | -0.7 | -2.0 |
| His | Pro | CAC | CCC | 2.6 | 4 | 0.8 | 0.1 |
| His | Pro | CAC | CCG | 23.5 | 29 | 1.3 | 0.1 |
| His | Pro | CAC | CCT | 4.5 | 4 | -0.1 | -0.6 |
| His | Arg | CAC | CGA | 1.8 | 0 | -1.8 | -1.6 |
| His | Arg | CAC | CGC | 19.6 | 15 | -1.1 | -0.2 |
| His | Arg | CAC | CGG | 2.5 | 3 | 0.1 | 0.4 |
| His | Arg | CAC | CGT | 27.7 | 23 | -0.8 | -0.0 |
| His | Leu | CAC | CTA | 2.0 | 1 | -0.5 | -0.5 |
| His | Leu | CAC | CTC | 8.2 | 8 | -0.0 | -0.0 |
| His | Leu | CAC | CTG | 53.4 | 49 | -0.4 | -0.2 |
| His | Leu | CAC | CTT | 7.1 | 5 | -0.6 | -0.5 |
| His | Glu | CAC | GAA | 44.1 | 27 | -6.6 | -1.3 |
| His | Asp | CAC | GAC | 23.9 | 27 | 0.4 | 0.4 |
| His | Glu | CAC | GAG | 18.3 | 11 | -2.9 | -0.6 |
| His | Asp | CAC | GAT | 26.9 | 27 | 0.0 | 0.0 |
| His | Ala | CAC | GCA | 18.4 | 13 | -1.6 | -1.3 |
| His | Ala | CAC | GCC | 18.8 | 27 | 3.5 | 4.2 |
| His | Ala | CAC | GCG | 30.0 | 36 | 1.2 | 1.7 |
| His | Ala | CAC | GCT | 17.4 | 19 | 0.2 | 0.3 |
| His | Gly | CAC | GGA | 4.0 | 3 | -0.2 | -0.3 |
| His | Gly | CAC | GGC | 28.2 | 40 | 5.0 | 3.7 |
| His | Gly | CAC | GGG | 6.8 | 8 | 0.2 | 0.1 |
| His | Gly | CAC | GGT | 30.3 | 45 | 7.1 | 5.5 |
| His | Val | CAC | GTA | 12.2 | 13 | 0.1 | 0.1 |
| His | Val | CAC | GTC | 11.6 | 17 | 2.5 | 2.5 |
| His | Val | CAC | GTG | 20.2 | 7 | -8.6 | -8.6 |
| His | Val | CAC | GTT | 22.4 | 31 | 3.3 | 3.3 |
| His | Ocr | CAC | TAA | 0.0 | 1 | 0.0 | 0.0 |
| His | Tyr | CAC | TAC | 13.9 | 22 | 4.7 | 0.8 |
| His | Amb | CAC | TAG | 0.0 | 0 | 0.0 | 0.0 |
| His | Tyr | CAC | TAT | 12.2 | 18 | 2.8 | 0.3 |
| His | Ser | CAC | TCA | 4.2 | 2 | -1.2 | -1.2 |
| His | Ser | CAC | TCC | 10.4 | 14 | 1.3 | 1.2 |
| His | Ser | CAC | TCG | 6.1 | 6 | -0.0 | -0.0 |
| His | Ser | CAC | TCT | 11.2 | 14 | 0.7 | 0.7 |
| His | Umb | CAC | TGA | 0.0 | 0 | 0.0 | 0.0 |
| His | Cys | CAC | TGC | 5.3 | 11 | 6.3 | 5.1 |
| His | Trp | CAC | TGG | 9.6 | 9 | -0.0 | -3.1 |
| His | Cys | CAC | TGT | 4.0 | 0 | -4.0 | -4.2 |
| His | Leu | CAC | TTA | 7.3 | 3 | -2.5 | -2.3 |
| His | Phe | CAC | TTC | 18.6 | 26 | 3.0 | 3.2 |
| His | Leu | CAC | TTG | 8.3 | 5 | -1.3 | -1.2 |
| His | Phe | CAC | TTT | 12.9 | 11 | -0.3 | -0.2 |
| | Page Totals: | | | 900.0 | 903 | 108.6 | 91.8 |

PAGE 18

ECO0.RXD/CPLIST.RXR January 11, 1989

| aa1 | aa2 | cod1 | cod2 | exp | obs | chis1 | chis2 |
|---|---|---|---|---|---|---|---|
| Gln | Lys | CAG | AAA | 93.9 | 64 | -9.5 | -2.4 |
| Gln | Asn | CAG | AAC | 67.1 | 51 | -3.9 | -3.1 |
| Gln | Lys | CAG | AAG | 30.6 | 27 | -0.4 | -0.1 |
| Gln | Asn | CAG | AAT | 33.8 | 32 | -0.1 | -0.0 |
| Gln | Thr | CAG | ACA | 12.6 | 11 | -0.2 | -0.1 |
| Gln | Thr | CAG | ACC | 60.7 | 40 | -7.0 | -6.1 |
| Gln | Thr | CAG | ACG | 26.7 | 21 | -1.2 | -0.9 |
| Gln | Thr | CAG | ACT | 27.5 | 26 | -0.1 | -0.0 |
| Gln | Arg | CAG | AGA | 3.3 | 3 | -0.0 | -0.0 |
| Gln | Ser | CAG | AGC | 38.6 | 34 | -0.5 | -0.1 |
| Gln | Arg | CAG | AGG | 2.1 | 2 | -0.0 | -0.0 |
| Gln | Ser | CAG | AGT | 15.5 | 8 | -3.7 | -2.9 |
| Gln | Ile | CAG | ATA | 6.3 | 11 | 3.6 | 2.7 |
| Gln | Ile | CAG | ATC | 75.4 | 71 | -0.3 | -1.3 |
| Gln | Met | CAG | ATG | 64.5 | 60 | -0.3 | -0.2 |
| Gln | Ile | CAG | ATT | 58.0 | 55 | -0.2 | -0.9 |
| Gln | Gln | CAG | CAA | 31.8 | 55 | 17.0 | 4.2 |
| Gln | His | CAG | CAC | 28.1 | 21 | -1.8 | -2.5 |
| Gln | Gln | CAG | CAG | 89.5 | 95 | 0.3 | 4.4 |
| Gln | His | CAG | CAT | 23.5 | 25 | 0.1 | 0.0 |
| Gln | Pro | CAG | CCA | 17.8 | 17 | -0.0 | -0.0 |
| Gln | Pro | CAG | CCC | 7.7 | 5 | -0.9 | -0.8 |
| Gln | Pro | CAG | CCG | 60.3 | 53 | -0.9 | -0.6 |
| Gln | Pro | CAG | CCT | 12.9 | 13 | 0.0 | 0.0 |
| Gln | Arg | CAG | CGA | 5.9 | 10 | 2.9 | 2.8 |
| Gln | Arg | CAG | CGC | 53.1 | 37 | -4.9 | -5.2 |
| Gln | Arg | CAG | CGG | 8.3 | 5 | -1.3 | -1.4 |
| Gln | Arg | CAG | CGT | 70.8 | 66 | -0.3 | -0.4 |
| Gln | Leu | CAG | CTA | 5.9 | 14 | 11.1 | 7.8 |
| Gln | Leu | CAG | CTC | 22.1 | 26 | 0.7 | 0.0 |
| Gln | Leu | CAG | CTG | 140.9 | 102 | -10.7 | -21.8 |
| Gln | Leu | CAG | CTT | 20.4 | 32 | 6.6 | 3.2 |
| Gln | Glu | CAG | GAA | 118.0 | 125 | 0.4 | 4.1 |
| Gln | Asp | CAG | GAC | 62.7 | 42 | -6.8 | -0.7 |
| Gln | Glu | CAG | GAG | 48.5 | 42 | -0.9 | -0.0 |
| Gln | Asp | CAG | GAT | 74.7 | 79 | 0.2 | 8.4 |
| Gln | Ala | CAG | GCA | 52.0 | 67 | 4.3 | 3.9 |
| Gln | Ala | CAG | GCC | 56.0 | 41 | -4.0 | -4.4 |
| Gln | Ala | CAG | GCG | 83.4 | 131 | 27.2 | 25.5 |
| Gln | Ala | CAG | GCT | 49.8 | 46 | -0.3 | -0.4 |
| Gln | Gly | CAG | GGA | 12.6 | 15 | 0.5 | 1.1 |
| Gln | Gly | CAG | GGC | 74.4 | 89 | 2.9 | 6.7 |
| Gln | Gly | CAG | GGG | 19.0 | 28 | 4.3 | 6.7 |
| Gln | Gly | CAG | GGT | 80.0 | 55 | -7.8 | -4.4 |
| Gln | Val | CAG | GTA | 32.1 | 34 | 0.1 | 0.1 |
| Gln | Val | CAG | GTC | 31.3 | 34 | 0.2 | 0.2 |
| Gln | Val | CAG | GTG | 57.2 | 71 | 3.3 | 3.1 |
| Gln | Val | CAG | GTT | 59.2 | 78 | 6.0 | 5.7 |
| Gln | Ocr | CAG | TAA | 0.0 | 5 | 0.0 | 0.0 |
| Gln | Tyr | CAG | TAC | 36.2 | 45 | 2.1 | 0.0 |
| Gln | Amb | CAG | TAG | 0.0 | 2 | 0.0 | 0.0 |
| Gln | Tyr | CAG | TAT | 33.8 | 48 | 6.0 | 0.6 |
| Gln | Ser | CAG | TCA | 12.8 | 11 | -0.2 | -0.1 |
| Gln | Ser | CAG | TCC | 27.6 | 18 | -3.3 | -2.3 |
| Gln | Ser | CAG | TCG | 18.1 | 16 | -0.2 | -0.0 |
| Gln | Ser | CAG | TCT | 29.6 | 39 | 3.0 | 4.7 |
| Gln | Umb | CAG | TGA | 0.0 | 1 | 0.0 | 0.0 |
| Gln | Cys | CAG | TGC | 13.6 | 16 | 0.4 | 2.7 |
| Gln | Trp | CAG | TGG | 27.0 | 31 | 0.6 | 0.6 |
| Gln | Cys | CAG | TGT | 10.0 | 4 | -3.6 | -1.9 |
| Gln | Leu | CAG | TTA | 22.5 | 25 | 0.3 | 0.0 |
| Gln | Phe | CAG | TTC | 47.0 | 65 | 6.9 | 4.6 |
| Gln | Leu | CAG | TTG | 24.6 | 39 | 8.5 | 4.2 |
| Gln | Phe | CAG | TTT | 37.8 | 40 | 0.1 | 0.0 |
| | Page Totals: | | | 2466.5 | 2474 | 195.1 | 172.8 |

PAGE 19

ECO0.RXD/CPLIST.RXR January 11, 1989

| aa1 | aa2 | cod1 | cod2 | exp | obs | chis1 | chis2 |
|---|---|---|---|---|---|---|---|
| His | Lys | CAT | AAA | 26.1 | 34 | 2.4 | 4.9 |
| His | Asn | CAT | AAC | 17.8 | 20 | 0.3 | 0.2 |
| His | Lys | CAT | AAG | 8.2 | 11 | 0.9 | 1.8 |
| His | Asn | CAT | AAT | 12.6 | 7 | -2.5 | -2.6 |
| His | Thr | CAT | ACA | 4.7 | 3 | -0.6 | -0.3 |
| His | Thr | CAT | ACC | 16.8 | 15 | -0.2 | -0.0 |
| His | Thr | CAT | ACG | 9.4 | 4 | -3.1 | -2.1 |
| His | Thr | CAT | ACT | 7.3 | 9 | 0.4 | 1.1 |
| His | Arg | CAT | AGA | 1.5 | 1 | -0.1 | -0.0 |
| His | Ser | CAT | AGC | 12.5 | 11 | -0.2 | -0.2 |
| His | Arg | CAT | AGG | 0.7 | 0 | -0.7 | -0.6 |
| His | Ser | CAT | AGT | 5.2 | 3 | -0.9 | -1.0 |
| His | Ile | CAT | ATA | 2.8 | 8 | 10.0 | 6.6 |
| His | Ile | CAT | ATC | 19.6 | 27 | 2.8 | 0.5 |
| His | Met | CAT | ATG | 19.6 | 33 | 9.2 | 5.4 |
| His | Ile | CAT | ATT | 19.8 | 23 | 0.5 | 0.0 |
| His | Gln | CAT | CAA | 11.2 | 9 | -0.4 | -1.0 |
| His | His | CAT | CAC | 8.8 | 5 | -1.6 | -1.5 |
| His | Gln | CAT | CAG | 23.5 | 33 | 3.8 | 1.7 |
| His | His | CAT | CAT | 10.9 | 15 | 1.6 | 1.7 |
| His | Pro | CAT | CCA | 5.8 | 5 | -0.1 | -0.9 |
| His | Pro | CAT | CCC | 3.2 | 3 | -0.0 | -0.3 |
| His | Pro | CAT | CCG | 17.7 | 35 | 17.0 | 6.1 |
| His | Pro | CAT | CCT | 4.5 | 5 | 0.0 | 0.2 |
| His | Arg | CAT | CGA | 2.1 | 1 | -0.6 | -0.4 |
| His | Arg | CAT | CGC | 17.2 | 18 | 0.0 | 0.8 |
| His | Arg | CAT | CGG | 3.1 | 5 | 1.2 | 2.1 |
| His | Arg | CAT | CGT | 19.1 | 15 | -0.9 | -0.1 |
| His | Leu | CAT | CTA | 2.4 | 3 | 0.1 | 0.2 |
| His | Leu | CAT | CTC | 7.2 | 3 | -2.4 | -2.3 |
| His | Leu | CAT | CTG | 40.2 | 52 | 3.5 | 4.3 |
| His | Leu | CAT | CTT | 7.4 | 11 | 1.8 | 2.0 |
| His | Glu | CAT | GAA | 33.1 | 30 | -0.3 | -0.9 |
| His | Asp | CAT | GAC | 15.8 | 20 | 1.1 | 1.0 |
| His | Glu | CAT | GAG | 14.9 | 16 | 0.1 | 1.9 |
| His | Asp | CAT | GAT | 23.7 | 17 | -1.9 | -2.0 |
| His | Ala | CAT | GCA | 14.7 | 13 | -0.2 | -0.1 |
| His | Ala | CAT | GCC | 18.5 | 17 | -0.1 | -0.0 |
| His | Ala | CAT | GCG | 24.6 | 14 | -4.5 | -4.0 |
| His | Ala | CAT | GCT | 12.5 | 11 | -0.2 | -0.1 |
| His | Gly | CAT | GGA | 5.0 | 1 | -3.2 | -3.4 |
| His | Gly | CAT | GGC | 21.2 | 16 | -1.3 | -1.8 |
| His | Gly | CAT | GGG | 7.2 | 1 | -5.3 | -5.7 |
| His | Gly | CAT | GGT | 21.4 | 16 | -1.3 | -1.8 |
| His | Val | CAT | GTA | 9.2 | 12 | 0.9 | 0.9 |
| His | Val | CAT | GTC | 10.4 | 9 | -0.2 | -0.2 |
| His | Val | CAT | GTG | 17.6 | 20 | 0.3 | 0.3 |
| His | Val | CAT | GTT | 15.3 | 10 | -1.8 | -1.8 |
| His | Ocr | CAT | TAA | 0.0 | 4 | 0.0 | 0.0 |
| His | Tyr | CAT | TAC | 10.0 | 11 | 0.1 | 0.3 |
| His | Amb | CAT | TAG | 0.0 | 0 | 0.0 | 0.0 |
| His | Tyr | CAT | TAT | 12.3 | 12 | -0.0 | -1.0 |
| His | Ser | CAT | TCA | 5.3 | 7 | 0.6 | 0.6 |
| His | Ser | CAT | TCC | 7.2 | 4 | -1.5 | -1.5 |
| His | Ser | CAT | TCG | 6.0 | 5 | -0.2 | -0.2 |
| His | Ser | CAT | TCT | 7.7 | 7 | -0.1 | -0.1 |
| His | Umb | CAT | TGA | 0.0 | 0 | 0.0 | 0.0 |
| His | Cys | CAT | TGC | 4.9 | 7 | 0.9 | 0.6 |
| His | Trp | CAT | TGG | 9.4 | 1 | -7.5 | -3.2 |
| His | Cys | CAT | TGT | 3.6 | 1 | -1.9 | -2.1 |
| His | Leu | CAT | TTA | 9.2 | 9 | -0.0 | -0.0 |
| His | Phe | CAT | TTC | 13.7 | 13 | -0.0 | -0.0 |
| His | Leu | CAT | TTG | 9.1 | 8 | -0.1 | -0.1 |
| His | Phe | CAT | TTT | 13.4 | 8 | -2.2 | -2.1 |
| | Page Totals: | | | 745.7 | 747 | 107.8 | 90.6 |

PAGE 20

ECOO.RXD/CPLIST.RXR January 11, 1989

| aa1 | aa2 | cod1 | cod2 | exp | obs | chis1 | chis2 |
|---|---|---|---|---|---|---|---|
| Pro | Lys | CCA | AAA | 22.7 | 22 | -0.0 | -0.1 |
| Pro | Asn | CCA | AAC | 14.8 | 10 | -1.5 | -1.2 |
| Pro | Lys | CCA | AAG | 7.0 | 4 | -1.2 | -0.9 |
| Pro | Asn | CCA | AAT | 9.9 | 13 | 1.0 | 1.4 |
| Pro | Thr | CCA | ACA | 3.6 | 6 | 1.5 | 1.6 |
| Pro | Thr | CCA | ACC | 13.2 | 13 | -0.0 | -0.0 |
| Pro | Thr | CCA | ACG | 6.7 | 12 | 4.3 | 4.6 |
| Pro | Thr | CCA | ACT | 6.3 | 9 | 1.2 | 1.3 |
| Pro | Arg | CCA | AGA | 1.5 | 0 | -1.5 | -1.2 |
| Pro | Ser | CCA | AGC | 8.7 | 8 | -0.1 | -0.0 |
| Pro | Arg | CCA | AGG | 0.6 | 0 | -0.6 | -0.5 |
| Pro | Ser | CCA | AGT | 3.9 | 4 | 0.0 | 0.0 |
| Pro | Ile | CCA | ATA | 2.6 | 3 | 0.1 | 0.2 |
| Pro | Ile | CCA | ATC | 16.3 | 19 | 0.4 | 1.0 |
| Pro | Met | CCA | ATG | 15.1 | 23 | 4.1 | 4.7 |
| Pro | Ile | CCA | ATT | 15.1 | 10 | -1.7 | -1.1 |
| Pro | Gln | CCA | CAA | 8.0 | 20 | 17.8 | 18.5 |
| Pro | His | CCA | CAC | 6.1 | 10 | 2.5 | 2.6 |
| Pro | Gln | CCA | CAG | 17.8 | 15 | -0.4 | -0.4 |
| Pro | His | CCA | CAT | 5.8 | 2 | -2.5 | -2.5 |
| Pro | Pro | CCA | CCA | 7.2 | 5 | -0.7 | -0.0 |
| Pro | Pro | CCA | CCC | 2.4 | 0 | -2.4 | -1.8 |
| Pro | Pro | CCA | CCG | 13.8 | 8 | -2.4 | -0.4 |
| Pro | Pro | CCA | CCT | 3.8 | 0 | -3.8 | -2.7 |
| Pro | Arg | CCA | CGA | 1.5 | 2 | 0.2 | 0.6 |
| Pro | Arg | CCA | CGC | 12.4 | 16 | 1.1 | 4.6 |
| Pro | Arg | CCA | CGG | 2.2 | 2 | -0.0 | -0.1 |
| Pro | Arg | CCA | CGT | 14.6 | 8 | -3.0 | -0.9 |
| Pro | Leu | CCA | CTA | 1.6 | 1 | -0.2 | -0.2 |
| Pro | Leu | CCA | CTC | 5.4 | 5 | -0.0 | -0.0 |
| Pro | Leu | CCA | CTG | 31.0 | 15 | -8.3 | -8.0 |
| Pro | Leu | CCA | CTT | 5.5 | 7 | 0.4 | 0.5 |
| Pro | Glu | CCA | GAA | 26.2 | 44 | 12.1 | 3.6 |
| Pro | Asp | CCA | GAC | 12.6 | 9 | -1.0 | -0.9 |
| Pro | Glu | CCA | GAG | 10.9 | 18 | 4.6 | 1.3 |
| Pro | Asp | CCA | GAT | 18.0 | 10 | -3.5 | -3.2 |
| Pro | Ala | CCA | GCA | 12.0 | 11 | -0.1 | -0.1 |
| Pro | Ala | CCA | GCC | 13.1 | 12 | -0.1 | -0.1 |
| Pro | Ala | CCA | GCG | 18.6 | 14 | -1.2 | -1.3 |
| Pro | Ala | CCA | GCT | 10.6 | 11 | 0.0 | 0.0 |
| Pro | Gly | CCA | GGA | 3.9 | 11 | 12.8 | 12.4 |
| Pro | Gly | CCA | GGC | 16.4 | 13 | -0.7 | -0.8 |
| Pro | Gly | CCA | GGG | 4.7 | 8 | 2.3 | 2.1 |
| Pro | Gly | CCA | GGT | 17.5 | 19 | 0.1 | 0.1 |
| Pro | Val | CCA | GTA | 7.6 | 13 | 3.8 | 1.3 |
| Pro | Val | CCA | GTC | 7.9 | 5 | -1.1 | -2.4 |
| Pro | Val | CCA | GTG | 13.0 | 13 | 0.0 | -0.6 |
| Pro | Val | CCA | GTT | 13.3 | 10 | -0.8 | -2.6 |
| Pro | Ocr | CCA | TAA | 0.0 | 0 | 0.0 | 0.0 |
| Pro | Tyr | CCA | TAC | 8.0 | 9 | 0.1 | 0.0 |
| Pro | Amb | CCA | TAG | 0.0 | 0 | 0.0 | 0.0 |
| Pro | Tyr | CCA | TAT | 9.6 | 9 | -0.0 | -0.2 |
| Pro | Ser | CCA | TCA | 4.0 | 6 | 1.0 | 1.1 |
| Pro | Ser | CCA | TCC | 6.2 | 6 | -0.0 | -0.0 |
| Pro | Ser | CCA | TCG | 4.2 | 3 | -0.3 | -0.3 |
| Pro | Ser | CCA | TCT | 6.5 | 5 | -0.3 | -0.3 |
| Pro | Umb | CCA | TGA | 0.0 | 0 | 0.0 | 0.0 |
| Pro | Cys | CCA | TGC | 3.4 | 4 | 0.1 | 0.2 |
| Pro | Trp | CCA | TGG | 6.7 | 1 | -4.9 | -5.5 |
| Pro | Cys | CCA | TGT | 2.7 | 0 | -2.7 | -2.5 |
| Pro | Leu | CCA | TTA | 6.9 | 15 | 9.6 | 9.9 |
| Pro | Phe | CCA | TTC | 10.8 | 3 | -5.7 | -6.7 |
| Pro | Leu | CCA | TTG | 6.4 | 15 | 11.6 | 12.0 |
| Pro | Phe | CCA | TTT | 10.2 | 12 | 0.3 | 0.1 |
| | Page Totals: | | | 578.9 | 581 | 146.0 | 134.9 |

PAGE 21

ECOO.RXD/CPLIST.RXR January 11, 1989

| aa1 | aa2 | cod1 | cod2 | exp | obs | chis1 | chis2 |
|---|---|---|---|---|---|---|---|
| Pro | Lys | CCC | AAA | 8.9 | 11 | 0.5 | 1.0 |
| Pro | Asn | CCC | AAC | 5.7 | 5 | -0.1 | -0.0 |
| Pro | Lys | CCC | AAG | 2.9 | 2 | -0.3 | -0.2 |
| Pro | Asn | CCC | AAT | 5.0 | 8 | 1.8 | 2.2 |
| Pro | Thr | CCC | ACA | 2.3 | 4 | 1.3 | 1.4 |
| Pro | Thr | CCC | ACC | 5.6 | 2 | -2.3 | -2.2 |
| Pro | Thr | CCC | ACG | 3.6 | 4 | 0.1 | 0.1 |
| Pro | Thr | CCC | ACT | 2.4 | 1 | -0.8 | -0.8 |
| Pro | Arg | CCC | AGA | 0.9 | 2 | 1.6 | 2.8 |
| Pro | Ser | CCC | AGC | 4.5 | 4 | -0.1 | -0.0 |
| Pro | Arg | CCC | AGG | 0.4 | 1 | 1.2 | 2.0 |
| Pro | Ser | CCC | AGT | 2.4 | 1 | -0.8 | -0.8 |
| Pro | Ile | CCC | ATA | 1.5 | 1 | -0.2 | -0.1 |
| Pro | Ile | CCC | ATC | 6.0 | 12 | 6.1 | 7.7 |
| Pro | Met | CCC | ATG | 6.5 | 3 | -1.9 | -1.8 |
| Pro | Ile | CCC | ATT | 7.4 | 9 | 0.3 | 0.7 |
| Pro | Gln | CCC | CAA | 4.5 | 1 | -2.7 | -2.7 |
| Pro | His | CCC | CAC | 2.6 | 2 | -0.1 | -0.1 |
| Pro | Gln | CCC | CAG | 7.7 | 4 | -1.8 | -1.7 |
| Pro | His | CCC | CAT | 3.2 | 3 | -0.0 | -0.0 |
| Pro | Pro | CCC | CCA | 2.4 | 4 | 1.0 | 2.9 |
| Pro | Pro | CCC | CCC | 2.5 | 1 | -0.9 | -0.4 |
| Pro | Pro | CCC | CCG | 5.6 | 2 | -2.3 | -1.0 |
| Pro | Pro | CCC | CCT | 1.9 | 2 | 0.0 | 0.3 |
| Pro | Arg | CCC | CGA | 0.8 | 0 | -0.8 | -0.6 |
| Pro | Arg | CCC | CGC | 6.2 | 3 | -1.7 | -0.6 |
| Pro | Arg | CCC | CGG | 1.5 | 0 | -1.5 | -1.2 |
| Pro | Arg | CCC | CGT | 5.4 | 4 | -0.4 | -0.0 |
| Pro | Leu | CCC | CTA | 1.0 | 0 | -1.0 | -1.0 |
| Pro | Leu | CCC | CTC | 2.9 | 2 | -0.3 | -0.3 |
| Pro | Leu | CCC | CTG | 12.9 | 5 | -4.9 | -4.7 |
| Pro | Leu | CCC | CTT | 3.0 | 2 | -0.3 | -0.3 |
| Pro | Glu | CCC | GAA | 10.9 | 6 | -2.2 | -4.3 |
| Pro | Asp | CCC | GAC | 4.6 | 7 | 1.2 | 1.4 |
| Pro | Glu | CCC | GAG | 5.3 | 2 | -2.0 | -3.3 |
| Pro | Asp | CCC | GAT | 8.3 | 12 | 1.7 | 1.9 |
| Pro | Ala | CCC | GCA | 5.6 | 8 | 1.0 | 0.9 |
| Pro | Ala | CCC | GCC | 6.8 | 8 | 0.2 | 0.2 |
| Pro | Ala | CCC | GCG | 8.8 | 3 | -3.8 | -4.0 |
| Pro | Ala | CCC | GCT | 4.1 | 14 | 24.0 | 23.1 |
| Pro | Gly | CCC | GGA | 2.1 | 3 | 0.4 | 0.3 |
| Pro | Gly | CCC | GGC | 7.0 | 14 | 7.1 | 6.8 |
| Pro | Gly | CCC | GGG | 2.6 | 1 | -1.0 | -1.0 |
| Pro | Gly | CCC | GGT | 6.2 | 9 | 1.3 | 1.2 |
| Pro | Val | CCC | GTA | 3.1 | 3 | -0.0 | -0.2 |
| Pro | Val | CCC | GTC | 4.1 | 5 | 0.2 | 0.0 |
| Pro | Val | CCC | GTG | 6.1 | 3 | -1.6 | -2.8 |
| Pro | Val | CCC | GTT | 4.9 | 4 | -0.2 | -0.7 |
| Pro | Ocr | CCC | TAA | 0.0 | 0 | 0.0 | 0.0 |
| Pro | Tyr | CCC | TAC | 3.2 | 6 | 2.6 | 1.9 |
| Pro | Amb | CCC | TAG | 0.0 | 0 | 0.0 | 0.0 |
| Pro | Tyr | CCC | TAT | 4.6 | 7 | 1.2 | 0.7 |
| Pro | Ser | CCC | TCA | 2.0 | 4 | 2.0 | 2.1 |
| Pro | Ser | CCC | TCC | 2.3 | 2 | -0.0 | -0.0 |
| Pro | Ser | CCC | TCG | 2.2 | 2 | -0.0 | -0.0 |
| Pro | Ser | CCC | TCT | 2.7 | 3 | 0.0 | 0.1 |
| Pro | Umb | CCC | TGA | 0.0 | 2 | 0.0 | 0.0 |
| Pro | Cys | CCC | TGC | 1.5 | 4 | 4.1 | 4.5 |
| Pro | Trp | CCC | TGG | 3.3 | 8 | 6.8 | 5.5 |
| Pro | Cys | CCC | TGT | 1.4 | 3 | 1.9 | 2.1 |
| Pro | Leu | CCC | TTA | 4.3 | 2 | -1.2 | -1.2 |
| Pro | Phe | CCC | TTC | 4.1 | 8 | 3.7 | 2.7 |
| Pro | Leu | CCC | TTG | 3.6 | 2 | -0.7 | -0.7 |
| Pro | Phe | CCC | TTT | 5.7 | 2 | -2.4 | -2.9 |
| | Page Totals: | | | 261.0 | 262 | 113.5 | 117.8 |

PAGE 22

ECOO.RXD/CPLIST.RXR January 11, 1989

| aa1 | aa2 | cod1 | cod2 | exp | obs | chis1 | chis2 |
|---|---|---|---|---|---|---|---|
| Pro | Lys | CCG | AAA | 73.6 | 69 | -0.3 | -0.0 |
| Pro | Asn | CCG | AAC | 51.8 | 52 | 0.0 | 0.1 |
| Pro | Lys | CCG | AAG | 23.7 | 27 | 0.5 | 1.2 |
| Pro | Asn | CCG | AAT | 22.3 | 17 | -1.3 | -0.9 |
| Pro | Thr | CCG | ACA | 8.3 | 9 | 0.1 | 0.1 |
| Pro | Thr | CCG | ACC | 49.4 | 46 | -0.2 | -0.1 |
| Pro | Thr | CCG | ACG | 20.0 | 22 | 0.2 | 0.3 |
| Pro | Thr | CCG | ACT | 21.0 | 27 | 1.7 | 2.0 |
| Pro | Arg | CCG | AGA | 1.8 | 0 | -1.8 | -1.4 |
| Pro | Ser | CCG | AGC | 28.4 | 17 | -4.6 | -4.3 |
| Pro | Arg | CCG | AGG | 1.0 | 1 | -0.0 | -0.1 |
| Pro | Ser | CCG | AGT | 9.6 | 4 | -3.3 | -3.1 |
| Pro | Ile | CCG | ATA | 3.3 | 4 | 0.1 | 0.3 |
| Pro | Ile | CCG | ATC | 62.1 | 45 | -4.7 | -2.7 |
| Pro | Met | CCG | ATG | 51.7 | 52 | 0.0 | 0.1 |
| Pro | Ile | CCG | ATT | 44.0 | 50 | 0.8 | 2.1 |
| Pro | Gln | CCG | CAA | 21.7 | 29 | 2.5 | 2.7 |
| Pro | His | CCG | CAC | 23.5 | 24 | 0.0 | 0.0 |
| Pro | Gln | CCG | CAG | 60.3 | 59 | -0.0 | -0.0 |
| Pro | His | CCG | CAT | 17.7 | 22 | 1.1 | 1.2 |
| Pro | Pro | CCG | CCA | 13.8 | 27 | 12.6 | 29.3 |
| Pro | Pro | CCG | CCC | 5.6 | 2 | -2.3 | -1.0 |
| Pro | Pro | CCG | CCG | 58.7 | 34 | -10.4 | -1.6 |
| Pro | Pro | CCG | CCT | 9.8 | 8 | -0.3 | -0.1 |
| Pro | Arg | CCG | CGA | 3.7 | 1 | -2.0 | -1.2 |
| Pro | Arg | CCG | CGC | 41.8 | 39 | -0.2 | -1.6 |
| Pro | Arg | CCG | CGG | 5.3 | 1 | -3.5 | -2.3 |
| Pro | Arg | CCG | CGT | 56.8 | 42 | -3.8 | -0.0 |
| Pro | Leu | CCG | CTA | 4.2 | 9 | 5.6 | 5.8 |
| Pro | Leu | CCG | CTC | 16.6 | 9 | -3.5 | -3.4 |
| Pro | Leu | CCG | CTG | 114.3 | 148 | 9.9 | 10.8 |
| Pro | Leu | CCG | CTT | 14.1 | 9 | -1.9 | -1.8 |
| Pro | Glu | CCG | GAA | 92.6 | 129 | 14.4 | 1.3 |
| Pro | Asp | CCG | GAC | 49.3 | 27 | -10.1 | -9.2 |
| Pro | Glu | CCG | GAG | 36.9 | 23 | -5.2 | -11.9 |
| Pro | Asp | CCG | GAT | 56.0 | 65 | 1.4 | 2.0 |
| Pro | Ala | CCG | GCA | 38.4 | 59 | 11.0 | 10.0 |
| Pro | Ala | CCG | GCC | 40.4 | 16 | -14.8 | -15.4 |
| Pro | Ala | CCG | GCG | 65.6 | 46 | -5.8 | -6.5 |
| Pro | Ala | CCG | GCT | 37.6 | 36 | -0.1 | -0.1 |
| Pro | Gly | CCG | GGA | 8.3 | 13 | 2.7 | 2.5 |
| Pro | Gly | CCG | GGC | 59.0 | 39 | -6.8 | -7.3 |
| Pro | Gly | CCG | GGG | 14.0 | 15 | 0.1 | 0.0 |
| Pro | Gly | CCG | GGT | 62.9 | 45 | -5.1 | -5.6 |
| Pro | Val | CCG | GTA | 26.1 | 51 | 23.7 | 10.7 |
| Pro | Val | CCG | GTC | 23.4 | 20 | -0.5 | -2.8 |
| Pro | Val | CCG | GTG | 46.0 | 61 | 4.9 | 0.3 |
| Pro | Val | CCG | GTT | 46.3 | 64 | 6.8 | 0.8 |
| Pro | Ocr | CCG | TAA | 0.0 | 0 | 0.0 | 0.0 |
| Pro | Tyr | CCG | TAC | 28.7 | 28 | -0.0 | -0.4 |
| Pro | Amb | CCG | TAG | 0.0 | 0 | 0.0 | 0.0 |
| Pro | Tyr | CCG | TAT | 25.3 | 14 | -5.1 | -6.8 |
| Pro | Ser | CCG | TCA | 8.9 | 16 | 5.8 | 6.1 |
| Pro | Ser | CCG | TCC | 21.6 | 22 | 0.0 | 0.0 |
| Pro | Ser | CCG | TCG | 13.3 | 14 | 0.0 | 0.1 |
| Pro | Ser | CCG | TCT | 22.3 | 28 | 1.5 | 1.7 |
| Pro | Umb | CCG | TGA | 0.0 | 1 | 0.0 | 0.0 |
| Pro | Cys | CCG | TGC | 11.2 | 10 | -0.1 | -0.1 |
| Pro | Trp | CCG | TGG | 20.3 | 29 | 3.7 | 2.1 |
| Pro | Cys | CCG | TGT | 8.1 | 3 | -3.2 | -2.9 |
| Pro | Leu | CCG | TTA | 14.8 | 12 | -0.5 | -0.5 |
| Pro | Phe | CCG | TTC | 39.4 | 50 | 2.8 | 1.0 |
| Pro | Leu | CCG | TTG | 17.2 | 27 | 5.6 | 5.9 |
| Pro | Phe | CCG | TTT | 27.5 | 37 | 3.3 | 1.5 |
| | | Page Totals: | | 1901.2 | 1905 | 224.1 | 197.0 |

PAGE 23

ECOO.RXD/CPLIST.RXR January 11, 1989

| aa1 | aa2 | cod1 | cod2 | exp | obs | chis1 | chis2 |
|---|---|---|---|---|---|---|---|
| Pro | Lys | CCT | AAA | 16.3 | 8 | -4.2 | -3.2 |
| Pro | Asn | CCT | AAC | 10.3 | 14 | 1.3 | 1.7 |
| Pro | Lys | CCT | AAG | 5.1 | 4 | -0.2 | -0.1 |
| Pro | Asn | CCT | AAT | 6.8 | 2 | -3.4 | -3.1 |
| Pro | Thr | CCT | ACA | 2.8 | 1 | -1.2 | -1.2 |
| Pro | Thr | CCT | ACC | 9.4 | 4 | -3.1 | -2.9 |
| Pro | Thr | CCT | ACG | 5.0 | 1 | -3.2 | -3.1 |
| Pro | Thr | CCT | ACT | 4.4 | 0 | -4.4 | -4.3 |
| Pro | Arg | CCT | AGA | 0.9 | 0 | -0.9 | -0.7 |
| Pro | Ser | CCT | AGC | 6.6 | 0 | -6.6 | -6.5 |
| Pro | Arg | CCT | AGG | 0.5 | 0 | -0.5 | -0.3 |
| Pro | Ser | CCT | AGT | 3.0 | 0 | -3.0 | -2.9 |
| Pro | Ile | CCT | ATA | 1.8 | 0 | -1.8 | -1.7 |
| Pro | Ile | CCT | ATC | 11.9 | 9 | -0.7 | -0.4 |
| Pro | Met | CCT | ATG | 11.0 | 4 | -4.4 | -4.2 |
| Pro | Ile | CCT | ATT | 11.0 | 7 | -1.4 | -1.0 |
| Pro | Gln | CCT | CAA | 6.3 | 3 | -1.7 | -1.6 |
| Pro | His | CCT | CAC | 4.5 | 2 | -1.4 | -1.4 |
| Pro | Gln | CCT | CAG | 12.9 | 6 | -3.7 | -3.5 |
| Pro | His | CCT | CAT | 4.5 | 2 | -1.4 | -1.4 |
| Pro | Pro | CCT | CCA | 3.8 | 4 | 0.0 | 0.6 |
| Pro | Pro | CCT | CCC | 1.9 | 2 | 0.0 | 0.3 |
| Pro | Pro | CCT | CCG | 9.8 | 6 | -1.4 | -0.1 |
| Pro | Pro | CCT | CCT | 4.5 | 1 | -2.7 | -1.5 |
| Pro | Arg | CCT | CGA | 1.3 | 0 | -1.3 | -1.0 |
| Pro | Arg | CCT | CGC | 8.7 | 11 | 0.6 | 2.9 |
| Pro | Arg | CCT | CGG | 1.7 | 0 | -1.7 | -1.3 |
| Pro | Arg | CCT | CGT | 10.9 | 6 | -2.2 | -0.6 |
| Pro | Leu | CCT | CTA | 1.4 | 0 | -1.4 | -1.3 |
| Pro | Leu | CCT | CTC | 4.0 | 1 | -2.3 | -2.2 |
| Pro | Leu | CCT | CTG | 22.8 | 7 | -10.9 | -10.7 |
| Pro | Leu | CCT | CTT | 4.4 | 6 | 0.6 | 0.6 |
| Pro | Glu | CCT | GAA | 19.1 | 27 | 3.2 | 0.3 |
| Pro | Asp | CCT | GAC | 8.8 | 18 | 9.6 | 10.4 |
| Pro | Glu | CCT | GAG | 8.2 | 16 | 7.4 | 3.1 |
| Pro | Asp | CCT | GAT | 12.9 | 18 | 2.0 | 2.4 |
| Pro | Ala | CCT | GCA | 9.2 | 13 | 1.6 | 1.4 |
| Pro | Ala | CCT | GCC | 9.5 | 15 | 3.2 | 3.0 |
| Pro | Ala | CCT | GCG | 13.1 | 25 | 10.9 | 10.2 |
| Pro | Ala | CCT | GCT | 7.9 | 16 | 8.4 | 7.9 |
| Pro | Gly | CCT | GGA | 2.5 | 4 | 0.9 | 0.8 |
| Pro | Gly | CCT | GGC | 12.0 | 25 | 14.2 | 13.6 |
| Pro | Gly | CCT | GGG | 3.9 | 4 | 0.0 | 0.0 |
| Pro | Gly | CCT | GGT | 13.1 | 17 | 1.1 | 1.0 |
| Pro | Val | CCT | GTA | 5.7 | 6 | 0.0 | 0.1 |
| Pro | Val | CCT | GTC | 5.8 | 7 | 0.3 | 0.0 |
| Pro | Val | CCT | GTG | 10.0 | 9 | -0.1 | -0.9 |
| Pro | Val | CCT | GTT | 9.1 | 14 | 2.6 | 0.7 |
| Pro | Ocr | CCT | TAA | 0.0 | 0 | 0.0 | 0.0 |
| Pro | Tyr | CCT | TAC | 5.7 | 11 | 5.1 | 3.8 |
| Pro | Amb | CCT | TAG | 0.0 | 0 | 0.0 | 0.0 |
| Pro | Tyr | CCT | TAT | 6.4 | 16 | 14.5 | 11.7 |
| Pro | Ser | CCT | TCA | 3.0 | 3 | 0.0 | 0.0 |
| Pro | Ser | CCT | TCC | 4.2 | 11 | 11.1 | 11.5 |
| Pro | Ser | CCT | TCG | 2.9 | 1 | -1.2 | -1.2 |
| Pro | Ser | CCT | TCT | 4.8 | 11 | 8.1 | 8.4 |
| Pro | Umb | CCT | TGA | 0.0 | 0 | 0.0 | 0.0 |
| Pro | Cys | CCT | TGC | 2.4 | 5 | 2.8 | 3.2 |
| Pro | Trp | CCT | TGG | 5.4 | 1 | -3.5 | -4.0 |
| Pro | Cys | CCT | TGT | 1.9 | 2 | 0.0 | 0.0 |
| Pro | Leu | CCT | TTA | 5.5 | 5 | -0.0 | -0.0 |
| Pro | Phe | CCT | TTC | 7.6 | 6 | -0.3 | -0.6 |
| Pro | Leu | CCT | TTG | 4.9 | 1 | -3.1 | -3.0 |
| Pro | Phe | CCT | TTT | 7.5 | 6 | -0.3 | -0.6 |
| | | Page Totals: | | 422.6 | 424 | 189.4 | 172.5 |

PAGE 24

ECOU.RXD/CPLIST.RXR January 11, 1989

| aa1 | aa2 | cod1 | cod2 | exp | obs | chis1 | chis2 |
|---|---|---|---|---|---|---|---|
| Arg | Lys | CGA | AAA | 6.3 | 7 | 0.1 | 0.1 |
| Arg | Asn | CGA | AAC | 4.1 | 5 | 0.2 | 0.2 |
| Arg | Lys | CGA | AAG | 2.3 | 5 | 3.0 | 3.1 |
| Arg | Asn | CGA | AAT | 3.4 | 4 | 0.1 | 0.1 |
| Arg | Thr | CGA | ACA | 1.4 | 1 | -0.1 | -0.1 |
| Arg | Thr | CGA | ACC | 3.7 | 1 | -1.9 | -1.7 |
| Arg | Thr | CGA | ACG | 2.2 | 2 | -0.0 | -0.0 |
| Arg | Thr | CGA | ACT | 1.8 | 0 | -1.8 | -1.7 |
| Arg | Arg | CGA | AGA | 0.4 | 0 | -0.4 | -0.4 |
| Arg | Ser | CGA | AGC | 3.0 | 4 | 0.4 | 1.0 |
| Arg | Arg | CGA | AGG | 0.5 | 0 | -0.5 | -0.4 |
| Arg | Ser | CGA | AGT | 2.0 | 1 | -0.5 | -0.2 |
| Arg | Ile | CGA | ATA | 1.0 | 1 | 0.0 | 0.0 |
| Arg | Ile | CGA | ATC | 4.6 | 1 | -2.9 | -3.0 |
| Arg | Met | CGA | ATG | 4.7 | 2 | -1.5 | -1.0 |
| Arg | Ile | CGA | ATT | 5.0 | 14 | 16.5 | 15.2 |
| Arg | Gln | CGA | CAA | 3.0 | 1 | -1.3 | -2.1 |
| Arg | His | CGA | CAC | 1.8 | 1 | -0.4 | -0.7 |
| Arg | Gln | CGA | CAG | 5.9 | 5 | -0.1 | -0.8 |
| Arg | His | CGA | CAT | 2.1 | 6 | 7.0 | 4.1 |
| Arg | Pro | CGA | CCA | 1.5 | 1 | -0.2 | -0.1 |
| Arg | Pro | CGA | CCC | 0.8 | 1 | 0.0 | 0.1 |
| Arg | Pro | CGA | CCG | 3.7 | 6 | 1.4 | 1.9 |
| Arg | Pro | CGA | CCT | 1.3 | 2 | 0.4 | 0.5 |
| Arg | Arg | CGA | CGA | 1.5 | 0 | -1.5 | -1.3 |
| Arg | Arg | CGA | CGC | 4.0 | 7 | 2.2 | 3.1 |
| Arg | Arg | CGA | CGG | 1.0 | 1 | 0.0 | 0.0 |
| Arg | Arg | CGA | CGT | 4.3 | 2 | -1.3 | -0.9 |
| Arg | Leu | CGA | CTA | 0.6 | 0 | -0.6 | -0.7 |
| Arg | Leu | CGA | CTC | 2.0 | 2 | -0.0 | -0.0 |
| Arg | Leu | CGA | CTG | 8.7 | 12 | 1.2 | 0.8 |
| Arg | Leu | CGA | CTT | 2.1 | 1 | -0.6 | -0.7 |
| Arg | Glu | CGA | GAA | 7.5 | 3 | -2.7 | -3.4 |
| Arg | Asp | CGA | GAC | 3.5 | 1 | -1.8 | -1.4 |
| Arg | Glu | CGA | GAG | 3.9 | 0 | -3.8 | -4.2 |
| Arg | Asp | CGA | GAT | 5.4 | 3 | -1.1 | -0.7 |
| Arg | Ala | CGA | GCA | 3.7 | 5 | 0.4 | 0.8 |
| Arg | Ala | CGA | GCC | 5.0 | 2 | -1.8 | -1.4 |
| Arg | Ala | CGA | GCG | 6.2 | 3 | -1.7 | -1.2 |
| Arg | Ala | CGA | GCT | 2.9 | 4 | 0.4 | 0.7 |
| Arg | Gly | CGA | GGA | 1.5 | 2 | 0.2 | 0.3 |
| Arg | Gly | CGA | GGC | 4.6 | 3 | -0.5 | -0.3 |
| Arg | Gly | CGA | GGG | 1.8 | 3 | 0.8 | 1.2 |
| Arg | Gly | CGA | GGT | 4.3 | 0 | -4.3 | -3.9 |
| Arg | Val | CGA | GTA | 2.2 | 3 | 0.3 | 0.2 |
| Arg | Val | CGA | GTC | 2.7 | 2 | -0.2 | -0.2 |
| Arg | Val | CGA | GTG | 4.4 | 3 | -0.4 | -0.6 |
| Arg | Val | CGA | GTT | 3.5 | 2 | -0.7 | -0.8 |
| Arg | Ocr | CGA | TAA | 0.0 | 1 | 0.0 | 0.0 |
| Arg | Tyr | CGA | TAC | 2.0 | 1 | -0.5 | -0.6 |
| Arg | Amb | CGA | TAG | 0.0 | 0 | 0.0 | 0.0 |
| Arg | Tyr | CGA | TAT | 2.8 | 2 | -0.2 | -0.3 |
| Arg | Ser | CGA | TCA | 1.6 | 1 | -0.2 | -0.1 |
| Arg | Ser | CGA | TCC | 1.7 | 3 | 1.0 | 1.9 |
| Arg | Ser | CGA | TCG | 1.7 | 1 | -0.3 | -0.1 |
| Arg | Ser | CGA | TCT | 2.2 | 4 | 1.6 | 2.9 |
| Arg | Umb | CGA | TGA | 0.0 | 1 | 0.0 | 0.0 |
| Arg | Cys | CGA | TGC | 1.2 | 1 | -0.0 | -0.0 |
| Arg | Trp | CGA | TGG | 2.1 | 3 | 0.4 | 0.0 |
| Arg | Cys | CGA | TGT | 0.8 | 1 | 0.0 | 0.0 |
| Arg | Leu | CGA | TTA | 2.7 | 12 | 32.4 | 29.8 |
| Arg | Phe | CGA | TTC | 2.8 | 5 | 1.8 | 0.7 |
| Arg | Leu | CGA | TTG | 2.5 | 4 | 1.0 | 0.8 |
| Arg | Phe | CGA | TTT | 3.5 | 7 | 3.5 | 1.5 |
| | Page Totals: | | | 181.3 | 182 | 112.2 | 106.0 |

ECOO.RXD/CPLIST.RXR January 11, 1989

| aa1 | aa2 | cod1 | cod2 | exp | obs | chis1 | chis2 |
|---|---|---|---|---|---|---|---|
| Arg | Lys | CGC | AAA | 59.8 | 44 | -4.2 | -3.8 |
| Arg | Asn | CGC | AAC | 42.4 | 30 | -3.6 | -3.5 |
| Arg | Lys | CGC | AAG | 19.9 | 13 | -2.4 | -2.2 |
| Arg | Asn | CGC | AAT | 22.8 | 27 | 0.8 | 0.8 |
| Arg | Thr | CGC | ACA | 8.4 | 7 | -0.2 | -0.1 |
| Arg | Thr | CGC | ACC | 39.7 | 36 | -0.3 | -0.0 |
| Arg | Thr | CGC | ACG | 19.0 | 19 | 0.0 | 0.1 |
| Arg | Thr | CGC | ACT | 16.2 | 14 | -0.3 | -0.1 |
| Arg | Arg | CGC | AGA | 1.9 | 1 | -0.4 | -0.3 |
| Arg | Ser | CGC | AGC | 27.3 | 21 | -1.4 | -0.1 |
| Arg | Arg | CGC | AGG | 1.1 | 2 | 0.8 | 1.1 |
| Arg | Ser | CGC | AGT | 10.0 | 20 | 10.1 | 17.3 |
| Arg | Ile | CGC | ATA | 3.9 | 2 | -0.9 | -1.0 |
| Arg | Ile | CGC | ATC | 47.9 | 33 | -4.7 | -5.7 |
| Arg | Met | CGC | ATG | 43.4 | 21 | -11.6 | -6.8 |
| Arg | Ile | CGC | ATT | 40.4 | 42 | 0.1 | 0.0 |
| Arg | Gln | CGC | CAA | 21.6 | 9 | -7.3 | -12.4 |
| Arg | His | CGC | CAC | 19.6 | 21 | 0.1 | 0.6 |
| Arg | Gln | CGC | CAG | 53.1 | 89 | 24.3 | 6.9 |
| Arg | His | CGC | CAT | 17.2 | 25 | 3.6 | 0.5 |
| Arg | Pro | CGC | CCA | 12.4 | 12 | -0.0 | -0.0 |
| Arg | Pro | CGC | CCC | 6.2 | 5 | -0.2 | -0.1 |
| Arg | Pro | CGC | CCG | 41.8 | 44 | 0.1 | 0.6 |
| Arg | Pro | CGC | CCT | 8.7 | 7 | -0.3 | -0.2 |
| Arg | Arg | CGC | CGA | 4.0 | 1 | -2.3 | -1.9 |
| Arg | Arg | CGC | CGC | 44.0 | 30 | -4.5 | -2.4 |
| Arg | Arg | CGC | CGG | 5.7 | 4 | -0.5 | -0.2 |
| Arg | Arg | CGC | CGT | 47.9 | 48 | 0.0 | 0.5 |
| Arg | Leu | CGC | CTA | 4.6 | 1 | -2.8 | -3.1 |
| Arg | Leu | CGC | CTC | 16.5 | 6 | -6.7 | -7.4 |
| Arg | Leu | CGC | CTG | 93.7 | 82 | -1.5 | -2.9 |
| Arg | Leu | CGC | CTT | 14.3 | 15 | 0.0 | 0.0 |
| Arg | Glu | CGC | GAA | 78.2 | 73 | -0.3 | -2.1 |
| Arg | Asp | CGC | GAC | 39.6 | 44 | 0.5 | 2.4 |
| Arg | Glu | CGC | GAG | 34.4 | 39 | 0.6 | 0.0 |
| Arg | Asp | CGC | GAT | 51.1 | 62 | 2.3 | 6.4 |
| Arg | Ala | CGC | GCA | 31.2 | 31 | -0.0 | -0.3 |
| Arg | Ala | CGC | GCC | 39.5 | 51 | 3.3 | 6.5 |
| Arg | Ala | CGC | GCG | 57.2 | 36 | -7.9 | -4.8 |
| Arg | Ala | CGC | GCT | 29.6 | 30 | 0.0 | 0.4 |
| Arg | Gly | CGC | GGA | 8.5 | 8 | -0.0 | -0.0 |
| Arg | Gly | CGC | GGC | 49.2 | 48 | -0.0 | -0.3 |
| Arg | Gly | CGC | GGG | 13.6 | 7 | -3.2 | -2.2 |
| Arg | Gly | CGC | GGT | 47.8 | 41 | -1.0 | -0.1 |
| Arg | Val | CGC | GTA | 20.9 | 40 | 17.6 | 14.7 |
| Arg | Val | CGC | GTC | 22.1 | 28 | 1.6 | 1.0 |
| Arg | Val | CGC | GTG | 40.0 | 62 | 12.1 | 9.4 |
| Arg | Val | CGC | GTT | 34.9 | 61 | 19.4 | 15.9 |
| Arg | Ocr | CGC | TAA | 0.0 | 5 | 0.0 | 0.0 |
| Arg | Tyr | CGC | TAC | 23.0 | 33 | 4.3 | 2.9 |
| Arg | Amb | CGC | TAG | 0.0 | 0 | 0.0 | 0.0 |
| Arg | Tyr | CGC | TAT | 22.8 | 21 | -0.1 | -0.5 |
| Arg | Ser | CGC | TCA | 8.3 | 5 | -1.3 | -0.5 |
| Arg | Ser | CGC | TCC | 17.4 | 13 | -1.1 | -0.1 |
| Arg | Ser | CGC | TCG | 12.8 | 8 | -1.8 | -0.6 |
| Arg | Ser | CGC | TCT | 17.9 | 8 | -5.5 | -3.0 |
| Arg | Umb | CGC | TGA | 0.0 | 0 | 0.0 | 0.0 |
| Arg | Cys | CGC | TGC | 10.2 | 10 | -0.0 | -0.0 |
| Arg | Trp | CGC | TGG | 18.3 | 39 | 23.6 | 10.2 |
| Arg | Cys | CGC | TGT | 7.5 | 10 | 0.9 | 1.1 |
| Arg | Leu | CGC | TTA | 15.3 | 19 | 0.9 | 0.5 |
| Arg | Phe | CGC | TTC | 30.8 | 43 | 4.8 | 0.5 |
| Arg | Leu | CGC | TTG | 18.1 | 10 | -3.6 | -4.3 |
| Arg | Phe | CGC | TTT | 26.6 | 31 | 0.7 | 0.2 |
| | Page Totals: | | | 1642.0 | 1647 | 214.6 | 173.4 |

ECOO.RXD/CPLIST.RXR January 11, 1989

| aa1 | aa2 | cod1 | cod2 | exp | obs | chis1 | chis2 |
|---|---|---|---|---|---|---|---|
| Arg | Lys | CGG | AAA | 8.3 | 6 | -0.6 | -0.6 |
| Arg | Asn | CGG | AAC | 5.4 | 2 | -2.2 | -2.1 |
| Arg | Lys | CGG | AAG | 3.1 | 7 | 5.1 | 5.2 |
| Arg | Asn | CGG | AAT | 4.8 | 2 | -1.7 | -1.6 |
| Arg | Thr | CGG | ACA | 2.0 | 2 | 0.0 | 0.0 |
| Arg | Thr | CGG | ACC | 4.9 | 1 | -3.1 | -2.8 |
| Arg | Thr | CGG | ACG | 3.7 | 2 | -0.8 | -0.6 |
| Arg | Thr | CGG | ACT | 2.3 | 3 | 0.2 | 0.3 |
| Arg | Arg | CGG | AGA | 0.8 | 0 | -0.8 | -0.7 |
| Arg | Ser | CGG | AGC | 4.5 | 1 | -2.7 | -1.9 |
| Arg | Arg | CGG | AGG | 0.4 | 0 | -0.4 | -0.4 |
| Arg | Ser | CGG | AGT | 2.3 | 3 | 0.2 | 0.7 |
| Arg | Ile | CGG | ATA | 1.5 | 0 | -1.5 | -1.6 |
| Arg | Ile | CGG | ATC | 6.1 | 5 | -0.2 | -0.3 |
| Arg | Met | CGG | ATG | 6.3 | 23 | 43.8 | 57.6 |
| Arg | Ile | CGG | ATT | 6.7 | 11 | 2.7 | 2.3 |
| Arg | Gln | CGG | CAA | 4.0 | 1 | -2.2 | -3.2 |
| Arg | His | CGG | CAC | 2.5 | 1 | -0.9 | -1.5 |
| Arg | Gln | CGG | CAG | 8.3 | 10 | 0.3 | 0.0 |
| Arg | His | CGG | CAT | 3.1 | 3 | -0.0 | -0.2 |
| Arg | Pro | CGG | CCA | 2.2 | 2 | -0.0 | -0.0 |
| Arg | Pro | CGG | CCC | 1.5 | 1 | -0.2 | -0.1 |
| Arg | Pro | CGG | CCG | 5.3 | 1 | -3.5 | -3.2 |
| Arg | Pro | CGG | CCT | 1.7 | 0 | -1.7 | -1.6 |
| Arg | Arg | CGG | CGA | 1.0 | 1 | 0.0 | 0.0 |
| Arg | Arg | CGG | CGC | 5.7 | 3 | -1.3 | -0.9 |
| Arg | Arg | CGG | CGG | 2.4 | 8 | 13.5 | 16.2 |
| Arg | Arg | CGG | CGT | 5.9 | 3 | -1.4 | -1.0 |
| Arg | Leu | CGG | CTA | 0.8 | 0 | -0.7 | -0.8 |
| Arg | Leu | CGG | CTC | 2.6 | 5 | 2.3 | 1.9 |
| Arg | Leu | CGG | CTG | 12.8 | 17 | 1.3 | 0.9 |
| Arg | Leu | CGG | CTT | 2.7 | 0 | -2.7 | -2.9 |
| Arg | Glu | CGG | GAA | 10.8 | 13 | 0.5 | 0.1 |
| Arg | Asp | CGG | GAC | 4.8 | 2 | -1.6 | -1.2 |
| Arg | Glu | CGG | GAG | 5.3 | 3 | -1.0 | -1.4 |
| Arg | Asp | CGG | GAT | 8.1 | 6 | -0.5 | -0.2 |
| Arg | Ala | CGG | GCA | 5.0 | 6 | 0.2 | 0.5 |
| Arg | Ala | CGG | GCC | 6.9 | 8 | 0.2 | 0.5 |
| Arg | Ala | CGG | GCG | 8.7 | 16 | 6.1 | 8.4 |
| Arg | Ala | CGG | GCT | 4.2 | 6 | 0.8 | 1.4 |
| Arg | Gly | CGG | GGA | 2.2 | 3 | 0.3 | 0.6 |
| Arg | Gly | CGG | GGC | 7.0 | 3 | -2.3 | -1.7 |
| Arg | Gly | CGG | GGG | 2.9 | 3 | 0.0 | 0.1 |
| Arg | Gly | CGG | GGT | 6.1 | 3 | -1.5 | -1.1 |
| Arg | Val | CGG | GTA | 3.0 | 11 | 21.6 | 19.7 |
| Arg | Val | CGG | GTC | 3.8 | 1 | -2.0 | -2.2 |
| Arg | Val | CGG | GTG | 6.4 | 8 | 0.4 | 0.2 |
| Arg | Val | CGG | GTT | 4.9 | 5 | 0.0 | 0.0 |
| Arg | Ocr | CGG | TAA | 0.0 | 1 | 0.0 | 0.0 |
| Arg | Tyr | CGG | TAC | 2.9 | 0 | -2.9 | -3.1 |
| Arg | Amb | CGG | TAG | 0.0 | 0 | 0.0 | 0.0 |
| Arg | Tyr | CGG | TAT | 4.2 | 4 | -0.0 | -0.1 |
| Arg | Ser | CGG | TCA | 1.8 | 1 | -0.4 | -0.2 |
| Arg | Ser | CGG | TCC | 2.4 | 0 | -2.4 | -1.9 |
| Arg | Ser | CGG | TCG | 2.2 | 0 | -2.2 | -1.8 |
| Arg | Ser | CGG | TCT | 2.6 | 0 | -2.6 | -2.1 |
| Arg | Umb | CGG | TGA | 0.0 | 1 | 0.0 | 0.0 |
| Arg | Cys | CGG | TGC | 1.7 | 2 | 0.1 | 0.1 |
| Arg | Trp | CGG | TGG | 3.4 | 2 | -0.6 | -1.3 |
| Arg | Cys | CGG | TGT | 1.2 | 5 | 12.4 | 13.1 |
| Arg | Leu | CGG | TTA | 4.0 | 2 | -1.0 | -1.1 |
| Arg | Phe | CGG | TTC | 4.1 | 3 | -0.3 | -0.9 |
| Arg | Leu | CGG | TTG | 3.6 | 5 | 0.6 | 0.4 |
| Arg | Phe | CGG | TTT | 5.2 | 7 | 0.6 | 0.0 |
| | Page Totals: | | | 254.2 | 254 | 163.1 | 178.4 |

PAGE 27

ECOO.RXD/CPLIST.RXR January 11, 1989

| aa1 | aa2 | cod1 | cod2 | exp | obs | chis1 | chis2 |
|---|---|---|---|---|---|---|---|
| Arg | Lys | CGT | AAA | 88.3 | 90 | 0.0 | 0.1 |
| Arg | Asn | CGT | AAC | 61.9 | 57 | -0.4 | -0.3 |
| Arg | Lys | CGT | AAG | 28.9 | 42 | 6.0 | 6.4 |
| Arg | Asn | CGT | AAT | 24.9 | 38 | 6.9 | 7.1 |
| Arg | Thr | CGT | ACA | 9.9 | 10 | 0.0 | 0.1 |
| Arg | Thr | CGT | ACC | 55.2 | 53 | -0.1 | -0.1 |
| Arg | Thr | CGT | ACG | 21.8 | 16 | -1.6 | -0.9 |
| Arg | Thr | CGT | ACT | 26.4 | 30 | 0.5 | 1.2 |
| Arg | Arg | CGT | AGA | 2.2 | 0 | -2.2 | -2.0 |
| Arg | Ser | CGT | AGC | 31.6 | 18 | -5.9 | -2.3 |
| Arg | Arg | CGT | AGG | 1.4 | 0 | -1.4 | -1.3 |
| Arg | Ser | CGT | AGT | 10.7 | 10 | -0.0 | -0.2 |
| Arg | Ile | CGT | ATA | 4.4 | 6 | 0.6 | 0.5 |
| Arg | Ile | CGT | ATC | 73.9 | 81 | 0.7 | 0.2 |
| Arg | Met | CGT | ATG | 57.8 | 49 | -1.3 | -0.0 |
| Arg | Ile | CGT | ATT | 48.4 | 56 | 1.2 | 0.6 |
| Arg | Gln | CGT | CAA | 24.8 | 20 | -0.9 | -4.2 |
| Arg | His | CGT | CAC | 27.7 | 38 | 3.8 | 0.2 |
| Arg | Gln | CGT | CAG | 70.8 | 108 | 19.5 | 3.6 |
| Arg | His | CGT | CAT | 19.1 | 27 | 3.2 | 0.3 |
| Arg | Pro | CGT | CCA | 14.6 | 7 | -4.0 | -3.2 |
| Arg | Pro | CGT | CCC | 5.4 | 3 | -1.1 | -0.8 |
| Arg | Pro | CGT | CCG | 56.8 | 56 | -0.0 | -0.2 |
| Arg | Pro | CGT | CCT | 10.9 | 12 | 0.1 | 0.3 |
| Arg | Arg | CGT | CGA | 4.3 | 5 | 0.1 | 0.3 |
| Arg | Arg | CGT | CGC | 47.9 | 52 | 0.4 | 1.8 |
| Arg | Arg | CGT | CGG | 5.9 | 7 | 0.2 | 0.6 |
| Arg | Arg | CGT | CGT | 77.8 | 72 | -0.4 | -0.1 |
| Arg | Leu | CGT | CTA | 4.5 | 1 | -2.7 | -3.0 |
| Arg | Leu | CGT | CTC | 18.7 | 11 | -3.2 | -3.9 |
| Arg | Leu | CGT | CTG | 133.1 | 167 | 8.7 | 5.1 |
| Arg | Leu | CGT | CTT | 16.7 | 20 | 0.7 | 0.3 |
| Arg | Glu | CGT | GAA | 112.7 | 140 | 6.6 | 2.0 |
| Arg | Asp | CGT | GAC | 60.1 | 52 | -1.1 | -0.0 |
| Arg | Glu | CGT | GAG | 45.0 | 53 | 1.4 | 0.2 |
| Arg | Asp | CGT | GAT | 64.6 | 43 | -7.2 | -3.4 |
| Arg | Ala | CGT | GCA | 46.3 | 27 | -8.0 | -5.3 |
| Arg | Ala | CGT | GCC | 44.9 | 31 | -4.3 | -2.2 |
| Arg | Ala | CGT | GCG | 73.4 | 67 | -0.6 | -0.0 |
| Arg | Ala | CGT | GCT | 46.8 | 49 | 0.1 | 1.1 |
| Arg | Gly | CGT | GGA | 9.1 | 9 | -0.0 | -0.1 |
| Arg | Gly | CGT | GGC | 66.9 | 58 | -1.2 | -0.1 |
| Arg | Gly | CGT | GGG | 14.8 | 11 | -1.0 | -0.4 |
| Arg | Gly | CGT | GGT | 74.5 | 80 | 0.4 | 2.5 |
| Arg | Val | CGT | GTA | 31.5 | 20 | -4.2 | -5.2 |
| Arg | Val | CGT | GTC | 26.2 | 16 | -4.0 | -4.9 |
| Arg | Val | CGT | GTG | 49.3 | 34 | -4.7 | -6.2 |
| Arg | Val | CGT | GTT | 56.1 | 35 | -7.9 | -9.8 |
| Arg | Ocr | CGT | TAA | 0.0 | 5 | 0.0 | 0.0 |
| Arg | Tyr | CGT | TAC | 33.8 | 36 | 0.1 | 0.0 |
| Arg | Amb | CGT | TAG | 0.0 | 0 | 0.0 | 0.0 |
| Arg | Tyr | CGT | TAT | 27.5 | 34 | 1.5 | 0.7 |
| Arg | Ser | CGT | TCA | 9.9 | 9 | -0.1 | -0.1 |
| Arg | Ser | CGT | TCC | 26.0 | 35 | 3.1 | 8.9 |
| Arg | Ser | CGT | TCG | 14.4 | 4 | -7.5 | -5.1 |
| Arg | Ser | CGT | TCT | 27.6 | 31 | 0.4 | 3.2 |
| Arg | Umb | CGT | TGA | 0.0 | 0 | 0.0 | 0.0 |
| Arg | Cys | CGT | TGC | 12.4 | 8 | -1.6 | -1.3 |
| Arg | Trp | CGT | TGG | 21.4 | 14 | -2.6 | -6.7 |
| Arg | Cys | CGT | TGT | 8.7 | 6 | -0.8 | -0.7 |
| Arg | Leu | CGT | TTA | 16.2 | 15 | -0.1 | -0.3 |
| Arg | Phe | CGT | TTC | 44.1 | 44 | -0.0 | -2.4 |
| Arg | Leu | CGT | TTG | 19.1 | 28 | 4.1 | 3.0 |
| Arg | Phe | CGT | TTT | 30.0 | 49 | 12.1 | 3.3 |
| | Page Totals: | | | 2199.7 | 2205 | 164.3 | 130.3 |

PAGE 28

ECO0.RXD/CPLIST.RXR January 11, 1989

| aa1 | aa2 | cod1 | cod2 | exp | obs | chis1 | chis2 |
|---|---|---|---|---|---|---|---|
| Leu | Lys | CTA | AAA | 6.9 | 13 | 5.5 | 3.8 |
| Leu | Asn | CTA | AAC | 4.5 | 6 | 0.5 | 0.3 |
| Leu | Lys | CTA | AAG | 2.1 | 3 | 0.4 | 0.2 |
| Leu | Asn | CTA | AAT | 3.5 | 0 | -3.5 | -3.7 |
| Leu | Thr | CTA | ACA | 1.7 | 1 | -0.3 | -0.3 |
| Leu | Thr | CTA | ACC | 4.1 | 8 | 3.8 | 3.0 |
| Leu | Thr | CTA | ACG | 2.6 | 2 | -0.1 | -0.2 |
| Leu | Thr | CTA | ACT | 2.1 | 0 | -2.1 | -2.2 |
| Leu | Arg | CTA | AGA | 0.5 | 1 | 0.4 | 0.4 |
| Leu | Ser | CTA | AGC | 3.1 | 3 | -0.0 | -0.1 |
| Leu | Arg | CTA | AGG | 0.2 | 1 | 2.4 | 2.1 |
| Leu | Ser | CTA | AGT | 1.6 | 2 | 0.1 | 0.0 |
| Leu | Ile | CTA | ATA | 1.1 | 2 | 0.9 | 1.0 |
| Leu | Ile | CTA | ATC | 4.8 | 5 | 0.0 | 0.1 |
| Leu | Met | CTA | ATG | 5.0 | 9 | 3.3 | 3.9 |
| Leu | Ile | CTA | ATT | 5.3 | 2 | -2.0 | -1.8 |
| Leu | Gln | CTA | CAA | 3.2 | 8 | 7.5 | 12.2 |
| Leu | His | CTA | CAC | 2.0 | 3 | 0.5 | 0.4 |
| Leu | Gln | CTA | CAG | 5.9 | 6 | 0.0 | 0.4 |
| Leu | His | CTA | CAT | 2.4 | 5 | 2.8 | 2.7 |
| Leu | Pro | CTA | CCA | 1.6 | 8 | 25.1 | 19.7 |
| Leu | Pro | CTA | CCC | 1.0 | 4 | 8.5 | 6.4 |
| Leu | Pro | CTA | CCG | 4.2 | 6 | 0.8 | 0.3 |
| Leu | Pro | CTA | CCT | 1.4 | 4 | 5.1 | 3.7 |
| Leu | Arg | CTA | CGA | 0.6 | 1 | 0.2 | 0.2 |
| Leu | Arg | CTA | CGC | 4.6 | 8 | 2.5 | 1.9 |
| Leu | Arg | CTA | CGG | 0.8 | 4 | 14.2 | 12.8 |
| Leu | Arg | CTA | CGT | 4.5 | 7 | 1.4 | 1.0 |
| Leu | Leu | CTA | CTA | 1.5 | 0 | -1.5 | -1.3 |
| Leu | Leu | CTA | CTC | 2.1 | 0 | -2.1 | -1.9 |
| Leu | Leu | CTA | CTG | 9.7 | 11 | 0.2 | 0.6 |
| Leu | Leu | CTA | CTT | 2.2 | 2 | -0.0 | -0.0 |
| Leu | Glu | CTA | GAA | 8.2 | 4 | -2.2 | -2.1 |
| Leu | Asp | CTA | GAC | 3.7 | 0 | -3.7 | -3.8 |
| Leu | Glu | CTA | GAG | 3.6 | 1 | -1.9 | -1.8 |
| Leu | Asp | CTA | GAT | 6.0 | 5 | -0.2 | -0.2 |
| Leu | Ala | CTA | GCA | 3.7 | 1 | -2.0 | -2.5 |
| Leu | Ala | CTA | GCC | 4.7 | 0 | -4.7 | -5.3 |
| Leu | Ala | CTA | GCG | 6.0 | 0 | -6.0 | -6.7 |
| Leu | Ala | CTA | GCT | 3.0 | 1 | -1.3 | -1.6 |
| Leu | Gly | CTA | GGA | 1.3 | 0 | -1.3 | -1.2 |
| Leu | Gly | CTA | GGC | 5.2 | 4 | -0.3 | -0.1 |
| Leu | Gly | CTA | GGG | 1.8 | 1 | -0.3 | -0.2 |
| Leu | Gly | CTA | GGT | 4.9 | 1 | -3.1 | -2.7 |
| Leu | Val | CTA | GTA | 2.6 | 1 | -0.9 | -0.8 |
| Leu | Val | CTA | GTC | 2.8 | 1 | -1.1 | -1.0 |
| Leu | Val | CTA | GTG | 4.3 | 1 | -2.6 | -2.4 |
| Leu | Val | CTA | GTT | 3.7 | 4 | 0.0 | 0.1 |
| Leu | Ocr | CTA | TAA | 0.0 | 0 | 0.0 | 0.0 |
| Leu | Tyr | CTA | TAC | 2.2 | 1 | -0.7 | -0.5 |
| Leu | Amb | CTA | TAG | 0.0 | 0 | 0.0 | 0.0 |
| Leu | Tyr | CTA | TAT | 3.2 | 3 | -0.0 | -0.0 |
| Leu | Ser | CTA | TCA | 1.6 | 4 | 3.5 | 2.6 |
| Leu | Ser | CTA | TCC | 1.9 | 3 | 0.7 | 0.3 |
| Leu | Ser | CTA | TCG | 1.7 | 0 | -1.7 | -1.9 |
| Leu | Ser | CTA | TCT | 2.2 | 0 | -2.2 | -2.4 |
| Leu | Umb | CTA | TGA | 0.0 | 0 | 0.0 | 0.0 |
| Leu | Cys | CTA | TGC | 1.1 | 1 | -0.0 | -0.0 |
| Leu | Trp | CTA | TGG | 2.4 | 1 | -0.8 | -0.5 |
| Leu | Cys | CTA | TGT | 1.1 | 3 | 3.5 | 4.6 |
| Leu | Leu | CTA | TTA | 2.7 | 5 | 1.9 | 2.7 |
| Leu | Phe | CTA | TTC | 3.1 | 3 | -0.0 | -0.0 |
| Leu | Leu | CTA | TTG | 2.4 | 4 | 1.1 | 1.6 |
| Leu | Phe | CTA | TTT | 4.0 | 4 | 0.0 | -0.1 |
| | | Page Totals: | | 191.4 | 192 | 144.9 | 138.6 |

PAGE 29

ECO0.RXD/CPLIST.RXR January 11, 1989

| aa1 | aa2 | cod1 | cod2 | exp | obs | chis1 | chis2 |
|---|---|---|---|---|---|---|---|
| Leu | Lys | CTC | AAA | 25.0 | 22 | -0.3 | -1.1 |
| Leu | Asn | CTC | AAC | 17.6 | 34 | 15.4 | 12.8 |
| Leu | Lys | CTC | AAG | 8.6 | 11 | 0.7 | 0.2 |
| Leu | Asn | CTC | AAT | 10.4 | 20 | 9.0 | 7.4 |
| Leu | Thr | CTC | ACA | 4.2 | 3 | -0.3 | -0.5 |
| Leu | Thr | CTC | ACC | 16.8 | 34 | 17.5 | 13.8 |
| Leu | Thr | CTC | ACG | 8.1 | 2 | -4.6 | -5.2 |
| Leu | Thr | CTC | ACT | 7.0 | 10 | 1.3 | 0.8 |
| Leu | Arg | CTC | AGA | 1.1 | 1 | -0.0 | -0.0 |
| Leu | Ser | CTC | AGC | 11.9 | 8 | -1.3 | -2.2 |
| Leu | Arg | CTC | AGG | 0.7 | 3 | 7.9 | 7.1 |
| Leu | Ser | CTC | AGT | 5.0 | 12 | 10.0 | 7.3 |
| Leu | Ile | CTC | ATA | 2.3 | 0 | -2.3 | -2.1 |
| Leu | Ile | CTC | ATC | 20.6 | 13 | -2.8 | -2.1 |
| Leu | Met | CTC | ATG | 19.0 | 4 | -11.8 | -10.9 |
| Leu | Ile | CTC | ATT | 18.0 | 13 | -1.4 | -0.9 |
| Leu | Gln | CTC | CAA | 9.6 | 0 | -9.6 | -7.6 |
| Leu | His | CTC | CAC | 8.2 | 10 | 0.4 | 0.4 |
| Leu | Gln | CTC | CAG | 22.1 | 7 | -10.4 | -6.3 |
| Leu | His | CTC | CAT | 7.2 | 7 | -0.0 | -0.0 |
| Leu | Pro | CTC | CCA | 5.4 | 1 | -3.5 | -4.4 |
| Leu | Pro | CTC | CCC | 2.9 | 4 | 0.4 | 0.1 |
| Leu | Pro | CTC | CCG | 16.6 | 3 | -11.1 | -13.8 |
| Leu | Pro | CTC | CCT | 4.0 | 5 | 0.2 | 0.0 |
| Leu | Arg | CTC | CGA | 2.0 | 0 | -2.0 | -2.2 |
| Leu | Arg | CTC | CGC | 16.5 | 2 | -12.7 | -13.8 |
| Leu | Arg | CTC | CGG | 2.6 | 0 | -2.6 | -2.7 |
| Leu | Arg | CTC | CGT | 18.7 | 4 | -11.5 | -12.8 |
| Leu | Leu | CTC | CTA | 2.1 | 0 | -2.1 | -1.9 |
| Leu | Leu | CTC | CTC | 9.7 | 2 | -6.1 | -5.1 |
| Leu | Leu | CTC | CTG | 39.3 | 9 | -23.4 | -19.6 |
| Leu | Leu | CTC | CTT | 6.8 | 3 | -2.1 | -1.5 |
| Leu | Glu | CTC | GAA | 32.7 | 40 | 1.6 | 1.9 |
| Leu | Asp | CTC | GAC | 15.9 | 50 | 72.8 | 68.1 |
| Leu | Glu | CTC | GAG | 14.6 | 13 | -0.2 | -0.1 |
| Leu | Asp | CTC | GAT | 21.3 | 58 | 63.3 | 58.8 |
| Leu | Ala | CTC | GCA | 14.1 | 11 | -0.7 | -1.5 |
| Leu | Ala | CTC | GCC | 17.0 | 25 | 3.7 | 1.8 |
| Leu | Ala | CTC | GCG | 24.1 | 10 | -8.3 | -10.9 |
| Leu | Ala | CTC | GCT | 12.0 | 10 | -0.3 | -0.9 |
| Leu | Gly | CTC | GGA | 4.3 | 9 | 5.3 | 6.5 |
| Leu | Gly | CTC | GGC | 20.4 | 42 | 22.7 | 28.4 |
| Leu | Gly | CTC | GGG | 6.2 | 8 | 0.5 | 0.9 |
| Leu | Gly | CTC | GGT | 21.4 | 32 | 5.2 | 7.5 |
| Leu | Val | CTC | GTA | 8.8 | 2 | -5.2 | -4.9 |
| Leu | Val | CTC | GTC | 10.0 | 5 | -2.5 | -2.2 |
| Leu | Val | CTC | GTG | 17.2 | 4 | -10.1 | -9.4 |
| Leu | Val | CTC | GTT | 15.0 | 7 | -4.3 | -3.8 |
| Leu | Ocr | CTC | TAA | 0.0 | 0 | 0.0 | 0.0 |
| Leu | Tyr | CTC | TAC | 9.5 | 15 | 3.3 | 4.7 |
| Leu | Amb | CTC | TAG | 0.0 | 0 | 0.0 | 0.0 |
| Leu | Tyr | CTC | TAT | 10.6 | 23 | 14.6 | 18.5 |
| Leu | Ser | CTC | TCA | 4.0 | 8 | 4.1 | 2.8 |
| Leu | Ser | CTC | TCC | 7.4 | 23 | 33.1 | 25.8 |
| Leu | Ser | CTC | TCG | 5.5 | 4 | -0.4 | -0.8 |
| Leu | Ser | CTC | TCT | 8.3 | 21 | 19.7 | 14.6 |
| Leu | Umb | CTC | TGA | 0.0 | 1 | 0.0 | 0.0 |
| Leu | Cys | CTC | TGC | 4.0 | 8 | 3.9 | 5.8 |
| Leu | Trp | CTC | TGG | 7.9 | 14 | 4.8 | 8.5 |
| Leu | Cys | CTC | TGT | 3.2 | 2 | -0.5 | -0.2 |
| Leu | Leu | CTC | TTA | 7.6 | 1 | -5.7 | -5.0 |
| Leu | Phe | CTC | TTC | 13.6 | 8 | -2.3 | -1.3 |
| Leu | Leu | CTC | TTG | 8.1 | 1 | -6.2 | -5.4 |
| Leu | Phe | CTC | TTT | 12.8 | 7 | -2.6 | -1.6 |
| | | Page Totals: | | 706.6 | 709 | 492.7 | 469.5 |

PAGE 30

ECOO.RXD/CPLIST.RXR January 11, 1989

| aa1 | aa2 | cod1 | cod2 | exp | obs | chis1 | chis2 |
|---|---|---|---|---|---|---|---|
| Leu | Lys | CTG | AAA | 174.0 | 219 | 11.6 | 3.6 |
| Leu | Asn | CTG | AAC | 122.0 | 109 | -1.4 | -3.1 |
| Leu | Lys | CTG | AAG | 54.5 | 42 | -2.9 | -5.6 |
| Leu | Asn | CTG | AAT | 54.4 | 59 | 0.4 | 0.0 |
| Leu | Thr | CTG | ACA | 21.0 | 13 | -3.1 | -4.2 |
| Leu | Thr | CTG | ACC | 112.9 | 121 | 0.6 | 0.0 |
| Leu | Thr | CTG | ACG | 48.5 | 51 | 0.1 | 0.0 |
| Leu | Thr | CTG | ACT | 49.8 | 51 | 0.0 | 0.1 |
| Leu | Arg | CTG | AGA | 4.1 | 1 | -2.3 | -2.6 |
| Leu | Ser | CTG | AGC | 69.5 | 40 | -12.5 | -18.9 |
| Leu | Arg | CTG | AGG | 2.9 | 0 | -2.9 | -3.1 |
| Leu | Ser | CTG | AGT | 23.8 | 11 | -6.9 | -9.4 |
| Leu | Ile | CTG | ATA | 8.8 | 9 | 0.0 | 0.1 |
| Leu | Ile | CTG | ATC | 146.4 | 116 | -6.3 | -3.6 |
| Leu | Met | CTG | ATG | 121.2 | 116 | -0.2 | -0.0 |
| Leu | Ile | CTG | ATT | 106.3 | 111 | 0.2 | 1.1 |
| Leu | Gln | CTG | CAA | 51.7 | 80 | 15.5 | 37.5 |
| Leu | His | CTG | CAC | 53.4 | 53 | -0.0 | -0.0 |
| Leu | Gln | CTG | CAG | 140.9 | 48 | -61.3 | -36.1 |
| Leu | His | CTG | CAT | 40.2 | 35 | -0.7 | -0.8 |
| Leu | Pro | CTG | CCA | 31.0 | 50 | 11.6 | 5.3 |
| Leu | Pro | CTG | CCC | 12.9 | 13 | 0.0 | 0.3 |
| Leu | Pro | CTG | CCG | 114.3 | 124 | 0.8 | 0.7 |
| Leu | Pro | CTG | CCT | 22.8 | 23 | 0.0 | 0.5 |
| Leu | Arg | CTG | CGA | 8.7 | 6 | -0.9 | -1.2 |
| Leu | Arg | CTG | CGC | 93.7 | 127 | 11.8 | 7.2 |
| Leu | Arg | CTG | CGG | 12.8 | 6 | -3.6 | -4.3 |
| Leu | Arg | CTG | CGT | 133.1 | 152 | 2.7 | 0.7 |
| Leu | Leu | CTG | CTA | 9.7 | 11 | 0.2 | 0.6 |
| Leu | Leu | CTG | CTC | 39.3 | 30 | -2.2 | -0.8 |
| Leu | Leu | CTG | CTG | 284.9 | 262 | -1.8 | -0.2 |
| Leu | Leu | CTG | CTT | 34.3 | 32 | -0.2 | -0.1 |
| Leu | Glu | CTG | GAA | 213.0 | 271 | 15.8 | 17.8 |
| Leu | Asp | CTG | GAC | 115.6 | 67 | -20.4 | -23.2 |
| Leu | Glu | CTG | GAG | 86.0 | 78 | -0.7 | -0.5 |
| Leu | Asp | CTG | GAT | 131.8 | 147 | 1.8 | 0.8 |
| Leu | Ala | CTG | GCA | 93.5 | 159 | 45.8 | 27.3 |
| Leu | Ala | CTG | GCC | 98.9 | 48 | -26.2 | -36.1 |
| Leu | Ala | CTG | GCG | 155.1 | 272 | 88.2 | 54.2 |
| Leu | Ala | CTG | GCT | 92.7 | 115 | 5.4 | 1.1 |
| Leu | Gly | CTG | GGA | 20.5 | 19 | -0.1 | -0.0 |
| Leu | Gly | CTG | GGC | 138.9 | 108 | -6.9 | -3.2 |
| Leu | Gly | CTG | GGG | 33.4 | 38 | 0.6 | 1.7 |
| Leu | Gly | CTG | GGT | 149.4 | 120 | -5.8 | -2.3 |
| Leu | Val | CTG | GTA | 61.3 | 85 | 9.2 | 11.8 |
| Leu | Val | CTG | GTC | 57.0 | 54 | -0.2 | -0.0 |
| Leu | Val | CTG | GTG | 107.7 | 174 | 40.9 | 48.8 |
| Leu | Val | CTG | GTT | 108.8 | 110 | 0.0 | 0.3 |
| Leu | Ocr | CTG | TAA | 0.0 | 7 | 0.0 | 0.0 |
| Leu | Tyr | CTG | TAC | 66.1 | 42 | -8.8 | -5.5 |
| Leu | Amb | CTG | TAG | 0.0 | 0 | 0.0 | 0.0 |
| Leu | Tyr | CTG | TAT | 58.2 | 45 | -3.0 | -1.2 |
| Leu | Ser | CTG | TCA | 20.3 | 14 | -2.0 | -3.5 |
| Leu | Ser | CTG | TCC | 50.6 | 23 | -15.1 | -20.4 |
| Leu | Ser | CTG | TCG | 31.1 | 28 | -0.3 | -1.5 |
| Leu | Ser | CTG | TCT | 54.0 | 48 | -0.7 | -2.8 |
| Leu | Umb | CTG | TGA | 0.0 | 0 | 0.0 | 0.0 |
| Leu | Cys | CTG | TGC | 25.3 | 16 | -3.4 | -1.6 |
| Leu | Trp | CTG | TGG | 46.6 | 41 | -0.7 | -0.1 |
| Leu | Cys | CTG | TGT | 17.9 | 11 | -2.7 | -1.3 |
| Leu | Leu | CTG | TTA | 36.0 | 31 | -0.7 | -0.1 |
| Leu | Phe | CTG | TTC | 93.4 | 90 | -0.1 | -0.6 |
| Leu | Leu | CTG | TTG | 42.7 | 45 | 0.1 | 1.2 |
| Leu | Phe | CTG | TTT | 67.2 | 61 | -0.6 | -0.0 |
| | | Page Totals: | | 4476.7 | 4488 | 470.7 | 420.6 |

PAGE 31

ECOO.RXD/CPLIST.RXR January 11, 1989

| aa1 | aa2 | cod1 | cod2 | exp | obs | chis1 | chis2 |
|---|---|---|---|---|---|---|---|
| Leu | Lys | CTT | AAA | 24.4 | 20 | -0.8 | -1.8 |
| Leu | Asn | CTT | AAC | 15.8 | 22 | 2.5 | 1.7 |
| Leu | Lys | CTT | AAG | 8.4 | 8 | -0.0 | -0.2 |
| Leu | Asn | CTT | AAT | 12.1 | 24 | 11.6 | 9.7 |
| Leu | Thr | CTT | ACA | 4.8 | 4 | -0.1 | -0.3 |
| Leu | Thr | CTT | ACC | 13.8 | 10 | -1.0 | -1.6 |
| Leu | Thr | CTT | ACG | 7.9 | 0 | -7.9 | -8.5 |
| Leu | Thr | CTT | ACT | 6.7 | 9 | 0.8 | 0.5 |
| Leu | Arg | CTT | AGA | 1.5 | 0 | -1.5 | -1.6 |
| Leu | Ser | CTT | AGC | 10.8 | 12 | 0.1 | 0.0 |
| Leu | Arg | CTT | AGG | 1.0 | 0 | -1.0 | -1.0 |
| Leu | Ser | CTT | AGT | 5.3 | 5 | -0.0 | -0.1 |
| Leu | Ile | CTT | ATA | 3.2 | 4 | 0.2 | 0.3 |
| Leu | Ile | CTT | ATC | 18.0 | 28 | 5.6 | 7.2 |
| Leu | Met | CTT | ATG | 16.5 | 4 | -9.5 | -8.7 |
| Leu | Ile | CTT | ATT | 18.1 | 13 | -1.4 | -1.0 |
| Leu | Gln | CTT | CAA | 10.4 | 3 | -5.3 | -3.3 |
| Leu | His | CTT | CAC | 7.1 | 5 | -0.6 | -0.7 |
| Leu | Gln | CTT | CAG | 20.4 | 5 | -11.6 | -7.7 |
| Leu | His | CTT | CAT | 7.4 | 4 | -1.6 | -1.6 |
| Leu | Pro | CTT | CCA | 5.5 | 4 | -0.4 | -0.9 |
| Leu | Pro | CTT | CCC | 3.0 | 1 | -1.3 | -1.7 |
| Leu | Pro | CTT | CCG | 14.1 | 3 | -8.8 | -11.0 |
| Leu | Pro | CTT | CCT | 4.4 | 7 | 1.5 | 0.7 |
| Leu | Arg | CTT | CGA | 2.1 | 0 | -2.1 | -2.3 |
| Leu | Arg | CTT | CGC | 14.3 | 4 | -7.4 | -8.3 |
| Leu | Arg | CTT | CGG | 2.7 | 1 | -1.1 | -1.2 |
| Leu | Arg | CTT | CGT | 16.7 | 13 | -0.8 | -1.3 |
| Leu | Leu | CTT | CTA | 2.2 | 1 | -0.7 | -0.5 |
| Leu | Leu | CTT | CTC | 6.8 | 5 | -0.5 | -0.2 |
| Leu | Leu | CTT | CTG | 34.3 | 10 | -17.2 | -14.0 |
| Leu | Leu | CTT | CTT | 9.6 | 4 | -3.2 | -2.4 |
| Leu | Glu | CTT | GAA | 29.5 | 25 | -0.7 | -0.6 |
| Leu | Asp | CTT | GAC | 13.8 | 19 | 2.0 | 1.6 |
| Leu | Glu | CTT | GAG | 13.3 | 30 | 20.9 | 21.8 |
| Leu | Asp | CTT | GAT | 20.9 | 44 | 25.5 | 23.1 |
| Leu | Ala | CTT | GCA | 13.8 | 9 | -1.6 | -2.7 |
| Leu | Ala | CTT | GCC | 15.4 | 28 | 10.4 | 6.6 |
| Leu | Ala | CTT | GCG | 20.7 | 17 | -0.6 | -1.7 |
| Leu | Ala | CTT | GCT | 11.7 | 20 | 5.8 | 3.5 |
| Leu | Gly | CTT | GGA | 5.2 | 6 | 0.1 | 0.3 |
| Leu | Gly | CTT | GGC | 18.2 | 26 | 3.4 | 5.1 |
| Leu | Gly | CTT | GGG | 6.5 | 5 | -0.4 | -0.2 |
| Leu | Gly | CTT | GGT | 18.6 | 13 | -1.7 | -1.0 |
| Leu | Val | CTT | GTA | 8.3 | 2 | -4.8 | -4.4 |
| Leu | Val | CTT | GTC | 9.4 | 8 | -0.2 | -0.1 |
| Leu | Val | CTT | GTG | 14.7 | 4 | -7.8 | -7.2 |
| Leu | Val | CTT | GTT | 13.9 | 8 | -2.5 | -2.1 |
| Leu | Ocr | CTT | TAA | 0.0 | 2 | 0.0 | 0.0 |
| Leu | Tyr | CTT | TAC | 8.5 | 12 | 1.5 | 2.4 |
| Leu | Amb | CTT | TAG | 0.0 | 0 | 0.0 | 0.0 |
| Leu | Tyr | CTT | TAT | 10.9 | 22 | 11.4 | 14.8 |
| Leu | Ser | CTT | TCA | 4.9 | 19 | 40.6 | 32.7 |
| Leu | Ser | CTT | TCC | 6.6 | 30 | 83.3 | 68.4 |
| Leu | Ser | CTT | TCG | 5.4 | 11 | 6.0 | 4.1 |
| Leu | Ser | CTT | TCT | 7.5 | 33 | 86.7 | 70.9 |
| Leu | Umb | CTT | TGA | 0.0 | 0 | 0.0 | 0.0 |
| Leu | Cys | CTT | TGC | 3.5 | 3 | -0.1 | -0.0 |
| Leu | Trp | CTT | TGG | 7.8 | 4 | -1.9 | -1.0 |
| Leu | Cys | CTT | TGT | 2.9 | 4 | 0.4 | 0.8 |
| Leu | Leu | CTT | TTA | 9.1 | 5 | -1.9 | -1.2 |
| Leu | Phe | CTT | TTC | 11.6 | 6 | -2.7 | -1.7 |
| Leu | Leu | CTT | TTG | 8.1 | 6 | -0.5 | -0.2 |
| Leu | Phe | CTT | TTT | 12.7 | 9 | -1.1 | -0.4 |
| | | Page Totals: | | 661.8 | 663 | 434.4 | 382.9 |

PAGE 32

ECOO.RXD/CPLIST.RXR January 11, 1989

| aa1 | aa2 | cod1 | cod2 | exp | obs | chis1 | chis2 |
|---|---|---|---|---|---|---|---|
| Glu | Lys | GAA | AAA | 154.8 | 166 | 0.8 | 1.1 |
| Glu | Asn | GAA | AAC | 100.0 | 135 | 12.3 | 5.2 |
| Glu | Lys | GAA | AAG | 48.7 | 31 | -6.4 | -11.6 |
| Glu | Asn | GAA | AAT | 47.2 | 50 | 0.2 | 0.1 |
| Glu | Thr | GAA | ACA | 18.7 | 21 | 0.3 | 0.5 |
| Glu | Thr | GAA | ACC | 93.4 | 114 | 4.5 | 6.8 |
| Glu | Thr | GAA | ACG | 36.9 | 43 | 1.0 | 1.7 |
| Glu | Thr | GAA | ACT | 42.5 | 40 | -0.2 | -0.0 |
| Glu | Arg | GAA | AGA | 4.8 | 6 | 0.3 | 0.4 |
| Glu | Ser | GAA | AGC | 54.0 | 60 | 0.7 | 2.4 |
| Glu | Arg | GAA | AGG | 2.6 | 4 | 0.8 | 0.8 |
| Glu | Ser | GAA | AGT | 19.8 | 21 | 0.1 | 0.5 |
| Glu | Ile | GAA | ATA | 9.4 | 15 | 3.4 | 2.8 |
| Glu | Ile | GAA | ATC | 122.7 | 126 | 0.1 | 0.0 |
| Glu | Met | GAA | ATG | 98.2 | 85 | -1.8 | -2.8 |
| Glu | Ile | GAA | ATT | 86.5 | 77 | -1.0 | -1.9 |
| Glu | Gln | GAA | CAA | 44.7 | 54 | 1.9 | 0.2 |
| Glu | His | GAA | CAC | 44.1 | 33 | -2.8 | -2.2 |
| Glu | Gln | GAA | CAG | 118.0 | 77 | -14.2 | -36.6 |
| Glu | His | GAA | CAT | 33.1 | 26 | -1.5 | -1.2 |
| Glu | Pro | GAA | CCA | 26.2 | 15 | -4.8 | -3.0 |
| Glu | Pro | GAA | CCC | 10.9 | 11 | 0.0 | 0.2 |
| Glu | Pro | GAA | CCG | 92.6 | 66 | -7.6 | -3.3 |
| Glu | Pro | GAA | CCT | 19.1 | 7 | -7.7 | -5.9 |
| Glu | Arg | GAA | CGA | 7.5 | 10 | 0.8 | 1.0 |
| Glu | Arg | GAA | CGC | 78.2 | 63 | -3.0 | -2.4 |
| Glu | Arg | GAA | CGG | 10.8 | 11 | 0.0 | 0.0 |
| Glu | Arg | GAA | CGT | 112.7 | 81 | -8.9 | -7.7 |
| Glu | Leu | GAA | CTA | 8.2 | 9 | 0.1 | 0.0 |
| Glu | Leu | GAA | CTC | 32.7 | 22 | -3.5 | -5.7 |
| Glu | Leu | GAA | CTG | 213.0 | 216 | 0.0 | 2.0 |
| Glu | Leu | GAA | CTT | 29.5 | 19 | -3.7 | -5.9 |
| Glu | Glu | GAA | GAA | 204.0 | 184 | -2.0 | -1.3 |
| Glu | Asp | GAA | GAC | 98.8 | 82 | -2.8 | -0.4 |
| Glu | Glu | GAA | GAG | 73.9 | 169 | 122.2 | 128.6 |
| Glu | Asp | GAA | GAT | 111.2 | 131 | 3.5 | 23.7 |
| Glu | Ala | GAA | GCA | 80.1 | 99 | 4.4 | 3.7 |
| Glu | Ala | GAA | GCC | 78.9 | 88 | 1.0 | 0.7 |
| Glu | Ala | GAA | GCG | 124.2 | 169 | 16.2 | 14.3 |
| Glu | Ala | GAA | GCT | 80.3 | 83 | 0.1 | 0.0 |
| Glu | Gly | GAA | GGA | 17.7 | 19 | 0.1 | 0.6 |
| Glu | Gly | GAA | GGC | 114.7 | 142 | 6.5 | 14.8 |
| Glu | Gly | GAA | GGG | 26.2 | 38 | 5.4 | 9.0 |
| Glu | Gly | GAA | GGT | 122.1 | 119 | -0.1 | -0.8 |
| Glu | Val | GAA | GTA | 52.8 | 37 | -4.7 | -5.2 |
| Glu | Val | GAA | GTC | 46.7 | 55 | 1.5 | 1.2 |
| Glu | Val | GAA | GTG | 83.0 | 144 | 44.8 | 41.9 |
| Glu | Val | GAA | GTT | 95.7 | 106 | 1.1 | 0.8 |
| Glu | Ocr | GAA | TAA | 0.0 | 5 | 0.0 | 0.0 |
| Glu | Tyr | GAA | TAC | 52.1 | 41 | -2.4 | -1.2 |
| Glu | Amb | GAA | TAG | 0.0 | 0 | 0.0 | 0.0 |
| Glu | Tyr | GAA | TAT | 48.8 | 47 | -0.1 | -0.1 |
| Glu | Ser | GAA | TCA | 18.6 | 17 | -0.1 | -0.0 |
| Glu | Ser | GAA | TCC | 42.6 | 37 | -0.7 | -0.1 |
| Glu | Ser | GAA | TCG | 24.9 | 20 | -1.0 | -0.3 |
| Glu | Ser | GAA | TCT | 45.7 | 26 | -8.5 | -5.9 |
| Glu | Umb | GAA | TGA | 0.0 | 0 | 0.0 | 0.0 |
| Glu | Cys | GAA | TGC | 20.1 | 3 | -14.6 | -9.9 |
| Glu | Trp | GAA | TGG | 37.2 | 25 | -4.0 | -2.3 |
| Glu | Cys | GAA | TGT | 14.8 | 13 | -0.2 | -0.3 |
| Glu | Leu | GAA | TTA | 31.8 | 28 | -0.5 | -1.6 |
| Glu | Phe | GAA | TTC | 71.7 | 31 | -23.1 | -18.9 |
| Glu | Leu | GAA | TTG | 34.2 | 28 | -1.1 | -2.7 |
| Glu | Phe | GAA | TTT | 53.7 | 36 | -5.8 | -3.8 |
| | Page Totals: | | | 3727.9 | 3736 | 372.9 | 409.9 |

ECOO.RXD/CPLIST.RXR January 11, 1989

| aa1 | aa2 | cod1 | cod2 | exp | obs | chis1 | chis2 |
|---|---|---|---|---|---|---|---|
| Asp | Lys | GAC | AAA | 81.1 | 75 | -0.5 | -1.0 |
| Asp | Asn | GAC | AAC | 56.7 | 48 | -1.3 | -1.5 |
| Asp | Lys | GAC | AAG | 24.8 | 39 | 8.1 | 6.8 |
| Asp | Asn | GAC | AAT | 21.5 | 17 | -1.0 | -1.0 |
| Asp | Thr | GAC | ACA | 8.5 | 6 | -0.7 | -0.4 |
| Asp | Thr | GAC | ACC | 50.7 | 51 | 0.0 | 0.5 |
| Asp | Thr | GAC | ACG | 18.2 | 10 | -3.7 | -2.6 |
| Asp | Thr | GAC | ACT | 23.9 | 22 | -0.1 | -0.0 |
| Asp | Arg | GAC | AGA | 2.3 | 8 | 14.6 | 18.2 |
| Asp | Ser | GAC | AGC | 27.2 | 65 | 52.5 | 52.2 |
| Asp | Arg | GAC | AGG | 1.4 | 0 | -1.4 | -1.2 |
| Asp | Ser | GAC | AGT | 9.3 | 16 | 4.9 | 4.9 |
| Asp | Ile | GAC | ATA | 4.1 | 4 | -0.0 | -0.1 |
| Asp | Ile | GAC | ATC | 66.8 | 56 | -1.8 | -4.2 |
| Asp | Met | GAC | ATG | 50.4 | 43 | -1.1 | -0.0 |
| Asp | Ile | GAC | ATT | 41.7 | 38 | -0.3 | -1.4 |
| Asp | Gln | GAC | CAA | 20.6 | 12 | -3.6 | -1.7 |
| Asp | His | GAC | CAC | 23.9 | 21 | -0.3 | -0.2 |
| Asp | Gln | GAC | CAG | 62.7 | 54 | -1.2 | -0.0 |
| Asp | His | GAC | CAT | 15.8 | 12 | -0.9 | -0.0 |
| Asp | Pro | GAC | CCA | 12.6 | 6 | -3.5 | -3.6 |
| Asp | Pro | GAC | CCC | 4.6 | 5 | 0.0 | 0.0 |
| Asp | Pro | GAC | CCG | 49.3 | 46 | -0.2 | -0.3 |
| Asp | Pro | GAC | CCT | 8.8 | 4 | -2.6 | -2.7 |
| Asp | Arg | GAC | CGA | 3.5 | 3 | -0.1 | -0.0 |
| Asp | Arg | GAC | CGC | 39.6 | 36 | -0.3 | -0.0 |
| Asp | Arg | GAC | CGG | 4.8 | 9 | 3.7 | 5.4 |
| Asp | Arg | GAC | CGT | 60.1 | 54 | -0.6 | -0.0 |
| Asp | Leu | GAC | CTA | 3.7 | 1 | -2.0 | -1.8 |
| Asp | Leu | GAC | CTC | 15.9 | 10 | -2.2 | -1.8 |
| Asp | Leu | GAC | CTG | 115.6 | 86 | -7.6 | -5.5 |
| Asp | Leu | GAC | CTT | 13.8 | 15 | 0.1 | 0.2 |
| Asp | Glu | GAC | GAA | 98.8 | 111 | 1.5 | 0.0 |
| Asp | Asp | GAC | GAC | 60.0 | 50 | -1.7 | -0.8 |
| Asp | Glu | GAC | GAG | 37.3 | 32 | -0.8 | -2.1 |
| Asp | Asp | GAC | GAT | 55.8 | 52 | -0.3 | -0.0 |
| Asp | Ala | GAC | GCA | 42.0 | 41 | -0.0 | -0.0 |
| Asp | Ala | GAC | GCC | 38.5 | 44 | 0.8 | 1.3 |
| Asp | Ala | GAC | GCG | 63.0 | 47 | -4.1 | -3.1 |
| Asp | Ala | GAC | GCT | 43.6 | 35 | -1.7 | -1.2 |
| Asp | Gly | GAC | GGA | 7.9 | 6 | -0.5 | -0.4 |
| Asp | Gly | GAC | GGC | 61.8 | 72 | 1.7 | 1.9 |
| Asp | Gly | GAC | GGG | 12.5 | 17 | 1.7 | 1.8 |
| Asp | Gly | GAC | GGT | 67.7 | 78 | 1.6 | 1.8 |
| Asp | Val | GAC | GTA | 28.1 | 36 | 2.2 | 0.5 |
| Asp | Val | GAC | GTC | 22.5 | 30 | 2.5 | 0.7 |
| Asp | Val | GAC | GTG | 42.9 | 44 | 0.0 | 0.5 |
| Asp | Val | GAC | GTT | 50.7 | 68 | 5.9 | 1.7 |
| Asp | Ocr | GAC | TAA | 0.0 | 3 | 0.0 | 0.0 |
| Asp | Tyr | GAC | TAC | 30.8 | 43 | 4.8 | 0.6 |
| Asp | Amb | GAC | TAG | 0.0 | 0 | 0.0 | 0.0 |
| Asp | Tyr | GAC | TAT | 24.9 | 29 | 0.7 | 0.1 |
| Asp | Ser | GAC | TCA | 8.0 | 3 | -3.1 | -3.1 |
| Asp | Ser | GAC | TCC | 23.6 | 36 | 6.6 | 6.5 |
| Asp | Ser | GAC | TCG | 12.1 | 12 | -0.0 | -0.0 |
| Asp | Ser | GAC | TCT | 24.8 | 15 | -3.9 | -3.9 |
| Asp | Umb | GAC | TGA | 0.0 | 0 | 0.0 | 0.0 |
| Asp | Cys | GAC | TGC | 10.7 | 9 | -0.3 | -0.1 |
| Asp | Trp | GAC | TGG | 19.7 | 47 | 37.7 | 23.4 |
| Asp | Cys | GAC | TGT | 7.6 | 4 | -1.7 | -0.5 |
| Asp | Leu | GAC | TTA | 14.2 | 14 | -0.0 | -0.0 |
| Asp | Phe | GAC | TTC | 40.4 | 47 | 1.1 | 0.1 |
| Asp | Leu | GAC | TTG | 16.0 | 19 | 0.6 | 0.9 |
| Asp | Phe | GAC | TTT | 25.9 | 24 | -0.1 | -0.8 |
| | Page Totals: | | | 1935.7 | 1940 | 208.2 | 177.4 |

ECOO.RXD/CPLIST.RXR January 11, 1989

| aa1 | aa2 | cod1 | cod2 | exp | obs | chis1 | chis2 |
|---|---|---|---|---|---|---|---|
| Glu | Lys | GAG | AAA | 58.8 | 92 | 18.8 | 8.3 |
| Glu | Asn | GAG | AAC | 38.5 | 34 | -0.5 | -1.8 |
| Glu | Lys | GAG | AAG | 20.1 | 39 | 17.9 | 10.6 |
| Glu | Asn | GAG | AAT | 21.3 | 11 | -5.0 | -6.8 |
| Glu | Thr | GAG | ACA | 8.2 | 9 | 0.1 | 0.2 |
| Glu | Thr | GAG | ACC | 36.1 | 9 | -20.3 | -18.8 |
| Glu | Thr | GAG | ACG | 17.1 | 9 | -3.8 | -3.3 |
| Glu | Thr | GAG | ACT | 16.0 | 12 | -1.0 | -0.7 |
| Glu | Arg | GAG | AGA | 2.5 | 0 | -2.5 | -2.4 |
| Glu | Ser | GAG | AGC | 23.4 | 21 | -0.2 | -0.0 |
| Glu | Arg | GAG | AGG | 1.5 | 2 | 0.2 | 0.2 |
| Glu | Ser | GAG | AGT | 9.2 | 7 | -0.5 | -0.2 |
| Glu | Ile | GAG | ATA | 4.6 | 5 | 0.0 | 0.0 |
| Glu | Ile | GAG | ATC | 46.3 | 55 | 1.6 | 0.9 |
| Glu | Met | GAG | ATG | 39.5 | 58 | 8.7 | 7.0 |
| Glu | Ile | GAG | ATT | 36.5 | 41 | 0.5 | 0.2 |
| Glu | Gln | GAG | CAA | 19.4 | 65 | 107.7 | 64.9 |
| Glu | His | GAG | CAC | 18.3 | 26 | 3.3 | 3.9 |
| Glu | Gln | GAG | CAG | 48.5 | 100 | 54.7 | 22.9 |
| Glu | His | GAG | CAT | 14.9 | 22 | 3.4 | 4.0 |
| Glu | Pro | GAG | CCA | 10.9 | 14 | 0.9 | 1.9 |
| Glu | Pro | GAG | CCC | 5.3 | 1 | -3.5 | -2.9 |
| Glu | Pro | GAG | CCG | 36.9 | 62 | 17.1 | 25.9 |
| Glu | Pro | GAG | CCT | 8.2 | 11 | 0.9 | 1.9 |
| Glu | Arg | GAG | CGA | 3.9 | 6 | 1.2 | 1.3 |
| Glu | Arg | GAG | CGC | 34.4 | 43 | 2.2 | 2.6 |
| Glu | Arg | GAG | CGG | 5.3 | 14 | 14.2 | 14.9 |
| Glu | Arg | GAG | CGT | 45.0 | 62 | 6.4 | 7.4 |
| Glu | Leu | GAG | CTA | 3.6 | 6 | 1.6 | 1.0 |
| Glu | Leu | GAG | CTC | 14.6 | 7 | -3.9 | -5.3 |
| Glu | Leu | GAG | CTG | 86.0 | 141 | 35.2 | 21.2 |
| Glu | Leu | GAG | CTT | 13.3 | 28 | 16.2 | 11.7 |
| Glu | Glu | GAG | GAA | 73.9 | 20 | -39.3 | -38.0 |
| Glu | Asp | GAG | GAC | 37.3 | 5 | -28.0 | -19.7 |
| Glu | Glu | GAG | GAG | 36.9 | 8 | -22.6 | -21.9 |
| Glu | Asp | GAG | GAT | 45.5 | 8 | -30.9 | -20.9 |
| Glu | Ala | GAG | GCA | 31.2 | 19 | -4.8 | -5.1 |
| Glu | Ala | GAG | GCC | 34.3 | 14 | -12.0 | -12.5 |
| Glu | Ala | GAG | GCG | 51.5 | 31 | -8.2 | -8.8 |
| Glu | Ala | GAG | GCT | 28.1 | 15 | -6.1 | -6.5 |
| Glu | Gly | GAG | GGA | 8.2 | 3 | -3.3 | -2.6 |
| Glu | Gly | GAG | GGC | 44.0 | 16 | -17.8 | -14.0 |
| Glu | Gly | GAG | GGG | 12.2 | 7 | -2.2 | -1.4 |
| Glu | Gly | GAG | GGT | 46.1 | 7 | -33.1 | -28.5 |
| Glu | Val | GAG | GTA | 19.8 | 5 | -11.0 | -11.4 |
| Glu | Val | GAG | GTC | 19.7 | 8 | -6.9 | -7.2 |
| Glu | Val | GAG | GTG | 35.0 | 22 | -4.8 | -5.2 |
| Glu | Val | GAG | GTT | 34.5 | 17 | -8.9 | -9.3 |
| Glu | Ocr | GAG | TAA | 0.0 | 7 | 0.0 | 0.0 |
| Glu | Tyr | GAG | TAC | 21.3 | 23 | 0.1 | 0.5 |
| Glu | Amb | GAG | TAG | 0.0 | 0 | 0.0 | 0.0 |
| Glu | Tyr | GAG | TAT | 21.5 | 23 | 0.1 | 0.4 |
| Glu | Ser | GAG | TCA | 8.2 | 10 | 0.4 | 0.8 |
| Glu | Ser | GAG | TCC | 15.8 | 16 | 0.0 | 0.2 |
| Glu | Ser | GAG | TCG | 11.3 | 13 | 0.3 | 0.7 |
| Glu | Ser | GAG | TCT | 17.8 | 17 | -0.0 | -0.0 |
| Glu | Umb | GAG | TGA | 0.0 | 0 | 0.0 | 0.0 |
| Glu | Cys | GAG | TGC | 8.6 | 15 | 4.7 | 10.7 |
| Glu | Trp | GAG | TGG | 15.7 | 23 | 3.4 | 5.4 |
| Glu | Cys | GAG | TGT | 6.3 | 7 | 0.1 | 1.0 |
| Glu | Leu | GAG | TTA | 14.8 | 20 | 1.9 | 0.8 |
| Glu | Phe | GAG | TTC | 28.1 | 44 | 9.0 | 12.5 |
| Glu | Leu | GAG | TTG | 15.9 | 31 | 14.5 | 10.0 |
| Glu | Phe | GAG | TTT | 23.5 | 53 | 37.0 | 44.8 |
| | | Page Totals: | | 1514.4 | 1519 | 665.7 | 556.0 |

PAGE 35

ECOO.RXD/CPLIST.RXR January 11, 1989

| aa1 | aa2 | cod1 | cod2 | exp | obs | chis1 | chis2 |
|---|---|---|---|---|---|---|---|
| Asp | Lys | GAT | AAA | 91.0 | 94 | 0.1 | 0.0 |
| Asp | Asn | GAT | AAC | 62.2 | 87 | 9.9 | 9.2 |
| Asp | Lys | GAT | AAG | 28.6 | 26 | -0.2 | -0.4 |
| Asp | Asn | GAT | AAT | 36.5 | 27 | -2.5 | -2.7 |
| Asp | Thr | GAT | ACA | 13.8 | 11 | -0.6 | -0.2 |
| Asp | Thr | GAT | ACC | 56.9 | 58 | 0.0 | 0.7 |
| Asp | Thr | GAT | ACG | 26.2 | 26 | -0.0 | -0.2 |
| Asp | Thr | GAT | ACT | 25.5 | 20 | -1.2 | -0.5 |
| Asp | Arg | GAT | AGA | 4.1 | 3 | -0.3 | -0.1 |
| Asp | Ser | GAT | AGC | 37.3 | 34 | -0.3 | -0.3 |
| Asp | Arg | GAT | AGG | 2.3 | 0 | -2.3 | -2.0 |
| Asp | Ser | GAT | AGT | 15.5 | 5 | -7.1 | -7.2 |
| Asp | Ile | GAT | ATA | 7.7 | 5 | -0.9 | -1.4 |
| Asp | Ile | GAT | ATC | 69.7 | 107 | 19.9 | 11.9 |
| Asp | Met | GAT | ATG | 60.3 | 54 | -0.7 | -0.0 |
| Asp | Ile | GAT | ATT | 59.7 | 65 | 0.5 | 0.0 |
| Asp | Gln | GAT | CAA | 31.6 | 27 | -0.7 | -0.0 |
| Asp | His | GAT | CAC | 26.9 | 30 | 0.4 | 3.4 |
| Asp | Gln | GAT | CAG | 74.7 | 68 | -0.6 | -0.3 |
| Asp | His | GAT | CAT | 23.7 | 9 | -9.1 | -5.2 |
| Asp | Pro | GAT | CCA | 18.0 | 13 | -1.4 | -1.5 |
| Asp | Pro | GAT | CCC | 8.3 | 8 | -0.0 | -0.0 |
| Asp | Pro | GAT | CCG | 56.0 | 68 | 2.6 | 2.3 |
| Asp | Pro | GAT | CCT | 12.9 | 22 | 6.4 | 6.2 |
| Asp | Arg | GAT | CGA | 5.4 | 0 | -5.4 | -4.8 |
| Asp | Arg | GAT | CGC | 51.1 | 54 | 0.2 | 1.9 |
| Asp | Arg | GAT | CGG | 8.1 | 7 | -0.1 | -0.0 |
| Asp | Arg | GAT | CGT | 64.6 | 43 | -7.2 | -3.3 |
| Asp | Leu | GAT | CTA | 6.0 | 1 | -4.1 | -3.9 |
| Asp | Leu | GAT | CTC | 21.3 | 36 | 10.2 | 12.0 |
| Asp | Leu | GAT | CTG | 131.8 | 125 | -0.3 | -0.0 |
| Asp | Leu | GAT | CTT | 20.9 | 20 | -0.0 | 0.0 |
| Asp | Glu | GAT | GAA | 111.2 | 139 | 6.9 | 2.1 |
| Asp | Asp | GAT | GAC | 55.8 | 72 | 4.7 | 7.0 |
| Asp | Glu | GAT | GAG | 45.5 | 42 | -0.3 | -1.4 |
| Asp | Asp | GAT | GAT | 82.3 | 66 | -3.2 | -1.8 |
| Asp | Ala | GAT | GCA | 50.0 | 37 | -3.4 | -2.6 |
| Asp | Ala | GAT | GCC | 55.0 | 71 | 4.7 | 6.1 |
| Asp | Ala | GAT | GCG | 79.0 | 75 | -0.2 | -0.0 |
| Asp | Ala | GAT | GCT | 45.8 | 52 | 0.8 | 1.4 |
| Asp | Gly | GAT | GGA | 14.3 | 8 | -2.8 | -2.7 |
| Asp | Gly | GAT | GGC | 70.4 | 75 | 0.3 | 0.4 |
| Asp | Gly | GAT | GGG | 19.9 | 3 | -14.4 | -14.2 |
| Asp | Gly | GAT | GGT | 75.2 | 67 | -0.9 | -0.7 |
| Asp | Val | GAT | GTA | 29.7 | 20 | -3.1 | -5.7 |
| Asp | Val | GAT | GTC | 31.6 | 40 | 2.2 | 0.4 |
| Asp | Val | GAT | GTG | 54.5 | 64 | 1.7 | 0.0 |
| Asp | Val | GAT | GTT | 54.2 | 57 | 0.1 | 0.4 |
| Asp | Ocr | GAT | TAA | 0.0 | 5 | 0.0 | 0.0 |
| Asp | Tyr | GAT | TAC | 32.4 | 43 | 3.5 | 0.2 |
| Asp | Amb | GAT | TAG | 0.0 | 0 | 0.0 | 0.0 |
| Asp | Tyr | GAT | TAT | 36.2 | 40 | 0.4 | 0.6 |
| Asp | Ser | GAT | TCA | 14.1 | 9 | -1.8 | -1.8 |
| Asp | Ser | GAT | TCC | 25.1 | 25 | -0.0 | -0.0 |
| Asp | Ser | GAT | TCG | 17.4 | 9 | -4.1 | -4.1 |
| Asp | Ser | GAT | TCT | 27.2 | 13 | -7.4 | -7.5 |
| Asp | Umb | GAT | TGA | 0.0 | 2 | 0.0 | 0.0 |
| Asp | Cys | GAT | TGC | 13.2 | 9 | -1.3 | -0.1 |
| Asp | Trp | GAT | TGG | 25.5 | 7 | -13.4 | -18.1 |
| Asp | Cys | GAT | TGT | 10.3 | 9 | -0.2 | -0.3 |
| Asp | Leu | GAT | TTA | 24.8 | 33 | 2.7 | 3.6 |
| Asp | Phe | GAT | TTC | 44.2 | 52 | 1.4 | 0.2 |
| Asp | Leu | GAT | TTG | 24.9 | 31 | 1.5 | 2.2 |
| Asp | Phe | GAT | TTT | 38.8 | 43 | 0.4 | 0.0 |
| | | Page Totals: | | 2366.7 | 2371 | 183.1 | 167.0 |

PAGE 36

ECDO.RXD/CPLIST.RXR January 11, 1989

| aa1 | aa2 | cod1 | cod2 | exp | obs | chis1 | chis2 |
|---|---|---|---|---|---|---|---|
| Ala | Lys | GCA | AAA | 71.3 | 63 | -1.0 | -1.1 |
| Ala | Asn | GCA | AAC | 44.8 | 34 | -2.6 | -1.2 |
| Ala | Lys | GCA | AAG | 21.3 | 5 | -12.4 | -12.7 |
| Ala | Asn | GCA | AAT | 24.5 | 18 | -1.7 | -0.8 |
| Ala | Thr | GCA | ACA | 9.9 | 18 | 6.5 | 7.9 |
| Ala | Thr | GCA | ACC | 40.7 | 52 | 3.1 | 4.9 |
| Ala | Thr | GCA | ACG | 17.3 | 28 | 6.6 | 8.4 |
| Ala | Thr | GCA | ACT | 21.1 | 20 | -0.1 | -0.0 |
| Ala | Arg | GCA | AGA | 2.7 | 1 | -1.1 | -1.1 |
| Ala | Ser | GCA | AGC | 23.7 | 25 | 0.1 | 0.1 |
| Ala | Arg | GCA | AGG | 1.7 | 2 | 0.1 | 0.1 |
| Ala | Ser | GCA | AGT | 11.0 | 9 | -0.4 | -0.3 |
| Ala | Ile | GCA | ATA | 5.4 | 8 | 1.3 | 1.7 |
| Ala | Ile | GCA | ATC | 52.1 | 33 | -7.0 | -5.5 |
| Ala | Met | GCA | ATG | 43.2 | 46 | 0.2 | 0.0 |
| Ala | Ile | GCA | ATT | 40.7 | 31 | -2.3 | -1.5 |
| Ala | Gln | GCA | CAA | 21.5 | 23 | 0.1 | 0.0 |
| Ala | His | GCA | CAC | 18.4 | 18 | -0.0 | 0.0 |
| Ala | Gln | GCA | CAG | 52.0 | 53 | 0.0 | 0.2 |
| Ala | His | GCA | CAT | 14.7 | 15 | 0.0 | 0.0 |
| Ala | Pro | GCA | CCA | 12.0 | 15 | 0.7 | 3.1 |
| Ala | Pro | GCA | CCC | 5.6 | 5 | -0.1 | -0.1 |
| Ala | Pro | GCA | CCG | 38.4 | 41 | 0.2 | 3.5 |
| Ala | Pro | GCA | CCT | 9.2 | 10 | 0.1 | 1.0 |
| Ala | Arg | GCA | CGA | 3.7 | 10 | 10.7 | 10.4 |
| Ala | Arg | GCA | CGC | 31.2 | 28 | -0.3 | -0.4 |
| Ala | Arg | GCA | CGG | 5.0 | 3 | -0.8 | -0.8 |
| Ala | Arg | GCA | CGT | 46.3 | 45 | -0.0 | -0.1 |
| Ala | Leu | GCA | CTA | 3.7 | 5 | 0.4 | 0.3 |
| Ala | Leu | GCA | CTC | 14.1 | 13 | -0.1 | -0.2 |
| Ala | Leu | GCA | CTG | 93.5 | 100 | 0.4 | 0.1 |
| Ala | Leu | GCA | CTT | 13.8 | 9 | -1.6 | -1.9 |
| Ala | Glu | GCA | GAA | 80.1 | 105 | 7.7 | 3.3 |
| Ala | Asp | GCA | GAC | 42.0 | 42 | 0.0 | 0.2 |
| Ala | Glu | GCA | GAG | 31.2 | 44 | 5.2 | 2.8 |
| Ala | Asp | GCA | GAT | 50.0 | 42 | -1.3 | -2.5 |
| Ala | Ala | GCA | GCA | 45.7 | 48 | 0.1 | 0.0 |
| Ala | Ala | GCA | GCC | 35.7 | 20 | -6.9 | -8.9 |
| Ala | Ala | GCA | GCG | 55.0 | 55 | 0.0 | 0.3 |
| Ala | Ala | GCA | GCT | 39.9 | 37 | -0.2 | -0.8 |
| Ala | Gly | GCA | GGA | 9.9 | 12 | 0.5 | 0.5 |
| Ala | Gly | GCA | GGC | 50.9 | 68 | 5.8 | 6.3 |
| Ala | Gly | GCA | GGG | 12.9 | 13 | 0.0 | 0.0 |
| Ala | Gly | GCA | GGT | 57.1 | 69 | 2.5 | 2.9 |
| Ala | Val | GCA | GTA | 23.6 | 21 | -0.3 | -0.1 |
| Ala | Val | GCA | GTC | 21.0 | 13 | -3.0 | -2.3 |
| Ala | Val | GCA | GTG | 37.4 | 43 | 0.8 | 1.7 |
| Ala | Val | GCA | GTT | 44.1 | 20 | -13.2 | -11.2 |
| Ala | Ocr | GCA | TAA | 0.0 | 4 | 0.0 | 0.0 |
| Ala | Tyr | GCA | TAC | 22.4 | 13 | -3.9 | -1.2 |
| Ala | Amb | GCA | TAG | 0.0 | 0 | 0.0 | 0.0 |
| Ala | Tyr | GCA | TAT | 23.5 | 12 | -5.6 | -2.3 |
| Ala | Ser | GCA | TCA | 9.8 | 20 | 10.6 | 11.2 |
| Ala | Ser | GCA | TCC | 18.3 | 9 | -4.7 | -4.4 |
| Ala | Ser | GCA | TCG | 11.0 | 15 | 1.4 | 1.6 |
| Ala | Ser | GCA | TCT | 21.5 | 22 | 0.0 | 0.0 |
| Ala | Umb | GCA | TGA | 0.0 | 2 | 0.0 | 0.0 |
| Ala | Cys | GCA | TGC | 8.5 | 3 | -3.6 | -4.5 |
| Ala | Trp | GCA | TGG | 17.2 | 19 | 0.2 | 0.0 |
| Ala | Cys | GCA | TGT | 6.3 | 6 | -0.0 | -0.2 |
| Ala | Leu | GCA | TTA | 17.5 | 36 | 19.7 | 18.0 |
| Ala | Phe | GCA | TTC | 30.9 | 40 | 2.7 | 3.1 |
| Ala | Leu | GCA | TTG | 16.4 | 23 | 2.6 | 2.2 |
| Ala | Phe | GCA | TTT | 26.6 | 24 | -0.3 | -0.2 |
| | | Page Totals: | | 1680.2 | 1686 | .164.9 | 162.3 |

PAGE 37

ECOO.RXD/CPLIST.RXR January 11, 1989

| aa1 | aa2 | cod1 | cod2 | exp | obs | chis1 | chis2 |
|---|---|---|---|---|---|---|---|
| Ala | Lys | GCC | AAA | 64.1 | 61 | -0.2 | -0.2 |
| Ala | Asn | GCC | AAC | 44.0 | 47 | 0.2 | 1.1 |
| Ala | Lys | GCC | AAG | 19.8 | 15 | -1.2 | -1.3 |
| Ala | Asn | GCC | AAT | 27.8 | 33 | 1.0 | 2.3 |
| Ala | Thr | GCC | ACA | 9.9 | 8 | -0.4 | -0.2 |
| Ala | Thr | GCC | ACC | 42.0 | 51 | 1.9 | 3.3 |
| Ala | Thr | GCC | ACG | 21.8 | 21 | -0.0 | -0.0 |
| Ala | Thr | GCC | ACT | 17.1 | 9 | -3.8 | -3.1 |
| Ala | Arg | GCC | AGA | 2.1 | 4 | 1.8 | 1.8 |
| Ala | Ser | GCC | AGC | 30.4 | 81 | 84.2 | 87.8 |
| Ala | Arg | GCC | AGG | 1.6 | 9 | 34.9 | 34.4 |
| Ala | Ser | GCC | AGT | 12.7 | 33 | 32.7 | 34.2 |
| Ala | Ile | GCC | ATA | 5.0 | 5 | -0.0 | -0.0 |
| Ala | Ile | GCC | ATC | 50.9 | 53 | 0.1 | 0.4 |
| Ala | Met | GCC | ATG | 46.5 | 18 | -17.4 | -19.7 |
| Ala | Ile | GCC | ATT | 46.4 | 58 | 2.9 | 4.4 |
| Ala | Gln | GCC | CAA | 25.3 | 9 | -10.5 | -12.2 |
| Ala | His | GCC | CAC | 18.8 | 13 | -1.8 | -1.6 |
| Ala | Gln | GCC | CAG | 56.0 | 54 | -0.1 | -0.6 |
| Ala | His | GCC | CAT | 18.5 | 17 | -0.1 | -0.1 |
| Ala | Pro | GCC | CCA | 13.1 | 3 | -7.8 | -5.3 |
| Ala | Pro | GCC | CCC | 6.8 | 1 | -4.9 | -3.6 |
| Ala | Pro | GCC | CCG | 40.4 | 11 | -21.4 | -14.0 |
| Ala | Pro | GCC | CCT | 9.5 | 5 | -2.1 | -0.9 |
| Ala | Arg | GCC | CGA | 5.0 | 5 | -0.0 | -0.0 |
| Ala | Arg | GCC | CGC | 39.5 | 39 | -0.0 | -0.0 |
| Ala | Arg | GCC | CGG | 6.9 | 5 | -0.5 | -0.5 |
| Ala | Arg | GCC | CGT | 44.9 | 41 | -0.3 | -0.4 |
| Ala | Leu | GCC | CTA | 4.7 | 1 | -2.9 | -3.1 |
| Ala | Leu | GCC | CTC | 17.0 | 10 | -2.9 | -3.2 |
| Ala | Leu | GCC | CTG | 98.9 | 56 | -18.6 | -20.6 |
| Ala | Leu | GCC | CTT | 15.4 | 5 | -7.0 | -7.4 |
| Ala | Glu | GCC | GAA | 78.9 | 68 | -1.5 | -4.0 |
| Ala | Asp | GCC | GAC | 38.5 | 52 | 4.7 | 2.8 |
| Ala | Glu | GCC | GAG | 34.3 | 35 | 0.0 | 0.2 |
| Ala | Asp | GCC | GAT | 55.0 | 90 | 22.3 | 16.4 |
| Ala | Ala | GCC | GCA | 35.7 | 31 | -0.6 | -1.4 |
| Ala | Ala | GCC | GCC | 52.4 | 67 | 4.0 | 1.9 |
| Ala | Ala | GCC | GCG | 64.1 | 58 | -0.6 | -1.8 |
| Ala | Ala | GCC | GCT | 32.5 | 48 | 7.4 | 4.8 |
| Ala | Gly | GCC | GGA | 9.9 | 28 | 32.9 | 33.8 |
| Ala | Gly | GCC | GGC | 52.9 | 7 | -39.9 | -39.2 |
| Ala | Gly | GCC | GGG | 15.7 | 36 | 26.3 | 27.1 |
| Ala | Gly | GCC | GGT | 50.6 | 72 | 9.0 | 9.7 |
| Ala | Val | GCC | GTA | 21.3 | 15 | -1.9 | -1.3 |
| Ala | Val | GCC | GTC | 25.6 | 21 | -0.8 | -0.4 |
| Ala | Val | GCC | GTG | 44.0 | 25 | -8.2 | -6.6 |
| Ala | Val | GCC | GTT | 36.9 | 55 | 8.9 | 11.7 |
| Ala | Ocr | GCC | TAA | 0.0 | 0 | 0.0 | 0.0 |
| Ala | Tyr | GCC | TAC | 22.5 | 21 | -0.1 | -0.6 |
| Ala | Amb | GCC | TAG | 0.0 | 0 | 0.0 | 0.0 |
| Ala | Tyr | GCC | TAT | 24.7 | 24 | -0.0 | -1.0 |
| Ala | Ser | GCC | TCA | 10.2 | 4 | -3.8 | -3.6 |
| Ala | Ser | GCC | TCC | 18.6 | 15 | -0.7 | -0.6 |
| Ala | Ser | GCC | TCG | 14.6 | 17 | 0.4 | 0.5 |
| Ala | Ser | GCC | TCT | 18.6 | 26 | 2.9 | 3.3 |
| Ala | Umb | GCC | TGA | 0.0 | 5 | 0.0 | 0.0 |
| Ala | Cys | GCC | TGC | 11.0 | 19 | 5.8 | 3.6 |
| Ala | Trp | GCC | TGG | 19.3 | 48 | 42.7 | 34.5 |
| Ala | Cys | GCC | TGT | 7.6 | 24 | 35.7 | 28.5 |
| Ala | Leu | GCC | TTA | 18.1 | 15 | -0.5 | -0.7 |
| Ala | Phe | GCC | TTC | 32.4 | 20 | -4.7 | -4.3 |
| Ala | Leu | GCC | TTG | 19.9 | 7 | -8.3 | -8.8 |
| Ala | Phe | GCC | TTT | 30.2 | 28 | -0.2 | -0.1 |
| | | Page Totals: | | 1758.6 | 1762 | 538.6 | 520.8 |

PAGE 38

ECOO.RXD/CPLIST.RXR January 11, 1989

| aa1 | aa2 | cod1 | cod2 | exp | obs | chis1 | chis2 |
|---|---|---|---|---|---|---|---|
| Ala | Lys | GCG | AAA | 99.7 | 144 | 19.7 | 18.5 |
| Ala | Asn | GCG | AAC | 69.2 | 50 | -5.3 | -2.8 |
| Ala | Lys | GCG | AAG | 31.4 | 47 | 7.8 | 7.3 |
| Ala | Asn | GCG | AAT | 34.8 | 29 | -1.0 | -0.2 |
| Ala | Thr | GCG | ACA | 12.9 | 15 | 0.3 | 0.7 |
| Ala | Thr | GCG | ACC | 66.6 | 44 | -7.7 | -5.6 |
| Ala | Thr | GCG | ACG | 30.1 | 32 | 0.1 | 0.5 |
| Ala | Thr | GCG | ACT | 26.6 | 26 | -0.0 | -0.0 |
| Ala | Arg | GCG | AGA | 2.8 | 4 | 0.5 | 0.5 |
| Ala | Ser | GCG | AGC | 41.2 | 13 | -19.3 | -18.6 |
| Ala | Arg | GCG | AGG | 1.8 | 4 | 2.8 | 2.7 |
| Ala | Ser | GCG | AGT | 16.7 | 7 | -5.7 | -5.4 |
| Ala | Ile | GCG | ATA | 5.8 | 6 | 0.0 | 0.0 |
| Ala | Ile | GCG | ATC | 81.1 | 56 | -7.7 | -5.7 |
| Ala | Met | GCG | ATG | 71.8 | 128 | 44.0 | 36.0 |
| Ala | Ile | GCG | ATT | 64.7 | 87 | 7.7 | 10.6 |
| Ala | Gln | GCG | CAA | 33.5 | 63 | 26.0 | 20.1 |
| Ala | His | GCG | CAC | 30.0 | 33 | 0.3 | 0.4 |
| Ala | Gln | GCG | CAG | 83.4 | 105 | 5.6 | 2.6 |
| Ala | His | GCG | CAT | 24.6 | 30 | 1.2 | 1.4 |
| Ala | Pro | GCG | CCA | 18.6 | 23 | 1.0 | 4.5 |
| Ala | Pro | GCG | CCC | 8.8 | 9 | 0.0 | 0.6 |
| Ala | Pro | GCG | CCG | 65.6 | 63 | -0.1 | -2.2 |
| Ala | Pro | GCG | CCT | 13.1 | 11 | -0.3 | -0.0 |
| Ala | Arg | GCG | CGA | 6.2 | 6 | -0.0 | -0.0 |
| Ala | Arg | GCG | CGC | 57.2 | 56 | -0.0 | -0.1 |
| Ala | Arg | GCG | CGG | 8.7 | 14 | 3.2 | 3.1 |
| Ala | Arg | GCG | CGT | 73.4 | 86 | 2.2 | 1.9 |
| Ala | Leu | GCG | CTA | 6.0 | 16 | 17.0 | 15.9 |
| Ala | Leu | GCG | CTC | 24.1 | 14 | -4.2 | -4.7 |
| Ala | Leu | GCG | CTG | 155.1 | 238 | 44.4 | 38.4 |
| Ala | Leu | GCG | CTT | 20.7 | 26 | 1.4 | 1.0 |
| Ala | Glu | GCG | GAA | 124.2 | 101 | -4.3 | -9.1 |
| Ala | Asp | GCG | GAC | 63.0 | 29 | -18.4 | -22.0 |
| Ala | Glu | GCG | GAG | 51.5 | 27 | -11.7 | -15.4 |
| Ala | Asp | GCG | GAT | 79.0 | 54 | -7.9 | -11.1 |
| Ala | Ala | GCG | GCA | 55.0 | 92 | 25.0 | 18.1 |
| Ala | Ala | GCG | GCC | 64.1 | 23 | -26.3 | -30.8 |
| Ala | Ala | GCG | GCG | 104.6 | 96 | -0.7 | -2.5 |
| Ala | Ala | GCG | GCT | 50.2 | 37 | -3.5 | -5.4 |
| Ala | Gly | GCG | GGA | 13.2 | 17 | 1.1 | 1.2 |
| Ala | Gly | GCG | GGC | 82.4 | 59 | -6.7 | -6.2 |
| Ala | Gly | GCG | GGG | 21.0 | 15 | -1.7 | -1.6 |
| Ala | Gly | GCG | GGT | 81.1 | 72 | -1.0 | -0.8 |
| Ala | Val | GCG | GTA | 33.1 | 63 | 27.1 | 32.5 |
| Ala | Val | GCG | GTC | 36.3 | 15 | -12.5 | -10.8 |
| Ala | Val | GCG | GTG | 66.9 | 92 | 9.5 | 13.3 |
| Ala | Val | GCG | GTT | 59.2 | 64 | 0.4 | 1.2 |
| Ala | Ocr | GCG | TAA | 0.0 | 7 | 0.0 | 0.0 |
| Ala | Tyr | GCG | TAC | 35.1 | 10 | -17.9 | -11.3 |
| Ala | Amb | GCG | TAG | 0.0 | 2 | 0.0 | 0.0 |
| Ala | Tyr | GCG | TAT | 35.3 | 8 | -21.1 | -14.2 |
| Ala | Ser | GCG | TCA | 12.6 | 4 | -5.8 | -5.6 |
| Ala | Ser | GCG | TCC | 28.3 | 9 | -13.1 | -12.7 |
| Ala | Ser | GCG | TCG | 20.2 | 16 | -0.9 | -0.7 |
| Ala | Ser | GCG | TCT | 28.7 | 17 | -4.7 | -4.4 |
| Ala | Umb | GCG | TGA | 0.0 | 0 | 0.0 | 0.0 |
| Ala | Cys | GCG | TGC | 15.0 | 7 | -4.3 | -5.8 |
| Ala | Trp | GCG | TGG | 27.2 | 17 | -3.9 | -5.4 |
| Ala | Cys | GCG | TGT | 10.8 | 8 | -0.7 | -1.4 |
| Ala | Leu | GCG | TTA | 23.3 | 48 | 26.2 | 24.0 |
| Ala | Phe | GCG | TTC | 49.6 | 53 | 0.2 | 0.4 |
| Ala | Leu | GCG | TTG | 27.7 | 38 | 3.9 | 3.2 |
| Ala | Phe | GCG | TTT | 41.6 | 47 | 0.7 | 1.0 |
| | | Page Totals: | | 2626.1 | 2632 | 497.6 | 484.2 |

ECOO.RXD/CPLIST.RXR January 11, 1989

| aa1 | aa2 | cod1 | cod2 | exp | obs | chis1 | chis2 |
|---|---|---|---|---|---|---|---|
| Ala | Lys | GCT | AAA | 72.1 | 53 | -5.0 | -5.4 |
| Ala | Asn | GCT | AAC | 45.8 | 57 | 2.7 | 5.5 |
| Ala | Lys | GCT | AAG | 20.8 | 17 | -0.7 | -0.8 |
| Ala | Asn | GCT | AAT | 20.0 | 16 | -0.8 | -0.3 |
| Ala | Thr | GCT | ACA | 8.0 | 2 | -4.5 | -4.1 |
| Ala | Thr | GCT | ACC | 39.5 | 30 | -2.3 | -1.4 |
| Ala | Thr | GCT | ACG | 14.0 | 11 | -0.6 | -0.4 |
| Ala | Thr | GCT | ACT | 22.5 | 10 | -7.0 | -5.9 |
| Ala | Arg | GCT | AGA | 1.9 | 0 | -1.9 | -1.9 |
| Ala | Ser | GCT | AGC | 21.8 | 3 | -16.2 | -15.8 |
| Ala | Arg | GCT | AGG | 1.2 | 0 | -1.2 | -1.2 |
| Ala | Ser | GCT | AGT | 8.4 | 0 | -8.4 | -8.2 |
| Ala | Ile | GCT | ATA | 4.0 | 1 | -2.3 | -2.1 |
| Ala | Ile | GCT | ATC | 54.4 | 58 | 0.2 | 0.8 |
| Ala | Met | GCT | ATG | 42.3 | 23 | -8.8 | -10.5 |
| Ala | Ile | GCT | ATT | 35.9 | 28 | -1.7 | -1.1 |
| Ala | Gln | GCT | CAA | 17.9 | 12 | -1.9 | -2.7 |
| Ala | His | GCT | CAC | 17.4 | 16 | -0.1 | -0.1 |
| Ala | Gln | GCT | CAG | 49.8 | 46 | -0.3 | -1.1 |
| Ala | His | GCT | CAT | 12.5 | 10 | -0.5 | -0.4 |
| Ala | Pro | GCT | CCA | 10.6 | 6 | -2.0 | -0.7 |
| Ala | Pro | GCT | CCC | 4.1 | 3 | -0.3 | -0.0 |
| Ala | Pro | GCT | CCG | 37.6 | 30 | -1.5 | -0.0 |
| Ala | Pro | GCT | CCT | 7.9 | 4 | -1.9 | -0.8 |
| Ala | Arg | GCT | CGA | 2.9 | 4 | 0.4 | 0.4 |
| Ala | Arg | GCT | CGC | 29.6 | 26 | -0.4 | -0.5 |
| Ala | Arg | GCT | CGG | 4.2 | 3 | -0.3 | -0.3 |
| Ala | Arg | GCT | CGT | 46.8 | 36 | -2.5 | -2.7 |
| Ala | Leu | GCT | CTA | 3.0 | 3 | 0.0 | 0.0 |
| Ala | Leu | GCT | CTC | 12.0 | 5 | -4.1 | -4.4 |
| Ala | Leu | GCT | CTG | 92.7 | 61 | -10.8 | -12.4 |
| Ala | Leu | GCT | CTT | 11.7 | 5 | -3.9 | -4.1 |
| Ala | Glu | GCT | GAA | 80.3 | 144 | 50.4 | 35.4 |
| Ala | Asp | GCT | GAC | 43.6 | 69 | 14.8 | 10.6 |
| Ala | Glu | GCT | GAG | 28.1 | 34 | 1.2 | 0.3 |
| Ala | Asp | GCT | GAT | 45.8 | 69 | 11.7 | 8.1 |
| Ala | Ala | GCT | GCA | 39.9 | 60 | 10.2 | 6.7 |
| Ala | Ala | GCT | GCC | 32.5 | 59 | 21.6 | 16.4 |
| Ala | Ala | GCT | GCG | 50.2 | 78 | 15.3 | 10.5 |
| Ala | Ala | GCT | GCT | 50.3 | 62 | 2.7 | 1.1 |
| Ala | Gly | GCT | GGA | 7.7 | 5 | -0.9 | -0.9 |
| Ala | Gly | GCT | GGC | 49.9 | 63 | 3.4 | 3.8 |
| Ala | Gly | GCT | GGG | 10.4 | 2 | -6.8 | -6.6 |
| Ala | Gly | GCT | GGT | 57.8 | 38 | -6.8 | -6.4 |
| Ala | Val | GCT | GTA | 25.0 | 27 | 0.2 | 0.5 |
| Ala | Val | GCT | GTC | 18.6 | 14 | -1.1 | -0.7 |
| Ala | Val | GCT | GTG | 34.2 | 19 | -6.7 | -5.4 |
| Ala | Val | GCT | GTT | 47.7 | 35 | -3.4 | -2.2 |
| Ala | Ocr | GCT | TAA | 0.0 | 8 | 0.0 | 0.0 |
| Ala | Tyr | GCT | TAC | 23.4 | 38 | 9.1 | 20.6 |
| Ala | Amb | GCT | TAG | 0.0 | 0 | 0.0 | 0.0 |
| Ala | Tyr | GCT | TAT | 19.4 | 37 | 15.9 | 30.5 |
| Ala | Ser | GCT | TCA | 7.7 | 10 | 0.7 | 0.8 |
| Ala | Ser | GCT | TCC | 18.4 | 23 | 1.1 | 1.3 |
| Ala | Ser | GCT | TCG | 9.3 | 11 | 0.3 | 0.4 |
| Ala | Ser | GCT | TCT | 21.6 | 38 | 12.4 | 13.3 |
| Ala | Umb | GCT | TGA | 0.0 | 0 | 0.0 | 0.0 |
| Ala | Cys | GCT | TGC | 7.5 | 7 | -0.0 | -0.2 |
| Ala | Trp | GCT | TGG | 15.1 | 2 | -11.4 | -12.7 |
| Ala | Cys | GCT | TGT | 5.5 | 7 | 0.4 | 0.1 |
| Ala | Leu | GCT | TTA | 13.1 | 10 | -0.7 | -0.9 |
| Ala | Phe | GCT | TTC | 32.4 | 26 | -1.3 | -1.1 |
| Ala | Leu | GCT | TTG | 12.9 | 13 | 0.0 | 0.0 |
| Ala | Phe | GCT | TTT | 22.7 | 23 | 0.0 | 0.0 |
| | | Page Totals: | | 1604.2 | 1610 | 306.2 | 293.7 |

ECOO.RXD/CPLIST.RXR January 11, 1989

| aa1 | aa2 | cod1 | cod2 | exp | obs | chis1 | chis2 |
|---|---|---|---|---|---|---|---|
| Gly | Lys | GGA | AAA | 15.8 | 22 | 2.4 | 0.6 |
| Gly | Asn | GGA | AAC | 9.1 | 3 | -4.1 | -3.8 |
| Gly | Lys | GGA | AAG | 5.1 | 3 | -0.9 | -1.5 |
| Gly | Asn | GGA | AAT | 9.5 | 10 | 0.0 | 0.1 |
| Gly | Thr | GGA | ACA | 3.9 | 8 | 4.5 | 5.6 |
| Gly | Thr | GGA | ACC | 8.8 | 10 | 0.2 | 0.4 |
| Gly | Thr | GGA | ACG | 5.3 | 8 | 1.4 | 2.0 |
| Gly | Thr | GGA | ACT | 4.7 | 9 | 4.0 | 5.1 |
| Gly | Arg | GGA | AGA | 1.7 | 1 | -0.3 | -0.3 |
| Gly | Ser | GGA | AGC | 6.5 | 8 | 0.4 | 0.3 |
| Gly | Arg | GGA | AGG | 0.9 | 0 | -0.9 | -1.0 |
| Gly | Ser | GGA | AGT | 4.0 | 9 | 6.4 | 6.0 |
| Gly | Ile | GGA | ATA | 2.9 | 6 | 3.4 | 2.3 |
| Gly | Ile | GGA | ATC | 10.1 | 1 | -8.2 | -9.6 |
| Gly | Met | GGA | ATG | 10.0 | 13 | 0.9 | 0.3 |
| Gly | Ile | GGA | ATT | 13.1 | 11 | -0.3 | -1.0 |
| Gly | Gln | GGA | CAA | 6.7 | 7 | 0.0 | 0.2 |
| Gly | His | GGA | CAC | 4.0 | 7 | 2.3 | 1.3 |
| Gly | Gln | GGA | CAG | 12.6 | 9 | -1.0 | -0.4 |
| Gly | His | GGA | CAT | 5.0 | 7 | 0.8 | 0.3 |
| Gly | Pro | GGA | CCA | 3.9 | 3 | -0.2 | -0.1 |
| Gly | Pro | GGA | CCC | 2.1 | 0 | -2.1 | -1.4 |
| Gly | Pro | GGA | CCG | 8.3 | 6 | -0.6 | -0.1 |
| Gly | Pro | GGA | CCT | 2.5 | 6 | 4.8 | 11.9 |
| Gly | Arg | GGA | CGA | 1.5 | 8 | 28.0 | 26.5 |
| Gly | Arg | GGA | CGC | 8.5 | 15 | 4.9 | 4.3 |
| Gly | Arg | GGA | CGG | 2.2 | 3 | 0.3 | 0.3 |
| Gly | Arg | GGA | CGT | 9.1 | 16 | 5.2 | 4.6 |
| Gly | Leu | GGA | CTA | 1.3 | 0 | -1.3 | -1.2 |
| Gly | Leu | GGA | CTC | 4.3 | 3 | -0.4 | -0.2 |
| Gly | Leu | GGA | CTG | 20.5 | 21 | 0.0 | 0.2 |
| Gly | Leu | GGA | CTT | 5.2 | 3 | -0.9 | -0.7 |
| Gly | Glu | GGA | GAA | 17.7 | 19 | 0.1 | 0.0 |
| Gly | Asp | GGA | GAC | 7.9 | 3 | -3.0 | -3.4 |
| Gly | Glu | GGA | GAG | 8.2 | 10 | 0.4 | 0.1 |
| Gly | Asp | GGA | GAT | 14.3 | 8 | -2.8 | -3.3 |
| Gly | Ala | GGA | GCA | 9.9 | 8 | -0.4 | -0.1 |
| Gly | Ala | GGA | GCC | 9.9 | 7 | -0.9 | -0.4 |
| Gly | Ala | GGA | GCG | 13.2 | 11 | -0.4 | -0.1 |
| Gly | Ala | GGA | GCT | 7.7 | 8 | 0.0 | 0.2 |
| Gly | Gly | GGA | GGA | 5.7 | 1 | -3.9 | -4.0 |
| Gly | Gly | GGA | GGC | 11.0 | 2 | -7.4 | -7.5 |
| Gly | Gly | GGA | GGG | 4.6 | 1 | -2.8 | -2.9 |
| Gly | Gly | GGA | GGT | 12.5 | 4 | -5.8 | -6.0 |
| Gly | Val | GGA | GTA | 5.5 | 4 | -0.4 | -0.3 |
| Gly | Val | GGA | GTC | 6.0 | 4 | -0.7 | -0.5 |
| Gly | Val | GGA | GTG | 9.6 | 2 | -6.0 | -5.6 |
| Gly | Val | GGA | GTT | 9.4 | 2 | -5.8 | -5.4 |
| Gly | Ocr | GGA | TAA | 0.0 | 1 | 0.0 | 0.0 |
| Gly | Tyr | GGA | TAC | 5.0 | 6 | 0.2 | 0.1 |
| Gly | Amb | GGA | TAG | 0.0 | 0 | 0.0 | 0.0 |
| Gly | Tyr | GGA | TAT | 8.2 | 15 | 5.6 | 4.0 |
| Gly | Ser | GGA | TCA | 3.8 | 2 | -0.9 | -1.0 |
| Gly | Ser | GGA | TCC | 3.9 | 2 | -1.0 | -1.0 |
| Gly | Ser | GGA | TCG | 3.4 | 5 | 0.7 | 0.6 |
| Gly | Ser | GGA | TCT | 5.0 | 2 | -1.8 | -1.9 |
| Gly | Umb | GGA | TGA | 0.0 | 1 | 0.0 | 0.0 |
| Gly | Cys | GGA | TGC | 2.3 | 5 | 3.2 | 2.6 |
| Gly | Trp | GGA | TGG | 5.1 | 4 | -0.2 | -0.3 |
| Gly | Cys | GGA | TGT | 1.9 | 3 | 0.6 | 0.4 |
| Gly | Leu | GGA | TTA | 7.1 | 16 | 11.3 | 13.3 |
| Gly | Phe | GGA | TTC | 6.6 | 11 | 2.9 | 2.0 |
| Gly | Leu | GGA | TTG | 5.3 | 7 | 0.5 | 0.8 |
| Gly | Phe | GGA | TTT | 9.0 | 20 | 13.4 | 10.6 |
| | | Page Totals: | | 428.6 | 430 | 174.1 | 171.7 |

ECOO.RXD/CPLIST.RXR January 11, 1989

| aa1 | aa2 | cod1 | cod2 | exp | obs | chis1 | chis2 |
|---|---|---|---|---|---|---|---|
| Gly | Lys | GGC | AAA | 94.1 | 71 | -5.7 | -14.3 |
| Gly | Asn | GGC | AAC | 65.8 | 60 | -0.5 | -0.2 |
| Gly | Lys | GGC | AAG | 28.6 | 30 | 0.1 | 0.4 |
| Gly | Asn | GGC | AAT | 30.2 | 45 | 7.3 | 8.5 |
| Gly | Thr | GGC | ACA | 11.6 | 16 | 1.7 | 2.7 |
| Gly | Thr | GGC | ACC | 61.0 | 48 | -2.8 | -1.2 |
| Gly | Thr | GGC | ACG | 24.8 | 38 | 7.0 | 10.1 |
| Gly | Thr | GGC | ACT | 26.2 | 22 | -0.7 | -0.2 |
| Gly | Arg | GGC | AGA | 2.4 | 3 | 0.2 | 0.1 |
| Gly | Ser | GGC | AGC | 35.5 | 46 | 3.1 | 2.5 |
| Gly | Arg | GGC | AGG | 1.4 | 2 | 0.3 | 0.2 |
| Gly | Ser | GGC | AGT | 13.1 | 26 | 12.6 | 11.7 |
| Gly | Ile | GGC | ATA | 4.9 | 2 | -1.7 | -2.3 |
| Gly | Ile | GGC | ATC | 75.6 | 59 | -3.6 | -8.5 |
| Gly | Met | GGC | ATG | 64.2 | 55 | -1.3 | -3.9 |
| Gly | Ile | GGC | ATT | 55.6 | 66 | 1.9 | 0.1 |
| Gly | Gln | GGC | CAA | 28.2 | 6 | -17.5 | -14.2 |
| Gly | His | GGC | CAC | 28.2 | 23 | -1.0 | -2.7 |
| Gly | Gln | GGC | CAG | 74.4 | 43 | -13.3 | -7.5 |
| Gly | His | GGC | CAT | 21.2 | 23 | 0.1 | 0.1 |
| Gly | Pro | GGC | CCA | 16.4 | 12 | -1.2 | -0.2 |
| Gly | Pro | GGC | CCC | 7.0 | 6 | -0.1 | -0.5 |
| Gly | Pro | GGC | CCG | 59.0 | 39 | -6.8 | -0.0 |
| Gly | Pro | GGC | CCT | 12.0 | 5 | -4.0 | -0.9 |
| Gly | Arg | GGC | CGA | 4.6 | 2 | -1.4 | -1.6 |
| Gly | Arg | GGC | CGC | 49.2 | 28 | -9.1 | -10.4 |
| Gly | Arg | GGC | CGG | 7.0 | 8 | 0.2 | 0.1 |
| Gly | Arg | GGC | CGT | 66.9 | 44 | -7.9 | -9.3 |
| Gly | Leu | GGC | CTA | 5.2 | 2 | -1.9 | -1.7 |
| Gly | Leu | GGC | CTC | 20.4 | 5 | -11.7 | -10.5 |
| Gly | Leu | GGC | CTG | 138.9 | 104 | -8.8 | -5.2 |
| Gly | Leu | GGC | CTT | 18.2 | 8 | -5.7 | -4.8 |
| Gly | Glu | GGC | GAA | 114.7 | 136 | 4.0 | 0.8 |
| Gly | Asp | GGC | GAC | 61.8 | 101 | 24.9 | 20.2 |
| Gly | Glu | GGC | GAG | 44.0 | 49 | 0.6 | 0.0 |
| Gly | Asp | GGC | GAT | 70.4 | 86 | 3.4 | 2.0 |
| Gly | Ala | GGC | GCA | 50.9 | 72 | 8.8 | 14.8 |
| Gly | Ala | GGC | GCC | 52.9 | 7 | -39.9 | -34.8 |
| Gly | Ala | GGC | GCG | 82.4 | 91 | 0.9 | 3.7 |
| Gly | Ala | GGC | GCT | 49.9 | 35 | -4.5 | -2.3 |
| Gly | Gly | GGC | GGA | 11.0 | 19 | 5.8 | 5.5 |
| Gly | Gly | GGC | GGC | 84.5 | 123 | 17.5 | 16.0 |
| Gly | Gly | GGC | GGG | 17.5 | 19 | 0.1 | 0.1 |
| Gly | Gly | GGC | GGT | 80.0 | 120 | 20.0 | 18.4 |
| Gly | Val | GGC | GTA | 31.2 | 68 | 43.5 | 49.2 |
| Gly | Val | GGC | GTC | 31.1 | 30 | -0.0 | -0.0 |
| Gly | Val | GGC | GTG | 57.5 | 69 | 2.3 | 3.6 |
| Gly | Val | GGC | GTT | 58.5 | 78 | 6.5 | 8.8 |
| Gly | Ocr | GGC | TAA | 0.0 | 1 | 0.0 | 0.0 |
| Gly | Tyr | GGC | TAC | 35.2 | 33 | -0.1 | -0.8 |
| Gly | Amb | GGC | TAG | 0.0 | 0 | 0.0 | 0.0 |
| Gly | Tyr | GGC | TAT | 31.8 | 30 | -0.1 | -0.6 |
| Gly | Ser | GGC | TCA | 10.4 | 10 | -0.0 | -0.0 |
| Gly | Ser | GGC | TCC | 26.8 | 17 | -3.6 | -4.0 |
| Gly | Ser | GGC | TCG | 16.3 | 11 | -1.7 | -2.0 |
| Gly | Ser | GGC | TCT | 27.2 | 15 | -5.5 | -6.0 |
| Gly | Umb | GGC | TGA | 0.0 | 2 | 0.0 | 0.0 |
| Gly | Cys | GGC | TGC | 13.1 | 13 | -0.0 | -0.1 |
| Gly | Trp | GGC | TGG | 25.7 | 45 | 14.5 | 12.4 |
| Gly | Cys | GGC | TGT | 9.9 | 13 | 1.0 | 0.5 |
| Gly | Leu | GGC | TTA | 19.7 | 18 | -0.1 | -0.0 |
| Gly | Phe | GGC | TTC | 48.5 | 63 | 4.3 | 2.0 |
| Gly | Leu | GGC | TTG | 22.7 | 12 | -5.1 | -4.1 |
| Gly | Phe | GGC | TTT | 35.7 | 47 | 3.6 | 1.7 |
| | | Page Totals: | | 2373.0 | 2380 | 363.3 | 351.0 |

ECOO.RXD/CPLIST.RXR January 11, 1989

| aa1 | aa2 | cod1 | cod2 | exp | obs | chis1 | chis2 |
|---|---|---|---|---|---|---|---|
| Gly | Lys | GGG | AAA | 22.1 | 24 | 0.2 | 0.2 |
| Gly | Asn | GGG | AAC | 14.6 | 0 | -14.6 | -14.1 |
| Gly | Lys | GGG | AAG | 6.9 | 4 | -1.2 | -2.1 |
| Gly | Asn | GGG | AAT | 10.8 | 9 | -0.3 | -0.2 |
| Gly | Thr | GGG | ACA | 4.1 | 1 | -2.3 | -2.0 |
| Gly | Thr | GGG | ACC | 13.6 | 2 | -9.9 | -8.9 |
| Gly | Thr | GGG | ACG | 8.0 | 9 | 0.1 | 0.3 |
| Gly | Thr | GGG | ACT | 5.9 | 7 | 0.2 | 0.5 |
| Gly | Arg | GGG | AGA | 1.0 | 0 | -1.0 | -1.0 |
| Gly | Ser | GGG | AGC | 10.7 | 4 | -4.2 | -4.4 |
| Gly | Arg | GGG | AGG | 0.7 | 0 | -0.7 | -0.7 |
| Gly | Ser | GGG | AGT | 4.8 | 4 | -0.1 | -0.2 |
| Gly | Ile | GGG | ATA | 2.4 | 2 | -0.1 | -0.2 |
| Gly | Ile | GGG | ATC | 15.9 | 32 | 16.3 | 10.7 |
| Gly | Met | GGG | ATG | 15.7 | 28 | 9.7 | 6.3 |
| Gly | Ile | GGG | ATT | 17.2 | 21 | 0.9 | 0.1 |
| Gly | Gln | GGG | CAA | 9.4 | 22 | 16.9 | 23.0 |
| Gly | His | GGG | CAC | 6.8 | 10 | 1.5 | 0.6 |
| Gly | Gln | GGG | CAG | 19.0 | 39 | 21.2 | 30.2 |
| Gly | His | GGG | CAT | 7.2 | 16 | 10.8 | 7.3 |
| Gly | Pro | GGG | CCA | 4.7 | 7 | 1.1 | 5.1 |
| Gly | Pro | GGG | CCC | 2.6 | 0 | -2.6 | -1.7 |
| Gly | Pro | GGG | CCG | 14.0 | 12 | -0.3 | -1.0 |
| Gly | Pro | GGG | CCT | 3.9 | 3 | -0.2 | -0.1 |
| Gly | Arg | GGG | CGA | 1.8 | 6 | 9.7 | 9.1 |
| Gly | Arg | GGG | CGC | 13.6 | 16 | 0.4 | 0.3 |
| Gly | Arg | GGG | CGG | 2.9 | 2 | -0.3 | -0.3 |
| Gly | Arg | GGG | CGT | 14.8 | 21 | 2.6 | 2.1 |
| Gly | Leu | GGG | CTA | 1.8 | 5 | 5.9 | 6.7 |
| Gly | Leu | GGG | CTC | 6.2 | 2 | -2.8 | -2.5 |
| Gly | Leu | GGG | CTG | 33.4 | 55 | 13.9 | 17.9 |
| Gly | Leu | GGG | CTT | 6.5 | 13 | 6.4 | 7.8 |
| Gly | Glu | GGG | GAA | 26.2 | 20 | -1.5 | -2.6 |
| Gly | Asp | GGG | GAC | 12.5 | 3 | -7.2 | -7.8 |
| Gly | Glu | GGG | GAG | 12.2 | 8 | -1.4 | -2.1 |
| Gly | Asp | GGG | GAT | 19.9 | 13 | -2.4 | -3.0 |
| Gly | Ala | GGG | GCA | 12.9 | 16 | 0.8 | 1.6 |
| Gly | Ala | GGG | GCC | 15.7 | 11 | -1.4 | -0.7 |
| Gly | Ala | GGG | GCG | 21.0 | 25 | 0.8 | 1.9 |
| Gly | Ala | GGG | GCT | 10.4 | 14 | 1.3 | 2.3 |
| Gly | Gly | GGG | GGA | 4.6 | 3 | -0.5 | -0.6 |
| Gly | Gly | GGG | GGC | 17.5 | 13 | -1.1 | -1.3 |
| Gly | Gly | GGG | GGG | 8.3 | 2 | -4.7 | -4.9 |
| Gly | Gly | GGG | GGT | 17.4 | 12 | -1.7 | -1.8 |
| Gly | Val | GGG | GTA | 7.3 | 11 | 1.8 | 2.3 |
| Gly | Val | GGG | GTC | 8.9 | 5 | -1.7 | -1.4 |
| Gly | Val | GGG | GTG | 15.1 | 5 | -6.7 | -6.1 |
| Gly | Val | GGG | GTT | 12.8 | 12 | -0.0 | -0.0 |
| Gly | Ocr | GGG | TAA | 0.0 | 7 | 0.0 | 0.0 |
| Gly | Tyr | GGG | TAC | 7.5 | 1 | -5.6 | -6.3 |
| Gly | Amb | GGG | TAG | 0.0 | 0 | 0.0 | 0.0 |
| Gly | Tyr | GGG | TAT | 9.8 | 7 | -0.8 | -1.3 |
| Gly | Ser | GGG | TCA | 4.2 | 0 | -4.2 | -4.3 |
| Gly | Ser | GGG | TCC | 5.9 | 0 | -5.9 | -6.0 |
| Gly | Ser | GGG | TCG | 5.4 | 6 | 0.1 | 0.0 |
| Gly | Ser | GGG | TCT | 6.6 | 1 | -4.8 | -4.9 |
| Gly | Umb | GGG | TGA | 0.0 | 0 | 0.0 | 0.0 |
| Gly | Cys | GGG | TGC | 3.6 | 1 | -1.8 | -2.1 |
| Gly | Trp | GGG | TGG | 7.3 | 3 | -2.5 | -2.7 |
| Gly | Cys | GGG | TGT | 2.5 | 0 | -2.5 | -2.7 |
| Gly | Leu | GGG | TTA | 8.2 | 12 | 1.8 | 2.5 |
| Gly | Phe | GGG | TTC | 10.3 | 8 | -0.5 | -0.9 |
| Gly | Leu | GGG | TTG | 8.0 | 15 | 6.0 | 7.4 |
| Gly | Phe | GGG | TTT | 11.8 | 8 | -1.2 | -1.8 |
| | Page Totals: | | | 616.1 | 618 | 231.4 | 251.2 |

PAGE 43

ECOO.RXD/CPLIST.RXR January 11, 1989

| aa1 | aa2 | cod1 | cod2 | exp | obs | chis1 | chis2 |
|---|---|---|---|---|---|---|---|
| Gly | Lys | GGT | AAA | 104.5 | 166 | 36.2 | 15.0 |
| Gly | Asn | GGT | AAC | 72.5 | 60 | -2.1 | -1.5 |
| Gly | Lys | GGT | AAG | 31.1 | 43 | 4.6 | 1.1 |
| Gly | Asn | GGT | AAT | 32.2 | 50 | 9.8 | 11.3 |
| Gly | Thr | GGT | ACA | 12.3 | 14 | 0.2 | 0.6 |
| Gly | Thr | GGT | ACC | 65.9 | 25 | -25.4 | -21.0 |
| Gly | Thr | GGT | ACG | 24.1 | 30 | 1.5 | 2.8 |
| Gly | Thr | GGT | ACT | 32.7 | 41 | 2.1 | 4.0 |
| Gly | Arg | GGT | AGA | 3.3 | 1 | -1.6 | -1.7 |
| Gly | Ser | GGT | AGC | 35.2 | 35 | -0.0 | -0.0 |
| Gly | Arg | GGT | AGG | 1.7 | 1 | -0.3 | -0.3 |
| Gly | Ser | GGT | AGT | 13.1 | 8 | -2.0 | -2.2 |
| Gly | Ile | GGT | ATA | 5.6 | 3 | -1.2 | -1.8 |
| Gly | Ile | GGT | ATC | 86.1 | 113 | 8.4 | 2.3 |
| Gly | Met | GGT | ATG | 66.9 | 79 | 2.2 | 0.2 |
| Gly | Ile | GGT | ATT | 57.4 | 79 | 8.2 | 2.9 |
| Gly | Gln | GGT | CAA | 27.8 | 16 | -5.0 | -2.9 |
| Gly | His | GGT | CAC | 30.3 | 34 | 0.4 | 0.0 |
| Gly | Gln | GGT | CAG | 80.0 | 84 | 0.2 | 2.8 |
| Gly | His | GGT | CAT | 21.4 | 22 | 0.0 | 0.2 |
| Gly | Pro | GGT | CCA | 17.5 | 7 | -6.3 | -1.6 |
| Gly | Pro | GGT | CCC | 6.2 | 0 | -6.2 | -4.0 |
| Gly | Pro | GGT | CCG | 62.9 | 42 | -6.9 | -0.1 |
| Gly | Pro | GGT | CCT | 13.1 | 4 | -6.3 | -2.3 |
| Gly | Arg | GGT | CGA | 4.3 | 1 | -2.6 | -2.7 |
| Gly | Arg | GGT | CGC | 47.8 | 52 | 0.4 | 0.1 |
| Gly | Arg | GGT | CGG | 6.1 | 7 | 0.1 | 0.1 |
| Gly | Arg | GGT | CGT | 74.5 | 103 | 10.9 | 8.5 |
| Gly | Leu | GGT | CTA | 4.9 | 2 | -1.7 | -1.4 |
| Gly | Leu | GGT | CTC | 21.4 | 3 | -15.9 | -14.5 |
| Gly | Leu | GGT | CTG | 149.4 | 168 | 2.3 | 5.6 |
| Gly | Leu | GGT | CTT | 18.6 | 14 | -1.1 | -0.7 |
| Gly | Glu | GGT | GAA | 122.1 | 143 | 3.6 | 0.6 |
| Gly | Asp | GGT | GAC | 67.7 | 56 | -2.0 | -3.2 |
| Gly | Glu | GGT | GAG | 46.1 | 44 | -0.1 | -0.8 |
| Gly | Asp | GGT | GAT | 75.2 | 76 | 0.0 | 0.1 |
| Gly | Ala | GGT | GCA | 57.1 | 42 | -4.0 | -1.8 |
| Gly | Ala | GGT | GCC | 50.6 | 47 | -0.3 | -0.0 |
| Gly | Ala | GGT | GCG | 81.1 | 76 | -0.3 | -0.1 |
| Gly | Ala | GGT | GCT | 57.8 | 57 | -0.0 | -0.4 |
| Gly | Gly | GGT | GGA | 12.5 | 13 | 0.0 | 0.0 |
| Gly | Gly | GGT | GGC | 80.0 | 52 | -9.8 | -10.6 |
| Gly | Gly | GGT | GGG | 17.4 | 14 | -0.7 | -0.8 |
| Gly | Gly | GGT | GGT | 102.7 | 97 | -0.3 | -0.5 |
| Gly | Val | GGT | GTA | 37.0 | 25 | -3.9 | -3.0 |
| Gly | Val | GGT | GTC | 30.4 | 16 | -6.8 | -5.8 |
| Gly | Val | GGT | GTG | 54.9 | 48 | -0.9 | -0.4 |
| Gly | Val | GGT | GTT | 68.3 | 44 | -8.6 | -6.8 |
| Gly | Ocr | GGT | TAA | 0.0 | 2 | 0.0 | 0.0 |
| Gly | Tyr | GGT | TAC | 40.4 | 53 | 4.0 | 1.8 |
| Gly | Amb | GGT | TAG | 0.0 | 0 | 0.0 | 0.0 |
| Gly | Tyr | GGT | TAT | 34.4 | 43 | 2.1 | 0.8 |
| Gly | Ser | GGT | TCA | 12.2 | 18 | 2.8 | 2.4 |
| Gly | Ser | GGT | TCC | 30.0 | 26 | -0.5 | -0.7 |
| Gly | Ser | GGT | TCG | 15.3 | 24 | 4.9 | 4.4 |
| Gly | Ser | GGT | TCT | 33.4 | 62 | 24.6 | 22.6 |
| Gly | Umb | GGT | TGA | 0.0 | 0 | 0.0 | 0.0 |
| Gly | Cys | GGT | TGC | 12.9 | 14 | 0.1 | 0.0 |
| Gly | Trp | GGT | TGG | 25.4 | 14 | -5.1 | -5.8 |
| Gly | Cys | GGT | TGT | 10.2 | 12 | 0.3 | 0.1 |
| Gly | Leu | GGT | TTA | 20.2 | 25 | 1.1 | 2.0 |
| Gly | Phe | GGT | TTC | 53.8 | 31 | -9.7 | -12.9 |
| Gly | Leu | GGT | TTG | 20.7 | 19 | -0.1 | -0.0 |
| Gly | Phe | GGT | TTT | 36.8 | 43 | 1.0 | 0.2 |
| | Page Totals: | | | 2536.7 | 2543 | 270.0 | 205.0 |

PAGE 44

ECOO.RXD/CPLIST.RXR January 11, 1989

| aa1 | aa2 | cod1 | cod2 | exp | obs | chis1 | chis2 |
|---|---|---|---|---|---|---|---|
| Val | Lys | GTA | AAA | 44.9 | 47 | 0.1 | 0.0 |
| Val | Asn | GTA | AAC | 28.2 | 16 | -5.3 | -5.7 |
| Val | Lys | GTA | AAG | 13.3 | 5 | -5.2 | -6.1 |
| Val | Asn | GTA | AAT | 13.7 | 7 | -3.3 | -3.5 |
| Val | Thr | GTA | ACA | 5.7 | 7 | 0.3 | 0.0 |
| Val | Thr | GTA | ACC | 25.3 | 19 | -1.6 | -4.4 |
| Val | Thr | GTA | ACG | 10.3 | 29 | 33.9 | 21.9 |
| Val | Thr | GTA | ACT | 13.8 | 21 | 3.8 | 1.1 |
| Val | Arg | GTA | AGA | 1.6 | 4 | 3.8 | 3.8 |
| Val | Ser | GTA | AGC | 14.8 | 13 | -0.2 | -0.7 |
| Val | Arg | GTA | AGG | 0.9 | 0 | -0.9 | -0.9 |
| Val | Ser | GTA | AGT | 5.9 | 6 | 0.0 | 0.1 |
| Val | Ile | GTA | ATA | 2.9 | 0 | -2.9 | -3.2 |
| Val | Ile | GTA | ATC | 35.3 | 26 | -2.4 | -4.5 |
| Val | Met | GTA | ATG | 27.7 | 33 | 1.0 | 2.5 |
| Val | Ile | GTA | ATT | 25.1 | 18 | -2.0 | -3.5 |
| Val | Gln | GTA | CAA | 12.2 | 12 | -0.0 | -0.2 |
| Val | His | GTA | CAC | 12.2 | 12 | -0.0 | -0.9 |
| Val | Gln | GTA | CAG | 32.1 | 34 | 0.1 | 1.4 |
| Val | His | GTA | CAT | 9.2 | 10 | 0.1 | 1.4 |
| Val | Pro | GTA | CCA | 7.6 | 6 | -0.3 | -0.3 |
| Val | Pro | GTA | CCC | 3.1 | 0 | -3.1 | -3.0 |
| Val | Pro | GTA | CCG | 26.1 | 46 | 15.2 | 15.5 |
| Val | Pro | GTA | CCT | 5.7 | 6 | 0.0 | 0.0 |
| Val | Arg | GTA | CGA | 2.2 | 2 | -0.0 | -0.0 |
| Val | Arg | GTA | CGC | 20.9 | 29 | 3.2 | 3.2 |
| Val | Arg | GTA | CGG | 3.0 | 10 | 16.6 | 16.6 |
| Val | Arg | GTA | CGT | 31.5 | 54 | 16.1 | 16.2 |
| Val | Leu | GTA | CTA | 2.6 | 4 | 0.8 | 0.9 |
| Val | Leu | GTA | CTC | 8.8 | 7 | -0.4 | -0.3 |
| Val | Leu | GTA | CTG | 61.3 | 81 | 6.4 | 7.6 |
| Val | Leu | GTA | CTT | 8.3 | 10 | 0.4 | 0.5 |
| Val | Glu | GTA | GAA | 52.8 | 59 | 0.7 | 0.1 |
| Val | Asp | GTA | GAC | 28.1 | 24 | -0.6 | -2.3 |
| Val | Glu | GTA | GAG | 19.8 | 18 | -0.2 | -0.5 |
| Val | Asp | GTA | GAT | 29.7 | 24 | -1.1 | -3.2 |
| Val | Ala | GTA | GCA | 23.6 | 21 | -0.3 | -0.0 |
| Val | Ala | GTA | GCC | 21.3 | 18 | -0.5 | -0.1 |
| Val | Ala | GTA | GCG | 33.1 | 21 | -4.4 | -2.8 |
| Val | Ala | GTA | GCT | 25.0 | 15 | -4.0 | -2.7 |
| Val | Gly | GTA | GGA | 5.5 | 4 | -0.4 | -0.2 |
| Val | Gly | GTA | GGC | 31.2 | 16 | -7.4 | -5.1 |
| Val | Gly | GTA | GGG | 7.3 | 10 | 1.0 | 1.8 |
| Val | Gly | GTA | GGT | 37.0 | 38 | 0.0 | 0.7 |
| Val | Val | GTA | GTA | 19.9 | 7 | -8.3 | -7.6 |
| Val | Val | GTA | GTC | 12.8 | 11 | -0.3 | -0.1 |
| Val | Val | GTA | GTG | 23.3 | 11 | -6.5 | -5.7 |
| Val | Val | GTA | GTT | 29.3 | 18 | -4.3 | -3.6 |
| Val | Ocr | GTA | TAA | 0.0 | 0 | 0.0 | 0.0 |
| Val | Tyr | GTA | TAC | 15.1 | 12 | -0.6 | -0.0 |
| Val | Amb | GTA | TAG | 0.0 | 0 | 0.0 | 0.0 |
| Val | Tyr | GTA | TAT | 13.6 | 9 | -1.5 | -0.4 |
| Val | Ser | GTA | TCA | 5.8 | 4 | -0.6 | -1.0 |
| Val | Ser | GTA | TCC | 12.7 | 16 | 0.9 | 0.2 |
| Val | Ser | GTA | TCG | 6.7 | 12 | 4.3 | 2.8 |
| Val | Ser | GTA | TCT | 13.8 | 14 | 0.0 | 0.1 |
| Val | Umb | GTA | TGA | 0.0 | 0 | 0.0 | 0.0 |
| Val | Cys | GTA | TGC | 5.5 | 2 | -2.3 | -3.4 |
| Val | Trp | GTA | TGG | 10.5 | 16 | 2.9 | 5.6 |
| Val | Cys | GTA | TGT | 4.3 | 12 | 13.5 | 8.3 |
| Val | Leu | GTA | TTA | 9.6 | 15 | 3.1 | 3.5 |
| Val | Phe | GTA | TTC | 20.7 | 30 | 4.2 | 5.7 |
| Val | Leu | GTA | TTG | 9.1 | 14 | 2.7 | 3.0 |
| Val | Phe | GTA | TTT | 15.6 | 16 | 0.0 | 0.1 |
| | Page Totals: | | | 1058.1 | 1061 | 205.5 | 200.8 |

PAGE 45

ECOO.RXD/CPLIST.RXR January 11, 1989

| aa1 | aa2 | cod1 | cod2 | exp | obs | chis1 | chis2 |
|---|---|---|---|---|---|---|---|
| Val | Lys | GTC | AAA | 37.5 | 27 | -2.9 | -4.5 |
| Val | Asn | GTC | AAC | 25.5 | 37 | 5.2 | 4.6 |
| Val | Lys | GTC | AAG | 11.8 | 10 | -0.3 | -0.6 |
| Val | Asn | GTC | AAT | 15.4 | 14 | -0.1 | -0.2 |
| Val | Thr | GTC | ACA | 5.9 | 9 | 1.7 | 0.5 |
| Val | Thr | GTC | ACC | 24.7 | 37 | 6.1 | 1.7 |
| Val | Thr | GTC | ACG | 11.6 | 12 | 0.0 | 0.3 |
| Val | Thr | GTC | ACT | 9.9 | 18 | 6.7 | 3.1 |
| Val | Arg | GTC | AGA | 1.7 | 4 | 3.2 | 3.2 |
| Val | Ser | GTC | AGC | 16.8 | 39 | 29.2 | 21.9 |
| Val | Arg | GTC | AGG | 1.0 | 3 | 4.2 | 4.2 |
| Val | Ser | GTC | AGT | 7.1 | 22 | 31.7 | 25.5 |
| Val | Ile | GTC | ATA | 3.3 | 2 | -0.5 | -0.8 |
| Val | Ile | GTC | ATC | 29.3 | 27 | -0.2 | -1.0 |
| Val | Met | GTC | ATG | 28.0 | 12 | -9.1 | -7.0 |
| Val | Ile | GTC | ATT | 27.1 | 28 | 0.0 | 0.2 |
| Val | Gln | GTC | CAA | 14.0 | 1 | -12.0 | -10.2 |
| Val | His | GTC | CAC | 11.6 | 1 | -9.7 | -6.8 |
| Val | Gln | GTC | CAG | 31.3 | 12 | -11.9 | -8.4 |
| Val | His | GTC | CAT | 10.4 | 4 | -3.9 | -1.8 |
| Val | Pro | GTC | CCA | 7.9 | 5 | -1.1 | -1.1 |
| Val | Pro | GTC | CCC | 4.1 | 2 | -1.1 | -1.0 |
| Val | Pro | GTC | CCG | 23.4 | 14 | -3.8 | -3.7 |
| Val | Pro | GTC | CCT | 5.8 | 6 | 0.0 | 0.0 |
| Val | Arg | GTC | CGA | 2.7 | 0 | -2.7 | -2.7 |
| Val | Arg | GTC | CGC | 22.1 | 19 | -0.4 | -0.4 |
| Val | Arg | GTC | CGG | 3.8 | 1 | -2.0 | -2.0 |
| Val | Arg | GTC | CGT | 26.2 | 9 | -11.3 | -11.3 |
| Val | Leu | GTC | CTA | 2.8 | 0 | -2.8 | -2.7 |
| Val | Leu | GTC | CTC | 10.0 | 7 | -0.9 | -0.7 |
| Val | Leu | GTC | CTG | 57.0 | 24 | -19.1 | -17.9 |
| Val | Leu | GTC | CTT | 9.4 | 2 | -5.8 | -5.5 |
| Val | Glu | GTC | GAA | 46.7 | 53 | 0.9 | 0.1 |
| Val | Asp | GTC | GAC | 22.5 | 17 | -1.3 | -3.2 |
| Val | Glu | GTC | GAG | 19.7 | 19 | -0.0 | -0.2 |
| Val | Asp | GTC | GAT | 31.6 | 50 | 10.7 | 4.8 |
| Val | Ala | GTC | GCA | 21.0 | 19 | -0.2 | -0.0 |
| Val | Ala | GTC | GCC | 25.6 | 35 | 3.4 | 5.7 |
| Val | Ala | GTC | GCG | 36.3 | 36 | -0.0 | -0.2 |
| Val | Ala | GTC | GCT | 18.6 | 17 | -0.1 | 0.0 |
| Val | Gly | GTC | GGA | 6.0 | 7 | 0.2 | 0.5 |
| Val | Gly | GTC | GGC | 31.1 | 36 | 0.8 | 2.3 |
| Val | Gly | GTC | GGG | 8.9 | 14 | 2.9 | 4.5 |
| Val | Gly | GTC | GGT | 30.4 | 54 | 18.4 | 26.2 |
| Val | Val | GTC | GTA | 12.8 | 5 | -4.8 | -4.3 |
| Val | Val | GTC | GTC | 17.8 | 19 | 0.1 | 0.2 |
| Val | Val | GTC | GTG | 25.2 | 23 | -0.2 | -0.1 |
| Val | Val | GTC | GTT | 22.5 | 25 | 0.3 | 0.5 |
| Val | Ocr | GTC | TAA | 0.0 | 0 | 0.0 | 0.0 |
| Val | Tyr | GTC | TAC | 13.2 | 10 | -0.8 | -0.1 |
| Val | Amb | GTC | TAG | 0.0 | 0 | 0.0 | 0.0 |
| Val | Tyr | GTC | TAT | 14.6 | 18 | 0.8 | 3.0 |
| Val | Ser | GTC | TCA | 5.9 | 6 | 0.0 | 0.1 |
| Val | Ser | GTC | TCC | 10.7 | 15 | 1.7 | 0.8 |
| Val | Ser | GTC | TCG | 8.1 | 5 | -1.2 | -1.8 |
| Val | Ser | GTC | TCT | 11.1 | 16 | 2.2 | 1.1 |
| Val | Umb | GTC | TGA | 0.0 | 2 | 0.0 | 0.0 |
| Val | Cys | GTC | TGC | 5.8 | 13 | 8.9 | 4.8 |
| Val | Trp | GTC | TGG | 11.5 | 24 | 13.5 | 20.7 |
| Val | Cys | GTC | TGT | 4.5 | 9 | 4.5 | 2.2 |
| Val | Leu | GTC | TTA | 10.7 | 6 | -2.1 | -1.9 |
| Val | Phe | GTC | TTC | 18.9 | 31 | 7.8 | 10.0 |
| Val | Leu | GTC | TTG | 11.5 | 1 | -9.6 | -9.3 |
| Val | Phe | GTC | TTT | 17.4 | 29 | 7.7 | 9.8 |
| | Page Totals: | | | 1019.3 | 1022 | 294.6 | 274.0 |

PAGE 46

ECOO.RXD/CPLIST.RXR January 11, 1989

| aa1 | aa2 | cod1 | cod2 | exp | obs | chis1 | chis2 |
|---|---|---|---|---|---|---|---|
| Val | Lys | GTG | AAA | 66.8 | 93 | 10.3 | 6.0 |
| Val | Asn | GTG | AAC | 47.2 | 30 | -6.3 | -6.9 |
| Val | Lys | GTG | AAG | 21.8 | 46 | 26.7 | 21.3 |
| Val | Asn | GTG | AAT | 24.5 | 29 | 0.8 | 0.6 |
| Val | Thr | GTG | ACA | 9.0 | 15 | 4.0 | 1.5 |
| Val | Thr | GTG | ACC | 44.4 | 47 | 0.2 | 0.8 |
| Val | Thr | GTG | ACG | 21.5 | 38 | 12.7 | 5.6 |
| Val | Thr | GTG | ACT | 17.8 | 26 | 3.8 | 0.9 |
| Val | Arg | GTG | AGA | 1.9 | 2 | 0.0 | 0.0 |
| Val | Ser | GTG | AGC | 29.1 | 20 | -2.9 | -4.8 |
| Val | Arg | GTG | AGG | 1.3 | 0 | -1.3 | -1.3 |
| Val | Ser | GTG | AGT | 11.3 | 15 | 1.2 | 0.5 |
| Val | Ile | GTG | ATA | 4.2 | 3 | -0.3 | -0.6 |
| Val | Ile | GTG | ATC | 55.7 | 68 | 2.7 | 0.6 |
| Val | Met | GTG | ATG | 49.2 | 73 | 11.5 | 18.2 |
| Val | Ile | GTG | ATT | 45.1 | 63 | 7.1 | 3.3 |
| Val | Gln | GTG | CAA | 22.7 | 19 | -0.6 | -0.0 |
| Val | His | GTG | CAC | 20.2 | 9 | -6.2 | -2.5 |
| Val | Gln | GTG | CAG | 57.2 | 53 | -0.3 | -0.2 |
| Val | His | GTG | CAT | 17.6 | 21 | 0.7 | 4.6 |
| Val | Pro | GTG | CCA | 13.0 | 14 | 0.1 | 0.1 |
| Val | Pro | GTG | CCC | 6.1 | 5 | -0.2 | -0.2 |
| Val | Pro | GTG | CCG | 46.0 | 48 | 0.1 | 0.1 |
| Val | Pro | GTG | CCT | 10.0 | 11 | 0.1 | 0.1 |
| Val | Arg | GTG | CGA | 4.4 | 2 | -1.3 | -1.3 |
| Val | Arg | GTG | CGC | 40.0 | 33 | -1.2 | -1.2 |
| Val | Arg | GTG | CGG | 6.4 | 6 | -0.0 | -0.0 |
| Val | Arg | GTG | CGT | 49.3 | 69 | 7.9 | 8.0 |
| Val | Leu | GTG | CTA | 4.3 | 6 | 0.6 | 0.8 |
| Val | Leu | GTG | CTC | 17.2 | 10 | -3.0 | -2.7 |
| Val | Leu | GTG | CTG | 107.7 | 153 | 19.1 | 22.1 |
| Val | Leu | GTG | CTT | 14.7 | 20 | 1.9 | 2.3 |
| Val | Glu | GTG | GAA | 83.0 | 71 | -1.7 | -3.8 |
| Val | Asp | GTG | GAC | 42.9 | 26 | -6.6 | -11.4 |
| Val | Glu | GTG | GAG | 35.0 | 20 | -6.4 | -8.3 |
| Val | Asp | GTG | GAT | 54.5 | 51 | -0.2 | -2.4 |
| Val | Ala | GTG | GCA | 37.4 | 30 | -1.5 | -0.5 |
| Val | Ala | GTG | GCC | 44.0 | 18 | -15.4 | -12.3 |
| Val | Ala | GTG | GCG | 66.9 | 81 | 3.0 | 6.5 |
| Val | Ala | GTG | GCT | 34.2 | 19 | -6.7 | -4.8 |
| Val | Gly | GTG | GGA | 9.6 | 7 | -0.7 | -0.3 |
| Val | Gly | GTG | GGC | 57.5 | 29 | -14.2 | -9.9 |
| Val | Gly | GTG | GGG | 15.1 | 13 | -0.3 | -0.0 |
| Val | Gly | GTG | GGT | 54.9 | 38 | -5.2 | -2.6 |
| Val | Val | GTG | GTA | 23.3 | 27 | 0.6 | 1.0 |
| Val | Val | GTG | GTC | 25.2 | 23 | -0.2 | -0.1 |
| Val | Val | GTG | GTG | 53.8 | 101 | 41.4 | 47.3 |
| Val | Val | GTG | GTT | 40.7 | 55 | 5.0 | 6.5 |
| Val | Ocr | GTG | TAA | 0.0 | 1 | 0.0 | 0.0 |
| Val | Tyr | GTG | TAC | 24.2 | 13 | -5.2 | -2.4 |
| Val | Amb | GTG | TAG | 0.0 | 1 | 0.0 | 0.0 |
| Val | Tyr | GTG | TAT | 25.2 | 9 | -10.4 | -6.6 |
| Val | Ser | GTG | TCA | 9.1 | 5 | -1.9 | -2.6 |
| Val | Ser | GTG | TCC | 19.6 | 5 | -10.9 | -13.0 |
| Val | Ser | GTG | TCG | 14.4 | 12 | -0.4 | -1.0 |
| Val | Ser | GTG | TCT | 20.1 | 10 | -5.1 | -6.8 |
| Val | Umb | GTG | TGA | 0.0 | 2 | 0.0 | 0.0 |
| Val | Cys | GTG | TGC | 10.9 | 5 | -3.2 | -5.3 |
| Val | Trp | GTG | TGG | 20.2 | 9 | -6.2 | -3.9 |
| Val | Cys | GTG | TGT | 7.4 | 5 | -0.8 | -1.9 |
| Val | Leu | GTG | TTA | 16.7 | 10 | -2.7 | -2.4 |
| Val | Phe | GTG | TTC | 35.3 | 32 | -0.3 | -0.0 |
| Val | Leu | GTG | TTG | 20.2 | 28 | 3.0 | 3.6 |
| Val | Phe | GTG | TTT | 29.6 | 21 | -2.5 | -1.7 |
| | | Page Totals: | | 1818.3 | 1824 | 296.6 | 287.7 |

PAGE 47

ECOO.RXD/CPLIST.RXR January 11, 1989

| aa1 | aa2 | cod1 | cod2 | exp | obs | chis1 | chis2 |
|---|---|---|---|---|---|---|---|
| Val | Lys | GTT | AAA | 81.1 | 67 | -2.5 | -4.8 |
| Val | Asn | GTT | AAC | 52.9 | 79 | 12.9 | 11.5 |
| Val | Lys | GTT | AAG | 23.8 | 30 | 1.6 | 0.7 |
| Val | Asn | GTT | AAT | 23.5 | 24 | 0.0 | 0.0 |
| Val | Thr | GTT | ACA | 9.8 | 6 | -1.5 | -2.9 |
| Val | Thr | GTT | ACC | 47.5 | 40 | -1.2 | -3.3 |
| Val | Thr | GTT | ACG | 16.6 | 13 | -0.8 | -2.5 |
| Val | Thr | GTT | ACT | 25.0 | 24 | -0.0 | -1.3 |
| Val | Arg | GTT | AGA | 3.0 | 1 | -1.3 | -1.3 |
| Val | Ser | GTT | AGC | 25.4 | 8 | -12.0 | -14.6 |
| Val | Arg | GTT | AGG | 1.5 | 0 | -1.5 | -1.5 |
| Val | Ser | GTT | AGT | 9.9 | 4 | -3.5 | -4.5 |
| Val | Ile | GTT | ATA | 5.4 | 6 | 0.1 | 0.0 |
| Val | Ile | GTT | ATC | 63.9 | 97 | 17.1 | 9.4 |
| Val | Met | GTT | ATG | 48.7 | 21 | -15.8 | -12.1 |
| Val | Ile | GTT | ATT | 42.4 | 40 | -0.1 | -1.1 |
| Val | Gln | GTT | CAA | 20.5 | 8 | -7.6 | -5.4 |
| Val | His | GTT | CAC | 22.4 | 19 | -0.5 | -0.3 |
| Val | Gln | GTT | CAG | 59.2 | 77 | 5.4 | 12.9 |
| Val | His | GTT | CAT | 15.3 | 13 | -0.3 | -0.2 |
| Val | Pro | GTT | CCA | 13.3 | 3 | -8.0 | -7.9 |
| Val | Pro | GTT | CCC | 4.9 | 9 | 3.5 | 3.6 |
| Val | Pro | GTT | CCG | 46.3 | 43 | -0.2 | -0.2 |
| Val | Pro | GTT | CCT | 9.1 | 13 | 1.7 | 1.7 |
| Val | Arg | GTT | CGA | 3.5 | 7 | 3.4 | 3.4 |
| Val | Arg | GTT | CGC | 34.9 | 28 | -1.4 | -1.4 |
| Val | Arg | GTT | CGG | 4.9 | 0 | -4.9 | -4.9 |
| Val | Arg | GTT | CGT | 56.1 | 41 | -4.0 | -4.0 |
| Val | Leu | GTT | CTA | 3.7 | 2 | -0.8 | -0.7 |
| Val | Leu | GTT | CTC | 15.0 | 16 | 0.1 | 0.1 |
| Val | Leu | GTT | CTG | 108.8 | 85 | -5.2 | -4.1 |
| Val | Leu | GTT | CTT | 13.9 | 10 | -1.1 | -0.9 |
| Val | Glu | GTT | GAA | 95.7 | 129 | 11.6 | 6.5 |
| Val | Asp | GTT | GAC | 50.7 | 73 | 9.8 | 3.3 |
| Val | Glu | GTT | GAG | 34.5 | 48 | 5.3 | 3.2 |
| Val | Asp | GTT | GAT | 54.2 | 100 | 38.8 | 21.8 |
| Val | Ala | GTT | GCA | 44.1 | 28 | -5.9 | -3.7 |
| Val | Ala | GTT | GCC | 36.9 | 53 | 7.0 | 11.0 |
| Val | Ala | GTT | GCG | 59.2 | 40 | -6.2 | -3.7 |
| Val | Ala | GTT | GCT | 47.7 | 74 | 14.5 | 21.3 |
| Val | Gly | GTT | GGA | 9.4 | 4 | -3.1 | -2.3 |
| Val | Gly | GTT | GGC | 58.5 | 55 | -0.2 | -0.1 |
| Val | Gly | GTT | GGG | 12.8 | 8 | -1.8 | -1.1 |
| Val | Gly | GTT | GGT | 68.3 | 65 | -0.2 | -0.2 |
| Val | Val | GTT | GTA | 29.3 | 14 | -8.0 | -7.1 |
| Val | Val | GTT | GTC | 22.5 | 27 | 0.9 | 1.4 |
| Val | Val | GTT | GTG | 40.7 | 22 | -8.6 | -7.5 |
| Val | Val | GTT | GTT | 61.9 | 54 | -1.0 | -0.5 |
| Val | Ocr | GTT | TAA | 0.0 | 7 | 0.0 | 0.0 |
| Val | Tyr | GTT | TAC | 27.3 | 30 | 0.3 | 2.6 |
| Val | Amb | GTT | TAG | 0.0 | 0 | 0.0 | 0.0 |
| Val | Tyr | GTT | TAT | 24.1 | 28 | 0.6 | 3.4 |
| Val | Ser | GTT | TCA | 9.5 | 14 | 2.2 | 1.1 |
| Val | Ser | GTT | TCC | 22.3 | 48 | 29.8 | 21.8 |
| Val | Ser | GTT | TCG | 11.3 | 11 | -0.0 | -0.2 |
| Val | Ser | GTT | TCT | 25.6 | 44 | 13.2 | 8.4 |
| Val | Umb | GTT | TGA | 0.0 | 1 | 0.0 | 0.0 |
| Val | Cys | GTT | TGC | 9.1 | 9 | -0.0 | -0.4 |
| Val | Trp | GTT | TGG | 17.8 | 2 | -14.0 | -11.4 |
| Val | Cys | GTT | TGT | 6.9 | 12 | 3.7 | 1.4 |
| Val | Leu | GTT | TTA | 16.4 | 21 | 1.3 | 1.6 |
| Val | Phe | GTT | TTC | 38.5 | 12 | -18.2 | -16.1 |
| Val | Leu | GTT | TTG | 15.4 | 8 | -3.6 | -3.3 |
| Val | Phe | GTT | TTT | 27.3 | 20 | -1.9 | -1.2 |
| | | Page Totals: | | 1889.7 | 1895 | 331.7 | 293.0 |

PAGE 48

ECOO.RXD/CPLIST.RXR January 11, 1989

| aa1 | aa2 | cod1 | cod2 | exp | obs | chis1 | chis2 |
|---|---|---|---|---|---|---|---|
| Tyr | Lys | TAC | AAA | 43.8 | 35 | -1.8 | -0.0 |
| Tyr | Asn | TAC | AAC | 34.4 | 33 | -0.1 | -0.7 |
| Tyr | Lys | TAC | AAG | 13.5 | 12 | -0.2 | -0.2 |
| Tyr | Asn | TAC | AAT | 13.9 | 12 | -0.3 | -0.0 |
| Tyr | Thr | TAC | ACA | 5.1 | 4 | -0.2 | -0.5 |
| Tyr | Thr | TAC | ACC | 29.3 | 54 | 20.8 | 14.1 |
| Tyr | Thr | TAC | ACG | 11.2 | 13 | 0.3 | 0.0 |
| Tyr | Thr | TAC | ACT | 13.2 | 10 | -0.8 | -1.5 |
| Tyr | Arg | TAC | AGA | 1.5 | 6 | 13.7 | 9.5 |
| Tyr | Ser | TAC | AGC | 16.2 | 37 | 26.9 | 22.5 |
| Tyr | Arg | TAC | AGG | 0.8 | 2 | 2.1 | 1.2 |
| Tyr | Ser | TAC | AGT | 5.9 | 6 | 0.0 | 0.0 |
| Tyr | Ile | TAC | ATA | 2.6 | 1 | -1.0 | -0.9 |
| Tyr | Ile | TAC | ATC | 36.3 | 44 | 1.6 | 2.7 |
| Tyr | Met | TAC | ATG | 29.2 | 25 | -0.6 | -0.1 |
| Tyr | Ile | TAC | ATT | 24.7 | 21 | -0.5 | -0.2 |
| Tyr | Gln | TAC | CAA | 12.8 | 7 | -2.6 | -5.9 |
| Tyr | His | TAC | CAC | 13.9 | 15 | 0.1 | 0.5 |
| Tyr | Gln | TAC | CAG | 36.2 | 34 | -0.1 | -4.1 |
| Tyr | His | TAC | CAT | 10.0 | 11 | 0.1 | 0.2 |
| Tyr | Pro | TAC | CCA | 8.0 | 6 | -0.5 | -0.8 |
| Tyr | Pro | TAC | CCC | 3.2 | 5 | 1.1 | 0.7 |
| Tyr | Pro | TAC | CCG | 28.7 | 30 | 0.1 | 0.0 |
| Tyr | Pro | TAC | CCT | 5.7 | 5 | -0.1 | -0.2 |
| Tyr | Arg | TAC | CGA | 2.0 | 3 | 0.5 | 0.1 |
| Tyr | Arg | TAC | CGC | 23.0 | 27 | 0.7 | 0.1 |
| Tyr | Arg | TAC | CGG | 2.9 | 2 | -0.3 | -0.7 |
| Tyr | Arg | TAC | CGT | 33.8 | 34 | 0.0 | 1.4 |
| Tyr | Leu | TAC | CTA | 2.2 | 2 | -0.0 | -0.0 |
| Tyr | Leu | TAC | CTC | 9.5 | 13 | 1.3 | 1.1 |
| Tyr | Leu | TAC | CTG | 66.1 | 66 | -0.0 | -0.1 |
| Tyr | Leu | TAC | CTT | 8.5 | 7 | -0.3 | -0.3 |
| Tyr | Glu | TAC | GAA | 52.1 | 29 | -10.2 | -1.3 |
| Tyr | Asp | TAC | GAC | 30.8 | 44 | 5.7 | 1.3 |
| Tyr | Glu | TAC | GAG | 21.3 | 10 | -6.0 | -1.5 |
| Tyr | Asp | TAC | GAT | 32.4 | 35 | 0.2 | 0.4 |
| Tyr | Ala | TAC | GCA | 22.4 | 15 | -2.4 | -1.0 |
| Tyr | Ala | TAC | GCC | 22.5 | 31 | 3.2 | 6.9 |
| Tyr | Ala | TAC | GCG | 35.1 | 20 | -6.5 | -3.5 |
| Tyr | Ala | TAC | GCT | 23.4 | 20 | -0.5 | -0.0 |
| Tyr | Gly | TAC | GGA | 5.0 | 4 | -0.2 | -0.3 |
| Tyr | Gly | TAC | GGC | 35.2 | 52 | 8.1 | 6.5 |
| Tyr | Gly | TAC | GGG | 7.5 | 4 | -1.6 | -1.8 |
| Tyr | Gly | TAC | GGT | 40.4 | 44 | 0.3 | 0.1 |
| Tyr | Val | TAC | GTA | 15.1 | 10 | -1.7 | -1.4 |
| Tyr | Val | TAC | GTC | 13.2 | 13 | -0.0 | -0.0 |
| Tyr | Val | TAC | GTG | 24.2 | 14 | -4.3 | -3.7 |
| Tyr | Val | TAC | GTT | 27.3 | 27 | -0.0 | -0.0 |
| Tyr | Ocr | TAC | TAA | 0.0 | 6 | 0.0 | 0.0 |
| Tyr | Tyr | TAC | TAC | 23.2 | 22 | -0.1 | -0.1 |
| Tyr | Amb | TAC | TAG | 0.0 | 1 | 0.0 | 0.0 |
| Tyr | Tyr | TAC | TAT | 16.4 | 13 | -0.7 | -0.2 |
| Tyr | Ser | TAC | TCA | 5.2 | 2 | -2.0 | -2.3 |
| Tyr | Ser | TAC | TCC | 13.6 | 20 | 3.0 | 2.0 |
| Tyr | Ser | TAC | TCG | 7.1 | 14 | 6.6 | 5.3 |
| Tyr | Ser | TAC | TCT | 14.1 | 11 | -0.7 | -1.1 |
| Tyr | Umb | TAC | TGA | 0.0 | 0 | 0.0 | 0.0 |
| Tyr | Cys | TAC | TGC | 6.4 | 8 | 0.4 | 0.8 |
| Tyr | Trp | TAC | TGG | 13.1 | 16 | 0.6 | 5.6 |
| Tyr | Cys | TAC | TGT | 4.8 | 5 | 0.0 | 0.1 |
| Tyr | Leu | TAC | TTA | 9.1 | 4 | -2.9 | -3.1 |
| Tyr | Phe | TAC | TTC | 25.3 | 34 | 3.0 | 1.0 |
| Tyr | Leu | TAC | TTG | 9.9 | 0 | -9.9 | -10.2 |
| Tyr | Phe | TAC | TTT | 16.2 | 13 | -0.6 | -1.6 |
| | Page Totals: | | | 1119.8 | 1123 | 160.0 | 133.5 |

ECOO.RXD/CPLIST.RXR January 11, 1989

| aa1 | aa2 | cod1 | cod2 | exp | obs | chis1 | chis2 |
|---|---|---|---|---|---|---|---|
| Tyr | Lys | TAT | AAA | 42.2 | 31 | -3.0 | -0.1 |
| Tyr | Asn | TAT | AAC | 28.9 | 32 | 0.3 | 2.6 |
| Tyr | Lys | TAT | AAG | 13.3 | 10 | -0.8 | -0.0 |
| Tyr | Asn | TAT | AAT | 20.3 | 4 | -13.0 | -9.8 |
| Tyr | Thr | TAT | ACA | 8.1 | 3 | -3.2 | -3.9 |
| Tyr | Thr | TAT | ACC | 25.4 | 29 | 0.5 | 0.0 |
| Tyr | Thr | TAT | ACG | 13.7 | 12 | -0.2 | -0.7 |
| Tyr | Thr | TAT | ACT | 12.0 | 6 | -3.0 | -4.0 |
| Tyr | Arg | TAT | AGA | 3.6 | 2 | -0.7 | -1.3 |
| Tyr | Ser | TAT | AGC | 17.3 | 14 | -0.6 | -1.1 |
| Tyr | Arg | TAT | AGG | 1.7 | 0 | -1.7 | -2.1 |
| Tyr | Ser | TAT | AGT | 8.6 | 1 | -6.7 | -7.2 |
| Tyr | Ile | TAT | ATA | 5.4 | 3 | -1.1 | -0.9 |
| Tyr | Ile | TAT | ATC | 30.2 | 28 | -0.2 | -0.0 |
| Tyr | Met | TAT | ATG | 28.3 | 22 | -1.4 | -0.1 |
| Tyr | Ile | TAT | ATT | 29.6 | 25 | -0.7 | -0.3 |
| Tyr | Gln | TAT | CAA | 15.9 | 20 | 1.0 | 0.1 |
| Tyr | His | TAT | CAC | 12.2 | 30 | 26.1 | 13.2 |
| Tyr | Gln | TAT | CAG | 33.8 | 70 | 38.8 | 14.1 |
| Tyr | His | TAT | CAT | 12.3 | 6 | -3.2 | -6.0 |
| Tyr | Pro | TAT | CCA | 9.6 | 2 | -6.0 | -6.8 |
| Tyr | Pro | TAT | CCC | 4.6 | 12 | 11.6 | 9.7 |
| Tyr | Pro | TAT | CCG | 25.3 | 31 | 1.3 | 0.5 |
| Tyr | Pro | TAT | CCT | 6.4 | 8 | 0.4 | 0.2 |
| Tyr | Arg | TAT | CGA | 2.8 | 2 | -0.2 | -0.6 |
| Tyr | Arg | TAT | CGC | 22.8 | 44 | 19.7 | 9.0 |
| Tyr | Arg | TAT | CGG | 4.2 | 5 | 0.2 | 0.0 |
| Tyr | Arg | TAT | CGT | 27.5 | 29 | 0.1 | 0.7 |
| Tyr | Leu | TAT | CTA | 3.2 | 4 | 0.2 | 0.2 |
| Tyr | Leu | TAT | CTC | 10.6 | 26 | 22.5 | 21.1 |
| Tyr | Leu | TAT | CTG | 58.2 | 73 | 3.7 | 2.9 |
| Tyr | Leu | TAT | CTT | 10.9 | 11 | 0.0 | 0.0 |
| Tyr | Glu | TAT | GAA | 48.8 | 42 | -0.9 | -2.1 |
| Tyr | Asp | TAT | GAC | 24.9 | 46 | 17.8 | 8.4 |
| Tyr | Glu | TAT | GAG | 21.5 | 18 | -0.6 | -0.7 |
| Tyr | Asp | TAT | GAT | 36.2 | 25 | -3.4 | -8.0 |
| Tyr | Ala | TAT | GCA | 23.5 | 17 | -1.8 | -0.5 |
| Tyr | Ala | TAT | GCC | 24.7 | 35 | 4.3 | 8.7 |
| Tyr | Ala | TAT | GCG | 35.3 | 26 | -2.4 | -0.7 |
| Tyr | Ala | TAT | GCT | 19.4 | 14 | -1.5 | -0.5 |
| Tyr | Gly | TAT | GGA | 8.2 | 7 | -0.2 | -0.3 |
| Tyr | Gly | TAT | GGC | 31.8 | 36 | 0.5 | 0.3 |
| Tyr | Gly | TAT | GGG | 9.8 | 3 | -4.7 | -5.1 |
| Tyr | Gly | TAT | GGT | 34.4 | 29 | -0.9 | -1.3 |
| Tyr | Val | TAT | GTA | 13.6 | 8 | -2.3 | -1.9 |
| Tyr | Val | TAT | GTC | 14.6 | 17 | 0.4 | 0.6 |
| Tyr | Val | TAT | GTG | 25.2 | 30 | 0.9 | 1.4 |
| Tyr | Val | TAT | GTT | 24.1 | 32 | 2.6 | 3.4 |
| Tyr | Ocr | TAT | TAA | 0.0 | 1 | 0.0 | 0.0 |
| Tyr | Tyr | TAT | TAC | 16.4 | 25 | 4.5 | 7.3 |
| Tyr | Amb | TAT | TAG | 0.0 | 0 | 0.0 | 0.0 |
| Tyr | Tyr | TAT | TAT | 24.5 | 12 | -6.3 | -4.5 |
| Tyr | Ser | TAT | TCA | 8.0 | 3 | -3.1 | -3.6 |
| Tyr | Ser | TAT | TCC | 11.7 | 18 | 3.4 | 2.4 |
| Tyr | Ser | TAT | TCG | 8.6 | 4 | -2.5 | -3.0 |
| Tyr | Ser | TAT | TCT | 12.8 | 8 | -1.8 | -2.4 |
| Tyr | Umb | TAT | TGA | 0.0 | 0 | 0.0 | 0.0 |
| Tyr | Cys | TAT | TGC | 6.6 | 6 | -0.1 | 0.0 |
| Tyr | Trp | TAT | TGG | 13.3 | 2 | -9.6 | -5.5 |
| Tyr | Cys | TAT | TGT | 5.3 | 2 | -2.1 | -1.7 |
| Tyr | Leu | TAT | TTA | 14.5 | 6 | -5.0 | -5.3 |
| Tyr | Phe | TAT | TTC | 21.5 | 28 | 2.0 | 0.5 |
| Tyr | Leu | TAT | TTG | 12.5 | 9 | -1.0 | -1.2 |
| Tyr | Phe | TAT | TTT | 20.9 | 20 | -0.0 | -0.6 |
| | Page Totals: | | | 1121.4 | 1124 | 258.9 | 200.9 |

ECOO.RXD/CPLIST.RXR January 11, 1989

| aa1 | aa2 | cod1 | cod2 | exp | obs | chis1 | chis2 |
|---|---|---|---|---|---|---|---|
| Ser | Lys | TCA | AAA | 16.3 | 19 | 0.5 | 2.6 |
| Ser | Asn | TCA | AAC | 9.8 | 10 | 0.0 | 0.1 |
| Ser | Lys | TCA | AAG | 5.3 | 5 | -0.0 | -0.1 |
| Ser | Asn | TCA | AAT | 9.4 | 3 | -4.4 | -3.8 |
| Ser | Thr | TCA | ACA | 3.6 | 5 | 0.5 | 0.4 |
| Ser | Thr | TCA | ACC | 8.6 | 12 | 1.4 | 1.0 |
| Ser | Thr | TCA | ACG | 5.3 | 10 | 4.3 | 3.7 |
| Ser | Thr | TCA | ACT | 4.8 | 2 | -1.6 | -1.8 |
| Ser | Arg | TCA | AGA | 1.6 | 3 | 1.3 | 0.9 |
| Ser | Ser | TCA | AGC | 6.7 | 3 | -2.0 | -1.7 |
| Ser | Arg | TCA | AGG | 0.8 | 0 | -0.8 | -0.9 |
| Ser | Ser | TCA | AGT | 4.0 | 3 | -0.2 | -0.1 |
| Ser | Ile | TCA | ATA | 2.7 | 3 | 0.0 | 0.1 |
| Ser | Ile | TCA | ATC | 10.6 | 7 | -1.2 | -0.8 |
| Ser | Met | TCA | ATG | 10.8 | 12 | 0.1 | 1.9 |
| Ser | Ile | TCA | ATT | 12.4 | 7 | -2.4 | -1.7 |
| Ser | Gln | TCA | CAA | 7.2 | 5 | -0.7 | -0.6 |
| Ser | His | TCA | CAC | 4.2 | 3 | -0.4 | -0.4 |
| Ser | Gln | TCA | CAG | 12.8 | 13 | 0.0 | 0.0 |
| Ser | His | TCA | CAT | 5.3 | 5 | -0.0 | -0.0 |
| Ser | Pro | TCA | CCA | 4.0 | 3 | -0.2 | -0.0 |
| Ser | Pro | TCA | CCC | 2.0 | 4 | 2.0 | 3.2 |
| Ser | Pro | TCA | CCG | 8.9 | 8 | -0.1 | -0.0 |
| Ser | Pro | TCA | CCT | 3.0 | 3 | 0.0 | 0.1 |
| Ser | Arg | TCA | CGA | 1.6 | 3 | 1.2 | 0.8 |
| Ser | Arg | TCA | CGC | 8.3 | 9 | 0.1 | 0.0 |
| Ser | Arg | TCA | CGG | 1.8 | 1 | -0.4 | -0.5 |
| Ser | Arg | TCA | CGT | 9.9 | 6 | -1.5 | -2.4 |
| Ser | Leu | TCA | CTA | 1.6 | 1 | -0.2 | -0.3 |
| Ser | Leu | TCA | CTC | 4.0 | 4 | 0.0 | 0.0 |
| Ser | Leu | TCA | CTG | 20.3 | 24 | 0.7 | 0.2 |
| Ser | Leu | TCA | CTT | 4.9 | 5 | 0.0 | 0.0 |
| Ser | Glu | TCA | GAA | 18.6 | 20 | 0.1 | 0.8 |
| Ser | Asp | TCA | GAC | 8.0 | 9 | 0.1 | 0.6 |
| Ser | Glu | TCA | GAG | 8.2 | 6 | -0.6 | -0.2 |
| Ser | Asp | TCA | GAT | 14.1 | 8 | -2.6 | -1.4 |
| Ser | Ala | TCA | GCA | 9.8 | 12 | 0.5 | 0.3 |
| Ser | Ala | TCA | GCC | 10.2 | 13 | 0.8 | 0.5 |
| Ser | Ala | TCA | GCG | 12.6 | 17 | 1.6 | 1.1 |
| Ser | Ala | TCA | GCT | 7.7 | 9 | 0.2 | 0.1 |
| Ser | Gly | TCA | GGA | 3.8 | 7 | 2.6 | 1.0 |
| Ser | Gly | TCA | GGC | 10.4 | 9 | -0.2 | -1.2 |
| Ser | Gly | TCA | GGG | 4.2 | 5 | 0.1 | 0.0 |
| Ser | Gly | TCA | GGT | 12.2 | 10 | -0.4 | -1.8 |
| Ser | Val | TCA | GTA | 5.8 | 9 | 1.7 | 1.5 |
| Ser | Val | TCA | GTC | 5.9 | 8 | 0.7 | 0.6 |
| Ser | Val | TCA | GTG | 9.1 | 6 | -1.1 | -1.2 |
| Ser | Val | TCA | GTT | 9.5 | 7 | -0.6 | -0.8 |
| Ser | Ocr | TCA | TAA | 0.0 | 1 | 0.0 | 0.0 |
| Ser | Tyr | TCA | TAC | 5.2 | 3 | -0.9 | -1.3 |
| Ser | Amb | TCA | TAG | 0.0 | 0 | 0.0 | 0.0 |
| Ser | Tyr | TCA | TAT | 8.0 | 4 | -2.0 | -2.7 |
| Ser | Ser | TCA | TCA | 5.1 | 8 | 1.6 | 2.2 |
| Ser | Ser | TCA | TCC | 4.3 | 7 | 1.7 | 2.2 |
| Ser | Ser | TCA | TCG | 3.3 | 5 | 0.9 | 1.2 |
| Ser | Ser | TCA | TCT | 5.4 | 5 | -0.0 | -0.0 |
| Ser | Umb | TCA | TGA | 0.0 | 2 | 0.0 | 0.0 |
| Ser | Cys | TCA | TGC | 2.1 | 5 | 3.8 | 1.8 |
| Ser | Trp | TCA | TGG | 4.9 | 7 | 0.9 | 0.4 |
| Ser | Cys | TCA | TGT | 2.0 | 1 | -0.5 | -1.0 |
| Ser | Leu | TCA | TTA | 7.1 | 12 | 3.3 | 2.3 |
| Ser | Phe | TCA | TTC | 7.0 | 5 | -0.6 | -0.4 |
| Ser | Leu | TCA | TTG | 4.9 | 6 | 0.2 | 0.1 |
| Ser | Phe | TCA | TTT | 8.7 | 5 | -1.6 | -1.3 |
| | | Page Totals: | | 430.5 | 432 | 60.5 | 60.5 |

PAGE 51

ECOO.RXD/CPLIST.RXR Janunry 11, 1989

| aa1 | aa2 | cod1 | cod2 | exp | obs | chis1 | chis2 |
|---|---|---|---|---|---|---|---|
| Ser | Lys | TCC | AAA | 35.1 | 20 | -6.5 | -2.5 |
| Ser | Asn | TCC | AAC | 24.8 | 23 | -0.1 | -0.0 |
| Ser | Lys | TCC | AAG | 10.9 | 13 | 0.4 | 1.9 |
| Ser | Asn | TCC | AAT | 10.7 | 13 | 0.5 | 1.0 |
| Ser | Thr | TCC | ACA | 4.2 | 7 | 1.9 | 1.6 |
| Ser | Thr | TCC | ACC | 21.9 | 32 | 4.7 | 3.6 |
| Ser | Thr | TCC | ACG | 8.4 | 10 | 0.3 | 0.2 |
| Ser | Thr | TCC | ACT | 10.3 | 11 | 0.0 | 0.0 |
| Ser | Arg | TCC | AGA | 1.2 | 1 | -0.0 | -0.1 |
| Ser | Ser | TCC | AGC | 12.4 | 38 | 52.6 | 59.7 |
| Ser | Arg | TCC | AGG | 0.6 | 2 | 3.1 | 2.5 |
| Ser | Ser | TCC | AGT | 4.7 | 12 | 11.6 | 13.4 |
| Ser | Ile | TCC | ATA | 2.1 | 5 | 3.9 | 4.8 |
| Ser | Ile | TCC | ATC | 29.1 | 37 | 2.2 | 4.0 |
| Ser | Met | TCC | ATG | 23.2 | 12 | -5.4 | -1.7 |
| Ser | Ile | TCC | ATT | 19.6 | 20 | 0.0 | 0.2 |
| Ser | Gln | TCC | CAA | 9.9 | 4 | -3.5 | -3.3 |
| Ser | His | TCC | CAC | 10.4 | 7 | -1.1 | -1.3 |
| Ser | Gln | TCC | CAG | 27.6 | 20 | -2.1 | -1.8 |
| Ser | His | TCC | CAT | 7.2 | 7 | -0.0 | -0.0 |
| Ser | Pro | TCC | CCA | 6.2 | 5 | -0.2 | -0.0 |
| Ser | Pro | TCC | CCC | 2.3 | 1 | -0.7 | -0.4 |
| Ser | Pro | TCC | CCG | 21.6 | 7 | -9.9 | -6.8 |
| Ser | Pro | TCC | CCT | 4.2 | 5 | 0.2 | 0.6 |
| Ser | Arg | TCC | CGA | 1.7 | 3 | 1.0 | 0.6 |
| Ser | Arg | TCC | CGC | 17.4 | 22 | 1.2 | 0.3 |
| Ser | Arg | TCC | CGG | 2.4 | 2 | -0.1 | -0.2 |
| Ser | Arg | TCC | CGT | 26.0 | 32 | 1.4 | 0.3 |
| Ser | Leu | TCC | CTA | 1.9 | 0 | -1.9 | -2.1 |
| Ser | Leu | TCC | CTC | 7.4 | 6 | -0.3 | -0.5 |
| Ser | Leu | TCC | CTG | 50.6 | 26 | -12.0 | -15.2 |
| Ser | Leu | TCC | CTT | 6.6 | 5 | -0.4 | -0.6 |
| Ser | Glu | TCC | GAA | 42.6 | 12 | -21.9 | -17.4 |
| Ser | Asp | TCC | GAC | 23.6 | 35 | 5.6 | 10.7 |
| Ser | Glu | TCC | GAG | 15.8 | 14 | -0.2 | -0.0 |
| Ser | Asp | TCC | GAT | 25.1 | 15 | -4.1 | -2.0 |
| Ser | Ala | TCC | GCA | 18.3 | 33 | 11.9 | 10.0 |
| Ser | Ala | TCC | GCC | 18.6 | 15 | -0.7 | -1.0 |
| Ser | Ala | TCC | GCG | 28.3 | 18 | -3.7 | -4.6 |
| Ser | Ala | TCC | GCT | 18.4 | 18 | -0.0 | -0.1 |
| Ser | Gly | TCC | GGA | 3.9 | 4 | 0.0 | 0.2 |
| Ser | Gly | TCC | GGC | 26.8 | 39 | 5.6 | 0.9 |
| Ser | Gly | TCC | GGG | 5.9 | 12 | 6.4 | 3.0 |
| Ser | Gly | TCC | GGT | 30.0 | 52 | 16.2 | 5.7 |
| Ser | Val | TCC | GTA | 12.7 | 17 | 1.5 | 1.1 |
| Ser | Val | TCC | GTC | 10.7 | 17 | 3.7 | 3.2 |
| Ser | Val | TCC | GTG | 19.6 | 19 | -0.0 | -0.1 |
| Ser | Val | TCC | GTT | 22.3 | 15 | -2.4 | -2.8 |
| Ser | Ocr | TCC | TAA | 0.0 | 0 | 0.0 | 0.0 |
| Ser | Tyr | TCC | TAC | 13.6 | 12 | -0.2 | -0.6 |
| Ser | Amb | TCC | TAG | 0.0 | 0 | 0.0 | 0.0 |
| Ser | Tyr | TCC | TAT | 11.7 | 8 | -1.2 | -1.9 |
| Ser | Ser | TCC | TCA | 4.3 | 6 | 0.7 | 1.0 |
| Ser | Ser | TCC | TCC | 13.3 | 9 | -1.4 | -1.0 |
| Ser | Ser | TCC | TCG | 5.5 | 2 | -2.3 | -1.9 |
| Ser | Ser | TCC | TCT | 10.9 | 13 | 0.4 | 0.8 |
| Ser | Umb | TCC | TGA | 0.0 | 5 | 0.0 | 0.0 |
| Ser | Cys | TCC | TGC | 5.0 | 16 | 24.0 | 14.0 |
| Ser | Trp | TCC | TGG | 8.6 | 18 | 10.5 | 7.2 |
| Ser | Cys | TCC | TGT | 3.6 | 4 | 0.0 | 0.1 |
| Ser | Leu | TCC | TTA | 6.9 | 4 | -1.2 | -1.6 |
| Ser | Phe | TCC | TTC | 17.4 | 19 | 0.1 | 0.3 |
| Ser | Leu | TCC | TTG | 7.6 | 4 | -1.7 | -2.2 |
| Ser | Phe | TCC | TTT | 12.1 | 4 | -5.4 | -4.9 |
| | | Page Totals: | | 865.3 | 867 | 261.8 | 231.5 |

PAGE 52

ECOO.RXD/CPLIST.RXR January 11, 1989

| aa1 | aa2 | cod1 | cod2 | exp | obs | chis1 | chis2 |
|---|---|---|---|---|---|---|---|
| Ser | Lys | TCG | AAA | 19.3 | 17 | -0.3 | -0.1 |
| Ser | Asn | TCG | AAC | 14.2 | 4 | -7.4 | -6.5 |
| Ser | Lys | TCG | AAG | 6.6 | 9 | 0.9 | 2.6 |
| Ser | Asn | TCG | AAT | 9.5 | 3 | -4.4 | -3.9 |
| Ser | Thr | TCG | ACA | 3.4 | 3 | -0.1 | -0.1 |
| Ser | Thr | TCG | ACC | 12.9 | 3 | -7.6 | -8.1 |
| Ser | Thr | TCG | ACG | 7.4 | 7 | -0.0 | -0.1 |
| Ser | Thr | TCG | ACT | 5.1 | 5 | -0.0 | -0.0 |
| Ser | Arg | TCG | AGA | 0.9 | 0 | -0.9 | -1.0 |
| Ser | Ser | TCG | AGC | 9.7 | 0 | -9.7 | -9.1 |
| Ser | Arg | TCG | AGG | 0.7 | 1 | 0.2 | 0.1 |
| Ser | Ser | TCG | AGT | 4.3 | 1 | -2.6 | -2.3 |
| Ser | Ile | TCG | ATA | 1.8 | 3 | 0.9 | 1.2 |
| Ser | Ile | TCG | ATC | 15.6 | 20 | 1.2 | 2.2 |
| Ser | Met | TCG | ATG | 15.2 | 27 | 9.2 | 21.3 |
| Ser | Ile | TCG | ATT | 15.4 | 13 | -0.4 | -0.1 |
| Ser | Gln | TCG | CAA | 7.8 | 11 | 1.3 | 1.5 |
| Ser | His | TCG | CAC | 6.1 | 3 | -1.6 | -1.7 |
| Ser | Gln | TCG | CAG | 18.1 | 17 | -0.1 | -0.0 |
| Ser | His | TCG | CAT | 6.0 | 13 | 8.1 | 7.3 |
| Ser | Pro | TCG | CCA | 4.2 | 8 | 3.5 | 5.8 |
| Ser | Pro | TCG | CCC | 2.2 | 3 | 0.3 | 0.8 |
| Ser | Pro | TCG | CCG | 13.3 | 12 | -0.1 | -0.1 |
| Ser | Pro | TCG | CCT | 2.9 | 5 | 1.5 | 2.7 |
| Ser | Arg | TCG | CGA | 1.7 | 2 | 0.1 | 0.0 |
| Ser | Arg | TCG | CGC | 12.8 | 17 | 1.4 | 0.5 |
| Ser | Arg | TCG | CGG | 2.2 | 4 | 1.4 | 0.9 |
| Ser | Arg | TCG | CGT | 14.4 | 17 | 0.5 | 0.0 |
| Ser | Leu | TCG | CTA | 1.7 | 5 | 6.5 | 5.5 |
| Ser | Leu | TCG | CTC | 5.5 | 8 | 1.2 | 0.7 |
| Ser | Leu | TCG | CTG | 31.1 | 82 | 83.2 | 69.0 |
| Ser | Leu | TCG | CTT | 5.4 | 11 | 6.0 | 4.7 |
| Ser | Glu | TCG | GAA | 24.9 | 15 | -3.9 | -2.2 |
| Ser | Asp | TCG | GAC | 12.1 | 3 | -6.9 | -5.3 |
| Ser | Glu | TCG | GAG | 11.3 | 5 | -3.5 | -2.5 |
| Ser | Asp | TCG | GAT | 17.4 | 9 | -4.1 | -2.4 |
| Ser | Ala | TCG | GCA | 11.0 | 15 | 1.4 | 1.0 |
| Ser | Ala | TCG | GCC | 14.6 | 4 | -7.7 | -8.4 |
| Ser | Ala | TCG | GCG | 20.2 | 17 | -0.5 | -0.9 |
| Ser | Ala | TCG | GCT | 9.3 | 9 | -0.0 | -0.1 |
| Ser | Gly | TCG | GGA | 3.4 | 1 | -1.7 | -2.5 |
| Ser | Gly | TCG | GGC | 16.3 | 7 | -5.3 | -8.8 |
| Ser | Gly | TCG | GGG | 5.4 | 1 | -3.6 | -4.9 |
| Ser | Gly | TCG | GGT | 15.3 | 9 | -2.6 | -5.3 |
| Ser | Val | TCG | GTA | 6.7 | 11 | 2.8 | 2.5 |
| Ser | Val | TCG | GTC | 8.1 | 9 | 0.1 | 0.1 |
| Ser | Val | TCG | GTG | 14.4 | 24 | 6.5 | 5.7 |
| Ser | Val | TCG | GTT | 11.3 | 13 | 0.3 | 0.2 |
| Ser | Ocr | TCG | TAA | 0.0 | 2 | 0.0 | 0.0 |
| Ser | Tyr | TCG | TAC | 7.1 | 2 | -3.7 | -4.4 |
| Ser | Amb | TCG | TAG | 0.0 | 0 | 0.0 | 0.0 |
| Ser | Tyr | TCG | TAT | 8.6 | 3 | -3.7 | -4.5 |
| Ser | Ser | TCG | TCA | 3.3 | 8 | 6.8 | 7.9 |
| Ser | Ser | TCG | TCC | 5.5 | 4 | -0.4 | -0.3 |
| Ser | Ser | TCG | TCG | 6.9 | 5 | -0.5 | -0.3 |
| Ser | Ser | TCG | TCT | 5.8 | 3 | -1.4 | -1.1 |
| Ser | Umb | TCG | TGA | 0.0 | 2 | 0.0 | 0.0 |
| Ser | Cys | TCG | TGC | 3.6 | 2 | -0.7 | -1.5 |
| Ser | Trp | TCG | TGG | 6.6 | 6 | -0.1 | -0.3 |
| Ser | Cys | TCG | TGT | 2.5 | 3 | 0.1 | 0.0 |
| Ser | Leu | TCG | TTA | 6.2 | 8 | 0.6 | 0.3 |
| Ser | Phe | TCG | TTC | 10.2 | 10 | -0.0 | -0.0 |
| Ser | Leu | TCG | TTG | 6.7 | 11 | 2.8 | 1.9 |
| Ser | Phe | TCG | TTT | 9.9 | 9 | -0.1 | -0.0 |
| | Page Totals: | | | 561.9 | 564 | 233.8 | 234.7 |

ECOO.RXD/CPLIST.RXR January 11, 1989

| aa1 | aa2 | cod1 | cod2 | exp | obs | chis1 | chis2 |
|---|---|---|---|---|---|---|---|
| Ser | Lys | TCT | AAA | 39.3 | 18 | -11.5 | -6.0 |
| Ser | Asn | TCT | AAC | 25.4 | 31 | 1.2 | 2.3 |
| Ser | Lys | TCT | AAG | 12.1 | 6 | -3.1 | -1.5 |
| Ser | Asn | TCT | AAT | 12.6 | 8 | -1.7 | -1.2 |
| Ser | Thr | TCT | ACA | 4.9 | 7 | 0.9 | 0.7 |
| Ser | Thr | TCT | ACC | 23.7 | 31 | 2.3 | 1.6 |
| Ser | Thr | TCT | ACG | 9.3 | 12 | 0.8 | 0.5 |
| Ser | Thr | TCT | ACT | 12.1 | 7 | -2.1 | -2.5 |
| Ser | Arg | TCT | AGA | 1.7 | 4 | 3.1 | 2.3 |
| Ser | Ser | TCT | AGC | 12.9 | 0 | -12.9 | -12.1 |
| Ser | Arg | TCT | AGG | 1.0 | 2 | 1.1 | 0.8 |
| Ser | Ser | TCT | AGT | 5.7 | 0 | -5.7 | -5.3 |
| Ser | Ile | TCT | ATA | 2.9 | 2 | -0.3 | -0.2 |
| Ser | Ile | TCT | ATC | 30.4 | 29 | -0.1 | -0.0 |
| Ser | Met | TCT | ATG | 24.1 | 10 | -8.3 | -3.6 |
| Ser | Ile | TCT | ATT | 22.3 | 21 | -0.1 | -0.0 |
| Ser | Gln | TCT | CAA | 10.9 | 7 | -1.4 | -1.2 |
| Ser | His | TCT | CAC | 11.2 | 15 | 1.3 | 1.0 |
| Ser | Gln | TCT | CAG | 29.6 | 31 | 0.1 | 0.2 |
| Ser | His | TCT | CAT | 7.7 | 1 | -5.9 | -6.2 |
| Ser | Pro | TCT | CCA | 6.5 | 1 | -4.6 | -3.6 |
| Ser | Pro | TCT | CCC | 2.7 | 4 | 0.7 | 1.4 |
| Ser | Pro | TCT | CCG | 22.3 | 22 | -0.0 | -0.6 |
| Ser | Pro | TCT | CCT | 4.8 | 6 | 0.3 | 1.0 |
| Ser | Arg | TCT | CGA | 2.2 | 1 | -0.6 | -0.8 |
| Ser | Arg | TCT | CGC | 17.9 | 22 | 0.9 | 0.2 |
| Ser | Arg | TCT | CGG | 2.6 | 0 | -2.6 | -2.9 |
| Ser | Arg | TCT | CGT | 27.6 | 16 | -4.9 | -7.2 |
| Ser | Leu | TCT | CTA | 2.2 | 5 | 3.7 | 3.0 |
| Ser | Leu | TCT | CTC | 8.3 | 4 | -2.2 | -2.7 |
| Ser | Leu | TCT | CTG | 54.0 | 55 | 0.0 | 0.2 |
| Ser | Leu | TCT | CTT | 7.5 | 12 | 2.7 | 1.8 |
| Ser | Glu | TCT | GAA | 45.7 | 56 | 2.3 | 6.1 |
| Ser | Asp | TCT | GAC | 24.8 | 31 | 1.6 | 4.4 |
| Ser | Glu | TCT | GAG | 17.8 | 13 | -1.3 | -0.5 |
| Ser | Asp | TCT | GAT | 27.2 | 16 | -4.6 | -2.4 |
| Ser | Ala | TCT | GCA | 21.5 | 22 | 0.0 | 0.0 |
| Ser | Ala | TCT | GCC | 18.6 | 17 | -0.1 | -0.3 |
| Ser | Ala | TCT | GCG | 28.7 | 38 | 3.0 | 2.1 |
| Ser | Ala | TCT | GCT | 21.6 | 34 | 7.1 | 5.6 |
| Ser | Gly | TCT | GGA | 5.0 | 1 | -3.2 | -4.4 |
| Ser | Gly | TCT | GGC | 27.2 | 35 | 2.2 | 0.0 |
| Ser | Gly | TCT | GGG | 6.6 | 3 | -2.0 | -3.4 |
| Ser | Gly | TCT | GGT | 33.4 | 49 | 7.3 | 1.3 |
| Ser | Val | TCT | GTA | 13.8 | 19 | 1.9 | 1.5 |
| Ser | Val | TCT | GTC | 11.1 | 13 | 0.3 | 0.2 |
| Ser | Val | TCT | GTG | 20.1 | 14 | -1.9 | -2.2 |
| Ser | Val | TCT | GTT | 25.6 | 29 | 0.4 | 0.2 |
| Ser | Ocr | TCT | TAA | 0.0 | 2 | 0.0 | 0.0 |
| Ser | Tyr | TCT | TAC | 14.1 | 21 | 3.4 | 1.9 |
| Ser | Amb | TCT | TAG | 0.0 | 0 | 0.0 | 0.0 |
| Ser | Tyr | TCT | TAT | 12.8 | 22 | 6.6 | 4.3 |
| Ser | Ser | TCT | TCA | 5.4 | 4 | -0.4 | -0.2 |
| Ser | Ser | TCT | TCC | 10.9 | 14 | 0.9 | 1.4 |
| Ser | Ser | TCT | TCG | 5.8 | 15 | 14.4 | 16.6 |
| Ser | Ser | TCT | TCT | 15.7 | 18 | 0.3 | 0.7 |
| Ser | Umb | TCT | TGA | 0.0 | 0 | 0.0 | 0.0 |
| Ser | Cys | TCT | TGC | 4.5 | 4 | -0.0 | -0.5 |
| Ser | Trp | TCT | TGG | 9.0 | 2 | -5.5 | -6.6 |
| Ser | Cys | TCT | TGT | 3.6 | 7 | 3.1 | 1.1 |
| Ser | Leu | TCT | TTA | 8.8 | 6 | -0.9 | -1.3 |
| Ser | Phe | TCT | TTC | 18.9 | 24 | 1.4 | 1.9 |
| Ser | Leu | TCT | TTG | 7.9 | 12 | 2.1 | 1.3 |
| Ser | Phe | TCT | TTT | 14.5 | 11 | -0.8 | -0.6 |
| | Page Totals: | | | 939.0 | 942 | 166.0 | 147.8 |

ECOO.RXD/CPLIST.RXR January 11, 1989

| aa1 | aa2 | cod1 | cod2 | exp | obs | chis1 | chis2 |
|---|---|---|---|---|---|---|---|
| Cys | Lys | TGC | AAA | 16.0 | 10 | -2.2 | -0.1 |
| Cys | Asn | TGC | AAC | 11.5 | 10 | -0.2 | -1.2 |
| Cys | Lys | TGC | AAG | 5.5 | 1 | -3.7 | -2.1 |
| Cys | Asn | TGC | AAT | 5.9 | 0 | -5.9 | -3.6 |
| Cys | Thr | TGC | ACA | 2.3 | 0 | -2.3 | -2.4 |
| Cys | Thr | TGC | ACC | 10.7 | 8 | -0.7 | -0.7 |
| Cys | Thr | TGC | ACG | 5.5 | 6 | 0.0 | 0.0 |
| Cys | Thr | TGC | ACT | 4.3 | 4 | -0.0 | -0.0 |
| Cys | Arg | TGC | AGA | 0.5 | 3 | 13.7 | 13.9 |
| Cys | Ser | TGC | AGC | 7.2 | 4 | -1.4 | -3.3 |
| Cys | Arg | TGC | AGG | 0.3 | 0 | -0.3 | -0.3 |
| Cys | Ser | TGC | AGT | 2.5 | 1 | -0.9 | -1.6 |
| Cys | Ile | TGC | ATA | 1.0 | 2 | 1.1 | 0.7 |
| Cys | Ile | TGC | ATC | 13.1 | 10 | -0.7 | -1.8 |
| Cys | Met | TGC | ATG | 11.3 | 5 | -3.5 | -1.8 |
| Cys | Ile | TGC | ATT | 10.6 | 16 | 2.8 | 1.1 |
| Cys | Gln | TGC | CAA | 5.2 | 2 | -2.0 | -0.9 |
| Cys | His | TGC | CAC | 5.3 | 10 | 4.3 | 0.2 |
| Cys | Gln | TGC | CAG | 13.6 | 16 | 0.4 | 3.3 |
| Cys | His | TGC | CAT | 4.9 | 8 | 2.0 | 0.0 |
| Cys | Pro | TGC | CCA | 3.4 | 4 | 0.1 | 0.1 |
| Cys | Pro | TGC | CCC | 1.5 | 0 | -1.5 | -1.5 |
| Cys | Pro | TGC | CCG | 11.2 | 21 | 8.5 | 8.0 |
| Cys | Pro | TGC | CCT | 2.4 | 1 | -0.8 | -0.8 |
| Cys | Arg | TGC | CGA | 1.2 | 3 | 2.7 | 2.7 |
| Cys | Arg | TGC | CGC | 10.2 | 7 | -1.0 | -0.9 |
| Cys | Arg | TGC | CGG | 1.7 | 5 | 6.5 | 6.7 |
| Cys | Arg | TGC | CGT | 12.4 | 16 | 1.0 | 1.2 |
| Cys | Leu | TGC | CTA | 1.1 | 0 | -1.1 | -0.9 |
| Cys | Leu | TGC | CTC | 4.0 | 5 | 0.2 | 0.9 |
| Cys | Leu | TGC | CTG | 25.3 | 26 | 0.0 | 1.4 |
| Cys | Leu | TGC | CTT | 3.5 | 3 | -0.1 | -0.0 |
| Cys | Glu | TGC | GAA | 20.1 | 19 | -0.1 | -0.0 |
| Cys | Asp | TGC | GAC | 10.7 | 9 | -0.3 | -0.2 |
| Cys | Glu | TGC | GAG | 8.6 | 4 | -2.5 | -1.9 |
| Cys | Asp | TGC | GAT | 13.2 | 11 | -0.4 | -0.7 |
| Cys | Ala | TGC | GCA | 8.5 | 10 | 0.3 | 0.7 |
| Cys | Ala | TGC | GCC | 11.0 | 12 | 0.1 | 0.4 |
| Cys | Ala | TGC | GCG | 15.0 | 9 | -2.4 | -1.5 |
| Cys | Ala | TGC | GCT | 7.5 | 4 | -1.7 | -1.1 |
| Cys | Gly | TGC | GGA | 2.3 | 2 | -0.0 | -0.3 |
| Cys | Gly | TGC | GGC | 13.1 | 15 | 0.3 | 0.3 |
| Cys | Gly | TGC | GGG | 3.6 | 2 | -0.7 | -1.5 |
| Cys | Gly | TGC | GGT | 12.9 | 17 | 1.3 | 0.0 |
| Cys | Val | TGC | GTA | 5.5 | 13 | 10.1 | 7.2 |
| Cys | Val | TGC | GTC | 5.8 | 8 | 0.8 | 0.3 |
| Cys | Val | TGC | GTG | 10.9 | 9 | -0.3 | -0.9 |
| Cys | Val | TGC | GTT | 9.1 | 4 | -2.9 | -3.9 |
| Cys | Ocr | TGC | TAA | 0.0 | 0 | 0.0 | 0.0 |
| Cys | Tyr | TGC | TAC | 6.4 | 11 | 3.3 | 1.4 |
| Cys | Amb | TGC | TAG | 0.0 | 0 | 0.0 | 0.0 |
| Cys | Tyr | TGC | TAT | 6.6 | 5 | -0.4 | -1.1 |
| Cys | Ser | TGC | TCA | 2.1 | 4 | 1.6 | 0.4 |
| Cys | Ser | TGC | TCC | 5.0 | 8 | 1.8 | 0.2 |
| Cys | Ser | TGC | TCG | 3.6 | 3 | -0.1 | -0.7 |
| Cys | Ser | TGC | TCT | 4.5 | 10 | 6.9 | 2.7 |
| Cys | Umb | TGC | TGA | 0.0 | 0 | 0.0 | 0.0 |
| Cys | Cys | TGC | TGC | 4.9 | 1 | -3.1 | -2.1 |
| Cys | Trp | TGC | TGG | 4.8 | 11 | 7.9 | 3.7 |
| Cys | Cys | TGC | TGT | 2.4 | 4 | 1.1 | 2.4 |
| Cys | Leu | TGC | TTA | 3.9 | 2 | -0.9 | -0.4 |
| Cys | Phe | TGC | TTC | 8.9 | 10 | 0.1 | 0.0 |
| Cys | Leu | TGC | TTG | 4.7 | 4 | -0.1 | -0.0 |
| Cys | Phe | TGC | TTT | 7.1 | 11 | 2.2 | 1.5 |
| | Page Totals: | | | 437.7 | 439 | 125.3 | 101.8 |

PAGE 55

ECOO.RXD/CPLIST.RXR January 11, 1989

| aa1 | aa2 | cod1 | cod2 | exp | obs | chis1 | chis2 |
|---|---|---|---|---|---|---|---|
| Trp | Lys | TGG | AAA | 31.2 | 27 | -0.6 | -0.4 |
| Trp | Asn | TGG | AAC | 22.8 | 21 | -0.1 | -0.0 |
| Trp | Lys | TGG | AAG | 9.8 | 13 | 1.1 | 1.3 |
| Trp | Asn | TGG | AAT | 13.2 | 11 | -0.4 | -0.0 |
| Trp | Thr | TGG | ACA | 5.0 | 8 | 1.9 | 3.1 |
| Trp | Thr | TGG | ACC | 19.9 | 15 | -1.2 | -0.3 |
| Trp | Thr | TGG | ACG | 10.0 | 9 | -0.1 | -0.0 |
| Trp | Thr | TGG | ACT | 8.7 | 6 | -0.8 | -0.3 |
| Trp | Arg | TGG | AGA | 1.5 | 3 | 1.5 | 1.0 |
| Trp | Ser | TGG | AGC | 13.7 | 13 | -0.0 | -0.0 |
| Trp | Arg | TGG | AGG | 0.8 | 0 | -0.8 | -0.9 |
| Trp | Ser | TGG | AGT | 5.8 | 5 | -0.1 | -0.0 |
| Trp | Ile | TGG | ATA | 3.1 | 4 | 0.3 | 0.3 |
| Trp | Ile | TGG | ATC | 23.6 | 25 | 0.1 | 0.1 |
| Trp | Met | TGG | ATG | 22.1 | 16 | -1.7 | 0.0 |
| Trp | Ile | TGG | ATT | 21.2 | 18 | -0.5 | -0.4 |
| Trp | Gln | TGG | CAA | 11.8 | 18 | 3.2 | 0.4 |
| Trp | His | TGG | CAC | 9.6 | 14 | 2.1 | 0.5 |
| Trp | Gln | TGG | CAG | 27.0 | 50 | 19.7 | 0.2 |
| Trp | His | TGG | CAT | 9.4 | 9 | -0.0 | -0.5 |
| Trp | Pro | TGG | CCA | 6.7 | 6 | -0.1 | -0.1 |
| Trp | Pro | TGG | CCC | 3.3 | 0 | -3.3 | -2.7 |
| Trp | Pro | TGG | CCG | 20.3 | 17 | -0.5 | -0.0 |
| Trp | Pro | TGG | CCT | 5.4 | 6 | 0.1 | 0.6 |
| Trp | Arg | TGG | CGA | 2.1 | 2 | -0.0 | -0.1 |
| Trp | Arg | TGG | CGC | 18.3 | 14 | -1.0 | -2.2 |
| Trp | Arg | TGG | CGG | 3.4 | 7 | 3.9 | 2.6 |
| Trp | Arg | TGG | CGT | 21.4 | 28 | 2.0 | 0.5 |
| Trp | Leu | TGG | CTA | 2.4 | 6 | 5.6 | 3.1 |
| Trp | Leu | TGG | CTC | 7.9 | 10 | 0.6 | 0.0 |
| Trp | Leu | TGG | CTG | 46.6 | 49 | 0.1 | 1.4 |
| Trp | Leu | TGG | CTT | 7.8 | 12 | 2.3 | 0.5 |
| Trp | Glu | TGG | GAA | 37.2 | 34 | -0.3 | -1.2 |
| Trp | Asp | TGG | GAC | 19.7 | 17 | -0.4 | -0.2 |
| Trp | Glu | TGG | GAG | 15.7 | 6 | -6.0 | -2.9 |
| Trp | Asp | TGG | GAT | 25.5 | 27 | 0.1 | 0.2 |
| Trp | Ala | TGG | GCA | 17.2 | 17 | -0.0 | -0.2 |
| Trp | Ala | TGG | GCC | 19.3 | 8 | -6.6 | -4.9 |
| Trp | Ala | TGG | GCG | 27.2 | 34 | 1.7 | 4.0 |
| Trp | Ala | TGG | GCT | 15.1 | 11 | -1.1 | -0.4 |
| Trp | Gly | TGG | GGA | 5.1 | 9 | 3.1 | 7.8 |
| Trp | Gly | TGG | GGC | 25.7 | 23 | -0.3 | -1.0 |
| Trp | Gly | TGG | GGG | 7.3 | 5 | -0.7 | -0.0 |
| Trp | Gly | TGG | GGT | 25.4 | 9 | -10.6 | -4.8 |
| Trp | Val | TGG | GTA | 10.5 | 21 | 10.4 | 12.2 |
| Trp | Val | TGG | GTC | 11.5 | 12 | 0.0 | 0.1 |
| Trp | Val | TGG | GTG | 20.2 | 11 | -4.2 | -3.5 |
| Trp | Val | TGG | GTT | 17.8 | 13 | -1.3 | -0.9 |
| Trp | Ocr | TGG | TAA | 0.0 | 4 | 0.0 | 0.0 |
| Trp | Tyr | TGG | TAC | 13.1 | 10 | -0.7 | -0.3 |
| Trp | Amb | TGG | TAG | 0.0 | 0 | 0.0 | 0.0 |
| Trp | Tyr | TGG | TAT | 13.3 | 14 | 0.0 | 0.3 |
| Trp | Ser | TGG | TCA | 4.9 | 7 | 0.9 | 1.4 |
| Trp | Ser | TGG | TCC | 8.6 | 5 | -1.5 | -1.1 |
| Trp | Ser | TGG | TCG | 6.6 | 9 | 0.8 | 1.3 |
| Trp | Ser | TGG | TCT | 9.0 | 6 | -1.0 | -0.7 |
| Trp | Umb | TGG | TGA | 0.0 | 0 | 0.0 | 0.0 |
| Trp | Cys | TGG | TGC | 4.8 | 11 | 7.9 | 0.8 |
| Trp | Trp | TGG | TGG | 15.9 | 16 | 0.0 | 0.0 |
| Trp | Cys | TGG | TGT | 3.7 | 4 | 0.0 | 1.0 |
| Trp | Leu | TGG | TTA | 9.7 | 17 | 5.4 | 1.9 |
| Trp | Phe | TGG | TTC | 18.0 | 16 | -0.2 | -0.6 |
| Trp | Leu | TGG | TTG | 9.7 | 11 | 0.2 | 0.1 |
| Trp | Phe | TGG | TTT | 15.1 | 20 | 1.6 | 0.8 |
| | Page Totals: | | | 848.2 | 849 | 122.7 | 78.2 |

PAGE 56

ECO0.RXD/CPLIST.RXR January 11, 1989

| aa1 | aa2 | cod1 | cod2 | exp | obs | chis1 | chis2 |
|---|---|---|---|---|---|---|---|
| Cys | Lys | TGT | AAA | 12.0 | 10 | -0.3 | -0.3 |
| Cys | Asn | TGT | AAC | 8.3 | 5 | -1.3 | -0.0 |
| Cys | Lys | TGT | AAG | 3.9 | 5 | 0.3 | 2.0 |
| Cys | Asn | TGT | AAT | 5.1 | 4 | -0.2 | -0.2 |
| Cys | Thr | TGT | ACA | 2.1 | 1 | -0.6 | -0.6 |
| Cys | Thr | TGT | ACC | 7.9 | 6 | -0.4 | -0.5 |
| Cys | Thr | TGT | ACG | 3.5 | 5 | 0.6 | 0.6 |
| Cys | Thr | TGT | ACT | 3.2 | 10 | 14.2 | 13.9 |
| Cys | Arg | TGT | AGA | 0.8 | 0 | -0.8 | -0.8 |
| Cys | Ser | TGT | AGC | 5.1 | 5 | -0.0 | -0.5 |
| Cys | Arg | TGT | AGG | 0.4 | 0 | -0.4 | -0.4 |
| Cys | Ser | TGT | AGT | 2.3 | 3 | 0.2 | 0.0 |
| Cys | Ile | TGT | ATA | 1.5 | 0 | -1.5 | -1.7 |
| Cys | Ile | TGT | ATC | 9.6 | 14 | 2.0 | 0.7 |
| Cys | Met | TGT | ATG | 8.8 | 11 | 0.6 | 2.3 |
| Cys | Ile | TGT | ATT | 8.1 | 9 | 0.1 | 0.0 |
| Cys | Gln | TGT | CAA | 4.5 | 2 | -1.4 | -0.6 |
| Cys | His | TGT | CAC | 4.0 | 3 | -0.2 | -1.9 |
| Cys | Gln | TGT | CAG | 10.0 | 5 | -2.5 | -0.8 |
| Cys | His | TGT | CAT | 3.6 | 8 | 5.2 | 0.7 |
| Cys | Pro | TGT | CCA | 2.7 | 2 | -0.2 | -0.2 |
| Cys | Pro | TGT | CCC | 1.4 | 0 | -1.4 | -1.4 |
| Cys | Pro | TGT | CCG | 8.1 | 4 | -2.0 | -2.1 |
| Cys | Pro | TGT | CCT | 1.9 | 1 | -0.4 | -0.4 |
| Cys | Arg | TGT | CGA | 0.8 | 1 | 0.0 | 0.0 |
| Cys | Arg | TGT | CGC | 7.5 | 3 | -2.7 | -2.6 |
| Cys | Arg | TGT | CGG | 1.2 | 1 | -0.0 | -0.0 |
| Cys | Arg | TGT | CGT | 8.7 | 6 | -0.8 | -0.8 |
| Cys | Leu | TGT | CTA | 1.1 | 0 | -1.1 | -0.9 |
| Cys | Leu | TGT | CTC | 3.2 | 5 | 1.0 | 2.1 |
| Cys | Leu | TGT | CTG | 17.9 | 10 | -3.5 | -1.4 |
| Cys | Leu | TGT | CTT | 2.9 | 1 | -1.3 | -0.8 |
| Cys | Glu | TGT | GAA | 14.8 | 16 | 0.1 | 0.5 |
| Cys | Asp | TGT | GAC | 7.6 | 11 | 1.5 | 1.9 |
| Cys | Glu | TGT | GAG | 6.3 | 6 | -0.0 | -0.0 |
| Cys | Asp | TGT | GAT | 10.3 | 9 | -0.2 | -0.1 |
| Cys | Ala | TGT | GCA | 6.3 | 4 | -0.9 | -0.5 |
| Cys | Ala | TGT | GCC | 7.6 | 5 | -0.9 | -0.5 |
| Cys | Ala | TGT | GCG | 10.8 | 13 | 0.4 | 1.1 |
| Cys | Ala | TGT | GCT | 5.5 | 8 | 1.1 | 1.9 |
| Cys | Gly | TGT | GGA | 1.9 | 5 | 4.9 | 2.4 |
| Cys | Gly | TGT | GGC | 9.9 | 9 | -0.1 | -1.2 |
| Cys | Gly | TGT | GGG | 2.5 | 8 | 11.7 | 6.5 |
| Cys | Gly | TGT | GGT | 10.2 | 16 | 3.3 | 0.5 |
| Cys | Val | TGT | GTA | 4.3 | 5 | 0.1 | 0.0 |
| Cys | Val | TGT | GTC | 4.5 | 6 | 0.5 | 0.2 |
| Cys | Val | TGT | GTG | 7.4 | 9 | 0.3 | 0.0 |
| Cys | Val | TGT | GTT | 6.9 | 8 | 0.2 | 0.0 |
| Cys | Ocr | TGT | TAA | 0.0 | 0 | 0.0 | 0.0 |
| Cys | Tyr | TGT | TAC | 4.8 | 3 | -0.7 | -1.4 |
| Cys | Amb | TGT | TAG | 0.0 | 0 | 0.0 | 0.0 |
| Cys | Tyr | TGT | TAT | 5.3 | 9 | 2.5 | 1.0 |
| Cys | Ser | TGT | TCA | 2.0 | 6 | 7.8 | 4.0 |
| Cys | Ser | TGT | TCC | 3.6 | 7 | 3.2 | 1.0 |
| Cys | Ser | TGT | TCG | 2.5 | 5 | 2.4 | 0.6 |
| Cys | Ser | TGT | TCT | 3.6 | 3 | -0.1 | -0.7 |
| Cys | Umb | TGT | TGA | 0.0 | 0 | 0.0 | 0.0 |
| Cys | Cys | TGT | TGC | 2.4 | 2 | -0.1 | -0.0 |
| Cys | Trp | TGT | TGG | 3.7 | 0 | -3.7 | -4.8 |
| Cys | Cys | TGT | TGT | 3.0 | 3 | 0.0 | 0.2 |
| Cys | Leu | TGT | TTA | 3.8 | 3 | -0.1 | -0.0 |
| Cys | Phe | TGT | TTC | 6.8 | 5 | -0.5 | -0.8 |
| Cys | Leu | TGT | TTG | 3.7 | 2 | -0.7 | -0.3 |
| Cys | Phe | TGT | TTT | 6.0 | 5 | -0.2 | -0.3 |
| | Page Totals: | | | 329.9 | 331 | 95.6 | 73.9 |

PAGE 57

ECO0.RXD/CPLIST.RXR January 11, 1989

| aa1 | aa2 | cod1 | cod2 | exp | obs | chis1 | chis2 |
|---|---|---|---|---|---|---|---|
| Leu | Lys | TTA | AAA | 28.3 | 31 | 0.3 | 0.0 |
| Leu | Asn | TTA | AAC | 17.0 | 5 | -8.5 | -9.4 |
| Leu | Lys | TTA | AAG | 8.7 | 8 | -0.1 | -0.3 |
| Leu | Asn | TTA | AAT | 16.8 | 21 | 1.1 | 0.6 |
| Leu | Thr | TTA | ACA | 7.1 | 14 | 6.7 | 5.2 |
| Leu | Thr | TTA | ACC | 15.4 | 24 | 4.9 | 3.3 |
| Leu | Thr | TTA | ACG | 9.4 | 18 | 8.0 | 6.2 |
| Leu | Thr | TTA | ACT | 7.9 | 12 | 2.2 | 1.4 |
| Leu | Arg | TTA | AGA | 2.9 | 3 | 0.0 | 0.0 |
| Leu | Ser | TTA | AGC | 12.2 | 28 | 20.6 | 14.8 |
| Leu | Arg | TTA | AGG | 1.6 | 0 | -1.6 | -1.7 |
| Leu | Ser | TTA | AGT | 7.4 | 14 | 5.8 | 3.8 |
| Leu | Ile | TTA | ATA | 5.6 | 4 | -0.5 | -0.3 |
| Leu | Ile | TTA | ATC | 17.8 | 13 | -1.3 | -0.8 |
| Leu | Met | TTA | ATG | 18.0 | 27 | 4.5 | 5.7 |
| Leu | Ile | TTA | ATT | 22.8 | 28 | 1.2 | 1.9 |
| Leu | Gln | TTA | CAA | 13.0 | 18 | 1.9 | 5.8 |
| Leu | His | TTA | CAC | 7.3 | 9 | 0.4 | 0.4 |
| Leu | Gln | TTA | CAG | 22.5 | 32 | 4.0 | 11.3 |
| Leu | His | TTA | CAT | 9.2 | 10 | 0.1 | 0.0 |
| Leu | Pro | TTA | CCA | 6.9 | 9 | 0.7 | 0.1 |
| Leu | Pro | TTA | CCC | 4.3 | 6 | 0.7 | 0.2 |
| Leu | Pro | TTA | CCG | 14.8 | 24 | 5.8 | 2.7 |
| Leu | Pro | TTA | CCT | 5.5 | 15 | 16.5 | 11.5 |
| Leu | Arg | TTA | CGA | 2.7 | 2 | -0.2 | -0.3 |
| Leu | Arg | TTA | CGC | 15.3 | 15 | -0.0 | -0.1 |
| Leu | Arg | TTA | CGG | 4.0 | 4 | 0.0 | 0.0 |
| Leu | Arg | TTA | CGT | 16.2 | 24 | 3.7 | 2.6 |
| Leu | Leu | TTA | CTA | 2.7 | 2 | -0.2 | -0.1 |
| Leu | Leu | TTA | CTC | 7.6 | 10 | 0.8 | 1.5 |
| Leu | Leu | TTA | CTG | 36.0 | 35 | -0.0 | -0.2 |
| Leu | Leu | TTA | CTT | 9.1 | 11 | 0.4 | 1.0 |
| Leu | Glu | TTA | GAA | 31.8 | 11 | -13.6 | -13.2 |
| Leu | Asp | TTA | GAC | 14.2 | 7 | -3.6 | -4.0 |
| Leu | Glu | TTA | GAG | 14.8 | 8 | -3.1 | -2.9 |
| Leu | Asp | TTA | GAT | 24.8 | 13 | -5.6 | -6.3 |
| Leu | Ala | TTA | GCA | 17.5 | 14 | -0.7 | -1.6 |
| Leu | Ala | TTA | GCC | 18.1 | 18 | -0.0 | -0.3 |
| Leu | Ala | TTA | GCG | 23.3 | 18 | -1.2 | -2.6 |
| Leu | Ala | TTA | GCT | 13.1 | 3 | -7.8 | -9.4 |
| Leu | Gly | TTA | GGA | 7.1 | 5 | -0.6 | -0.4 |
| Leu | Gly | TTA | GGC | 19.7 | 16 | -0.7 | -0.3 |
| Leu | Gly | TTA | GGG | 8.2 | 12 | 1.8 | 2.6 |
| Leu | Gly | TTA | GGT | 20.2 | 21 | 0.0 | 0.3 |
| Leu | Val | TTA | GTA | 9.6 | 8 | -0.3 | -0.1 |
| Leu | Val | TTA | GTC | 10.7 | 6 | -2.1 | -1.8 |
| Leu | Val | TTA | GTG | 16.7 | 6 | -6.9 | -6.2 |
| Leu | Val | TTA | GTT | 16.4 | 5 | -7.9 | -7.2 |
| Leu | Ocr | TTA | TAA | 0.0 | 0 | 0.0 | 0.0 |
| Leu | Tyr | TTA | TAC | 9.1 | 5 | -1.8 | -1.3 |
| Leu | Amb | TTA | TAG | 0.0 | 0 | 0.0 | 0.0 |
| Leu | Tyr | TTA | TAT | 14.5 | 11 | -0.8 | -0.4 |
| Leu | Ser | TTA | TCA | 7.1 | 6 | -0.2 | -0.5 |
| Leu | Ser | TTA | TCC | 6.9 | 9 | 0.7 | 0.2 |
| Leu | Ser | TTA | TCG | 6.2 | 12 | 5.6 | 3.7 |
| Leu | Ser | TTA | TCT | 8.8 | 10 | 0.2 | 0.0 |
| Leu | Umb | TTA | TGA | 0.0 | 3 | 0.0 | 0.0 |
| Leu | Cys | TTA | TGC | 3.9 | 4 | 0.0 | 0.1 |
| Leu | Trp | TTA | TGG | 9.7 | 7 | -0.8 | -0.2 |
| Leu | Cys | TTA | TGT | 3.8 | 7 | 2.8 | 4.3 |
| Leu | Leu | TTA | TTA | 16.7 | 17 | 0.0 | 0.3 |
| Leu | Phe | TTA | TTC | 12.3 | 8 | -1.5 | -0.8 |
| Leu | Leu | TTA | TTG | 9.9 | 12 | 0.5 | 1.1 |
| Leu | Phe | TTA | TTT | 16.9 | 12 | -1.4 | -0.6 |
| | Page Totals: | | | 767.4 | 770 | 174.3 | 165.8 |

PAGE 58

ECOO.RXD/CPLIST.RXR January 11, 1989

| aa1 | aa2 | cod1 | cod2 | exp | obs | chis1 | chis2 |
|---|---|---|---|---|---|---|---|
| Phe | Lys | TTC | AAA | 60.2 | 47 | -2.9 | -0.6 |
| Phe | Asn | TTC | AAC | 43.6 | 58 | 4.8 | 0.3 |
| Phe | Lys | TTC | AAG | 19.0 | 16 | -0.5 | -0.0 |
| Phe | Asn | TTC | AAT | 18.9 | 18 | -0.0 | -1.3 |
| Phe | Thr | TTC | ACA | 7.0 | 5 | -0.6 | -1.0 |
| Phe | Thr | TTC | ACC | 38.8 | 55 | 6.8 | 3.2 |
| Phe | Thr | TTC | ACG | 15.5 | 9 | -2.7 | -4.0 |
| Phe | Thr | TTC | ACT | 17.7 | 17 | -0.0 | -0.4 |
| Phe | Arg | TTC | AGA | 1.8 | 5 | 5.7 | 4.9 |
| Phe | Ser | TTC | AGC | 22.6 | 37 | 9.2 | 4.1 |
| Phe | Arg | TTC | AGG | 1.2 | 3 | 2.7 | 2.3 |
| Phe | Ser | TTC | AGT | 7.8 | 7 | -0.1 | -0.5 |
| Phe | Ile | TTC | ATA | 3.9 | 1 | -2.2 | -2.0 |
| Phe | Ile | TTC | ATC | 50.5 | 35 | -4.8 | -3.5 |
| Phe | Met | TTC | ATG | 41.7 | 13 | -19.7 | -3.2 |
| Phe | Ile | TTC | ATT | 35.6 | 21 | -6.0 | -4.8 |
| Phe | Gln | TTC | CAA | 16.3 | 3 | -10.8 | -8.9 |
| Phe | His | TTC | CAC | 18.6 | 23 | 1.1 | 0.8 |
| Phe | Gln | TTC | CAG | 47.0 | 72 | 13.3 | 23.1 |
| Phe | His | TTC | CAT | 13.7 | 19 | 2.0 | 1.8 |
| Phe | Pro | TTC | CCA | 10.8 | 12 | 0.1 | 0.1 |
| Phe | Pro | TTC | CCC | 4.1 | 11 | 11.5 | 11.2 |
| Phe | Pro | TTC | CCG | 39.4 | 56 | 7.0 | 6.5 |
| Phe | Pro | TTC | CCT | 7.6 | 8 | 0.0 | 0.0 |
| Phe | Arg | TTC | CGA | 2.8 | 0 | -2.8 | -3.0 |
| Phe | Arg | TTC | CGC | 30.8 | 49 | 10.7 | 7.5 |
| Phe | Arg | TTC | CGG | 4.1 | 8 | 3.9 | 3.0 |
| Phe | Arg | TTC | CGT | 44.1 | 68 | 13.0 | 8.8 |
| Phe | Leu | TTC | CTA | 3.1 | 0 | -3.1 | -2.6 |
| Phe | Leu | TTC | CTC | 13.6 | 45 | 72.9 | 98.9 |
| Phe | Leu | TTC | CTG | 93.4 | 78 | -2.6 | -0.0 |
| Phe | Leu | TTC | CTT | 11.6 | 12 | 0.0 | 0.5 |
| Phe | Glu | TTC | GAA | 71.7 | 58 | -2.6 | -2.0 |
| Phe | Asp | TTC | GAC | 40.4 | 47 | 1.1 | 0.0 |
| Phe | Glu | TTC | GAG | 28.1 | 18 | -3.6 | -3.2 |
| Phe | Asp | TTC | GAT | 44.2 | 32 | -3.4 | -6.7 |
| Phe | Ala | TTC | GCA | 30.9 | 17 | -6.2 | -7.5 |
| Phe | Ala | TTC | GCC | 32.4 | 45 | 5.0 | 3.4 |
| Phe | Ala | TTC | GCG | 49.6 | 20 | -17.7 | -20.2 |
| Phe | Ala | TTC | GCT | 32.4 | 31 | -0.1 | -0.3 |
| Phe | Gly | TTC | GGA | 6.6 | 2 | -3.2 | -3.7 |
| Phe | Gly | TTC | GGC | 48.5 | 31 | -6.3 | -8.4 |
| Phe | Gly | TTC | GGG | 10.3 | 12 | 0.3 | 0.1 |
| Phe | Gly | TTC | GGT | 53.8 | 56 | 0.1 | 0.0 |
| Phe | Val | TTC | GTA | 20.7 | 8 | -7.8 | -5.6 |
| Phe | Val | TTC | GTC | 18.9 | 15 | -0.8 | -0.1 |
| Phe | Val | TTC | GTG | 35.3 | 20 | -6.6 | -3.7 |
| Phe | Val | TTC | GTT | 38.5 | 34 | -0.5 | -0.0 |
| Phe | Ocr | TTC | TAA | 0.0 | 2 | 0.0 | 0.0 |
| Phe | Tyr | TTC | TAC | 25.3 | 28 | 0.3 | 1.1 |
| Phe | Amb | TTC | TAG | 0.0 | 0 | 0.0 | 0.0 |
| Phe | Tyr | TTC | TAT | 21.5 | 18 | -0.6 | -0.1 |
| Phe | Ser | TTC | TCA | 7.0 | 6 | -0.1 | -0.6 |
| Phe | Ser | TTC | TCC | 17.4 | 22 | 1.2 | 0.1 |
| Phe | Ser | TTC | TCG | 10.2 | 24 | 18.6 | 11.9 |
| Phe | Ser | TTC | TCT | 18.9 | 25 | 1.9 | 0.3 |
| Phe | Umb | TTC | TGA | 0.0 | 3 | 0.0 | 0.0 |
| Phe | Cys | TTC | TGC | 8.9 | 17 | 7.4 | 2.7 |
| Phe | Trp | TTC | TGG | 18.0 | 27 | 4.6 | 7.1 |
| Phe | Cys | TTC | TGT | 6.8 | 6 | -0.1 | -0.9 |
| Phe | Leu | TTC | TTA | 12.3 | 7 | -2.3 | -1.1 |
| Phe | Phe | TTC | TTC | 40.5 | 53 | 3.9 | 1.5 |
| Phe | Leu | TTC | TTG | 13.7 | 7 | -3.2 | -1.8 |
| Phe | Phe | TTC | TTT | 24.5 | 36 | 5.4 | 2.8 |
| | | Page Totals: | | 1534.1 | 1538 | 338.3 | 309.6 |

PAGE 59

ECOO.RXD/CPLIST.RXR January 11, 1989

| aa1 | aa2 | cod1 | cod2 | exp | obs | chis1 | chis2 |
|---|---|---|---|---|---|---|---|
| Leu | Lys | TTG | AAA | 27.4 | 31 | 0.5 | 0.0 |
| Leu | Asn | TTG | AAC | 19.4 | 13 | -2.1 | -2.8 |
| Leu | Lys | TTG | AAG | 9.3 | 10 | 0.1 | 0.0 |
| Leu | Asn | TTG | AAT | 13.7 | 12 | -0.2 | -0.4 |
| Leu | Thr | TTG | ACA | 4.8 | 5 | 0.0 | 0.0 |
| Leu | Thr | TTG | ACC | 17.0 | 14 | -0.5 | -1.0 |
| Leu | Thr | TTG | ACG | 10.0 | 8 | -0.4 | -0.7 |
| Leu | Thr | TTG | ACT | 7.2 | 8 | 0.1 | 0.0 |
| Leu | Arg | TTG | AGA | 1.2 | 5 | 12.9 | 11.6 |
| Leu | Ser | TTG | AGC | 13.3 | 12 | -0.1 | -0.6 |
| Leu | Arg | TTG | AGG | 0.9 | 4 | 11.6 | 10.5 |
| Leu | Ser | TTG | AGT | 6.3 | 15 | 12.0 | 8.7 |
| Leu | Ile | TTG | ATA | 3.3 | 8 | 6.5 | 7.4 |
| Leu | Ile | TTG | ATC | 20.0 | 20 | 0.0 | 0.1 |
| Leu | Met | TTG | ATG | 20.2 | 30 | 4.7 | 6.0 |
| Leu | Ile | TTG | ATT | 20.6 | 29 | 3.4 | 4.7 |
| Leu | Gln | TTG | CAA | 12.1 | 11 | -0.1 | -0.2 |
| Leu | His | TTG | CAC | 8.3 | 10 | 0.3 | 0.3 |
| Leu | Gln | TTG | CAG | 24.6 | 48 | 22.3 | 42.0 |
| Leu | His | TTG | CAT | 9.1 | 13 | 1.7 | 1.6 |
| Leu | Pro | TTG | CCA | 6.4 | 12 | 4.9 | 2.8 |
| Leu | Pro | TTG | CCC | 3.6 | 5 | 0.6 | 0.2 |
| Leu | Pro | TTG | CCG | 17.2 | 20 | 0.5 | 0.0 |
| Leu | Pro | TTG | CCT | 4.9 | 9 | 3.5 | 1.9 |
| Leu | Arg | TTG | CGA | 2.5 | 4 | 1.0 | 0.7 |
| Leu | Arg | TTG | CGC | 18.1 | 21 | 0.5 | 0.1 |
| Leu | Arg | TTG | CGG | 3.6 | 3 | -0.1 | -0.2 |
| Leu | Arg | TTG | CGT | 19.1 | 37 | 16.7 | 13.4 |
| Leu | Leu | TTG | CTA | 2.4 | 6 | 5.5 | 7.0 |
| Leu | Leu | TTG | CTC | 8.1 | 13 | 3.0 | 4.6 |
| Leu | Leu | TTG | CTG | 42.7 | 67 | 13.8 | 21.5 |
| Leu | Leu | TTG | CTT | 8.1 | 10 | 0.5 | 1.1 |
| Leu | Glu | TTG | GAA | 34.2 | 7 | -21.6 | -21.1 |
| Leu | Asp | TTG | GAC | 16.0 | 3 | -10.5 | -11.0 |
| Leu | Glu | TTG | GAG | 15.9 | 2 | -12.1 | -11.9 |
| Leu | Asp | TTG | GAT | 24.9 | 10 | -8.9 | -9.6 |
| Leu | Ala | TTG | GCA | 16.4 | 9 | -3.3 | -4.9 |
| Leu | Ala | TTG | GCC | 19.9 | 9 | -5.9 | -8.0 |
| Leu | Ala | TTG | GCG | 27.7 | 21 | -1.6 | -3.3 |
| Leu | Ala | TTG | GCT | 12.9 | 10 | -0.7 | -1.4 |
| Leu | Gly | TTG | GGA | 5.3 | 3 | -1.0 | -0.8 |
| Leu | Gly | TTG | GGC | 22.7 | 9 | -8.3 | -6.8 |
| Leu | Gly | TTG | GGG | 8.0 | 12 | 2.0 | 2.8 |
| Leu | Gly | TTG | GGT | 20.7 | 14 | -2.1 | -1.3 |
| Leu | Val | TTG | GTA | 9.1 | 7 | -0.5 | -0.3 |
| Leu | Val | TTG | GTC | 11.5 | 8 | -1.0 | -0.8 |
| Leu | Val | TTG | GTG | 20.2 | 11 | -4.2 | -3.6 |
| Leu | Val | TTG | GTT | 15.4 | 10 | -1.9 | -1.5 |
| Leu | Ocr | TTG | TAA | 0.0 | 1 | 0.0 | 0.0 |
| Leu | Tyr | TTG | TAC | 9.9 | 4 | -3.5 | -2.8 |
| Leu | Amb | TTG | TAG | 0.0 | 2 | 0.0 | 0.0 |
| Leu | Tyr | TTG | TAT | 12.5 | 13 | 0.0 | 0.2 |
| Leu | Ser | TTG | TCA | 4.9 | 7 | 0.9 | 0.4 |
| Leu | Ser | TTG | TCC | 7.6 | 2 | -4.1 | -5.1 |
| Leu | Ser | TTG | TCG | 6.7 | 13 | 5.9 | 3.9 |
| Leu | Ser | TTG | TCT | 7.9 | 6 | -0.5 | -1.0 |
| Leu | Umb | TTG | TGA | 0.0 | 0 | 0.0 | 0.0 |
| Leu | Cys | TTG | TGC | 4.7 | 2 | -1.5 | -1.0 |
| Leu | Trp | TTG | TGG | 9.7 | 3 | -4.6 | -3.2 |
| Leu | Cys | TTG | TGT | 3.7 | 4 | 0.0 | 0.2 |
| Leu | Leu | TTG | TTA | 9.9 | 11 | 0.1 | 0.5 |
| Leu | Phe | TTG | TTC | 13.7 | 19 | 2.1 | 4.0 |
| Leu | Leu | TTG | TTG | 12.8 | 23 | 8.0 | 11.4 |
| Leu | Phe | TTG | TTT | 14.6 | 17 | 0.4 | 1.3 |
| | | Page Totals: | | 784.2 | 785 | 247.5 | 276.3 |

PAGE 60

ECOO.RXD/CPLIST.RXR January 11, 1989

| aa1 | aa2 | cod1 | cod2 | exp | obs | chis1 | chis2 |
|---|---|---|---|---|---|---|---|
| Phe | Lys | TTT | AAA | 46.4 | 48 | 0.1 | 1.5 |
| Phe | Asn | TTT | AAC | 30.8 | 39 | 2.2 | 0.0 |
| Phe | Lys | TTT | AAG | 14.7 | 11 | -0.9 | -0.2 |
| Phe | Asn | TTT | AAT | 21.7 | 28 | 1.8 | 0.0 |
| Phe | Thr | TTT | ACA | 8.4 | 3 | -3.5 | -4.3 |
| Phe | Thr | TTT | ACC | 27.9 | 40 | 5.2 | 2.5 |
| Phe | Thr | TTT | ACG | 15.7 | 13 | -0.5 | -1.2 |
| Phe | Thr | TTT | ACT | 13.3 | 19 | 2.4 | 1.2 |
| Phe | Arg | TTT | AGA | 2.6 | 1 | -1.0 | -1.1 |
| Phe | Ser | TTT | AGC | 19.7 | 11 | -3.9 | -6.4 |
| Phe | Arg | TTT | AGG | 1.4 | 1 | -0.1 | -0.2 |
| Phe | Ser | TTT | AGT | 10.0 | 9 | -0.1 | -0.6 |
| Phe | Ile | TTT | ATA | 5.7 | 2 | -2.4 | -2.1 |
| Phe | Ile | TTT | ATC | 33.9 | 52 | 9.7 | 12.3 |
| Phe | Met | TTT | ATG | 32.9 | 25 | -1.9 | -4.0 |
| Phe | Ile | TTT | ATT | 34.0 | 44 | 3.0 | 4.3 |
| Phe | Gln | TTT | CAA | 17.6 | 4 | -10.5 | -8.5 |
| Phe | His | TTT | CAC | 12.9 | 8 | -1.9 | -2.1 |
| Phe | Gln | TTT | CAG | 37.8 | 25 | -4.3 | -2.0 |
| Phe | His | TTT | CAT | 13.4 | 10 | -0.9 | -1.0 |
| Phe | Pro | TTT | CCA | 10.2 | 5 | -2.6 | -2.7 |
| Phe | Pro | TTT | CCC | 5.7 | 5 | -0.1 | -0.1 |
| Phe | Pro | TTT | CCG | 27.5 | 13 | -7.6 | -7.9 |
| Phe | Pro | TTT | CCT | 7.5 | 4 | -1.6 | -1.7 |
| Phe | Arg | TTT | CGA | 3.5 | 0 | -3.5 | -3.8 |
| Phe | Arg | TTT | CGC | 26.6 | 15 | -5.1 | -6.5 |
| Phe | Arg | TTT | CGG | 5.2 | 0 | -5.2 | -5.6 |
| Phe | Arg | TTT | CGT | 30.0 | 16 | -6.5 | -8.2 |
| Phe | Leu | TTT | CTA | 4.0 | 3 | -0.3 | -0.0 |
| Phe | Leu | TTT | CTC | 12.8 | 14 | 0.1 | 1.0 |
| Phe | Leu | TTT | CTG | 67.2 | 29 | -21.7 | -13.4 |
| Phe | Leu | TTT | CTT | 12.7 | 7 | -2.5 | -1.2 |
| Phe | Glu | TTT | GAA | 53.7 | 73 | 6.9 | 8.3 |
| Phe | Asp | TTT | GAC | 25.9 | 44 | 12.6 | 7.1 |
| Phe | Glu | TTT | GAG | 23.5 | 23 | -0.0 | -0.0 |
| Phe | Asp | TTT | GAT | 38.8 | 47 | 1.7 | 0.2 |
| Phe | Ala | TTT | GCA | 26.6 | 22 | -0.8 | -1.4 |
| Phe | Ala | TTT | GCC | 30.2 | 67 | 44.9 | 38.4 |
| Phe | Ala | TTT | GCG | 41.6 | 36 | -0.7 | -1.5 |
| Phe | Ala | TTT | GCT | 22.7 | 44 | 20.0 | 16.6 |
| Phe | Gly | TTT | GGA | 9.0 | 6 | -1.0 | -1.4 |
| Phe | Gly | TTT | GGC | 35.7 | 48 | 4.2 | 2.5 |
| Phe | Gly | TTT | GGG | 11.8 | 3 | -6.5 | -7.3 |
| Phe | Gly | TTT | GGT | 36.8 | 69 | 28.2 | 22.4 |
| Phe | Val | TTT | GTA | 15.6 | 9 | -2.8 | -1.6 |
| Phe | Val | TTT | GTC | 17.4 | 31 | 10.6 | 16.6 |
| Phe | Val | TTT | GTG | 29.6 | 15 | -7.2 | -4.5 |
| Phe | Val | TTT | GTT | 27.3 | 45 | 11.5 | 19.0 |
| Phe | Ocr | TTT | TAA | 0.0 | 4 | 0.0 | 0.0 |
| Phe | Tyr | TTT | TAC | 16.2 | 11 | -1.7 | -0.9 |
| Phe | Amb | TTT | TAG | 0.0 | 0 | 0.0 | 0.0 |
| Phe | Tyr | TTT | TAT | 20.9 | 19 | -0.2 | -0.0 |
| Phe | Ser | TTT | TCA | 8.7 | 12 | 1.3 | 0.3 |
| Phe | Ser | TTT | TCC | 12.1 | 10 | -0.4 | -1.3 |
| Phe | Ser | TTT | TCG | 9.9 | 12 | 0.4 | 0.0 |
| Phe | Ser | TTT | TCT | 14.5 | 12 | -0.4 | -1.5 |
| Phe | Umb | TTT | TGA | 0.0 | 2 | 0.0 | 0.0 |
| Phe | Cys | TTT | TGC | 7.1 | 10 | 1.2 | 0.1 |
| Phe | Trp | TTT | TGG | 15.1 | 3 | -9.7 | -8.4 |
| Phe | Cys | TTT | TGT | 6.0 | 4 | -0.7 | -1.8 |
| Phe | Leu | TTT | TTA | 16.9 | 16 | -0.0 | -0.2 |
| Phe | Phe | TTT | TTC | 24.5 | 22 | -0.3 | -1.0 |
| Phe | Leu | TTT | TTG | 14.6 | 14 | -0.0 | -0.2 |
| Phe | Phe | TTT | TTT | 30.3 | 22 | -2.3 | -4.0 |
| | Page Totals: | | | 1256.5 | 1259 | 291.4 | 276.3 |

Grand Totals:

| exp | obs | chis1 | chis2 |
|---|---|---|---|
| 78403 | 78615 | 14363.0 | 12995.9 |

YEAST.RXD/CPLIST.RXR February 7, 1989

| aa1 | aa2 | cod1 | cod2 | exp | obs | chis1 | chis2 |
|---|---|---|---|---|---|---|---|
| Lys | Lys | AAA | AAA | 125.8 | 114 | -1.11 | -3.2 |
| Lys | Asn | AAA | AAC | 68.1 | 62 | -0.54 | -0.2 |
| Lys | Lys | AAA | AAG | 95.8 | 76 | -4.10 | -7.0 |
| Lys | Asn | AAA | AAT | 90.9 | 90 | -0.01 | -0.1 |
| Lys | Thr | AAA | ACA | 45.3 | 46 | 0.01 | 0.1 |
| Lys | Thr | AAA | ACC | 34.6 | 27 | -1.67 | -1.3 |
| Lys | Thr | AAA | ACG | 19.2 | 30 | 6.04 | 6.8 |
| Lys | Thr | AAA | ACT | 59.4 | 30 | -14.58 | -13.4 |
| Lys | Arg | AAA | AGA | 68.5 | 70 | 0.03 | 3.0 |
| Lys | Ser | AAA | AGC | 21.0 | 23 | 0.20 | 0.5 |
| Lys | Arg | AAA | AGG | 23.8 | 45 | 18.81 | 7.6 |
| Lys | Ser | AAA | AGT | 32.4 | 37 | 0.66 | 1.3 |
| Lys | Ile | AAA | ATA | 42.0 | 51 | 1.95 | 1.7 |
| Lys | Ile | AAA | ATC | 46.4 | 45 | -0.04 | -0.1 |
| Lys | Met | AAA | ATG | 62.0 | 43 | -5.84 | -0.1 |
| Lys | Ile | AAA | ATT | 88.2 | 92 | 0.17 | 0.1 |
| Lys | Gln | AAA | CAA | 78.6 | 69 | -1.17 | -3.7 |
| Lys | His | AAA | CAC | 20.8 | 14 | -2.23 | -0.3 |
| Lys | Gln | AAA | CAG | 27.9 | 38 | 3.62 | 1.6 |
| Lys | His | AAA | CAT | 36.6 | 21 | -6.62 | -1.9 |
| Lys | Pro | AAA | CCA | 58.6 | 55 | -0.22 | -0.0 |
| Lys | Pro | AAA | CCC | 18.3 | 9 | -4.71 | -3.8 |
| Lys | Pro | AAA | CCG | 12.1 | 15 | 0.67 | 1.2 |
| Lys | Pro | AAA | CCT | 35.8 | 38 | 0.14 | 0.7 |
| Lys | Arg | AAA | CGA | 7.9 | 13 | 3.38 | 1.0 |
| Lys | Arg | AAA | CGC | 5.7 | 9 | 1.95 | 0.5 |
| Lys | Arg | AAA | CGG | 3.5 | 2 | -0.66 | -1.3 |
| Lys | Arg | AAA | CGT | 22.9 | 22 | -0.03 | -1.6 |
| Lys | Leu | AAA | CTA | 34.4 | 59 | 17.62 | 16.8 |
| Lys | Leu | AAA | CTC | 11.6 | 8 | -1.14 | -1.2 |
| Lys | Leu | AAA | CTG | 26.8 | 34 | 1.94 | 1.7 |
| Lys | Leu | AAA | CTT | 28.9 | 26 | -0.29 | -0.4 |
| Lys | Glu | AAA | GAA | 139.9 | 140 | 0.00 | 0.2 |
| Lys | Asp | AAA | GAC | 57.3 | 57 | -0.00 | -0.1 |
| Lys | Glu | AAA | GAG | 52.4 | 56 | 0.25 | 0.0 |
| Lys | Asp | AAA | GAT | 111.4 | 107 | -0.17 | -0.0 |
| Lys | Ala | AAA | GCA | 45.5 | 45 | -0.00 | -0.1 |
| Lys | Ala | AAA | GCC | 41.6 | 40 | -0.06 | -0.2 |
| Lys | Ala | AAA | GCG | 15.9 | 9 | -2.97 | -3.2 |
| Lys | Ala | AAA | GCT | 68.7 | 62 | -0.65 | -1.0 |
| Lys | Gly | AAA | GGA | 25.2 | 17 | -2.69 | -1.6 |
| Lys | Gly | AAA | GGC | 24.8 | 11 | -7.66 | -6.0 |
| Lys | Gly | AAA | GGG | 16.3 | 14 | -0.31 | -0.1 |
| Lys | Gly | AAA | GGT | 92.2 | 86 | -0.42 | -0.0 |
| Lys | Val | AAA | GTA | 30.6 | 31 | 0.01 | 0.3 |
| Lys | Val | AAA | GTC | 37.3 | 25 | -4.07 | -2.6 |
| Lys | Val | AAA | GTG | 27.3 | 32 | 0.79 | 1.8 |
| Lys | Val | AAA | GTT | 72.1 | 83 | 1.65 | 4.0 |
| Lys | Ocr | AAA | TAA | 0.0 | 9 | 0.00 | 0.0 |
| Lys | Tyr | AAA | TAC | 45.0 | 72 | 16.19 | 6.5 |
| Lys | Amb | AAA | TAG | 0.0 | 3 | 0.00 | 0.0 |
| Lys | Tyr | AAA | TAT | 50.7 | 55 | 0.37 | 0.4 |
| Lys | Ser | AAA | TCA | 46.7 | 56 | 1.87 | 3.2 |
| Lys | Ser | AAA | TCC | 37.5 | 40 | 0.17 | 0.6 |
| Lys | Ser | AAA | TCG | 18.5 | 23 | 1.09 | 1.7 |
| Lys | Ser | AAA | TCT | 69.8 | 63 | -0.67 | -0.1 |
| Lys | Umb | AAA | TGA | 0.0 | 3 | 0.00 | 0.0 |
| Lys | Cys | AAA | TGC | 10.7 | 10 | -0.05 | -0.1 |
| Lys | Trp | AAA | TGG | 29.0 | 53 | 19.84 | 7.6 |
| Lys | Cys | AAA | TGT | 21.8 | 18 | -0.67 | -0.0 |
| Lys | Leu | AAA | TTA | 70.9 | 97 | 9.57 | 8.8 |
| Lys | Phe | AAA | TTC | 51.4 | 55 | 0.26 | 1.0 |
| Lys | Leu | AAA | TTG | 85.8 | 69 | -3.30 | -3.7 |
| Lys | Phe | AAA | TTT | 67.9 | 70 | 0.07 | 0.7 |
| | | Page Totals: | | 2817.7 | 2824 | 177.956 | 139.9 |

PAGE 1

YEAST.RXD/CPLIST.RXR February 7, 1989

| aa1 | aa2 | cod1 | cod2 | exp | obs | chis1 | chis2 |
|---|---|---|---|---|---|---|---|
| Asn | Lys | AAC | AAA | 68.1 | 69 | 0.01 | 0.3 |
| Asn | Asn | AAC | AAC | 56.8 | 47 | -1.70 | -1.7 |
| Asn | Lys | AAC | AAG | 74.2 | 86 | 1.89 | 3.3 |
| Asn | Asn | AAC | AAT | 55.0 | 53 | -0.07 | -0.1 |
| Asn | Thr | AAC | ACA | 27.1 | 23 | -0.62 | -0.0 |
| Asn | Thr | AAC | ACC | 29.7 | 28 | -0.10 | -0.5 |
| Asn | Thr | AAC | ACG | 11.3 | 10 | -0.15 | -0.0 |
| Asn | Thr | AAC | ACT | 43.0 | 39 | -0.37 | -0.3 |
| Asn | Arg | AAC | AGA | 49.1 | 53 | 0.31 | 3.0 |
| Asn | Ser | AAC | AGC | 13.3 | 15 | 0.23 | 0.5 |
| Asn | Arg | AAC | AGG | 13.5 | 15 | 0.17 | 1.1 |
| Asn | Ser | AAC | AGT | 20.1 | 26 | 1.74 | 2.6 |
| Asn | Ile | AAC | ATA | 22.5 | 23 | 0.01 | 0.4 |
| Asn | Ile | AAC | ATC | 35.3 | 37 | 0.08 | 0.4 |
| Asn | Met | AAC | ATG | 42.0 | 42 | 0.00 | -0.1 |
| Asn | Ile | AAC | ATT | 58.3 | 66 | 1.03 | 0.1 |
| Asn | Gln | AAC | CAA | 56.3 | 51 | -0.49 | -0.5 |
| Asn | His | AAC | CAC | 15.5 | 14 | -0.14 | -0.4 |
| Asn | Gln | AAC | CAG | 16.9 | 16 | -0.05 | -0.3 |
| Asn | His | AAC | CAT | 22.5 | 22 | -0.01 | -1.3 |
| Asn | Pro | AAC | CCA | 43.2 | 49 | 0.79 | 1.9 |
| Asn | Pro | AAC | CCC | 11.1 | 4 | -4.57 | -3.9 |
| Asn | Pro | AAC | CCG | 7.1 | 2 | -3.62 | -3.2 |
| Asn | Pro | AAC | CCT | 21.8 | 23 | 0.06 | 0.3 |
| Asn | Arg | AAC | CGA | 4.0 | 4 | 0.00 | 0.1 |
| Asn | Arg | AAC | CGC | 3.5 | 6 | 1.86 | 3.2 |
| Asn | Arg | AAC | CGG | 1.9 | 4 | 2.22 | 3.4 |
| Asn | Arg | AAC | CGT | 15.4 | 9 | -2.64 | -1.3 |
| Asn | Leu | AAC | CTA | 21.5 | 23 | 0.11 | 0.3 |
| Asn | Leu | AAC | CTC | 7.0 | 7 | 0.00 | 0.0 |
| Asn | Leu | AAC | CTG | 16.3 | 18 | 0.18 | 0.4 |
| Asn | Leu | AAC | CTT | 16.7 | 24 | 3.23 | 4.0 |
| Asn | Glu | AAC | GAA | 93.0 | 93 | 0.00 | -1.1 |
| Asn | Asp | AAC | GAC | 44.4 | 45 | 0.01 | 0.2 |
| Asn | Glu | AAC | GAG | 31.2 | 27 | -0.57 | -1.7 |
| Asn | Asp | AAC | GAT | 69.0 | 73 | 0.23 | 0.0 |
| Asn | Ala | AAC | GCA | 27.7 | 24 | -0.50 | -0.4 |
| Asn | Ala | AAC | GCC | 33.3 | 24 | -2.61 | -2.5 |
| Asn | Ala | AAC | GCG | 9.3 | 6 | -1.15 | -1.1 |
| Asn | Ala | AAC | GCT | 58.1 | 41 | -5.02 | -4.7 |
| Asn | Gly | AAC | GGA | 14.1 | 23 | 5.63 | 1.4 |
| Asn | Gly | AAC | GGC | 17.0 | 18 | 0.06 | 0.6 |
| Asn | Gly | AAC | GGG | 10.2 | 9 | -0.13 | -1.2 |
| Asn | Gly | AAC | GGT | 76.1 | 75 | -0.02 | -5.0 |
| Asn | Val | AAC | GTA | 17.2 | 22 | 1.33 | 0.1 |
| Asn | Val | AAC | GTC | 32.3 | 38 | 1.01 | 0.0 |
| Asn | Val | AAC | GTG | 18.1 | 13 | -1.43 | -3.3 |
| Asn | Val | AAC | GTT | 52.7 | 53 | 0.00 | 1.4 |
| Asn | Ocr | AAC | TAA | 0.0 | 4 | 0.00 | 0.0 |
| Asn | Tyr | AAC | TAC | 35.9 | 36 | 0.00 | 0.2 |
| Asn | Amb | AAC | TAG | 0.0 | 1 | 0.00 | 0.0 |
| Asn | Tyr | AAC | TAT | 29.9 | 31 | 0.04 | 0.3 |
| Asn | Ser | AAC | TCA | 27.5 | 23 | -0.74 | -0.3 |
| Asn | Ser | AAC | TCC | 28.6 | 28 | -0.01 | -0.0 |
| Asn | Ser | AAC | TCG | 10.9 | 8 | -0.77 | -0.5 |
| Asn | Ser | AAC | TCT | 50.8 | 56 | 0.54 | 1.4 |
| Asn | Umb | AAC | TGA | 0.0 | 2 | 0.00 | 0.0 |
| Asn | Cys | AAC | TGC | 6.3 | 3 | -1.71 | -2.1 |
| Asn | Trp | AAC | TGG | 19.7 | 33 | 8.94 | 11.6 |
| Asn | Cys | AAC | TGT | 15.6 | 23 | 3.54 | 2.3 |
| Asn | Leu | AAC | TTA | 42.4 | 38 | -0.46 | -0.2 |
| Asn | Phe | AAC | TTC | 39.7 | 31 | -1.90 | -1.1 |
| Asn | Leu | AAC | TTG | 67.6 | 77 | 1.30 | 2.3 |
| Asn | Phe | AAC | TTT | 41.3 | 38 | -0.26 | -0.0 |
| | | Page Totals: | | 1919.2 | 1924 | 68.3851 | 86.1 |

PAGE 2

YEAST.RXD/CPLIST.RXR February 7, 1989

| aa1 | aa2 | cod1 | cod2 | exp | obs | chis1 | chis2 |
|---|---|---|---|---|---|---|---|
| Lys | Lys | AAG | AAA | 95.8 | 132 | 13.65 | 8.3 |
| Lys | Asn | AAG | AAC | 74.2 | 84 | 1.31 | 2.3 |
| Lys | Lys | AAG | AAG | 124.6 | 152 | 6.02 | 2.5 |
| Lys | Asn | AAG | AAT | 68.2 | 53 | -3.38 | -2.3 |
| Lys | Thr | AAG | ACA | 34.5 | 45 | 3.19 | 3.9 |
| Lys | Thr | AAG | ACC | 43.8 | 40 | -0.32 | -0.2 |
| Lys | Thr | AAG | ACG | 14.2 | 12 | -0.33 | -0.2 |
| Lys | Thr | AAG | ACT | 62.7 | 75 | 2.42 | 3.2 |
| Lys | Arg | AAG | AGA | 79.9 | 112 | 12.92 | 1.4 |
| Lys | Ser | AAG | AGC | 16.6 | 20 | 0.69 | 1.2 |
| Lys | Arg | AAG | AGG | 17.7 | 21 | 0.63 | 0.1 |
| Lys | Ser | AAG | AGT | 24.3 | 19 | -1.14 | -0.7 |
| Lys | Ile | AAG | ATA | 28.1 | 34 | 1.22 | 1.0 |
| Lys | Ile | AAG | ATC | 53.8 | 48 | -0.63 | -0.8 |
| Lys | Met | AAG | ATG | 59.1 | 45 | -3.37 | -0.1 |
| Lys | Ile | AAG | ATT | 83.7 | 77 | -0.54 | -0.7 |
| Lys | Gln | AAG | CAA | 80.7 | 104 | 6.72 | 2.4 |
| Lys | His | AAG | CAC | 24.0 | 20 | -0.65 | -0.1 |
| Lys | Gln | AAG | CAG | 22.3 | 21 | -0.07 | -0.5 |
| Lys | His | AAG | CAT | 30.6 | 32 | 0.07 | 2.8 |
| Lys | Pro | AAG | CCA | 66.4 | 55 | -1.97 | -0.8 |
| Lys | Pro | AAG | CCC | 14.5 | 21 | 2.89 | 4.1 |
| Lys | Pro | AAG | CCG | 8.6 | 5 | -1.48 | -1.1 |
| Lys | Pro | AAG | CCT | 29.5 | 29 | -0.01 | -0.1 |
| Lys | Arg | AAG | CGA | 4.8 | 5 | 0.01 | 0.2 |
| Lys | Arg | AAG | CGC | 4.2 | 4 | -0.01 | -0.3 |
| Lys | Arg | AAG | CGG | 2.6 | 3 | 0.05 | 0.0 |
| Lys | Arg | AAG | CGT | 22.2 | 25 | 0.35 | 0.3 |
| Lys | Leu | AAG | CTA | 29.0 | 37 | 2.21 | 2.0 |
| Lys | Leu | AAG | CTC | 9.0 | 10 | 0.11 | 0.1 |
| Lys | Leu | AAG | CTG | 20.5 | 25 | 0.99 | 0.9 |
| Lys | Leu | AAG | CTT | 22.1 | 22 | -0.00 | -0.0 |
| Lys | Glu | AAG | GAA | 142.1 | 153 | 0.84 | 0.2 |
| Lys | Asp | AAG | GAC | 65.4 | 68 | 0.11 | 0.4 |
| Lys | Glu | AAG | GAG | 44.1 | 45 | 0.02 | 0.0 |
| Lys | Asp | AAG | GAT | 96.6 | 86 | -1.15 | -0.5 |
| Lys | Ala | AAG | GCA | 37.1 | 49 | 3.83 | 3.2 |
| Lys | Ala | AAG | GCC | 49.9 | 56 | 0.76 | 0.5 |
| Lys | Ala | AAG | GCG | 12.4 | 10 | -0.46 | -0.6 |
| Lys | Ala | AAG | GCT | 93.0 | 102 | 0.87 | 0.5 |
| Lys | Gly | AAG | GGA | 19.2 | 26 | 2.45 | 4.1 |
| Lys | Gly | AAG | GGC | 22.2 | 35 | 7.45 | 10.7 |
| Lys | Gly | AAG | GGG | 13.3 | 11 | -0.39 | -0.1 |
| Lys | Gly | AAG | GGT | 121.3 | 106 | -1.94 | -0.2 |
| Lys | Val | AAG | GTA | 22.7 | 14 | -3.35 | -2.3 |
| Lys | Val | AAG | GTC | 49.5 | 42 | -1.13 | -0.3 |
| Lys | Val | AAG | GTG | 24.5 | 13 | -5.36 | -4.1 |
| Lys | Val | AAG | GTT | 81.4 | 79 | -0.07 | -0.2 |
| Lys | Ocr | AAG | TAA | 0.0 | 0 | 0.00 | 0.0 |
| Lys | Tyr | AAG | TAC | 51.0 | 65 | 3.85 | 0.3 |
| Lys | Amb | AAG | TAG | 0.0 | 2 | 0.00 | 0.0 |
| Lys | Tyr | AAG | TAT | 39.0 | 28 | -3.09 | -7.2 |
| Lys | Ser | AAG | TCA | 34.0 | 27 | -1.43 | -0.8 |
| Lys | Ser | AAG | TCC | 42.0 | 30 | -3.41 | -2.4 |
| Lys | Ser | AAG | TCG | 13.8 | 16 | 0.36 | 0.7 |
| Lys | Ser | AAG | TCT | 72.0 | 51 | -6.13 | -4.3 |
| Lys | Umb | AAG | TGA | 0.0 | 1 | 0.00 | 0.0 |
| Lys | Cys | AAG | TGC | 8.2 | 8 | -0.00 | -0.1 |
| Lys | Trp | AAG | TGG | 26.8 | 17 | -3.60 | -8.2 |
| Lys | Cys | AAG | TGT | 21.0 | 17 | -0.76 | -0.1 |
| Lys | Leu | AAG | TTA | 58.5 | 37 | -7.89 | -8.3 |
| Lys | Phe | AAG | TTC | 58.1 | 43 | -3.91 | -2.4 |
| Lys | Leu | AAG | TTG | 104.3 | 84 | -3.96 | -4.4 |
| Lys | Phe | AAG | TTT | 54.6 | 49 | -0.58 | -0.1 |
| | Page Totals: | | | 2749.7 | 2757 | 138.484 | 111.9 |

PAGE 3

YEAST.RXD/CPLIST.RXR February 7, 1989

| aa1 | aa2 | cod1 | cod2 | exp | obs | chis1 | chis2 |
|---|---|---|---|---|---|---|---|
| Asn | Lys | AAT | AAA | 90.9 | 74 | -3.15 | -1.8 |
| Asn | Asn | AAT | AAC | 55.0 | 58 | 0.16 | 0.2 |
| Asn | Lys | AAT | AAG | 68.2 | 58 | -1.52 | -0.7 |
| Asn | Asn | AAT | AAT | 83.4 | 92 | 0.88 | 0.9 |
| Asn | Thr | AAT | ACA | 36.7 | 29 | -1.62 | -0.1 |
| Asn | Thr | AAT | ACC | 26.4 | 17 | -3.33 | -1.0 |
| Asn | Thr | AAT | ACG | 16.5 | 17 | 0.01 | 0.8 |
| Asn | Thr | AAT | ACT | 45.4 | 32 | -3.94 | -0.8 |
| Asn | Arg | AAT | AGA | 49.7 | 30 | -7.79 | -3.5 |
| Asn | Ser | AAT | AGC | 18.7 | 22 | 0.58 | 1.1 |
| Asn | Arg | AAT | AGG | 19.8 | 15 | -1.17 | -0.2 |
| Asn | Ser | AAT | AGT | 28.3 | 22 | -1.39 | -0.8 |
| Asn | Ile | AAT | ATA | 34.4 | 41 | 1.27 | 0.0 |
| Asn | Ile | AAT | ATC | 33.7 | 46 | 4.53 | 1.2 |
| Asn | Met | AAT | ATG | 48.1 | 44 | -0.35 | -0.1 |
| Asn | Ile | AAT | ATT | 67.9 | 81 | 2.51 | 0.0 |
| Asn | Gln | AAT | CAA | 60.5 | 51 | -1.50 | -0.0 |
| Asn | His | AAT | CAC | 15.3 | 11 | -1.20 | -0.0 |
| Asn | Gln | AAT | CAG | 23.2 | 11 | -6.39 | -3.4 |
| Asn | His | AAT | CAT | 28.9 | 16 | -5.78 | -1.7 |
| Asn | Pro | AAT | CCA | 41.4 | 38 | -0.28 | -0.0 |
| Asn | Pro | AAT | CCC | 14.3 | 13 | -0.12 | -0.0 |
| Asn | Pro | AAT | CCG | 10.0 | 12 | 0.41 | 0.8 |
| Asn | Pro | AAT | CCT | 27.8 | 24 | -0.51 | -0.1 |
| Asn | Arg | AAT | CGA | 6.8 | 7 | 0.01 | 0.3 |
| Asn | Arg | AAT | CGC | 4.8 | 4 | -0.13 | -0.0 |
| Asn | Arg | AAT | CGG | 2.8 | 2 | -0.24 | -0.1 |
| Asn | Arg | AAT | CGT | 17.0 | 11 | -2.09 | -0.8 |
| Asn | Leu | AAT | CTA | 27.6 | 14 | -6.73 | -5.9 |
| Asn | Leu | AAT | CTC | 10.2 | 10 | -0.00 | -0.0 |
| Asn | Leu | AAT | CTG | 22.1 | 17 | -1.16 | -0.8 |
| Asn | Leu | AAT | CTT | 24.2 | 25 | 0.02 | 0.1 |
| Asn | Glu | AAT | GAA | 102.1 | 139 | 13.34 | 5.7 |
| Asn | Asp | AAT | GAC | 44.0 | 57 | 3.85 | 2.0 |
| Asn | Glu | AAT | GAG | 40.7 | 38 | -0.18 | -1.2 |
| Asn | Asp | AAT | GAT | 86.8 | 88 | 0.02 | 0.3 |
| Asn | Ala | AAT | GCA | 37.0 | 42 | 0.66 | 0.8 |
| Asn | Ala | AAT | GCC | 29.5 | 37 | 1.90 | 2.1 |
| Asn | Ala | AAT | GCG | 12.4 | 19 | 3.46 | 3.6 |
| Asn | Ala | AAT | GCT | 49.0 | 61 | 2.92 | 3.2 |
| Asn | Gly | AAT | GGA | 20.0 | 28 | 3.24 | 0.3 |
| Asn | Gly | AAT | GGC | 20.2 | 27 | 2.32 | 0.1 |
| Asn | Gly | AAT | GGG | 13.2 | 20 | 3.45 | 0.6 |
| Asn | Gly | AAT | GGT | 65.5 | 101 | 19.29 | 3.7 |
| Asn | Val | AAT | GTA | 24.5 | 27 | 0.26 | 0.1 |
| Asn | Val | AAT | GTC | 27.7 | 45 | 10.83 | 4.6 |
| Asn | Val | AAT | GTG | 22.5 | 27 | 0.89 | 0.0 |
| Asn | Val | AAT | GTT | 52.8 | 68 | 4.35 | 0.5 |
| Asn | Ocr | AAT | TAA | 0.0 | 0 | 0.00 | 0.0 |
| Asn | Tyr | AAT | TAC | 35.0 | 25 | -2.86 | -1.8 |
| Asn | Amb | AAT | TAG | 0.0 | 2 | 0.00 | 0.0 |
| Asn | Tyr | AAT | TAT | 40.7 | 40 | -0.01 | -0.1 |
| Asn | Ser | AAT | TCA | 40.1 | 35 | -0.64 | -0.2 |
| Asn | Ser | AAT | TCC | 28.9 | 23 | -1.19 | -0.7 |
| Asn | Ser | AAT | TCG | 15.9 | 10 | -2.18 | -1.7 |
| Asn | Ser | AAT | TCT | 56.1 | 52 | -0.30 | -0.0 |
| Asn | Umb | AAT | TGA | 0.0 | 1 | 0.00 | 0.0 |
| Asn | Cys | AAT | TGC | 9.0 | 8 | -0.10 | -0.3 |
| Asn | Trp | AAT | TGG | 22.1 | 6 | -11.74 | -10.4 |
| Asn | Cys | AAT | TGT | 17.4 | 18 | 0.02 | 0.0 |
| Asn | Leu | AAT | TTA | 55.9 | 52 | -0.28 | -0.0 |
| Asn | Phe | AAT | TTC | 38.7 | 39 | 0.00 | 0.2 |
| Asn | Leu | AAT | TTG | 63.5 | 54 | -1.41 | -0.8 |
| Asn | Phe | AAT | TTT | 55.8 | 57 | 0.03 | 0.4 |
| | Page Totals: | | | 2186.6 | 2190 | 152.484 | 72.5 |

PAGE 4

YEAST.RXD/CPLIST.RXR February 7, 1989

| aa1 | aa2 | cod1 | cod2 | exp | obs | chis1 | chis2 |
|---|---|---|---|---|---|---|---|
| Thr | Lys | ACA | AAA | 45.3 | 44 | -0.03 | -0.4 |
| Thr | Asn | ACA | AAC | 27.1 | 27 | -0.00 | -0.1 |
| Thr | Lys | ACA | AAG | 34.5 | 43 | 2.09 | 0.9 |
| Thr | Asn | ACA | AAT | 36.7 | 45 | 1.87 | 3.1 |
| Thr | Thr | ACA | ACA | 21.7 | 24 | 0.25 | 0.0 |
| Thr | Thr | ACA | ACC | 13.9 | 9 | -1.74 | -2.3 |
| Thr | Thr | ACA | ACG | 8.4 | 7 | -0.24 | -0.4 |
| Thr | Thr | ACA | ACT | 22.6 | 27 | 0.85 | 0.4 |
| Thr | Arg | ACA | AGA | 25.3 | 47 | 18.67 | 25.1 |
| Thr | Ser | ACA | AGC | 8.8 | 5 | -1.62 | -2.4 |
| Thr | Arg | ACA | AGG | 9.8 | 11 | 0.16 | 0.5 |
| Thr | Ser | ACA | AGT | 13.9 | 17 | 0.72 | 0.1 |
| Thr | Ile | ACA | ATA | 16.8 | 14 | -0.46 | -0.4 |
| Thr | Ile | ACA | ATC | 17.8 | 15 | -0.44 | -0.4 |
| Thr | Met | ACA | ATG | 25.1 | 24 | -0.04 | -0.4 |
| Thr | Ile | ACA | ATT | 34.7 | 30 | -0.65 | -0.6 |
| Thr | Gln | ACA | CAA | 30.4 | 21 | -2.90 | -2.2 |
| Thr | His | ACA | CAC | 8.0 | 5 | -1.12 | -0.4 |
| Thr | Gln | ACA | CAG | 11.9 | 11 | -0.06 | -0.0 |
| Thr | His | ACA | CAT | 14.6 | 15 | 0.01 | 0.7 |
| Thr | Pro | ACA | CCA | 22.1 | 24 | 0.16 | 0.0 |
| Thr | Pro | ACA | CCC | 7.6 | 7 | -0.04 | -0.1 |
| Thr | Pro | ACA | CCG | 5.5 | 5 | -0.04 | -0.1 |
| Thr | Pro | ACA | CCT | 14.9 | 25 | 6.80 | 5.7 |
| Thr | Arg | ACA | CGA | 3.3 | 5 | 0.82 | 1.3 |
| Thr | Arg | ACA | CGC | 2.3 | 0 | -2.33 | -2.1 |
| Thr | Arg | ACA | CGG | 1.5 | 1 | -0.14 | -0.1 |
| Thr | Arg | ACA | CGT | 9.2 | 7 | -0.54 | -0.2 |
| Thr | Leu | ACA | CTA | 14.1 | 6 | -4.61 | -4.2 |
| Thr | Leu | ACA | CTC | 5.1 | 0 | -5.11 | -4.9 |
| Thr | Leu | ACA | CTG | 11.1 | 6 | -2.36 | -2.1 |
| Thr | Leu | ACA | CTT | 12.3 | 4 | -5.63 | -5.3 |
| Thr | Glu | ACA | GAA | 50.4 | 47 | -0.23 | -0.2 |
| Thr | Asp | ACA | GAC | 22.1 | 18 | -0.76 | -0.8 |
| Thr | Glu | ACA | GAG | 20.5 | 19 | -0.11 | -0.1 |
| Thr | Asp | ACA | GAT | 42.9 | 52 | 1.92 | 1.8 |
| Thr | Ala | ACA | GCA | 19.6 | 12 | -2.93 | -4.2 |
| Thr | Ala | ACA | GCC | 16.1 | 11 | -1.59 | -2.5 |
| Thr | Ala | ACA | GCG | 6.5 | 11 | 3.05 | 2.0 |
| Thr | Ala | ACA | GCT | 26.3 | 22 | -0.69 | -1.6 |
| Thr | Gly | ACA | GGA | 9.9 | 11 | 0.12 | 0.0 |
| Thr | Gly | ACA | GGC | 10.5 | 21 | 10.59 | 8.5 |
| Thr | Gly | ACA | GGG | 6.7 | 4 | -1.06 | -1.4 |
| Thr | Gly | ACA | GGT | 35.9 | 36 | 0.00 | 0.2 |
| Thr | Val | ACA | GTA | 12.1 | 17 | 2.01 | 1.2 |
| Thr | Val | ACA | GTC | 14.6 | 7 | -3.95 | -4.9 |
| Thr | Val | ACA | GTG | 12.0 | 10 | -0.34 | -0.7 |
| Thr | Val | ACA | GTT | 27.7 | 26 | -0.11 | -0.5 |
| Thr | Ocr | ACA | TAA | 0.0 | 1 | 0.00 | 0.0 |
| Thr | Tyr | ACA | TAC | 17.7 | 19 | 0.10 | 2.4 |
| Thr | Amb | ACA | TAG | 0.0 | 0 | 0.00 | 0.0 |
| Thr | Tyr | ACA | TAT | 20.2 | 22 | 0.17 | 3.1 |
| Thr | Ser | ACA | TCA | 19.2 | 24 | 1.19 | 0.3 |
| Thr | Ser | ACA | TCC | 14.4 | 20 | 2.21 | 0.9 |
| Thr | Ser | ACA | TCG | 8.0 | 11 | 1.16 | 0.5 |
| Thr | Ser | ACA | TCT | 27.2 | 28 | 0.02 | 0.2 |
| Thr | Umb | ACA | TGA | 0.0 | 1 | 0.00 | 0.0 |
| Thr | Cys | ACA | TGC | 4.4 | 4 | -0.03 | -0.0 |
| Thr | Trp | ACA | TGG | 11.6 | 14 | 0.50 | 2.0 |
| Thr | Cys | ACA | TGT | 8.7 | 8 | -0.06 | -0.0 |
| Thr | Leu | ACA | TTA | 28.3 | 32 | 0.49 | 0.8 |
| Thr | Phe | ACA | TTC | 19.9 | 13 | -2.38 | -3.0 |
| Thr | Leu | ACA | TTG | 32.0 | 28 | -0.49 | -0.3 |
| Thr | Phe | ACA | TTT | 27.3 | 31 | 0.51 | 0.2 |
| | Page Totals: | | | 1108.6 | 1111 | 101.313 | 111.3 |

PAGE 5

YEAST.RXD/CPLIST.RXR February 7, 1989

| aa1 | aa2 | cod1 | cod2 | exp | obs | chis1 | chis2 |
|---|---|---|---|---|---|---|---|
| Thr | Lys | ACC | AAA | 34.6 | 44 | 2.56 | 1.3 |
| Thr | Asn | ACC | AAC | 29.7 | 35 | 0.95 | 1.7 |
| Thr | Lys | ACC | AAG | 43.8 | 71 | 16.97 | 12.2 |
| Thr | Asn | ACC | AAT | 26.4 | 33 | 1.67 | 2.6 |
| Thr | Thr | ACC | ACA | 13.9 | 20 | 2.66 | 1.8 |
| Thr | Thr | ACC | ACC | 21.1 | 32 | 5.60 | 4.0 |
| Thr | Thr | ACC | ACG | 5.5 | 4 | -0.41 | -0.6 |
| Thr | Thr | ACC | ACT | 24.9 | 36 | 4.91 | 3.4 |
| Thr | Arg | ACC | AGA | 30.3 | 32 | 0.09 | 0.7 |
| Thr | Ser | ACC | AGC | 6.5 | 7 | 0.05 | 0.0 |
| Thr | Arg | ACC | AGG | 6.7 | 4 | -1.07 | -0.7 |
| Thr | Ser | ACC | AGT | 10.0 | 14 | 1.56 | 0.7 |
| Thr | Ile | ACC | ATA | 10.5 | 18 | 5.35 | 5.6 |
| Thr | Ile | ACC | ATC | 22.0 | 26 | 0.72 | 0.8 |
| Thr | Met | ACC | ATG | 23.4 | 23 | -0.01 | -0.6 |
| Thr | Ile | ACC | ATT | 33.6 | 43 | 2.64 | 2.9 |
| Thr | Gln | ACC | CAA | 30.6 | 23 | -1.88 | -1.3 |
| Thr | His | ACC | CAC | 9.1 | 8 | -0.14 | -0.0 |
| Thr | Gln | ACC | CAG | 8.5 | 3 | -3.57 | -3.2 |
| Thr | His | ACC | CAT | 12.3 | 10 | -0.42 | -0.0 |
| Thr | Pro | ACC | CCA | 26.0 | 14 | -5.55 | -6.4 |
| Thr | Pro | ACC | CCC | 6.1 | 6 | -0.00 | -0.0 |
| Thr | Pro | ACC | CCG | 3.2 | 4 | 0.18 | 0.1 |
| Thr | Pro | ACC | CCT | 12.0 | 6 | -3.00 | -3.4 |
| Thr | Arg | ACC | CGA | 1.8 | 2 | 0.03 | 0.1 |
| Thr | Arg | ACC | CGC | 1.7 | 1 | -0.29 | -0.2 |
| Thr | Arg | ACC | CGG | 0.9 | 0 | -0.89 | -0.8 |
| Thr | Arg | ACC | CGT | 8.9 | 2 | -5.35 | -4.6 |
| Thr | Leu | ACC | CTA | 11.6 | 10 | -0.23 | -0.1 |
| Thr | Leu | ACC | CTC | 3.6 | 5 | 0.58 | 0.7 |
| Thr | Leu | ACC | CTG | 8.2 | 1 | -6.31 | -6.0 |
| Thr | Leu | ACC | CTT | 8.9 | 4 | -2.66 | -2.4 |
| Thr | Glu | ACC | GAA | 52.8 | 39 | -3.59 | -1.2 |
| Thr | Asp | ACC | GAC | 26.5 | 16 | -4.18 | -4.3 |
| Thr | Glu | ACC | GAG | 15.7 | 17 | 0.10 | 0.7 |
| Thr | Asp | ACC | GAT | 37.9 | 41 | 0.26 | 0.2 |
| Thr | Ala | ACC | GCA | 15.1 | 24 | 5.26 | 3.3 |
| Thr | Ala | ACC | GCC | 20.7 | 15 | -1.57 | -2.6 |
| Thr | Ala | ACC | GCG | 4.6 | 5 | 0.03 | 0.0 |
| Thr | Ala | ACC | GCT | 36.7 | 40 | 0.30 | 0.0 |
| Thr | Gly | ACC | GGA | 7.2 | 6 | -0.20 | -0.4 |
| Thr | Gly | ACC | GGC | 9.3 | 9 | -0.01 | -0.1 |
| Thr | Gly | ACC | GGG | 5.2 | 5 | -0.01 | -0.1 |
| Thr | Gly | ACC | GGT | 49.9 | 44 | -0.71 | -1.7 |
| Thr | Val | ACC | GTA | 8.9 | 9 | 0.00 | 0.0 |
| Thr | Val | ACC | GTC | 20.9 | 20 | -0.04 | -0.3 |
| Thr | Val | ACC | GTG | 10.1 | 12 | 0.34 | 0.1 |
| Thr | Val | ACC | GTT | 32.9 | 30 | -0.25 | -0.9 |
| Thr | Ocr | ACC | TAA | 0.0 | 1 | 0.00 | 0.0 |
| Thr | Tyr | ACC | TAC | 21.3 | 11 | -4.95 | -1.6 |
| Thr | Amb | ACC | TAG | 0.0 | 0 | 0.00 | 0.0 |
| Thr | Tyr | ACC | TAT | 15.1 | 12 | -0.64 | -0.0 |
| Thr | Ser | ACC | TCA | 13.7 | 17 | 0.79 | 0.2 |
| Thr | Ser | ACC | TCC | 17.1 | 16 | -0.07 | -0.5 |
| Thr | Ser | ACC | TCG | 5.5 | 4 | -0.38 | -0.7 |
| Thr | Ser | ACC | TCT | 28.3 | 25 | -0.39 | -1.5 |
| Thr | Umb | ACC | TGA | 0.0 | 0 | 0.00 | 0.0 |
| Thr | Cys | ACC | TGC | 3.4 | 4 | 0.10 | 0.4 |
| Thr | Trp | ACC | TGG | 10.5 | 6 | -1.96 | -0.8 |
| Thr | Cys | ACC | TGT | 9.2 | 8 | -0.15 | -0.0 |
| Thr | Leu | ACC | TTA | 23.0 | 22 | -0.05 | -0.0 |
| Thr | Phe | ACC | TTC | 23.8 | 26 | 0.21 | 0.0 |
| Thr | Leu | ACC | TTG | 41.4 | 36 | -0.69 | -0.4 |
| Thr | Phe | ACC | TTT | 21.5 | 26 | 0.95 | 0.5 |
| | Page Totals: | | | 1084.3 | 1087 | 106.491 | 91.6 |

PAGE 6

YEAST.RXD/CPLIST.RXR February 7, 1989

| aa1 | aa2 | cod1 | cod2 | exp | obs | chis1 | chis2 |
|---|---|---|---|---|---|---|---|
| Thr | Lys | ACG | AAA | 19.2 | 29 | 4.97 | 3.4 |
| Thr | Asn | ACG | AAC | 11.3 | 6 | -2.48 | -2.0 |
| Thr | Lys | ACG | AAG | 14.2 | 12 | -0.33 | -0.7 |
| Thr | Asn | ACG | AAT | 16.5 | 18 | 0.13 | 0.4 |
| Thr | Thr | ACG | ACA | 8.4 | 9 | 0.04 | 0.0 |
| Thr | Thr | ACG | ACC | 5.5 | 5 | -0.04 | -0.1 |
| Thr | Thr | ACG | ACG | 4.7 | 1 | -2.88 | -3.2 |
| Thr | Thr | ACG | ACT | 9.4 | 7 | -0.62 | -0.9 |
| Thr | Arg | ACG | AGA | 10.2 | 15 | 2.23 | 3.5 |
| Thr | Ser | ACG | AGC | 4.1 | 5 | 0.20 | 0.0 |
| Thr | Arg | ACG | AGG | 4.5 | 4 | -0.06 | -0.0 |
| Thr | Ser | ACG | AGT | 6.1 | 6 | -0.00 | -0.1 |
| Thr | Ile | ACG | ATA | 7.4 | 6 | -0.28 | -0.3 |
| Thr | Ile | ACG | ATC | 7.0 | 9 | 0.55 | 0.3 |
| Thr | Met | ACG | ATG | 10.7 | 12 | 0.17 | 1.1 |
| Thr | Ile | ACG | ATT | 14.2 | 17 | 0.54 | 0.6 |
| Thr | Gln | ACG | CAA | 12.5 | 17 | 1.61 | 2.1 |
| Thr | His | ACG | CAC | 3.3 | 2 | -0.53 | -0.2 |
| Thr | Gln | ACG | CAG | 5.5 | 5 | -0.04 | -0.0 |
| Thr | His | ACG | CAT | 6.4 | 5 | -0.29 | -0.0 |
| Thr | Pro | ACG | CCA | 8.9 | 12 | 1.08 | 0.8 |
| Thr | Pro | ACG | CCC | 3.3 | 2 | -0.48 | -0.6 |
| Thr | Pro | ACG | CCG | 2.4 | 6 | 5.28 | 4.8 |
| Thr | Pro | ACG | CCT | 6.2 | 8 | 0.56 | 0.4 |
| Thr | Arg | ACG | CGA | 1.6 | 2 | 0.10 | 0.2 |
| Thr | Arg | ACG | CGC | 1.1 | 2 | 0.76 | 1.0 |
| Thr | Arg | ACG | CGG | 0.7 | 1 | 0.17 | 0.3 |
| Thr | Arg | ACG | CGT | 3.6 | 1 | -1.91 | -1.6 |
| Thr | Leu | ACG | CTA | 5.9 | 10 | 2.79 | 3.2 |
| Thr | Leu | ACG | CTC | 2.2 | 1 | -0.67 | -0.6 |
| Thr | Leu | ACG | CTG | 4.9 | 6 | 0.24 | 0.3 |
| Thr | Leu | ACG | CTT | 5.3 | 4 | -0.34 | -0.3 |
| Thr | Glu | ACG | GAA | 20.7 | 24 | 0.52 | 1.8 |
| Thr | Asp | ACG | GAC | 9.4 | 8 | -0.21 | -0.2 |
| Thr | Glu | ACG | GAG | 9.1 | 8 | -0.14 | -0.0 |
| Thr | Asp | ACG | GAT | 18.7 | 18 | -0.03 | -0.0 |
| Thr | Ala | ACG | GCA | 8.2 | 10 | 0.39 | 0.1 |
| Thr | Ala | ACG | GCC | 6.2 | 6 | -0.01 | -0.1 |
| Thr | Ala | ACG | GCG | 2.9 | 1 | -1.24 | -1.5 |
| Thr | Ala | ACG | GCT | 10.3 | 10 | -0.01 | -0.1 |
| Thr | Gly | ACG | GGA | 4.6 | 4 | -0.09 | -0.2 |
| Thr | Gly | ACG | GGC | 4.4 | 4 | -0.04 | -0.1 |
| Thr | Gly | ACG | GGG | 3.1 | 3 | -0.00 | -0.0 |
| Thr | Gly | ACG | GGT | 13.7 | 7 | -3.28 | -4.0 |
| Thr | Val | ACG | GTA | 5.3 | 7 | 0.57 | 0.3 |
| Thr | Val | ACG | GTC | 5.8 | 2 | -2.49 | -2.9 |
| Thr | Val | ACG | GTG | 4.9 | 8 | 1.96 | 1.4 |
| Thr | Val | ACG | GTT | 11.3 | 7 | -1.60 | -2.2 |
| Thr | Ocr | ACG | TAA | 0.0 | 0 | 0.00 | 0.0 |
| Thr | Tyr | ACG | TAC | 7.2 | 4 | -1.42 | -0.4 |
| Thr | Amb | ACG | TAG | 0.0 | 0 | 0.00 | 0.0 |
| Thr | Tyr | ACG | TAT | 8.6 | 8 | -0.04 | -0.4 |
| Thr | Ser | ACG | TCA | 8.6 | 15 | 4.81 | 3.0 |
| Thr | Ser | ACG | TCC | 5.9 | 6 | 0.00 | 0.1 |
| Thr | Ser | ACG | TCG | 3.5 | 8 | 5.75 | 4.2 |
| Thr | Ser | ACG | TCT | 11.6 | 12 | 0.02 | 0.1 |
| Thr | Umb | ACG | TGA | 0.0 | 1 | 0.00 | 0.0 |
| Thr | Cys | ACG | TGC | 1.9 | 3 | 0.59 | 1.1 |
| Thr | Trp | ACG | TGG | 4.7 | 2 | -1.51 | -0.9 |
| Thr | Cys | ACG | TGT | 3.8 | 2 | -0.82 | -0.5 |
| Thr | Leu | ACG | TTA | 11.6 | 7 | -1.81 | -1.6 |
| Thr | Phe | ACG | TTC | 8.2 | 6 | -0.61 | -0.8 |
| Thr | Leu | ACG | TTG | 13.4 | 14 | 0.03 | 0.1 |
| Thr | Phe | ACG | TTT | 12.1 | 8 | -1.41 | -1.8 |
| | Page Totals: | | | 467.0 | 468 | 63.7713 | 63.0 |

PAGE 7

YEAST.RXD/CPLIST.RXR February 7, 1989

| aa1 | aa2 | cod1 | cod2 | exp | obs | chis1 | chis2 |
|---|---|---|---|---|---|---|---|
| Thr | Lys | ACT | AAA | 59.4 | 51 | -1.20 | -2.6 |
| Thr | Asn | ACT | AAC | 43.0 | 27 | -5.94 | -4.6 |
| Thr | Lys | ACT | AAG | 62.7 | 43 | -6.19 | -8.8 |
| Thr | Asn | ACT | AAT | 45.4 | 32 | -3.94 | -2.8 |
| Thr | Thr | ACT | ACA | 22.6 | 24 | 0.08 | 0.0 |
| Thr | Thr | ACT | ACC | 24.9 | 18 | -1.93 | -2.8 |
| Thr | Thr | ACT | ACG | 9.4 | 8 | -0.22 | -0.4 |
| Thr | Thr | ACT | ACT | 42.2 | 45 | 0.19 | 0.0 |
| Thr | Arg | ACT | AGA | 44.4 | 30 | -4.66 | -2.7 |
| Thr | Ser | ACT | AGC | 10.8 | 10 | -0.06 | -0.4 |
| Thr | Arg | ACT | AGG | 11.2 | 7 | -1.56 | -1.0 |
| Thr | Ser | ACT | AGT | 16.6 | 14 | -0.42 | -1.2 |
| Thr | Ile | ACT | ATA | 18.1 | 20 | 0.21 | 0.3 |
| Thr | Ile | ACT | ATC | 30.4 | 28 | -0.19 | -0.1 |
| Thr | Met | ACT | ATG | 36.4 | 21 | -6.51 | -3.0 |
| Thr | Ile | ACT | ATT | 52.0 | 36 | -4.93 | -4.7 |
| Thr | Gln | ACT | CAA | 48.0 | 61 | 3.53 | 5.0 |
| Thr | His | ACT | CAC | 13.1 | 13 | -0.00 | -0.4 |
| Thr | Gln | ACT | CAG | 13.8 | 13 | -0.05 | -0.0 |
| Thr | His | ACT | CAT | 19.6 | 14 | -1.61 | -0.3 |
| Thr | Pro | ACT | CCA | 39.3 | 54 | 5.54 | 4.1 |
| Thr | Pro | ACT | CCC | 9.1 | 5 | -1.87 | -2.2 |
| Thr | Pro | ACT | CCG | 5.7 | 5 | -0.09 | -0.2 |
| Thr | Pro | ACT | CCT | 19.4 | 17 | -0.29 | -0.5 |
| Thr | Arg | ACT | CGA | 3.3 | 1 | -1.59 | -1.3 |
| Thr | Arg | ACT | CGC | 2.8 | 0 | -2.83 | -2.6 |
| Thr | Arg | ACT | CGG | 1.5 | 0 | -1.47 | -1.3 |
| Thr | Arg | ACT | CGT | 13.5 | 7 | -3.14 | -2.3 |
| Thr | Leu | ACT | CTA | 18.9 | 17 | -0.19 | -0.1 |
| Thr | Leu | ACT | CTC | 5.6 | 6 | 0.03 | 0.1 |
| Thr | Leu | ACT | CTG | 13.2 | 10 | -0.79 | -0.6 |
| Thr | Leu | ACT | CTT | 14.9 | 10 | -1.62 | -1.3 |
| Thr | Glu | ACT | GAA | 82.9 | 60 | -6.32 | -2.3 |
| Thr | Asp | ACT | GAC | 37.4 | 47 | 2.45 | 2.3 |
| Thr | Glu | ACT | GAG | 26.6 | 31 | 0.75 | 2.5 |
| Thr | Asp | ACT | GAT | 61.0 | 58 | -0.15 | -0.2 |
| Thr | Ala | ACT | GCA | 23.8 | 39 | 9.78 | 6.4 |
| Thr | Ala | ACT | GCC | 28.6 | 35 | 1.43 | 0.4 |
| Thr | Ala | ACT | GCG | 7.5 | 11 | 1.67 | 1.0 |
| Thr | Ala | ACT | GCT | 52.8 | 62 | 1.61 | 0.3 |
| Thr | Gly | ACT | GGA | 11.8 | 8 | -1.22 | -1.7 |
| Thr | Gly | ACT | GGC | 14.1 | 11 | -0.67 | -1.1 |
| Thr | Gly | ACT | GGG | 8.4 | 10 | 0.32 | 0.1 |
| Thr | Gly | ACT | GGT | 68.9 | 100 | 14.06 | 9.2 |
| Thr | Val | ACT | GTA | 14.4 | 23 | 5.19 | 3.6 |
| Thr | Val | ACT | GTC | 28.0 | 32 | 0.57 | 0.1 |
| Thr | Val | ACT | GTG | 15.0 | 19 | 1.08 | 0.5 |
| Thr | Val | ACT | GTT | 48.8 | 66 | 6.05 | 3.3 |
| Thr | Ocr | ACT | TAA | 0.0 | 0 | 0.00 | 0.0 |
| Thr | Tyr | ACT | TAC | 30.1 | 20 | -3.39 | -0.3 |
| Thr | Amb | ACT | TAG | 0.0 | 0 | 0.00 | 0.0 |
| Thr | Tyr | ACT | TAT | 26.0 | 14 | -5.53 | -1.6 |
| Thr | Ser | ACT | TCA | 23.5 | 23 | -0.01 | -0.4 |
| Thr | Ser | ACT | TCC | 25.4 | 36 | 4.48 | 2.0 |
| Thr | Ser | ACT | TCG | 9.3 | 12 | 0.80 | 0.2 |
| Thr | Ser | ACT | TCT | 44.2 | 49 | 0.51 | 0.0 |
| Thr | Umb | ACT | TGA | 0.0 | 2 | 0.00 | 0.0 |
| Thr | Cys | ACT | TGC | 4.9 | 7 | 0.86 | 1.8 |
| Thr | Trp | ACT | TGG | 16.8 | 14 | -0.47 | -0.0 |
| Thr | Cys | ACT | TGT | 12.7 | 6 | -3.51 | -2.2 |
| Thr | Leu | ACT | TTA | 37.8 | 62 | 15.43 | 17.8 |
| Thr | Phe | ACT | TTC | 34.6 | 44 | 2.53 | 1.5 |
| Thr | Leu | ACT | TTG | 59.2 | 78 | 5.99 | 7.6 |
| Thr | Phe | ACT | TTT | 36.6 | 40 | 0.32 | 0.1 |
| | Page Totals: | | | 1662.1 | 1666 | 159.999 | 127.7 |

PAGE 8

YEAST.RXD/CPLIST.RXR February 7, 1989

| aa1 | aa2 | cod1 | cod2 | exp | obs | chis1 | chis2 |
|---|---|---|---|---|---|---|---|
| Arg | Lys | AGA | AAA | 68.5 | 70 | 0.03 | 0.2 |
| Arg | Asn | AGA | AAC | 49.1 | 60 | 2.42 | 3.6 |
| Arg | Lys | AGA | AAG | 79.9 | 93 | 2.16 | 0.6 |
| Arg | Asn | AGA | AAT | 49.7 | 47 | -0.14 | -0.0 |
| Arg | Thr | AGA | ACA | 25.3 | 20 | -1.10 | -1.3 |
| Arg | Thr | AGA | ACC | 30.3 | 41 | 3.76 | 3.2 |
| Arg | Thr | AGA | ACG | 10.2 | 13 | 0.75 | 0.6 |
| Arg | Thr | AGA | ACT | 44.4 | 48 | 0.29 | 0.1 |
| Arg | Arg | AGA | AGA | 64.1 | 83 | 5.55 | 0.2 |
| Arg | Ser | AGA | AGC | 11.0 | 11 | -0.00 | -0.5 |
| Arg | Arg | AGA | AGG | 12.7 | 21 | 5.39 | 1.8 |
| Arg | Ser | AGA | AGT | 17.4 | 14 | -0.66 | -0.0 |
| Arg | Ile | AGA | ATA | 20.4 | 21 | 0.02 | 0.1 |
| Arg | Ile | AGA | ATC | 37.7 | 47 | 2.31 | 0.6 |
| Arg | Met | AGA | ATG | 42.8 | 43 | 0.00 | 1.1 |
| Arg | Ile | AGA | ATT | 60.3 | 67 | 0.75 | 0.0 |
| Arg | Gln | AGA | CAA | 56.6 | 45 | -2.38 | -0.3 |
| Arg | His | AGA | CAC | 16.4 | 21 | 1.28 | 0.0 |
| Arg | Gln | AGA | CAG | 15.5 | 11 | -1.32 | -0.4 |
| Arg | His | AGA | CAT | 22.8 | 31 | 2.97 | 0.1 |
| Arg | Pro | AGA | CCA | 46.1 | 49 | 0.18 | 0.2 |
| Arg | Pro | AGA | CCC | 10.3 | 4 | -3.81 | -3.8 |
| Arg | Pro | AGA | CCG | 6.2 | 4 | -0.78 | -0.8 |
| Arg | Pro | AGA | CCT | 21.6 | 25 | 0.52 | 0.5 |
| Arg | Arg | AGA | CGA | 3.5 | 3 | -0.06 | -0.4 |
| Arg | Arg | AGA | CGC | 3.0 | 5 | 1.40 | 0.5 |
| Arg | Arg | AGA | CGG | 1.7 | 2 | 0.06 | 0.0 |
| Arg | Arg | AGA | CGT | 16.7 | 16 | -0.03 | -1.0 |
| Arg | Leu | AGA | CTA | 21.0 | 20 | -0.04 | -0.0 |
| Arg | Leu | AGA | CTC | 6.7 | 7 | 0.02 | 0.0 |
| Arg | Leu | AGA | CTG | 14.3 | 19 | 1.56 | 1.6 |
| Arg | Leu | AGA | CTT | 16.4 | 13 | -0.70 | -0.7 |
| Arg | Glu | AGA | GAA | 97.6 | 99 | 0.02 | 0.0 |
| Arg | Asp | AGA | GAC | 43.2 | 34 | -1.95 | -0.8 |
| Arg | Glu | AGA | GAG | 30.2 | 28 | -0.16 | -0.2 |
| Arg | Asp | AGA | GAT | 69.3 | 66 | -0.15 | -0.1 |
| Arg | Ala | AGA | GCA | 27.2 | 23 | -0.64 | -0.4 |
| Arg | Ala | AGA | GCC | 34.7 | 24 | -3.28 | -2.6 |
| Arg | Ala | AGA | GCG | 8.4 | 11 | 0.81 | 1.1 |
| Arg | Ala | AGA | GCT | 65.0 | 53 | -2.21 | -1.4 |
| Arg | Gly | AGA | GGA | 13.4 | 14 | 0.02 | 0.4 |
| Arg | Gly | AGA | GGC | 14.7 | 12 | -0.48 | -0.1 |
| Arg | Gly | AGA | GGG | 9.2 | 8 | -0.15 | -0.0 |
| Arg | Gly | AGA | GGT | 86.5 | 73 | -2.11 | -0.1 |
| Arg | Val | AGA | GTA | 16.5 | 18 | 0.14 | 0.3 |
| Arg | Val | AGA | GTC | 34.5 | 33 | -0.07 | -0.0 |
| Arg | Val | AGA | GTG | 16.5 | 16 | -0.01 | -0.0 |
| Arg | Val | AGA | GTT | 58.0 | 53 | -0.43 | -0.2 |
| Arg | Ocr | AGA | TAA | 0.0 | 0 | 0.00 | 0.0 |
| Arg | Tyr | AGA | TAC | 35.0 | 37 | 0.11 | 0.3 |
| Arg | Amb | AGA | TAG | 0.0 | 0 | 0.00 | 0.0 |
| Arg | Tyr | AGA | TAT | 28.8 | 30 | 0.05 | 0.3 |
| Arg | Ser | AGA | TCA | 25.0 | 22 | -0.35 | -0.2 |
| Arg | Ser | AGA | TCC | 28.7 | 17 | -4.75 | -1.7 |
| Arg | Ser | AGA | TCG | 9.4 | 10 | 0.04 | 0.8 |
| Arg | Ser | AGA | TCT | 51.7 | 42 | -1.81 | -0.0 |
| Arg | Umb | AGA | TGA | 0.0 | 2 | 0.00 | 0.0 |
| Arg | Cys | AGA | TGC | 5.9 | 8 | 0.78 | 0.2 |
| Arg | Trp | AGA | TGG | 18.6 | 25 | 2.17 | 0.0 |
| Arg | Cys | AGA | TGT | 14.7 | 8 | -3.05 | -4.8 |
| Arg | Leu | AGA | TTA | 44.0 | 56 | 3.30 | 3.5 |
| Arg | Phe | AGA | TTC | 39.3 | 40 | 0.01 | 0.0 |
| Arg | Leu | AGA | TTG | 71.9 | 60 | -1.96 | -1.8 |
| Arg | Phe | AGA | TTT | 39.8 | 49 | 2.15 | 1.3 |
| | Page Totals: | | | 1939.7 | 1945 | 75.6104 | 46.8 |

PAGE 9

YEAST.RXD/CPLIST.RXR February 7, 1989

| aa1 | aa2 | cod1 | cod2 | exp | obs | chis1 | chis2 |
|---|---|---|---|---|---|---|---|
| Ser | Lys | AGC | AAA | 21.0 | 23 | 0.20 | 0.0 |
| Ser | Asn | AGC | AAC | 13.3 | 10 | -0.80 | -0.6 |
| Ser | Lys | AGC | AAG | 16.6 | 22 | 1.74 | 0.5 |
| Ser | Asn | AGC | AAT | 18.7 | 20 | 0.09 | 0.3 |
| Ser | Thr | AGC | ACA | 8.8 | 16 | 5.97 | 3.9 |
| Ser | Thr | AGC | ACC | 6.5 | 2 | -3.07 | -3.8 |
| Ser | Thr | AGC | ACG | 4.1 | 3 | -0.30 | -0.6 |
| Ser | Thr | AGC | ACT | 10.8 | 14 | 0.94 | 0.3 |
| Ser | Arg | AGC | AGA | 11.0 | 15 | 1.43 | 1.6 |
| Ser | Ser | AGC | AGC | 6.1 | 7 | 0.13 | 0.0 |
| Ser | Arg | AGC | AGG | 4.8 | 4 | -0.12 | -0.1 |
| Ser | Ser | AGC | AGT | 7.0 | 11 | 2.27 | 1.1 |
| Ser | Ile | AGC | ATA | 7.8 | 9 | 0.18 | 0.3 |
| Ser | Ile | AGC | ATC | 7.8 | 10 | 0.65 | 0.9 |
| Ser | Met | AGC | ATG | 11.3 | 8 | -0.96 | -0.2 |
| Ser | Ile | AGC | ATT | 15.4 | 24 | 4.75 | 5.9 |
| Ser | Gln | AGC | CAA | 14.3 | 13 | -0.12 | -0.0 |
| Ser | His | AGC | CAC | 4.1 | 4 | -0.00 | -0.0 |
| Ser | Gln | AGC | CAG | 5.6 | 2 | -2.27 | -1.9 |
| Ser | His | AGC | CAT | 6.6 | 5 | -0.40 | -0.6 |
| Ser | Pro | AGC | CCA | 9.8 | 12 | 0.48 | 0.1 |
| Ser | Pro | AGC | CCC | 3.6 | 2 | -0.68 | -1.0 |
| Ser | Pro | AGC | CCG | 2.8 | 0 | -2.84 | -3.2 |
| Ser | Pro | AGC | CCT | 6.6 | 9 | 0.92 | 0.3 |
| Ser | Arg | AGC | CGA | 1.7 | 0 | -1.67 | -1.6 |
| Ser | Arg | AGC | CGC | 1.4 | 0 | -1.35 | -1.3 |
| Ser | Arg | AGC | CGG | 0.9 | 0 | -0.85 | -0.8 |
| Ser | Arg | AGC | CGT | 3.8 | 0 | -3.76 | -3.7 |
| Ser | Leu | AGC | CTA | 6.5 | 3 | -1.87 | -2.1 |
| Ser | Leu | AGC | CTC | 2.4 | 1 | -0.80 | -0.9 |
| Ser | Leu | AGC | CTG | 5.3 | 6 | 0.10 | 0.0 |
| Ser | Leu | AGC | CTT | 5.7 | 6 | 0.02 | 0.0 |
| Ser | Glu | AGC | GAA | 23.3 | 23 | -0.00 | -0.9 |
| Ser | Asp | AGC | GAC | 10.7 | 6 | -2.04 | -0.8 |
| Ser | Glu | AGC | GAG | 9.9 | 15 | 2.61 | 6.1 |
| Ser | Asp | AGC | GAT | 19.8 | 20 | 0.00 | 0.9 |
| Ser | Ala | AGC | GCA | 8.6 | 6 | -0.78 | -0.6 |
| Ser | Ala | AGC | GCC | 6.7 | 9 | 0.79 | 1.1 |
| Ser | Ala | AGC | GCG | 3.2 | 3 | -0.01 | -0.0 |
| Ser | Ala | AGC | GCT | 11.6 | 8 | -1.10 | -0.8 |
| Ser | Gly | AGC | GGA | 4.8 | 5 | 0.01 | 0.0 |
| Ser | Gly | AGC | GGC | 5.0 | 7 | 0.78 | 0.9 |
| Ser | Gly | AGC | GGG | 3.3 | 2 | -0.52 | -0.5 |
| Ser | Gly | AGC | GGT | 15.3 | 26 | 7.56 | 8.3 |
| Ser | Val | AGC | GTA | 5.7 | 3 | -1.29 | -1.2 |
| Ser | Val | AGC | GTC | 6.5 | 5 | -0.33 | -0.3 |
| Ser | Val | AGC | GTG | 5.3 | 2 | -2.07 | -1.9 |
| Ser | Val | AGC | GTT | 12.0 | 10 | -0.32 | -0.2 |
| Ser | Ocr | AGC | TAA | 0.0 | 0 | 0.00 | 0.0 |
| Ser | Tyr | AGC | TAC | 8.3 | 6 | -0.66 | -1.0 |
| Ser | Amb | AGC | TAG | 0.0 | 0 | 0.00 | 0.0 |
| Ser | Tyr | AGC | TAT | 9.2 | 13 | 1.61 | 0.9 |
| Ser | Ser | AGC | TCA | 9.3 | 15 | 3.49 | 1.7 |
| Ser | Ser | AGC | TCC | 6.7 | 4 | -1.09 | -1.8 |
| Ser | Ser | AGC | TCG | 3.9 | 3 | -0.23 | -0.5 |
| Ser | Ser | AGC | TCT | 12.5 | 11 | -0.18 | -0.8 |
| Ser | Umb | AGC | TGA | 0.0 | 0 | 0.00 | 0.0 |
| Ser | Cys | AGC | TGC | 2.5 | 4 | 0.85 | 2.0 |
| Ser | Trp | AGC | TGG | 5.1 | 3 | -0.88 | -0.4 |
| Ser | Cys | AGC | TGT | 4.0 | 2 | -0.99 | -0.4 |
| Ser | Leu | AGC | TTA | 12.6 | 15 | 0.45 | 0.2 |
| Ser | Phe | AGC | TTC | 8.7 | 4 | -2.55 | -2.9 |
| Ser | Leu | AGC | TTG | 15.0 | 12 | -0.60 | -0.9 |
| Ser | Phe | AGC | TTT | 12.7 | 12 | -0.04 | -0.1 |
| | Page Totals: | | | 513.9 | 515 | 75.5656 | 76.0 |

PAGE 10

YEAST.RXD/CPLIST.RXR February 7, 1989

| aa1 | aa2 | cod1 | cod2 | exp | obs | chis1 | chis2 |
|---|---|---|---|---|---|---|---|
| Arg | Lys | AGG | AAA | 23.8 | 28 | 0.73 | 0.2 |
| Arg | Asn | AGG | AAC | 13.5 | 9 | -1.49 | -1.2 |
| Arg | Lys | AGG | AAG | 17.7 | 20 | 0.31 | 0.1 |
| Arg | Asn | AGG | AAT | 19.8 | 19 | -0.03 | -0.0 |
| Arg | Thr | AGG | ACA | 9.8 | 16 | 4.00 | 3.6 |
| Arg | Thr | AGG | ACC | 6.7 | 11 | 2.80 | 2.5 |
| Arg | Thr | AGG | ACG | 4.5 | 8 | 2.63 | 2.4 |
| Arg | Thr | AGG | ACT | 11.2 | 10 | -0.13 | -0.2 |
| Arg | Arg | AGG | AGA | 12.7 | 6 | -3.55 | -5.9 |
| Arg | Ser | AGG | AGC | 4.8 | 4 | -0.12 | -0.0 |
| Arg | Arg | AGG | AGG | 6.6 | 8 | 0.29 | 0.0 |
| Arg | Ser | AGG | AGT | 7.3 | 4 | -1.51 | -0.6 |
| Arg | Ile | AGG | ATA | 9.5 | 17 | 5.87 | 3.8 |
| Arg | Ile | AGG | ATC | 8.2 | 8 | -0.01 | -0.2 |
| Arg | Met | AGG | ATG | 12.9 | 8 | -1.88 | -0.8 |
| Arg | Ile | AGG | ATT | 17.2 | 12 | -1.55 | -2.7 |
| Arg | Gln | AGG | CAA | 14.9 | 8 | -3.19 | -1.8 |
| Arg | His | AGG | CAC | 4.0 | 5 | 0.28 | 0.0 |
| Arg | Gln | AGG | CAG | 6.5 | 5 | -0.33 | -0.1 |
| Arg | His | AGG | CAT | 7.3 | 7 | -0.01 | -0.6 |
| Arg | Pro | AGG | CCA | 10.2 | 16 | 3.28 | 3.3 |
| Arg | Pro | AGG | CCC | 3.9 | 3 | -0.21 | -0.2 |
| Arg | Pro | AGG | CCG | 2.9 | 5 | 1.56 | 1.6 |
| Arg | Pro | AGG | CCT | 7.1 | 9 | 0.52 | 0.5 |
| Arg | Arg | AGG | CGA | 1.8 | 2 | 0.02 | 0.0 |
| Arg | Arg | AGG | CGC | 1.2 | 2 | 0.46 | 0.1 |
| Arg | Arg | AGG | CGG | 0.9 | 3 | 5.05 | 3.4 |
| Arg | Arg | AGG | CGT | 4.4 | 9 | 4.71 | 2.3 |
| Arg | Leu | AGG | CTA | 7.1 | 8 | 0.11 | 0.1 |
| Arg | Leu | AGG | CTC | 2.7 | 4 | 0.60 | 0.6 |
| Arg | Leu | AGG | CTG | 6.0 | 12 | 6.03 | 6.2 |
| Arg | Leu | AGG | CTT | 6.1 | 1 | -4.30 | -4.2 |
| Arg | Glu | AGG | GAA | 25.8 | 25 | -0.02 | -0.0 |
| Arg | Asp | AGG | GAC | 11.3 | 14 | 0.63 | 1.2 |
| Arg | Glu | AGG | GAG | 11.0 | 16 | 2.28 | 2.2 |
| Arg | Asp | AGG | GAT | 22.4 | 19 | -0.51 | -0.1 |
| Arg | Ala | AGG | GCA | 9.7 | 14 | 1.95 | 2.4 |
| Arg | Ala | AGG | GCC | 7.2 | 10 | 1.11 | 1.4 |
| Arg | Ala | AGG | GCG | 3.3 | 4 | 0.15 | 0.2 |
| Arg | Ala | AGG | GCT | 12.0 | 18 | 2.96 | 3.6 |
| Arg | Gly | AGG | GGA | 5.4 | 4 | -0.37 | -0.1 |
| Arg | Gly | AGG | GGC | 5.3 | 3 | -0.97 | -0.6 |
| Arg | Gly | AGG | GGG | 3.7 | 1 | -1.93 | -1.5 |
| Arg | Gly | AGG | GGT | 15.6 | 13 | -0.42 | -0.0 |
| Arg | Val | AGG | GTA | 6.3 | 4 | -0.85 | -0.7 |
| Arg | Val | AGG | GTC | 6.8 | 5 | -0.47 | -0.4 |
| Arg | Val | AGG | GTG | 6.2 | 2 | -2.81 | -2.6 |
| Arg | Val | AGG | GTT | 12.8 | 11 | -0.26 | -0.2 |
| Arg | Ocr | AGG | TAA | 0.0 | 0 | 0.00 | 0.0 |
| Arg | Tyr | AGG | TAC | 8.5 | 4 | -2.41 | -3.4 |
| Arg | Amb | AGG | TAG | 0.0 | 0 | 0.00 | 0.0 |
| Arg | Tyr | AGG | TAT | 10.6 | 8 | -0.66 | -1.5 |
| Arg | Ser | AGG | TCA | 9.9 | 11 | 0.11 | 1.1 |
| Arg | Ser | AGG | TCC | 7.1 | 2 | -3.63 | -2.4 |
| Arg | Ser | AGG | TCG | 4.0 | 0 | -4.04 | -3.3 |
| Arg | Ser | AGG | TCT | 13.1 | 11 | -0.34 | -0.0 |
| Arg | Umb | AGG | TGA | 0.0 | 0 | 0.00 | 0.0 |
| Arg | Cys | AGG | TGC | 2.3 | 1 | -0.74 | -1.1 |
| Arg | Trp | AGG | TGG | 5.5 | 4 | -0.41 | -1.4 |
| Arg | Cys | AGG | TGT | 4.3 | 9 | 5.02 | 3.1 |
| Arg | Leu | AGG | TTA | 14.5 | 16 | 0.16 | 0.2 |
| Arg | Phe | AGG | TTC | 9.7 | 11 | 0.19 | 0.1 |
| Arg | Leu | AGG | TTG | 15.8 | 11 | -1.45 | -1.4 |
| Arg | Phe | AGG | TTT | 14.6 | 21 | 2.85 | 2.2 |
| | Page Totals: | | | 557.8 | 559 | 97.3028 | 87.6 |

PAGE 11

YEAST.RXD/CPLIST.RXR February 7, 1989

| aa1 | aa2 | cod1 | cod2 | exp | obs | chis1 | chis2 |
|---|---|---|---|---|---|---|---|
| Ser | Lys | AGT | AAA | 32.4 | 31 | -0.06 | -1.0 |
| Ser | Asn | AGT | AAC | 20.1 | 18 | -0.22 | -0.1 |
| Ser | Lys | AGT | AAG | 24.3 | 26 | 0.13 | 0.1 |
| Ser | Asn | AGT | AAT | 28.3 | 28 | -0.00 | -0.0 |
| Ser | Thr | AGT | ACA | 13.9 | 13 | -0.05 | -0.4 |
| Ser | Thr | AGT | ACC | 10.0 | 13 | 0.87 | 0.3 |
| Ser | Thr | AGT | ACG | 6.1 | 11 | 4.01 | 2.6 |
| Ser | Thr | AGT | ACT | 16.6 | 18 | 0.11 | 0.0 |
| Ser | Arg | AGT | AGA | 17.4 | 8 | -5.08 | -4.8 |
| Ser | Ser | AGT | AGC | 7.0 | 13 | 5.11 | 3.0 |
| Ser | Arg | AGT | AGG | 7.3 | 7 | -0.01 | -0.0 |
| Ser | Ser | AGT | AGT | 12.7 | 14 | 0.14 | 0.0 |
| Ser | Ile | AGT | ATA | 12.3 | 11 | -0.13 | -0.0 |
| Ser | Ile | AGT | ATC | 11.9 | 10 | -0.30 | -0.2 |
| Ser | Met | AGT | ATG | 17.9 | 9 | -4.43 | -2.2 |
| Ser | Ile | AGT | ATT | 23.9 | 18 | -1.45 | -1.0 |
| Ser | Gln | AGT | CAA | 21.3 | 17 | -0.87 | -0.4 |
| Ser | His | AGT | CAC | 5.8 | 5 | -0.11 | -0.2 |
| Ser | Gln | AGT | CAG | 8.8 | 1 | -6.93 | -6.2 |
| Ser | His | AGT | CAT | 10.0 | 9 | -0.10 | -0.3 |
| Ser | Pro | AGT | CCA | 14.9 | 4 | -8.01 | -9.8 |
| Ser | Pro | AGT | CCC | 5.1 | 3 | -0.88 | -1.3 |
| Ser | Pro | AGT | CCG | 4.2 | 2 | -1.16 | -1.6 |
| Ser | Pro | AGT | CCT | 10.0 | 7 | -0.88 | -1.6 |
| Ser | Arg | AGT | CGA | 2.5 | 2 | -0.11 | -0.1 |
| Ser | Arg | AGT | CGC | 1.9 | 2 | 0.01 | 0.0 |
| Ser | Arg | AGT | CGG | 1.2 | 0 | -1.24 | -1.2 |
| Ser | Arg | AGT | CGT | 6.3 | 3 | -1.69 | -1.6 |
| Ser | Leu | AGT | CTA | 10.3 | 2 | -6.65 | -7.2 |
| Ser | Leu | AGT | CTC | 3.6 | 7 | 3.31 | 2.8 |
| Ser | Leu | AGT | CTG | 8.3 | 4 | -2.22 | -2.5 |
| Ser | Leu | AGT | CTT | 8.7 | 12 | 1.28 | 0.9 |
| Ser | Glu | AGT | GAA | 35.9 | 42 | 1.06 | 5.8 |
| Ser | Asp | AGT | GAC | 16.4 | 14 | -0.35 | -0.0 |
| Ser | Glu | AGT | GAG | 14.9 | 11 | -1.04 | -0.1 |
| Ser | Asp | AGT | GAT | 31.2 | 44 | 5.29 | 13.5 |
| Ser | Ala | AGT | GCA | 13.6 | 10 | -0.96 | -0.7 |
| Ser | Ala | AGT | GCC | 10.8 | 11 | 0.00 | 0.0 |
| Ser | Ala | AGT | GCG | 4.6 | 6 | 0.40 | 0.6 |
| Ser | Ala | AGT | GCT | 17.6 | 23 | 1.68 | 2.3 |
| Ser | Gly | AGT | GGA | 7.4 | 7 | -0.02 | -0.0 |
| Ser | Gly | AGT | GGC | 7.5 | 7 | -0.03 | -0.0 |
| Ser | Gly | AGT | GGG | 4.8 | 11 | 7.95 | 8.5 |
| Ser | Gly | AGT | GGT | 22.9 | 34 | 5.43 | 6.2 |
| Ser | Val | AGT | GTA | 8.9 | 12 | 1.11 | 1.3 |
| Ser | Val | AGT | GTC | 10.1 | 16 | 3.42 | 3.9 |
| Ser | Val | AGT | GTG | 8.1 | 15 | 5.78 | 6.4 |
| Ser | Val | AGT | GTT | 18.9 | 19 | 0.00 | 0.0 |
| Ser | Ocr | AGT | TAA | 0.0 | 3 | 0.00 | 0.0 |
| Ser | Tyr | AGT | TAC | 13.0 | 9 | -1.22 | -1.9 |
| Ser | Amb | AGT | TAG | 0.0 | 0 | 0.00 | 0.0 |
| Ser | Tyr | AGT | TAT | 14.5 | 14 | -0.02 | -0.2 |
| Ser | Ser | AGT | TCA | 14.7 | 20 | 1.93 | 0.6 |
| Ser | Ser | AGT | TCC | 10.3 | 9 | -0.15 | -0.7 |
| Ser | Ser | AGT | TCG | 6.1 | 6 | -0.00 | -0.1 |
| Ser | Ser | AGT | TCT | 19.3 | 22 | 0.37 | 0.0 |
| Ser | Umb | AGT | TGA | 0.0 | 1 | 0.00 | 0.0 |
| Ser | Cys | AGT | TGC | 3.3 | 2 | -0.48 | -0.1 |
| Ser | Trp | AGT | TGG | 8.4 | 8 | -0.02 | -0.2 |
| Ser | Cys | AGT | TGT | 6.3 | 0 | -6.26 | -5.0 |
| Ser | Leu | AGT | TTA | 20.0 | 26 | 1.80 | 1.2 |
| Ser | Phe | AGT | TTC | 14.2 | 25 | 8.19 | 6.8 |
| Ser | Leu | AGT | TTG | 22.7 | 21 | -0.12 | -0.3 |
| Ser | Phe | AGT | TTT | 20.5 | 17 | -0.59 | -0.9 |
| | Page Totals: | | | 791.3 | 793 | 113.198 | 120.9 |

PAGE 12

YEAST.RXD/CPLIST.RXR February 7, 1989

| aa1 | aa2 | cod1 | cod2 | exp | obs | chis1 | chis2 |
|---|---|---|---|---|---|---|---|
| Ile | Lys | ATA | AAA | 42.0 | 41 | -0.02 | -0.2 |
| Ile | Asn | ATA | AAC | 22.5 | 27 | 0.88 | 0.0 |
| Ile | Lys | ATA | AAG | 28.1 | 30 | 0.12 | 0.8 |
| Ile | Asn | ATA | AAT | 34.4 | 51 | 8.01 | 2.7 |
| Ile | Thr | ATA | ACA | 16.8 | 16 | -0.04 | -0.0 |
| Ile | Thr | ATA | ACC | 10.5 | 7 | -1.17 | -1.2 |
| Ile | Thr | ATA | ACG | 7.4 | 7 | -0.03 | -0.0 |
| Ile | Thr | ATA | ACT | 18.1 | 12 | -2.03 | -2.0 |
| Ile | Arg | ATA | AGA | 20.4 | 26 | 1.57 | 1.5 |
| Ile | Ser | ATA | AGC | 7.8 | 7 | -0.08 | -0.2 |
| Ile | Arg | ATA | AGG | 9.5 | 9 | -0.03 | -0.0 |
| Ile | Ser | ATA | AGT | 12.3 | 13 | 0.05 | 0.0 |
| Ile | Ile | ATA | ATA | 19.3 | 15 | -0.97 | -0.6 |
| Ile | Ile | ATA | ATC | 13.5 | 17 | 0.91 | 1.4 |
| Ile | Met | ATA | ATG | 21.2 | 31 | 4.52 | 4.3 |
| Ile | Ile | ATA | ATT | 28.7 | 19 | -3.28 | -2.4 |
| Ile | Gln | ATA | CAA | 24.5 | 22 | -0.26 | -1.0 |
| Ile | His | ATA | CAC | 6.6 | 8 | 0.28 | 0.4 |
| Ile | Gln | ATA | CAG | 10.4 | 11 | 0.03 | 0.0 |
| Ile | His | ATA | CAT | 12.0 | 8 | -1.33 | -1.1 |
| Ile | Pro | ATA | CCA | 15.8 | 15 | -0.04 | -0.4 |
| Ile | Pro | ATA | CCC | 6.3 | 4 | -0.84 | -1.3 |
| Ile | Pro | ATA | CCG | 4.6 | 5 | 0.04 | 0.0 |
| Ile | Pro | ATA | CCT | 11.6 | 17 | 2.47 | 1.3 |
| Ile | Arg | ATA | CGA | 3.2 | 6 | 2.34 | 2.3 |
| Ile | Arg | ATA | CGC | 2.1 | 3 | 0.36 | 0.3 |
| Ile | Arg | ATA | CGG | 1.5 | 5 | 8.00 | 7.9 |
| Ile | Arg | ATA | CGT | 6.6 | 2 | -3.23 | -3.3 |
| Ile | Leu | ATA | CTA | 11.7 | 9 | -0.61 | -0.6 |
| Ile | Leu | ATA | CTC | 4.8 | 1 | -2.99 | -3.0 |
| Ile | Leu | ATA | CTG | 10.1 | 19 | 7.88 | 8.1 |
| Ile | Leu | ATA | CTT | 10.6 | 11 | 0.01 | 0.0 |
| Ile | Glu | ATA | GAA | 42.2 | 49 | 1.08 | 2.4 |
| Ile | Asp | ATA | GAC | 17.7 | 22 | 1.06 | 1.2 |
| Ile | Glu | ATA | GAG | 18.2 | 19 | 0.03 | 0.2 |
| Ile | Asp | ATA | GAT | 37.5 | 25 | -4.16 | -3.9 |
| Ile | Ala | ATA | GCA | 16.3 | 12 | -1.15 | -1.2 |
| Ile | Ala | ATA | GCC | 11.0 | 4 | -4.45 | -4.5 |
| Ile | Ala | ATA | GCG | 6.0 | 2 | -2.62 | -2.6 |
| Ile | Ala | ATA | GCT | 17.9 | 7 | -6.63 | -6.7 |
| Ile | Gly | ATA | GGA | 9.6 | 7 | -0.69 | -0.4 |
| Ile | Gly | ATA | GGC | 8.8 | 2 | -5.21 | -4.5 |
| Ile | Gly | ATA | GGG | 5.7 | 4 | -0.51 | -0.3 |
| Ile | Gly | ATA | GGT | 23.4 | 14 | -3.76 | -2.6 |
| Ile | Val | ATA | GTA | 11.1 | 13 | 0.33 | 0.4 |
| Ile | Val | ATA | GTC | 10.8 | 11 | 0.01 | 0.0 |
| Ile | Val | ATA | GTG | 9.8 | 11 | 0.15 | 0.2 |
| Ile | Val | ATA | GTT | 20.8 | 16 | -1.12 | -1.0 |
| Ile | Ocr | ATA | TAA | 0.0 | 1 | 0.00 | 0.0 |
| Ile | Tyr | ATA | TAC | 14.2 | 13 | -0.11 | 0.0 |
| Ile | Amb | ATA | TAG | 0.0 | 0 | 0.00 | 0.0 |
| Ile | Tyr | ATA | TAT | 17.7 | 15 | -0.40 | -0.1 |
| Ile | Ser | ATA | TCA | 17.1 | 34 | 16.70 | 14.0 |
| Ile | Ser | ATA | TCC | 11.1 | 11 | -0.00 | -0.1 |
| Ile | Ser | ATA | TCG | 6.8 | 3 | -2.14 | -2.5 |
| Ile | Ser | ATA | TCT | 22.1 | 28 | 1.59 | 0.9 |
| Ile | Umb | ATA | TGA | 0.0 | 1 | 0.00 | 0.0 |
| Ile | Cys | ATA | TGC | 3.8 | 2 | -0.88 | -1.4 |
| Ile | Trp | ATA | TGG | 9.6 | 14 | 2.01 | 0.7 |
| Ile | Cys | ATA | TGT | 7.4 | 8 | 0.04 | 0.1 |
| Ile | Leu | ATA | TTA | 24.5 | 31 | 1.70 | 1.8 |
| Ile | Phe | ATA | TTC | 15.7 | 25 | 5.47 | 6.2 |
| Ile | Leu | ATA | TTG | 24.9 | 20 | -0.97 | -0.9 |
| Ile | Phe | ATA | TTT | 24.2 | 25 | 0.03 | 0.1 |
| | | Page Totals: | | 921.0 | 923 | 119.443 | 108.9 |

YEAST.RXD/CPLIST.RXR February 7, 1989

| aa1 | aa2 | cod1 | cod2 | exp | obs | chis1 | chis2 |
|---|---|---|---|---|---|---|---|
| Ile | Lys | ATC | AAA | 46.4 | 78 | 21.49 | 30.7 |
| Ile | Asn | ATC | AAC | 35.3 | 67 | 28.46 | 15.5 |
| Ile | Lys | ATC | AAG | 53.8 | 74 | 7.58 | 13.1 |
| Ile | Asn | ATC | AAT | 33.7 | 44 | 3.18 | 0.5 |
| Ile | Thr | ATC | ACA | 17.8 | 28 | 5.85 | 5.9 |
| Ile | Thr | ATC | ACC | 22.0 | 24 | 0.18 | 0.2 |
| Ile | Thr | ATC | ACG | 7.0 | 8 | 0.13 | 0.1 |
| Ile | Thr | ATC | ACT | 30.4 | 58 | 25.03 | 25.2 |
| Ile | Arg | ATC | AGA | 37.7 | 61 | 14.43 | 14.0 |
| Ile | Ser | ATC | AGC | 7.8 | 11 | 1.36 | 1.0 |
| Ile | Arg | ATC | AGG | 8.2 | 7 | -0.18 | -0.2 |
| Ile | Ser | ATC | AGT | 11.9 | 17 | 2.19 | 1.5 |
| Ile | Ile | ATC | ATA | 13.5 | 11 | -0.46 | -0.2 |
| Ile | Ile | ATC | ATC | 30.3 | 33 | 0.24 | 0.7 |
| Ile | Met | ATC | ATG | 29.7 | 32 | 0.18 | 0.1 |
| Ile | Ile | ATC | ATT | 42.9 | 59 | 6.06 | 8.5 |
| Ile | Gln | ATC | CAA | 39.4 | 37 | -0.15 | -1.0 |
| Ile | His | ATC | CAC | 11.8 | 7 | -1.97 | -1.7 |
| Ile | Gln | ATC | CAG | 10.2 | 11 | 0.06 | 0.0 |
| Ile | His | ATC | CAT | 15.8 | 16 | 0.00 | 0.0 |
| Ile | Pro | ATC | CCA | 33.1 | 36 | 0.26 | 0.0 |
| Ile | Pro | ATC | CCC | 7.5 | 5 | -0.81 | -1.3 |
| Ile | Pro | ATC | CCG | 4.4 | 4 | -0.03 | -0.2 |
| Ile | Pro | ATC | CCT | 15.2 | 13 | -0.33 | -0.9 |
| Ile | Arg | ATC | CGA | 2.4 | 0 | -2.40 | -2.4 |
| Ile | Arg | ATC | CGC | 2.2 | 1 | -0.63 | -0.6 |
| Ile | Arg | ATC | CGG | 1.1 | 2 | 0.73 | 0.7 |
| Ile | Arg | ATC | CGT | 11.0 | 10 | -0.08 | -0.1 |
| Ile | Leu | ATC | CTA | 14.8 | 14 | -0.04 | -0.0 |
| Ile | Leu | ATC | CTC | 4.5 | 4 | -0.05 | -0.0 |
| Ile | Leu | ATC | CTG | 10.4 | 5 | -2.81 | -2.8 |
| Ile | Leu | ATC | CTT | 11.5 | 12 | 0.02 | 0.0 |
| Ile | Glu | ATC | GAA | 67.2 | 42 | -9.47 | -6.8 |
| Ile | Asp | ATC | GAC | 31.3 | 16 | -7.46 | -7.2 |
| Ile | Glu | ATC | GAG | 20.5 | 19 | -0.10 | -0.0 |
| Ile | Asp | ATC | GAT | 47.1 | 47 | -0.00 | -0.0 |
| Ile | Ala | ATC | GCA | 18.9 | 10 | -4.15 | -4.2 |
| Ile | Ala | ATC | GCC | 25.6 | 14 | -5.27 | -5.4 |
| Ile | Ala | ATC | GCG | 5.8 | 7 | 0.26 | 0.2 |
| Ile | Ala | ATC | GCT | 44.0 | 24 | -9.12 | -9.3 |
| Ile | Gly | ATC | GGA | 9.3 | 9 | -0.01 | -0.0 |
| Ile | Gly | ATC | GGC | 11.0 | 11 | -0.00 | -0.1 |
| Ile | Gly | ATC | GGG | 6.7 | 11 | 2.78 | 3.9 |
| Ile | Gly | ATC | GGT | 61.5 | 38 | -8.95 | -5.9 |
| Ile | Val | ATC | GTA | 11.3 | 6 | -2.50 | -2.4 |
| Ile | Val | ATC | GTC | 24.3 | 20 | -0.75 | -0.6 |
| Ile | Val | ATC | GTG | 12.3 | 7 | -2.28 | -2.2 |
| Ile | Val | ATC | GTT | 41.6 | 23 | -8.30 | -7.9 |
| Ile | Ocr | ATC | TAA | 0.0 | 2 | 0.00 | 0.0 |
| Ile | Tyr | ATC | TAC | 24.9 | 13 | -5.70 | -4.2 |
| Ile | Amb | ATC | TAG | 0.0 | 0 | 0.00 | 0.0 |
| Ile | Tyr | ATC | TAT | 19.6 | 17 | -0.34 | -0.0 |
| Ile | Ser | ATC | TCA | 17.4 | 11 | -2.33 | -3.0 |
| Ile | Ser | ATC | TCC | 21.0 | 18 | -0.42 | -0.8 |
| Ile | Ser | ATC | TCG | 6.8 | 7 | 0.01 | 0.0 |
| Ile | Ser | ATC | TCT | 36.1 | 39 | 0.24 | 0.0 |
| Ile | Umb | ATC | TGA | 0.0 | 1 | 0.00 | 0.0 |
| Ile | Cys | ATC | TGC | 4.1 | 1 | -2.36 | -3.0 |
| Ile | Trp | ATC | TGG | 13.4 | 15 | 0.20 | 0.0 |
| Ile | Cys | ATC | TGT | 10.8 | 14 | 0.96 | 0.2 |
| Ile | Leu | ATC | TTA | 29.7 | 25 | -0.73 | -0.7 |
| Ile | Phe | ATC | TTC | 29.0 | 25 | -0.55 | -0.4 |
| Ile | Leu | ATC | TTG | 49.9 | 50 | 0.00 | 0.0 |
| Ile | Phe | ATC | TTT | 27.4 | 24 | -0.43 | -0.3 |
| | | Page Totals: | | 1351.8 | 1355 | 203.065 | 198.0 |

YEAST.RXD/CPLIST.RXR February 7, 1989

| aa1 | aa2 | cod1 | cod2 | exp | obs | chis1 | chis2 |
|---|---|---|---|---|---|---|---|
| Met | Lys | ATG | AAA | 62.0 | 61 | -0.02 | -0.0 |
| Met | Asn | ATG | AAC | 42.0 | 40 | -0.10 | -0.2 |
| Met | Lys | ATG | AAG | 59.1 | 58 | -0.02 | -0.0 |
| Met | Asn | ATG | AAT | 48.1 | 52 | 0.32 | 0.2 |
| Met | Thr | ATG | ACA | 25.1 | 24 | -0.04 | -0.0 |
| Met | Thr | ATG | ACC | 23.4 | 27 | 0.56 | 0.8 |
| Met | Thr | ATG | ACG | 10.7 | 8 | -0.66 | -0.5 |
| Met | Thr | ATG | ACT | 36.4 | 34 | -0.16 | -0.1 |
| Met | Arg | ATG | AGA | 42.8 | 59 | 6.11 | 1.1 |
| Met | Ser | ATG | AGC | 11.3 | 8 | -0.96 | -2.7 |
| Met | Arg | ATG | AGG | 12.9 | 18 | 1.99 | 0.4 |
| Met | Ser | ATG | AGT | 17.9 | 25 | 2.81 | 0.3 |
| Met | Ile | ATG | ATA | 21.2 | 19 | -0.23 | -0.1 |
| Met | Ile | ATG | ATC | 29.7 | 17 | -5.41 | -2.3 |
| Met | Met | ATG | ATG | 40.7 | 32 | -1.87 | 0.0 |
| Met | Ile | ATG | ATT | 52.0 | 49 | -0.17 | -0.9 |
| Met | Gln | ATG | CAA | 46.8 | 33 | -4.07 | -0.0 |
| Met | His | ATG | CAC | 13.4 | 10 | -0.85 | -0.0 |
| Met | Gln | ATG | CAG | 15.2 | 10 | -1.80 | -0.0 |
| Met | His | ATG | CAT | 20.9 | 16 | -1.13 | -0.0 |
| Met | Pro | ATG | CCA | 37.6 | 30 | -1.54 | -0.6 |
| Met | Pro | ATG | CCC | 10.1 | 17 | 4.78 | 6.5 |
| Met | Pro | ATG | CCG | 6.3 | 4 | -0.86 | -0.6 |
| Met | Pro | ATG | CCT | 19.9 | 17 | -0.41 | -0.1 |
| Met | Arg | ATG | CGA | 3.8 | 2 | -0.84 | -1.4 |
| Met | Arg | ATG | CGC | 3.0 | 8 | 8.23 | 5.3 |
| Met | Arg | ATG | CGG | 1.9 | 0 | -1.89 | -2.3 |
| Met | Arg | ATG | CGT | 14.0 | 7 | -3.50 | -5.7 |
| Met | Leu | ATG | CTA | 19.1 | 25 | 1.82 | 2.8 |
| Met | Leu | ATG | CTC | 6.5 | 5 | -0.35 | -0.2 |
| Met | Leu | ATG | CTG | 14.4 | 18 | 0.90 | 1.5 |
| Met | Leu | ATG | CTT | 16.2 | 25 | 4.79 | 6.4 |
| Met | Glu | ATG | GAA | 80.6 | 64 | -3.42 | -0.0 |
| Met | Asp | ATG | GAC | 36.7 | 40 | 0.30 | 0.2 |
| Met | Glu | ATG | GAG | 28.5 | 22 | -1.49 | -0.0 |
| Met | Asp | ATG | GAT | 63.3 | 77 | 2.96 | 0.1 |
| Met | Ala | ATG | GCA | 26.0 | 31 | 0.98 | 0.0 |
| Met | Ala | ATG | GCC | 26.7 | 35 | 2.61 | 0.2 |
| Met | Ala | ATG | GCG | 8.3 | 10 | 0.37 | 0.0 |
| Met | Ala | ATG | GCT | 47.5 | 55 | 1.19 | 0.1 |
| Met | Gly | ATG | GGA | 13.7 | 7 | -3.27 | -4.5 |
| Met | Gly | ATG | GGC | 14.5 | 14 | -0.02 | -0.3 |
| Met | Gly | ATG | GGG | 9.3 | 11 | 0.29 | 0.0 |
| Met | Gly | ATG | GGT | 64.1 | 82 | 5.00 | 1.4 |
| Met | Val | ATG | GTA | 15.8 | 14 | -0.20 | -0.1 |
| Met | Val | ATG | GTC | 25.7 | 30 | 0.72 | 1.0 |
| Met | Val | ATG | GTG | 16.1 | 10 | -2.28 | -2.0 |
| Met | Val | ATG | GTT | 45.7 | 46 | 0.00 | 0.1 |
| Met | Ocr | ATG | TAA | 0.0 | 2 | 0.00 | 0.0 |
| Met | Tyr | ATG | TAC | 29.3 | 22 | -1.82 | -0.1 |
| Met | Amb | ATG | TAG | 0.0 | 0 | 0.00 | 0.0 |
| Met | Tyr | ATG | TAT | 27.4 | 23 | -0.72 | -0.1 |
| Met | Ser | ATG | TCA | 24.9 | 41 | 10.49 | 3.1 |
| Met | Ser | ATG | TCC | 23.1 | 31 | 2.67 | 0.1 |
| Met | Ser | ATG | TCG | 9.7 | 8 | -0.29 | -1.4 |
| Met | Ser | ATG | TCT | 41.8 | 48 | 0.93 | 0.3 |
| Met | Umb | ATG | TGA | 0.0 | 2 | 0.00 | 0.0 |
| Met | Cys | ATG | TGC | 6.1 | 7 | 0.15 | 0.5 |
| Met | Trp | ATG | TGG | 17.5 | 19 | 0.12 | 0.0 |
| Met | Cys | ATG | TGT | 13.1 | 10 | -0.72 | -0.2 |
| Met | Leu | ATG | TTA | 39.2 | 31 | -1.70 | -0.9 |
| Met | Phe | ATG | TTC | 33.0 | 28 | -0.77 | -2.6 |
| Met | Leu | ATG | TTG | 55.2 | 37 | -6.01 | -4.2 |
| Met | Phe | ATG | TTT | 38.2 | 54 | 6.50 | 2.3 |
| | | Page Totals: | | 1665.0 | 1669 | 117.185 | 69.0 |

PAGE 15

YEAST.RXD/CPLIST.RXR February 7, 1989

| aa1 | aa2 | cod1 | cod2 | exp | obs | chis1 | chis2 |
|---|---|---|---|---|---|---|---|
| Ile | Lys | ATT | AAA | 88.2 | 47 | -19.23 | -13.5 |
| Ile | Asn | ATT | AAC | 58.3 | 61 | 0.13 | 0.9 |
| Ile | Lys | ATT | AAG | 83.7 | 40 | -22.84 | -16.9 |
| Ile | Asn | ATT | AAT | 67.9 | 47 | -6.46 | -13.6 |
| Ile | Thr | ATT | ACA | 34.7 | 22 | -4.67 | -4.6 |
| Ile | Thr | ATT | ACC | 33.6 | 32 | -0.07 | -0.1 |
| Ile | Thr | ATT | ACG | 14.2 | 14 | -0.00 | -0.0 |
| Ile | Thr | ATT | ACT | 52.0 | 36 | -4.93 | -4.9 |
| Ile | Arg | ATT | AGA | 60.3 | 45 | -3.87 | -4.1 |
| Ile | Ser | ATT | AGC | 15.4 | 10 | -1.91 | -2.5 |
| Ile | Arg | ATT | AGG | 17.2 | 12 | -1.55 | -1.6 |
| Ile | Ser | ATT | AGT | 23.9 | 9 | -9.28 | -10.5 |
| Ile | Ile | ATT | ATA | 28.7 | 22 | -1.56 | -1.0 |
| Ile | Ile | ATT | ATC | 42.9 | 47 | 0.40 | 1.1 |
| Ile | Met | ATT | ATG | 52.0 | 41 | -2.32 | -2.5 |
| Ile | Ile | ATT | ATT | 80.2 | 60 | -5.08 | -3.2 |
| Ile | Gln | ATT | CAA | 66.4 | 87 | 6.37 | 2.4 |
| Ile | His | ATT | CAC | 17.9 | 15 | -0.46 | -0.3 |
| Ile | Gln | ATT | CAG | 20.2 | 22 | 0.16 | 0.0 |
| Ile | His | ATT | CAT | 29.4 | 36 | 1.49 | 2.1 |
| Ile | Pro | ATT | CCA | 52.9 | 64 | 2.33 | 0.5 |
| Ile | Pro | ATT | CCC | 13.6 | 22 | 5.22 | 3.2 |
| Ile | Pro | ATT | CCG | 8.6 | 10 | 0.22 | 0.0 |
| Ile | Pro | ATT | CCT | 28.2 | 29 | 0.03 | 0.2 |
| Ile | Arg | ATT | CGA | 5.0 | 2 | -1.81 | -1.8 |
| Ile | Arg | ATT | CGC | 4.1 | 6 | 0.94 | 0.9 |
| Ile | Arg | ATT | CGG | 2.2 | 0 | -2.20 | -2.2 |
| Ile | Arg | ATT | CGT | 19.8 | 19 | -0.03 | -0.0 |
| Ile | Leu | ATT | CTA | 28.1 | 23 | -0.91 | -0.8 |
| Ile | Leu | ATT | CTC | 8.9 | 13 | 1.93 | 2.0 |
| Ile | Leu | ATT | CTG | 19.6 | 9 | -5.74 | -5.6 |
| Ile | Leu | ATT | CTT | 23.0 | 31 | 2.77 | 2.9 |
| Ile | Glu | ATT | GAA | 116.2 | 117 | 0.01 | 0.7 |
| Ile | Asp | ATT | GAC | 51.2 | 56 | 0.44 | 0.6 |
| Ile | Glu | ATT | GAG | 39.5 | 37 | -0.15 | -0.0 |
| Ile | Asp | ATT | GAT | 88.8 | 104 | 2.60 | 3.1 |
| Ile | Ala | ATT | GCA | 36.4 | 39 | 0.19 | 0.2 |
| Ile | Ala | ATT | GCC | 38.3 | 69 | 24.59 | 24.1 |
| Ile | Ala | ATT | GCG | 11.2 | 15 | 1.29 | 1.2 |
| Ile | Ala | ATT | GCT | 68.8 | 99 | 13.22 | 12.8 |
| Ile | Gly | ATT | GGA | 18.5 | 17 | -0.11 | -0.0 |
| Ile | Gly | ATT | GGC | 20.2 | 21 | 0.03 | 0.4 |
| Ile | Gly | ATT | GGG | 12.4 | 17 | 1.69 | 2.8 |
| Ile | Gly | ATT | GGT | 95.1 | 107 | 1.50 | 4.6 |
| Ile | Val | ATT | GTA | 22.5 | 24 | 0.11 | 0.2 |
| Ile | Val | ATT | GTC | 37.5 | 50 | 4.18 | 4.6 |
| Ile | Val | ATT | GTG | 22.6 | 25 | 0.25 | 0.3 |
| Ile | Val | ATT | GTT | 67.5 | 82 | 3.11 | 3.6 |
| Ile | Ocr | ATT | TAA | 0.0 | 3 | 0.00 | 0.0 |
| Ile | Tyr | ATT | TAC | 40.6 | 44 | 0.28 | 1.3 |
| Ile | Amb | ATT | TAG | 0.0 | 0 | 0.00 | 0.0 |
| Ile | Tyr | ATT | TAT | 38.5 | 40 | 0.06 | 0.7 |
| Ile | Ser | ATT | TCA | 35.8 | 29 | -1.28 | -2.1 |
| Ile | Ser | ATT | TCC | 33.5 | 35 | 0.06 | 0.0 |
| Ile | Ser | ATT | TCG | 13.3 | 15 | 0.23 | 0.1 |
| Ile | Ser | ATT | TCT | 59.9 | 84 | 9.67 | 6.7 |
| Ile | Umb | ATT | TGA | 0.0 | 2 | 0.00 | 0.0 |
| Ile | Cys | ATT | TGC | 8.0 | 12 | 2.03 | 0.8 |
| Ile | Trp | ATT | TGG | 23.6 | 25 | 0.09 | 0.2 |
| Ile | Cys | ATT | TGT | 18.9 | 25 | 1.96 | 0.4 |
| Ile | Leu | ATT | TTA | 57.2 | 62 | 0.40 | 0.5 |
| Ile | Phe | ATT | TTC | 46.3 | 48 | 0.07 | 0.2 |
| Ile | Leu | ATT | TTG | 79.9 | 82 | 0.06 | 0.1 |
| Ile | Phe | ATT | TTT | 53.9 | 44 | -1.81 | -1.3 |
| | | Page Totals: | | 2356.9 | 2362 | 188.402 | 179.2 |

PAGE 16

YEAST.RXD/CPLIST.RXR February 7, 1989

| aa1 | aa2 | cod1 | cod2 | exp | obs | chis1 | chis2 |
|---|---|---|---|---|---|---|---|
| Gln | Lys | CAA | AAA | 78.6 | 59 | -4.88 | -0.7 |
| Gln | Asn | CAA | AAC | 56.3 | 56 | -0.00 | -0.0 |
| Gln | Lys | CAA | AAG | 80.7 | 85 | 0.23 | 4.4 |
| Gln | Asn | CAA | AAT | 60.5 | 70 | 1.48 | 1.3 |
| Gln | Thr | CAA | ACA | 30.4 | 42 | 4.44 | 4.0 |
| Gln | Thr | CAA | ACC | 30.6 | 32 | 0.07 | 0.0 |
| Gln | Thr | CAA | ACG | 12.5 | 11 | -0.18 | -0.2 |
| Gln | Thr | CAA | ACT | 48.0 | 48 | 0.00 | 0.0 |
| Gln | Arg | CAA | AGA | 56.6 | 71 | 3.65 | 0.4 |
| Gln | Ser | CAA | AGC | 14.3 | 14 | -0.01 | -0.0 |
| Gln | Arg | CAA | AGG | 14.9 | 15 | 0.00 | 0.3 |
| Gln | Ser | CAA | ACT | 21.3 | 29 | 2.77 | 4.2 |
| Gln | Ile | CAA | ATA | 24.5 | 29 | 0.81 | 1.0 |
| Gln | Ile | CAA | ATC | 39.4 | 45 | 0.79 | 1.0 |
| Gln | Met | CAA | ATG | 46.8 | 48 | 0.03 | 0.6 |
| Gln | Ile | CAA | ATT | 66.4 | 51 | -3.59 | -3.1 |
| Gln | Gln | CAA | CAA | 69.7 | 75 | 0.40 | 4.3 |
| Gln | His | CAA | CAC | 16.6 | 13 | -0.77 | -1.0 |
| Gln | Gln | CAA | CAG | 19.0 | 32 | 8.94 | 1.4 |
| Gln | His | CAA | CAT | 26.0 | 28 | 0.15 | 0.0 |
| Gln | Pro | CAA | CCA | 49.8 | 33 | -5.64 | -0.8 |
| Gln | Pro | CAA | CCC | 12.2 | 14 | 0.27 | 2.2 |
| Gln | Pro | CAA | CCG | 7.7 | 9 | 0.23 | 1.6 |
| Gln | Pro | CAA | CCT | 25.7 | 20 | -1.25 | -0.0 |
| Gln | Arg | CAA | CGA | 4.8 | 5 | 0.01 | 0.1 |
| Gln | Arg | CAA | CGC | 3.6 | 3 | -0.11 | -0.4 |
| Gln | Arg | CAA | CGG | 2.1 | 2 | -0.00 | -0.1 |
| Gln | Arg | CAA | CGT | 18.9 | 21 | 0.22 | 0.1 |
| Gln | Leu | CAA | CTA | 24.6 | 22 | -0.27 | -1.6 |
| Gln | Leu | CAA | CTC | 7.5 | 6 | -0.31 | -0.9 |
| Gln | Leu | CAA | CTG | 17.5 | 24 | 2.39 | 0.6 |
| Gln | Leu | CAA | CTT | 19.1 | 28 | 4.12 | 1.4 |
| Gln | Glu | CAA | GAA | 108.3 | 120 | 1.27 | 0.8 |
| Gln | Asp | CAA | GAC | 47.5 | 35 | -3.27 | -2.1 |
| Gln | Glu | CAA | GAG | 35.8 | 38 | 0.13 | 0.1 |
| Gln | Asp | CAA | GAT | 78.7 | 76 | -0.10 | -0.0 |
| Gln | Ala | CAA | GCA | 31.8 | 25 | -1.44 | -2.0 |
| Gln | Ala | CAA | GCC | 38.2 | 34 | -0.46 | -0.8 |
| Gln | Ala | CAA | GCG | 9.8 | 15 | 2.72 | 2.2 |
| Gln | Ala | CAA | GCT | 64.9 | 68 | 0.15 | 0.0 |
| Gln | Gly | CAA | GGA | 15.8 | 10 | -2.10 | -0.9 |
| Gln | Gly | CAA | GGC | 18.4 | 12 | -2.20 | -0.9 |
| Gln | Gly | CAA | GGG | 11.5 | 8 | -1.06 | -0.4 |
| Gln | Gly | CAA | GGT | 87.5 | 84 | -0.14 | -1.0 |
| Gln | Val | CAA | GTA | 19.5 | 15 | -1.04 | -0.2 |
| Gln | Val | CAA | GTC | 34.3 | 26 | -2.03 | -0.4 |
| Gln | Val | CAA | GTG | 20.2 | 24 | 0.72 | 2.7 |
| Gln | Val | CAA | GTT | 60.7 | 49 | -2.27 | -0.2 |
| Gln | Ocr | CAA | TAA | 0.0 | 2 | 0.00 | 0.0 |
| Gln | Tyr | CAA | TAC | 38.2 | 44 | 0.90 | 0.1 |
| Gln | Amb | CAA | TAG | 0.0 | 1 | 0.00 | 0.0 |
| Gln | Tyr | CAA | TAT | 34.2 | 36 | 0.09 | 0.6 |
| Gln | Ser | CAA | TCA | 30.3 | 28 | -0.18 | -0.0 |
| Gln | Ser | CAA | TCC | 31.1 | 23 | -2.12 | -1.2 |
| Gln | Ser | CAA | TCG | 11.7 | 12 | 0.01 | 0.1 |
| Gln | Ser | CAA | TCT | 56.2 | 50 | -0.69 | -0.1 |
| Gln | Umb | CAA | TGA | 0.0 | 1 | 0.00 | 0.0 |
| Gln | Cys | CAA | TGC | 7.2 | 7 | -0.01 | -0.0 |
| Gln | Trp | CAA | TGG | 21.1 | 27 | 1.63 | 0.9 |
| Gln | Cys | CAA | TGT | 16.7 | 16 | -0.03 | 0.0 |
| Gln | Leu | CAA | TTA | 48.9 | 60 | 2.50 | 0.1 |
| Gln | Phe | CAA | TTC | 43.1 | 44 | 0.02 | 0.0 |
| Gln | Leu | CAA | TTG | 74.9 | 86 | 1.64 | 0.0 |
| Gln | Phe | CAA | TTT | 46.6 | 39 | -1.22 | -1.2 |
| | | Page Totals: | | 2149.8 | 2155 | 80.1233 | 56.8 |

YEAST.RXD/CPLIST.RXR February 7, 1989

| aa1 | aa2 | cod1 | cod2 | exp | obs | chis1 | chis2 |
|---|---|---|---|---|---|---|---|
| His | Lys | CAC | AAA | 20.8 | 11 | -4.63 | -1.4 |
| His | Asn | CAC | AAC | 15.5 | 8 | -3.61 | -3.4 |
| His | Lys | CAC | AAG | 24.0 | 28 | 0.69 | 5.6 |
| His | Asn | CAC | AAT | 15.3 | 19 | 0.90 | 1.0 |
| His | Thr | CAC | ACA | 8.0 | 8 | 0.00 | 0.3 |
| His | Thr | CAC | ACC | 9.1 | 5 | -1.87 | -0.9 |
| His | Thr | CAC | ACG | 3.3 | 2 | -0.53 | -0.2 |
| His | Thr | CAC | ACT | 13.1 | 10 | -0.74 | -0.1 |
| His | Arg | CAC | AGA | 16.4 | 32 | 14.79 | 10.6 |
| His | Ser | CAC | AGC | 4.1 | 7 | 2.00 | 3.1 |
| His | Arg | CAC | AGG | 4.0 | 6 | 1.06 | 0.6 |
| His | Ser | CAC | AGT | 5.8 | 5 | -0.11 | -0.0 |
| His | Ile | CAC | ATA | 6.6 | 8 | 0.28 | 0.2 |
| His | Ile | CAC | ATC | 11.8 | 11 | -0.06 | -0.1 |
| His | Met | CAC | ATG | 13.4 | 13 | -0.01 | -0.4 |
| His | Ile | CAC | ATT | 17.9 | 21 | 0.54 | 0.4 |
| His | Gln | CAC | CAA | 16.6 | 12 | -1.26 | -0.5 |
| His | His | CAC | CAC | 7.5 | 15 | 7.63 | 1.7 |
| His | Gln | CAC | CAG | 4.8 | 4 | -0.13 | -0.0 |
| His | His | CAC | CAT | 7.5 | 10 | 0.84 | 0.1 |
| His | Pro | CAC | CCA | 14.1 | 19 | 1.67 | 0.0 |
| His | Pro | CAC | CCC | 3.5 | 8 | 5.98 | 2.6 |
| His | Pro | CAC | CCG | 2.3 | 1 | -0.76 | -1.4 |
| His | Pro | CAC | CCT | 7.0 | 10 | 1.32 | 0.1 |
| His | Arg | CAC | CGA | 1.1 | 1 | -0.02 | -0.1 |
| His | Arg | CAC | CGC | 1.1 | 3 | 3.38 | 2.7 |
| His | Arg | CAC | CGG | 0.7 | 1 | 0.14 | 0.1 |
| His | Arg | CAC | CGT | 4.5 | 3 | -0.52 | -0.8 |
| His | Leu | CAC | CTA | 6.8 | 6 | -0.10 | -0.3 |
| His | Leu | CAC | CTC | 2.2 | 3 | 0.32 | 0.2 |
| His | Leu | CAC | CTG | 4.9 | 3 | -0.75 | -1.0 |
| His | Leu | CAC | CTT | 5.4 | 9 | 2.35 | 1.6 |
| His | Glu | CAC | GAA | 29.3 | 26 | -0.36 | -0.0 |
| His | Asp | CAC | GAC | 14.1 | 17 | 0.60 | 0.2 |
| His | Glu | CAC | GAG | 9.4 | 6 | -1.25 | -0.8 |
| His | Asp | CAC | GAT | 20.6 | 21 | 0.01 | 0.1 |
| His | Ala | CAC | GCA | 8.4 | 5 | -1.38 | -0.4 |
| His | Ala | CAC | GCC | 10.8 | 9 | -0.29 | -0.0 |
| His | Ala | CAC | GCG | 2.8 | 1 | -1.17 | -0.7 |
| His | Ala | CAC | GCT | 19.3 | 11 | -3.59 | -1.2 |
| His | Gly | CAC | GGA | 4.3 | 6 | 0.69 | 0.8 |
| His | Gly | CAC | GGC | 5.2 | 5 | -0.01 | -0.0 |
| His | Gly | CAC | GGG | 2.9 | 2 | -0.29 | -0.2 |
| His | Gly | CAC | GGT | 26.2 | 33 | 1.75 | 2.3 |
| His | Val | CAC | GTA | 5.1 | 3 | -0.84 | -0.8 |
| His | Val | CAC | GTC | 10.8 | 8 | -0.72 | -0.7 |
| His | Val | CAC | GTG | 5.6 | 6 | 0.03 | 0.0 |
| His | Val | CAC | GTT | 17.6 | 18 | 0.01 | 0.0 |
| His | Ocr | CAC | TAA | 0.0 | 1 | 0.00 | 0.0 |
| His | Tyr | CAC | TAC | 11.0 | 16 | 2.25 | 0.9 |
| His | Amb | CAC | TAG | 0.0 | 0 | 0.00 | 0.0 |
| His | Tyr | CAC | TAT | 8.8 | 11 | 0.55 | 0.1 |
| His | Ser | CAC | TCA | 8.0 | 5 | -1.10 | -0.6 |
| His | Ser | CAC | TCC | 8.9 | 8 | -0.10 | -0.0 |
| His | Ser | CAC | TCG | 3.4 | 2 | -0.55 | -0.3 |
| His | Ser | CAC | TCT | 15.2 | 8 | -3.44 | -2.2 |
| His | Umb | CAC | TGA | 0.0 | 1 | 0.00 | 0.0 |
| His | Cys | CAC | TGC | 1.9 | 2 | 0.01 | 0.0 |
| His | Trp | CAC | TGG | 6.4 | 11 | 3.34 | 0.0 |
| His | Cys | CAC | TGT | 4.7 | 3 | -0.60 | -0.9 |
| His | Leu | CAC | TTA | 13.5 | 8 | -2.22 | -3.0 |
| His | Phe | CAC | TTC | 12.8 | 14 | 0.11 | 0.1 |
| His | Leu | CAC | TTG | 21.4 | 22 | 0.02 | 0.1 |
| His | Phe | CAC | TTT | 12.1 | 10 | -0.36 | -1.4 |
| | | Page Totals: | | 599.4 | 601 | 86.6156 | 59.3 |

YEAST.RXD/CPLIST.RXR February 7, 1989

| aa1 | aa2 | cod1 | cod2 | exp | obs | chis1 | chis2 |
|---|---|---|---|---|---|---|---|
| Gln | Lys | CAG | AAA | 27.9 | 21 | -1.72 | -0.3 |
| Gln | Asn | CAG | AAC | 16.9 | 14 | -0.50 | -0.5 |
| Gln | Lys | CAG | AAG | 22.3 | 11 | -5.72 | -3.2 |
| Gln | Asn | CAG | AAT | 23.2 | 18 | -1.15 | -1.2 |
| Gln | Thr | CAG | ACA | 11.9 | 4 | -5.22 | -5.4 |
| Gln | Thr | CAG | ACC | 8.5 | 9 | 0.03 | 0.0 |
| Gln | Thr | CAG | ACG | 5.5 | 6 | 0.05 | 0.0 |
| Gln | Thr | CAG | ACT | 13.8 | 12 | -0.23 | -0.3 |
| Gln | Arg | CAG | AGA | 15.5 | 12 | -0.80 | -2.1 |
| Gln | Ser | CAG | AGC | 5.6 | 4 | -0.43 | -0.3 |
| Gln | Arg | CAG | AGG | 6.5 | 8 | 0.36 | 0.0 |
| Gln | Ser | CAG | AGT | 8.8 | 7 | -0.37 | -0.2 |
| Gln | Ile | CAG | ATA | 10.4 | 14 | 1.22 | 1.4 |
| Gln | Ile | CAG | ATC | 10.2 | 7 | -1.00 | -0.9 |
| Gln | Met | CAG | ATG | 15.2 | 9 | -2.56 | -1.8 |
| Gln | Ile | CAG | ATT | 20.2 | 22 | 0.16 | 0.2 |
| Gln | Gln | CAG | CAA | 19.0 | 32 | 8.94 | 1.4 |
| Gln | His | CAG | CAC | 4.8 | 5 | 0.01 | 0.0 |
| Gln | Gln | CAG | CAG | 10.2 | 22 | 13.65 | 4.7 |
| Gln | His | CAG | CAT | 8.7 | 12 | 1.29 | 1.0 |
| Gln | Pro | CAG | CCA | 12.4 | 10 | -0.45 | -0.0 |
| Gln | Pro | CAG | CCC | 5.0 | 3 | -0.82 | -0.2 |
| Gln | Pro | CAG | CCG | 3.4 | 5 | 0.76 | 2.1 |
| Gln | Pro | CAG | CCT | 8.9 | 3 | -3.88 | -2.2 |
| Gln | Arg | CAG | CGA | 2.4 | 6 | 5.62 | 3.8 |
| Gln | Arg | CAG | CGC | 1.5 | 2 | 0.20 | 0.1 |
| Gln | Arg | CAG | CGG | 1.0 | 0 | -0.97 | -1.1 |
| Gln | Arg | CAG | CGT | 5.2 | 10 | 4.47 | 2.6 |
| Gln | Leu | CAG | CTA | 8.7 | 13 | 2.10 | 0.8 |
| Gln | Leu | CAG | CTC | 3.3 | 4 | 0.15 | 0.0 |
| Gln | Leu | CAG | CTG | 7.5 | 5 | -0.85 | -1.6 |
| Gln | Leu | CAG | CTT | 7.4 | 8 | 0.05 | 0.1 |
| Gln | Glu | CAG | GAA | 31.6 | 21 | -3.57 | -3.9 |
| Gln | Asp | CAG | GAC | 14.8 | 16 | 0.11 | 0.3 |
| Gln | Glu | CAG | GAG | 13.7 | 14 | 0.01 | 0.0 |
| Gln | Asp | CAG | GAT | 26.7 | 31 | 0.68 | 1.3 |
| Gln | Ala | CAG | GCA | 12.0 | 18 | 3.00 | 2.4 |
| Gln | Ala | CAG | GCC | 9.6 | 10 | 0.02 | 0.0 |
| Gln | Ala | CAG | GCG | 4.3 | 10 | 7.46 | 6.7 |
| Gln | Ala | CAG | GCT | 15.6 | 14 | -0.16 | -0.3 |
| Gln | Gly | CAG | GGA | 6.8 | 12 | 4.01 | 6.5 |
| Gln | Gly | CAG | GGC | 6.9 | 11 | 2.49 | 4.4 |
| Gln | Gly | CAG | GGG | 4.5 | 3 | -0.48 | -0.2 |
| Gln | Gly | CAG | GGT | 19.9 | 7 | -8.33 | -5.9 |
| Gln | Val | CAG | GTA | 7.7 | 8 | 0.01 | 0.3 |
| Gln | Val | CAG | GTC | 8.9 | 7 | -0.41 | -0.0 |
| Gln | Val | CAG | GTG | 7.7 | 6 | -0.35 | -0.0 |
| Gln | Val | CAG | GTT | 15.6 | 14 | -0.17 | -0.0 |
| Gln | Ocr | CAG | TAA | 0.0 | 0 | 0.00 | 0.0 |
| Gln | Tyr | CAG | TAC | 11.3 | 13 | 0.25 | 0.0 |
| Gln | Amb | CAG | TAG | 0.0 | 1 | 0.00 | 0.0 |
| Gln | Tyr | CAG | TAT | 12.0 | 22 | 8.27 | 3.9 |
| Gln | Ser | CAG | TCA | 11.8 | 14 | 0.42 | 0.9 |
| Gln | Ser | CAG | TCC | 9.0 | 8 | -0.11 | -0.0 |
| Gln | Ser | CAG | TCG | 5.0 | 6 | 0.22 | 0.4 |
| Gln | Ser | CAG | TCT | 16.4 | 11 | -1.78 | -1.2 |
| Gln | Umb | CAG | TGA | 0.0 | 1 | 0.00 | 0.0 |
| Gln | Cys | CAG | TGC | 2.4 | 2 | -0.06 | -0.0 |
| Gln | Trp | CAG | TGG | 7.0 | 3 | -2.32 | -2.7 |
| Gln | Cys | CAG | TGT | 5.1 | 5 | -0.00 | -0.0 |
| Gln | Leu | CAG | TTA | 15.9 | 19 | 0.62 | 0.0 |
| Gln | Phe | CAG | TTC | 12.0 | 11 | -0.09 | -0.1 |
| Gln | Leu | CAG | TTG | 20.0 | 24 | 0.82 | 0.0 |
| Gln | Phe | CAG | TTT | 16.9 | 24 | 2.97 | 3.1 |
| | Page Totals: | | | 682.4 | 684 | 114.936 | 84.4 |

PAGE 19

YEAST.RXD/CPLIST.RXR February 7, 1989

| aa1 | aa2 | cod1 | cod2 | exp | obs | chis1 | chis2 |
|---|---|---|---|---|---|---|---|
| His | Lys | CAT | AAA | 36.6 | 18 | -9.41 | -3.2 |
| His | Asn | CAT | AAC | 22.5 | 23 | 0.01 | 0.0 |
| His | Lys | CAT | AAG | 30.6 | 27 | -0.42 | -0.7 |
| His | Asn | CAT | AAT | 28.9 | 31 | 0.15 | 0.2 |
| His | Thr | CAT | ACA | 14.6 | 16 | 0.13 | 1.2 |
| His | Thr | CAT | ACC | 12.3 | 11 | -0.13 | -0.1 |
| His | Thr | CAT | ACG | 6.4 | 4 | -0.87 | -0.3 |
| His | Thr | CAT | ACT | 19.6 | 16 | -0.67 | -0.0 |
| His | Arg | CAT | AGA | 22.8 | 15 | -2.66 | -4.1 |
| His | Ser | CAT | AGC | 6.6 | 4 | -1.05 | -0.6 |
| His | Arg | CAT | AGG | 7.3 | 3 | -2.53 | -3.2 |
| His | Ser | CAT | AGT | 10.0 | 9 | -0.10 | -0.0 |
| His | Ile | CAT | ATA | 12.0 | 11 | -0.08 | -0.1 |
| His | Ile | CAT | ATC | 15.8 | 13 | -0.49 | -0.6 |
| His | Met | CAT | ATG | 20.9 | 15 | -1.64 | -0.3 |
| His | Ile | CAT | ATT | 29.4 | 32 | 0.23 | 0.1 |
| His | Gln | CAT | CAA | 26.0 | 29 | 0.34 | 1.4 |
| His | His | CAT | CAC | 7.5 | 10 | 0.84 | 0.1 |
| His | Gln | CAT | CAG | 8.7 | 5 | -1.55 | -1.0 |
| His | His | CAT | CAT | 14.4 | 18 | 0.90 | 0.4 |
| His | Pro | CAT | CCA | 20.1 | 21 | 0.04 | 1.2 |
| His | Pro | CAT | CCC | 6.0 | 5 | -0.16 | -1.1 |
| His | Pro | CAT | CCG | 3.9 | 7 | 2.43 | 0.7 |
| His | Pro | CAT | CCT | 12.1 | 20 | 5.20 | 1.0 |
| His | Arg | CAT | CGA | 2.4 | 2 | -0.06 | -0.1 |
| His | Arg | CAT | CGC | 1.7 | 4 | 2.99 | 2.3 |
| His | Arg | CAT | CGG | 1.0 | 0 | -0.97 | -1.1 |
| His | Arg | CAT | CGT | 7.6 | 8 | 0.02 | 0.0 |
| His | Leu | CAT | CTA | 11.5 | 10 | -0.19 | -0.5 |
| His | Leu | CAT | CTC | 3.9 | 4 | 0.00 | 0.0 |
| His | Leu | CAT | CTG | 8.4 | 8 | -0.02 | -0.1 |
| His | Leu | CAT | CTT | 9.6 | 10 | 0.01 | 0.0 |
| His | Glu | CAT | GAA | 44.4 | 42 | -0.12 | -0.0 |
| His | Asp | CAT | GAC | 19.4 | 20 | 0.02 | 0.0 |
| His | Glu | CAT | GAG | 16.2 | 17 | 0.04 | 0.3 |
| His | Asp | CAT | GAT | 36.2 | 39 | 0.21 | 0.0 |
| His | Ala | CAT | GCA | 15.3 | 13 | -0.34 | -0.1 |
| His | Ala | CAT | GCC | 14.2 | 8 | -2.70 | -0.9 |
| His | Ala | CAT | GCG | 5.0 | 4 | -0.19 | -0.0 |
| His | Ala | CAT | GCT | 24.5 | 28 | 0.51 | 3.9 |
| His | Gly | CAT | GGA | 7.7 | 5 | -0.94 | -0.8 |
| His | Gly | CAT | GGC | 8.1 | 9 | 0.10 | 0.2 |
| His | Gly | CAT | GGG | 5.3 | 4 | -0.32 | -0.3 |
| His | Gly | CAT | GGT | 33.1 | 26 | -1.52 | -1.2 |
| His | Val | CAT | GTA | 9.3 | 6 | -1.15 | -1.1 |
| His | Val | CAT | GTC | 13.4 | 17 | 0.97 | 1.0 |
| His | Val | CAT | GTG | 9.1 | 9 | -0.00 | 0.0 |
| His | Val | CAT | GTT | 25.0 | 28 | 0.35 | 0.4 |
| His | Ocr | CAT | TAA | 0.0 | 2 | 0.00 | 0.0 |
| His | Tyr | CAT | TAC | 15.3 | 19 | 0.91 | 0.1 |
| His | Amb | CAT | TAG | 0.0 | 0 | 0.00 | 0.0 |
| His | Tyr | CAT | TAT | 16.5 | 13 | -0.76 | -1.8 |
| His | Ser | CAT | TCA | 15.4 | 12 | -0.73 | -0.2 |
| His | Ser | CAT | TCC | 12.5 | 12 | -0.02 | -0.1 |
| His | Ser | CAT | TCG | 5.8 | 7 | 0.27 | 0.7 |
| His | Ser | CAT | TCT | 23.1 | 26 | 0.37 | 1.5 |
| His | Umb | CAT | TGA | 0.0 | 1 | 0.00 | 0.0 |
| His | Cys | CAT | TGC | 3.6 | 2 | -0.73 | -1.0 |
| His | Trp | CAT | TGG | 9.6 | 17 | 5.78 | 0.0 |
| His | Cys | CAT | TGT | 7.7 | 13 | 3.67 | 2.3 |
| His | Leu | CAT | TTA | 23.6 | 30 | 1.73 | 0.7 |
| His | Phe | CAT | TTC | 17.4 | 31 | 10.57 | 5.0 |
| His | Leu | CAT | TTG | 29.5 | 40 | 3.75 | 2.0 |
| His | Phe | CAT | TTT | 22.2 | 22 | -0.00 | -0.8 |
| | Page Totals: | | | 929.0 | 931 | 75.0534 | 52.2 |

PAGE 20

YEAST.RXD/CPLIST.RXR February 7, 1989

| aa1 | aa2 | cod1 | cod2 | exp | obs | chis1 | chis2 |
|---|---|---|---|---|---|---|---|
| Pro | Lys | CCA | AAA | 58.6 | 54 | -0.36 | -0.8 |
| Pro | Asn | CCA | AAC | 43.2 | 51 | 1.43 | 2.3 |
| Pro | Lys | CCA | AAG | 66.4 | 90 | 8.35 | 6.4 |
| Pro | Asn | CCA | AAT | 41.4 | 41 | -0.00 | -0.0 |
| Pro | Thr | CCA | ACA | 22.1 | 28 | 1.57 | 0.6 |
| Pro | Thr | CCA | ACC | 26.0 | 19 | -1.89 | -3.2 |
| Pro | Thr | CCA | ACG | 8.9 | 11 | 0.49 | 0.2 |
| Pro | Thr | CCA | ACT | 39.3 | 38 | -0.04 | -0.6 |
| Pro | Arg | CCA | AGA | 46.1 | 68 | 10.36 | 11.0 |
| Pro | Ser | CCA | AGC | 9.8 | 11 | 0.14 | 0.0 |
| Pro | Arg | CCA | AGG | 10.2 | 10 | -0.00 | -0.0 |
| Pro | Ser | CCA | AGT | 14.9 | 24 | 5.50 | 3.8 |
| Pro | Ile | CCA | ATA | 15.8 | 9 | -2.93 | -2.7 |
| Pro | Ile | CCA | ATC | 33.1 | 38 | 0.74 | 1.0 |
| Pro | Met | CCA | ATG | 37.6 | 52 | 5.51 | 5.4 |
| Pro | Ile | CCA | ATT | 52.9 | 63 | 1.93 | 2.5 |
| Pro | Gln | CCA | CAA | 49.8 | 41 | -1.54 | -1.7 |
| Pro | His | CCA | CAC | 14.1 | 14 | -0.00 | -0.2 |
| Pro | Gln | CCA | CAG | 12.4 | 14 | 0.22 | 0.2 |
| Pro | His | CCA | CAT | 20.1 | 19 | -0.06 | -0.6 |
| Pro | Pro | CCA | CCA | 47.7 | 32 | -5.16 | -2.0 |
| Pro | Pro | CCA | CCC | 9.0 | 10 | 0.10 | 0.6 |
| Pro | Pro | CCA | CCG | 5.3 | 7 | 0.52 | 1.3 |
| Pro | Pro | CCA | CCT | 19.7 | 12 | -2.98 | -1.4 |
| Pro | Arg | CCA | CGA | 2.8 | 1 | -1.15 | -1.1 |
| Pro | Arg | CCA | CGC | 2.5 | 4 | 0.85 | 0.9 |
| Pro | Arg | CCA | CGG | 1.2 | 2 | 0.49 | 0.5 |
| Pro | Arg | CCA | CGT | 14.9 | 11 | -1.04 | -1.0 |
| Pro | Leu | CCA | CTA | 18.1 | 10 | -3.62 | -2.9 |
| Pro | Leu | CCA | CTC | 5.1 | 7 | 0.70 | 1.0 |
| Pro | Leu | CCA | CTG | 11.9 | 15 | 0.80 | 1.3 |
| Pro | Leu | CCA | CTT | 13.8 | 15 | 0.11 | 0.3 |
| Pro | Glu | CCA | GAA | 86.1 | 116 | 10.38 | 0.0 |
| Pro | Asp | CCA | GAC | 38.2 | 19 | -9.67 | -5.5 |
| Pro | Glu | CCA | GAG | 25.6 | 46 | 16.23 | 4.2 |
| Pro | Asp | CCA | GAT | 61.4 | 51 | -1.75 | -0.0 |
| Pro | Ala | CCA | GCA | 23.3 | 16 | -2.29 | -0.2 |
| Pro | Ala | CCA | GCC | 30.8 | 28 | -0.25 | -0.9 |
| Pro | Ala | CCA | GCG | 6.8 | 5 | -0.45 | -0.0 |
| Pro | Ala | CCA | GCT | 57.2 | 38 | -6.45 | -0.7 |
| Pro | Gly | CCA | GGA | 10.9 | 11 | 0.00 | 0.1 |
| Pro | Gly | CCA | GGC | 12.9 | 21 | 5.08 | 3.0 |
| Pro | Gly | CCA | GGG | 7.6 | 7 | -0.05 | -0.3 |
| Pro | Gly | CCA | GGT | 76.8 | 69 | -0.79 | -3.3 |
| Pro | Val | CCA | GTA | 13.6 | 7 | -3.18 | -3.5 |
| Pro | Val | CCA | GTC | 29.5 | 21 | -2.46 | -2.9 |
| Pro | Val | CCA | GTG | 14.3 | 16 | 0.21 | 0.1 |
| Pro | Val | CCA | GTT | 53.2 | 44 | -1.57 | -2.1 |
| Pro | Ocr | CCA | TAA | 0.0 | 0 | 0.00 | 0.0 |
| Pro | Tyr | CCA | TAC | 30.8 | 33 | 0.16 | 0.2 |
| Pro | Amb | CCA | TAG | 0.0 | 0 | 0.00 | 0.0 |
| Pro | Tyr | CCA | TAT | 24.6 | 25 | 0.01 | 0.0 |
| Pro | Ser | CCA | TCA | 22.9 | 24 | 0.06 | 0.0 |
| Pro | Ser | CCA | TCC | 25.5 | 13 | -6.12 | -7.7 |
| Pro | Ser | CCA | TCG | 8.3 | 12 | 1.67 | 1.0 |
| Pro | Ser | CCA | TCT | 44.6 | 42 | -0.15 | -0.8 |
| Pro | Umb | CCA | TGA | 0.0 | 1 | 0.00 | 0.0 |
| Pro | Cys | CCA | TGC | 4.8 | 4 | -0.15 | -0.1 |
| Pro | Trp | CCA | TGG | 17.5 | 22 | 1.17 | 0.7 |
| Pro | Cys | CCA | TGT | 12.9 | 9 | -1.15 | -0.0 |
| Pro | Leu | CCA | TTA | 37.2 | 43 | 0.92 | 1.9 |
| Pro | Phe | CCA | TTC | 35.4 | 34 | -0.05 | -0.0 |
| Pro | Leu | CCA | TTG | 62.2 | 56 | -0.63 | -0.1 |
| Pro | Phe | CCA | TTT | 34.5 | 34 | -0.01 | -0.1 |
| | Page Totals: | | | 1684.0 | 1688 | 133.660 | 97.1 |

PAGE 21

YEAST.RXD/CPLIST.RXR February 7, 1989

| aa1 | aa2 | cod1 | cod2 | exp | obs | chis1 | chis2 |
|---|---|---|---|---|---|---|---|
| Pro | Lys | CCC | AAA | 18.3 | 17 | -0.09 | -0.2 |
| Pro | Asn | CCC | AAC | 11.1 | 11 | -0.00 | -0.0 |
| Pro | Lys | CCC | AAG | 14.5 | 28 | 12.52 | 11.1 |
| Pro | Asn | CCC | AAT | 14.3 | 20 | 2.25 | 2.9 |
| Pro | Thr | CCC | ACA | 7.6 | 13 | 3.87 | 2.6 |
| Pro | Thr | CCC | ACC | 6.1 | 9 | 1.41 | 0.8 |
| Pro | Thr | CCC | ACG | 3.3 | 5 | 0.95 | 0.6 |
| Pro | Thr | CCC | ACT | 9.1 | 10 | 0.08 | 0.0 |
| Pro | Arg | CCC | AGA | 10.3 | 4 | -3.81 | -3.7 |
| Pro | Ser | CCC | AGC | 3.6 | 0 | -3.55 | -3.8 |
| Pro | Arg | CCC | AGG | 3.9 | 2 | -0.93 | -0.9 |
| Pro | Ser | CCC | AGT | 5.1 | 5 | -0.00 | -0.1 |
| Pro | Ile | CCC | ATA | 6.3 | 10 | 2.17 | 2.4 |
| Pro | Ile | CCC | ATC | 7.5 | 8 | 0.04 | 0.1 |
| Pro | Met | CCC | ATG | 10.1 | 7 | -0.93 | -0.9 |
| Pro | Ile | CCC | ATT | 13.6 | 12 | -0.18 | -0.1 |
| Pro | Gln | CCC | CAA | 12.2 | 11 | -0.11 | -0.1 |
| Pro | His | CCC | CAC | 3.5 | 6 | 1.88 | 1.1 |
| Pro | Gln | CCC | CAG | 5.0 | 1 | -3.23 | -3.3 |
| Pro | His | CCC | CAT | 6.0 | 5 | -0.16 | -0.5 |
| Pro | Pro | CCC | CCA | 9.0 | 8 | -0.12 | -0.0 |
| Pro | Pro | CCC | CCC | 4.4 | 3 | -0.42 | -0.2 |
| Pro | Pro | CCC | CCG | 2.2 | 0 | -2.21 | -1.9 |
| Pro | Pro | CCC | CCT | 5.9 | 3 | -1.39 | -0.8 |
| Pro | Arg | CCC | CGA | 1.2 | 0 | -1.23 | -1.2 |
| Pro | Arg | CCC | CGC | 1.1 | 1 | -0.00 | -0.0 |
| Pro | Arg | CCC | CGG | 0.7 | 0 | -0.67 | -0.7 |
| Pro | Arg | CCC | CGT | 3.4 | 4 | 0.11 | 0.1 |
| Pro | Leu | CCC | CTA | 5.6 | 2 | -2.34 | -2.0 |
| Pro | Leu | CCC | CTC | 2.2 | 3 | 0.33 | 0.5 |
| Pro | Leu | CCC | CTG | 4.6 | 2 | -1.49 | -1.3 |
| Pro | Leu | CCC | CTT | 4.9 | 2 | -1.74 | -1.5 |
| Pro | Glu | CCC | GAA | 20.6 | 24 | 0.57 | 0.4 |
| Pro | Asp | CCC | GAC | 9.8 | 11 | 0.15 | 0.9 |
| Pro | Glu | CCC | GAG | 8.6 | 10 | 0.24 | 0.2 |
| Pro | Asp | CCC | GAT | 17.6 | 7 | -6.37 | -4.2 |
| Pro | Ala | CCC | GCA | 7.8 | 4 | -1.88 | -0.7 |
| Pro | Ala | CCC | GCC | 6.9 | 1 | -5.06 | -3.5 |
| Pro | Ala | CCC | GCG | 2.8 | 1 | -1.18 | -0.6 |
| Pro | Ala | CCC | GCT | 11.1 | 12 | 0.08 | 1.5 |
| Pro | Gly | CCC | GGA | 4.3 | 3 | -0.37 | -0.7 |
| Pro | Gly | CCC | GGC | 4.5 | 8 | 2.68 | 1.7 |
| Pro | Gly | CCC | GGG | 3.0 | 1 | -1.37 | -1.7 |
| Pro | Gly | CCC | GGT | 14.9 | 16 | 0.08 | 0.0 |
| Pro | Val | CCC | GTA | 5.1 | 8 | 1.71 | 1.5 |
| Pro | Val | CCC | GTC | 6.4 | 11 | 3.32 | 3.0 |
| Pro | Val | CCC | GTG | 5.1 | 5 | -0.00 | -0.0 |
| Pro | Val | CCC | GTT | 11.1 | 15 | 1.42 | 1.2 |
| Pro | Ocr | CCC | TAA | 0.0 | 0 | 0.00 | 0.0 |
| Pro | Tyr | CCC | TAC | 7.4 | 5 | -0.79 | -0.8 |
| Pro | Amb | CCC | TAG | 0.0 | 0 | 0.00 | 0.0 |
| Pro | Tyr | CCC | TAT | 7.8 | 7 | -0.09 | -0.1 |
| Pro | Ser | CCC | TCA | 7.7 | 8 | 0.01 | 0.0 |
| Pro | Ser | CCC | TCC | 6.3 | 6 | -0.01 | -0.1 |
| Pro | Ser | CCC | TCG | 3.2 | 4 | 0.22 | 0.1 |
| Pro | Ser | CCC | TCT | 10.6 | 16 | 2.79 | 1.8 |
| Pro | Umb | CCC | TGA | 0.0 | 0 | 0.00 | 0.0 |
| Pro | Cys | CCC | TGC | 1.8 | 2 | 0.02 | 0.5 |
| Pro | Trp | CCC | TGG | 4.6 | 4 | -0.08 | -0.2 |
| Pro | Cys | CCC | TGT | 3.4 | 3 | -0.05 | -0.2 |
| Pro | Leu | CCC | TTA | 10.6 | 17 | 3.80 | 4.9 |
| Pro | Phe | CCC | TTC | 8.3 | 10 | 0.33 | 0.6 |
| Pro | Leu | CCC | TTG | 13.6 | 13 | -0.03 | -0.0 |
| Pro | Phe | CCC | TTT | 10.7 | 9 | -0.28 | -0.1 |
| | Page Totals: | | | 452.0 | 453 | 85.2192 | 76.5 |

PAGE 22

YEAST.RXD/CPLIST.RXR February 7, 1989

| aa1 | aa2 | cod1 | cod2 | exp | obs | chis1 | chis2 |
|---|---|---|---|---|---|---|---|
| Pro | Lys | CCG | AAA | 12.1 | 14 | 0.28 | 0.2 |
| Pro | Asn | CCG | AAC | 7.1 | 9 | 0.54 | 0.7 |
| Pro | Lys | CCG | AAG | 8.6 | 3 | -3.61 | -3.9 |
| Pro | Asn | CCG | AAT | 10.0 | 10 | 0.00 | 0.0 |
| Pro | Thr | CCG | ACA | 5.5 | 9 | 2.27 | 1.5 |
| Pro | Thr | CCG | ACC | 3.2 | 2 | -0.47 | -0.7 |
| Pro | Thr | CCG | ACG | 2.4 | 4 | 1.02 | 0.7 |
| Pro | Thr | CCG | ACT | 5.7 | 3 | -1.29 | -1.7 |
| Pro | Arg | CCG | AGA | 6.2 | 4 | -0.78 | -0.7 |
| Pro | Ser | CCG | AGC | 2.8 | 4 | 0.48 | 0.3 |
| Pro | Arg | CCG | AGG | 2.9 | 3 | 0.01 | 0.0 |
| Pro | Ser | CCG | AGT | 4.2 | 3 | -0.35 | -0.5 |
| Pro | Ile | CCG | ATA | 4.6 | 2 | -1.44 | -1.3 |
| Pro | Ile | CCG | ATC | 4.4 | 6 | 0.60 | 0.7 |
| Pro | Met | CCG | ATG | 6.3 | 6 | -0.02 | -0.0 |
| Pro | Ile | CCG | ATT | 8.6 | 7 | -0.31 | -0.2 |
| Pro | Gln | CCG | CAA | 7.7 | 10 | 0.71 | 0.7 |
| Pro | His | CCG | CAC | 2.3 | 2 | -0.05 | -0.2 |
| Pro | Gln | CCG | CAG | 3.4 | 6 | 2.01 | 1.9 |
| Pro | His | CCG | CAT | 3.9 | 10 | 9.46 | 7.0 |
| Pro | Pro | CCG | CCA | 5.3 | 8 | 1.34 | 2.5 |
| Pro | Pro | CCG | CCC | 2.2 | 4 | 1.45 | 2.3 |
| Pro | Pro | CCG | CCG | 2.8 | 1 | -1.14 | -0.8 |
| Pro | Pro | CCG | CCT | 3.7 | 5 | 0.43 | 1.0 |
| Pro | Arg | CCG | CGA | 1.1 | 0 | -1.11 | -1.1 |
| Pro | Arg | CCG | CGC | 0.8 | 0 | -0.78 | -0.8 |
| Pro | Arg | CCG | CGG | 0.6 | 1 | 0.23 | 0.2 |
| Pro | Arg | CCG | CGT | 2.2 | 1 | -0.68 | -0.7 |
| Pro | Leu | CCG | CTA | 3.9 | 3 | -0.20 | -0.1 |
| Pro | Leu | CCG | CTC | 1.4 | 1 | -0.14 | -0.1 |
| Pro | Leu | CCG | CTG | 3.3 | 3 | -0.03 | -0.0 |
| Pro | Leu | CCG | CTT | 3.2 | 3 | -0.01 | -0.0 |
| Pro | Glu | CCG | GAA | 12.9 | 11 | -0.27 | -2.2 |
| Pro | Asp | CCG | GAC | 5.9 | 7 | 0.21 | 0.8 |
| Pro | Glu | CCG | GAG | 5.9 | 11 | 4.34 | 1.2 |
| Pro | Asp | CCG | GAT | 11.4 | 18 | 3.79 | 7.2 |
| Pro | Ala | CCG | GCA | 4.9 | 2 | -1.74 | -0.8 |
| Pro | Ala | CCG | GCC | 3.7 | 3 | -0.13 | -0.0 |
| Pro | Ala | CCG | GCG | 2.1 | 0 | -2.08 | -1.6 |
| Pro | Ala | CCG | GCT | 5.7 | 3 | -1.31 | -0.4 |
| Pro | Gly | CCG | GGA | 2.9 | 5 | 1.58 | 1.0 |
| Pro | Gly | CCG | GGC | 2.7 | 3 | 0.03 | 0.0 |
| Pro | Gly | CCG | GGG | 2.0 | 5 | 4.48 | 3.4 |
| Pro | Gly | CCG | GGT | 7.5 | 5 | -0.80 | -1.3 |
| Pro | Val | CCG | GTA | 3.5 | 4 | 0.08 | 0.1 |
| Pro | Val | CCG | GTC | 3.6 | 5 | 0.59 | 0.5 |
| Pro | Val | CCG | GTG | 3.1 | 1 | -1.38 | -1.5 |
| Pro | Val | CCG | GTT | 6.3 | 4 | -0.85 | -1.0 |
| Pro | Ocr | CCG | TAA | 0.0 | 0 | 0.00 | 0.0 |
| Pro | Tyr | CCG | TAC | 4.1 | 2 | -1.07 | -1.1 |
| Pro | Amb | CCG | TAG | 0.0 | 0 | 0.00 | 0.0 |
| Pro | Tyr | CCG | TAT | 5.4 | 9 | 2.45 | 2.4 |
| Pro | Ser | CCG | TCA | 5.3 | 2 | -2.03 | -2.4 |
| Pro | Ser | CCG | TCC | 3.5 | 4 | 0.06 | 0.0 |
| Pro | Ser | CCG | TCG | 2.5 | 2 | -0.11 | -0.2 |
| Pro | Ser | CCG | TCT | 6.6 | 8 | 0.30 | 0.1 |
| Pro | Umb | CCG | TGA | 0.0 | 0 | 0.00 | 0.0 |
| Pro | Cys | CCG | TGC | 1.1 | 0 | -1.05 | -0.7 |
| Pro | Trp | CCG | TGG | 2.7 | 3 | 0.03 | 0.0 |
| Pro | Cys | CCG | TGT | 2.1 | 1 | -0.57 | -0.1 |
| Pro | Leu | CCG | TTA | 7.1 | 5 | -0.64 | -0.4 |
| Pro | Phe | CCG | TTC | 4.7 | 1 | -2.94 | -2.6 |
| Pro | Leu | CCG | TTG | 7.6 | 5 | -0.86 | -0.6 |
| Pro | Phe | CCG | TTT | 7.4 | 10 | 0.94 | 1.4 |
| | | Page Totals: | | 286.5 | 286 | 69.9172 | 67.7 |

PAGE 23

YEAST.RXD/CPLIST.RXR February 7, 1989

| aa1 | aa2 | cod1 | cod2 | exp | obs | chis1 | chis2 |
|---|---|---|---|---|---|---|---|
| Pro | Lys | CCT | AAA | 35.8 | 27 | -2.14 | -2.8 |
| Pro | Asn | CCT | AAC | 21.8 | 10 | -6.40 | -5.7 |
| Pro | Lys | CCT | AAG | 29.5 | 20 | -3.03 | -3.7 |
| Pro | Asn | CCT | AAT | 27.8 | 17 | -4.17 | -3.4 |
| Pro | Thr | CCT | ACA | 14.9 | 18 | 0.63 | 0.2 |
| Pro | Thr | CCT | ACC | 12.0 | 9 | -0.75 | -1.3 |
| Pro | Thr | CCT | ACG | 6.2 | 13 | 7.63 | 5.8 |
| Pro | Thr | CCT | ACT | 19.4 | 19 | -0.01 | -0.2 |
| Pro | Arg | CCT | AGA | 21.6 | 14 | -2.70 | -2.6 |
| Pro | Ser | CCT | AGC | 6.6 | 3 | -1.92 | -2.3 |
| Pro | Arg | CCT | AGG | 7.1 | 4 | -1.35 | -1.3 |
| Pro | Ser | CCT | AGT | 10.0 | 8 | -0.39 | -0.7 |
| Pro | Ile | CCT | ATA | 11.6 | 8 | -1.14 | -1.0 |
| Pro | Ile | CCT | ATC | 15.2 | 7 | -4.46 | -4.2 |
| Pro | Met | CCT | ATG | 19.9 | 9 | -5.94 | -6.0 |
| Pro | Ile | CCT | ATT | 28.2 | 27 | -0.05 | -0.0 |
| Pro | Gln | CCT | CAA | 25.7 | 33 | 2.09 | 1.9 |
| Pro | His | CCT | CAC | 7.0 | 10 | 1.32 | 0.6 |
| Pro | Gln | CCT | CAG | 8.9 | 10 | 0.15 | 0.1 |
| Pro | His | CCT | CAT | 12.1 | 12 | -0.00 | -0.2 |
| Pro | Pro | CCT | CCA | 19.7 | 22 | 0.28 | 1.5 |
| Pro | Pro | CCT | CCC | 5.9 | 4 | -0.58 | -0.2 |
| Pro | Pro | CCT | CCG | 3.7 | 3 | -0.14 | -0.0 |
| Pro | Pro | CCT | CCT | 13.7 | 16 | 0.38 | 1.5 |
| Pro | Arg | CCT | CGA | 2.3 | 3 | 0.23 | 0.3 |
| Pro | Arg | CCT | CGC | 1.8 | 3 | 0.85 | 0.9 |
| Pro | Arg | CCT | CGG | 0.9 | 0 | -0.91 | -0.9 |
| Pro | Arg | CCT | CGT | 7.9 | 12 | 2.11 | 2.2 |
| Pro | Leu | CCT | CTA | 11.2 | 11 | -0.00 | -0.0 |
| Pro | Leu | CCT | CTC | 3.7 | 3 | -0.12 | -0.1 |
| Pro | Leu | CCT | CTG | 8.2 | 8 | -0.01 | -0.0 |
| Pro | Leu | CCT | CTT | 9.4 | 14 | 2.21 | 3.0 |
| Pro | Glu | CCT | GAA | 43.4 | 56 | 3.64 | 0.1 |
| Pro | Asp | CCT | GAC | 18.4 | 12 | -2.20 | -0.8 |
| Pro | Glu | CCT | GAG | 16.0 | 17 | 0.07 | 0.8 |
| Pro | Asp | CCT | GAT | 34.6 | 42 | 1.60 | 5.5 |
| Pro | Ala | CCT | GCA | 15.2 | 16 | 0.04 | 1.7 |
| Pro | Ala | CCT | GCC | 14.8 | 12 | -0.54 | -0.0 |
| Pro | Ala | CCT | GCG | 4.9 | 3 | -0.76 | -0.2 |
| Pro | Ala | CCT | GCT | 24.7 | 26 | 0.07 | 2.7 |
| Pro | Gly | CCT | GGA | 7.5 | 10 | 0.80 | 0.3 |
| Pro | Gly | CCT | GGC | 8.3 | 20 | 16.37 | 12.3 |
| Pro | Gly | CCT | GGG | 4.9 | 7 | 0.89 | 0.4 |
| Pro | Gly | CCT | GGT | 33.1 | 37 | 0.47 | 0.0 |
| Pro | Val | CCT | GTA | 9.2 | 16 | 5.10 | 4.6 |
| Pro | Val | CCT | GTC | 13.1 | 15 | 0.28 | 0.2 |
| Pro | Val | CCT | GTG | 9.4 | 9 | -0.02 | -0.0 |
| Pro | Val | CCT | GTT | 24.7 | 36 | 5.21 | 4.4 |
| Pro | Ocr | CCT | TAA | 0.0 | 1 | 0.00 | 0.0 |
| Pro | Tyr | CCT | TAC | 14.9 | 14 | -0.06 | -0.1 |
| Pro | Amb | CCT | TAG | 0.0 | 0 | 0.00 | 0.0 |
| Pro | Tyr | CCT | TAT | 15.7 | 16 | 0.01 | 0.0 |
| Pro | Ser | CCT | TCA | 14.8 | 21 | 2.63 | 1.6 |
| Pro | Ser | CCT | TCC | 13.0 | 24 | 9.35 | 7.1 |
| Pro | Ser | CCT | TCG | 5.9 | 9 | 1.67 | 1.1 |
| Pro | Ser | CCT | TCT | 22.8 | 28 | 1.21 | 0.5 |
| Pro | Umb | CCT | TGA | 0.0 | 0 | 0.00 | 0.0 |
| Pro | Cys | CCT | TGC | 3.3 | 2 | -0.49 | -0.0 |
| Pro | Trp | CCT | TGG | 9.3 | 7 | -0.56 | -0.8 |
| Pro | Cys | CCT | TGT | 7.2 | 4 | -1.43 | -0.2 |
| Pro | Leu | CCT | TTA | 22.5 | 19 | -0.55 | -0.2 |
| Pro | Phe | CCT | TTC | 16.7 | 17 | 0.00 | 0.1 |
| Pro | Leu | CCT | TTG | 28.1 | 21 | -1.78 | -1.1 |
| Pro | Phe | CCT | TTT | 21.7 | 15 | -2.07 | -1.3 |
| | | Page Totals: | | 907.1 | 909 | 113.943 | 102.7 |

PAGE 24

YEAST.RXD/CPLIST.RXR February 7, 1989

| aa1 | aa2 | cod1 | cod2 | exp | obs | chis1 | chis2 |
|---|---|---|---|---|---|---|---|
| Arg | Lys | CGA | AAA | 7.9 | 5 | -1.04 | -1.4 |
| Arg | Asn | CGA | AAC | 4.0 | 1 | -2.22 | -2.1 |
| Arg | Lys | CGA | AAG | 4.8 | 8 | 2.09 | 1.5 |
| Arg | Asn | CGA | AAT | 6.8 | 5 | -0.47 | -0.3 |
| Arg | Thr | CGA | ACA | 3.3 | 1 | -1.64 | -1.7 |
| Arg | Thr | CGA | ACC | 1.8 | 1 | -0.33 | -0.4 |
| Arg | Thr | CGA | ACG | 1.6 | 0 | -1.59 | -1.6 |
| Arg | Thr | CGA | ACT | 3.3 | 3 | -0.02 | -0.0 |
| Arg | Arg | CGA | AGA | 3.5 | 5 | 0.69 | 0.1 |
| Arg | Ser | CGA | AGC | 1.7 | 2 | 0.07 | 0.3 |
| Arg | Arg | CGA | AGG | 1.8 | 6 | 9.80 | 6.5 |
| Arg | Ser | CGA | AGT | 2.5 | 3 | 0.09 | 0.4 |
| Arg | Ile | CGA | ATA | 3.2 | 3 | -0.02 | -0.1 |
| Arg | Ile | CGA | ATC | 2.4 | 7 | 8.85 | 7.0 |
| Arg | Met | CGA | ATG | 3.8 | 3 | -0.16 | -0.0 |
| Arg | Ile | CGA | ATT | 5.0 | 6 | 0.19 | 0.0 |
| Arg | Gln | CGA | CAA | 4.8 | 4 | -0.13 | -0.0 |
| Arg | His | CGA | CAC | 1.1 | 0 | -1.14 | -1.5 |
| Arg | Gln | CGA | CAG | 2.4 | 5 | 2.96 | 4.4 |
| Arg | His | CGA | CAT | 2.4 | 6 | 5.54 | 2.9 |
| Arg | Pro | CGA | CCA | 2.8 | 4 | 0.52 | 0.5 |
| Arg | Pro | CGA | CCC | 1.2 | 0 | -1.23 | -1.2 |
| Arg | Pro | CGA | CCG | 1.1 | 0 | -1.11 | -1.1 |
| Arg | Pro | CGA | CCT | 2.3 | 2 | -0.03 | -0.0 |
| Arg | Arg | CGA | CGA | 1.3 | 3 | 2.38 | 1.3 |
| Arg | Arg | CGA | CGC | 0.5 | 0 | -0.47 | -0.6 |
| Arg | Arg | CGA | CGG | 0.4 | 1 | 1.16 | 0.7 |
| Arg | Arg | CGA | CGT | 1.3 | 0 | -1.25 | -1.5 |
| Arg | Leu | CGA | CTA | 2.2 | 1 | -0.63 | -0.6 |
| Arg | Leu | CGA | CTC | 0.9 | 1 | 0.00 | 0.0 |
| Arg | Leu | CGA | CTG | 2.1 | 2 | -0.00 | -0.0 |
| Arg | Leu | CGA | CTT | 2.0 | 3 | 0.47 | 0.5 |
| Arg | Glu | CGA | GAA | 7.4 | 7 | -0.02 | -0.0 |
| Arg | Asp | CGA | GAC | 3.3 | 1 | -1.63 | -1.4 |
| Arg | Glu | CGA | GAG | 3.5 | 7 | 3.43 | 3.4 |
| Arg | Asp | CGA | GAT | 6.8 | 8 | 0.22 | 0.5 |
| Arg | Ala | CGA | GCA | 3.1 | 1 | -1.39 | -1.3 |
| Arg | Ala | CGA | GCC | 1.8 | 0 | -1.80 | -1.7 |
| Arg | Ala | CGA | GCG | 1.3 | 3 | 2.25 | 2.5 |
| Arg | Ala | CGA | GCT | 2.8 | 0 | -2.79 | -2.7 |
| Arg | Gly | CGA | GGA | 1.8 | 2 | 0.02 | 0.1 |
| Arg | Gly | CGA | GGC | 1.5 | 0 | -1.50 | -1.3 |
| Arg | Gly | CGA | GGG | 1.1 | 0 | -1.09 | -1.0 |
| Arg | Gly | CGA | GGT | 3.3 | 3 | -0.02 | -0.0 |
| Arg | Val | CGA | GTA | 2.2 | 4 | 1.49 | 1.7 |
| Arg | Val | CGA | GTC | 1.7 | 1 | -0.31 | -0.3 |
| Arg | Val | CGA | GTG | 1.9 | 0 | -1.86 | -1.8 |
| Arg | Val | CGA | GTT | 3.2 | 0 | -3.19 | -3.1 |
| Arg | Ocr | CGA | TAA | 0.0 | 1 | 0.00 | 0.0 |
| Arg | Tyr | CGA | TAC | 2.4 | 0 | -2.37 | -2.7 |
| Arg | Amb | CGA | TAG | 0.0 | 0 | 0.00 | 0.0 |
| Arg | Tyr | CGA | TAT | 3.3 | 9 | 9.69 | 7.0 |
| Arg | Ser | CGA | TCA | 3.5 | 1 | -1.77 | -1.2 |
| Arg | Ser | CGA | TCC | 1.9 | 3 | 0.65 | 1.4 |
| Arg | Ser | CGA | TCG | 1.4 | 1 | -0.13 | -0.0 |
| Arg | Ser | CGA | TCT | 4.1 | 3 | -0.31 | -0.0 |
| Arg | Umb | CGA | TGA | 0.0 | 0 | 0.00 | 0.0 |
| Arg | Cys | CGA | TGC | 0.8 | 2 | 1.83 | 1.3 |
| Arg | Trp | CGA | TGG | 1.7 | 4 | 2.97 | 1.4 |
| Arg | Cys | CGA | TGT | 1.3 | 3 | 2.37 | 1.6 |
| Arg | Leu | CGA | TTA | 4.3 | 3 | -0.40 | -0.4 |
| Arg | Phe | CGA | TTC | 2.5 | 3 | 0.08 | 0.0 |
| Arg | Leu | CGA | TTG | 4.3 | 7 | 1.69 | 1.7 |
| Arg | Phe | CGA | TTT | 4.5 | 1 | -2.72 | -2.9 |
| | | Page Totals: | | 168.6 | 169 | 98.2907 | 85.0 |

YEAST.RXD/CPLIST.RXR February 7, 1989

| aa1 | aa2 | cod1 | cod2 | exp | obs | chis1 | chis2 |
|---|---|---|---|---|---|---|---|
| Arg | Lys | CGC | AAA | 5.7 | 10 | 3.29 | 2.5 |
| Arg | Asn | CGC | AAC | 3.5 | 7 | 3.61 | 4.1 |
| Arg | Lys | CGC | AAG | 4.2 | 7 | 1.83 | 1.3 |
| Arg | Asn | CGC | AAT | 4.8 | 2 | -1.63 | -1.5 |
| Arg | Thr | CGC | ACA | 2.3 | 3 | 0.19 | 0.2 |
| Arg | Thr | CGC | ACC | 1.7 | 2 | 0.05 | 0.0 |
| Arg | Thr | CGC | ACG | 1.1 | 1 | -0.01 | -0.0 |
| Arg | Thr | CGC | ACT | 2.8 | 1 | -1.19 | -1.2 |
| Arg | Arg | CGC | AGA | 3.0 | 7 | 5.50 | 3.1 |
| Arg | Ser | CGC | AGC | 1.4 | 2 | 0.31 | 0.8 |
| Arg | Arg | CGC | AGG | 1.2 | 2 | 0.46 | 0.1 |
| Arg | Ser | CGC | AGT | 1.9 | 3 | 0.65 | 1.4 |
| Arg | Ile | CGC | ATA | 2.1 | 0 | -2.13 | -2.4 |
| Arg | Ile | CGC | ATC | 2.2 | 1 | -0.63 | -0.8 |
| Arg | Met | CGC | ATG | 3.0 | 3 | -0.00 | -0.1 |
| Arg | Ile | CGC | ATT | 4.1 | 3 | -0.27 | -0.5 |
| Arg | Gln | CGC | CAA | 3.6 | 6 | 1.56 | 2.7 |
| Arg | His | CGC | CAC | 1.1 | 2 | 0.77 | 0.3 |
| Arg | Gln | CGC | CAG | 1.5 | 1 | -0.15 | -0.1 |
| Arg | His | CGC | CAT | 1.7 | 1 | -0.31 | -0.7 |
| Arg | Pro | CGC | CCA | 2.5 | 3 | 0.09 | 0.1 |
| Arg | Pro | CGC | CCC | 1.1 | 0 | -1.05 | -1.1 |
| Arg | Pro | CGC | CCG | 0.8 | 0 | -0.78 | -0.8 |
| Arg | Pro | CGC | CCT | 1.8 | 0 | -1.77 | -1.8 |
| Arg | Arg | CGC | CGA | 0.5 | 2 | 4.96 | 3.5 |
| Arg | Arg | CGC | CGC | 0.6 | 0 | -0.64 | -0.8 |
| Arg | Arg | CGC | CGG | 0.3 | 0 | -0.31 | -0.4 |
| Arg | Arg | CGC | CGT | 1.1 | 2 | 0.86 | 0.4 |
| Arg | Leu | CGC | CTA | 1.8 | 1 | -0.38 | -0.4 |
| Arg | Leu | CGC | CTC | 0.7 | 0 | -0.65 | -0.6 |
| Arg | Leu | CGC | CTG | 1.5 | 1 | -0.19 | -0.2 |
| Arg | Leu | CGC | CTT | 1.6 | 1 | -0.23 | -0.2 |
| Arg | Glu | CGC | GAA | 6.1 | 7 | 0.14 | 0.1 |
| Arg | Asp | CGC | GAC | 2.9 | 2 | -0.29 | -0.2 |
| Arg | Glu | CGC | GAG | 2.7 | 3 | 0.02 | 0.0 |
| Arg | Asp | CGC | GAT | 5.2 | 3 | -0.91 | -0.7 |
| Arg | Ala | CGC | GCA | 2.4 | 2 | -0.06 | -0.0 |
| Arg | Ala | CGC | GCC | 1.8 | 1 | -0.32 | -0.3 |
| Arg | Ala | CGC | GCG | 1.0 | 1 | 0.00 | -0.0 |
| Arg | Ala | CGC | GCT | 3.0 | 2 | -0.32 | -0.3 |
| Arg | Gly | CGC | GGA | 1.3 | 2 | 0.45 | 0.7 |
| Arg | Gly | CGC | GGC | 1.3 | 0 | -1.29 | -1.1 |
| Arg | Gly | CGC | GGG | 0.9 | 0 | -0.86 | -0.8 |
| Arg | Gly | CGC | GGT | 3.8 | 3 | -0.16 | -0.0 |
| Arg | Val | CGC | GTA | 1.7 | 2 | 0.06 | 0.1 |
| Arg | Val | CGC | GTC | 1.7 | 2 | 0.05 | 0.1 |
| Arg | Val | CGC | GTG | 1.5 | 1 | -0.17 | -0.1 |
| Arg | Val | CGC | GTT | 3.2 | 3 | -0.01 | -0.0 |
| Arg | Ocr | CGC | TAA | 0.0 | 2 | 0.00 | 0.0 |
| Arg | Tyr | CGC | TAC | 2.0 | 4 | 1.89 | 1.2 |
| Arg | Amb | CGC | TAG | 0.0 | 0 | 0.00 | 0.0 |
| Arg | Tyr | CGC | TAT | 2.3 | 1 | -0.76 | -1.0 |
| Arg | Ser | CGC | TCA | 2.3 | 3 | 0.19 | 0.7 |
| Arg | Ser | CGC | TCC | 1.8 | 0 | -1.78 | -1.4 |
| Arg | Ser | CGC | TCG | 1.2 | 3 | 2.90 | 4.5 |
| Arg | Ser | CGC | TCT | 3.2 | 4 | 0.22 | 0.8 |
| Arg | Umb | CGC | TGA | 0.0 | 1 | 0.00 | 0.0 |
| Arg | Cys | CGC | TGC | 0.5 | 0 | -0.51 | -0.6 |
| Arg | Trp | CGC | TGG | 1.3 | 3 | 2.16 | 1.0 |
| Arg | Cys | CGC | TGT | 1.0 | 1 | -0.00 | -0.0 |
| Arg | Leu | CGC | TTA | 3.3 | 1 | -1.58 | -1.6 |
| Arg | Phe | CGC | TTC | 2.3 | 2 | -0.04 | -0.1 |
| Arg | Leu | CGC | TTG | 3.9 | 1 | -2.14 | -2.1 |
| Arg | Phe | CGC | TTT | 3.3 | 2 | -0.54 | -0.6 |
| | | Page Totals: | | 135.7 | 136 | 56.2767 | 54.0 |

YEAST.RXD/CPLIST.RXR February 7, 1989

| aa1 | aa2 | cod1 | cod2 | exp | obs | chis1 | chis2 |
|---|---|---|---|---|---|---|---|
| Arg | Lys | CGG | AAA | 3.5 | 8 | 5.71 | 4.7 |
| Arg | Asn | CGG | AAC | 1.9 | 0 | -1.93 | -1.8 |
| Arg | Lys | CGG | AAG | 2.6 | 2 | -0.15 | -0.2 |
| Arg | Asn | CGG | AAT | 2.8 | 2 | -0.24 | -0.2 |
| Arg | Thr | CGG | ACA | 1.5 | 0 | -1.45 | -1.5 |
| Arg | Thr | CGG | ACC | 0.9 | 0 | -0.89 | -0.9 |
| Arg | Thr | CGG | ACG | 0.7 | 2 | 2.71 | 2.6 |
| Arg | Thr | CGG | ACT | 1.5 | 0 | -1.47 | -1.5 |
| Arg | Arg | CGG | AGA | 1.7 | 0 | -1.68 | -2.1 |
| Arg | Ser | CGG | AGC | 0.9 | 0 | -0.85 | -0.7 |
| Arg | Arg | CGG | AGG | 0.9 | 0 | -0.89 | -1.1 |
| Arg | Ser | CGG | AGT | 1.2 | 0 | -1.24 | -1.0 |
| Arg | Ile | CGG | ATA | 1.5 | 1 | -0.18 | -0.3 |
| Arg | Ile | CGG | ATC | 1.1 | 1 | -0.01 | -0.0 |
| Arg | Met | CGG | ATG | 1.9 | 0 | -1.89 | -1.6 |
| Arg | Ile | CGG | ATT | 2.2 | 3 | 0.29 | 0.1 |
| Arg | Gln | CGG | CAA | 2.1 | 3 | 0.44 | 0.9 |
| Arg | His | CGG | CAC | 0.7 | 0 | -0.69 | -0.9 |
| Arg | Gln | CGG | CAG | 1.0 | 2 | 1.09 | 1.6 |
| Arg | His | CGG | CAT | 1.0 | 2 | 1.11 | 0.5 |
| Arg | Pro | CGG | CCA | 1.2 | 0 | -1.23 | -1.2 |
| Arg | Pro | CGG | CCC | 0.7 | 0 | -0.67 | -0.7 |
| Arg | Pro | CGG | CCG | 0.6 | 0 | -0.63 | -0.6 |
| Arg | Pro | CGG | CCT | 0.9 | 2 | 1.29 | 1.3 |
| Arg | Arg | CGG | CGA | 0.4 | 0 | -0.36 | -0.4 |
| Arg | Arg | CGG | CGC | 0.3 | 0 | -0.31 | -0.4 |
| Arg | Arg | CGG | CGG | 0.4 | 0 | -0.44 | -0.5 |
| Arg | Arg | CGG | CGT | 0.6 | 3 | 9.85 | 7.1 |
| Arg | Leu | CGG | CTA | 1.0 | 3 | 4.29 | 4.4 |
| Arg | Leu | CGG | CTC | 0.5 | 0 | -0.45 | -0.4 |
| Arg | Leu | CGG | CTG | 1.1 | 2 | 0.87 | 0.9 |
| Arg | Leu | CGG | CTT | 0.9 | 2 | 1.20 | 1.2 |
| Arg | Glu | CGG | GAA | 3.3 | 6 | 2.25 | 2.2 |
| Arg | Asp | CGG | GAC | 1.7 | 2 | 0.06 | 0.1 |
| Arg | Glu | CGG | GAG | 1.8 | 0 | -1.83 | -1.8 |
| Arg | Asp | CGG | GAT | 3.0 | 1 | -1.29 | -1.1 |
| Arg | Ala | CGG | GCA | 1.4 | 3 | 1.71 | 1.9 |
| Arg | Ala | CGG | GCC | 0.9 | 0 | -0.89 | -0.9 |
| Arg | Ala | CGG | GCG | 0.7 | 0 | -0.71 | -0.7 |
| Arg | Ala | CGG | GCT | 1.4 | 2 | 0.28 | 0.3 |
| Arg | Gly | CGG | GGA | 0.9 | 2 | 1.27 | 1.8 |
| Arg | Gly | CGG | GGC | 0.8 | 0 | -0.75 | -0.7 |
| Arg | Gly | CGG | GGG | 0.5 | 0 | -0.53 | -0.5 |
| Arg | Gly | CGG | GGT | 1.8 | 0 | -1.79 | -1.6 |
| Arg | Val | CGG | GTA | 1.0 | 0 | -1.00 | -1.0 |
| Arg | Val | CGG | GTC | 0.9 | 0 | -0.86 | -0.8 |
| Arg | Val | CGG | GTG | 1.0 | 1 | 0.00 | 0.0 |
| Arg | Val | CGG | GTT | 1.4 | 1 | -0.13 | -0.1 |
| Arg | Ocr | CGG | TAA | 0.0 | 0 | 0.00 | 0.0 |
| Arg | Tyr | CGG | TAC | 1.3 | 3 | 2.32 | 1.6 |
| Arg | Amb | CGG | TAG | 0.0 | 0 | 0.00 | 0.0 |
| Arg | Tyr | CGG | TAT | 1.4 | 2 | 0.24 | 0.1 |
| Arg | Ser | CGG | TCA | 1.4 | 3 | 1.96 | 3.3 |
| Arg | Ser | CGG | TCC | 0.9 | 1 | 0.02 | 0.1 |
| Arg | Ser | CGG | TCG | 0.8 | 3 | 5.93 | 8.4 |
| Arg | Ser | CGG | TCT | 1.7 | 0 | -1.66 | -1.3 |
| Arg | Umb | CGG | TGA | 0.0 | 0 | 0.00 | 0.0 |
| Arg | Cys | CGG | TGC | 0.4 | 0 | -0.39 | -0.5 |
| Arg | Trp | CGG | TGG | 0.8 | 1 | 0.04 | 0.0 |
| Arg | Cys | CGG | TGT | 0.5 | 0 | -0.53 | -0.6 |
| Arg | Leu | CGG | TTA | 2.0 | 1 | -0.49 | -0.5 |
| Arg | Phe | CGG | TTC | 1.3 | 4 | 5.42 | 4.9 |
| Arg | Leu | CGG | TTG | 2.0 | 0 | -1.97 | -2.0 |
| Arg | Phe | CGG | TTT | 2.0 | 5 | 4.44 | 4.0 |
| | | Page Totals: | | 78.8 | 79 | 87.2156 | 86.1 |

PAGE 27

YEAST.RXD/CPLIST.RXR February 7, 1989

| aa1 | aa2 | cod1 | cod2 | exp | obs | chis1 | chis2 |
|---|---|---|---|---|---|---|---|
| Arg | Lys | CGT | AAA | 22.9 | 17 | -1.51 | -2.4 |
| Arg | Asn | CGT | AAC | 15.4 | 10 | -1.88 | -1.5 |
| Arg | Lys | CGT | AAG | 22.2 | 16 | -1.74 | -2.6 |
| Arg | Asn | CGT | AAT | 17.0 | 18 | 0.06 | 0.2 |
| Arg | Thr | CGT | ACA | 9.2 | 9 | -0.01 | -0.0 |
| Arg | Thr | CGT | ACC | 8.9 | 7 | -0.41 | -0.5 |
| Arg | Thr | CGT | ACG | 3.6 | 1 | -1.91 | -2.0 |
| Arg | Thr | CGT | ACT | 13.5 | 7 | -3.14 | -3.4 |
| Arg | Arg | CGT | AGA | 16.7 | 10 | -2.69 | -5.4 |
| Arg | Ser | CGT | AGC | 3.8 | 0 | -3.76 | -3.0 |
| Arg | Arg | CGT | AGG | 4.4 | 2 | -1.33 | -2.2 |
| Arg | Ser | CGT | AGT | 6.3 | 1 | -4.41 | -3.3 |
| Arg | Ile | CGT | ATA | 6.6 | 6 | -0.06 | -0.3 |
| Arg | Ile | CGT | ATC | 11.0 | 11 | 0.00 | 0.1 |
| Arg | Met | CGT | ATG | 14.0 | 10 | -1.14 | -0.3 |
| Arg | Ile | CGT | ATT | 19.8 | 25 | 1.38 | 0.4 |
| Arg | Gln | CGT | CAA | 18.9 | 23 | 0.87 | 2.8 |
| Arg | His | CGT | CAC | 4.5 | 6 | 0.47 | 0.0 |
| Arg | Gln | CGT | CAG | 5.2 | 1 | -3.38 | -2.7 |
| Arg | His | CGT | CAT | 7.6 | 9 | 0.25 | 0.1 |
| Arg | Pro | CGT | CCA | 14.9 | 14 | -0.06 | -0.1 |
| Arg | Pro | CGT | CCC | 3.4 | 7 | 3.81 | 3.8 |
| Arg | Pro | CGT | CCG | 2.2 | 2 | -0.03 | -0.0 |
| Arg | Pro | CGT | CCT | 7.9 | 5 | -1.07 | -1.1 |
| Arg | Arg | CGT | CGA | 1.3 | 1 | -0.05 | -0.2 |
| Arg | Arg | CGT | CGC | 1.1 | 2 | 0.86 | 0.4 |
| Arg | Arg | CGT | CGG | 0.6 | 0 | -0.59 | -0.7 |
| Arg | Arg | CGT | CGT | 7.8 | 16 | 8.64 | 4.3 |
| Arg | Leu | CGT | CTA | 7.3 | 10 | 0.96 | 1.0 |
| Arg | Leu | CGT | CTC | 2.1 | 2 | -0.00 | -0.0 |
| Arg | Leu | CGT | CTG | 5.1 | 4 | -0.25 | -0.2 |
| Arg | Leu | CGT | CTT | 5.8 | 3 | -1.38 | -1.3 |
| Arg | Glu | CGT | GAA | 31.4 | 25 | -1.31 | -1.3 |
| Arg | Asp | CGT | GAC | 13.7 | 17 | 0.82 | 1.5 |
| Arg | Glu | CGT | GAG | 10.3 | 9 | -0.17 | -0.2 |
| Arg | Asp | CGT | GAT | 23.4 | 23 | -0.01 | -0.1 |
| Arg | Ala | CGT | GCA | 9.6 | 6 | -1.34 | -1.1 |
| Arg | Ala | CGT | GCC | 10.5 | 14 | 1.20 | 1.5 |
| Arg | Ala | CGT | GCG | 2.9 | 7 | 5.69 | 6.2 |
| Arg | Ala | CGT | GCT | 18.1 | 22 | 0.86 | 1.2 |
| Arg | Gly | CGT | GGA | 4.8 | 4 | -0.13 | -0.0 |
| Arg | Gly | CGT | GGC | 5.2 | 11 | 6.35 | 8.9 |
| Arg | Gly | CGT | GGG | 3.1 | 7 | 4.75 | 6.5 |
| Arg | Gly | CGT | GGT | 26.0 | 24 | -0.16 | -0.1 |
| Arg | Val | CGT | GTA | 6.0 | 10 | 2.70 | 3.1 |
| Arg | Val | CGT | GTC | 10.3 | 20 | 9.09 | 10.1 |
| Arg | Val | CGT | GTG | 5.9 | 9 | 1.62 | 1.9 |
| Arg | Val | CGT | GTT | 18.4 | 16 | -0.32 | -0.2 |
| Arg | Ocr | CGT | TAA | 0.0 | 0 | 0.00 | 0.0 |
| Arg | Tyr | CGT | TAC | 10.7 | 21 | 10.06 | 6.3 |
| Arg | Amb | CGT | TAG | 0.0 | 1 | 0.00 | 0.0 |
| Arg | Tyr | CGT | TAT | 10.2 | 15 | 2.22 | 0.9 |
| Arg | Ser | CGT | TCA | 9.0 | 4 | -2.80 | -1.5 |
| Arg | Ser | CGT | TCC | 8.9 | 12 | 1.08 | 3.2 |
| Arg | Ser | CGT | TCG | 3.6 | 4 | 0.04 | 0.4 |
| Arg | Ser | CGT | TCT | 16.0 | 15 | -0.06 | -0.3 |
| Arg | Umb | CGT | TGA | 0.0 | 0 | 0.00 | 0.0 |
| Arg | Cys | CGT | TGC | 2.0 | 5 | 4.78 | 3.3 |
| Arg | Trp | CGT | TGG | 5.9 | 7 | 0.21 | 0.1 |
| Arg | Cys | CGT | TGT | 5.1 | 8 | 1.67 | 0.7 |
| Arg | Leu | CGT | TTA | 14.9 | 22 | 3.35 | 3.5 |
| Arg | Phe | CGT | TTC | 12.1 | 7 | -2.12 | -2.5 |
| Arg | Leu | CGT | TTG | 20.9 | 18 | -0.40 | -0.4 |
| Arg | Phe | CGT | TTT | 13.6 | 7 | -3.23 | -3.7 |
| | | Page Totals: | | 623.6 | 625 | 116.617 | 117.2 |

PAGE 28

YEAST.RXD/CPLIST.RXR February 7, 1989

| aa1 | aa2 | cod1 | cod2 | exp | obs | chis1 | chis2 |
|---|---|---|---|---|---|---|---|
| Leu | Lys | CTA | AAA | 34.4 | 40 | 0.92 | 0.0 |
| Leu | Asn | CTA | AAC | 21.5 | 21 | -0.01 | -0.0 |
| Leu | Lys | CTA | AAG | 29.0 | 32 | 0.31 | 0.0 |
| Leu | Asn | CTA | AAT | 27.6 | 27 | -0.02 | -0.0 |
| Leu | Thr | CTA | ACA | 14.1 | 14 | -0.00 | -0.0 |
| Leu | Thr | CTA | ACC | 11.6 | 10 | -0.23 | -0.3 |
| Leu | Thr | CTA | ACG | 5.9 | 7 | 0.19 | 0.2 |
| Leu | Thr | CTA | ACT | 18.9 | 15 | -0.81 | -0.9 |
| Leu | Arg | CTA | AGA | 21.0 | 26 | 1.21 | 0.8 |
| Leu | Ser | CTA | AGC | 6.5 | 7 | 0.04 | 0.0 |
| Leu | Arg | CTA | AGG | 7.1 | 5 | -0.62 | -0.8 |
| Leu | Ser | CTA | AGT | 10.3 | 12 | 0.29 | 0.1 |
| Leu | Ile | CTA | ATA | 11.7 | 9 | -0.61 | -0.0 |
| Leu | Ile | CTA | ATC | 14.8 | 10 | -1.55 | -0.3 |
| Leu | Met | CTA | ATG | 19.1 | 12 | -2.64 | -1.8 |
| Leu | Ile | CTA | ATT | 28.1 | 18 | -3.61 | -0.8 |
| Leu | Gln | CTA | CAA | 24.6 | 27 | 0.23 | 0.0 |
| Leu | His | CTA | CAC | 6.8 | 4 | -1.17 | -0.9 |
| Leu | Gln | CTA | CAG | 8.7 | 11 | 0.60 | 0.2 |
| Leu | His | CTA | CAT | 11.5 | 12 | 0.03 | 0.2 |
| Leu | Pro | CTA | CCA | 18.1 | 24 | 1.93 | 0.1 |
| Leu | Pro | CTA | CCC | 5.6 | 6 | 0.02 | 0.1 |
| Leu | Pro | CTA | CCG | 3.9 | 10 | 9.72 | 5.7 |
| Leu | Pro | CTA | CCT | 11.2 | 12 | 0.06 | 0.2 |
| Leu | Arg | CTA | CGA | 2.2 | 3 | 0.32 | 0.3 |
| Leu | Arg | CTA | CGC | 1.8 | 3 | 0.75 | 0.6 |
| Leu | Arg | CTA | CGG | 1.0 | 0 | -0.97 | -1.0 |
| Leu | Arg | CTA | CGT | 7.3 | 4 | -1.52 | -1.7 |
| Leu | Leu | CTA | CTA | 13.0 | 13 | 0.00 | 0.1 |
| Leu | Leu | CTA | CTC | 3.8 | 4 | 0.02 | 0.1 |
| Leu | Leu | CTA | CTG | 8.5 | 11 | 0.71 | 1.3 |
| Leu | Leu | CTA | CTT | 9.5 | 8 | -0.23 | -0.1 |
| Leu | Glu | CTA | GAA | 42.3 | 43 | 0.01 | 0.0 |
| Leu | Asp | CTA | GAC | 18.7 | 26 | 2.83 | 2.5 |
| Leu | Glu | CTA | GAG | 16.1 | 21 | 1.52 | 1.1 |
| Leu | Asp | CTA | GAT | 34.2 | 30 | -0.52 | -0.7 |
| Leu | Ala | CTA | GCA | 14.3 | 20 | 2.27 | 3.0 |
| Leu | Ala | CTA | GCC | 13.5 | 12 | -0.17 | -0.1 |
| Leu | Ala | CTA | GCG | 4.7 | 5 | 0.02 | 0.1 |
| Leu | Ala | CTA | GCT | 22.9 | 10 | -7.25 | -6.4 |
| Leu | Gly | CTA | GGA | 7.6 | 7 | -0.04 | -0.0 |
| Leu | Gly | CTA | GGC | 8.4 | 5 | -1.37 | -1.3 |
| Leu | Gly | CTA | GGG | 5.0 | 3 | -0.79 | -0.7 |
| Leu | Gly | CTA | GGT | 31.6 | 34 | 0.19 | 0.3 |
| Leu | Val | CTA | GTA | 9.5 | 13 | 1.34 | 2.0 |
| Leu | Val | CTA | GTC | 12.7 | 11 | -0.22 | -0.1 |
| Leu | Val | CTA | GTG | 9.2 | 7 | -0.53 | -0.3 |
| Leu | Val | CTA | GTT | 23.4 | 16 | -2.33 | -1.5 |
| Leu | Ocr | CTA | TAA | 0.0 | 1 | 0.00 | 0.0 |
| Leu | Tyr | CTA | TAC | 14.4 | 1 | -12.45 | -11.1 |
| Leu | Amb | CTA | TAG | 0.0 | 1 | 0.00 | 0.0 |
| Leu | Tyr | CTA | TAT | 15.2 | 21 | 2.25 | 3.8 |
| Leu | Ser | CTA | TCA | 14.7 | 22 | 3.69 | 2.3 |
| Leu | Ser | CTA | TCC | 12.2 | 10 | -0.39 | -0.8 |
| Leu | Ser | CTA | TCG | 5.8 | 13 | 9.09 | 7.2 |
| Leu | Ser | CTA | TCT | 21.6 | 24 | 0.27 | 0.0 |
| Leu | Umb | CTA | TGA | 0.0 | 0 | 0.00 | 0.0 |
| Leu | Cys | CTA | TGC | 3.2 | 4 | 0.20 | 0.0 |
| Leu | Trp | CTA | TGG | 9.2 | 6 | -1.11 | -0.5 |
| Leu | Cys | CTA | TGT | 7.1 | 14 | 6.81 | 3.9 |
| Leu | Leu | CTA | TTA | 22.1 | 24 | 0.16 | 0.7 |
| Leu | Phe | CTA | TTC | 16.4 | 15 | -0.11 | -0.0 |
| Leu | Leu | CTA | TTG | 27.7 | 26 | -0.11 | -0.0 |
| Leu | Phe | CTA | TTT | 20.9 | 23 | 0.21 | 0.4 |
| | Page Totals: | | | 883.1 | 885 | 89.5753 | 69.3 |

PAGE 29

YEAST.RXD/CPLIST.RXR February 7, 1989

| aa1 | aa2 | cod1 | cod2 | exp | obs | chis1 | chis2 |
|---|---|---|---|---|---|---|---|
| Leu | Lys | CTC | AAA | 11.6 | 18 | 3.48 | 1.6 |
| Leu | Asn | CTC | AAC | 7.0 | 9 | 0.60 | 0.9 |
| Leu | Lys | CTC | AAG | 9.0 | 13 | 1.78 | 0.7 |
| Leu | Asn | CTC | AAT | 10.2 | 13 | 0.80 | 1.1 |
| Leu | Thr | CTC | ACA | 5.1 | 3 | -0.87 | -0.9 |
| Leu | Thr | CTC | ACC | 3.6 | 7 | 3.31 | 3.2 |
| Leu | Thr | CTC | ACG | 2.2 | 6 | 6.41 | 6.2 |
| Leu | Thr | CTC | ACT | 5.6 | 4 | -0.46 | -0.5 |
| Leu | Arg | CTC | AGA | 6.7 | 5 | -0.41 | -0.5 |
| Leu | Ser | CTC | AGC | 2.4 | 1 | -0.80 | -1.0 |
| Leu | Arg | CTC | AGG | 2.7 | 4 | 0.60 | 0.5 |
| Leu | Ser | CTC | AGT | 3.6 | 2 | -0.69 | -0.9 |
| Leu | Ile | CTC | ATA | 4.8 | 7 | 1.03 | 2.7 |
| Leu | Ile | CTC | ATC | 4.5 | 2 | -1.38 | -0.7 |
| Leu | Met | CTC | ATG | 6.5 | 4 | -0.97 | -0.7 |
| Leu | Ile | CTC | ATT | 8.9 | 6 | -0.93 | -0.1 |
| Leu | Gln | CTC | CAA | 7.5 | 3 | -2.71 | -3.3 |
| Leu | His | CTC | CAC | 2.2 | 0 | -2.16 | -2.0 |
| Leu | Gln | CTC | CAG | 3.3 | 5 | 0.88 | 0.5 |
| Leu | His | CTC | CAT | 3.9 | 3 | -0.21 | -0.1 |
| Leu | Pro | CTC | CCA | 5.1 | 5 | -0.00 | -0.3 |
| Leu | Pro | CTC | CCC | 2.2 | 4 | 1.59 | 0.7 |
| Leu | Pro | CTC | CCG | 1.4 | 1 | -0.14 | -0.3 |
| Leu | Pro | CTC | CCT | 3.7 | 3 | -0.12 | -0.5 |
| Leu | Arg | CTC | CGA | 0.9 | 2 | 1.21 | 1.1 |
| Leu | Arg | CTC | CGC | 0.7 | 2 | 2.83 | 2.6 |
| Leu | Arg | CTC | CGG | 0.5 | 1 | 0.67 | 0.6 |
| Leu | Arg | CTC | CGT | 2.1 | 5 | 4.02 | 3.7 |
| Leu | Leu | CTC | CTA | 3.8 | 1 | -2.02 | -1.7 |
| Leu | Leu | CTC | CTC | 2.3 | 1 | -0.70 | -0.6 |
| Leu | Leu | CTC | CTG | 3.2 | 2 | -0.42 | -0.3 |
| Leu | Leu | CTC | CTT | 3.4 | 1 | -1.66 | -1.4 |
| Leu | Glu | CTC | GAA | 12.5 | 7 | -2.42 | -2.8 |
| Leu | Asp | CTC | GAC | 5.8 | 2 | -2.53 | -2.6 |
| Leu | Glu | CTC | GAG | 5.9 | 5 | -0.13 | -0.2 |
| Leu | Asp | CTC | GAT | 11.3 | 16 | 1.96 | 1.7 |
| Leu | Ala | CTC | GCA | 5.3 | 2 | -2.06 | -1.8 |
| Leu | Ala | CTC | GCC | 3.7 | 4 | 0.02 | 0.1 |
| Leu | Ala | CTC | GCG | 1.8 | 3 | 0.82 | 1.0 |
| Leu | Ala | CTC | GCT | 6.1 | 1 | -4.31 | -4.0 |
| Leu | Gly | CTC | GGA | 2.9 | 2 | -0.26 | -0.2 |
| Leu | Gly | CTC | GGC | 2.7 | 3 | 0.04 | 0.1 |
| Leu | Gly | CTC | GGG | 1.9 | 2 | 0.01 | 0.0 |
| Leu | Gly | CTC | GGT | 7.9 | 6 | -0.46 | -0.4 |
| Leu | Val | CTC | GTA | 3.4 | 4 | 0.12 | 0.2 |
| Leu | Val | CTC | GTC | 3.7 | 1 | -1.95 | -1.7 |
| Leu | Val | CTC | GTG | 3.1 | 4 | 0.29 | 0.5 |
| Leu | Val | CTC | GTT | 6.5 | 9 | 0.97 | 1.4 |
| Leu | Ocr | CTC | TAA | 0.0 | 1 | 0.00 | 0.0 |
| Leu | Tyr | CTC | TAC | 4.5 | 7 | 1.37 | 2.1 |
| Leu | Amb | CTC | TAG | 0.0 | 0 | 0.00 | 0.0 |
| Leu | Tyr | CTC | TAT | 5.1 | 4 | -0.25 | -0.1 |
| Leu | Ser | CTC | TCA | 5.1 | 6 | 0.16 | 0.0 |
| Leu | Ser | CTC | TCC | 3.4 | 8 | 6.10 | 4.9 |
| Leu | Ser | CTC | TCG | 2.1 | 2 | -0.00 | -0.0 |
| Leu | Ser | CTC | TCT | 6.7 | 6 | -0.06 | -0.2 |
| Leu | Umb | CTC | TGA | 0.0 | 0 | 0.00 | 0.0 |
| Leu | Cys | CTC | TGC | 1.2 | 2 | 0.63 | 0.3 |
| Leu | Trp | CTC | TGG | 3.1 | 1 | -1.42 | -1.0 |
| Leu | Cys | CTC | TGT | 2.1 | 2 | -0.00 | -0.1 |
| Leu | Leu | CTC | TTA | 7.2 | 5 | -0.69 | -0.4 |
| Leu | Phe | CTC | TTC | 5.3 | 9 | 2.68 | 3.0 |
| Leu | Leu | CTC | TTG | 8.0 | 11 | 1.10 | 1.8 |
| Leu | Phe | CTC | TTT | 7.1 | 8 | 0.12 | 0.2 |
| | Page Totals: | | | 285.3 | 286 | 78.7651 | 74.9 |

PAGE 30

YEAST.RXD/CPLIST.RXR February 7, 1989

| aa1 | aa2 | cod1 | cod2 | exp | obs | chis1 | chis2 |
|---|---|---|---|---|---|---|---|
| Leu | Lys | CTG | AAA | 26.8 | 41 | 7.54 | 3.5 |
| Leu | Asn | CTG | AAC | 16.3 | 13 | -0.66 | -0.4 |
| Leu | Lys | CTG | AAG | 20.5 | 21 | 0.01 | 0.3 |
| Leu | Asn | CTG | AAT | 22.1 | 22 | -0.00 | -0.0 |
| Leu | Thr | CTG | ACA | 11.1 | 15 | 1.35 | 1.2 |
| Leu | Thr | CTG | ACC | 8.2 | 5 | -1.24 | -1.3 |
| Leu | Thr | CTG | ACG | 4.9 | 5 | 0.00 | 0.0 |
| Leu | Thr | CTG | ACT | 13.2 | 14 | 0.04 | 0.0 |
| Leu | Arg | CTG | AGA | 14.3 | 8 | -2.76 | -3.1 |
| Leu | Ser | CTG | AGC | 5.3 | 2 | -2.03 | -2.4 |
| Leu | Arg | CTG | AGG | 6.0 | 5 | -0.16 | -0.2 |
| Leu | Ser | CTG | AGT | 8.3 | 8 | -0.01 | -0.1 |
| Leu | Ile | CTG | ATA | 10.1 | 10 | -0.00 | -0.5 |
| Leu | Ile | CTG | ATC | 10.4 | 7 | -1.12 | -0.2 |
| Leu | Met | CTG | ATG | 14.4 | 10 | -1.35 | -0.8 |
| Leu | Ile | CTG | ATT | 19.6 | 16 | -0.66 | -0.0 |
| Leu | Gln | CTG | CAA | 17.5 | 21 | 0.69 | 0.2 |
| Leu | His | CTG | CAC | 4.9 | 6 | 0.24 | 0.4 |
| Leu | Gln | CTG | CAG | 7.5 | 3 | -2.72 | -3.3 |
| Leu | His | CTG | CAT | 8.4 | 10 | 0.29 | 0.6 |
| Leu | Pro | CTG | CCA | 11.9 | 14 | 0.37 | 0.0 |
| Leu | Pro | CTG | CCC | 4.6 | 4 | -0.08 | -0.5 |
| Leu | Pro | CTG | CCG | 3.3 | 6 | 2.15 | 0.9 |
| Leu | Pro | CTG | CCT | 8.2 | 4 | -2.15 | -3.7 |
| Leu | Arg | CTG | CGA | 2.1 | 2 | -0.00 | -0.0 |
| Leu | Arg | CTG | CGC | 1.5 | 0 | -1.54 | -1.6 |
| Leu | Arg | CTG | CGG | 1.1 | 0 | -1.05 | -1.1 |
| Leu | Arg | CTG | CGT | 5.1 | 7 | 0.68 | 0.5 |
| Leu | Leu | CTG | CTA | 8.5 | 9 | 0.03 | 0.2 |
| Leu | Leu | CTG | CTC | 3.2 | 1 | -1.47 | -1.2 |
| Leu | Leu | CTG | CTG | 8.2 | 7 | -0.19 | -0.0 |
| Leu | Leu | CTG | CTT | 7.3 | 9 | 0.39 | 0.8 |
| Leu | Glu | CTG | GAA | 28.7 | 45 | 9.28 | 7.7 |
| Leu | Asp | CTG | GAC | 13.6 | 13 | -0.02 | -0.1 |
| Leu | Glu | CTG | GAG | 12.2 | 9 | -0.84 | -1.1 |
| Leu | Asp | CTG | GAT | 24.9 | 28 | 0.38 | 0.3 |
| Leu | Ala | CTG | GCA | 11.0 | 10 | -0.10 | -0.0 |
| Leu | Ala | CTG | GCC | 9.0 | 9 | 0.00 | 0.0 |
| Leu | Ala | CTG | GCG | 4.1 | 7 | 2.08 | 2.5 |
| Leu | Ala | CTG | GCT | 14.1 | 15 | 0.06 | 0.2 |
| Leu | Gly | CTG | GGA | 6.1 | 7 | 0.13 | 0.2 |
| Leu | Gly | CTG | GGC | 6.3 | 7 | 0.08 | 0.1 |
| Leu | Gly | CTG | GGG | 4.1 | 4 | -0.00 | -0.0 |
| Leu | Gly | CTG | GGT | 18.6 | 23 | 1.06 | 1.2 |
| Leu | Val | CTG | GTA | 7.5 | 13 | 4.09 | 5.2 |
| Leu | Val | CTG | GTC | 8.3 | 9 | 0.05 | 0.2 |
| Leu | Val | CTG | GTG | 7.1 | 7 | -0.00 | -0.0 |
| Leu | Val | CTG | GTT | 15.1 | 14 | -0.09 | -0.0 |
| Leu | Ocr | CTG | TAA | 0.0 | 1 | 0.00 | 0.0 |
| Leu | Tyr | CTG | TAC | 10.1 | 18 | 6.11 | 8.4 |
| Leu | Amb | CTG | TAG | 0.0 | 0 | 0.00 | 0.0 |
| Leu | Tyr | CTG | TAT | 12.1 | 6 | -3.07 | -2.3 |
| Leu | Ser | CTG | TCA | 11.2 | 9 | -0.45 | -0.9 |
| Leu | Ser | CTG | TCC | 8.7 | 9 | 0.01 | 0.0 |
| Leu | Ser | CTG | TCG | 4.9 | 2 | -1.72 | -2.1 |
| Leu | Ser | CTG | TCT | 15.5 | 12 | -0.81 | -1.5 |
| Leu | Umb | CTG | TGA | 0.0 | 0 | 0.00 | 0.0 |
| Leu | Cys | CTG | TGC | 2.5 | 2 | -0.11 | -0.3 |
| Leu | Trp | CTG | TGG | 7.1 | 6 | -0.16 | -0.0 |
| Leu | Cys | CTG | TGT | 5.2 | 0 | -5.17 | -6.1 |
| Leu | Leu | CTG | TTA | 16.1 | 13 | -0.60 | -0.2 |
| Leu | Phe | CTG | TTC | 12.1 | 15 | 0.69 | 0.9 |
| Leu | Leu | CTG | TTG | 18.4 | 21 | 0.36 | 1.0 |
| Leu | Phe | CTG | TTT | 16.0 | 8 | -4.02 | -3.7 |
| | | Page Totals: | | 645.6 | 647 | 74.5191 | 75.3 |

YEAST.RXD/CPLIST.RXR February 7, 1989

| aa1 | aa2 | cod1 | cod2 | exp | obs | chis1 | chis2 |
|---|---|---|---|---|---|---|---|
| Leu | Lys | CTT | AAA | 28.9 | 12 | -9.88 | -13.4 |
| Leu | Asn | CTT | AAC | 16.7 | 12 | -1.31 | -0.9 |
| Leu | Lys | CTT | AAG | 22.1 | 7 | -10.33 | -13.3 |
| Leu | Asn | CTT | AAT | 24.2 | 11 | -7.23 | -6.3 |
| Leu | Thr | CTT | ACA | 12.3 | 4 | -5.63 | -5.8 |
| Leu | Thr | CTT | ACC | 8.9 | 4 | -2.66 | -2.8 |
| Leu | Thr | CTT | ACG | 5.3 | 3 | -1.03 | -1.1 |
| Leu | Thr | CTT | ACT | 14.9 | 6 | -5.33 | -5.5 |
| Leu | Arg | CTT | AGA | 16.4 | 5 | -7.92 | -8.5 |
| Leu | Ser | CTT | AGC | 5.7 | 0 | -5.67 | -6.2 |
| Leu | Arg | CTT | AGG | 6.1 | 1 | -4.30 | -4.5 |
| Leu | Ser | CTT | AGT | 8.7 | 1 | -6.79 | -7.6 |
| Leu | Ile | CTT | ATA | 10.6 | 10 | -0.04 | -0.3 |
| Leu | Ile | CTT | ATC | 11.5 | 10 | -0.20 | -0.1 |
| Leu | Met | CTT | ATG | 16.2 | 10 | -2.37 | -1.6 |
| Leu | Ile | CTT | ATT | 23.0 | 13 | -4.36 | -1.5 |
| Leu | Gln | CTT | CAA | 19.1 | 20 | 0.04 | 0.0 |
| Leu | His | CTT | CAC | 5.4 | 6 | 0.06 | 0.2 |
| Leu | Gln | CTT | CAG | 7.4 | 4 | -1.57 | -2.1 |
| Leu | His | CTT | CAT | 9.6 | 13 | 1.18 | 1.8 |
| Leu | Pro | CTT | CCA | 13.8 | 16 | 0.36 | 0.1 |
| Leu | Pro | CTT | CCC | 4.9 | 5 | 0.00 | 0.2 |
| Leu | Pro | CTT | CCG | 3.2 | 4 | 0.21 | 0.0 |
| Leu | Pro | CTT | CCT | 9.4 | 6 | -1.25 | -2.7 |
| Leu | Arg | CTT | CGA | 2.0 | 2 | -0.00 | -0.0 |
| Leu | Arg | CTT | CGC | 1.6 | 0 | -1.61 | -1.7 |
| Leu | Arg | CTT | CGG | 0.9 | 4 | 9.99 | 9.4 |
| Leu | Arg | CTT | CGT | 5.8 | 7 | 0.23 | 0.1 |
| Leu | Leu | CTT | CTA | 9.5 | 12 | 0.67 | 1.3 |
| Leu | Leu | CTT | CTC | 3.4 | 2 | -0.55 | -0.4 |
| Leu | Leu | CTT | CTG | 7.3 | 9 | 0.39 | 0.8 |
| Leu | Leu | CTT | CTT | 9.8 | 10 | 0.00 | 0.1 |
| Leu | Glu | CTT | GAA | 33.5 | 34 | 0.01 | 0.0 |
| Leu | Asp | CTT | GAC | 14.4 | 15 | 0.02 | 0.0 |
| Leu | Glu | CTT | GAG | 13.5 | 10 | -0.91 | -1.2 |
| Leu | Asp | CTT | GAT | 28.7 | 26 | -0.25 | -0.4 |
| Leu | Ala | CTT | GCA | 12.6 | 9 | -1.04 | -0.8 |
| Leu | Ala | CTT | GCC | 10.0 | 9 | -0.11 | -0.0 |
| Leu | Ala | CTT | GCG | 4.1 | 5 | 0.22 | 0.3 |
| Leu | Ala | CTT | GCT | 16.8 | 24 | 3.14 | 4.1 |
| Leu | Gly | CTT | GGA | 6.8 | 8 | 0.22 | 0.3 |
| Leu | Gly | CTT | GGC | 6.7 | 6 | -0.07 | -0.1 |
| Leu | Gly | CTT | GGG | 4.4 | 3 | -0.43 | -0.4 |
| Leu | Gly | CTT | GGT | 23.0 | 27 | 0.71 | 0.8 |
| Leu | Val | CTT | GTA | 8.1 | 7 | -0.15 | -0.0 |
| Leu | Val | CTT | GTC | 9.4 | 14 | 2.31 | 3.2 |
| Leu | Val | CTT | GTG | 7.9 | 8 | 0.00 | 0.1 |
| Leu | Val | CTT | GTT | 18.3 | 16 | -0.30 | -0.1 |
| Leu | Ocr | CTT | TAA | 0.0 | 0 | 0.00 | 0.0 |
| Leu | Tyr | CTT | TAC | 11.2 | 17 | 3.01 | 4.6 |
| Leu | Amb | CTT | TAG | 0.0 | 0 | 0.00 | 0.0 |
| Leu | Tyr | CTT | TAT | 13.0 | 22 | 6.21 | 8.8 |
| Leu | Ser | CTT | TCA | 13.0 | 22 | 6.17 | 4.3 |
| Leu | Ser | CTT | TCC | 9.8 | 13 | 1.07 | 0.5 |
| Leu | Ser | CTT | TCG | 5.2 | 8 | 1.49 | 0.9 |
| Leu | Ser | CTT | TCT | 17.5 | 40 | 28.82 | 22.8 |
| Leu | Umb | CTT | TGA | 0.0 | 1 | 0.00 | 0.0 |
| Leu | Cys | CTT | TGC | 2.8 | 4 | 0.47 | 0.1 |
| Leu | Trp | CTT | TGG | 7.5 | 8 | 0.03 | 0.4 |
| Leu | Cys | CTT | TGT | 5.8 | 17 | 21.57 | 15.2 |
| Leu | Leu | CTT | TTA | 18.6 | 27 | 3.85 | 5.9 |
| Leu | Phe | CTT | TTC | 12.6 | 35 | 39.93 | 42.5 |
| Leu | Leu | CTT | TTG | 21.4 | 43 | 21.76 | 28.0 |
| Leu | Phe | CTT | TTT | 18.2 | 14 | -0.96 | -0.8 |
| | | Page Totals: | | 719.5 | 721 | 238.352 | 246.7 |

YEAST.RXD/CPLIST.RXR February 7, 1989

| aa1 | aa2 | cod1 | cod2 | exp | obs | chis1 | chis2 |
|---|---|---|---|---|---|---|---|
| Glu | Lys | GAA | AAA | 139.9 | 133 | -0.34 | -1.2 |
| Glu | Asn | GAA | AAC | 93.0 | 101 | 0.68 | 0.1 |
| Glu | Lys | GAA | AAG | 142.1 | 162 | 2.79 | 1.3 |
| Glu | Asn | GAA | AAT | 102.1 | 109 | 0.47 | 0.3 |
| Glu | Thr | GAA | ACA | 50.4 | 50 | -0.00 | -0.1 |
| Glu | Thr | GAA | ACC | 52.8 | 54 | 0.03 | 0.3 |
| Glu | Thr | GAA | ACG | 20.7 | 24 | 0.52 | 0.9 |
| Glu | Thr | GAA | ACT | 82.9 | 71 | -1.70 | -0.8 |
| Glu | Arg | GAA | AGA | 97.6 | 99 | 0.02 | 0.0 |
| Glu | Ser | GAA | AGC | 23.3 | 24 | 0.02 | 1.4 |
| Glu | Arg | GAA | AGG | 25.8 | 42 | 10.21 | 9.7 |
| Glu | Ser | GAA | AGT | 35.9 | 41 | 0.74 | 5.0 |
| Glu | Ile | GAA | ATA | 42.2 | 42 | -0.00 | -0.2 |
| Glu | Ile | GAA | ATC | 67.2 | 66 | -0.02 | -0.4 |
| Glu | Met | GAA | ATG | 80.6 | 87 | 0.51 | 1.3 |
| Glu | Ile | GAA | ATT | 116.2 | 139 | 4.49 | 2.2 |
| Glu | Gln | GAA | CAA | 108.3 | 115 | 0.42 | 0.7 |
| Glu | His | GAA | CAC | 29.3 | 31 | 0.10 | 0.0 |
| Glu | Gln | GAA | CAG | 31.6 | 33 | 0.06 | 0.3 |
| Glu | His | GAA | CAT | 44.4 | 42 | -0.12 | -0.6 |
| Glu | Pro | GAA | CCA | 86.1 | 42 | -22.59 | -7.2 |
| Glu | Pro | GAA | CCC | 20.6 | 6 | -10.32 | -5.5 |
| Glu | Pro | GAA | CCG | 12.9 | 6 | -3.65 | -1.3 |
| Glu | Pro | GAA | CCT | 43.4 | 52 | 1.69 | 12.6 |
| Glu | Arg | GAA | CGA | 7.4 | 8 | 0.05 | 0.0 |
| Glu | Arg | GAA | CGC | 6.1 | 5 | -0.19 | -0.2 |
| Glu | Arg | GAA | CGG | 3.3 | 2 | -0.50 | -0.5 |
| Glu | Arg | GAA | CGT | 31.4 | 33 | 0.08 | 0.0 |
| Glu | Leu | GAA | CTA | 42.3 | 53 | 2.73 | 0.9 |
| Glu | Leu | GAA | CTC | 12.5 | 14 | 0.18 | 0.0 |
| Glu | Leu | GAA | CTG | 28.7 | 30 | 0.06 | 0.1 |
| Glu | Leu | GAA | CTT | 33.5 | 33 | -0.01 | -0.4 |
| Glu | Glu | GAA | GAA | 202.1 | 205 | 0.04 | 1.2 |
| Glu | Asp | GAA | GAC | 84.5 | 81 | -0.14 | -1.4 |
| Glu | Glu | GAA | GAG | 64.6 | 81 | 4.14 | 1.5 |
| Glu | Asp | GAA | GAT | 141.3 | 168 | 5.05 | 1.2 |
| Glu | Ala | GAA | GCA | 53.7 | 46 | -1.12 | -0.7 |
| Glu | Ala | GAA | GCC | 63.7 | 74 | 1.66 | 2.6 |
| Glu | Ala | GAA | GCG | 17.3 | 15 | -0.29 | -0.2 |
| Glu | Ala | GAA | GCT | 111.2 | 97 | -1.81 | -1.0 |
| Glu | Gly | GAA | GGA | 27.4 | 27 | -0.01 | -0.2 |
| Glu | Gly | GAA | GGC | 30.2 | 25 | -0.90 | -0.2 |
| Glu | Gly | GAA | GGG | 19.0 | 19 | 0.00 | -0.2 |
| Glu | Gly | GAA | GGT | 149.7 | 136 | -1.25 | -0.0 |
| Glu | Val | GAA | GTA | 34.1 | 36 | 0.10 | 0.3 |
| Glu | Val | GAA | GTC | 59.9 | 52 | -1.04 | -0.6 |
| Glu | Val | GAA | GTG | 34.6 | 38 | 0.34 | 0.6 |
| Glu | Val | GAA | GTT | 107.1 | 109 | 0.03 | 0.3 |
| Glu | Ocr | GAA | TAA | 0.0 | 6 | 0.00 | 0.0 |
| Glu | Tyr | GAA | TAC | 64.7 | 68 | 0.17 | 0.0 |
| Glu | Amb | GAA | TAG | 0.0 | 2 | 0.00 | 0.0 |
| Glu | Tyr | GAA | TAT | 58.0 | 63 | 0.43 | 0.0 |
| Glu | Ser | GAA | TCA | 52.0 | 42 | -1.92 | -0.0 |
| Glu | Ser | GAA | TCC | 54.0 | 41 | -3.11 | -0.1 |
| Glu | Ser | GAA | TCG | 20.3 | 13 | -2.65 | -0.7 |
| Glu | Ser | GAA | TCT | 95.6 | 68 | -7.98 | -1.1 |
| Glu | Umb | GAA | TGA | 0.0 | 2 | 0.00 | 0.0 |
| Glu | Cys | GAA | TGC | 11.7 | 7 | -1.88 | -0.5 |
| Glu | Trp | GAA | TGG | 36.4 | 30 | -1.13 | -0.0 |
| Glu | Cys | GAA | TGT | 28.7 | 28 | -0.02 | -1.6 |
| Glu | Leu | GAA | TTA | 86.4 | 99 | 1.85 | 0.2 |
| Glu | Phe | GAA | TTC | 73.9 | 59 | -3.01 | -2.6 |
| Glu | Leu | GAA | TTG | 131.1 | 144 | 1.27 | 0.0 |
| Glu | Phe | GAA | TTT | 81.0 | 87 | 0.44 | 0.7 |
| | Page Totals: | | | 3708.5 | 3717 | 109.102 | 75.1 |

YEAST.RXD/CPLIST.RXR February 7, 1989

| aa1 | aa2 | cod1 | cod2 | exp | obs | chis1 | chis2 |
|---|---|---|---|---|---|---|---|
| Asp | Lys | GAC | AAA | 57.3 | 69 | 2.41 | 11.8 |
| Asp | Asn | GAC | AAC | 44.4 | 40 | -0.43 | -0.1 |
| Asp | Lys | GAC | AAG | 65.4 | 60 | -0.44 | -1.2 |
| Asp | Asn | GAC | AAT | 44.0 | 47 | 0.21 | 2.4 |
| Asp | Thr | GAC | ACA | 22.1 | 15 | -2.29 | -1.5 |
| Asp | Thr | GAC | ACC | 26.5 | 31 | 0.75 | 1.6 |
| Asp | Thr | GAC | ACG | 9.4 | 5 | -2.07 | -1.6 |
| Asp | Thr | GAC | ACT | 37.4 | 51 | 4.93 | 7.4 |
| Asp | Arg | GAC | AGA | 43.2 | 31 | -3.43 | -0.1 |
| Asp | Ser | GAC | AGC | 10.7 | 10 | -0.04 | -0.1 |
| Asp | Arg | GAC | AGG | 11.3 | 6 | -2.51 | -0.8 |
| Asp | Ser | GAC | AGT | 16.4 | 20 | 0.79 | 2.5 |
| Asp | Ile | GAC | ATA | 17.7 | 20 | 0.30 | 0.1 |
| Asp | Ile | GAC | ATC | 31.3 | 23 | -2.19 | -5.6 |
| Asp | Met | GAC | ATG | 36.7 | 38 | 0.05 | 0.9 |
| Asp | Ile | GAC | ATT | 51.2 | 69 | 6.16 | 0.9 |
| Asp | Gln | GAC | CAA | 47.5 | 42 | -0.63 | -2.6 |
| Asp | His | GAC | CAC | 14.1 | 11 | -0.68 | -0.4 |
| Asp | Gln | GAC | CAG | 14.8 | 10 | -1.53 | -0.0 |
| Asp | His | GAC | CAT | 19.4 | 20 | 0.02 | 0.2 |
| Asp | Pro | GAC | CCA | 38.2 | 37 | -0.04 | -0.0 |
| Asp | Pro | GAC | CCC | 9.8 | 10 | 0.00 | 0.1 |
| Asp | Pro | GAC | CCG | 5.9 | 5 | -0.13 | -0.1 |
| Asp | Pro | GAC | CCT | 18.4 | 23 | 1.17 | 1.8 |
| Asp | Arg | GAC | CGA | 3.3 | 0 | -3.33 | -2.5 |
| Asp | Arg | GAC | CGC | 2.9 | 3 | 0.00 | 0.3 |
| Asp | Arg | GAC | CGG | 1.7 | 2 | 0.06 | 0.4 |
| Asp | Arg | GAC | CGT | 13.7 | 17 | 0.82 | 4.3 |
| Asp | Leu | GAC | CTA | 18.7 | 22 | 0.57 | 0.0 |
| Asp | Leu | GAC | CTC | 5.8 | 4 | -0.58 | -1.1 |
| Asp | Leu | GAC | CTG | 13.6 | 12 | -0.18 | -0.9 |
| Asp | Leu | GAC | CTT | 14.4 | 14 | -0.01 | -0.4 |
| Asp | Glu | GAC | GAA | 84.5 | 92 | 0.67 | 1.4 |
| Asp | Asp | GAC | GAC | 43.0 | 57 | 4.57 | 0.3 |
| Asp | Glu | GAC | GAG | 27.9 | 30 | 0.16 | 0.6 |
| Asp | Asp | GAC | GAT | 61.0 | 59 | -0.07 | -3.5 |
| Asp | Ala | GAC | GCA | 24.0 | 17 | -2.03 | -2.4 |
| Asp | Ala | GAC | GCC | 29.4 | 17 | -5.22 | -5.8 |
| Asp | Ala | GAC | GCG | 7.9 | 7 | -0.11 | -0.2 |
| Asp | Ala | GAC | GCT | 51.4 | 42 | -1.73 | -2.3 |
| Asp | Gly | GAC | GGA | 12.4 | 9 | -0.92 | -0.8 |
| Asp | Gly | GAC | GGC | 14.5 | 13 | -0.16 | -0.1 |
| Asp | Gly | GAC | GGG | 8.9 | 16 | 5.68 | 5.9 |
| Asp | Gly | GAC | GGT | 70.1 | 58 | -2.10 | -1.8 |
| Asp | Val | GAC | GTA | 14.7 | 17 | 0.36 | 0.1 |
| Asp | Val | GAC | GTC | 29.6 | 12 | -10.43 | -12.1 |
| Asp | Val | GAC | GTG | 15.9 | 16 | 0.00 | 0.1 |
| Asp | Val | GAC | GTT | 47.3 | 42 | -0.60 | -1.5 |
| Asp | Ocr | GAC | TAA | 0.0 | 0 | 0.00 | 0.0 |
| Asp | Tyr | GAC | TAC | 31.4 | 44 | 5.04 | 3.5 |
| Asp | Amb | GAC | TAG | 0.0 | 0 | 0.00 | 0.0 |
| Asp | Tyr | GAC | TAT | 25.2 | 37 | 5.50 | 4.0 |
| Asp | Ser | GAC | TCA | 21.9 | 14 | -2.83 | -1.2 |
| Asp | Ser | GAC | TCC | 24.7 | 19 | -1.30 | -0.2 |
| Asp | Ser | GAC | TCG | 9.0 | 7 | -0.43 | -0.1 |
| Asp | Ser | GAC | TCT | 42.2 | 49 | 1.09 | 4.5 |
| Asp | Umb | GAC | TGA | 0.0 | 1 | 0.00 | 0.0 |
| Asp | Cys | GAC | TGC | 5.3 | 3 | -1.00 | -0.6 |
| Asp | Trp | GAC | TGG | 16.8 | 18 | 0.09 | 0.5 |
| Asp | Cys | GAC | TGT | 13.3 | 22 | 5.72 | 8.9 |
| Asp | Leu | GAC | TTA | 36.6 | 37 | 0.01 | 0.7 |
| Asp | Phe | GAC | TTC | 35.4 | 43 | 1.64 | 0.2 |
| Asp | Leu | GAC | TTG | 60.8 | 77 | 4.31 | 0.6 |
| Asp | Phe | GAC | TTT | 35.2 | 29 | -1.08 | -2.9 |
| | Page Totals: | | | 1667.0 | 1671 | 103.594 | 120.5 |

YEAST.RXD/CPLIST.RXR February 7, 1989

| aa1 | aa2 | cod1 | cod2 | exp | obs | chis1 | chis2 |
|---|---|---|---|---|---|---|---|
| Glu | Lys | GAG | AAA | 52.4 | 53 | 0.01 | 0.1 |
| Glu | Asn | GAG | AAC | 31.2 | 35 | 0.46 | 0.0 |
| Glu | Lys | GAG | AAG | 44.1 | 47 | 0.19 | 0.0 |
| Glu | Asn | GAG | AAT | 40.7 | 56 | 5.78 | 2.2 |
| Glu | Thr | GAG | ACA | 20.5 | 14 | -2.08 | -1.6 |
| Glu | Thr | GAG | ACC | 15.7 | 20 | 1.16 | 1.7 |
| Glu | Thr | GAG | ACG | 9.1 | 4 | -2.89 | -2.5 |
| Glu | Thr | GAG | ACT | 26.6 | 28 | 0.08 | 0.3 |
| Glu | Arg | GAG | AGA | 30.2 | 14 | -8.67 | -9.0 |
| Glu | Ser | GAG | AGC | 9.9 | 11 | 0.12 | 1.1 |
| Glu | Arg | GAG | AGG | 11.0 | 11 | 0.00 | 0.0 |
| Glu | Ser | GAG | AGT | 14.9 | 18 | 0.63 | 2.9 |
| Glu | Ile | GAG | ATA | 18.2 | 16 | -0.27 | -0.5 |
| Glu | Ile | GAG | ATC | 20.5 | 16 | -0.97 | -1.5 |
| Glu | Met | GAG | ATG | 28.5 | 17 | -4.65 | -3.8 |
| Glu | Ile | GAG | ATT | 39.5 | 42 | 0.16 | 0.0 |
| Glu | Gln | GAG | CAA | 35.8 | 47 | 3.47 | 0.8 |
| Glu | His | GAG | CAC | 9.4 | 7 | -0.63 | -0.9 |
| Glu | Gln | GAG | CAG | 13.7 | 23 | 6.37 | 3.4 |
| Glu | His | GAG | CAT | 16.2 | 26 | 5.99 | 4.4 |
| Glu | Pro | GAG | CCA | 25.6 | 21 | -0.83 | -0.3 |
| Glu | Pro | GAG | CCC | 8.6 | 9 | 0.02 | 1.2 |
| Glu | Pro | GAG | CCG | 5.9 | 3 | -1.45 | -0.4 |
| Glu | Pro | GAG | CCT | 16.0 | 22 | 2.30 | 9.0 |
| Glu | Arg | GAG | CGA | 3.5 | 4 | 0.06 | 0.1 |
| Glu | Arg | GAG | CGC | 2.7 | 2 | -0.20 | -0.2 |
| Glu | Arg | GAG | CGG | 1.8 | 0 | -1.83 | -1.9 |
| Glu | Arg | GAG | CGT | 10.3 | 14 | 1.31 | 1.2 |
| Glu | Leu | GAG | CTA | 16.1 | 24 | 3.93 | 2.2 |
| Glu | Leu | GAG | CTC | 5.9 | 4 | -0.60 | -1.0 |
| Glu | Leu | GAG | CTG | 12.2 | 17 | 1.88 | 0.9 |
| Glu | Leu | GAG | CTT | 13.5 | 17 | 0.90 | 0.3 |
| Glu | Glu | GAG | GAA | 64.6 | 76 | 2.00 | 0.4 |
| Glu | Asp | GAG | GAC | 27.9 | 20 | -2.23 | -3.6 |
| Glu | Glu | GAG | GAG | 28.3 | 32 | 0.48 | 0.0 |
| Glu | Asp | GAG | GAT | 51.4 | 64 | 3.10 | 1.1 |
| Glu | Ala | GAG | GCA | 21.2 | 28 | 2.18 | 2.8 |
| Glu | Ala | GAG | GCC | 18.8 | 13 | -1.81 | -1.5 |
| Glu | Ala | GAG | GCG | 7.4 | 7 | -0.02 | -0.0 |
| Glu | Ala | GAG | GCT | 30.2 | 32 | 0.11 | 0.3 |
| Glu | Gly | GAG | GGA | 11.5 | 12 | 0.03 | 0.3 |
| Glu | Gly | GAG | GGC | 11.7 | 12 | 0.01 | 0.2 |
| Glu | Gly | GAG | GGG | 8.0 | 10 | 0.50 | 1.1 |
| Glu | Gly | GAG | GGT | 40.2 | 27 | -4.36 | -2.3 |
| Glu | Val | GAG | GTA | 14.2 | 20 | 2.38 | 2.9 |
| Glu | Val | GAG | GTC | 16.7 | 11 | -1.93 | -1.6 |
| Glu | Val | GAG | GTG | 13.3 | 9 | -1.37 | -1.1 |
| Glu | Val | GAG | GTT | 30.9 | 25 | -1.14 | -0.8 |
| Glu | Ocr | GAG | TAA | 0.0 | 2 | 0.00 | 0.0 |
| Glu | Tyr | GAG | TAC | 20.9 | 29 | 3.13 | 1.9 |
| Glu | Amb | GAG | TAG | 0.0 | 0 | 0.00 | 0.0 |
| Glu | Tyr | GAG | TAT | 22.1 | 18 | -0.75 | -1.4 |
| Glu | Ser | GAG | TCA | 20.3 | 16 | -0.92 | -0.0 |
| Glu | Ser | GAG | TCC | 16.8 | 12 | -1.37 | -0.2 |
| Glu | Ser | GAG | TCG | 8.6 | 5 | -1.49 | -0.5 |
| Glu | Ser | GAG | TCT | 30.1 | 17 | -5.73 | -2.2 |
| Glu | Umb | GAG | TGA | 0.0 | 0 | 0.00 | 0.0 |
| Glu | Cys | GAG | TGC | 4.7 | 3 | -0.58 | -0.1 |
| Glu | Trp | GAG | TGG | 12.7 | 10 | -0.58 | -0.0 |
| Glu | Cys | GAG | TGT | 9.4 | 4 | -3.13 | -1.5 |
| Glu | Leu | GAG | TTA | 31.2 | 21 | -3.33 | -5.2 |
| Glu | Phe | GAG | TTC | 23.4 | 25 | 0.10 | 0.2 |
| Glu | Leu | GAG | TTG | 39.4 | 43 | 0.33 | 0.0 |
| Glu | Phe | GAG | TTT | 30.9 | 35 | 0.55 | 0.7 |
| | Page Totals: | | | 1277.1 | 1280 | 105.508 | 89.2 |

PAGE 35

YEAST.RXD/CPLIST.RXR February 7, 1989

| aa1 | aa2 | cod1 | cod2 | exp | obs | chis1 | chis2 |
|---|---|---|---|---|---|---|---|
| Asp | Lys | GAT | AAA | 111.4 | 89 | -4.49 | 0.0 |
| Asp | Asn | GAT | AAC | 69.0 | 43 | -9.80 | -4.2 |
| Asp | Lys | GAT | AAG | 96.6 | 46 | -26.46 | -12.6 |
| Asp | Asn | GAT | AAT | 86.8 | 78 | -0.90 | -0.2 |
| Asp | Thr | GAT | ACA | 42.9 | 33 | -2.29 | -1.2 |
| Asp | Thr | GAT | ACC | 37.9 | 42 | 0.45 | 1.3 |
| Asp | Thr | GAT | ACG | 18.7 | 10 | -4.07 | -3.2 |
| Asp | Thr | GAT | ACT | 61.0 | 52 | -1.33 | -0.4 |
| Asp | Arg | GAT | AGA | 69.3 | 45 | -8.49 | -1.1 |
| Asp | Ser | GAT | AGC | 19.8 | 19 | -0.03 | -0.2 |
| Asp | Arg | GAT | AGG | 22.4 | 13 | -3.94 | -0.9 |
| Asp | Ser | GAT | AGT | 31.2 | 29 | -0.15 | -0.2 |
| Asp | Ile | GAT | ATA | 37.5 | 44 | 1.13 | 0.0 |
| Asp | Ile | GAT | ATC | 47.1 | 74 | 15.37 | 5.4 |
| Asp | Met | GAT | ATG | 63.3 | 51 | -2.40 | -0.5 |
| Asp | Ile | GAT | ATT | 88.8 | 98 | 0.95 | 0.7 |
| Asp | Gln | GAT | CAA | 78.7 | 42 | -17.14 | -2.9 |
| Asp | His | GAT | CAC | 20.6 | 11 | -4.44 | -3.6 |
| Asp | Gln | GAT | CAG | 26.7 | 22 | -0.84 | -0.7 |
| Asp | His | GAT | CAT | 36.2 | 43 | 1.27 | 2.3 |
| Asp | Pro | GAT | CCA | 61.4 | 54 | -0.88 | -0.3 |
| Asp | Pro | GAT | CCC | 17.6 | 14 | -0.73 | -0.4 |
| Asp | Pro | GAT | CCG | 11.4 | 8 | -1.02 | -0.7 |
| Asp | Pro | GAT | CCT | 34.6 | 36 | 0.06 | 0.3 |
| Asp | Arg | GAT | CGA | 6.8 | 5 | -0.46 | -0.0 |
| Asp | Arg | GAT | CGC | 5.2 | 4 | -0.27 | -0.0 |
| Asp | Arg | GAT | CGG | 3.0 | 3 | 0.00 | 0.3 |
| Asp | Arg | GAT | CGT | 23.4 | 27 | 0.55 | 4.8 |
| Asp | Leu | GAT | CTA | 34.2 | 34 | -0.00 | -0.8 |
| Asp | Leu | GAT | CTC | 11.3 | 14 | 0.65 | 0.1 |
| Asp | Leu | GAT | CTG | 24.9 | 29 | 0.67 | 0.0 |
| Asp | Leu | GAT | CTT | 28.7 | 28 | -0.02 | -0.8 |
| Asp | Glu | GAT | GAA | 141.3 | 192 | 18.20 | 1.8 |
| Asp | Asp | GAT | GAC | 61.0 | 97 | 21.25 | 6.3 |
| Asp | Glu | GAT | GAG | 51.4 | 62 | 2.19 | 0.0 |
| Asp | Asp | GAT | GAT | 117.1 | 135 | 2.75 | 0.6 |
| Asp | Ala | GAT | GCA | 44.9 | 51 | 0.83 | 0.5 |
| Asp | Ala | GAT | GCC | 43.5 | 54 | 2.56 | 1.9 |
| Asp | Ala | GAT | GCG | 14.8 | 21 | 2.61 | 2.2 |
| Asp | Ala | GAT | GCT | 74.4 | 90 | 3.25 | 2.3 |
| Asp | Gly | GAT | GGA | 23.9 | 25 | 0.05 | 0.1 |
| Asp | Gly | GAT | GGC | 24.4 | 20 | -0.79 | -0.7 |
| Asp | Gly | GAT | GGG | 16.1 | 19 | 0.52 | 0.6 |
| Asp | Gly | GAT | GGT | 101.1 | 108 | 0.47 | 0.7 |
| Asp | Val | GAT | GTA | 28.8 | 25 | -0.50 | -1.1 |
| Asp | Val | GAT | GTC | 41.4 | 60 | 8.36 | 5.6 |
| Asp | Val | GAT | GTG | 27.5 | 30 | 0.23 | 0.0 |
| Asp | Val | GAT | GTT | 75.6 | 98 | 6.66 | 3.7 |
| Asp | Ocr | GAT | TAA | 0.0 | 0 | 0.00 | 0.0 |
| Asp | Tyr | GAT | TAC | 46.7 | 38 | -1.61 | -2.6 |
| Asp | Amb | GAT | TAG | 0.0 | 1 | 0.00 | 0.0 |
| Asp | Tyr | GAT | TAT | 48.0 | 41 | -1.02 | -1.9 |
| Asp | Ser | GAT | TCA | 44.8 | 33 | -3.09 | -0.8 |
| Asp | Ser | GAT | TCC | 38.1 | 31 | -1.33 | -0.1 |
| Asp | Ser | GAT | TCG | 17.7 | 18 | 0.00 | 0.5 |
| Asp | Ser | GAT | TCT | 69.9 | 48 | -6.83 | -2.4 |
| Asp | Umb | GAT | TGA | 0.0 | 2 | 0.00 | 0.0 |
| Asp | Cys | GAT | TGC | 9.6 | 7 | -0.69 | -0.3 |
| Asp | Trp | GAT | TGG | 28.3 | 23 | -0.98 | -0.3 |
| Asp | Cys | GAT | TGT | 22.7 | 13 | -4.16 | -2.5 |
| Asp | Leu | GAT | TTA | 69.0 | 74 | 0.36 | 0.4 |
| Asp | Phe | GAT | TTC | 53.2 | 62 | 1.46 | 0.1 |
| Asp | Leu | GAT | TTG | 92.0 | 129 | 14.92 | 4.8 |
| Asp | Phe | GAT | TTT | 66.9 | 81 | 2.99 | 0.4 |
| | Page Totals: | | | 2821.9 | 2828 | 221.924 | 95.3 |

PAGE 36

YEAST.RXD/CPLIST.RXR February 7, 1989

| aa1 | aa2 | cod1 | cod2 | exp | obs | chis1 | chis2 |
|---|---|---|---|---|---|---|---|
| Ala | Lys | GCA | AAA | 45.5 | 37 | -1.57 | -2.0 |
| Ala | Asn | GCA | AAC | 27.7 | 31 | 0.38 | 0.2 |
| Ala | Lys | GCA | AAG | 37.1 | 43 | 0.94 | 0.7 |
| Ala | Asn | GCA | AAT | 37.0 | 35 | -0.11 | -0.3 |
| Ala | Thr | GCA | ACA | 19.6 | 24 | 1.00 | 0.4 |
| Ala | Thr | GCA | ACC | 15.1 | 11 | -1.11 | -1.7 |
| Ala | Thr | GCA | ACG | 8.2 | 4 | -2.16 | -2.7 |
| Ala | Thr | GCA | ACT | 23.8 | 17 | -1.92 | -2.9 |
| Ala | Arg | GCA | AGA | 27.2 | 38 | 4.32 | 4.2 |
| Ala | Ser | GCA | AGC | 8.6 | 12 | 1.36 | 1.5 |
| Ala | Arg | GCA | AGG | 9.7 | 16 | 4.17 | 4.1 |
| Ala | Ser | GCA | AGT | 13.6 | 16 | 0.42 | 0.5 |
| Ala | Ile | GCA | ATA | 16.3 | 12 | -1.15 | -1.5 |
| Ala | Ile | GCA | ATC | 18.9 | 21 | 0.25 | 0.1 |
| Ala | Met | GCA | ATG | 26.0 | 28 | 0.16 | 0.3 |
| Ala | Ile | GCA | ATT | 36.4 | 33 | -0.32 | -0.7 |
| Ala | Gln | GCA | CAA | 31.8 | 39 | 1.64 | 0.4 |
| Ala | His | GCA | CAC | 8.4 | 6 | -0.69 | -0.1 |
| Ala | Gln | GCA | CAG | 12.0 | 13 | 0.08 | 0.0 |
| Ala | His | GCA | CAT | 15.3 | 15 | -0.01 | -0.4 |
| Ala | Pro | GCA | CCA | 23.3 | 20 | -0.47 | -0.2 |
| Ala | Pro | GCA | CCC | 7.8 | 7 | -0.09 | -0.0 |
| Ala | Pro | GCA | CCG | 4.9 | 0 | -4.93 | -4.6 |
| Ala | Pro | GCA | CCT | 15.2 | 17 | 0.21 | 0.5 |
| Ala | Arg | GCA | CGA | 3.1 | 0 | -3.07 | -3.1 |
| Ala | Arg | GCA | CGC | 2.4 | 1 | -0.80 | -0.8 |
| Ala | Arg | GCA | CGG | 1.4 | 2 | 0.22 | 0.2 |
| Ala | Arg | GCA | CGT | 9.6 | 7 | -0.70 | -0.7 |
| Ala | Leu | GCA | CTA | 14.3 | 12 | -0.37 | -0.5 |
| Ala | Leu | GCA | CTC | 5.3 | 4 | -0.32 | -0.4 |
| Ala | Leu | GCA | CTG | 11.0 | 12 | 0.08 | 0.0 |
| Ala | Leu | GCA | CTT | 12.6 | 7 | -2.50 | -2.7 |
| Ala | Glu | GCA | GAA | 53.7 | 50 | -0.26 | -0.0 |
| Ala | Asp | GCA | GAC | 24.0 | 34 | 4.19 | 6.9 |
| Ala | Glu | GCA | GAG | 21.2 | 19 | -0.23 | -0.0 |
| Ala | Asp | GCA | GAT | 44.9 | 42 | -0.19 | -0.0 |
| Ala | Ala | GCA | GCA | 22.3 | 23 | 0.02 | 0.9 |
| Ala | Ala | GCA | GCC | 17.7 | 12 | -1.85 | -4.7 |
| Ala | Ala | GCA | GCG | 6.4 | 7 | 0.05 | 0.1 |
| Ala | Ala | GCA | GCT | 29.3 | 43 | 6.41 | 1.1 |
| Ala | Gly | GCA | GGA | 10.3 | 7 | -1.08 | -1.0 |
| Ala | Gly | GCA | GGC | 11.4 | 17 | 2.82 | 3.1 |
| Ala | Gly | GCA | GGG | 6.8 | 7 | 0.01 | 0.0 |
| Ala | Gly | GCA | GGT | 39.4 | 45 | 0.78 | 1.0 |
| Ala | Val | GCA | GTA | 12.2 | 9 | -0.82 | -0.4 |
| Ala | Val | GCA | GTC | 16.1 | 8 | -4.05 | -3.0 |
| Ala | Val | GCA | GTG | 12.6 | 15 | 0.48 | 1.2 |
| Ala | Val | GCA | GTT | 30.1 | 15 | -7.56 | -5.5 |
| Ala | Ocr | GCA | TAA | 0.0 | 2 | 0.00 | 0.0 |
| Ala | Tyr | GCA | TAC | 19.0 | 17 | -0.21 | -0.1 |
| Ala | Amb | GCA | TAG | 0.0 | 1 | 0.00 | 0.0 |
| Ala | Tyr | GCA | TAT | 20.7 | 24 | 0.54 | 2.9 |
| Ala | Ser | GCA | TCA | 19.1 | 25 | 1.80 | 2.1 |
| Ala | Ser | GCA | TCC | 15.3 | 19 | 0.92 | 1.1 |
| Ala | Ser | GCA | TCG | 7.4 | 7 | -0.02 | -0.0 |
| Ala | Ser | GCA | TCT | 27.7 | 31 | 0.39 | 0.5 |
| Ala | Umb | GCA | TGA | 0.0 | 1 | 0.00 | 0.0 |
| Ala | Cys | GCA | TGC | 4.3 | 6 | 0.66 | 1.0 |
| Ala | Trp | GCA | TGG | 12.1 | 13 | 0.07 | 0.2 |
| Ala | Cys | GCA | TGT | 9.3 | 12 | 0.81 | 1.3 |
| Ala | Leu | GCA | TTA | 28.9 | 30 | 0.04 | 0.0 |
| Ala | Phe | GCA | TTC | 21.0 | 19 | -0.18 | -0.0 |
| Ala | Leu | GCA | TTG | 35.1 | 28 | -1.43 | -1.8 |
| Ala | Phe | GCA | TTT | 28.5 | 30 | 0.08 | 1.0 |
| | Page Totals: | | | 1155.5 | 1158 | 75.4844 | 79.4 |

PAGE 37

YEAST.RXD/CPLIST.RXR February 7, 1989

| aa1 | aa2 | cod1 | cod2 | exp | obs | chis1 | chis2 |
|---|---|---|---|---|---|---|---|
| Ala | Lys | GCC | AAA | 41.6 | 54 | 3.72 | 3.0 |
| Ala | Asn | GCC | AAC | 33.3 | 56 | 15.42 | 13.5 |
| Ala | Lys | GCC | AAG | 49.9 | 83 | 22.03 | 19.9 |
| Ala | Asn | GCC | AAT | 29.5 | 38 | 2.45 | 1.8 |
| Ala | Thr | GCC | ACA | 16.1 | 24 | 3.94 | 2.5 |
| Ala | Thr | GCC | ACC | 20.7 | 28 | 2.58 | 1.4 |
| Ala | Thr | GCC | ACG | 6.2 | 14 | 9.80 | 7.9 |
| Ala | Thr | GCC | ACT | 28.6 | 33 | 0.67 | 0.1 |
| Ala | Arg | GCC | AGA | 34.7 | 42 | 1.55 | 1.5 |
| Ala | Ser | GCC | AGC | 6.7 | 5 | -0.43 | -0.4 |
| Ala | Arg | GCC | AGG | 7.2 | 7 | -0.00 | -0.0 |
| Ala | Ser | GCC | AGT | 10.8 | 5 | -3.10 | -2.9 |
| Ala | Ile | GCC | ATA | 11.0 | 15 | 1.46 | 1.0 |
| Ala | Ile | GCC | ATC | 25.6 | 35 | 3.44 | 2.5 |
| Ala | Met | GCC | ATG | 26.7 | 34 | 2.02 | 2.4 |
| Ala | Ile | GCC | ATT | 38.3 | 62 | 14.65 | 11.8 |
| Ala | Gln | GCC | CAA | 38.2 | 33 | -0.70 | -2.0 |
| Ala | His | GCC | CAC | 10.8 | 10 | -0.05 | -0.1 |
| Ala | Gln | GCC | CAG | 9.6 | 7 | -0.70 | -1.2 |
| Ala | His | GCC | CAT | 14.2 | 10 | -1.24 | -0.3 |
| Ala | Pro | GCC | CCA | 30.8 | 22 | -2.50 | -1.6 |
| Ala | Pro | GCC | CCC | 6.9 | 4 | -1.23 | -1.0 |
| Ala | Pro | GCC | CCG | 3.7 | 2 | -0.77 | -0.6 |
| Ala | Pro | GCC | CCT | 14.8 | 6 | -5.26 | -4.5 |
| Ala | Arg | GCC | CGA | 1.8 | 1 | -0.36 | -0.4 |
| Ala | Arg | GCC | CGC | 1.8 | 3 | 0.90 | 0.9 |
| Ala | Arg | GCC | CGG | 0.9 | 0 | -0.89 | -0.9 |
| Ala | Arg | GCC | CGT | 10.5 | 6 | -1.90 | -1.9 |
| Ala | Leu | GCC | CTA | 13.5 | 8 | -2.26 | -2.5 |
| Ala | Leu | GCC | CTC | 3.7 | 3 | -0.14 | -0.2 |
| Ala | Leu | GCC | CTG | 9.0 | 7 | -0.43 | -0.5 |
| Ala | Leu | GCC | CTT | 10.0 | 13 | 0.87 | 0.7 |
| Ala | Glu | GCC | GAA | 63.7 | 49 | -3.40 | -1.9 |
| Ala | Asp | GCC | GAC | 29.4 | 21 | -2.40 | -1.2 |
| Ala | Glu | GCC | GAG | 18.8 | 8 | -6.24 | -5.3 |
| Ala | Asp | GCC | GAT | 43.5 | 32 | -3.02 | -1.4 |
| Ala | Ala | GCC | GCA | 17.7 | 18 | 0.00 | 0.8 |
| Ala | Ala | GCC | GCC | 28.7 | 33 | 0.65 | 0.2 |
| Ala | Ala | GCC | GCG | 5.2 | 4 | -0.26 | -0.9 |
| Ala | Ala | GCC | GCT | 43.6 | 62 | 7.74 | 1.0 |
| Ala | Gly | GCC | GGA | 8.0 | 3 | -3.12 | -3.0 |
| Ala | Gly | GCC | GGC | 10.9 | 6 | -2.23 | -2.1 |
| Ala | Gly | GCC | GGG | 6.2 | 7 | 0.11 | 0.1 |
| Ala | Gly | GCC | GGT | 60.5 | 57 | -0.21 | -0.1 |
| Ala | Val | GCC | GTA | 9.8 | 7 | -0.79 | -0.4 |
| Ala | Val | GCC | GTC | 23.3 | 19 | -0.80 | -0.2 |
| Ala | Val | GCC | GTG | 11.7 | 5 | -3.84 | -3.0 |
| Ala | Val | GCC | GTT | 39.2 | 40 | 0.02 | 0.6 |
| Ala | Ocr | GCC | TAA | 0.0 | 2 | 0.00 | 0.0 |
| Ala | Tyr | GCC | TAC | 23.7 | 15 | -3.22 | -1.0 |
| Ala | Amb | GCC | TAG | 0.0 | 0 | 0.00 | 0.0 |
| Ala | Tyr | GCC | TAT | 18.0 | 12 | -2.00 | -0.5 |
| Ala | Ser | GCC | TCA | 15.5 | 11 | -1.30 | -1.2 |
| Ala | Ser | GCC | TCC | 20.2 | 21 | 0.03 | 0.1 |
| Ala | Ser | GCC | TCG | 5.9 | 5 | -0.12 | -0.1 |
| Ala | Ser | GCC | TCT | 33.9 | 30 | -0.45 | -0.3 |
| Ala | Umb | GCC | TGA | 0.0 | 0 | 0.00 | 0.0 |
| Ala | Cys | GCC | TGC | 3.4 | 3 | -0.04 | -0.0 |
| Ala | Trp | GCC | TGG | 12.1 | 11 | -0.10 | -0.0 |
| Ala | Cys | GCC | TGT | 10.0 | 6 | -1.60 | -1.2 |
| Ala | Leu | GCC | TTA | 27.4 | 26 | -0.08 | -0.2 |
| Ala | Phe | GCC | TTC | 26.9 | 15 | -5.26 | -3.1 |
| Ala | Leu | GCC | TTG | 47.8 | 37 | -2.43 | -2.9 |
| Ala | Phe | GCC | TTT | 25.0 | 25 | 0.00 | -0.4 |
| | Page Totals: | | | 1256.8 | 1260 | 158.896 | 125.4 |

PAGE 38

YEAST.RXD/CPLIST.RXR February 7, 1989

| aa1 | aa2 | cod1 | cod2 | exp | obs | chis1 | chis2 |
|---|---|---|---|---|---|---|---|
| Ala | Lys | GCG | AAA | 15.9 | 12 | -0.94 | -1.1 |
| Ala | Asn | GCG | AAC | 9.3 | 13 | 1.51 | 1.2 |
| Ala | Lys | GCG | AAG | 12.4 | 13 | 0.03 | 0.0 |
| Ala | Asn | GCG | AAT | 12.4 | 9 | -0.95 | -1.2 |
| Ala | Thr | GCG | ACA | 6.5 | 9 | 0.93 | 0.5 |
| Ala | Thr | GCG | ACC | 4.6 | 3 | -0.57 | -0.8 |
| Ala | Thr | GCG | ACG | 2.9 | 3 | 0.00 | 0.0 |
| Ala | Thr | GCG | ACT | 7.5 | 6 | -0.29 | -0.5 |
| Ala | Arg | GCG | AGA | 8.4 | 10 | 0.31 | 0.3 |
| Ala | Ser | GCG | AGC | 3.2 | 0 | -3.20 | -3.1 |
| Ala | Arg | GCG | AGG | 3.3 | 1 | -1.59 | -1.6 |
| Ala | Ser | GCG | AGT | 4.6 | 3 | -0.58 | -0.5 |
| Ala | Ile | GCG | ATA | 6.0 | 3 | -1.46 | -1.7 |
| Ala | Ile | GCG | ATC | 5.8 | 3 | -1.34 | -1.5 |
| Ala | Met | GCG | ATG | 8.3 | 10 | 0.37 | 0.5 |
| Ala | Ile | GCG | ATT | 11.2 | 1 | -9.29 | -9.8 |
| Ala | Gln | GCG | CAA | 9.8 | 15 | 2.72 | 1.6 |
| Ala | His | GCG | CAC | 2.8 | 2 | -0.24 | -0.0 |
| Ala | Gln | GCG | CAG | 4.3 | 2 | -1.25 | -1.6 |
| Ala | His | GCG | CAT | 5.0 | 5 | 0.00 | 0.2 |
| Ala | Pro | GCG | CCA | 6.8 | 7 | 0.01 | 0.1 |
| Ala | Pro | GCG | CCC | 2.8 | 2 | -0.24 | -0.2 |
| Ala | Pro | GCG | CCG | 2.1 | 3 | 0.41 | 0.6 |
| Ala | Pro | GCG | CCT | 4.9 | 7 | 0.86 | 1.2 |
| Ala | Arg | GCG | CGA | 1.3 | 0 | -1.29 | -1.3 |
| Ala | Arg | GCG | CGC | 1.0 | 1 | 0.00 | 0.0 |
| Ala | Arg | GCG | CGG | 0.7 | 0 | -0.71 | -0.7 |
| Ala | Arg | GCG | CGT | 2.9 | 4 | 0.40 | 0.4 |
| Ala | Leu | GCG | CTA | 4.7 | 6 | 0.35 | 0.3 |
| Ala | Leu | GCG | CTC | 1.8 | 6 | 9.94 | 9.5 |
| Ala | Leu | GCG | CTG | 4.1 | 4 | -0.00 | -0.0 |
| Ala | Leu | GCG | CTT | 4.1 | 10 | 8.71 | 8.2 |
| Ala | Glu | GCG | GAA | 17.3 | 19 | 0.18 | 0.5 |
| Ala | Asp | GCG | GAC | 7.9 | 11 | 1.19 | 2.0 |
| Ala | Glu | GCG | GAG | 7.4 | 4 | -1.58 | -1.3 |
| Ala | Asp | GCG | GAT | 14.8 | 14 | -0.04 | -0.0 |
| Ala | Ala | GCG | GCA | 6.4 | 8 | 0.40 | 0.0 |
| Ala | Ala | GCG | GCC | 5.2 | 6 | 0.14 | 0.0 |
| Ala | Ala | GCG | GCG | 3.3 | 1 | -1.64 | -2.4 |
| Ala | Ala | GCG | GCT | 8.4 | 11 | 0.78 | 0.0 |
| Ala | Gly | GCG | GGA | 3.6 | 4 | 0.04 | 0.1 |
| Ala | Gly | GCG | GGC | 3.8 | 4 | 0.02 | 0.0 |
| Ala | Gly | GCG | GGG | 2.4 | 1 | -0.80 | -0.8 |
| Ala | Gly | GCG | GGT | 11.5 | 10 | -0.19 | -0.1 |
| Ala | Val | GCG | GTA | 4.6 | 0 | -4.63 | -4.2 |
| Ala | Val | GCG | GTC | 4.9 | 3 | -0.72 | -0.5 |
| Ala | Val | GCG | GTG | 4.2 | 2 | -1.13 | -0.8 |
| Ala | Val | GCG | GTT | 8.9 | 11 | 0.49 | 1.1 |
| Ala | Ocr | GCG | TAA | 0.0 | 0 | 0.00 | 0.0 |
| Ala | Tyr | GCG | TAC | 6.1 | 7 | 0.14 | 0.8 |
| Ala | Amb | GCG | TAG | 0.0 | 0 | 0.00 | 0.0 |
| Ala | Tyr | GCG | TAT | 6.8 | 15 | 9.83 | 15.8 |
| Ala | Ser | GCG | TCA | 6.3 | 2 | -2.92 | -2.8 |
| Ala | Ser | GCG | TCC | 4.9 | 4 | -0.16 | -0.1 |
| Ala | Ser | GCG | TCG | 3.0 | 3 | 0.00 | 0.0 |
| Ala | Ser | GCG | TCT | 8.9 | 14 | 2.99 | 3.2 |
| Ala | Umb | GCG | TGA | 0.0 | 0 | 0.00 | 0.0 |
| Ala | Cys | GCG | TGC | 1.3 | 2 | 0.35 | 0.5 |
| Ala | Trp | GCG | TGG | 3.7 | 2 | -0.75 | -0.7 |
| Ala | Cys | GCG | TGT | 3.2 | 1 | -1.47 | -1.3 |
| Ala | Leu | GCG | TTA | 9.4 | 9 | -0.02 | -0.0 |
| Ala | Phe | GCG | TTC | 6.3 | 6 | -0.02 | -0.0 |
| Ala | Leu | GCG | TTG | 10.7 | 15 | 1.78 | 1.5 |
| Ala | Phe | GCG | TTT | 9.0 | 14 | 2.78 | 4.8 |
| | | Page Totals: | | 375.2 | 376 | 87.6491 | 95.7 |

PAGE 39

YEAST.RXD/CPLIST.RXR February 7, 1989

| aa1 | aa2 | cod1 | cod2 | exp | obs | chis1 | chis2 |
|---|---|---|---|---|---|---|---|
| Ala | Lys | GCT | AAA | 68.7 | 59 | -1.37 | -1.8 |
| Ala | Asn | GCT | AAC | 58.1 | 40 | -5.62 | -6.7 |
| Ala | Lys | GCT | AAG | 93.0 | 72 | -4.74 | -5.7 |
| Ala | Asn | GCT | AAT | 49.0 | 43 | -0.74 | -1.2 |
| Ala | Thr | GCT | ACA | 26.3 | 35 | 2.90 | 1.5 |
| Ala | Thr | GCT | ACC | 36.7 | 31 | -0.88 | -1.9 |
| Ala | Thr | GCT | ACG | 10.3 | 8 | -0.50 | -0.9 |
| Ala | Thr | GCT | ACT | 52.8 | 59 | 0.73 | 0.1 |
| Ala | Arg | GCT | AGA | 65.0 | 46 | -5.54 | -5.7 |
| Ala | Ser | GCT | AGC | 11.6 | 6 | -2.68 | -2.5 |
| Ala | Arg | GCT | AGG | 12.0 | 10 | -0.34 | -0.4 |
| Ala | Ser | GCT | AGT | 17.6 | 15 | -0.37 | -0.3 |
| Ala | Ile | GCT | ATA | 17.9 | 14 | -0.85 | -1.2 |
| Ala | Ile | GCT | ATC | 44.0 | 50 | 0.81 | 0.3 |
| Ala | Met | GCT | ATG | 47.5 | 34 | -3.83 | -3.3 |
| Ala | Ile | GCT | ATT | 68.8 | 66 | -0.12 | -0.5 |
| Ala | Gln | GCT | CAA | 64.9 | 85 | 6.22 | 2.4 |
| Ala | His | GCT | CAC | 19.3 | 19 | -0.01 | -0.6 |
| Ala | Gln | GCT | CAG | 15.6 | 12 | -0.83 | -1.6 |
| Ala | His | GCT | CAT | 24.5 | 16 | -2.93 | -0.9 |
| Ala | Pro | GCT | CCA | 57.2 | 63 | 0.59 | 1.6 |
| Ala | Pro | GCT | CCC | 11.1 | 9 | -0.38 | -0.2 |
| Ala | Pro | GCT | CCG | 5.7 | 7 | 0.28 | 0.5 |
| Ala | Pro | GCT | CCT | 24.7 | 33 | 2.82 | 4.2 |
| Ala | Arg | GCT | CGA | 2.8 | 3 | 0.02 | 0.0 |
| Ala | Arg | GCT | CGC | 3.0 | 4 | 0.36 | 0.3 |
| Ala | Arg | GCT | CGG | 1.4 | 2 | 0.28 | 0.3 |
| Ala | Arg | GCT | CGT | 18.1 | 27 | 4.43 | 4.3 |
| Ala | Leu | GCT | CTA | 22.9 | 19 | -0.66 | -0.8 |
| Ala | Leu | GCT | CTC | 6.1 | 7 | 0.12 | 0.1 |
| Ala | Leu | GCT | CTG | 14.1 | 12 | -0.31 | -0.4 |
| Ala | Leu | GCT | CTT | 16.8 | 26 | 5.11 | 4.5 |
| Ala | Glu | GCT | GAA | 111.2 | 121 | 0.87 | 2.7 |
| Ala | Asp | GCT | GAC | 51.4 | 39 | -3.00 | -1.2 |
| Ala | Glu | GCT | GAG | 30.2 | 33 | 0.26 | 0.8 |
| Ala | Asp | GCT | GAT | 74.4 | 70 | -0.26 | -0.1 |
| Ala | Ala | GCT | GCA | 29.3 | 44 | 7.38 | 1.4 |
| Ala | Ala | GCT | GCC | 43.6 | 63 | 8.61 | 1.3 |
| Ala | Ala | GCT | GCG | 8.4 | 7 | -0.24 | -1.2 |
| Ala | Ala | GCT | GCT | 90.6 | 117 | 7.72 | 0.1 |
| Ala | Gly | GCT | GGA | 13.2 | 13 | -0.00 | -0.0 |
| Ala | Gly | GCT | GGC | 17.6 | 14 | -0.74 | -0.6 |
| Ala | Gly | GCT | GGG | 9.8 | 6 | -1.49 | -1.4 |
| Ala | Gly | GCT | GGT | 110.8 | 119 | 0.61 | 1.0 |
| Ala | Val | GCT | GTA | 16.2 | 17 | 0.04 | 0.4 |
| Ala | Val | GCT | GTC | 43.4 | 53 | 2.14 | 4.8 |
| Ala | Val | GCT | GTG | 19.0 | 19 | 0.00 | 0.2 |
| Ala | Val | GCT | GTT | 71.6 | 74 | 0.08 | 1.3 |
| Ala | Ocr | GCT | TAA | 0.0 | 9 | 0.00 | 0.0 |
| Ala | Tyr | GCT | TAC | 41.8 | 26 | -5.97 | -2.0 |
| Ala | Amb | GCT | TAG | 0.0 | 0 | 0.00 | 0.0 |
| Ala | Tyr | GCT | TAT | 29.7 | 20 | -3.14 | -0.8 |
| Ala | Ser | GCT | TCA | 26.1 | 25 | -0.04 | -0.0 |
| Ala | Ser | GCT | TCC | 36.1 | 39 | 0.23 | 0.4 |
| Ala | Ser | GCT | TCG | 9.6 | 8 | -0.28 | -0.2 |
| Ala | Ser | GCT | TCT | 60.5 | 64 | 0.21 | 0.4 |
| Ala | Umb | GCT | TGA | 0.0 | 1 | 0.00 | 0.0 |
| Ala | Cys | GCT | TGC | 5.7 | 8 | 0.97 | 1.4 |
| Ala | Trp | GCT | TGG | 22.2 | 22 | -0.00 | -0.0 |
| Ala | Cys | GCT | TGT | 16.5 | 12 | -1.22 | -0.7 |
| Ala | Leu | GCT | TTA | 46.4 | 47 | 0.01 | 0.0 |
| Ala | Phe | GCT | TTC | 47.9 | 38 | -2.03 | -0.4 |
| Ala | Leu | GCT | TTG | 88.0 | 111 | 6.01 | 4.8 |
| Ala | Phe | GCT | TTT | 42.2 | 34 | -1.60 | -0.2 |
| | | Page Totals: | | 2200.4 | 2205 | 112.500 | 86.5 |

PAGE 40

YEAST.RXD/CPLIST.RXR February 7, 1989

| aa1 | aa2 | cod1 | cod2 | exp | obs | chis1 | chis2 |
|---|---|---|---|---|---|---|---|
| Gly | Lys | GGA | AAA | 25.2 | 27 | 0.12 | 0.2 |
| Gly | Asn | GGA | AAC | 14.1 | 13 | -0.08 | -0.1 |
| Gly | Lys | GGA | AAG | 19.2 | 16 | -0.52 | -0.4 |
| Gly | Asn | GGA | AAT | 20.0 | 31 | 6.11 | 5.5 |
| Gly | Thr | GGA | ACA | 9.9 | 7 | -0.86 | -0.9 |
| Gly | Thr | GGA | ACC | 7.2 | 7 | -0.01 | -0.0 |
| Gly | Thr | GGA | ACG | 4.6 | 4 | -0.09 | -0.1 |
| Gly | Thr | GGA | ACT | 11.8 | 10 | -0.27 | -0.3 |
| Gly | Arg | GGA | AGA | 13.4 | 15 | 0.18 | 0.9 |
| Gly | Ser | GGA | AGC | 4.8 | 6 | 0.31 | 0.4 |
| Gly | Arg | GGA | AGG | 5.4 | 2 | -2.15 | -1.6 |
| Gly | Ser | GGA | AGT | 7.4 | 8 | 0.05 | 0.1 |
| Gly | Ile | GGA | ATA | 9.6 | 14 | 2.04 | 1.2 |
| Gly | Ile | GGA | ATC | 9.3 | 10 | 0.06 | 0.0 |
| Gly | Met | GGA | ATG | 13.7 | 14 | 0.01 | 0.3 |
| Gly | Ile | GGA | ATT | 18.5 | 24 | 1.67 | 0.7 |
| Gly | Gln | GGA | CAA | 15.8 | 25 | 5.43 | 2.8 |
| Gly | His | GGA | CAC | 4.3 | 5 | 0.12 | 0.1 |
| Gly | Gln | GGA | CAG | 6.8 | 8 | 0.22 | 0.0 |
| Gly | His | GGA | CAT | 7.7 | 8 | 0.01 | 0.0 |
| Gly | Pro | GGA | CCA | 10.9 | 13 | 0.42 | 1.4 |
| Gly | Pro | GGA | CCC | 4.3 | 6 | 0.72 | 1.4 |
| Gly | Pro | GGA | CCG | 2.9 | 1 | -1.22 | -0.9 |
| Gly | Pro | GGA | CCT | 7.5 | 10 | 0.80 | 1.8 |
| Gly | Arg | GGA | CGA | 1.8 | 1 | -0.38 | -0.2 |
| Gly | Arg | GGA | CGC | 1.3 | 0 | -1.25 | -1.1 |
| Gly | Arg | GGA | CGG | 0.9 | 1 | 0.01 | 0.0 |
| Gly | Arg | GGA | CGT | 4.8 | 3 | -0.66 | -0.3 |
| Gly | Leu | GGA | CTA | 7.6 | 7 | -0.04 | -0.0 |
| Gly | Leu | GGA | CTC | 2.9 | 5 | 1.59 | 2.3 |
| Gly | Leu | GGA | CTG | 6.1 | 6 | -0.00 | -0.1 |
| Gly | Leu | GGA | CTT | 6.8 | 5 | -0.46 | -0.2 |
| Gly | Glu | GGA | GAA | 27.4 | 33 | 1.15 | 2.2 |
| Gly | Asp | GGA | GAC | 12.4 | 13 | 0.03 | 0.6 |
| Gly | Glu | GGA | GAG | 11.5 | 9 | -0.52 | -0.3 |
| Gly | Asp | GGA | GAT | 23.9 | 18 | -1.45 | -0.2 |
| Gly | Ala | GGA | GCA | 10.3 | 7 | -1.08 | -0.9 |
| Gly | Ala | GGA | GCC | 8.0 | 4 | -1.99 | -1.8 |
| Gly | Ala | GGA | GCG | 3.6 | 3 | -0.11 | -0.1 |
| Gly | Ala | GGA | GCT | 13.2 | 7 | -2.88 | -2.5 |
| Gly | Gly | GGA | GGA | 7.2 | 7 | -0.01 | -0.1 |
| Gly | Gly | GGA | GGC | 6.1 | 4 | -0.75 | -1.1 |
| Gly | Gly | GGA | GGG | 3.9 | 3 | -0.19 | -0.3 |
| Gly | Gly | GGA | GGT | 17.8 | 10 | -3.41 | -4.5 |
| Gly | Val | GGA | GTA | 7.1 | 7 | -0.00 | -0.2 |
| Gly | Val | GGA | GTC | 7.5 | 3 | -2.74 | -3.8 |
| Gly | Val | GGA | GTG | 6.4 | 6 | -0.02 | -0.3 |
| Gly | Val | GGA | GTT | 14.1 | 5 | -5.89 | -7.9 |
| Gly | Ocr | GGA | TAA | 0.0 | 0 | 0.00 | 0.0 |
| Gly | Tyr | GGA | TAC | 9.8 | 7 | -0.78 | -0.8 |
| Gly | Amb | GGA | TAG | 0.0 | 0 | 0.00 | 0.0 |
| Gly | Tyr | GGA | TAT | 10.9 | 11 | 0.00 | 0.0 |
| Gly | Ser | GGA | TCA | 10.3 | 6 | -1.78 | -1.5 |
| Gly | Ser | GGA | TCC | 7.3 | 5 | -0.75 | -0.6 |
| Gly | Ser | GGA | TCG | 4.2 | 3 | -0.35 | -0.3 |
| Gly | Ser | GGA | TCT | 13.9 | 14 | 0.00 | 0.0 |
| Gly | Umb | GGA | TGA | 0.0 | 0 | 0.00 | 0.0 |
| Gly | Cys | GGA | TGC | 2.5 | 3 | 0.12 | 0.0 |
| Gly | Trp | GGA | TGG | 6.4 | 10 | 2.05 | 0.3 |
| Gly | Cys | GGA | TGT | 4.7 | 4 | -0.10 | -0.9 |
| Gly | Leu | GGA | TTA | 14.5 | 13 | -0.15 | -0.0 |
| Gly | Phe | GGA | TTC | 10.4 | 17 | 4.26 | 1.6 |
| Gly | Leu | GGA | TTG | 17.4 | 18 | 0.02 | 0.4 |
| Gly | Phe | GGA | TTT | 15.2 | 32 | 18.75 | 10.4 |
| | | Page Totals: | | 593.6 | 594 | 79.2073 | 69.1 |

PAGE 41

YEAST.RXD/CPLIST.RXR February 7, 1989

| aa1 | aa2 | cod1 | cod2 | exp | obs | chis1 | chis2 |
|---|---|---|---|---|---|---|---|
| Gly | Lys | GGC | AAA | 24.8 | 22 | -0.31 | -0.2 |
| Gly | Asn | GGC | AAC | 17.0 | 15 | -0.23 | -0.3 |
| Gly | Lys | GGC | AAG | 22.2 | 24 | 0.15 | 0.2 |
| Gly | Asn | GGC | AAT | 20.2 | 12 | -3.30 | -3.6 |
| Gly | Thr | GGC | ACA | 10.5 | 4 | -4.00 | -4.1 |
| Gly | Thr | GGC | ACC | 9.3 | 8 | -0.17 | -0.2 |
| Gly | Thr | GGC | ACG | 4.4 | 3 | -0.46 | -0.5 |
| Gly | Thr | GGC | ACT | 14.1 | 17 | 0.61 | 0.6 |
| Gly | Arg | GGC | AGA | 14.7 | 11 | -0.91 | -0.3 |
| Gly | Ser | GGC | AGC | 5.0 | 3 | -0.81 | -0.7 |
| Gly | Arg | GGC | AGG | 5.3 | 6 | 0.11 | 0.4 |
| Gly | Ser | GGC | AGT | 7.5 | 9 | 0.32 | 0.5 |
| Gly | Ile | GGC | ATA | 8.8 | 13 | 2.06 | 1.2 |
| Gly | Ile | GGC | ATC | 11.0 | 8 | -0.84 | -1.4 |
| Gly | Met | GGC | ATG | 14.5 | 6 | -4.97 | -3.6 |
| Gly | Ile | GGC | ATT | 20.2 | 17 | -0.50 | -1.1 |
| Gly | Gln | GGC | CAA | 18.4 | 37 | 18.94 | 12.6 |
| Gly | His | GGC | CAC | 5.2 | 14 | 14.67 | 13.3 |
| Gly | Gln | GGC | CAG | 6.9 | 10 | 1.43 | 0.6 |
| Gly | His | GGC | CAT | 8.1 | 8 | -0.00 | -0.0 |
| Gly | Pro | GGC | CCA | 12.9 | 23 | 7.90 | 12.4 |
| Gly | Pro | GGC | CCC | 4.5 | 3 | -0.51 | -0.2 |
| Gly | Pro | GGC | CCG | 2.7 | 0 | -2.72 | -2.4 |
| Gly | Pro | GGC | CCT | 8.3 | 10 | 0.34 | 1.1 |
| Gly | Arg | GGC | CGA | 1.5 | 2 | 0.16 | 0.4 |
| Gly | Arg | GGC | CGC | 1.3 | 1 | -0.06 | -0.0 |
| Gly | Arg | GGC | CGG | 0.8 | 0 | -0.75 | -0.7 |
| Gly | Arg | GGC | CGT | 5.2 | 10 | 4.34 | 6.4 |
| Gly | Leu | GGC | CTA | 8.4 | 13 | 2.54 | 4.0 |
| Gly | Leu | GGC | CTC | 2.7 | 2 | -0.17 | -0.1 |
| Gly | Leu | GGC | CTG | 6.3 | 3 | -1.73 | -1.2 |
| Gly | Leu | GGC | CTT | 6.7 | 7 | 0.01 | 0.2 |
| Gly | Glu | GGC | GAA | 30.2 | 13 | -9.80 | -8.1 |
| Gly | Asp | GGC | GAC | 14.5 | 14 | -0.02 | -0.2 |
| Gly | Glu | GGC | GAG | 11.7 | 15 | 0.92 | 1.5 |
| Gly | Asp | GGC | GAT | 24.4 | 17 | -2.23 | -0.6 |
| Gly | Ala | GGC | GCA | 11.4 | 13 | 0.24 | 0.4 |
| Gly | Ala | GGC | GCC | 10.9 | 4 | -4.40 | -4.0 |
| Gly | Ala | GGC | GCG | 3.8 | 2 | -0.82 | -0.7 |
| Gly | Ala | GGC | GCT | 17.6 | 18 | 0.01 | 0.1 |
| Gly | Gly | GGC | GGA | 6.1 | 7 | 0.12 | 0.0 |
| Gly | Gly | GGC | GGC | 8.4 | 5 | -1.39 | -1.9 |
| Gly | Gly | GGC | GGG | 4.0 | 3 | -0.25 | -0.4 |
| Gly | Gly | GGC | GGT | 23.9 | 21 | -0.35 | -0.9 |
| Gly | Val | GGC | GTA | 6.9 | 11 | 2.42 | 1.1 |
| Gly | Val | GGC | GTC | 9.6 | 9 | -0.03 | -0.4 |
| Gly | Val | GGC | GTG | 7.3 | 5 | -0.70 | -1.4 |
| Gly | Val | GGC | GTT | 17.3 | 16 | -0.09 | -0.8 |
| Gly | Ocr | GGC | TAA | 0.0 | 0 | 0.00 | 0.0 |
| Gly | Tyr | GGC | TAC | 12.1 | 15 | 0.68 | 0.6 |
| Gly | Amb | GGC | TAG | 0.0 | 0 | 0.00 | 0.0 |
| Gly | Tyr | GGC | TAT | 11.3 | 12 | 0.05 | 0.0 |
| Gly | Ser | GGC | TCA | 10.3 | 13 | 0.71 | 1.0 |
| Gly | Ser | GGC | TCC | 9.1 | 15 | 3.82 | 4.4 |
| Gly | Ser | GGC | TCG | 4.3 | 4 | -0.03 | -0.0 |
| Gly | Ser | GGC | TCT | 16.0 | 16 | 0.00 | -0.0 |
| Gly | Umb | GGC | TGA | 0.0 | 0 | 0.00 | 0.0 |
| Gly | Cys | GGC | TGC | 2.3 | 7 | 9.48 | 4.8 |
| Gly | Trp | GGC | TGG | 7.0 | 17 | 14.15 | 6.3 |
| Gly | Cys | GGC | TGT | 5.4 | 11 | 5.98 | 2.0 |
| Gly | Leu | GGC | TTA | 15.7 | 15 | -0.03 | -0.1 |
| Gly | Phe | GGC | TTC | 12.8 | 5 | -4.77 | -7.1 |
| Gly | Leu | GGC | TTG | 21.0 | 21 | 0.00 | -0.3 |
| Gly | Phe | GGC | TTT | 15.2 | 16 | 0.04 | 0.3 |
| | | Page Totals: | | 659.5 | 661 | 139.579 | 124.0 |

PAGE 42

YEAST.RXD/CPLIST.RXR February 7, 1989

| aa1 | aa2 | cod1 | cod2 | exp | obs | chis1 | chis2 |
|---|---|---|---|---|---|---|---|
| Gly | Lys | GGG | AAA | 16.3 | 22 | 2.03 | 2.3 |
| Gly | Asn | GGG | AAC | 10.2 | 9 | -0.13 | -0.2 |
| Gly | Lys | GGG | AAG | 13.3 | 15 | 0.22 | 0.3 |
| Gly | Asn | GGG | AAT | 13.2 | 13 | -0.00 | -0.0 |
| Gly | Thr | GGG | ACA | 6.7 | 11 | 2.83 | 2.7 |
| Gly | Thr | GGG | ACC | 5.2 | 5 | -0.01 | -0.0 |
| Gly | Thr | GGG | ACG | 3.1 | 0 | -3.12 | -3.1 |
| Gly | Thr | GGG | ACT | 8.4 | 8 | -0.02 | -0.0 |
| Gly | Arg | GGG | AGA | 9.2 | 7 | -0.51 | -0.1 |
| Gly | Ser | GGG | AGC | 3.3 | 5 | 0.86 | 1.0 |
| Gly | Arg | GGG | AGG | 3.7 | 3 | -0.12 | -0.0 |
| Gly | Ser | GGG | AGT | 4.8 | 2 | -1.64 | -1.5 |
| Gly | Ile | GGG | ATA | 5.7 | 2 | -2.40 | -2.9 |
| Gly | Ile | GGG | ATC | 6.7 | 7 | 0.01 | 0.0 |
| Gly | Met | GGG | ATG | 9.3 | 10 | 0.05 | 0.4 |
| Gly | Ile | GGG | ATT | 12.4 | 9 | -0.94 | -1.5 |
| Gly | Gln | GGG | CAA | 11.5 | 7 | -1.76 | -2.8 |
| Gly | His | GGG | CAC | 2.9 | 5 | 1.49 | 1.3 |
| Gly | Gln | GGG | CAG | 4.5 | 11 | 9.54 | 6.9 |
| Gly | His | GGG | CAT | 5.3 | 6 | 0.09 | 0.0 |
| Gly | Pro | GGG | CCA | 7.6 | 10 | 0.74 | 1.7 |
| Gly | Pro | GGG | CCC | 3.0 | 2 | -0.36 | -0.2 |
| Gly | Pro | GGG | CCG | 2.0 | 5 | 4.48 | 6.1 |
| Gly | Pro | GGG | CCT | 4.9 | 7 | 0.89 | 1.8 |
| Gly | Arg | GGG | CGA | 1.1 | 0 | -1.09 | -1.0 |
| Gly | Arg | GGG | CGC | 0.9 | 2 | 1.52 | 2.1 |
| Gly | Arg | GGG | CGG | 0.5 | 1 | 0.41 | 0.6 |
| Gly | Arg | GGG | CGT | 3.1 | 5 | 1.11 | 1.9 |
| Gly | Leu | GGG | CTA | 5.0 | 9 | 3.25 | 4.6 |
| Gly | Leu | GGG | CTC | 1.9 | 5 | 5.11 | 6.5 |
| Gly | Leu | GGG | CTG | 4.1 | 2 | -1.06 | -0.7 |
| Gly | Leu | GGG | CTT | 4.4 | 4 | -0.03 | -0.0 |
| Gly | Glu | GGG | GAA | 19.0 | 15 | -0.85 | -0.4 |
| Gly | Asp | GGG | GAC | 8.9 | 6 | -0.94 | -0.3 |
| Gly | Glu | GGG | GAG | 8.0 | 4 | -2.00 | -1.6 |
| Gly | Asp | GGG | GAT | 16.1 | 11 | -1.61 | -0.5 |
| Gly | Ala | GGG | GCA | 6.8 | 6 | -0.09 | -0.0 |
| Gly | Ala | GGG | GCC | 6.2 | 2 | -2.83 | -2.6 |
| Gly | Ala | GGG | GCG | 2.4 | 3 | 0.16 | 0.2 |
| Gly | Ala | GGG | GCT | 9.8 | 8 | -0.34 | -0.2 |
| Gly | Gly | GGG | GGA | 3.9 | 0 | -3.87 | -4.2 |
| Gly | Gly | GGG | GGC | 4.0 | 1 | -2.25 | -2.6 |
| Gly | Gly | GGG | GGG | 3.6 | 1 | -1.89 | -2.2 |
| Gly | Gly | GGG | GGT | 13.2 | 6 | -3.96 | -4.9 |
| Gly | Val | GGG | GTA | 4.4 | 2 | -1.34 | -1.9 |
| Gly | Val | GGG | GTC | 5.6 | 0 | -5.57 | -6.5 |
| Gly | Val | GGG | GTG | 4.5 | 5 | 0.05 | 0.0 |
| Gly | Val | GGG | GTT | 9.8 | 9 | -0.06 | -0.5 |
| Gly | Ocr | GGG | TAA | 0.0 | 0 | 0.00 | 0.0 |
| Gly | Tyr | GGG | TAC | 6.6 | 6 | -0.06 | -0.1 |
| Gly | Amb | GGG | TAG | 0.0 | 0 | 0.00 | 0.0 |
| Gly | Tyr | GGG | TAT | 7.4 | 8 | 0.06 | 0.1 |
| Gly | Ser | GGG | TCA | 6.6 | 8 | 0.30 | 0.4 |
| Gly | Ser | GGG | TCC | 5.2 | 5 | -0.01 | -0.0 |
| Gly | Ser | GGG | TCG | 2.9 | 0 | -2.90 | -2.8 |
| Gly | Ser | GGG | TCT | 9.7 | 5 | -2.25 | -2.0 |
| Gly | Umb | GGG | TGA | 0.0 | 0 | 0.00 | 0.0 |
| Gly | Cys | GGG | TGC | 1.8 | 0 | -1.80 | -2.4 |
| Gly | Trp | GGG | TGG | 4.0 | 3 | -0.25 | -1.0 |
| Gly | Cys | GGG | TGT | 3.2 | 5 | 0.98 | 0.1 |
| Gly | Leu | GGG | TTA | 9.7 | 10 | 0.01 | 0.2 |
| Gly | Phe | GGG | TTC | 7.6 | 25 | 40.32 | 27.8 |
| Gly | Leu | GGG | TTG | 12.3 | 21 | 6.12 | 9.0 |
| Gly | Phe | GGG | TTT | 9.9 | 24 | 20.17 | 12.3 |
| | Page Totals: | | | 407.1 | 408 | 150.847 | 141.2 |

PAGE 43

YEAST.RXD/CPLIST.RXR February 7, 1989

| aa1 | aa2 | cod1 | cod2 | exp | obs | chis1 | chis2 |
|---|---|---|---|---|---|---|---|
| Gly | Lys | GGT | AAA | 92.2 | 101 | 0.83 | 1.2 |
| Gly | Asn | GGT | AAC | 76.1 | 83 | 0.63 | 0.4 |
| Gly | Lys | GGT | AAG | 121.3 | 101 | -3.41 | -2.7 |
| Gly | Asn | GGT | AAT | 65.5 | 65 | -0.00 | -0.0 |
| Gly | Thr | GGT | ACA | 35.9 | 26 | -2.74 | -2.9 |
| Gly | Thr | GGT | ACC | 49.9 | 60 | 2.03 | 1.8 |
| Gly | Thr | GGT | ACG | 13.7 | 17 | 0.80 | 0.7 |
| Gly | Thr | GGT | ACT | 68.9 | 79 | 1.49 | 1.3 |
| Gly | Arg | GGT | AGA | 86.5 | 78 | -0.84 | -0.1 |
| Gly | Ser | GGT | AGC | 15.3 | 6 | -5.62 | -5.1 |
| Gly | Arg | GGT | AGG | 15.6 | 7 | -4.70 | -3.2 |
| Gly | Ser | GGT | AGT | 22.9 | 13 | -4.25 | -3.7 |
| Gly | Ile | GGT | ATA | 23.4 | 21 | -0.24 | -0.8 |
| Gly | Ile | GGT | ATC | 61.5 | 61 | -0.00 | -0.6 |
| Gly | Met | GGT | ATG | 64.1 | 60 | -0.26 | -0.2 |
| Gly | Ile | GGT | ATT | 95.1 | 122 | 7.63 | 3.2 |
| Gly | Gln | GGT | CAA | 87.5 | 78 | -1.03 | -4.5 |
| Gly | His | GGT | CAC | 26.2 | 26 | -0.00 | -0.1 |
| Gly | Gln | GGT | CAG | 19.9 | 18 | -0.17 | -0.9 |
| Gly | His | GGT | CAT | 33.1 | 25 | -1.98 | -2.7 |
| Gly | Pro | GGT | CCA | 76.8 | 53 | -7.36 | -2.8 |
| Gly | Pro | GGT | CCC | 14.9 | 12 | -0.57 | -0.1 |
| Gly | Pro | GGT | CCG | 7.5 | 5 | -0.80 | -0.3 |
| Gly | Pro | GGT | CCT | 33.1 | 17 | -7.80 | -4.8 |
| Gly | Arg | GGT | CGA | 3.3 | 3 | -0.02 | -0.0 |
| Gly | Arg | GGT | CGC | 3.8 | 1 | -2.03 | -1.6 |
| Gly | Arg | GGT | CGG | 1.8 | 1 | -0.35 | -0.2 |
| Gly | Arg | GGT | CGT | 26.0 | 25 | -0.04 | -0.2 |
| Gly | Leu | GGT | CTA | 31.6 | 34 | 0.19 | 1.2 |
| Gly | Leu | GGT | CTC | 7.9 | 8 | 0.00 | 0.1 |
| Gly | Leu | GGT | CTG | 18.6 | 10 | -3.96 | -2.6 |
| Gly | Leu | GGT | CTT | 23.0 | 19 | -0.69 | -0.1 |
| Gly | Glu | GGT | GAA | 149.7 | 146 | -0.09 | -0.3 |
| Gly | Asp | GGT | GAC | 70.1 | 69 | -0.02 | -1.6 |
| Gly | Glu | GGT | GAG | 40.2 | 42 | 0.08 | 0.6 |
| Gly | Asp | GGT | GAT | 101.1 | 81 | -3.99 | -0.2 |
| Gly | Ala | GGT | GCA | 39.4 | 37 | -0.15 | -0.0 |
| Gly | Ala | GGT | GCC | 60.5 | 68 | 0.92 | 1.7 |
| Gly | Ala | GGT | GCG | 11.5 | 6 | -2.60 | -2.3 |
| Gly | Ala | GGT | GCT | 110.8 | 125 | 1.82 | 3.3 |
| Gly | Gly | GGT | GGA | 17.8 | 22 | 1.00 | 0.4 |
| Gly | Gly | GGT | GGC | 23.9 | 28 | 0.70 | 0.2 |
| Gly | Gly | GGT | GGG | 13.2 | 22 | 5.79 | 4.0 |
| Gly | Gly | GGT | GGT | 164.2 | 209 | 12.25 | 5.3 |
| Gly | Val | GGT | GTA | 21.6 | 33 | 6.03 | 2.5 |
| Gly | Val | GGT | GTC | 60.2 | 78 | 5.29 | 0.9 |
| Gly | Val | GGT | GTG | 26.3 | 30 | 0.53 | 0.0 |
| Gly | Val | GGT | GTT | 97.9 | 137 | 15.66 | 4.7 |
| Gly | Ocr | GGT | TAA | 0.0 | 1 | 0.00 | 0.0 |
| Gly | Tyr | GGT | TAC | 56.9 | 70 | 2.99 | 2.8 |
| Gly | Amb | GGT | TAG | 0.0 | 1 | 0.00 | 0.0 |
| Gly | Tyr | GGT | TAT | 40.3 | 27 | -4.36 | -4.5 |
| Gly | Ser | GGT | TCA | 34.4 | 33 | -0.05 | -0.0 |
| Gly | Ser | GGT | TCC | 46.9 | 55 | 1.39 | 2.1 |
| Gly | Ser | GGT | TCG | 12.5 | 7 | -2.41 | -2.1 |
| Gly | Ser | GGT | TCT | 80.5 | 91 | 1.38 | 2.4 |
| Gly | Umb | GGT | TGA | 0.0 | 0 | 0.00 | 0.0 |
| Gly | Cys | GGT | TGC | 8.1 | 12 | 1.94 | 0.1 |
| Gly | Trp | GGT | TGG | 28.5 | 31 | 0.21 | 1.3 |
| Gly | Cys | GGT | TGT | 24.7 | 29 | 0.76 | 0.6 |
| Gly | Leu | GGT | TTA | 63.4 | 54 | -1.38 | -0.1 |
| Gly | Phe | GGT | TTC | 64.1 | 68 | 0.23 | 1.1 |
| Gly | Leu | GGT | TTG | 115.8 | 79 | -11.72 | -5.9 |
| Gly | Phe | GGT | TTT | 56.0 | 43 | -3.00 | -8.8 |
| | Page Totals: | | | 2962.8 | 2969 | 151.214 | 109.9 |

PAGE 44

YEAST.RXD/CPLIST.RXR February 7, 1989

| aa1 | aa2 | cod1 | cod2 | exp | obs | chis1 | chis2 |
|---|---|---|---|---|---|---|---|
| Val | Lys | GTA | AAA | 30.6 | 26 | -0.68 | -0.9 |
| Val | Asn | GTA | AAC | 17.2 | 13 | -1.03 | -1.0 |
| Val | Lys | GTA | AAG | 22.7 | 19 | -0.61 | -0.7 |
| Val | Asn | GTA | AAT | 24.5 | 36 | 5.44 | 5.5 |
| Val | Thr | GTA | ACA | 12.1 | 11 | -0.09 | -0.2 |
| Val | Thr | GTA | ACC | 8.9 | 5 | -1.69 | -1.9 |
| Val | Thr | GTA | ACG | 5.3 | 4 | -0.30 | -0.4 |
| Val | Thr | GTA | ACT | 14.4 | 14 | -0.01 | -0.1 |
| Val | Arg | GTA | AGA | 16.5 | 13 | -0.73 | -0.4 |
| Val | Ser | GTA | AGC | 5.7 | 7 | 0.29 | 0.2 |
| Val | Arg | GTA | AGG | 6.3 | 8 | 0.45 | 0.7 |
| Val | Ser | GTA | AGT | 8.9 | 11 | 0.51 | 0.3 |
| Val | Ile | GTA | ATA | 11.1 | 8 | -0.86 | -0.6 |
| Val | Ile | GTA | ATC | 11.3 | 6 | -2.50 | -2.0 |
| Val | Met | GTA | ATG | 15.8 | 8 | -3.84 | -2.7 |
| Val | Ile | GTA | ATT | 22.5 | 17 | -1.32 | -0.8 |
| Val | Gln | GTA | CAA | 19.5 | 16 | -0.63 | -0.0 |
| Val | His | GTA | CAC | 5.1 | 3 | -0.84 | -0.6 |
| Val | Gln | GTA | CAG | 7.7 | 8 | 0.01 | 0.5 |
| Val | His | GTA | CAT | 9.3 | 6 | -1.15 | -0.7 |
| Val | Pro | GTA | CCA | 13.6 | 19 | 2.18 | 0.3 |
| Val | Pro | GTA | CCC | 5.1 | 6 | 0.17 | 0.0 |
| Val | Pro | GTA | CCG | 3.5 | 10 | 12.30 | 7.5 |
| Val | Pro | GTA | CCT | 9.2 | 3 | -4.14 | -6.2 |
| Val | Arg | GTA | CGA | 2.2 | 1 | -0.65 | -0.5 |
| Val | Arg | GTA | CGC | 1.7 | 3 | 1.05 | 1.3 |
| Val | Arg | GTA | CGG | 1.0 | 2 | 1.01 | 1.2 |
| Val | Arg | GTA | CGT | 6.0 | 8 | 0.68 | 1.0 |
| Val | Leu | GTA | CTA | 9.5 | 8 | -0.22 | -0.3 |
| Val | Leu | GTA | CTC | 3.4 | 5 | 0.81 | 0.7 |
| Val | Leu | GTA | CTG | 7.5 | 12 | 2.74 | 2.5 |
| Val | Leu | GTA | CTT | 8.1 | 6 | -0.54 | -0.6 |
| Val | Glu | GTA | GAA | 34.1 | 33 | -0.04 | -0.3 |
| Val | Asp | GTA | GAC | 14.7 | 16 | 0.12 | 0.1 |
| Val | Glu | GTA | GAG | 14.2 | 21 | 3.27 | 5.8 |
| Val | Asp | GTA | GAT | 28.8 | 36 | 1.81 | 1.6 |
| Val | Ala | GTA | GCA | 12.2 | 30 | 26.20 | 22.6 |
| Val | Ala | GTA | GCC | 9.8 | 11 | 0.15 | 0.0 |
| Val | Ala | GTA | GCG | 4.6 | 6 | 0.41 | 0.2 |
| Val | Ala | GTA | GCT | 16.2 | 12 | -1.10 | -1.6 |
| Val | Gly | GTA | GGA | 7.1 | 4 | -1.33 | -1.3 |
| Val | Gly | GTA | GGC | 6.9 | 7 | 0.00 | 0.0 |
| Val | Gly | GTA | GGG | 4.4 | 5 | 0.07 | 0.1 |
| Val | Gly | GTA | GGT | 21.6 | 20 | -0.12 | -0.1 |
| Val | Val | GTA | GTA | 10.2 | 3 | -5.07 | -5.4 |
| Val | Val | GTA | GTC | 9.5 | 7 | -0.66 | -0.8 |
| Val | Val | GTA | GTG | 7.7 | 11 | 1.37 | 1.1 |
| Val | Val | GTA | GTT | 17.3 | 14 | -0.63 | -0.9 |
| Val | Ocr | GTA | TAA | 0.0 | 3 | 0.00 | 0.0 |
| Val | Tyr | GTA | TAC | 11.1 | 10 | -0.10 | -0.0 |
| Val | Amb | GTA | TAG | 0.0 | 0 | 0.00 | 0.0 |
| Val | Tyr | GTA | TAT | 13.0 | 14 | 0.07 | 0.4 |
| Val | Ser | GTA | TCA | 12.8 | 10 | -0.63 | -0.9 |
| Val | Ser | GTA | TCC | 9.3 | 9 | -0.01 | -0.1 |
| Val | Ser | GTA | TCG | 5.0 | 9 | 3.19 | 2.6 |
| Val | Ser | GTA | TCT | 17.6 | 21 | 0.64 | 0.3 |
| Val | Umb | GTA | TGA | 0.0 | 0 | 0.00 | 0.0 |
| Val | Cys | GTA | TGC | 2.8 | 1 | -1.15 | -1.1 |
| Val | Trp | GTA | TGG | 7.3 | 7 | -0.01 | -0.0 |
| Val | Cys | GTA | TGT | 5.9 | 4 | -0.60 | -0.6 |
| Val | Leu | GTA | TTA | 18.1 | 19 | 0.04 | 0.0 |
| Val | Phe | GTA | TTC | 12.7 | 9 | -1.07 | -1.2 |
| Val | Leu | GTA | TTG | 20.1 | 19 | -0.06 | -0.1 |
| Val | Phe | GTA | TTT | 18.0 | 27 | 4.55 | 4.0 |
| | | Page Totals: | | 718.5 | 720 | 103.965 | 95.7 |

PAGE 45

YEAST.RXD/CPLIST.RXR February 7, 1989

| aa1 | aa2 | cod1 | cod2 | exp | obs | chis1 | chis2 |
|---|---|---|---|---|---|---|---|
| Val | Lys | GTC | AAA | 37.3 | 63 | 17.67 | 16.4 |
| Val | Asn | GTC | AAC | 32.3 | 37 | 0.68 | 0.7 |
| Val | Lys | GTC | AAG | 49.5 | 81 | 20.11 | 18.6 |
| Val | Asn | GTC | AAT | 27.7 | 35 | 1.93 | 2.0 |
| Val | Thr | GTC | ACA | 14.6 | 21 | 2.81 | 2.3 |
| Val | Thr | GTC | ACC | 20.9 | 29 | 3.17 | 2.5 |
| Val | Thr | GTC | ACG | 5.8 | 7 | 0.25 | 0.2 |
| Val | Thr | GTC | ACT | 28.0 | 33 | 0.89 | 0.5 |
| Val | Arg | GTC | AGA | 34.5 | 41 | 1.22 | 2.3 |
| Val | Ser | GTC | AGC | 6.5 | 7 | 0.05 | 0.0 |
| Val | Arg | GTC | AGG | 6.8 | 7 | 0.01 | 0.1 |
| Val | Ser | GTC | AGT | 10.1 | 20 | 9.66 | 8.1 |
| Val | Ile | GTC | ATA | 10.8 | 11 | 0.01 | 0.1 |
| Val | Ile | GTC | ATC | 24.3 | 35 | 4.74 | 6.6 |
| Val | Met | GTC | ATG | 25.7 | 33 | 2.08 | 4.2 |
| Val | Ile | GTC | ATT | 37.5 | 39 | 0.06 | 0.4 |
| Val | Gln | GTC | CAA | 34.3 | 20 | -5.99 | -2.3 |
| Val | His | GTC | CAC | 10.8 | 13 | 0.45 | 1.0 |
| Val | Gln | GTC | CAG | 8.9 | 5 | -1.73 | -0.7 |
| Val | His | GTC | CAT | 13.4 | 16 | 0.51 | 1.1 |
| Val | Pro | GTC | CCA | 29.5 | 26 | -0.42 | -3.1 |
| Val | Pro | GTC | CCC | 6.4 | 12 | 4.92 | 2.1 |
| Val | Pro | GTC | CCG | 3.6 | 3 | -0.09 | -0.5 |
| Val | Pro | GTC | CCT | 13.1 | 10 | -0.72 | -2.4 |
| Val | Arg | GTC | CGA | 1.7 | 2 | 0.04 | 0.1 |
| Val | Arg | GTC | CGC | 1.7 | 2 | 0.05 | 0.1 |
| Val | Arg | GTC | CGG | 0.9 | 2 | 1.51 | 1.8 |
| Val | Arg | GTC | CGT | 10.3 | 12 | 0.28 | 0.6 |
| Val | Leu | GTC | CTA | 12.7 | 7 | -2.55 | -2.8 |
| Val | Leu | GTC | CTC | 3.7 | 4 | 0.03 | 0.0 |
| Val | Leu | GTC | CTG | 8.3 | 7 | -0.22 | -0.3 |
| Val | Leu | GTC | CTT | 9.4 | 6 | -1.20 | -1.3 |
| Val | Glu | GTC | GAA | 59.9 | 35 | -10.36 | -6.0 |
| Val | Asp | GTC | GAC | 29.6 | 24 | -1.04 | -1.2 |
| Val | Glu | GTC | GAG | 16.7 | 13 | -0.81 | -0.2 |
| Val | Asp | GTC | GAT | 41.4 | 40 | -0.05 | -0.1 |
| Val | Ala | GTC | GCA | 16.1 | 11 | -1.60 | -2.2 |
| Val | Ala | GTC | GCC | 23.3 | 17 | -1.71 | -2.4 |
| Val | Ala | GTC | GCG | 4.9 | 2 | -1.70 | -2.0 |
| Val | Ala | GTC | GCT | 43.4 | 22 | -10.53 | -12.6 |
| Val | Gly | GTC | GGA | 7.5 | 5 | -0.86 | -0.9 |
| Val | Gly | GTC | GGC | 9.6 | 10 | 0.02 | 0.0 |
| Val | Gly | GTC | GGG | 5.6 | 3 | -1.19 | -1.2 |
| Val | Gly | GTC | GGT | 60.2 | 62 | 0.06 | 0.1 |
| Val | Val | GTC | GTA | 9.5 | 10 | 0.03 | 0.0 |
| Val | Val | GTC | GTC | 27.2 | 22 | -1.00 | -1.4 |
| Val | Val | GTC | GTG | 10.7 | 11 | 0.01 | 0.0 |
| Val | Val | GTC | GTT | 37.1 | 40 | 0.23 | 0.1 |
| Val | Ocr | GTC | TAA | 0.0 | 0 | 0.00 | 0.0 |
| Val | Tyr | GTC | TAC | 22.9 | 17 | -1.51 | -0.7 |
| Val | Amb | GTC | TAG | 0.0 | 0 | 0.00 | 0.0 |
| Val | Tyr | GTC | TAT | 16.4 | 13 | -0.69 | -0.3 |
| Val | Ser | GTC | TCA | 14.3 | 6 | -4.85 | -5.5 |
| Val | Ser | GTC | TCC | 19.4 | 21 | 0.13 | 0.0 |
| Val | Ser | GTC | TCG | 5.5 | 3 | -1.10 | -1.3 |
| Val | Ser | GTC | TCT | 32.0 | 31 | -0.03 | -0.2 |
| Val | Umb | GTC | TGA | 0.0 | 0 | 0.00 | 0.0 |
| Val | Cys | GTC | TGC | 3.1 | 3 | -0.00 | -0.0 |
| Val | Trp | GTC | TGG | 12.1 | 12 | -0.00 | -0.1 |
| Val | Cys | GTC | TGT | 9.9 | 12 | 0.44 | 0.5 |
| Val | Leu | GTC | TTA | 25.6 | 18 | -2.26 | -2.6 |
| Val | Phe | GTC | TTC | 26.6 | 29 | 0.22 | 0.1 |
| Val | Leu | GTC | TTG | 46.4 | 42 | -0.42 | -0.6 |
| Val | Phe | GTC | TTT | 22.7 | 23 | 0.01 | 0.0 |
| | | Page Totals: | | 1200.1 | 1203 | 128.884 | 127.0 |

PAGE 46

YEAST.RXD/CPLIST.RXR February 7, 1989

| aa1 | aa2 | cod1 | cod2 | exp | obs | chis1 | chis2 |
|---|---|---|---|---|---|---|---|
| Val | Lys | GTG | AAA | 27.3 | 28 | 0.02 | 0.0 |
| Val | Asn | GTG | AAC | 18.1 | 20 | 0.20 | 0.2 |
| Val | Lys | GTG | AAG | 24.5 | 30 | 1.26 | 1.0 |
| Val | Asn | GTG | AAT | 22.5 | 18 | -0.91 | -0.9 |
| Val | Thr | GTG | ACA | 12.0 | 14 | 0.32 | 0.2 |
| Val | Thr | GTG | ACC | 10.1 | 4 | -3.71 | -4.0 |
| Val | Thr | GTG | ACG | 4.9 | 6 | 0.25 | 0.2 |
| Val | Thr | GTG | ACT | 15.0 | 10 | -1.66 | -2.0 |
| Val | Arg | GTG | AGA | 16.5 | 13 | -0.73 | -0.4 |
| Val | Ser | GTG | AGC | 5.3 | 4 | -0.33 | -0.5 |
| Val | Arg | GTG | AGG | 6.2 | 5 | -0.22 | -0.1 |
| Val | Ser | GTG | AGT | 8.1 | 8 | -0.00 | -0.0 |
| Val | Ile | GTG | ATA | 9.8 | 19 | 8.62 | 10.4 |
| Val | Ile | GTG | ATC | 12.3 | 5 | -4.33 | -3.7 |
| Val | Met | GTG | ATG | 16.1 | 13 | -0.58 | -0.1 |
| Val | Ile | GTG | ATT | 22.6 | 20 | -0.30 | -0.1 |
| Val | Gln | GTG | CAA | 20.2 | 23 | 0.39 | 2.5 |
| Val | His | GTG | CAC | 5.6 | 8 | 1.07 | 1.6 |
| Val | Gln | GTG | CAG | 7.7 | 8 | 0.02 | 0.5 |
| Val | His | GTG | CAT | 9.1 | 4 | -2.82 | -2.2 |
| Val | Pro | GTG | CCA | 14.3 | 15 | 0.04 | 0.4 |
| Val | Pro | GTG | CCC | 5.1 | 8 | 1.60 | 0.4 |
| Val | Pro | GTG | CCG | 3.1 | 3 | -0.00 | -0.2 |
| Val | Pro | GTG | CCT | 9.4 | 8 | -0.21 | -1.2 |
| Val | Arg | GTG | CGA | 1.9 | 5 | 5.29 | 6.1 |
| Val | Arg | GTG | CGC | 1.5 | 0 | -1.51 | -1.4 |
| Val | Arg | GTG | CGG | 1.0 | 0 | -0.97 | -0.9 |
| Val | Arg | GTG | CGT | 5.9 | 3 | -1.43 | -1.2 |
| Val | Leu | GTG | CTA | 9.2 | 9 | -0.00 | -0.0 |
| Val | Leu | GTG | CTC | 3.1 | 4 | 0.29 | 0.2 |
| Val | Leu | GTG | CTG | 7.1 | 8 | 0.12 | 0.1 |
| Val | Leu | GTG | CTT | 7.9 | 7 | -0.09 | -0.1 |
| Val | Glu | GTG | GAA | 34.6 | 46 | 3.80 | 7.9 |
| Val | Asp | GTG | GAC | 15.9 | 23 | 3.16 | 3.0 |
| Val | Glu | GTG | GAG | 13.3 | 22 | 5.76 | 9.1 |
| Val | Asp | GTG | GAT | 27.5 | 30 | 0.23 | 0.2 |
| Val | Ala | GTG | GCA | 12.6 | 16 | 0.95 | 0.5 |
| Val | Ala | GTG | GCC | 11.7 | 16 | 1.57 | 1.0 |
| Val | Ala | GTG | GCG | 4.2 | 6 | 0.80 | 0.6 |
| Val | Ala | GTG | GCT | 19.0 | 17 | -0.20 | -0.5 |
| Val | Gly | GTG | GGA | 6.4 | 10 | 2.09 | 2.1 |
| Val | Gly | GTG | GGC | 7.3 | 11 | 1.94 | 1.9 |
| Val | Gly | GTG | GGG | 4.5 | 3 | -0.51 | -0.5 |
| Val | Gly | GTG | GGT | 26.3 | 18 | -2.61 | -2.6 |
| Val | Val | GTG | GTA | 7.7 | 14 | 5.06 | 4.4 |
| Val | Val | GTG | GTC | 10.7 | 16 | 2.65 | 2.2 |
| Val | Val | GTG | GTG | 10.0 | 8 | -0.42 | -0.6 |
| Val | Val | GTG | GTT | 19.2 | 16 | -0.52 | -0.8 |
| Val | Ocr | GTG | TAA | 0.0 | 4 | 0.00 | 0.0 |
| Val | Tyr | GTG | TAC | 11.7 | 3 | -6.50 | -5.6 |
| Val | Amb | GTG | TAG | 0.0 | 0 | 0.00 | 0.0 |
| Val | Tyr | GTG | TAT | 12.2 | 12 | -0.00 | -0.1 |
| Val | Ser | GTG | TCA | 11.3 | 10 | -0.15 | -0.3 |
| Val | Ser | GTG | TCC | 10.0 | 11 | 0.10 | 0.0 |
| Val | Ser | GTG | TCG | 4.9 | 5 | 0.00 | 0.0 |
| Val | Ser | GTG | TCT | 17.4 | 13 | -1.13 | -1.6 |
| Val | Umb | GTG | TGA | 0.0 | 0 | 0.00 | 0.0 |
| Val | Cys | GTG | TGC | 2.7 | 0 | -2.70 | -2.7 |
| Val | Trp | GTG | TGG | 7.0 | 4 | -1.29 | -0.8 |
| Val | Cys | GTG | TGT | 5.7 | 2 | -2.40 | -2.4 |
| Val | Leu | GTG | TTA | 17.6 | 12 | -1.76 | -2.0 |
| Val | Phe | GTG | TTC | 13.1 | 14 | 0.06 | 0.0 |
| Val | Leu | GTG | TTG | 22.1 | 20 | -0.20 | -0.3 |
| Val | Phe | GTG | TTT | 16.9 | 16 | -0.05 | -0.1 |
| | Page Totals: | | | 726.4 | 728 | 87.887 | 96.5 |

PAGE 47

YEAST.RXD/CPLIST.RXR February 7, 1989

| aa1 | aa2 | cod1 | cod2 | exp | obs | chis1 | chis2 |
|---|---|---|---|---|---|---|---|
| Val | Lys | GTT | AAA | 72.1 | 46 | -9.45 | -10.3 |
| Val | Asn | GTT | AAC | 52.7 | 49 | -0.26 | -0.2 |
| Val | Lys | GTT | AAG | 81.4 | 59 | -6.16 | -6.9 |
| Val | Asn | GTT | AAT | 52.8 | 39 | -3.62 | -3.5 |
| Val | Thr | GTT | ACA | 27.7 | 25 | -0.27 | -0.5 |
| Val | Thr | GTT | ACC | 32.9 | 42 | 2.53 | 1.8 |
| Val | Thr | GTT | ACG | 11.3 | 8 | -0.94 | -1.2 |
| Val | Thr | GTT | ACT | 48.8 | 50 | 0.03 | 0.0 |
| Val | Arg | GTT | AGA | 58.0 | 46 | -2.48 | -1.3 |
| Val | Ser | GTT | AGC | 12.0 | 14 | 0.35 | 0.1 |
| Val | Arg | GTT | AGG | 12.8 | 8 | -1.82 | -1.4 |
| Val | Ser | GTT | AGT | 18.9 | 11 | -3.33 | -4.0 |
| Val | Ile | GTT | ATA | 20.8 | 18 | -0.39 | -0.1 |
| Val | Ile | GTT | ATC | 41.6 | 36 | -0.75 | -0.2 |
| Val | Met | GTT | ATG | 45.7 | 39 | -0.97 | -0.1 |
| Val | Ile | GTT | ATT | 67.5 | 60 | -0.84 | -0.2 |
| Val | Gln | GTT | CAA | 60.7 | 53 | -0.99 | -0.2 |
| Val | His | GTT | CAC | 17.6 | 13 | -1.20 | -0.6 |
| Val | Gln | GTT | CAG | 15.6 | 10 | -2.03 | -0.6 |
| Val | His | GTT | CAT | 25.0 | 25 | -0.00 | -0.2 |
| Val | Pro | GTT | CCA | 53.2 | 80 | 13.57 | 2.9 |
| Val | Pro | GTT | CCC | 11.1 | 17 | 3.21 | 0.8 |
| Val | Pro | GTT | CCG | 6.3 | 7 | 0.07 | 0.1 |
| Val | Pro | GTT | CCT | 24.7 | 35 | 4.33 | 0.6 |
| Val | Arg | GTT | CGA | 3.2 | 0 | -3.19 | -3.0 |
| Val | Arg | GTT | CGC | 3.2 | 2 | -0.44 | -0.3 |
| Val | Arg | GTT | CGG | 1.4 | 3 | 1.69 | 2.0 |
| Val | Arg | GTT | CGT | 18.4 | 20 | 0.13 | 0.4 |
| Val | Leu | GTT | CTA | 23.4 | 19 | -0.82 | -1.0 |
| Val | Leu | GTT | CTC | 6.5 | 9 | 0.97 | 0.8 |
| Val | Leu | GTT | CTG | 15.1 | 17 | 0.23 | 0.1 |
| Val | Leu | GTT | CTT | 18.3 | 32 | 10.20 | 9.4 |
| Val | Glu | GTT | GAA | 107.1 | 94 | -1.61 | -0.0 |
| Val | Asp | GTT | GAC | 47.3 | 58 | 2.40 | 2.1 |
| Val | Glu | GTT | GAG | 30.9 | 10 | -14.17 | -10.9 |
| Val | Asp | GTT | GAT | 75.6 | 57 | -4.56 | -4.9 |
| Val | Ala | GTT | GCA | 30.1 | 28 | -0.14 | -0.5 |
| Val | Ala | GTT | GCC | 39.2 | 49 | 2.48 | 1.3 |
| Val | Ala | GTT | GCG | 8.9 | 6 | -0.95 | -1.3 |
| Val | Ala | GTT | GCT | 71.6 | 99 | 10.49 | 6.9 |
| Val | Gly | GTT | GGA | 14.1 | 21 | 3.36 | 3.4 |
| Val | Gly | GTT | GGC | 17.3 | 12 | -1.61 | -1.6 |
| Val | Gly | GTT | GGG | 9.8 | 6 | -1.46 | -1.5 |
| Val | Gly | GTT | GGT | 97.9 | 109 | 1.27 | 1.3 |
| Val | Val | GTT | GTA | 17.3 | 16 | -0.10 | -0.2 |
| Val | Val | GTT | GTC | 37.1 | 48 | 3.21 | 2.3 |
| Val | Val | GTT | GTG | 19.2 | 15 | -0.91 | -1.2 |
| Val | Val | GTT | GTT | 71.0 | 83 | 2.03 | 1.2 |
| Val | Ocr | GTT | TAA | 0.0 | 3 | 0.00 | 0.0 |
| Val | Tyr | GTT | TAC | 38.0 | 36 | -0.11 | -0.0 |
| Val | Amb | GTT | TAG | 0.0 | 0 | 0.00 | 0.0 |
| Val | Tyr | GTT | TAT | 31.4 | 38 | 1.41 | 3.1 |
| Val | Ser | GTT | TCA | 27.8 | 41 | 6.22 | 4.6 |
| Val | Ser | GTT | TCC | 32.2 | 45 | 5.12 | 3.6 |
| Val | Ser | GTT | TCG | 10.8 | 8 | -0.72 | -1.0 |
| Val | Ser | GTT | TCT | 56.9 | 58 | 0.02 | 0.1 |
| Val | Umb | GTT | TGA | 0.0 | 0 | 0.00 | 0.0 |
| Val | Cys | GTT | TGC | 6.3 | 3 | -1.71 | -1.7 |
| Val | Trp | GTT | TGG | 20.8 | 19 | -0.15 | -0.0 |
| Val | Cys | GTT | TGT | 17.2 | 28 | 6.85 | 7.1 |
| Val | Leu | GTT | TTA | 48.2 | 55 | 0.95 | 0.7 |
| Val | Phe | GTT | TTC | 43.5 | 46 | 0.14 | 0.0 |
| Val | Leu | GTT | TTG | 77.2 | 93 | 3.23 | 2.5 |
| Val | Phe | GTT | TTT | 43.9 | 38 | -0.78 | -1.1 |
| | Page Totals: | | | 2109.1 | 2114 | 155.391 | 121.2 |

PAGE 48

YEAST.RXD/CPLIST.RXR February 7, 1989

| aa1 | aa2 | cod1 | cod2 | exp | obs | chis1 | chis2 |
|---|---|---|---|---|---|---|---|
| Tyr | Lys | TAC | AAA | 45.0 | 57 | 3.20 | 4.3 |
| Tyr | Asn | TAC | AAC | 35.9 | 46 | 2.84 | 1.3 |
| Tyr | Lys | TAC | AAG | 51.0 | 60 | 1.59 | 2.4 |
| Tyr | Asn | TAC | AAT | 35.0 | 40 | 0.72 | 0.1 |
| Tyr | Thr | TAC | ACA | 17.7 | 25 | 3.05 | 4.3 |
| Tyr | Thr | TAC | ACC | 21.3 | 16 | -1.30 | -0.8 |
| Tyr | Thr | TAC | ACG | 7.2 | 10 | 1.10 | 1.6 |
| Tyr | Thr | TAC | ACT | 30.1 | 38 | 2.07 | 3.4 |
| Tyr | Arg | TAC | AGA | 35.0 | 46 | 3.44 | 2.2 |
| Tyr | Ser | TAC | AGC | 8.3 | 10 | 0.33 | 0.1 |
| Tyr | Arg | TAC | AGG | 8.5 | 12 | 1.40 | 1.0 |
| Tyr | Ser | TAC | AGT | 13.0 | 20 | 3.79 | 2.7 |
| Tyr | Ile | TAC | ATA | 14.2 | 12 | -0.35 | -0.1 |
| Tyr | Ile | TAC | ATC | 24.9 | 22 | -0.34 | -0.1 |
| Tyr | Met | TAC | ATG | 29.3 | 31 | 0.10 | 0.6 |
| Tyr | Ile | TAC | ATT | 40.6 | 31 | -2.28 | -1.3 |
| Tyr | Gln | TAC | CAA | 38.2 | 28 | -2.70 | -1.9 |
| Tyr | His | TAC | CAC | 11.0 | 16 | 2.25 | 0.6 |
| Tyr | Gln | TAC | CAG | 11.3 | 17 | 2.85 | 3.6 |
| Tyr | His | TAC | CAT | 15.3 | 16 | 0.03 | 0.3 |
| Tyr | Pro | TAC | CCA | 30.8 | 34 | 0.34 | 0.5 |
| Tyr | Pro | TAC | CCC | 7.4 | 5 | -0.79 | -0.7 |
| Tyr | Pro | TAC | CCG | 4.1 | 2 | -1.07 | -1.0 |
| Tyr | Pro | TAC | CCT | 14.9 | 9 | -2.36 | -2.1 |
| Tyr | Arg | TAC | CGA | 2.4 | 5 | 2.94 | 2.5 |
| Tyr | Arg | TAC | CGC | 2.0 | 1 | -0.53 | -0.6 |
| Tyr | Arg | TAC | CGG | 1.3 | 0 | -1.28 | -1.3 |
| Tyr | Arg | TAC | CGT | 10.7 | 18 | 5.08 | 4.1 |
| Tyr | Leu | TAC | CTA | 14.4 | 7 | -3.79 | -2.4 |
| Tyr | Leu | TAC | CTC | 4.5 | 6 | 0.49 | 1.1 |
| Tyr | Leu | TAC | CTG | 10.1 | 7 | -0.97 | -0.4 |
| Tyr | Leu | TAC | CTT | 11.2 | 4 | -4.62 | -3.3 |
| Tyr | Glu | TAC | GAA | 64.7 | 49 | -3.80 | -0.1 |
| Tyr | Asp | TAC | GAC | 31.4 | 33 | 0.08 | 1.2 |
| Tyr | Glu | TAC | GAG | 20.9 | 14 | -2.28 | -0.4 |
| Tyr | Asp | TAC | GAT | 46.7 | 70 | 11.66 | 2.0 |
| Tyr | Ala | TAC | GCA | 19.0 | 12 | -2.57 | -2.3 |
| Tyr | Ala | TAC | GCC | 23.7 | 20 | -0.59 | -0.4 |
| Tyr | Ala | TAC | GCG | 6.1 | 4 | -0.71 | -0.6 |
| Tyr | Ala | TAC | GCT | 41.8 | 28 | -4.55 | -3.9 |
| Tyr | Gly | TAC | GGA | 9.8 | 5 | -2.32 | -2.6 |
| Tyr | Gly | TAC | GGC | 12.1 | 17 | 1.96 | 1.6 |
| Tyr | Gly | TAC | GGG | 6.6 | 4 | -1.04 | -1.2 |
| Tyr | Gly | TAC | GGT | 56.9 | 39 | -5.65 | -6.6 |
| Tyr | Val | TAC | GTA | 11.1 | 7 | -1.50 | -2.4 |
| Tyr | Val | TAC | GTC | 22.9 | 27 | 0.74 | 0.1 |
| Tyr | Val | TAC | GTG | 11.7 | 12 | 0.01 | 0.1 |
| Tyr | Val | TAC | GTT | 38.0 | 43 | 0.65 | 0.0 |
| Tyr | Ocr | TAC | TAA | 0.0 | 4 | 0.00 | 0.0 |
| Tyr | Tyr | TAC | TAC | 28.7 | 35 | 1.36 | 0.7 |
| Tyr | Amb | TAC | TAG | 0.0 | 0 | 0.00 | 0.0 |
| Tyr | Tyr | TAC | TAT | 20.6 | 29 | 3.42 | 2.4 |
| Tyr | Ser | TAC | TCA | 17.4 | 10 | -3.13 | -4.0 |
| Tyr | Ser | TAC | TCC | 19.4 | 11 | -3.60 | -4.6 |
| Tyr | Ser | TAC | TCG | 6.8 | 4 | -1.14 | -1.5 |
| Tyr | Ser | TAC | TCT | 34.4 | 43 | 2.14 | 1.0 |
| Tyr | Umb | TAC | TGA | 0.0 | 1 | 0.00 | 0.0 |
| Tyr | Cys | TAC | TGC | 4.1 | 6 | 0.87 | 0.3 |
| Tyr | Trp | TAC | TGG | 14.6 | 12 | -0.47 | -0.4 |
| Tyr | Cys | TAC | TGT | 11.1 | 15 | 1.40 | 0.3 |
| Tyr | Leu | TAC | TTA | 28.3 | 15 | -6.27 | -3.7 |
| Tyr | Phe | TAC | TTC | 28.9 | 24 | -0.82 | -0.2 |
| Tyr | Leu | TAC | TTG | 48.4 | 51 | 0.14 | 2.0 |
| Tyr | Phe | TAC | TTT | 27.9 | 29 | 0.04 | 0.6 |
| | | Page Totals: | | 1320.7 | 1324 | 124.919 | 99.9 |

PAGE 49

YEAST.RXD/CPLIST.RXR February 7, 1989

| aa1 | aa2 | cod1 | cod2 | exp | obs | chis1 | chis2 |
|---|---|---|---|---|---|---|---|
| Tyr | Lys | TAT | AAA | 50.7 | 40 | -2.26 | -1.6 |
| Tyr | Asn | TAT | AAC | 29.9 | 24 | -1.15 | -2.1 |
| Tyr | Lys | TAT | AAG | 39.0 | 22 | -7.40 | -6.5 |
| Tyr | Asn | TAT | AAT | 40.7 | 43 | 0.14 | 0.0 |
| Tyr | Thr | TAT | ACA | 20.2 | 7 | -8.58 | -7.5 |
| Tyr | Thr | TAT | ACC | 15.1 | 18 | 0.55 | 1.0 |
| Tyr | Thr | TAT | ACG | 8.6 | 2 | -5.09 | -4.6 |
| Tyr | Thr | TAT | ACT | 26.0 | 21 | -0.96 | -0.5 |
| Tyr | Arg | TAT | AGA | 28.8 | 17 | -4.86 | -5.9 |
| Tyr | Ser | TAT | AGC | 9.2 | 8 | -0.15 | -0.3 |
| Tyr | Arg | TAT | AGG | 10.6 | 7 | -1.25 | -1.6 |
| Tyr | Ser | TAT | AGT | 14.5 | 11 | -0.83 | -1.3 |
| Tyr | Ile | TAT | ATA | 17.7 | 12 | -1.82 | -1.3 |
| Tyr | Ile | TAT | ATC | 19.6 | 23 | 0.60 | 1.2 |
| Tyr | Met | TAT | ATG | 27.4 | 21 | -1.51 | -0.7 |
| Tyr | Ile | TAT | ATT | 38.5 | 46 | 1.45 | 2.7 |
| Tyr | Gln | TAT | CAA | 34.2 | 32 | -0.14 | -0.0 |
| Tyr | His | TAT | CAC | 8.8 | 11 | 0.55 | 0.0 |
| Tyr | Gln | TAT | CAG | 12.0 | 14 | 0.32 | 0.6 |
| Tyr | His | TAT | CAT | 16.5 | 19 | 0.37 | 0.0 |
| Tyr | Pro | TAT | CCA | 24.6 | 30 | 1.16 | 1.5 |
| Tyr | Pro | TAT | CCC | 7.8 | 10 | 0.60 | 0.7 |
| Tyr | Pro | TAT | CCG | 5.4 | 6 | 0.07 | 0.1 |
| Tyr | Pro | TAT | CCT | 15.7 | 12 | -0.88 | -0.7 |
| Tyr | Arg | TAT | CGA | 3.3 | 4 | 0.14 | 0.1 |
| Tyr | Arg | TAT | CGC | 2.3 | 2 | -0.05 | -0.1 |
| Tyr | Arg | TAT | CGG | 1.4 | 0 | -1.42 | -1.5 |
| Tyr | Arg | TAT | CGT | 10.2 | 11 | 0.06 | 0.0 |
| Tyr | Leu | TAT | CTA | 15.2 | 15 | -0.00 | -0.3 |
| Tyr | Leu | TAT | CTC | 5.1 | 2 | -1.91 | -1.3 |
| Tyr | Leu | TAT | CTG | 12.1 | 14 | 0.30 | 1.2 |
| Tyr | Leu | TAT | CTT | 13.0 | 11 | -0.31 | -0.0 |
| Tyr | Glu | TAT | GAA | 58.0 | 50 | -1.10 | -0.3 |
| Tyr | Asp | TAT | GAC | 25.2 | 36 | 4.61 | 0.5 |
| Tyr | Glu | TAT | GAG | 22.1 | 19 | -0.43 | -0.1 |
| Tyr | Asp | TAT | GAT | 48.0 | 53 | 0.52 | 1.0 |
| Tyr | Ala | TAT | GCA | 20.7 | 26 | 1.38 | 1.8 |
| Tyr | Ala | TAT | GCC | 18.0 | 18 | 0.00 | -0.0 |
| Tyr | Ala | TAT | GCG | 6.8 | 8 | 0.21 | 0.3 |
| Tyr | Ala | TAT | GCT | 29.7 | 45 | 7.95 | 9.1 |
| Tyr | Gly | TAT | GGA | 10.9 | 18 | 4.69 | 4.1 |
| Tyr | Gly | TAT | GGC | 11.3 | 15 | 1.24 | 1.0 |
| Tyr | Gly | TAT | GGG | 7.4 | 10 | 0.96 | 0.8 |
| Tyr | Gly | TAT | GGT | 40.3 | 52 | 3.43 | 2.7 |
| Tyr | Val | TAT | GTA | 13.0 | 10 | -0.70 | -1.5 |
| Tyr | Val | TAT | GTC | 16.4 | 24 | 3.55 | 1.7 |
| Tyr | Val | TAT | GTG | 12.2 | 15 | 0.65 | 0.1 |
| Tyr | Val | TAT | GTT | 31.4 | 38 | 1.41 | 0.2 |
| Tyr | Ocr | TAT | TAA | 0.0 | 0 | 0.00 | 0.0 |
| Tyr | Tyr | TAT | TAC | 20.6 | 15 | -1.53 | -2.1 |
| Tyr | Amb | TAT | TAG | 0.0 | 0 | 0.00 | 0.0 |
| Tyr | Tyr | TAT | TAT | 25.9 | 22 | -0.58 | -1.0 |
| Tyr | Ser | TAT | TCA | 20.9 | 18 | -0.40 | -0.9 |
| Tyr | Ser | TAT | TCC | 15.8 | 21 | 1.73 | 1.0 |
| Tyr | Ser | TAT | TCG | 8.1 | 10 | 0.43 | 0.2 |
| Tyr | Ser | TAT | TCT | 30.1 | 46 | 8.36 | 5.8 |
| Tyr | Umb | TAT | TGA | 0.0 | 2 | 0.00 | 0.0 |
| Tyr | Cys | TAT | TGC | 4.7 | 2 | -1.58 | -2.2 |
| Tyr | Trp | TAT | TGG | 12.8 | 15 | 0.37 | 0.5 |
| Tyr | Cys | TAT | TGT | 10.2 | 12 | 0.33 | 0.0 |
| Tyr | Leu | TAT | TTA | 31.6 | 27 | -0.66 | -0.0 |
| Tyr | Phe | TAT | TTC | 23.1 | 24 | 0.04 | 0.5 |
| Tyr | Leu | TAT | TTG | 37.2 | 41 | 0.39 | 2.4 |
| Tyr | Phe | TAT | TTT | 31.2 | 23 | -2.15 | -0.9 |
| | | Page Totals: | | 1227.4 | 1230 | 98.2711 | 89.6 |

PAGE 50

YEAST.RXD/CPLIST.RXR February 7, 1989

| aa1 | aa2 | cod1 | cod2 | exp | obs | chis1 | chis2 |
|---|---|---|---|---|---|---|---|
| Ser | Lys | TCA | AAA | 46.7 | 65 | 7.22 | 2.5 |
| Ser | Asn | TCA | AAC | 27.5 | 38 | 4.01 | 5.2 |
| Ser | Lys | TCA | AAG | 34.0 | 36 | 0.12 | 0.2 |
| Ser | Asn | TCA | AAT | 40.1 | 37 | -0.23 | -0.0 |
| Ser | Thr | TCA | ACA | 19.2 | 18 | -0.08 | -0.6 |
| Ser | Thr | TCA | ACC | 13.7 | 17 | 0.79 | 0.2 |
| Ser | Thr | TCA | ACG | 8.6 | 8 | -0.04 | -0.3 |
| Ser | Thr | TCA | ACT | 23.5 | 22 | -0.09 | -0.7 |
| Ser | Arg | TCA | AGA | 25.0 | 37 | 5.82 | 6.5 |
| Ser | Ser | TCA | AGC | 9.3 | 16 | 4.82 | 2.7 |
| Ser | Arg | TCA | AGG | 9.9 | 18 | 6.53 | 7.0 |
| Ser | Ser | TCA | AGT | 14.7 | 14 | -0.03 | -0.5 |
| Ser | Ile | TCA | ATA | 17.1 | 23 | 2.04 | 2.8 |
| Ser | Ile | TCA | ATC | 17.4 | 8 | -5.05 | -4.4 |
| Ser | Met | TCA | ATG | 24.9 | 22 | -0.33 | -0.1 |
| Ser | Ile | TCA | ATT | 35.8 | 20 | -6.96 | -5.8 |
| Ser | Gln | TCA | CAA | 30.3 | 26 | -0.62 | -0.1 |
| Ser | His | TCA | CAC | 8.0 | 6 | -0.48 | -0.7 |
| Ser | Gln | TCA | CAG | 11.8 | 21 | 7.25 | 9.5 |
| Ser | His | TCA | CAT | 15.4 | 18 | 0.46 | 0.2 |
| Ser | Pro | TCA | CCA | 22.9 | 31 | 2.90 | 1.0 |
| Ser | Pro | TCA | CCC | 7.7 | 11 | 1.39 | 0.6 |
| Ser | Pro | TCA | CCG | 5.3 | 10 | 4.24 | 2.7 |
| Ser | Pro | TCA | CCT | 14.8 | 18 | 0.71 | 0.1 |
| Ser | Arg | TCA | CGA | 3.5 | 2 | -0.63 | -0.6 |
| Ser | Arg | TCA | CGC | 2.3 | 2 | -0.05 | -0.0 |
| Ser | Arg | TCA | CGG | 1.4 | 0 | -1.36 | -1.3 |
| Ser | Arg | TCA | CGT | 9.0 | 1 | -7.14 | -7.0 |
| Ser | Leu | TCA | CTA | 14.7 | 15 | 0.01 | 0.0 |
| Ser | Leu | TCA | CTC | 5.1 | 2 | -1.89 | -2.1 |
| Ser | Leu | TCA | CTG | 11.2 | 5 | -3.46 | -3.9 |
| Ser | Leu | TCA | CTT | 13.0 | 5 | -4.95 | -5.5 |
| Ser | Glu | TCA | GAA | 52.0 | 37 | -4.33 | -0.6 |
| Ser | Asp | TCA | GAC | 21.9 | 16 | -1.58 | -0.2 |
| Ser | Glu | TCA | GAG | 20.3 | 14 | -1.97 | -0.4 |
| Ser | Asp | TCA | GAT | 44.8 | 29 | -5.55 | -1.6 |
| Ser | Ala | TCA | GCA | 19.1 | 18 | -0.07 | -0.0 |
| Ser | Ala | TCA | GCC | 15.5 | 9 | -2.72 | -2.3 |
| Ser | Ala | TCA | GCG | 6.3 | 4 | -0.83 | -0.7 |
| Ser | Ala | TCA | GCT | 26.1 | 21 | -0.98 | -0.6 |
| Ser | Gly | TCA | GGA | 10.3 | 17 | 4.40 | 4.9 |
| Ser | Gly | TCA | GGC | 10.3 | 5 | -2.72 | -2.5 |
| Ser | Gly | TCA | GGG | 6.6 | 2 | -3.20 | -3.0 |
| Ser | Gly | TCA | GGT | 34.4 | 18 | -7.78 | -7.1 |
| Ser | Val | TCA | GTA | 12.8 | 15 | 0.36 | 0.5 |
| Ser | Val | TCA | GTC | 14.3 | 13 | -0.13 | -0.1 |
| Ser | Val | TCA | GTG | 11.3 | 11 | -0.01 | 0.0 |
| Ser | Val | TCA | GTT | 27.8 | 18 | -3.48 | -3.0 |
| Ser | Ocr | TCA | TAA | 0.0 | 1 | 0.00 | 0.0 |
| Ser | Tyr | TCA | TAC | 17.4 | 25 | 3.35 | 2.0 |
| Ser | Amb | TCA | TAG | 0.0 | 1 | 0.00 | 0.0 |
| Ser | Tyr | TCA | TAT | 20.9 | 24 | 0.46 | 0.1 |
| Ser | Ser | TCA | TCA | 23.6 | 29 | 1.21 | 0.1 |
| Ser | Ser | TCA | TCC | 15.2 | 17 | 0.21 | 0.0 |
| Ser | Ser | TCA | TCG | 8.3 | 12 | 1.70 | 0.7 |
| Ser | Ser | TCA | TCT | 28.6 | 33 | 0.67 | 0.0 |
| Ser | Umb | TCA | TGA | 0.0 | 0 | 0.00 | 0.0 |
| Ser | Cys | TCA | TGC | 4.7 | 9 | 3.89 | 7.3 |
| Ser | Trp | TCA | TGG | 11.2 | 11 | -0.00 | -0.3 |
| Ser | Cys | TCA | TGT | 9.0 | 12 | 1.00 | 3.3 |
| Ser | Leu | TCA | TTA | 29.1 | 33 | 0.53 | 0.2 |
| Ser | Phe | TCA | TTC | 19.9 | 18 | -0.18 | -0.4 |
| Ser | Leu | TCA | TTG | 32.6 | 50 | 9.33 | 7.3 |
| Ser | Phe | TCA | TTT | 29.1 | 35 | 1.19 | 0.6 |
| | Page Totals: | | | 1126.8 | 1129 | 145.546 | 124.7 |

PAGE 51

YEAST.RXD/CPLIST.RXR February 7, 1989

| aa1 | aa2 | cod1 | cod2 | exp | obs | chis1 | chis2 |
|---|---|---|---|---|---|---|---|
| Ser | Lys | TCC | AAA | 37.5 | 53 | 6.44 | 2.4 |
| Ser | Asn | TCC | AAC | 28.6 | 24 | -0.73 | -0.4 |
| Ser | Lys | TCC | AAG | 42.0 | 77 | 29.23 | 17.5 |
| Ser | Asn | TCC | AAT | 28.9 | 41 | 5.11 | 6.5 |
| Ser | Thr | TCC | ACA | 14.4 | 23 | 5.19 | 3.0 |
| Ser | Thr | TCC | ACC | 17.1 | 29 | 8.27 | 5.1 |
| Ser | Thr | TCC | ACG | 5.9 | 11 | 4.39 | 2.9 |
| Ser | Thr | TCC | ACT | 25.4 | 37 | 5.36 | 2.6 |
| Ser | Arg | TCC | AGA | 28.7 | 34 | 0.99 | 1.2 |
| Ser | Ser | TCC | AGC | 6.7 | 6 | -0.07 | -0.4 |
| Ser | Arg | TCC | AGG | 7.1 | 4 | -1.33 | -1.2 |
| Ser | Ser | TCC | AGT | 10.3 | 20 | 9.24 | 5.7 |
| Ser | Ile | TCC | ATA | 11.1 | 10 | -0.12 | -0.0 |
| Ser | Ile | TCC | ATC | 21.0 | 31 | 4.78 | 6.1 |
| Ser | Met | TCC | ATG | 23.1 | 35 | 6.08 | 13.3 |
| Ser | Ile | TCC | ATT | 33.5 | 41 | 1.66 | 2.6 |
| Ser | Gln | TCC | CAA | 31.1 | 23 | -2.12 | -1.1 |
| Ser | His | TCC | CAC | 8.9 | 10 | 0.13 | 0.0 |
| Ser | Gln | TCC | CAG | 9.0 | 11 | 0.45 | 0.9 |
| Ser | His | TCC | CAT | 12.5 | 12 | -0.02 | -0.1 |
| Ser | Pro | TCC | CCA | 25.5 | 15 | -4.32 | -6.6 |
| Ser | Pro | TCC | CCC | 6.3 | 5 | -0.25 | -0.6 |
| Ser | Pro | TCC | CCG | 3.5 | 2 | -0.67 | -1.0 |
| Ser | Pro | TCC | CCT | 13.0 | 4 | -6.22 | -7.8 |
| Ser | Arg | TCC | CGA | 1.9 | 1 | -0.42 | -0.4 |
| Ser | Arg | TCC | CGC | 1.8 | 0 | -1.78 | -1.7 |
| Ser | Arg | TCC | CGG | 0.9 | 1 | 0.02 | 0.0 |
| Ser | Arg | TCC | CGT | 8.9 | 10 | 0.14 | 0.2 |
| Ser | Leu | TCC | CTA | 12.2 | 11 | -0.11 | -0.3 |
| Ser | Leu | TCC | CTC | 3.4 | 2 | -0.59 | -0.7 |
| Ser | Leu | TCC | CTG | 8.7 | 7 | -0.35 | -0.5 |
| Ser | Leu | TCC | CTT | 9.8 | 4 | -3.40 | -3.8 |
| Ser | Glu | TCC | GAA | 54.0 | 33 | -8.14 | -2.6 |
| Ser | Asp | TCC | GAC | 24.7 | 16 | -3.04 | -0.9 |
| Ser | Glu | TCC | GAG | 16.8 | 10 | -2.75 | -0.9 |
| Ser | Asp | TCC | GAT | 38.1 | 26 | -3.85 | -0.9 |
| Ser | Ala | TCC | GCA | 15.3 | 9 | -2.56 | -2.1 |
| Ser | Ala | TCC | GCC | 20.2 | 16 | -0.89 | -0.6 |
| Ser | Ala | TCC | GCG | 4.9 | 2 | -1.70 | -1.5 |
| Ser | Ala | TCC | GCT | 36.1 | 20 | -7.18 | -6.1 |
| Ser | Gly | TCC | GGA | 7.3 | 4 | -1.52 | -1.4 |
| Ser | Gly | TCC | GGC | 9.1 | 9 | -0.00 | -0.0 |
| Ser | Gly | TCC | GGG | 5.2 | 1 | -3.41 | -3.3 |
| Ser | Gly | TCC | GGT | 46.9 | 51 | 0.35 | 0.6 |
| Ser | Val | TCC | GTA | 9.3 | 11 | 0.31 | 0.4 |
| Ser | Val | TCC | GTC | 19.4 | 23 | 0.66 | 0.9 |
| Ser | Val | TCC | GTG | 10.0 | 13 | 0.90 | 1.1 |
| Ser | Val | TCC | GTT | 32.2 | 32 | -0.00 | -0.0 |
| Ser | Ocr | TCC | TAA | 0.0 | 0 | 0.00 | 0.0 |
| Ser | Tyr | TCC | TAC | 19.4 | 12 | -2.79 | -3.9 |
| Ser | Amb | TCC | TAG | 0.0 | 0 | 0.00 | 0.0 |
| Ser | Tyr | TCC | TAT | 15.8 | 12 | -0.90 | -1.5 |
| Ser | Ser | TCC | TCA | 15.2 | 14 | -0.10 | -0.7 |
| Ser | Ser | TCC | TCC | 19.8 | 21 | 0.08 | 0.1 |
| Ser | Ser | TCC | TCG | 6.1 | 7 | 0.15 | 0.0 |
| Ser | Ser | TCC | TCT | 29.5 | 29 | -0.01 | -0.7 |
| Ser | Umb | TCC | TGA | 0.0 | 0 | 0.00 | 0.0 |
| Ser | Cys | TCC | TGC | 3.0 | 2 | -0.34 | -0.1 |
| Ser | Trp | TCC | TGG | 10.7 | 8 | -0.68 | -0.1 |
| Ser | Cys | TCC | TGT | 8.1 | 4 | -2.09 | -0.9 |
| Ser | Leu | TCC | TTA | 24.0 | 19 | -1.03 | -1.5 |
| Ser | Phe | TCC | TTC | 22.1 | 26 | 0.68 | 0.3 |
| Ser | Leu | TCC | TTG | 40.0 | 39 | -0.03 | -0.2 |
| Ser | Phe | TCC | TTT | 22.9 | 24 | 0.05 | 0.0 |
| | Page Totals: | | | 1084.4 | 1087 | 156.181 | 130.3 |

PAGE 52

YEAST.RXD/CPLIST.RXR February 7, 1989

| aa1 | aa2 | cod1 | cod2 | exp | obs | chis1 | chis2 |
|---|---|---|---|---|---|---|---|
| Ser | Lys | TCG | AAA | 18.5 | 20 | 0.12 | 0.1 |
| Ser | Asn | TCG | AAC | 10.9 | 16 | 2.38 | 3.0 |
| Ser | Lys | TCG | AAG | 13.8 | 21 | 3.80 | 1.8 |
| Ser | Asn | TCG | AAT | 15.9 | 13 | -0.52 | -0.3 |
| Ser | Thr | TCG | ACA | 8.0 | 8 | 0.00 | 0.1 |
| Ser | Thr | TCG | ACC | 5.5 | 3 | -1.10 | -1.6 |
| Ser | Thr | TCG | ACG | 3.5 | 4 | 0.07 | 0.0 |
| Ser | Thr | TCG | ACT | 9.3 | 10 | 0.06 | 0.0 |
| Ser | Arg | TCG | AGA | 9.4 | 18 | 7.92 | 8.4 |
| Ser | Ser | TCG | AGC | 3.9 | 3 | -0.23 | -0.5 |
| Ser | Arg | TCG | AGG | 4.0 | 1 | -2.29 | -2.2 |
| Ser | Ser | TCG | AGT | 6.1 | 6 | -0.00 | -0.1 |
| Ser | Ile | TCG | ATA | 6.8 | 9 | 0.69 | 1.0 |
| Ser | Ile | TCG | ATC | 6.8 | 5 | -0.48 | -0.3 |
| Ser | Met | TCG | ATG | 9.7 | 8 | -0.29 | 0.0 |
| Ser | Ile | TCG | ATT | 13.3 | 14 | 0.04 | 0.2 |
| Ser | Gln | TCG | CAA | 11.7 | 12 | 0.01 | 0.1 |
| Ser | His | TCG | CAC | 3.4 | 8 | 6.41 | 5.4 |
| Ser | Gln | TCG | CAG | 5.0 | 5 | 0.00 | 0.0 |
| Ser | His | TCG | CAT | 5.8 | 10 | 3.12 | 2.4 |
| Ser | Pro | TCG | CCA | 8.3 | 16 | 7.21 | 4.7 |
| Ser | Pro | TCG | CCC | 3.2 | 3 | -0.01 | -0.1 |
| Ser | Pro | TCG | CCG | 2.5 | 3 | 0.09 | 0.0 |
| Ser | Pro | TCG | CCT | 5.9 | 7 | 0.22 | 0.0 |
| Ser | Arg | TCG | CGA | 1.4 | 1 | -0.13 | -0.1 |
| Ser | Arg | TCG | CGC | 1.2 | 0 | -1.16 | -1.1 |
| Ser | Arg | TCG | CGG | 0.8 | 1 | 0.05 | 0.1 |
| Ser | Arg | TCG | CGT | 3.6 | 3 | -0.11 | -0.1 |
| Ser | Leu | TCG | CTA | 5.8 | 9 | 1.82 | 1.4 |
| Ser | Leu | TCG | CTC | 2.1 | 2 | -0.00 | -0.0 |
| Ser | Leu | TCG | CTG | 4.9 | 10 | 5.29 | 4.6 |
| Ser | Leu | TCG | CTT | 5.2 | 2 | -1.98 | -2.2 |
| Ser | Glu | TCG | GAA | 20.3 | 19 | -0.09 | -0.4 |
| Ser | Asp | TCG | GAC | 9.0 | 4 | -2.76 | -1.5 |
| Ser | Glu | TCG | GAG | 8.6 | 6 | -0.77 | -0.1 |
| Ser | Asp | TCG | GAT | 17.7 | 10 | -3.36 | -1.4 |
| Ser | Ala | TCG | GCA | 7.4 | 8 | 0.05 | 0.1 |
| Ser | Ala | TCG | GCC | 5.9 | 5 | -0.12 | -0.1 |
| Ser | Ala | TCG | GCG | 3.0 | 3 | 0.00 | 0.0 |
| Ser | Ala | TCG | GCT | 9.6 | 5 | -2.23 | -1.9 |
| Ser | Gly | TCG | GGA | 4.2 | 5 | 0.14 | 0.2 |
| Ser | Gly | TCG | GGC | 4.3 | 2 | -1.27 | -1.2 |
| Ser | Gly | TCG | GGG | 2.9 | 0 | -2.90 | -2.8 |
| Ser | Gly | TCG | GGT | 12.5 | 9 | -0.98 | -0.8 |
| Ser | Val | TCG | GTA | 5.0 | 3 | -0.80 | -0.7 |
| Ser | Val | TCG | GTC | 5.5 | 3 | -1.10 | -1.0 |
| Ser | Val | TCG | GTG | 4.9 | 6 | 0.23 | 0.3 |
| Ser | Val | TCG | GTT | 10.8 | 3 | -5.62 | -5.3 |
| Ser | Ocr | TCG | TAA | 0.0 | 1 | 0.00 | 0.0 |
| Ser | Tyr | TCG | TAC | 6.8 | 9 | 0.72 | 0.4 |
| Ser | Amb | TCG | TAG | 0.0 | 0 | 0.00 | 0.0 |
| Ser | Tyr | TCG | TAT | 8.1 | 13 | 2.93 | 2.0 |
| Ser | Ser | TCG | TCA | 8.3 | 6 | -0.62 | -1.3 |
| Ser | Ser | TCG | TCC | 6.1 | 9 | 1.43 | 0.6 |
| Ser | Ser | TCG | TCG | 4.5 | 6 | 0.48 | 0.1 |
| Ser | Ser | TCG | TCT | 10.8 | 12 | 0.12 | 0.0 |
| Ser | Umb | TCG | TGA | 0.0 | 0 | 0.00 | 0.0 |
| Ser | Cys | TCG | TGC | 1.8 | 2 | 0.03 | 0.3 |
| Ser | Trp | TCG | TGG | 4.3 | 5 | 0.11 | 0.6 |
| Ser | Cys | TCG | TGT | 3.5 | 1 | -1.76 | -1.1 |
| Ser | Leu | TCG | TTA | 11.3 | 8 | -0.97 | -1.3 |
| Ser | Phe | TCG | TTC | 7.5 | 7 | -0.03 | -0.1 |
| Ser | Leu | TCG | TTG | 12.7 | 10 | -0.58 | -0.8 |
| Ser | Phe | TCG | TTT | 11.1 | 14 | 0.75 | 0.5 |
| | | Page Totals: | | 444.1 | 445 | 80.5402 | 68.9 |

PAGE 53

YEAST.RXD/CPLIST.RXR February 7, 1989

| aa1 | aa2 | cod1 | cod2 | exp | obs | chis1 | chis2 |
|---|---|---|---|---|---|---|---|
| Ser | Lys | TCT | AAA | 69.8 | 63 | -0.67 | -3.6 |
| Ser | Asn | TCT | AAC | 50.8 | 37 | -3.74 | -2.7 |
| Ser | Lys | TCT | AAG | 72.0 | 53 | -5.01 | -10.5 |
| Ser | Asn | TCT | AAT | 56.1 | 42 | -3.53 | -2.5 |
| Ser | Thr | TCT | ACA | 27.2 | 21 | -1.42 | -3.0 |
| Ser | Thr | TCT | ACC | 28.3 | 28 | -0.00 | -0.4 |
| Ser | Thr | TCT | ACG | 11.6 | 11 | -0.03 | -0.3 |
| Ser | Thr | TCT | ACT | 44.2 | 43 | -0.03 | -0.9 |
| Ser | Arg | TCT | AGA | 51.7 | 34 | -6.04 | -5.5 |
| Ser | Ser | TCT | AGC | 12.5 | 12 | -0.02 | -0.4 |
| Ser | Arg | TCT | AGG | 13.1 | 9 | -1.29 | -1.2 |
| Ser | Ser | TCT | AGT | 19.3 | 13 | -2.07 | -3.8 |
| Ser | Ile | TCT | ATA | 22.1 | 25 | 0.39 | 0.8 |
| Ser | Ile | TCT | ATC | 36.1 | 31 | -0.72 | -0.3 |
| Ser | Met | TCT | ATG | 41.8 | 24 | -7.56 | -3.2 |
| Ser | Ile | TCT | ATT | 59.9 | 43 | -4.78 | -3.4 |
| Ser | Gln | TCT | CAA | 56.2 | 57 | 0.01 | 0.5 |
| Ser | His | TCT | CAC | 15.2 | 19 | 0.93 | 0.4 |
| Ser | Gln | TCT | CAG | 16.4 | 16 | -0.01 | -0.1 |
| Ser | His | TCT | CAT | 23.1 | 21 | -0.19 | -0.6 |
| Ser | Pro | TCT | CCA | 44.6 | 74 | 19.39 | 11.1 |
| Ser | Pro | TCT | CCC | 10.6 | 18 | 5.22 | 3.1 |
| Ser | Pro | TCT | CCG | 6.6 | 13 | 6.23 | 4.1 |
| Ser | Pro | TCT | CCT | 22.8 | 25 | 0.22 | 0.0 |
| Ser | Arg | TCT | CGA | 4.1 | 6 | 0.85 | 0.9 |
| Ser | Arg | TCT | CGC | 3.2 | 3 | -0.01 | -0.0 |
| Ser | Arg | TCT | CGG | 1.7 | 7 | 17.10 | 17.7 |
| Ser | Arg | TCT | CGT | 16.0 | 31 | 14.13 | 15.1 |
| Ser | Leu | TCT | CTA | 21.6 | 23 | 0.09 | 0.0 |
| Ser | Leu | TCT | CTC | 6.7 | 7 | 0.02 | 0.0 |
| Ser | Leu | TCT | CTG | 15.5 | 20 | 1.28 | 0.8 |
| Ser | Leu | TCT | CTT | 17.5 | 18 | 0.01 | 0.0 |
| Ser | Glu | TCT | GAA | 95.6 | 72 | -5.84 | -0.4 |
| Ser | Asp | TCT | GAC | 42.2 | 40 | -0.12 | -0.9 |
| Ser | Glu | TCT | GAG | 30.1 | 27 | -0.33 | -0.3 |
| Ser | Asp | TCT | GAT | 69.9 | 58 | -2.01 | -0.0 |
| Ser | Ala | TCT | GCA | 27.7 | 37 | 3.10 | 4.2 |
| Ser | Ala | TCT | GCC | 33.9 | 44 | 3.00 | 4.2 |
| Ser | Ala | TCT | GCG | 8.9 | 16 | 5.77 | 6.7 |
| Ser | Ala | TCT | GCT | 60.5 | 67 | 0.71 | 1.5 |
| Ser | Gly | TCT | GGA | 13.9 | 17 | 0.71 | 0.9 |
| Ser | Gly | TCT | GGC | 16.0 | 11 | -1.56 | -1.4 |
| Ser | Gly | TCT | GGG | 9.7 | 8 | -0.29 | -0.2 |
| Ser | Gly | TCT | GGT | 80.5 | 78 | -0.08 | -0.0 |
| Ser | Val | TCT | GTA | 17.6 | 15 | -0.39 | -0.3 |
| Ser | Val | TCT | GTC | 32.0 | 33 | 0.03 | 0.1 |
| Ser | Val | TCT | GTG | 17.4 | 25 | 3.28 | 3.9 |
| Ser | Val | TCT | GTT | 56.9 | 46 | -2.08 | -1.5 |
| Ser | Ocr | TCT | TAA | 0.0 | 3 | 0.00 | 0.0 |
| Ser | Tyr | TCT | TAC | 34.4 | 44 | 2.67 | 1.2 |
| Ser | Amb | TCT | TAG | 0.0 | 1 | 0.00 | 0.0 |
| Ser | Tyr | TCT | TAT | 30.1 | 34 | 0.50 | 0.0 |
| Ser | Ser | TCT | TCA | 28.6 | 36 | 1.90 | 0.3 |
| Ser | Ser | TCT | TCC | 29.5 | 38 | 2.45 | 0.5 |
| Ser | Ser | TCT | TCG | 10.8 | 18 | 4.73 | 2.5 |
| Ser | Ser | TCT | TCT | 56.7 | 62 | 0.50 | 0.1 |
| Ser | Umb | TCT | TGA | 0.0 | 1 | 0.00 | 0.0 |
| Ser | Cys | TCT | TGC | 6.4 | 4 | -0.92 | -0.2 |
| Ser | Trp | TCT | TGG | 19.4 | 14 | -1.50 | -0.3 |
| Ser | Cys | TCT | TGT | 15.3 | 12 | -0.71 | -0.0 |
| Ser | Leu | TCT | TTA | 44.0 | 54 | 2.26 | 1.3 |
| Ser | Phe | TCT | TTC | 39.0 | 55 | 6.52 | 4.8 |
| Ser | Leu | TCT | TTG | 67.8 | 97 | 12.58 | 9.3 |
| Ser | Phe | TCT | TTT | 42.5 | 26 | -6.37 | -7.8 |
| | | Page Totals: | | 1935.5 | 1940 | 175.888 | 151.3 |

PAGE 54

YEAST.RXD/CPLIST.RXR February 7, 1989

| aa1 | aa2 | cod1 | cod2 | exp | obs | chis1 | chis2 |
|---|---|---|---|---|---|---|---|
| Cys | Lys | TGC | AAA | 10.7 | 12 | 0.16 | 1.1 |
| Cys | Asn | TGC | AAC | 6.3 | 7 | 0.08 | 0.2 |
| Cys | Lys | TGC | AAG | 8.2 | 11 | 1.00 | 2.7 |
| Cys | Asn | TGC | AAT | 9.0 | 6 | -0.97 | -0.8 |
| Cys | Thr | TGC | ACA | 4.4 | 2 | -1.30 | -0.6 |
| Cys | Thr | TGC | ACC | 3.4 | 4 | 0.10 | 0.6 |
| Cys | Thr | TGC | ACG | 1.9 | 1 | -0.45 | -0.2 |
| Cys | Thr | TGC | ACT | 4.9 | 0 | -4.94 | -3.9 |
| Cys | Arg | TGC | AGA | 5.9 | 4 | -0.59 | -0.2 |
| Cys | Ser | TGC | AGC | 2.5 | 3 | 0.09 | 0.1 |
| Cys | Arg | TGC | AGG | 2.3 | 2 | -0.04 | -0.0 |
| Cys | Ser | TGC | AGT | 3.3 | 3 | -0.02 | -0.0 |
| Cys | Ile | TGC | ATA | 3.8 | 3 | -0.18 | -0.4 |
| Cys | Ile | TGC | ATC | 4.1 | 4 | -0.00 | -0.1 |
| Cys | Met | TGC | ATG | 6.1 | 4 | -0.70 | -1.9 |
| Cys | Ile | TGC | ATT | 8.0 | 10 | 0.51 | 0.1 |
| Cys | Gln | TGC | CAA | 7.2 | 14 | 6.36 | 5.4 |
| Cys | His | TGC | CAC | 1.9 | 9 | 26.70 | 10.7 |
| Cys | Gln | TGC | CAG | 2.4 | 2 | -0.06 | -0.1 |
| Cys | His | TGC | CAT | 3.6 | 7 | 3.14 | 0.1 |
| Cys | Pro | TGC | CCA | 4.8 | 6 | 0.28 | 0.1 |
| Cys | Pro | TGC | CCC | 1.8 | 1 | -0.36 | -0.5 |
| Cys | Pro | TGC | CCG | 1.1 | 1 | -0.00 | -0.0 |
| Cys | Pro | TGC | CCT | 3.3 | 5 | 0.93 | 0.6 |
| Cys | Arg | TGC | CGA | 0.8 | 1 | 0.05 | 0.2 |
| Cys | Arg | TGC | CGC | 0.5 | 0 | -0.51 | -0.4 |
| Cys | Arg | TGC | CGG | 0.4 | 0 | -0.39 | -0.3 |
| Cys | Arg | TGC | CGT | 2.0 | 6 | 8.43 | 11.3 |
| Cys | Leu | TGC | CTA | 3.2 | 1 | -1.52 | -1.7 |
| Cys | Leu | TGC | CTC | 1.2 | 1 | -0.02 | -0.0 |
| Cys | Leu | TGC | CTG | 2.5 | 2 | -0.11 | -0.2 |
| Cys | Leu | TGC | CTT | 2.8 | 4 | 0.47 | 0.3 |
| Cys | Glu | TGC | GAA | 11.7 | 11 | -0.04 | -0.0 |
| Cys | Asp | TGC | GAC | 5.3 | 3 | -1.00 | -1.5 |
| Cys | Glu | TGC | GAG | 4.7 | 1 | -2.86 | -2.7 |
| Cys | Asp | TGC | GAT | 9.6 | 8 | -0.25 | -0.8 |
| Cys | Ala | TGC | GCA | 4.3 | 2 | -1.24 | -1.3 |
| Cys | Ala | TGC | GCC | 3.4 | 2 | -0.55 | -0.6 |
| Cys | Ala | TGC | GCG | 1.3 | 0 | -1.32 | -1.3 |
| Cys | Ala | TGC | GCT | 5.7 | 6 | 0.02 | 0.0 |
| Cys | Gly | TGC | GGA | 2.5 | 1 | -0.87 | -1.2 |
| Cys | Gly | TGC | GGC | 2.3 | 1 | -0.75 | -1.1 |
| Cys | Gly | TGC | GGG | 1.8 | 2 | 0.02 | 0.0 |
| Cys | Gly | TGC | GGT | 8.1 | 8 | -0.00 | -0.2 |
| Cys | Val | TGC | GTA | 2.8 | 0 | -2.79 | -2.4 |
| Cys | Val | TGC | GTC | 3.1 | 4 | 0.26 | 0.7 |
| Cys | Val | TGC | GTG | 2.7 | 2 | -0.18 | -0.0 |
| Cys | Val | TGC | GTT | 6.3 | 8 | 0.47 | 1.3 |
| Cys | Ocr | TGC | TAA | 0.0 | 0 | 0.00 | 0.0 |
| Cys | Tyr | TGC | TAC | 4.1 | 2 | -1.08 | -0.0 |
| Cys | Amb | TGC | TAG | 0.0 | 0 | 0.00 | 0.0 |
| Cys | Tyr | TGC | TAT | 4.7 | 3 | -0.63 | -0.1 |
| Cys | Ser | TGC | TCA | 4.7 | 5 | 0.02 | 0.0 |
| Cys | Ser | TGC | TCC | 3.0 | 5 | 1.33 | 1.2 |
| Cys | Ser | TGC | TCG | 1.8 | 2 | 0.03 | 0.0 |
| Cys | Ser | TGC | TCT | 6.4 | 6 | -0.03 | -0.1 |
| Cys | Umb | TGC | TGA | 0.0 | 0 | 0.00 | 0.0 |
| Cys | Cys | TGC | TGC | 3.4 | 3 | -0.06 | -0.1 |
| Cys | Trp | TGC | TGG | 2.7 | 3 | 0.03 | 2.5 |
| Cys | Cys | TGC | TGT | 2.8 | 4 | 0.51 | 0.4 |
| Cys | Leu | TGC | TTA | 6.9 | 10 | 1.39 | 1.0 |
| Cys | Phe | TGC | TTC | 5.2 | 7 | 0.66 | 0.5 |
| Cys | Leu | TGC | TTG | 7.2 | 7 | -0.01 | -0.1 |
| Cys | Phe | TGC | TTT | 6.8 | 8 | 0.20 | 0.1 |
| | | Page Totals: | | 259.3 | 260 | 79.05 | 65.9 |

PAGE 55

YEAST.RXD/CPLIST.RXR February 7, 1989

| aa1 | aa2 | cod1 | cod2 | exp | obs | chis1 | chis2 |
|---|---|---|---|---|---|---|---|
| Trp | Lys | TGG | AAA | 29.0 | 27 | -0.14 | -0.7 |
| Trp | Asn | TGG | AAC | 19.7 | 17 | -0.38 | -0.7 |
| Trp | Lys | TGG | AAG | 26.8 | 17 | -3.60 | -0.8 |
| Trp | Asn | TGG | AAT | 22.1 | 27 | 1.08 | 0.6 |
| Trp | Thr | TGG | ACA | 11.6 | 10 | -0.22 | -1.1 |
| Trp | Thr | TGG | ACC | 10.5 | 8 | -0.61 | -1.7 |
| Trp | Thr | TGG | ACG | 4.7 | 5 | 0.03 | 0.1 |
| Trp | Thr | TGG | ACT | 16.8 | 29 | 8.87 | 4.0 |
| Trp | Arg | TGG | AGA | 18.6 | 28 | 4.71 | 1.0 |
| Trp | Ser | TGG | AGC | 5.1 | 7 | 0.69 | 0.4 |
| Trp | Arg | TGG | AGG | 5.5 | 7 | 0.41 | 0.0 |
| Trp | Ser | TGG | AGT | 8.4 | 8 | -0.02 | -0.1 |
| Trp | Ile | TGG | ATA | 9.6 | 7 | -0.71 | -0.0 |
| Trp | Ile | TGG | ATC | 13.4 | 10 | -0.85 | -0.0 |
| Trp | Met | TGG | ATG | 17.5 | 13 | -1.17 | 0.0 |
| Trp | Ile | TGG | ATT | 23.6 | 16 | -2.43 | -0.0 |
| Trp | Gln | TGG | CAA | 21.1 | 17 | -0.81 | -0.9 |
| Trp | His | TGG | CAC | 6.4 | 4 | -0.89 | -2.0 |
| Trp | Gln | TGG | CAG | 7.0 | 1 | -5.18 | -2.7 |
| Trp | His | TGG | CAT | 9.6 | 16 | 4.33 | 1.3 |
| Trp | Pro | TGG | CCA | 17.5 | 14 | -0.69 | -0.1 |
| Trp | Pro | TGG | CCC | 4.6 | 1 | -2.81 | -1.7 |
| Trp | Pro | TGG | CCG | 2.7 | 4 | 0.62 | 2.1 |
| Trp | Pro | TGG | CCT | 9.3 | 6 | -1.16 | -0.1 |
| Trp | Arg | TGG | CGA | 1.7 | 3 | 0.93 | 0.3 |
| Trp | Arg | TGG | CGC | 1.3 | 1 | -0.08 | -0.2 |
| Trp | Arg | TGG | CGG | 0.8 | 2 | 1.67 | 0.9 |
| Trp | Arg | TGG | CGT | 5.9 | 1 | -4.06 | -5.4 |
| Trp | Leu | TGG | CTA | 9.2 | 7 | -0.53 | -0.2 |
| Trp | Leu | TGG | CTC | 3.1 | 1 | -1.42 | -1.1 |
| Trp | Leu | TGG | CTG | 7.1 | 8 | 0.13 | 0.4 |
| Trp | Leu | TGG | CTT | 7.5 | 6 | -0.30 | -0.1 |
| Trp | Glu | TGG | GAA | 36.4 | 47 | 3.07 | 0.5 |
| Trp | Asp | TGG | GAC | 16.8 | 26 | 5.09 | 1.1 |
| Trp | Glu | TGG | GAG | 12.7 | 23 | 8.31 | 1.3 |
| Trp | Asp | TGG | GAT | 28.3 | 31 | 0.27 | 0.6 |
| Trp | Ala | TGG | GCA | 12.1 | 14 | 0.31 | 2.0 |
| Trp | Ala | TGG | GCC | 12.1 | 14 | 0.31 | 1.9 |
| Trp | Ala | TGG | GCG | 3.7 | 3 | -0.12 | -0.0 |
| Trp | Ala | TGG | GCT | 22.2 | 9 | -7.83 | -4.3 |
| Trp | Gly | TGG | GGA | 6.4 | 6 | -0.02 | -0.1 |
| Trp | Gly | TGG | GGC | 7.0 | 6 | -0.15 | -0.0 |
| Trp | Gly | TGG | GGG | 4.0 | 6 | 1.01 | 2.0 |
| Trp | Gly | TGG | GGT | 28.5 | 21 | -1.99 | -0.4 |
| Trp | Val | TGG | GTA | 7.3 | 5 | -0.70 | -0.2 |
| Trp | Val | TGG | GTC | 12.1 | 8 | -1.38 | -0.5 |
| Trp | Val | TGG | GTG | 7.0 | 6 | -0.14 | -0.0 |
| Trp | Val | TGG | GTT | 20.8 | 21 | 0.00 | 0.6 |
| Trp | Ocr | TGG | TAA | 0.0 | 1 | 0.00 | 0.0 |
| Trp | Tyr | TGG | TAC | 14.6 | 18 | 0.78 | 0.1 |
| Trp | Amb | TGG | TAG | 0.0 | 0 | 0.00 | 0.0 |
| Trp | Tyr | TGG | TAT | 12.8 | 14 | 0.11 | 0.1 |
| Trp | Ser | TGG | TCA | 11.2 | 8 | -0.93 | -1.4 |
| Trp | Ser | TGG | TCC | 10.7 | 12 | 0.16 | 0.0 |
| Trp | Ser | TGG | TCG | 4.3 | 1 | -2.53 | -2.9 |
| Trp | Ser | TGG | TCT | 19.4 | 28 | 3.82 | 2.3 |
| Trp | Umb | TGG | TGA | 0.0 | 0 | 0.00 | 0.0 |
| Trp | Cys | TGG | TGC | 2.7 | 10 | 19.31 | 1.9 |
| Trp | Trp | TGG | TGG | 12.2 | 9 | -0.82 | 0.0 |
| Trp | Cys | TGG | TGT | 6.2 | 11 | 3.81 | 0.9 |
| Trp | Leu | TGG | TTA | 18.1 | 19 | 0.05 | 0.5 |
| Trp | Phe | TGG | TTC | 16.8 | 15 | -0.19 | -1.1 |
| Trp | Leu | TGG | TTG | 25.0 | 22 | -0.36 | -0.0 |
| Trp | Phe | TGG | TTT | 18.1 | 26 | 3.41 | 1.0 |
| | | Page Totals: | | 767.0 | 768 | 118.478 | 58.7 |

PAGE 56

YEAST.RXD/CPLIST.RXR February 7, 1989

| aa1 | aa2 | cod1 | cod2 | exp | obs | chis1 | chis2 |
|---|---|---|---|---|---|---|---|
| Cys | Lys | TGT | AAA | 21.8 | 20 | -0.15 | -0.2 |
| Cys | Asn | TGT | AAC | 15.6 | 14 | -0.16 | -0.0 |
| Cys | Lys | TGT | AAG | 21.0 | 8 | -8.05 | -5.1 |
| Cys | Asn | TGT | AAT | 17.4 | 19 | 0.14 | 0.3 |
| Cys | Thr | TGT | ACA | 8.7 | 9 | 0.01 | 0.6 |
| Cys | Thr | TGT | ACC | 9.2 | 6 | -1.10 | -0.2 |
| Cys | Thr | TGT | ACG | 3.8 | 5 | 0.41 | 1.3 |
| Cys | Thr | TGT | ACT | 12.7 | 12 | -0.03 | -0.4 |
| Cys | Arg | TGT | AGA | 14.7 | 3 | -9.31 | -7.2 |
| Cys | Ser | TGT | AGC | 4.0 | 4 | 0.00 | 0.0 |
| Cys | Arg | TGT | AGG | 4.3 | 3 | -0.41 | -0.1 |
| Cys | Ser | TGT | AGT | 6.3 | 2 | -2.90 | -3.1 |
| Cys | Ile | TGT | ATA | 7.4 | 5 | -0.80 | -1.5 |
| Cys | Ile | TGT | ATC | 10.8 | 14 | 0.96 | 0.2 |
| Cys | Met | TGT | ATG | 13.1 | 21 | 4.83 | 0.9 |
| Cys | Ile | TGT | ATT | 18.9 | 25 | 1.96 | 0.5 |
| Cys | Gln | TGT | CAA | 16.7 | 12 | -1.32 | -1.8 |
| Cys | His | TGT | CAC | 4.7 | 7 | 1.16 | 0.1 |
| Cys | Gln | TGT | CAG | 5.1 | 5 | -0.00 | -0.0 |
| Cys | His | TGT | CAT | 7.7 | 7 | -0.06 | -2.7 |
| Cys | Pro | TGT | CCA | 12.9 | 13 | 0.00 | 0.1 |
| Cys | Pro | TGT | CCC | 3.4 | 3 | -0.05 | -0.1 |
| Cys | Pro | TGT | CCG | 2.1 | 0 | -2.10 | -2.3 |
| Cys | Pro | TGT | CCT | 7.2 | 11 | 1.99 | 1.2 |
| Cys | Arg | TGT | CGA | 1.3 | 3 | 2.37 | 3.4 |
| Cys | Arg | TGT | CGC | 1.0 | 2 | 0.97 | 1.5 |
| Cys | Arg | TGT | CGG | 0.5 | 1 | 0.43 | 0.7 |
| Cys | Arg | TGT | CGT | 5.1 | 8 | 1.67 | 3.1 |
| Cys | Leu | TGT | CTA | 7.1 | 10 | 1.22 | 0.8 |
| Cys | Leu | TGT | CTC | 2.1 | 3 | 0.39 | 0.3 |
| Cys | Leu | TGT | CTG | 5.2 | 6 | 0.13 | 0.1 |
| Cys | Leu | TGT | CTT | 5.8 | 6 | 0.01 | 0.0 |
| Cys | Glu | TGT | GAA | 28.7 | 30 | 0.06 | 0.3 |
| Cys | Asp | TGT | GAC | 13.3 | 14 | 0.04 | 0.1 |
| Cys | Glu | TGT | GAG | 9.4 | 10 | 0.03 | 0.1 |
| Cys | Asp | TGT | GAT | 22.7 | 33 | 4.65 | 1.9 |
| Cys | Ala | TGT | GCA | 9.3 | 10 | 0.06 | 0.0 |
| Cys | Ala | TGT | GCC | 10.0 | 8 | -0.40 | -0.4 |
| Cys | Ala | TGT | GCG | 3.2 | 3 | -0.01 | -0.0 |
| Cys | Ala | TGT | GCT | 16.5 | 23 | 2.58 | 2.5 |
| Cys | Gly | TGT | GGA | 4.7 | 4 | -0.10 | -0.4 |
| Cys | Gly | TGT | GGC | 5.4 | 6 | 0.08 | 0.0 |
| Cys | Gly | TGT | GGG | 3.2 | 4 | 0.19 | 0.0 |
| Cys | Gly | TGT | GGT | 24.7 | 35 | 4.31 | 1.4 |
| Cys | Val | TGT | GTA | 5.9 | 3 | -1.40 | -0.8 |
| Cys | Val | TGT | GTC | 9.9 | 6 | -1.54 | -0.7 |
| Cys | Val | TGT | GTG | 5.7 | 6 | 0.02 | 0.2 |
| Cys | Val | TGT | GTT | 17.2 | 17 | -0.00 | -0.3 |
| Cys | Ocr | TGT | TAA | 0.0 | 0 | 0.00 | 0.0 |
| Cys | Tyr | TGT | TAC | 11.1 | 6 | -2.32 | -0.0 |
| Cys | Amb | TGT | TAG | 0.0 | 0 | 0.00 | 0.0 |
| Cys | Tyr | TGT | TAT | 10.2 | 5 | -2.62 | -0.0 |
| Cys | Ser | TGT | TCA | 9.0 | 11 | 0.44 | 0.3 |
| Cys | Ser | TGT | TCC | 8.1 | 12 | 1.85 | 1.6 |
| Cys | Ser | TGT | TCG | 3.5 | 2 | -0.63 | -0.7 |
| Cys | Ser | TGT | TCT | 15.3 | 15 | -0.01 | -0.0 |
| Cys | Umb | TGT | TGA | 0.0 | 3 | 0.00 | 0.0 |
| Cys | Cys | TGT | TGC | 2.8 | 2 | -0.23 | -0.3 |
| Cys | Trp | TGT | TGG | 6.2 | 1 | -4.32 | -1.1 |
| Cys | Cys | TGT | TGT | 7.0 | 8 | 0.15 | 0.0 |
| Cys | Leu | TGT | TTA | 14.7 | 15 | 0.01 | 0.0 |
| Cys | Phe | TGT | TTC | 11.8 | 18 | 3.28 | 2.6 |
| Cys | Leu | TGT | TTG | 19.7 | 18 | -0.15 | -0.4 |
| Cys | Phe | TGT | TTT | 13.5 | 6 | -4.19 | -4.7 |
| | Page Totals: | | | 599.6 | 601 | 80.7339 | 61.1 |

YEAST.RXD/CPLIST.RXR February 7, 1989

| aa1 | aa2 | cod1 | cod2 | exp | obs | chis1 | chis2 |
|---|---|---|---|---|---|---|---|
| Leu | Lys | TTA | AAA | 70.9 | 56 | -3.15 | -7.9 |
| Leu | Asn | TTA | AAC | 42.4 | 28 | -4.91 | -3.8 |
| Leu | Lys | TTA | AAG | 58.5 | 49 | -1.53 | -4.8 |
| Leu | Asn | TTA | AAT | 55.9 | 33 | -9.41 | -7.7 |
| Leu | Thr | TTA | ACA | 28.3 | 41 | 5.72 | 5.3 |
| Leu | Thr | TTA | ACC | 23.0 | 21 | -0.18 | -0.2 |
| Leu | Thr | TTA | ACG | 11.6 | 10 | -0.21 | -0.3 |
| Leu | Thr | TTA | ACT | 37.8 | 39 | 0.04 | 0.0 |
| Leu | Arg | TTA | AGA | 44.0 | 52 | 1.47 | 0.9 |
| Leu | Ser | TTA | AGC | 12.6 | 20 | 4.30 | 2.8 |
| Leu | Arg | TTA | AGG | 14.5 | 13 | -0.15 | -0.3 |
| Leu | Ser | TTA | AGT | 20.0 | 31 | 6.05 | 3.9 |
| Leu | Ile | TTA | ATA | 24.5 | 20 | -0.84 | -0.0 |
| Leu | Ile | TTA | ATC | 29.7 | 24 | -1.08 | -0.0 |
| Leu | Met | TTA | ATG | 39.2 | 44 | 0.60 | 1.7 |
| Leu | Ile | TTA | ATT | 57.2 | 37 | -7.14 | -1.5 |
| Leu | Gln | TTA | CAA | 48.9 | 60 | 2.50 | 0.8 |
| Leu | His | TTA | CAC | 13.5 | 16 | 0.47 | 1.0 |
| Leu | Gln | TTA | CAG | 15.9 | 20 | 1.08 | 0.4 |
| Leu | His | TTA | CAT | 23.6 | 23 | -0.02 | -0.0 |
| Leu | Pro | TTA | CCA | 37.2 | 45 | 1.65 | 0.0 |
| Leu | Pro | TTA | CCC | 10.6 | 16 | 2.70 | 0.6 |
| Leu | Pro | TTA | CCG | 7.1 | 15 | 8.69 | 4.4 |
| Leu | Pro | TTA | CCT | 22.5 | 36 | 8.08 | 2.5 |
| Leu | Arg | TTA | CGA | 4.3 | 8 | 3.16 | 2.8 |
| Leu | Arg | TTA | CGC | 3.3 | 2 | -0.50 | -0.6 |
| Leu | Arg | TTA | CGG | 2.0 | 2 | 0.00 | 0.0 |
| Leu | Arg | TTA | CGT | 14.9 | 18 | 0.63 | 0.4 |
| Leu | Leu | TTA | CTA | 22.1 | 30 | 2.81 | 4.7 |
| Leu | Leu | TTA | CTC | 7.2 | 10 | 1.06 | 1.7 |
| Leu | Leu | TTA | CTG | 16.1 | 28 | 8.77 | 12.0 |
| Leu | Leu | TTA | CTT | 18.6 | 20 | 0.11 | 0.5 |
| Leu | Glu | TTA | GAA | 86.4 | 94 | 0.67 | 0.2 |
| Leu | Asp | TTA | GAC | 36.6 | 33 | -0.35 | -0.5 |
| Leu | Glu | TTA | GAG | 31.2 | 24 | -1.66 | -2.2 |
| Leu | Asp | TTA | GAT | 69.0 | 63 | -0.53 | -0.8 |
| Leu | Ala | TTA | GCA | 28.9 | 19 | -3.37 | -2.6 |
| Leu | Ala | TTA | GCC | 27.4 | 24 | -0.43 | -0.2 |
| Leu | Ala | TTA | GCG | 9.4 | 11 | 0.28 | 0.5 |
| Leu | Ala | TTA | GCT | 46.4 | 41 | -0.62 | -0.2 |
| Leu | Gly | TTA | GGA | 14.5 | 19 | 1.41 | 1.6 |
| Leu | Gly | TTA | GGC | 15.7 | 14 | -0.19 | -0.2 |
| Leu | Gly | TTA | GGG | 9.7 | 15 | 2.92 | 3.1 |
| Leu | Gly | TTA | GGT | 63.4 | 65 | 0.04 | 0.1 |
| Leu | Val | TTA | GTA | 18.1 | 14 | -0.94 | -0.5 |
| Leu | Val | TTA | GTC | 25.6 | 20 | -1.22 | -0.6 |
| Leu | Val | TTA | GTG | 17.6 | 16 | -0.14 | -0.0 |
| Leu | Val | TTA | GTT | 48.2 | 48 | -0.00 | -0.2 |
| Leu | Ocr | TTA | TAA | 0.0 | 3 | 0.00 | 0.0 |
| Leu | Tyr | TTA | TAC | 28.3 | 31 | 0.25 | 1.1 |
| Leu | Amb | TTA | TAG | 0.0 | 3 | 0.00 | 0.0 |
| Leu | Tyr | TTA | TAT | 31.6 | 28 | -0.40 | -0.0 |
| Leu | Ser | TTA | TCA | 29.1 | 39 | 3.38 | 1.7 |
| Leu | Ser | TTA | TCC | 24.0 | 21 | -0.37 | -1.0 |
| Leu | Ser | TTA | TCG | 11.3 | 11 | -0.01 | -0.1 |
| Leu | Ser | TTA | TCT | 44.0 | 52 | 1.45 | 0.3 |
| Leu | Umb | TTA | TGA | 0.0 | 2 | 0.00 | 0.0 |
| Leu | Cys | TTA | TGC | 6.9 | 10 | 1.39 | 0.4 |
| Leu | Trp | TTA | TGG | 18.1 | 24 | 1.93 | 4.6 |
| Leu | Cys | TTA | TGT | 14.7 | 16 | 0.12 | 0.1 |
| Leu | Leu | TTA | TTA | 49.2 | 33 | -5.35 | -3.2 |
| Leu | Phe | TTA | TTC | 33.0 | 27 | -1.10 | -0.8 |
| Leu | Leu | TTA | TTG | 55.5 | 49 | -0.76 | -0.1 |
| Leu | Phe | TTA | TTT | 42.6 | 42 | -0.01 | -0.0 |
| | Page Totals: | | | 1774.2 | 1778 | 120.321 | 100.5 |

YEAST.RXD/CPLIST.RXR February 7, 1989

| aa1 | aa2 | cod1 | cod2 | exp | obs | chis1 | chis2 |
|---|---|---|---|---|---|---|---|
| Phe | Lys | TTC | AAA | 51.4 | 77 | 12.78 | 21.6 |
| Phe | Asn | TTC | AAC | 39.7 | 59 | 9.42 | 6.4 |
| Phe | Lys | TTC | AAG | 58.1 | 67 | 1.37 | 4.6 |
| Phe | Asn | TTC | AAT | 38.7 | 64 | 16.60 | 12.3 |
| Phe | Thr | TTC | ACA | 19.9 | 15 | -1.19 | -0.9 |
| Phe | Thr | TTC | ACC | 23.8 | 25 | 0.06 | 0.2 |
| Phe | Thr | TTC | ACG | 8.2 | 8 | -0.01 | -0.0 |
| Phe | Thr | TTC | ACT | 34.6 | 37 | 0.16 | 0.4 |
| Phe | Arg | TTC | AGA | 39.3 | 28 | -3.27 | -0.5 |
| Phe | Ser | TTC | AGC | 8.7 | 14 | 3.21 | 3.4 |
| Phe | Arg | TTC | AGG | 9.7 | 17 | 5.59 | 10.6 |
| Phe | Ser | TTC | AGT | 14.2 | 15 | 0.04 | 0.1 |
| Phe | Ile | TTC | ATA | 15.7 | 14 | -0.19 | -0.3 |
| Phe | Ile | TTC | ATC | 29.0 | 41 | 4.98 | 4.0 |
| Phe | Met | TTC | ATG | 33.0 | 34 | 0.03 | 0.1 |
| Phe | Ile | TTC | ATT | 46.3 | 54 | 1.30 | 0.7 |
| Phe | Gln | TTC | CAA | 43.1 | 67 | 13.25 | 5.7 |
| Phe | His | TTC | CAC | 12.8 | 20 | 4.04 | 0.5 |
| Phe | Gln | TTC | CAG | 12.0 | 14 | 0.32 | 0.0 |
| Phe | His | TTC | CAT | 17.4 | 31 | 10.57 | 2.6 |
| Phe | Pro | TTC | CCA | 35.4 | 43 | 1.64 | 1.5 |
| Phe | Pro | TTC | CCC | 8.3 | 16 | 7.06 | 6.8 |
| Phe | Pro | TTC | CCG | 4.7 | 7 | 1.09 | 1.0 |
| Phe | Pro | TTC | CCT | 16.7 | 22 | 1.67 | 1.5 |
| Phe | Arg | TTC | CGA | 2.5 | 1 | -0.93 | -0.6 |
| Phe | Arg | TTC | CGC | 2.3 | 3 | 0.21 | 0.7 |
| Phe | Arg | TTC | CGG | 1.3 | 2 | 0.35 | 0.8 |
| Phe | Arg | TTC | CGT | 12.1 | 12 | -0.00 | -0.5 |
| Phe | Leu | TTC | CTA | 16.4 | 23 | 2.71 | 3.3 |
| Phe | Leu | TTC | CTC | 5.3 | 12 | 8.68 | 9.4 |
| Phe | Leu | TTC | CTG | 12.1 | 9 | -0.80 | -0.6 |
| Phe | Leu | TTC | CTT | 12.6 | 18 | 2.33 | 2.8 |
| Phe | Glu | TTC | GAA | 73.9 | 59 | -3.01 | -5.6 |
| Phe | Asp | TTC | GAC | 35.4 | 23 | -4.34 | -4.7 |
| Phe | Glu | TTC | GAG | 23.4 | 19 | -0.84 | -1.6 |
| Phe | Asp | TTC | GAT | 53.2 | 48 | -0.51 | -0.7 |
| Phe | Ala | TTC | GCA | 21.0 | 8 | -8.01 | -6.5 |
| Phe | Ala | TTC | GCC | 26.9 | 9 | -11.90 | -9.9 |
| Phe | Ala | TTC | GCG | 6.3 | 3 | -1.74 | -1.3 |
| Phe | Ala | TTC | GCT | 47.9 | 24 | -11.90 | -8.9 |
| Phe | Gly | TTC | GGA | 10.4 | 6 | -1.83 | -2.3 |
| Phe | Gly | TTC | GGC | 12.8 | 4 | -6.07 | -6.9 |
| Phe | Gly | TTC | GGG | 7.6 | 6 | -0.32 | -0.5 |
| Phe | Gly | TTC | GGT | 64.1 | 53 | -1.93 | -3.5 |
| Phe | Val | TTC | GTA | 12.7 | 3 | -7.39 | -7.3 |
| Phe | Val | TTC | GTC | 26.6 | 15 | -5.05 | -4.9 |
| Phe | Val | TTC | GTG | 13.1 | 10 | -0.75 | -0.7 |
| Phe | Val | TTC | GTT | 43.5 | 26 | -7.06 | -6.9 |
| Phe | Ocr | TTC | TAA | 0.0 | 4 | 0.00 | 0.0 |
| Phe | Tyr | TTC | TAC | 28.9 | 36 | 1.76 | 0.0 |
| Phe | Amb | TTC | TAG | 0.0 | 2 | 0.00 | 0.0 |
| Phe | Tyr | TTC | TAT | 23.1 | 26 | 0.37 | 0.3 |
| Phe | Ser | TTC | TCA | 19.9 | 20 | 0.00 | 0.0 |
| Phe | Ser | TTC | TCC | 22.1 | 22 | -0.00 | -0.0 |
| Phe | Ser | TTC | TCG | 7.5 | 7 | -0.03 | -0.0 |
| Phe | Ser | TTC | TCT | 39.0 | 41 | 0.10 | 0.2 |
| Phe | Umb | TTC | TGA | 0.0 | 0 | 0.00 | 0.0 |
| Phe | Cys | TTC | TGC | 5.2 | 4 | -0.26 | -0.1 |
| Phe | Trp | TTC | TGG | 16.8 | 11 | -1.98 | -1.2 |
| Phe | Cys | TTC | TGT | 11.8 | 12 | 0.00 | 0.1 |
| Phe | Leu | TTC | TTA | 33.0 | 27 | -1.10 | -0.8 |
| Phe | Phe | TTC | TTC | 36.8 | 20 | -7.67 | -2.7 |
| Phe | Leu | TTC | TTG | 55.0 | 56 | 0.02 | 0.2 |
| Phe | Phe | TTC | TTT | 32.4 | 25 | -1.70 | -0.0 |
| | | Page Totals: | | 1495.4 | 1498 | 203.511 | 182.1 |

PAGE 59

YEAST.RXD/CPLIST.RXR February 7, 1989

| aa1 | aa2 | cod1 | cod2 | exp | obs | chis1 | chis2 |
|---|---|---|---|---|---|---|---|
| Leu | Lys | TTG | AAA | 85.8 | 141 | 35.44 | 18.5 |
| Leu | Asn | TTG | AAC | 67.6 | 88 | 6.14 | 8.7 |
| Leu | Lys | TTG | AAG | 104.3 | 145 | 15.85 | 5.4 |
| Leu | Asn | TTG | AAT | 63.5 | 80 | 4.31 | 6.3 |
| Leu | Thr | TTG | ACA | 32.0 | 22 | -3.11 | -3.3 |
| Leu | Thr | TTG | ACC | 41.4 | 48 | 1.07 | 0.9 |
| Leu | Thr | TTG | ACG | 13.4 | 23 | 6.95 | 6.6 |
| Leu | Thr | TTG | ACT | 59.2 | 72 | 2.78 | 2.4 |
| Leu | Arg | TTG | AGA | 71.9 | 85 | 2.40 | 1.5 |
| Leu | Ser | TTG | AGC | 15.0 | 25 | 6.65 | 4.5 |
| Leu | Arg | TTG | AGG | 15.8 | 22 | 2.45 | 2.0 |
| Leu | Ser | TTG | AGT | 22.7 | 32 | 3.86 | 2.1 |
| Leu | Ile | TTG | ATA | 24.9 | 19 | -1.41 | -0.0 |
| Leu | Ile | TTG | ATC | 49.9 | 42 | -1.25 | -0.2 |
| Leu | Met | TTG | ATG | 55.2 | 59 | 0.26 | 1.3 |
| Leu | Ile | TTG | ATT | 79.9 | 76 | -0.19 | -2.6 |
| Leu | Gln | TTG | CAA | 74.9 | 74 | -0.01 | -0.8 |
| Leu | His | TTG | CAC | 21.4 | 13 | -3.30 | -2.4 |
| Leu | Gln | TTG | CAG | 20.0 | 31 | 6.10 | 3.9 |
| Leu | His | TTG | CAT | 29.5 | 25 | -0.68 | -0.2 |
| Leu | Pro | TTG | CCA | 62.2 | 80 | 5.07 | 0.1 |
| Leu | Pro | TTG | CCC | 13.6 | 23 | 6.48 | 2.3 |
| Leu | Pro | TTG | CCG | 7.6 | 9 | 0.28 | 0.0 |
| Leu | Pro | TTG | CCT | 28.1 | 21 | -1.78 | -5.3 |
| Leu | Arg | TTG | CGA | 4.3 | 4 | -0.02 | -0.0 |
| Leu | Arg | TTG | CGC | 3.9 | 2 | -0.91 | -1.0 |
| Leu | Arg | TTG | CGG | 2.0 | 4 | 2.08 | 1.9 |
| Leu | Arg | TTG | CGT | 20.9 | 17 | -0.73 | -1.0 |
| Leu | Leu | TTG | CTA | 27.7 | 28 | 0.00 | 0.3 |
| Leu | Leu | TTG | CTC | 8.0 | 5 | -1.14 | -0.7 |
| Leu | Leu | TTG | CTG | 18.4 | 12 | -2.24 | -1.4 |
| Leu | Leu | TTG | CTT | 21.4 | 19 | -0.27 | -0.0 |
| Leu | Glu | TTG | GAA | 131.1 | 135 | 0.12 | 0.0 |
| Leu | Asp | TTG | GAC | 60.8 | 64 | 0.17 | 0.1 |
| Leu | Glu | TTG | GAG | 39.4 | 44 | 0.54 | 0.2 |
| Leu | Asp | TTG | GAT | 92.0 | 103 | 1.33 | 0.9 |
| Leu | Ala | TTG | GCA | 35.1 | 33 | -0.12 | -0.0 |
| Leu | Ala | TTG | GCC | 47.8 | 51 | 0.22 | 0.7 |
| Leu | Ala | TTG | GCG | 10.7 | 6 | -2.03 | -1.7 |
| Leu | Ala | TTG | GCT | 88.0 | 96 | 0.73 | 1.8 |
| Leu | Gly | TTG | GGA | 17.4 | 8 | -5.08 | -4.9 |
| Leu | Gly | TTG | GGC | 21.0 | 27 | 1.72 | 1.9 |
| Leu | Gly | TTG | GGG | 12.3 | 12 | -0.01 | -0.0 |
| Leu | Gly | TTG | GGT | 115.8 | 101 | -1.90 | -1.5 |
| Leu | Val | TTG | GTA | 20.1 | 19 | -0.06 | -0.0 |
| Leu | Val | TTG | GTC | 46.4 | 49 | 0.15 | 0.8 |
| Leu | Val | TTG | GTG | 22.1 | 22 | -0.00 | -0.1 |
| Leu | Val | TTG | GTT | 77.2 | 58 | -4.78 | -2.7 |
| Leu | Ocr | TTG | TAA | 0.0 | 4 | 0.00 | 0.0 |
| Leu | Tyr | TTG | TAC | 48.4 | 30 | -7.02 | -4.5 |
| Leu | Amb | TTG | TAG | 0.0 | 2 | 0.00 | 0.0 |
| Leu | Tyr | TTG | TAT | 37.2 | 25 | -3.99 | -2.3 |
| Leu | Ser | TTG | TCA | 32.6 | 20 | -4.85 | -6.8 |
| Leu | Ser | TTG | TCC | 40.0 | 43 | 0.22 | 0.0 |
| Leu | Ser | TTG | TCG | 12.7 | 9 | -1.08 | -1.7 |
| Leu | Ser | TTG | TCT | 67.8 | 47 | -6.38 | -9.8 |
| Leu | Umb | TTG | TGA | 0.0 | 0 | 0.00 | 0.0 |
| Leu | Cys | TTG | TGC | 7.2 | 6 | -0.20 | -0.7 |
| Leu | Trp | TTG | TGG | 25.0 | 15 | -4.01 | -1.9 |
| Leu | Cys | TTG | TGT | 19.7 | 15 | -1.13 | -2.9 |
| Leu | Leu | TTG | TTA | 55.5 | 34 | -8.33 | -5.5 |
| Leu | Phe | TTG | TTC | 55.0 | 31 | -10.45 | -9.4 |
| Leu | Leu | TTG | TTG | 104.8 | 55 | -23.63 | -17.4 |
| Leu | Phe | TTG | TTT | 52.4 | 56 | 0.24 | 0.5 |
| | | Page Totals: | | 2561.7 | 2566 | 215.705 | 168.3 |

PAGE 60

YEAST.RXD/CPLIST.RXR February 7, 1989

| aa1 | aa2 | cod1 | cod2 | exp | obs | chis1 | chis2 |
|---|---|---|---|---|---|---|---|
| Phe | Lys | TTT | AAA | 67.9 | 44 | -8.41 | -4.4 |
| Phe | Asn | TTT | AAC | 41.3 | 35 | -0.96 | -1.9 |
| Phe | Lys | TTT | AAG | 54.6 | 18 | -24.54 | -19.2 |
| Phe | Asn | TTT | AAT | 55.8 | 30 | -11.94 | -14.9 |
| Phe | Thr | TTT | ACA | 27.3 | 25 | -0.19 | -0.1 |
| Phe | Thr | TTT | ACC | 21.5 | 19 | -0.29 | -0.1 |
| Phe | Thr | TTT | ACG | 12.1 | 7 | -2.17 | -1.9 |
| Phe | Thr | TTT | ACT | 36.6 | 41 | 0.54 | 1.0 |
| Phe | Arg | TTT | AGA | 39.8 | 32 | -1.51 | -0.0 |
| Phe | Ser | TTT | AGC | 12.7 | 9 | -1.08 | -1.0 |
| Phe | Arg | TTT | AGG | 14.6 | 8 | -2.95 | -1.2 |
| Phe | Ser | TTT | AGT | 20.5 | 7 | -8.86 | -8.6 |
| Phe | Ile | TTT | ATA | 24.2 | 23 | -0.06 | -0.2 |
| Phe | Ile | TTT | ATC | 27.4 | 16 | -4.75 | -5.5 |
| Phe | Met | TTT | ATG | 38.2 | 36 | -0.13 | -0.1 |
| Phe | Ile | TTT | ATT | 53.9 | 56 | 0.08 | 0.0 |
| Phe | Gln | TTT | CAA | 46.6 | 47 | 0.00 | 0.9 |
| Phe | His | TTT | CAC | 12.1 | 17 | 2.01 | 0.0 |
| Phe | Gln | TTT | CAG | 16.9 | 10 | -2.82 | -4.8 |
| Phe | His | TTT | CAT | 22.2 | 18 | -0.78 | -4.5 |
| Phe | Pro | TTT | CCA | 34.5 | 22 | -4.55 | -4.8 |
| Phe | Pro | TTT | CCC | 10.7 | 10 | -0.05 | -0.1 |
| Phe | Pro | TTT | CCG | 7.4 | 3 | -2.59 | -2.7 |
| Phe | Pro | TTT | CCT | 21.7 | 18 | -0.63 | -0.7 |
| Phe | Arg | TTT | CGA | 4.5 | 6 | 0.50 | 1.5 |
| Phe | Arg | TTT | CGC | 3.3 | 4 | 0.13 | 0.6 |
| Phe | Arg | TTT | CGG | 2.0 | 1 | -0.51 | -0.2 |
| Phe | Arg | TTT | CGT | 13.6 | 4 | -6.80 | -4.5 |
| Phe | Leu | TTT | CTA | 20.9 | 15 | -1.68 | -1.4 |
| Phe | Leu | TTT | CTC | 7.1 | 4 | -1.35 | -1.2 |
| Phe | Leu | TTT | CTG | 16.0 | 16 | 0.00 | -0.0 |
| Phe | Leu | TTT | CTT | 18.2 | 14 | -0.96 | -0.7 |
| Phe | Glu | TTT | GAA | 81.0 | 116 | 15.08 | 9.0 |
| Phe | Asp | TTT | GAC | 35.2 | 46 | 3.34 | 2.9 |
| Phe | Glu | TTT | GAG | 30.9 | 33 | 0.14 | 0.0 |
| Phe | Asp | TTT | GAT | 66.9 | 77 | 1.53 | 1.2 |
| Phe | Ala | TTT | GCA | 28.5 | 37 | 2.55 | 4.6 |
| Phe | Ala | TTT | GCC | 25.0 | 43 | 12.94 | 17.7 |
| Phe | Ala | TTT | GCG | 9.0 | 10 | 0.11 | 0.4 |
| Phe | Ala | TTT | GCT | 42.2 | 55 | 3.86 | 7.0 |
| Phe | Gly | TTT | GGA | 15.2 | 19 | 0.98 | 0.5 |
| Phe | Gly | TTT | GGC | 15.2 | 21 | 2.20 | 1.4 |
| Phe | Gly | TTT | GGG | 9.9 | 10 | 0.00 | 0.0 |
| Phe | Gly | TTT | GGT | 56.0 | 85 | 15.08 | 10.7 |
| Phe | Val | TTT | GTA | 18.0 | 24 | 2.03 | 2.1 |
| Phe | Val | TTT | GTC | 22.7 | 28 | 1.26 | 1.3 |
| Phe | Val | TTT | GTG | 16.9 | 24 | 2.99 | 3.1 |
| Phe | Val | TTT | GTT | 43.9 | 66 | 11.19 | 11.6 |
| Phe | Ocr | TTT | TAA | 0.0 | 4 | 0.00 | 0.0 |
| Phe | Tyr | TTT | TAC | 27.9 | 36 | 2.36 | 0.0 |
| Phe | Amb | TTT | TAG | 0.0 | 1 | 0.00 | 0.0 |
| Phe | Tyr | TTT | TAT | 31.2 | 41 | 3.09 | 0.1 |
| Phe | Ser | TTT | TCA | 29.1 | 31 | 0.12 | 0.2 |
| Phe | Ser | TTT | TCC | 22.9 | 23 | 0.00 | 0.0 |
| Phe | Ser | TTT | TCG | 11.1 | 16 | 2.15 | 2.3 |
| Phe | Ser | TTT | TCT | 42.5 | 42 | -0.00 | -0.0 |
| Phe | Umb | TTT | TGA | 0.0 | 0 | 0.00 | 0.0 |
| Phe | Cys | TTT | TGC | 6.8 | 8 | 0.20 | 0.4 |
| Phe | Trp | TTT | TGG | 18.1 | 21 | 0.45 | 1.1 |
| Phe | Cys | TTT | TGT | 13.5 | 11 | -0.47 | -0.2 |
| Phe | Leu | TTT | TTA | 42.6 | 39 | -0.30 | -0.1 |
| Phe | Phe | TTT | TTC | 32.4 | 32 | -0.01 | -1.7 |
| Phe | Leu | TTT | TTG | 52.4 | 49 | -0.23 | -0.1 |
| Phe | Phe | TTT | TTT | 46.5 | 39 | -1.21 | -0.2 |
| | Page Totals: | | | 1699.4 | 1702 | 179.744 | 168.6 |

Grand Totals:

| exp | obs | chis1 | chis2 |
|---|---|---|---|
| 75457 | 75623 | 7308.25 | 6217.31 |

What is claimed is:

1. A method for determining relative native codon pairing preferences in an organism, comprising the steps of:

obtaining nucleotide sequence data for said organism;

determining from said data the number of codons represented in at least a portion of said sequence and the frequency of usage of at least some individual codons in said portion;

determining from said individual codon frequencies the expected number of occurrences of at least some codon pairs, if said codons are paired in a radon manner;

comparing the expected number with the actual number of occurrences to determine said relative condon pairing preferences;

determining preferred amino acid pairings of said organism and eliminating any amino acid pair bias prior to determining said codon pairing preferences; and altering a gene for expression in said organism by substituting at least one codon for an existing codon in said gene to alter codon pairing in accordance with said codon pairing preferences to change the translational kinetics of said gene in a predetermined manner.

2. The method of claim 1, in which said codon pairing is altered to increase the translational kinetics of at least a portion of said gene.

3. The method of claim 2, in which said codon pairing is altered to increase the number of codon pairs that, in comparison to random codon pair usage, are the more abundant and yet more under-represented codon pairs in said organism.

4. The method of claim 1, in which said codon pairing is altered to decrease the translational kinetics of at least a portion of said gene.

5. The method of claim 4, in which said codon pairing is altered to increase the number of codon pairs that, in comparison to random codon pair usage, are the less abundant and yet more over-represented codon pairs in said organism.

6. The method of claim 1, wherein at least 100% of the existing condons pairs are changed.

7. The method of claim 1, further comprising the step of constructing a synthetic gene coding for a predetermined polypeptide for expression in said organism, and selecting codons for amino acids of said polypeptide in accordance with the relative native condon pairing preferences of said organism to achieve a desired level of translational kinetics of said gene.

8. The method of claim 7, wherein at least 10% of said codon pairs are selected in accordance with the relative native codon pairing preferences of said organism.

9. The method of claim 7, in which said codon pairing is selected to increase the number of codon pairs that, in comparison to random codon pair usage, are underrepresented codon pairs in said organism.

10. The method of claim 7, in which said codon pairing is selected to increase the number of codon pairs that, in comparison to random codon pair usage, are over-represented codon pairs in said organism.

11. A method for making at least a portion of a synthetic gene coding for a polypeptide, wherein said gene is intended for expression in a particular organism, comprising the steps of:

obtaining information regarding the relationship between codon pairing and translational kinetics for said organism; and for at least one amino acid pair in said polypeptide, selecting from among possible codon pairs a pair that provides desired translational kinetics; and providing said selected codon pair in said gene in place of a less-preferred pair.

12. The method of claim 11, wherein at least three codon pairs are selected and provided in accordance with said information.

13. The method of claim 11, wherein said selected codon pair is preferred by said organism in genes expressed at low levels of less than about 1000 copies per cell.

14. The method of claim 11, wherein said selected codon pair is preferred by said organism in genes expressed at intermediate levels of from about 1000 to about 10,000 copies per cell.

15. The method of claim 11, wherein said selected codon pair is preferred by said organism in genes expressed at high levels of greater than about 10,000 copies per cell.

16. The method of claim 11, wherein said selecting step affects at least 10% of the codons of said gene.

17. A method for altering a gene of a first organism for expression in a second organism, comprising the steps of:

obtaining information regarding native codon pairing preferences for at least some genes of said second organism; and replacing one or more existing codon pairs of said gene of said first organism in accordance with said information with codon pairs coding for the same amino acids but for which said second organism has different preferences that it does for said existing codon pairs, to alter the translational kinetics of said pairs in a predetermined manner.

18. The method of claim 17, wherein said replacing step alters at least one codon pair to a pair over-represented or under-represented in said genes of said second organism to the same general degree as was said replaced pair in said first organism.

19. The method of claim 17, wherein said replacing step increases the translational speed of said codon pairs.

20. The method of claim 17, wherein said replacing step decreases the translational speed of said codon pairs.

21. A method for expressing a gene in an organism, said gene having altered translational kinetics, comprising the steps of:

introducing a gene prepared according to the method of claim 1 into said organism; and expressing said gene in said organism.

22. A method for expressing a gene in an organism, said gene having altered translational kinetics, comprising the steps of:

introducing a gene prepared according to the method of claim 7 into said organism; and expressing said gene in said organism.

23. A method for expressing a gene in an organism, said gene having altered translational kinetics, comprising the steps of:

introducing a gene prepared according to the method of claim 19 into said organism; and expressing said gene in said organism.

24. A method for expressing a gene in an organism, said gene having altered translational kinetics, introducing a gene prepared according to the method of claim 20 into said organism; and expressing said gene in said organism.

25. A heterologous DNA sequence coding for a predetermined polypeptide for expression in a first organism, comprising:

a plurality of codon pairs coding for amino acid pairs of acid polypeptide, wherein at least three of said pairs have been selected from among possible codon pairs to correspond to nonrandom codon pair usage patterns of genes expressed at a level within a predetermined range in said first organism.

26. The DNA sequence of claim 25, wherein said predetermined range of expression is levels greater than about 10,000 copies per cell.

27. The DNA sequence of claim 25, wherein said predetermined range of expression is between about 1000 and 10,000 copies per cell.

28. The DNA sequence of claim 25, wherein said predetermined range of expression is below about 1000 copies per cell.

29. A DNA sequence altered for expression in a host organism other than the one to which it is native, wherein at least three codon pairs of the native sequence have been changed to codon pairs preferred by said host organism in genes expressed at a predetermined level.

30. The sequence of claim 29, wherein said alterations conform the pattern of translational kinetics of said altered sequence in said host organism to that of said native sequence in said native organism.

31. An organism expressing an exogenous gene native to a different species, wherein said exogenous gene has been tailored for expression in said organism by rational replacement of existing codon pairs with codon pairs producing desired translational kinetics in said organism.

32. The organism of claim 31, wherein said replacement condon pairs are those that, in comparison to random codon pair usage, are under-represented in said organism.

33. The organism of claim 31, wherein said replacement codon pairs are those that, in comparison to random condon pair usage, are over-represented in said organism.

34. A method for determining the type of organism from which a sample of nucleic acid originated, comprising:

determining the nucleotide sequence of said sample; and comparing the codon pairings in said sequence with codon pairing preferences for several possible organisms.

35. A method for determining the evolutionary origin of a nucleic acid sample, comprising the steps of:

determining the nucleotide sequence of said sample; and comparing the codon pairings in said sequence with codon pairing preferences of genes to which the sample may be related.

36. A method for altering the translational kinetics of only a portion of a gene, comprising the steps of:

obtaining, for an organism in which said gene is to be expressed, data regarding the relationship between codon pairing and translational kinetics; and altering at least one codon pairing in said portion in accordance with said data.

37. The method of claim 36, wherein said alteration introduces a translational pause in said portion.

38. The method of claim 36, wherein said alteration increases the speed with which said portion is translated.

39. A method for controlling protein folding during expression of an exogenous gene in an engineered organism, comprising the steps of:

obtaining data relating to codon pair preferences and relative representation of codon pairs for both a first organism to which said gene is native and a second organism in which said gene is to be expressed;

identifying at least one codon pair in said gene that is over- or under-represented to a different extent in said first organism than in said second organism; and altering said identified codon pair to a pair coding for the same amino acid that is represented to generally the same degree in said second organism as the identified pair is in said first organism.

40. The method of claim 39, wherein said identified codon pair is over-represented to a greater degree in said first organism than in said second organism.

41. The method of claim 39, wherein said identified codon pair is under-represented to a greater degree in said first organism than in said second organism.

42. The method of claim 39, further comprising the step of expressing said gene in an organism.

43. A method for introducing a translational pause site into a gene to be expressed in a particular organism, comprising the steps of:

obtaining, for said organism, information regarding relative representation of codon pairs; and introducing into said desired pause site an over-represented codon pair.

44. The method of claim 43, wherein said over-represented codon pair is also at least one standard deviation less abundant than the mean value for codon pairs in said organism.

* * * * *

UNITED STATES PATENT AND TRADEMARK OFFICE

CERTIFICATE OF CORRECTION

PATENT NO. : 5,082,767
DATED : January 21, 1992
INVENTOR(S) : Hatfield, et. al.

It is certified that error appears in the above-indentified patent and that said Letters Patent is hereby corrected as shown below:

Column 199, line 43, after "at least", delete "100%" and replace with--10%--.
Column 199, line 49, after "native", delete "condon" and replace with--codon--.
Column 201, line 2, after "kinetics, " --comprising the steps of:-- should be inserted.
Column 201, line 10, after "pairs of", delete "acid" and replace with --said--.
Column 201, line 41, after "replacement", delete "condon" and replace with--codon--.
Column 201, line 46, after "randon", delete "condon" and replace with--codon--.

Signed and Sealed this

Twenty-eighth Day of June, 1994

Attest:

BRUCE LEHMAN

*Attesting Officer*

*Commissioner of Patents and Trademarks*